US012502424B2

(12) United States Patent
Arnaud Barbe et al.

(10) Patent No.: US 12,502,424 B2
(45) Date of Patent: Dec. 23, 2025

(54) COMPOSITIONS FOR USE IN TREATMENT OF ACNE

(71) Applicant: SANOFI PASTEUR INC., Swiftwater, PA (US)

(72) Inventors: Nadège Arnaud Barbe, Paris (FR); Danilo Casimiro, Cambridge, MA (US); Andreas Karlsson, Paris (FR); Isabelle Legastelois, Paris (FR); Noëlle Mistretta, Paris (FR); Geneviève Renauld, Paris (FR); Bachra Mohamed Rokbi, Paris (FR); Khang Tran, Cambridge, MA (US); Monica Wu, Cambridge, MA (US)

(73) Assignee: SANOFI PASTEUR INC., Swiftwater, PA (US)

( * ) Notice: Subject to any disclaimer, the term of this patent is extended or adjusted under 35 U.S.C. 154(b) by 0 days.

(21) Appl. No.: 18/654,557

(22) Filed: May 3, 2024

(65) Prior Publication Data

US 2024/0374698 A1 Nov. 14, 2024

Related U.S. Application Data

(60) Provisional application No. 63/464,523, filed on May 5, 2023.

(30) Foreign Application Priority Data

Jun. 29, 2023 (EP) .................................... 23306076
Nov. 8, 2023 (EP) .................................... 23306927

(51) Int. Cl.

*A61K 39/05* (2006.01)
*A61P 37/04* (2006.01)
*C07K 14/005* (2006.01)
*C07K 14/195* (2006.01)
*A61K 39/00* (2006.01)

(52) U.S. Cl.

CPC .............. *A61K 39/05* (2013.01); *A61P 37/04* (2018.01); *C07K 14/005* (2013.01); *C07K 14/195* (2013.01); *A61K 2039/53* (2013.01); *A61K 2039/6018* (2013.01); *A61K 2039/70* (2013.01); *C07K 2319/03* (2013.01)

(58) Field of Classification Search

None
See application file for complete search history.

(56) References Cited

U.S. PATENT DOCUMENTS

| | | | |
|---|---|---|---|
| 8,784,830 | B2 | 7/2014 | Hasumi et al. |
| 9,340,769 | B2 | 5/2016 | Gallo et al. |
| 9,528,997 | B2 | 12/2016 | Rogéet al. |
| 9,637,525 | B2 | 5/2017 | Foster et al. |
| 9,669,089 | B2 | 6/2017 | Thess et al. |
| 9,675,668 | B2 | 6/2017 | Bancel et al. |
| 9,782,462 | B2 | 10/2017 | Bancel et al. |
| 9,895,432 | B2 | 2/2018 | Hasumi et al. |
| 10,030,053 | B2 | 7/2018 | Compans et al. |
| 10,323,078 | B2 | 6/2019 | Dupin et al. |
| 10,364,473 | B2 | 7/2019 | Li et al. |
| 10,426,825 | B2 | 10/2019 | Hasumi et al. |
| 10,988,754 | B2 | 4/2021 | Fotin-Mleczek et al. |
| 11,020,468 | B2 | 6/2021 | Hasumi et al. |
| 11,129,885 | B2 | 9/2021 | Luo |
| 11,512,118 | B2 | 11/2022 | Foster et al. |
| 2002/0142978 | A1 | 10/2002 | Raz et al. |
| 2020/0038499 | A1 | 2/2020 | Narayanan et al. |
| 2020/0392482 | A1 | 12/2020 | Zhang et al. |
| 2020/0399322 | A1 | 12/2020 | Baumhof et al. |
| 2021/0123092 | A1 | 4/2021 | Li et al. |
| 2022/0040281 | A1 | 2/2022 | Schwendt et al. |
| 2022/0040285 | A1 | 2/2022 | Weissman et al. |
| 2023/0145420 | A1 | 5/2023 | Vukovich et al. |
| 2024/0139302 | A1 * | 5/2024 | Selak ..................... A61K 39/00 |

FOREIGN PATENT DOCUMENTS

| | | | | |
|---|---|---|---|---|
| CZ | 25164 | U1 | 4/2013 | |
| WO | WO 2001/081581 | A2 | 11/2001 | |
| WO | WO 2003/033515 | A1 | 4/2003 | |
| WO | WO 2010/005474 | A1 | 1/2010 | |
| WO | WO 2012/006372 | A1 | 1/2012 | |
| WO | WO 2013/006825 | A1 | 1/2013 | |
| WO | WO 2017/019982 | A1 | 2/2017 | |
| WO | WO 2018/175783 | A1 | 9/2018 | |
| WO | WO-2018176031 | A1 * | 9/2018 | ............ A61K 39/21 |
| WO | WO 2019/079612 | A1 | 4/2019 | |
| WO | WO 2019/079618 | A2 | 4/2019 | |
| WO | WO 2021/165543 | A1 | 8/2021 | |

(Continued)

OTHER PUBLICATIONS

Liu PF, Nakatsuji T, Zhu W, Gallo RL, Huang CM. Passive immunoprotection targeting a secreted CAMP factor of Propionibacterium acnes as a novel immunotherapeutic for acne vulgaris. Vaccine. Apr. 12, 2011;29(17):3230-8. (Year: 2011).*

Embry A, Meng X, Cantwell A, Dube PH, Xiang Y. Enhancement of immune response to an antigen delivered by vaccinia virus by displaying the antigen on the surface of intracellular mature virion. Vaccine. Jul. 26, 2011;29(33):5331-9. (Year: 2011).*

(Continued)

*Primary Examiner* — Benjamin P Blumel

(74) *Attorney, Agent, or Firm* — LATHROP GPM LLP; James H. Velema, Esq.; Michael J. Spellberg, Esq.

(57) ABSTRACT

This invention relates to compositions (e.g. immunogenic compositions) which can be used to immunise against *C. acnes*. The compositions comprise *C. acnes* antigens and antigen combinations, used in the form of nucleic acids (e.g. mRNAs) encoding antigenic proteins or in the form of recombinant protein antigens.

68 Claims, 84 Drawing Sheets

Specification includes a Sequence Listing.

(56) References Cited

FOREIGN PATENT DOCUMENTS

| | | | | |
|---|---|---|---|---|
| WO | WO-2022099003 A1 * | 5/2022 | ........... | A61K 39/145 |
| WO | WO 2022/204491 A1 | 9/2022 | | |
| WO | WO 2023/214082 A2 | 11/2023 | | |
| WO | WO 2024/133515 A1 | 6/2024 | | |
| WO | WO 2024/188165 A1 | 9/2024 | | |

OTHER PUBLICATIONS

NCBI Reference Sequence: WP_002518322.1 (2023); note that this protein is identical to AAT82444.1, 2014 (Year: 2023).*

Grange et al., "Characterization of a Propionibacterium acnes Surface Protein as a Fibrinogen-Binding Protein", Sci. Rep., Jul. 25, 2017, 7(1): 6428.

Jahns et al., "An increased incidence of Propionibacterium acnes biofilms in acne vulgaris: a case-control study", Br. J. Dermatol., Jul. 2012, 167(1): 50-58. Epub Jun. 1, 2012.

Liu et al., "Passive immunoprotection targeting a secreted CAMP factor of Propionibacterium acnes as a novel immunotherapeutic for acne vulgaris", Vaccine, Apr. 12, 2011, 29(17): 3230-3238. Epub Feb. 26, 2011.

Lodes et al., "Variable expression of immunoreactive surface proteins of Propionibacterium acnes", Microbiology (Reading), Dec. 2006, 152(Pt 12): 3667-3681.

Maruggi et al., "Immunogenicity and protective efficacy induced by self-amplifying mRNA vaccines encoding bacterial antigens", Vaccine, Jan. 5, 2017, 35(2): 361-368. Epub Dec. 7, 2016.

McDowell et al., "Propionibacterium acnes types I and II represent phylogenetically distinct groups", J Clin Microbiol., Jan. 2005, 43(1): 326-334.

McDowell et al., "A new phylogenetic group of Propionibacterium acnes", J. Med. Microbiol., Feb. 2008, 57(Pt 2): 218-224.

McDowell et al., "A novel multilocus sequence typing scheme for the opportunistic pathogen Propionibacterium acnes and characterization of type I cell surface-associated antigens", Microbiology (Reading), Jul. 2011, 157(Pt 7): 1990-2003. Epub Apr. 21, 2011.

McDowell et al., "An expanded multilocus sequence typing scheme for propionibacterium acnes: investigation of 'pathogenic', 'commensal' and antibiotic resistant strains", PLoS One, 2012, 7(7): e41480. Epub Jul. 30, 2012.

McDowell et al., "The opportunistic pathogen Propionibacterium acnes: insights into typing, human disease, clonal diversification and CAMP factor evolution", PLoS One, Sep. 13, 2013, 8(9): e70897.

McLaughlin et al., "Propionibacterium acnes and Acne Vulgaris: New Insights from the Integration of Population Genetic, Multi-Omic, Biochemical and Host-Microbe Studies", Microorganisms, May 13, 2019, 7(5): 128.

Nagata et al., "Immunohistochemical Detection of Propionibacterium acnes in the Retinal Granulomas in Patients with Ocular Sarcoidosis", Sci. Rep., Nov. 9, 2017, 7(1): 15226.

Nakatsuji et al., "Vaccination targeting a surface sialidase of P. acnes: implication for new treatment of acne vulgaris", PLoS One, Feb. 6, 2008, 3(2): e1551.

Nakatsuji et al., "Propionibacterium acnes CAMP factor and host acid sphingomyelinase contribute to bacterial virulence: potential targets for inflammatory acne treatment", PLoS One, Apr. 12, 2011, 6(4): e14797.

Parvin et al., "A Therapeutic Oral Vaccine Candidate against Propionibacterium acnes: Preparation and Immunological Evaluation of Nanoparticles Encapsulated Sialidase-CAMP Fusion Protein", Human and Animal Health, 2020, 63: e20190427.

Sanofi, "Innovation to drive sustainable growth in Vaccines", Vaccines Investor Event, Presentation, Jun. 29, 2023.

Toyoda et al., "An Overview of Topical Antibiotics for Acne Treatment", Dermatology, 1998, 196(1): 130-134.

Tunney et al., "Detection of prosthetic hip infection at revision arthroplasty by immunofluorescence microscopy and PCR amplification of the bacterial 16S rRNA gene", J. Clin. Microbiol., Oct. 1999, 37(10): 3281-3290.

Valanne et al., "CAMP factor homologues in Propionibacterium acnes: a new protein family differentially expressed by types I and II", Microbiology (Reading), May 2005, 151(Pt 5): 1369-1379.

Wang et al., "The Anti-Inflammatory Activities of Propionibacterium acnes CAMP Factor-Targeted Acne Vaccines", J. Invest. Dermatol., Nov. 2018, 138(11): 2355-2364. Epub Jun. 30, 2018.

Xue et al., "RNA encoding the MPT83 antigen induces protective immune responses against *Mycobacterium tuberculosis* infection", Infect. Immun., Nov. 2004, 72(11): 6324-6329.

Yang et al., "Specific humoral immune response induced by propionibacterium acnes can prevent Actinobacillus pleuropneumoniae infection in mice", Clin. Vaccine Immunol., Mar. 2014, 21(3): 407-416. Epub Jan. 15, 2014.

Extended European Search Report for European Patent Application No. 23306076.3, dated Dec. 22, 2023.

* cited by examiner

Figure 5

| Expected localization | Supernatant | | | | | | Transmembrane | | | |
|---|---|---|---|---|---|---|---|---|---|---|
| Construct | WT | | Mutated Linker | | Mutated C-Ter Helix | | WT C-Ter (HA) TMB | | WT N-Ter (NA) TMB | |
| | G(+) | G(-) | G(+) | G(-) | G(+) | G(-) | G(+) | G(-) | G(+) | G(-) |
| Detection using pAb | + | + | + | (+) | + | + | + | + | - | - |
| Co-hemolytic activity | +++ | +++ | + | - | - | - | - | - | Protein with co-hemolytic activity detected in supernatant by pAb | |
| Detection using mAb G05 | + | + | + | (+) | Not detected | Not detected | Not detected | +/- | Not done | Not done |
| Detection using mAbs D07 | + | + | Not detected | Not detected | + | + | Not detected | Not detected | Not done | Not done |

Anti-DsA1 IgG

Anti-PITP IgG

Co-hemolytic Neutralizing titer on purified IgG D42

Co-hemolytic neutralising titer on purified IgG D42

Figure 43

| Score | Comparative expression level |
|---|---|
| 4 | High level of expression |
| 3 | Medium level of expression |
| 2 | Low level of expression |
| 1 | Traces |
| 0 | No expression |
| ND | No data |

| | | | Total Lysate | Intracellular | Transmembrane | Supernatant |
|---|---|---|---|---|---|---|
| CAMP2 | / | No SS-TMB | 4 | 4 | 1 | 0 |
| | SS | Flu HA-A | 1 | 0 | 0 | 3 |
| | | Flu HA-B | 1 | 0 | 0 | 3 |
| | | Rabies-G | 1 | 0 | 0 | 3 |
| | | VZV-gI | 1 | 0 | 0 | 3 |
| | | Ebola-GP | 1 | 0 | 0 | 3 |
| | SS-TMB | Flu HA-A | 2 | 0 | 2 | 0 |
| | | Flu HA-B | 4 | ND | ND | 0 |
| | | Rabies-G | 4 | ND | ND | 0 |
| | | VZV-gI | 3 | 0 | 2 | 0 |
| | | Ebola-GP | 4 | ND | ND | 0 |
| PITP | / | No SS-TMB | 3 | 3 | 0 | 1 |
| | SS | Flu HA-A | 2 | 1 | 0 | 4 |
| | | Flu HA-B | 2 | 1 | 0 | 4 |
| | | Rabies-G | 2 | 1 | 0 | 4 |
| | | VZV-gI | 2 | 1 | 0 | 4 |
| | | Ebola-GP | 2 | 1 | 0 | 4 |
| | SS-TMB | Flu HA-A | 4 | 3 | 4 | 3 |
| | | Flu HA-B | 4 | 3 | 4 | 3 |
| | | Rabies-G | 4 | 3 | 4 | 3 |
| | | VZV-gI | 4 | 3 | 4 | 3 |
| | | Ebola-GP | 4 | ND | ND | 2 |

COMPOSITIONS FOR USE IN TREATMENT OF ACNE

RELATED APPLICATIONS

This application claims priority to U.S. Provisional Patent Application Ser. No. 63/464,523, filed May 5, 2023. European Patent Application Nos. 23306927.7, filed Nov. 8, 2023, and 23306076.3, filed Jun. 29, 2023, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on Jul. 29, 2024, is named 754424_SA9-378_ST26.xml and is 533.111 bytes in size.

FIELD OF THE INVENTION

The invention is in the field of treating and preventing Cutibacterium *acnes* (*C. acnes*) infections, such as acne vulgaris. In particular, the invention relates to antigens and antigen combinations which can be used to immunise against *C. acnes*, used in the form of nucleic acids (e.g. mRNAs) encoding antigenic proteins or in the form of recombinant protein antigens.

BACKGROUND

Cutibacterium *acnes* (*C. acnes*, previously named *Propionibacterium acnes*) is a gram-positive bacterium known for its role in skin disorders such as acne vulgaris. *C. acnes* is a skin commensal which predominantly resides within sebaceous follicles which provide a unique lipid-rich environment due to secretion of sebum. Apart from skin. *C. acnes* has also been found in the conjunctiva, respiratory tract, genitourinary tract and gastrointestinal tract of humans and other animals.

Acne is a disease of pilosebaceous units in the skin, affecting more than 85% of adolescents and more than 20% of population continues to experience symptoms well beyond the teenage period. Acne vulgaris manifests in different severity grades: mild, moderate and severe. Moderate and severe acne account for more than one third of all cases and require medical treatment. Acne can appear also after the puberty, as an adult-onset condition, often associated with hormonal fluctuations which are more prevalent in women. *C. acnes* is also thought to play a role in other severe types of acne, such as acne conglobata, acne fulminans and cystic acne. In addition to dermatological pathology. *C. acnes* has also been found in corneal ulcers, and is a common cause of chronic endophthalmitis following cataract surgery. Various other inflammatory diseases have been associated with *C. acnes*, including postoperative prosthetic implant- and device-related infections (implant-associated infections), endocarditis, sarcoidosis, osteomyelitis, allergic alveolitis, pulmonary angitis, the SAPHO syndrome (synovitis, acne, pustulosis, hyperostosis, osteitis) and inflammation of lumbar nerve roots leading to sciatica. More recent studies suggest potential pathogenetic role of *C. acnes* also in non-infectious diseases such as prostatic cancer, due to its ability to persist intracellularly which may lead to altered gene expression.

Phylogenetic studies based on multilocus gene sequencing, as well as whole-genome analyses of isolates from the Human Microbiome Project (HMP) have provided valuable insights into the genetic population structure of *C. acnes*. The Multi Locus Sequence Typing (MLST) generates different sequences defined as distinct alleles which are then used to generate sequence types (STs) for every *C. acnes* isolate. Two different MLST typing schemes have been developed which divide *C. acnes* into closely related clusters IA1, IA2, IB, IC, II, and III (McDowell et al. 2012) or I-1a, I-1b, I-2, II, and III (Lomholt and Kilian 2010), according to MLST8 or MLST9 typing schemes, respectively. There has been some suggestion that only the strains of type IA1 should be targeted in the context of a therapeutic (McLaughlin et al. 2019-page 23: O'Neill and Gallo 2018-page 4, second column, end of the first long paragraph), as these are most commonly isolated from the skin of acne patients, whereas others can be found on both acne-prone and healthy skin. However, other phylotypes have also been shown to be associated with acne (WO2021/165543). For example, *C. acnes* strains from phylotypes IA2, IC or II have been isolated from inflamed lesions of human subjects (WO2021/165543).

*C. acnes* strains can be divided into groups using genomic sequencing of 16S rDNA sequence called a ribotype (RT). This system allowed comparison of the *C. acnes* strain populations in individuals based on the 16S rDNA sequences. The top 10 major ribotypes were highly abundant while also a significant number of rare ribotypes were identified. According to the analysis of the top 10 ribotypes, both disease-specific and health-specific associations could be identified (Fitz-Gibbon et al. 2013: Tomida et al. 2013: Mclaughlin et al. 2019). The three most abundant ribotypes (RT1, RT2, and RT3) were fairly evenly distributed among acne and normal individuals. However, ribotypes RT4, RT5, RT7, RT8, RT9, and RT10 were found predominantly in acne patients, while RT6 was strongly associated with normal skin. A phylogenetic tree based on unique single-nucleotide polymorphism positions in the core genome obtained from these 71 *C. acnes* genomes suggested that the 16S rDNA ribotypes to a large extent represent the relationship of the lineages, and that the 16S rDNA sequence is a useful molecular marker to distinguish major *C. acnes* lineages (Fitz-Gibbon et al. 2013: Tomida et al. 2013).

Current treatments target one or two steps in acne pathogenesis, including benzoyl peroxide, topical retinoids, and topical or oral antibiotics. Nevertheless, antibiotic resistance is a concern in acne. In addition, oral isotretinoin, which is recommended in more severe cases, is associated with adverse effects, the most important one being teratogenicity. There is a need for an effective *C. acnes* vaccine.

DISCLOSURE OF THE INVENTION

The present inventors have provided *C. acnes* antigens and antigen combinations which can be used to immunise against *C. acnes*.

In particular, the inventors showed that antigens derived from *C. acnes* CAMP2, DsA1, DsA2 and/or PITP polypeptides, alone or in combination, elicited an antibody response when delivered by mRNAs encoding the relevant antigens or in the form of recombinant polypeptides.

Accordingly, the invention provides *C. acnes* CAMP2 polypeptides, modified *C. acnes* CAMP2 polypeptides, *C. acnes* DsA1 polypeptides, *C. acnes* DsA2 polypeptides, *C. acnes* PITP polypeptides, chimeric *C. acnes* DsA1/DsA2 polypeptides, chimeric *C. acnes* DsA1/DsA2/PITP polypeptides and chimeric *C. acnes* DsA1/DsA2/PITP/CAMP2 polypeptides and nucleic acids comprising a nucleotide sequence encoding such polypeptides.

Polypeptide antigens described herein may be delivered by. i.e. in the form of, a nucleic acid (e.g. mRNA) comprising a nucleotide sequence encoding said polypeptide or as. i.e. in the form of, a recombinant protein.

CAMP2

Christie-Atkins-Munch-Petersen (CAMP) factor 2, or CAMP2, is a polypeptide belonging to the CAMP factor superfamily, whose members are known for their co-hemolytic and cytotoxic properties. *C. acnes* CAMP factors 1-5 (or CAMP1-5) are thought to be the causative agents of a co-hemolytic reaction of *C. acnes* with both sheep and human erythrocytes (Choudhury, 1978, Sörensen et al. Journal of Microbiological Methods (2010) 83 (2):211-216). The amino acid sequences of *C. acnes* CAMP factors 1-5 have a low degree of sequence identity between them (e.g. around 50% for CAMP2 and CAMP4 amino acid sequences and even less for others). Native *C. acnes* CAMP2 polypeptide is a secreted protein.

CAMP2 has been identified as a putative acne-associated virulence factor (Holland et al (2010)). The expression and secretion of CAMP proteins by different *C. acnes* strains has been suggested as one of the factors contributing to *C. acnes* resistance to opsonophagocytic killing. It has been reported that CAMP2 is able to induce killing of phagocytic cells in an in vitro assay involving co-cultivation with *C. acnes* (Wang et al. 2018). Furthermore, anti-CAMP2 neutralizing antibodies were shown to significantly decrease inflammation induced by *C. acnes* in a mouse ear model (Liu et al. 2011, Vaccine. 29:3230-3238).

The inventors have recognised that *C. acnes* CAMP2 polypeptides may be used to elicit an immune response against a *C. acnes* infection. In particular, the inventors have demonstrated that *C. acnes* CAMP2 polypeptides elicit an antibody (e.g. IgG) response. Notably, *C. acnes* CAMP2 polypeptides elicited an antibody (e.g. IgG) response, when delivered as a mRNA encoding the antigen, as well as in the form of recombinant protein. Furthermore, the inventors demonstrated that an antibody (e.g. IgG) response was elicited when a mRNA encoding a *C. acnes* CAMP2 polypeptide was delivered in lipid nanoparticle (LNP). Antibodies induced by *C. acnes* CAMP2 polypeptides reduced the co-hemolytic activity of CAMP2. *C. acnes* CAMP2 polypeptides may therefore elicit antibodies in a subject, e.g. antibodies that can neutralise biological activity of CAMP2 polypeptide, such as CAMP2 inflammatory activity.

The inventors have therefore demonstrated that *C. acnes* CAMP2 polypeptides (e.g. delivered in the form of a mRNA encoding the antigen or as a recombinant protein) are suitable vaccine antigens that may be used alone, in combination with other *C. acnes* antigens described herein, such as one or more of *C. acnes* DsA1 polypeptides, *C. acnes* DsA2 polypeptides, *C. acnes* PITP polypeptides, chimeric *C. acnes* DsA1/DsA2 polypeptides and chimeric *C. acnes* DsA1/DsA2/PITP polypeptides (e.g. delivered in the form of a mRNA encoding the antigen or as a recombinant protein) described herein, or as chimeric *C. acnes* DsA1/DsA2/PITP/CAMP2 polypeptides. CAMP2 polypeptides may elicit antibodies that neutralise CAMP2 inflammatory activity whilst immunisation with one or more of these other *C. acnes* antigens may elicit antibodies that bind to the surface of *C. acnes* bacteria and recruit effector cells (e.g. effector cells of the immune system (e.g. innate immune system) such as phagocytes).

Accordingly, in one aspect, the invention provides a nucleic acid that comprises a nucleotide sequence encoding a *C. acnes* CAMP2 polypeptide. Typically, the nucleic acid is a messenger RNA (mRNA). In a preferred embodiment, the nucleic acid is a non-naturally occurring nucleic acid, e.g. a non-naturally occurring mRNA. Thus, the nucleic acid may be a synthetic nucleic acid (e.g. a synthetic mRNA). In a further aspect, the invention provides a polypeptide comprising the amino acid sequence of a *C. acnes* CAMP2 polypeptide. A *C. acnes* CAMP2 polypeptide for use in the present invention, e.g. delivered as a mRNA and/or in a LNP, may elicit antibodies in a subject. Such antibodies may neutralise biological activity of CAMP2 polypeptide, such as CAMP2 inflammatory activity. Such antibodies may neutralise CAMP2 polypeptide co-hemolytic activity. Neutralisation of CAMP2 inflammatory activity may be determined as reduction in pro-inflammatory cytokines such as IL-1b and/or IL-6. Neutralisation of co-hemolytic activity may be determined in an in vitro co-hemolytic assay.

The amino acid sequence of a native *C. acnes* CAMP2 antigen is provided in SEQ ID NO: 202:

```
                                  (SEQ ID NO: 202)
        10         20         30         40
MKKTHLVAPL LVGAMLVPAA LSAPSAHAVE PITTISATST

        50         60         70         80
HELSASDARN SIQLLNAHIA TLQSVQKSVP GSDYSDQIRD

        90        100        110        120
LLKAAFDLRG LIETLAHGGI PFYDPSTIMP RIKLVATTID

       130        140        150        160
TIHTATTTLQ NKVRPAHVEL GLEVTKAVLL TANPASTAKE

       170        180        190        200
LDAEGAALKA RLEKVSQYPD LTPNDVATVY VRTNFSKTIW

       210        220        230        240
QVRANRDRYI LGHKSAAVYK TLNHAITKAV GVRLNPKTTV

       250        260
GNIQAARTEL LAAYQTAFNS PDVKKAA
```

The native signal peptide sequence corresponds to residues 1-28 in the amino acid sequence of CAMP2 of *C. acnes* (SEQ ID NO: 202) and is shown underlined. Residues 29-267 of SEQ ID NO: 202 correspond to the mature form of full-length CAMP2 polypeptide of *C. acnes* (without the native signal peptide sequence).

The N-terminal domain and C-terminal domain of *C. acnes* CAMP2 are shown in bold (N terminal domain) and in bold and underlined text (C terminal domain). The N-terminal domain of *C. acnes* CAMP2 polypeptide corresponds to amino acid residues 29-176 of *C. acnes* CAMP2 polypeptide in SEQ ID NO: 202. The C-terminal domain of *C. acnes* CAMP2 polypeptide corresponds to amino acid residues 189-267 of *C. acnes* CAMP2 polypeptide in SEQ ID NO: 202. A linker domain is positioned between N-terminus and C-terminus domains. The linker domain corresponds to amino acid residues 177-188 of SEQ ID NO: 202.

A "*C. acnes* CAMP2 polypeptide" includes a mature form of a full-length native CAMP2 polypeptide of *C. acnes* without its native signal peptide sequence, and immunogenic variants thereof. An immunogenic variant of a native *C. acnes* CAMP2 polypeptide is capable of eliciting an immune response (e.g. an antigen specific immune response) in a subject, for example an antibody response. Immunogenic variants of a native *C. acnes* CAMP2 polypeptide include immunogenic fragments of a native *C. acnes* CAMP2 polypeptide. Immunogenic *C. acnes* CAMP2 fragments include fragments of a native *C. acnes* CAMP2 polypeptide that are at least 50, at least 75, at least 100, at least 125, at least 150, at least 175, at least 200 or at least 225 amino acids long.

Exemplary *C. acnes* CAMP2 polypeptide sequences include a native *C. acnes* CAMP2 polypeptide sequence in SEQ ID NO: 203 which lacks the native secretion signal peptide sequence of the *C. acnes* CAMP2 polypeptide. Other exemplary *C. acnes* polypeptide sequences are set out in SEQ ID NOs 313-338. These are naturally occurring CAMP2 polypeptides from different strains of *C. acnes* and include the native secretion signal peptide sequence of the *C. acnes* CAMP2 polypeptide. The corresponding sequences of the CAMP2 polypeptide but without the native secretion signal peptide sequences are provided in SEQ ID NOs 339-363.

Analysis of 430 CAMP2 polypeptide sequences from naturally occurring strains of *C. acnes* showed that there were only 27 different CAMP2 sequences (SEQ ID NOs 202 and 313-338) when the native secretion signal peptide sequence was included in the alignment and only 26 different CAMP2 sequences when the native secretion signal peptide sequence was excluded (SEQ ID NOs 203 and 339-363). Sequence variation between those CAMP2 polypeptides was concentrated at certain residues (FIGS. 44A-44C and Table 1).

TABLE 1

Analysis of naturally occurring CAMP2 polypeptide variants

| Position within CAMP2 sequence (without signal peptide) | Residue in strain KPA171202* | Number of sequences identical to KPA171202 (out of 430 sequences analysed) | % of sequences identical to KPA171202 (out of 430 sequences analysed) | Residue in strains other than KPA171202 | Number of sequences with variant at that position | % of sequences with variant sequence |
|---|---|---|---|---|---|---|
| 6 | T | 429 | 99.8% | I | 1 | 0.2% |
| 9 | A | 429 | 99.8% | T | 1 | 0.2% |
| 11 | S | 424 | 98.6% | A | 6 | 1.4% |
| 18 | S | 348 | 80.9% | N | 82 | 19.1% |
| 19 | D | 347 | 80.7% | E/Y** | 82/1 | 19%/0.2% |
| 21 | R | 417 | 97.0% | H | 13 | 3.0% |
| 24 | I | 340 | 79.1% | M/L/T | 82/6/2 | 19%/1.4%/0.5% |
| 29 | A | 418 | 97.2% | P | 12 | 2.8% |
| 30 | H | 342 | 79.5% | R | 88 | 20.5% |
| 37 | V | 421 | 97.9% | A | 9 | 2.1% |
| 48 | D | 424 | 98.6% | N | 6 | 1.4% |
| 61 | R | 397 | 92.3% | H | 33 | 7.7% |
| 65 | E | 424 | 98.6% | D | 6 | 1.4% |
| 68 | A | 429 | 99.8% | T | 1 | 0.2% |
| 76 | D | 429 | 99.8% | N | 1 | 0.2% |
| 87 | V | 424 | 98.6% | A | 6 | 1.4% |
| 91 | I | 347 | 80.7% | V | 83 | 19.3% |
| 92 | D | 429 | 99.8% | G | 1 | 0.2% |
| 98 | T | 429 | 99.8% | K | 1 | 0.2% |
| 100 | T | 429 | 99.8% | I | 1 | 0.2% |
| 106 | R | 319 | 74.2% | S | 111 | 25.8% |
| 118 | K | 427 | 99.3% | N | 3 | 0.7% |
| 128 | S | 355 | 82.6% | T | 75 | 17.4% |
| 138 | A | 355 | 82.6% | T | 75 | 17.4% |
| 143 | R | 427 | 99.3% | H | 3 | 0.7% |
| 145 | E | 422 | 98.1% | D/K | 6/2 | 1.4%/0.5% |
| 154 | T | 424 | 98.6% | A | 6 | 1.4% |
| 169 | K | 424 | 98.6% | R | 6 | 1.4% |
| 177 | N | 342 | 79.5% | D | 88 | 20.5% |
| 179 | D | 423 | 98.4% | N/H | 6/16 | 1.4%/3.7% |
| 189 | A | 424 | 98.6% | E | 6 | 1.4% |
| 207 | N | 348 | 80.9% | D/A | 80/2 | 18.6%/0.5% |
| 221 | E | 424 | 98.6% | K | 6 | 1.4% |
| 223 | L | 429 | 99.8% | F | 1 | 23.3% |

*SEQ ID NO: 203 is the CAMP2 sequence of strain KPA171202 without the secretion signal peptide sequence.

**If more than one CAMP2 variant was found at a particular position, all alternative residues are indicated using "/" and their corresponding frequencies are likewise indicated using "/" in the final two columns.

In some embodiments, the *C. acnes* CAMP2 polypeptide comprises an amino acid substitution at one or more positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 203. In some embodiments, the *C. acnes* CAMP2 polypeptide comprises an amino acid substitution at one or more positions corresponding to residues T6 (e.g. T6I), A9 (e.g. A9T), S11 (e.g. S11A), S18 (e.g. S18N), D19 (e.g. D19E or D19Y), R21 (e.g. R21H), I24 (e.g. I24M, I24L or I24T), A29 (e.g. A29P), H30 (e.g. H30R), V37 (e.g. V37A), D48 (e.g. D48N), R61 (e.g. R61H), E65 (e.g. E65D), A68 (e.g. A68T), D76 (e.g. D76N), V87 (e.g. V87A), I91 (e.g. I91V), D92 (e.g. D92G), T98 (e.g. T98K), T100 (e.g. T100I), R106 (e.g. R106S), K118 (e.g. K118N), S128 (e.g. S128T), A138 (e.g. A138T), R143 (e.g. R143H), E145 (e.g. E145D or E145K), T154 (e.g. T154A), K169 (e.g. K169R), N177 (e.g. N177D), D179 (e.g. D179N or D179H), A189 (e.g. A189E), N207 (e.g. N207D or N207A), E221 (e.g. E221K) and/or L223 (e.g. L223F) of SEQ ID NO: 203.

In some embodiments, the *C. acnes* CAMP2 polypeptide comprises the sequence of any one of SEQ ID NO: 203, SEQ ID NO: 43-58, SEQ ID NO: 1-4, SEQ ID NO: 10-16, or SEQ ID NO: 339-363 (e.g. SEQ ID NO: 203) or a sequence having at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. Typically, sequence variation is at the positions listed above, i.e. positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 203. Thus, in some embodiments, the *C. acnes* CAMP2 polypeptide comprises an amino acid substitution at one or more positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 203. In some embodiments, the *C. acnes* CAMP2 polypeptide comprises a sequence having at least 90% identity to any one of SEQ ID NO: 203, SEQ ID NO: 43-58, SEQ ID NO: 1-4, SEQ ID NO: 10-16 or SEQ ID NO: 339-363 (e.g. SEQ ID NO: 203). In some embodiments, the *C. acnes* CAMP2 polypeptide comprises a sequence having at least 95% identity to any one of SEQ ID NO 203, SEQ ID NO: 43-58, SEQ ID NO: 1-4, SEQ ID NO: 10-16 or SEQ ID NO: 339-363 (e.g. SEQ ID NO: 203). Typically, the *C. acnes* CAMP2 polypeptide comprises a sequence having at least 85% identity to any one of SEQ ID NO: 203, SEQ ID NO: 43-58, SEQ ID NO: 1-4, SEQ ID NO: 10-16 or SEQ ID NO: 339-363 (e.g. SEQ ID NO: 203). In some embodiments, the *C. acnes* CAMP2 polypeptide comprises, consists essentially of or consists of (e.g. comprises) an amino acid sequence according to SEQ ID NO: 203.

In some embodiments, a nucleic acid comprising a nucleotide sequence encoding a *C. acnes* CAMP2 polypeptide comprises a nucleotide sequence according to any one of SEQ ID NO: 153-167, SEQ ID NO: 87-89, or SEQ ID NO: 95-101 or a sequence that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, the nucleic acid comprises a nucleotide sequence that is least 75% identical to any one of SEQ ID NO: 153-167, SEQ ID NO: 87-89, or SEQ ID NO: 95-101.

Modified CAMP2

The inventors have generated modified *C. acnes* CAMP2 polypeptides comprising a *C. acnes* CAMP2 polypeptide sequence and a heterologous transmembrane domain (TMB) sequence. The inclusion of a heterologous TMB sequence may be advantageous as such a sequence may localise the antigen to the cell membrane when the antigen is expressed in a cell e.g. in a eukaryotic cell (such as a cell in a subject). The inclusion of a heterologous TMB sequence may reduce antigen intracellular localisation relative to the antigen without the TMB sequence. The inventors have shown that such modified *C. acnes* CAMP2 polypeptides which comprise a TMB domain sequence elicited an antibody (e.g. IgG) response. Antibodies induced by modified *C. acnes* CAMP2 polypeptides reduced the co-hemolytic activity of *C. acnes* CAMP2 polypeptide. *C. acnes* CAMP2 polypeptides may elicit antibodies in a subject, e.g. antibodies that can neutralise biological activity of CAMP2 polypeptide, such as CAMP2 inflammatory activity.

Moreover, modified *C. acnes* CAMP2 polypeptides elicited higher antibody titres relative to *C. acnes* CAMP2 polypeptides lacking a TMB domain. Inclusion of a TMB sequence may therefore enhance immunogenicity (e.g. antibody response) in a subject of a *C. acnes* CAMP2 polypeptide. Inclusion of a TMB sequence in a modified *C. acnes* CAMP2 polypeptide may elicit a stronger antibody response. e.g. a higher antibody titre, in a subject compared to a CAMP2 polypeptide without a TMB sequence. A surface-expressed antigen (e.g. a modified *C. acnes* CAMP2 polypeptide) may enhance B cell activation in a subject leading to enhanced antigen-specific B cell response (e.g. enhanced antigen-specific antibody response such as higher antibody titres) in a subject.

The inventors have therefore demonstrated that these modified *C. acnes* CAMP2 polypeptides are suitable vaccine antigens that may be used either alone or in combination with other *C. acnes* antigens described herein, such as one or more of *C. acnes* DsA1 polypeptides, *C. acnes* DsA2 polypeptides, *C. acnes* PITP polypeptides, chimeric *C. acnes* DsA1/DsA2 polypeptides and chimeric *C. acnes* DsA1/DsA2/PITP polypeptides described herein. These modified *C. acnes* CAMP2 polypeptides, when used alone or in combination with one or more other antigens described herein, may elicit an immune response against infection. A modified *C. acnes* CAMP2 polypeptide as described herein may be delivered by a nucleic acid comprising a nucleotide sequence encoding the modified *C. acnes* CAMP2 polypeptide.

Accordingly, in one aspect, the invention provides a nucleic acid comprising a nucleotide sequence encoding a modified *C. acnes* CAMP2 polypeptide, wherein the modified *C. acnes* CAMP2 polypeptide comprises an amino acid sequence comprising a *C. acnes* CAMP2 polypeptide sequence and a heterologous transmembrane domain sequence. A heterologous TMB sequence is capable of localising the antigen to the cell membrane when the antigen is expressed in a cell (e.g. a eukaryotic cell such as a cell in a subject). This may enhance immunogenicity (e.g. antibody response such as antibody titre) elicited in a subject, e.g. relative to the antigen lacking the TMB sequence.

In a further aspect, the invention provides a polypeptide comprising the amino acid sequence of a modified *C. acnes* CAMP2 polypeptide.

In certain embodiments, the heterologous transmembrane domain sequence is a TMB sequence of a eukaryotic transmembrane polypeptide (a eukaryotic transmembrane sequence), a TMB sequence of a prokaryotic transmembrane polypeptide (a prokaryotic transmembrane sequence), or a TMB sequence of a viral transmembrane protein (a viral transmembrane domain sequence). In certain embodiments, the heterologous transmembrane domain is a TMB sequence of a viral transmembrane protein.

In certain embodiments, the heterologous TMB sequence is positioned at the N-terminus of the modified *C. acnes* CAMP2 polypeptide. In other embodiments, the heterologous TMB sequence is positioned at the C-terminus of the modified *C. acnes* CAMP2 polypeptide.

Typically, a nucleic acid described herein encoding the modified *C. acnes* CAMP2 polypeptide that comprises a transmembrane domain also comprises a nucleotide sequence encoding a secretion signal peptide sequence.

Additional detail regarding TMB domains suitable for use in the present invention is provided herein below. Exemplary TMB sequences are described herein below.

In certain embodiments, the heterologous transmembrane domain comprises a hemagglutinin (HA) transmembrane domain sequence from influenza A or influenza B virus, preferably from influenza A virus.

In certain embodiments, a transmembrane domain (TMB) sequence is directly fused to a *C. acnes* CAMP2 polypeptide described herein (i.e., there is no linker, such as an amino acid linker, connecting the TMB sequence to the *C. acnes* CAMP2 polypeptide in the modified *C. acnes* CAMP2 polypeptide described herein). In other embodiments of the modified *C. acnes* CAMP2 polypeptide described herein, a TMB sequence of the disclosure is attached to a *C. acnes* CAMP2 polypeptide described herein with a linker. Preferred linkers are set out herein below in section "Linkers".

In some embodiments, the modified *C. acnes* CAMP2 polypeptide comprises a *C. acnes* CAMP2 polypeptide sequence which comprises a sequence according to any one of SEQ ID NO: 203, SEQ ID NO: 43-58, SEQ ID NO: 1-4, SEQ ID NO: 10-16, or SEQ ID NO: 339-363 (e.g. SEQ ID NO: 203) or a sequence having at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. Typically, variation in the *C. acnes* CAMP2 polypeptide sequence may be at the positions set out herein above. Thus, *C. acnes* CAMP2 polypeptide sequence variation may typically be at positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 203 as set out herein above. In some embodiments, the *C. acnes* CAMP2 polypeptide sequence comprises an amino acid substitution at one or more positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 203. In some embodiments, the *C. acnes* CAMP2 polypeptide comprises an amino acid substitution at one or more positions corresponding to residues T6 (e.g. T6I), A9 (e.g. A9T), S11 (e.g. S11A), S18 (e.g. S18N), D19 (e.g. D19E or D19Y), R21 (e.g. R21H), I24 (e.g. I24M, I24L or I24T), A29 (e.g. A29P), H30 (e.g. H30R), V37 (e.g. V37A), D48 (e.g. D48N), R61 (e.g. R61H), E65 (e.g. E65D), A68 (e.g. A68T), D76 (e.g. D76N), V87 (e.g. V87A), I91 (e.g. I91V), D92 (e.g. D92G), T98 (e.g. T98K), T100 (e.g. T100I), R106 (e.g. R106S), K118 (e.g. K118N), S128 (e.g. S128T), A138 (e.g. A138T), R143 (e.g. R143H), E145 (e.g. E145 D or E145K), T154 (e.g. T154A), K169 (e.g. K169R), N177 (e.g. N177D), D179 (e.g. D179N or D179H), A189 (e.g. A189E), N207 (e.g. N207D or N207A), E221 (e.g. E221K) and/or L223 (e.g. L223F) of SEQ ID NO: 203. In some embodiments, the modified *C. acnes* CAMP2 polypeptide comprises a *C. acnes* CAMP2 polypeptide sequence which comprises a sequence having at least 90% identity to any one of SEQ ID NO 203, SEQ ID NO: 43-58, SEQ ID NO: 1-4, SEQ ID NO: 10-16 or SEQ ID NO: 339-363 (e.g. SEQ ID NO: 203). In some embodiments, the modified *C. acnes* CAMP2 polypeptide comprises a *C. acnes* CAMP2 polypeptide sequence which comprises a sequence having at least 95% identity to any one of SEQ ID NO 203, SEQ ID NO: 43-58, SEQ ID NO: 1-4, SEQ ID NO: 10-16 or SEQ ID NO: 339-363 (e.g. SEQ ID NO: 203). Typically, the modified *C. acnes* CAMP2 polypeptide comprises a *C. acnes* CAMP2 polypeptide sequence which comprises a sequence having at least 85% identity to any one of SEQ ID NO: 203, SEQ ID NO: 43-58, SEQ ID NO: 1-4, SEQ ID NO: 10-16 or SEQ ID NO: 339-363 (e.g. SEQ ID NO: 203).

In some embodiments, the modified *C. acnes* CAMP2 polypeptide comprises a sequence according to any one of SEQ ID NO: 207 or SEQ ID NO: 5-9 (e.g. SEQ ID NO: 207) or a sequence having at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. Typically, sequence variation is at the positions set out herein above, i.e. positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 207. Thus, in some embodiments, the modified *C. acnes* CAMP2 polypeptide comprises an amino acid substitution at one or more positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 relative to the residue numbering in SEQ ID NO: 207. In some embodiments, the modified *C. acnes* CAMP2 polypeptide comprises a sequence having at least 90% identity to any one of SEQ ID NO: 203, SEQ ID NO: 207, SEQ ID NO: 43-58, SEQ ID NO: 1-16 or SEQ ID NO: 339-363 (e.g., SEQ ID NO: 207). In some embodiments, the modified *C. acnes* CAMP2 polypeptide comprises a sequence having at least 95% identity to any one of SEQ ID NO: 203, SEQ ID NO: 207, SEQ ID NO: 43-58, SEQ ID NO: 1-16 or SEQ ID NO: 339-363 (e.g., SEQ ID NO: 207). In some embodiments, the modified *C. acnes* CAMP2 polypeptide comprises a sequence having at least 85% identity to any one of SEQ ID NO: 203, SEQ ID NO: 207, SEQ ID NO: 43-58, SEQ ID NO: 1-16 or SEQ ID NO: 339-363 (e.g., SEQ ID NO: 207).

In some embodiments, a nucleic acid comprising a nucleotide sequence encoding a modified *C. acnes* CAMP2 polypeptide comprises a nucleotide sequence according to any one of SEQ ID NO: 153-167, SEQ ID NO: 87-89 or SEQ ID NO: 95-101 or a sequence that has at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. In some embodiments, a nucleic acid comprising a nucleotide sequence encoding a modified *C. acnes* CAMP2 polypeptide comprises a nucleotide sequence according to any one of SEQ ID NO: 90-94 or SEQ ID NO: 391-392 (e.g., SEQ ID NO: 91) or a sequence that has at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. In some embodiments, the nucleic acid comprises a nucleotide sequence that is at least 75% or 85% (e.g., 75%) identical to any one of SEQ ID NO: 153-167, SEQ ID NO: 391-392 or SEQ ID NO: 87-101 (e.g., SEQ ID NO: 91).

The sequences of SEQ ID NOs: 90, 91, 391 and 392 were aligned. Variation was found at the positions indicated in SEQ ID NOs 398 and 399. In some embodiments, the nucleic acid comprising a nucleotide sequence encoding a modified *C. acnes* CAMP2 polypeptide comprises a nucleotide sequence according to SEQ ID NO: 398, wherein the nucleotides at positions 66; 78; 81; 87; 102; 120; 150; 222; 232; 234; 261; 298; 321; 339; 351; 367; 420; 423; 435; 438; 456; 462; 468; 478; 516; 528; 541; 546; 574; 583; 648; 664; 684; 706; 711; 735; 834 are each independently selected from A or C; the nucleotides at positions 480; 660; 849 are each independently selected from A, C or G; the nucleotides at positions 171; 282; 318; 375; 432; 675; 738 are each independently selected from A, C or T; the nucleotides at positions 6; 57; 93; 114; 168; 246; 300; 363; 384; 396; 405; 447; 459; 543; 585; 591; 609; 666; 708; 714; 857 are each independently selected from A or G: the nucleotides at positions 73; 97; 103; 118; 169; 181; 190; 283; 433; 493; 553; 745; 769; 775; 793; 805; 808; 826; 841; 850 are each independently selected from A or T; the nucleotides at positions 18; 27; 54; 98; 119; 153; 162; 170; 182; 191; 210; 213; 240; 264; 284; 312; 369; 390; 408; 434; 441; 483; 494; 554; 573; 603; 690; 746; 770; 774; 776; 794; 806; 809; 827; 842; 851; 855 are each independently selected from C or G; and the nucleotides at positions 30; 33; 36; 48; 51; 108; 111; 117; 123; 135; 177; 183; 186; 189; 207; 219; 225; 243; 255; 258; 267; 270; 276; 279; 285; 297; 327; 372; 378; 402; 426; 429; 448; 453; 465; 477; 501; 507; 519; 522; 531; 537; 549; 564; 582; 594; 615; 624; 636; 672; 693; 696; 702; 729; 741; 750; 753; 771; 780; 795; 804; 807; 810; 828; 837; 840; 852 are each independently selected from C or T. In some embodiments, the nucleic acid comprising a nucleotide sequence encoding a modified *C. acnes* CAMP2 polypeptide comprises a nucleotide sequence according to SEQ ID NO: 399, wherein the nucleotides at positions 66; 81; 87; 102; 222; 232; 234; 261; 298; 321; 339; 351; 420; 438; 456; 462; 468; 478; 516; 528; 541; 546; 574; 583; 648; 660; 664; 684; 706; 711; 735; 834 are each independently selected from A or C; the nucleotide at position 849 is selected from A, C or G; the nucleotides at positions 318; 432; 675 are each independently selected from A, C or T; the nucleotides at positions 6; 57; 93; 168; 300; 363; 384; 396; 405; 447; 459; 480; 543; 585; 609; 666; 708; 714; 857 are each independently selected from A or G; the nucleotides at positions 73; 97; 103; 118; 169; 181; 283; 433; 493; 745; 769; 793; 805; 808; 826; 841; 850 are each independently selected from A or T; the nucleotides at positions 18; 27; 54; 98; 119; 153; 170; 182; 213; 264; 284; 312; 369; 390; 408; 434; 483; 494; 573; 603; 746; 770; 774; 794; 806; 809; 827; 842; 851; 855 are each independently selected from C or G; and the nucleotides at positions 30; 33; 36; 48; 117; 123; 135; 171; 177; 183; 186; 189; 225; 243; 255; 258; 267; 270; 276; 282; 285; 297; 327; 372; 375; 378; 426; 453; 465; 477; 501; 519; 522; 531; 549; 564; 582; 624; 636; 672; 693; 696; 738; 741; 750; 753; 771; 780; 795; 807; 810; 828; 837; 840; 852 are each independently selected from C or T. Typically, the nucleic acid comprising a nucleotide sequence according to SEQ ID NO: 398 or 399 encodes a sequence according to SEQ ID NO: 6.

In some embodiments, the nucleic acid comprises a nucleotide sequence that is at least 75% or 85% (e.g., 75%) identical to any one of SEQ ID NO: 153-167, SEQ ID NO: 391-392 or SEQ ID NO: 87-101 (e.g., SEQ ID NO: 91).

In one embodiment, the nucleic acid of the invention is a mRNA comprising or consisting of (e.g., consisting of) the following structural elements:

(i) a 5' cap with the following structure:

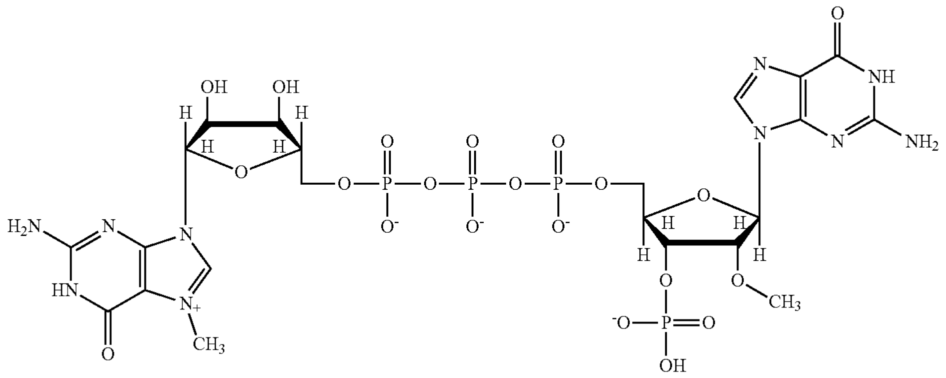

(ii) a 5' untranslated region (5' UTR) having the nucleic acid sequence according to SEQ ID NO: 265;

(iii) a protein coding region having the nucleic acid sequence according to SEQ ID NO: 90, SEQ ID NO: 391-392 or SEQ ID NO: 91 (e.g., SEQ ID NO: 91);

(iv) a 3' untranslated region (3' UTR) having the nucleic acid sequence according to SEQ ID NO: 266; and (v) a poly A tail, optionally wherein the poly A tail comprises at least 75 adenosine nucleotides (such as about 80 adenosine nucleotides) or at least 100 adenosine nucleotides (such as about 115 adenosine nucleotides), e.g., wherein the poly A tail comprises at least 100 adenosine nucleotides.

In some embodiments, the mRNA is chemically modified and the chemical modification comprises N1-methylpseudouridine in place of every uridine. The mRNA may be encapsulated in a LNP.

DsA1

*C. acnes* dermatan sulfate-adhesin 1 (DsA1), also known as P22 or P022, was identified as a putative *C. acnes* virulence factor (Lodes et al. 2006 (Microbiology (Reading). 2006 December; 152 (Pt 12):3667-3681); McDowell et al., 2011). This protein is found in abundance in both acne-affected and healthy follicular samples (Bek-Thomsen et al., 2014). *C. acnes* DsA1 polypeptides, derivatives and fragments thereof are described in WO2021/165543.

The inventors have demonstrated that mRNAs encoding different *C. acnes* DsA1 polypeptides and recombinant *C. acnes* DsA1 proteins elicit an antibody (e.g. IgG) response. Antibodies induced by *C. acnes* DsA1 polypeptides were shown to bind to the surface of *C. acnes* bacteria and recruit effector cells (e.g. effector cells of the immune system such as phagocytes). Antibodies induced by *C. acnes* DsA1 polypeptides were shown to elicit opsonophagocytic killing in vitro.

*C. acnes* DsA1 polypeptides of the invention may induce an immune response against a broad range of different *C. acnes* strains, phylotypes and variants which cause disease (a cross-reactive immune response).

The inventors have demonstrated that *C. acnes* DsA1 polypeptides are suitable vaccine antigens that may be used in combination with one or more other *C. acnes* antigens that can elicit antibody responses in a subject, such as *C. acnes* DsA2 polypeptides described herein. *C. acnes* PITP polypeptides described herein, and *C. acnes* CAMP2 polypeptides described herein. *C. acnes* CAMP2 polypeptides may elicit antibodies in a subject, e.g., antibodies that can neutralise biological activity of CAMP2 polypeptide, such as CAMP2 inflammatory activity.

Accordingly, in one aspect, the invention provides a nucleic acid that comprises a nucleotide sequence encoding a *C. acnes* DsA1 polypeptide. In a further aspect, the invention provides a polypeptide comprising the amino acid sequence of a *C. acnes* DsA1 polypeptide. A *C. acnes* DsA1 polypeptide for use in the present invention, e.g. delivered as a mRNA or as a recombinant protein, may elicit antibodies in a subject. Such antibodies may opsonize *C. acnes* bacteria. Opsonization may target immune effector cells such as phagocytes to *C. acnes* bacteria. This may lead to killing of *C. acnes* bacteria by such immune effector cells (e.g., phagocytic killing). Antibody binding to *C. acnes* cell surface may be measured e.g., using in vitro surface binding assays. In vitro opsonophagocytic killing assays may be used to evaluate antibodies for their ability to induce opsonization and killing of *C. acnes* strains of different genetic types by phagocytic cells.

The amino acid sequence of a native mature form of full-length *C. acnes* DsA1 polypeptide (without a signal peptide sequence) is provided in SEQ ID NO: 204:

SSNRPRSVAQAAIATDGKGIIDKDCRDAVINDAKLRAAIAGALVKAGFSS

ADAVALAPRIAKEMAKEGVLLINHHKLKALIGAQLGLLTDAKIQRAAAAV

DLGIKATLAATIIPNALHSAAFKDAVVANLVAAGVDKKLAKATAVAIAAT

ALNPALGPIAKTEAIKAEIAAQAALLVGRGVHLKKAAIEHIIGRSFDAAV

ATAIVSSPILNARIVTHLVRAGIDKSLAVQIAPRIIDRLAKEPLLALNTA

KLMKNITRQIVDVITADKAIKTAEQLEKELPALDDLVKKACSCPKPTPTP

TPTPTPTPKPTPTPTPKPTPTPKPKPTPAPAPTSGATSDESTSRSGGHSQ

GGSGTHYIHHGVAPVLTHSSDLPSTGF

A native mature *C. acnes* DsA1 polypeptide typically comprises a N-terminal swapping region ("NSR"), a first conserved sub-domain ("CSD1"), a first swapping region ("SR1"), a second conserved sub-domain ("CSD2"), a second swapping region ("SR2"), a third conserved sub-domain ("CSD3"), a Pro-Thr repeat containing region ("PT repeat region"-shown in bold above), and a C-terminal region ("CTR"; often with an LPXTG motif close to the C-terminus). The C-terminal LPXTG motif is thought to be critical for cell-wall anchoring of the protein.

For example, in the native *C. acnes* DsA1 polypeptide of SEQ ID NO: 204, the N-terminal swapping region ("NSR") corresponds to amino acid residues 1-20 the first conserved sub-domain ("CSD1") corresponds to amino acid residues 21-102, the first swapping region ("SR1") corresponds to amino acid residues 103-119, the second conserved sub-domain ("CSD2") corresponds to amino acid residues 120-239, the second swapping region ("SR2") corresponds to amino acid residues 240-249, the third conserved sub-domain ("CSD3") corresponds to amino acid residues 250-295, the Pro-Thr repeat containing region ("PT repeat region") corresponds to amino acid residues 296-333, and the C-terminal region ("CTR") corresponds to amino acid residues 334-377 (with the LPXTG motif corresponding to amino acid residues 372-376).

The sequence of naturally occurring DsA1 polypeptides are for the most part highly identical and differ (besides point mutations and rare exceptions specifically of the presence of the terminal LPXTG motif) only in the length and composition of the PT repeat region. More detailed sequence analyses of DsA1 have been described elsewhere (WO2021/165543). As is known in the art, the positions of the NSR, CSD1, SR1, CSD2, SR2, CSD3, PT repeat region and CTR within other native *C. acnes* DsA1 polypeptides may be determined by aligning the polypeptide sequence of a given DsA1 polypeptide with that of SEQ ID NO: 204, and identifying the regions of the DsA1 polypeptide which have high sequence identity to that of the NSR, CSD1, SR1, CSD2, SR2, CSD3, PT repeat region and CTR of SEQ ID NO: 204, respectively.

A "*C. acnes* DsA1 polypeptide" includes a mature form of a full-length native DsA1 polypeptide of *C. acnes* without its native signal peptide sequence, and immunogenic variants thereof. An immunogenic variant of a native *C. acnes* DsA1 polypeptide is capable of eliciting an immune response (e.g. an antigen specific immune response) in a subject, for example an antibody response. Immunogenic variants of a native *C. acnes* DsA1 polypeptide include immunogenic fragments of a native *C. acnes* DsA1 polypeptide. Immunogenic *C. acnes* DsA1 fragments include fragments of a native *C. acnes* DsA1 polypeptide that are at least 50, at least 75, at least 100, at least 125, at least 150, at least 175, at least 200, at least 225, at least 250, at least 275, at least 300, at least 325 or at least 350 amino acids long. In some embodiments, an immunogenic *C. acnes* DsA1 fragment comprises a CSD2 domain of a *C. acnes* DsA1 polypeptide. In some embodiments, immunogenic variants exclude sequence motifs that are found in a subject (e.g. human) proteome, e.g. sequence motifs of 8 or more, 9 or more, 10 or more, 11 or more, 12 or more, 13 or more, 14 or more or 15 or more (e.g. 8 or more) amino acids in length. Excluded subject proteome sequence motifs are typically 8 or more amino acids in length. This helps minimise unwanted cross-reactivity due to homology between the antigen and self protein.

Exemplary *C. acnes* DsA1 polypeptide sequences include a native *C. acnes* DsA1 polypeptide sequence of SEQ ID NO: 204 which lacks the native secretion signal peptide sequence of the *C. acnes* DsA1 polypeptide.

In some embodiments, the *C. acnes* DsA1 polypeptide comprises the sequence of any one of SEQ ID NO: 204, SEQ ID NO: 17-19 or SEQ ID NO: 59-61 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. In some embodiments, the *C. acnes* DsA1 polypeptide comprises a sequence having at least 90% identity to any one of SEQ ID NO: 204, SEQ ID NO: 17-19 or SEQ ID NO: 59-61. In some embodiments, the *C. acnes* DsA1 polypeptide comprises a sequence having at least 95% identity to any one of SEQ ID NO: 204, SEQ ID NO: 17-19 or SEQ ID NO: 59-61.

In some embodiments, a nucleic acid comprising a nucleotide sequence encoding a *C. acnes* DsA1 polypeptide comprises a nucleotide sequence according to any one of SEQ ID NO: 102-104 or SEQ ID NO: 168-170 or a sequence that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, the nucleic acid comprises a nucleotide sequence that is least 75% identical to any one of SEQ ID NO: 102-104 or SEQ ID NO: 168-170.

DsA2

*C. acnes* dermatan sulfate-adhesin 2 (DsA2) is also known as P27 or P027. DsA2 was identified as a putative *C. acnes* virulence factor (Lodes et al, 2006 (Microbiology (Reading). 2006 December; 152 (Pt 12):3667-3681); McDowell et al., 2011). This protein is found in both acne-affected and healthy follicular samples (Bek-Thomsen et al., 2014). DsA1 and DsA2 proteins are homologues (paralogues) with a typical sequence identity between 60-71%, depending on which region of the protein is aligned. Excluding PT-region length polymorphism, a high degree of typically >90% sequence identity can be seen within intact DsA1 and DsA2 proteins, respectively. *C. acnes* DsA2 polypeptides, derivatives and fragments thereof are described in WO2021/165543.

The inventors have demonstrated that mRNAs encoding different *C. acnes* DsA2 polypeptides and recombinant *C. acnes* DsA2 proteins elicit an antibody (e.g. IgG) response. Antibodies induced by *C. acnes* DsA2 polypeptides were shown to bind to the surface of *C. acnes* bacteria and recruit effector cells (e.g. effector cells of the immune system such as phagocytes). Antibodies induced by *C. acnes* DsA2 polypeptides were shown to elicit opsonophagocytic killing in vitro.

*C. acnes* DsA2 polypeptides of the invention may induce an immune response against a broad range of different *C. acnes* strains, phylotypes and variants which cause disease (a cross-reactive immune response).

The inventors have demonstrated that *C. acnes* DsA2 polypeptides are suitable vaccine antigens that may be used in combination with one or more other *C. acnes* antigens that can elicit antibody responses in a subject, such as *C. acnes* DsA1 polypeptides described herein. *C. acnes* PITP polypeptides described herein, and *C. acnes* CAMP2 polypeptides described herein. *C. acnes* CAMP2 polypeptides may elicit antibodies in a subject, e.g., antibodies that can neutralise biological activity of CAMP2 polypeptide, such as CAMP2 inflammatory activity.

Accordingly, in one aspect, the invention provides a nucleic acid that comprises a nucleotide sequence encoding a *C. acnes* DsA2 polypeptide. In a further aspect, the invention provides a polypeptide comprising the amino acid sequence of a *C. acnes* DsA2 polypeptide. A *C. acnes* DsA2 polypeptide for use in the present invention, e.g. delivered as a mRNA or as a recombinant protein, may elicit antibodies in a subject. Such antibodies may opsonize *C. acnes* bacteria. Opsonization may target immune effector cells such as phagocytes to *C. acnes* bacteria. This may lead to killing of *C. acnes* bacteria by such immune effector cells (e.g., phagocytic killing). Antibody binding to *C. acnes* cell surface may be measured e.g. using in vitro surface binding assays. In vitro opsonophagocytic killing assays may be used to evaluate antibodies for their ability to induce opsonization and killing of *C. acnes* strains of different genetic types by phagocytic cells.

The amino acid sequence of a native mature form of full-length *C. acnes* DsA2 polypeptide (without a signal peptide sequence) is provided in SEQ ID NO: 205:

```
ASNGNSSITQSAAFSPRATTKISEDCRKAIINDLKLRGAIVGALVKAGLS
AADAAALAPRIAAEMAAEGTLTINHHRLKVLVASQLGLVADAAVQHAAAA
IDLSFKAILGASIIPNALGSAAFKNAVIANLVAAGIDKHLARATAVAIVA
TALNPALGPIAKFELIKAEIAAQAALLIRRGVHLQKAAIEHVIGRAFDAA
VATAIISSPILSARIVTHLVRAGIDKSIAISLAPHIVKRLAKEPLLAFNT
AKLVKDIARQIVDIRNTQEAIAVYKQLKAELPTLDGLVQKACTPEPTPTP
TPTPTPTPTPAPTPTPAPTPTPAPTPAPTPTPAPTPTPTPTPTPTPTPTH
GATTTTPISRTTDRHNLGSHHTRIAAPALIHAKALPATGTGA
```

A native mature *C. acnes* DsA2 polypeptide typically comprises a N-terminal swapping region ("NSR"), a first conserved sub-domain ("CSD1"), a first swapping region ("SR1"), a second conserved sub-domain ("CSD2"), a second swapping region ("SR2"), a third conserved sub-domain ("CSD3"), a Pro-Thr repeat containing region ("PT repeat region"), and a C-terminal region ("CTR"; often with an LPXTG motif close to the C-terminus). The C-terminal LPXTG motif is thought to be critical for cell-wall anchoring of the protein.

For example, in the native *C. acnes* DsA2 polypeptide of SEQ ID NO: 205, the N-terminal swapping region ("NSR") corresponds to amino acid residues 1-21, the first conserved sub-domain ("CSD1") corresponds to amino acid residues 22-103, the first swapping region ("SR1") corresponds to amino acid residues 104-120, the second conserved subdomain ("CSD2") corresponds to amino acid residues 121-240, the second swapping region ("SR2") corresponds to amino acid residues 241-250, the third conserved subdomain ("CSD3") corresponds to amino acid residues 251-295, the Pro-Thr repeat containing region ("PT repeat region") corresponds to amino acid residues 296-349, and the C-terminal region ("CTR") corresponds to amino acid residues 350-392 (with the LPXTG motif corresponding to amino acid residues 385-389).

The sequence of naturally occurring DsA2 polypeptides are for the most part highly identical and differ (besides point mutations and rare exceptions specifically of the presence of the terminal LPXTG motif) only in the length and composition of the PT repeat region. More detailed sequence analyses of DsA2 have been described elsewhere (WO2021/165543). As is known in the art, the positions of the NSR, CSD1, SR1, CSD2, SR2, CSD3, PT repeat region and CTR within other native *C. acnes* DsA2 polypeptides may be determined by aligning the polypeptide sequence of a given DsA2 polypeptide with that of SEQ ID NO: 205, and identifying the regions of the DsA2 polypeptide which have high sequence identity to that of the NSR, CSD1, SR1, CSD2, SR2, CSD3, PT repeat region and CTR of SEQ ID NO: 205, respectively.

A "*C. acnes* DsA2 polypeptide" includes a mature form of a full-length native DsA2 polypeptide of *C. acnes* without its native signal peptide sequence, and immunogenic variants thereof. An immunogenic variant of a native *C. acnes* DsA2 polypeptide is capable of eliciting an immune response (e.g. an antigen specific immune response) in a subject, for example an antibody response. Immunogenic variants of a native *C. acnes* DsA2 polypeptide include immunogenic fragments of a native *C. acnes* DsA2 polypeptide. Immunogenic *C. acnes* DsA2 fragments include fragments of a native *C. acnes* DsA2 polypeptide that are at least 50, at least 75, at least 100, at least 125, at least 150, at least 175, at least 200, at least 225, at least 250, at least 275, at least 300, at least 325, at least 350 or at least 375 amino acids long. In some embodiments, an immunogenic *C. acnes* DsA2 fragment comprises a CSD2 domain of a *C. acnes* DsA2 polypeptide. In some embodiments, immunogenic variants exclude sequence motifs that are found in a subject (e.g. human) proteome, e.g. sequence motifs of 8 or more, 9 or more, 10 or more, 11 or more, 12 or more, 13 or more, 14 or more or 15 or more (e.g. 8 or more) amino acids in length. Excluded subject proteome sequence motifs are typically 8 or more amino acids in length. As explained further above, this helps minimise unwanted cross-reactivity due to homology between the antigen and self protein.

Exemplary *C. acnes* DsA2 polypeptide sequences include a native *C. acnes* DsA2 polypeptide sequence in SEQ ID NO: 205 which lacks the native secretion signal peptide sequence of the *C. acnes* DsA2 polypeptide.

In some embodiments, the *C. acnes* DsA2 polypeptide comprises the sequence of any one of SEQ ID NO: 205, SEQ ID NO: 20-27 or SEQ ID NO: 62-69 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. In some embodiments, the *C. acnes* DsA2 polypeptide comprises a sequence having at least 90% identity to any one of SEQ ID NO: 205, SEQ ID NO: 20-27 or SEQ ID NO: 62-69. In some embodiments, the *C. acnes* DsA2 polypeptide comprises a sequence having at least 95% identity to any one of SEQ ID NO: 205, SEQ ID NO: 20-27 or SEQ ID NO: 62-69.

In some embodiments, a nucleic acid comprising a nucleotide sequence encoding a *C. acnes* DsA2 polypeptide comprises a nucleotide sequence according to any one of SEQ ID NO: 105-112 or SEQ ID NO: 171-178 or a sequence that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, the nucleic acid comprises a nucleotide sequence that is least 75% identical to any one of SEQ ID NO: 105-112 or SEQ ID NO: 171-178.

PITP

*C. acnes* putative iron-transport protein (PITP), also known as P28 or P028, is a protein involved in the iron uptake mechanism by *C. acnes* (Lodes et al., 2006). Iron uptake plays a role in bacterial survival in the host tissue. Under iron limiting conditions, the expression of PITP increases on the cell surface (Lodes et al., 2006). *C. acnes* PITP polypeptides, derivatives and fragments thereof are described in WO2021/165543.

*C. acnes* PITP polypeptides of the invention may induce an immune response against a broad range of different *C. acnes* strains, phylotypes and variants which are able to cause disease. *C. acnes* PITP polypeptides were shown to elicit antibodies that bind to the surface of *C. acnes* bacteria and recruit effector cells (e.g. effector cells of the innate immune system such as phagocytes). The combination of a *C. acnes* PITP polypeptide of the invention with *C. acnes* DsA1 and/or DsA2 polypeptides (delivered as a mRNA or in the form of a recombinant protein) may elicit an immune response against a greater number of *C. acnes* strains or phylotypes compared to use of individual antigens.

The inventors have demonstrated that mRNAs encoding different *C. acnes* PITP polypeptides and recombinant *C. acnes* PITP proteins elicit an antibody (e.g. IgG) response. Antibodies elicited by *C. acnes* PITP polypeptides were shown to bind to the surface of *C. acnes* bacteria. Antibodies elicited by *C. acnes* PITP polypeptides were shown to elicit opsonophagocytic killing in vitro. Antibodies elicited by *C. acnes* PITP polypeptides were also shown to be cross-reactive across a range of *C. acnes* strains.

The inventors have demonstrated that *C. acnes* PITP polypeptides are suitable vaccine antigens that may be used in combination with one or more other *C. acnes* antigens that can elicit antibody responses in a subject, such as *C. acnes* DsA1 polypeptides described herein, *C. acnes* DsA2 polypeptides described herein, and *C. acnes* CAMP2 polypeptides described herein, *C. acnes* CAMP2 polypeptides may elicit antibodies in a subject, e.g. antibodies that can neutralise biological activity of CAMP2 polypeptide, such as CAMP2 inflammatory activity.

Accordingly, in one aspect, the invention provides a nucleic acid that comprises a nucleotide sequence encoding a *C. acnes* PITP polypeptide. In a further aspect, the invention provides a polypeptide comprising the amino acid sequence of a *C. acnes* PITP polypeptide. A *C. acnes* PITP polypeptide for use in the present invention, e.g. delivered as a mRNA or as a recombinant protein, may elicit antibodies in a subject. Such antibodies may opsonize *C. acnes* bacteria. Opsonization may target immune effector cells such as phagocytes to *C. acnes* bacteria. This may lead to killing of *C. acnes* bacteria by such immune effector cells (e.g. phagocytic killing). Antibody binding to *C. acnes* cell surface may be measured e.g. using in vitro surface binding assays. In vitro opsonophagocytic killing assays may be used to evaluate antibodies for their ability to induce opsonization and killing of *C. acnes* strains of different genetic types by phagocytic cells.

The amino acid sequence of a native mature form of full-length *C. acnes* PITP polypeptide (without a signal peptide sequence) is provided in SEQ ID NO: 206:

```
AGPTVTVIPVGREGGDITISGKGFSTTGFGVYVAVAPASVPEFYGNSDKF
YGYDPSKDTTESPSTIWVYTPSQKAIGSRFAQGRPMNNDGSFTITMKAPP
FEQGKDFVVLTTKAHGVGKTDHSDDTRTPVTYREATPAPTGPKTPIAPSK
QPSKQAAPSKQVKPSKQAGPNKQSTTPQQKTAEHRSQTPAAHRTMTKQVC
TIGASKVTSGSLTWGIRTSFTSYLRGPIANGSWKLSGGANWNGSAFTFPL
TSGSFDPATKSGSLKYSGSVHMTGHHGILDMTLAEPSLQIKGSTGHLYLD
VKSSSMDGKKTNYGRVDFATFGVSVSGNAAIKGSPVKLTATGAKAFAGFY
RAGEPMNPLSTNLTLSAEKVCHNVTVDAVTGKVIGDDSGKGAGRGLPVTG
AEGPSSDEIDLGIVGGLALTAVVSTVVVCRRYAARI
```

A native, mature *C. acnes* PITP polypeptide typically comprises an extended neocarzinostatin family domain ("ENFD"), a first swapping region ("SR1"), a heme binding domain ("HbD"), a second swapping region ("SR2": which includes the first four N-terminal residues of a LPXTG motif (i.e. including LPXT, but not G)), and a hydrophobic C-terminal region ("hLAR"; which includes the C-terminal Gly residue of a LPXTG motif). The LPXTG motif is thought to be critical for cell-wall anchoring of the protein.

For example, in the native *C. acnes* PITP polypeptide of SEQ ID NO: 206, the extended neocarzinostatin family domain ("ENFD") corresponds to amino acid residues 1-133, the first swapping region ("SR1") corresponds to amino acid residues 134-206, the heme binding domain ("HbD") corresponds to amino acid residues 207-365, the second swapping region ("SR2") corresponds to amino acid residues 366-399, and the hydrophobic C-terminal region ("hLAR") corresponds to amino acid residues 400-436. The LPXTG motif corresponds to amino acid residues 396-400.

The sequence of naturally occurring PITP polypeptides are for the most part highly identical and differ (besides point mutations) only in the N- and in the C-terminus. More detailed sequence analyses of DsA1 have been described elsewhere (WO2021/165543). As is known in the art, the positions of the ENFD, SR1, HbD, SR2 and hLAR within other native *C. acnes* PITP polypeptides may be determined by aligning the polypeptide sequence of a given PITP polypeptide with that of SEQ ID NO: 206, and identifying the regions of the PITP polypeptide which have high sequence identity to that of the ENFD, SR1, HbD, SR2 and hLAR of SEQ ID NO: 206, respectively.

A "*C. acnes* PITP polypeptide" includes a mature form of a full-length native PITP polypeptide of *C. acnes* without its native signal peptide sequence, and immunogenic variants thereof. An immunogenic variant of a native *C. acnes* PITP polypeptide is capable of eliciting an immune response (e.g. an antigen specific immune response) in a subject, for example an antibody response. Immunogenic variants of a native *C. acnes* PITP polypeptide include immunogenic fragments of a native *C. acnes* PITP polypeptide. Immunogenic *C. acnes* PITP fragments include fragments of a native *C. acnes* PITP polypeptide that are at least 50, at least 75, at least 100, at least 125, at least 150, at least 175, at least 200, at least 225, at least 250, at least 275, at least 300, at least 325, at least 350, at least 375, at least 400 or at least 425 amino acids long. In some embodiments, an immunogenic *C. acnes* PITP fragment comprises a ENFD and/or a HbD (e.g. a ENFD) domain of a *C. acnes* PITP polypeptide. In some embodiments, immunogenic variants exclude sequence motifs that are found in a subject (e.g. human) proteome, e.g. sequence motifs of 8 or more, 9 or more, 10 or more, 11 or more, 12 or more, 13 or more, 14 or more or 15 or more (e.g. 8 or more) amino acids in length. Excluded subject proteome sequence motifs are typically 8 or more amino acids in length. As explained further above, this helps minimise unwanted cross-reactivity due to homology between the antigen and self protein.

Exemplary *C. acnes* PITP polypeptide sequences include a native *C. acnes* PITP polypeptide sequence in SEQ ID NO: 206 which lacks the native secretion signal peptide sequence of the *C. acnes* PITP polypeptide.

In some embodiments, the *C. acnes* PITP polypeptide comprises the sequence of any one of SEQ ID NO: 206, SEQ ID NO: 31-37, SEQ ID NO: 73-79 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto. In some embodiments, the *C. acnes* PITP polypeptide comprises a sequence having at least 90% identity to any one of SEQ ID NO 206, SEQ ID NO: 31-37 or SEQ ID NO: 73-79. In some embodiments, the *C. acnes* PITP polypeptide comprises a sequence having at least 95% identity to any one of SEQ ID NO: 206, SEQ ID NO: 31-37 or SEQ ID NO: 73-79. In some embodiments, the *C. acnes* PITP polypeptide comprises, consists of or consists essentially of (e.g. comprises) an amino acid sequence according to SEQ ID NO: 73. Typically, the *C. acnes* PITP polypeptide comprises an amino acid sequence according to SEQ ID NO: 73 or a sequence that has at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity thereto.

In some embodiments, a nucleic acid comprising a nucleotide sequence encoding a *C. acnes* PITP polypeptide comprises a nucleotide sequence according to any one of SEQ ID NO: 115, SEQ ID NO: 117-121, SEQ ID NO: 182-188 (e.g., SEQ ID NO: 182) or a sequence that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, the nucleic acid comprises a nucleotide sequence that is least 75% identical to any one of SEQ ID NO: 115. SEQ ID NO: 117-121. SEQ ID NO: 182-188 (e.g., SEQ ID NO: 182 or SEQ ID NO: 115, such as SEQ ID NO: 182).

In one embodiment, the nucleic acid of the invention is a mRNA comprising or consisting of (e.g. consisting of) the following structural elements:

(i) a 5' cap with the following structure:

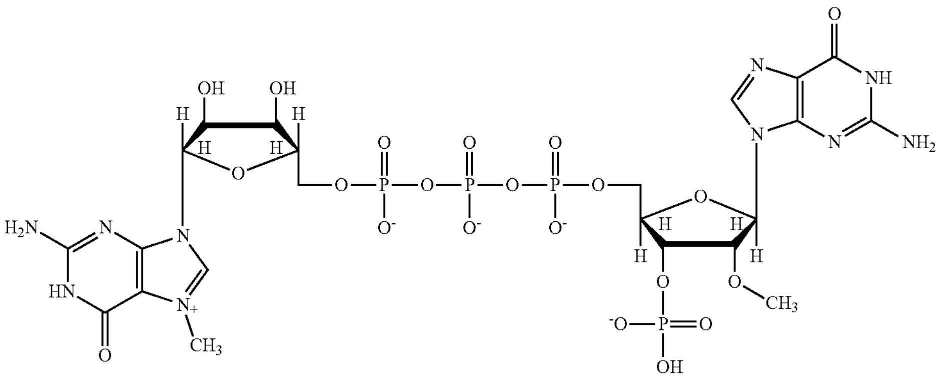

(ii) a 5' untranslated region (5' UTR) having the nucleic acid sequence according to SEQ ID NO: 265;

(iii) a protein coding region having the nucleic acid sequence according to SEQ ID NO: 115;

(iv) a 3' untranslated region (3' UTR) having the nucleic acid sequence according to SEQ ID NO: 266; and (v) a poly A tail, optionally wherein the poly A tail comprises at least 75 adenosine nucleotides (such as about 80 adenosine nucleotides) or at least 100 adenosine nucleotides (such as about 115 adenosine nucleotides), e.g., wherein the poly A tail comprises at least 100 adenosine nucleotides.

In some embodiments, the mRNA is chemically modified and the chemical modification comprises N1-methylpseudouridine in place of every uridine. The mRNA may be encapsulated in a LNP.

Chimeric DsA1/DsA2

Chimeric *C. acnes* DsA1/DsA2 polypeptides have been described previously (WO2021/165543).

*C. acnes* DsA1 and DsA2 proteins are homologues (paralogues) with a typical sequence identity between 60-71%, depending on which region of the protein is aligned. Excluding PT-region length polymorphism, a high degree of typically >90% sequence identity can be seen within intact DsA1 and DsA2 proteins, respectively. *C. acnes* DsA1 and *C. acnes* DsA2 are differentially expressed on the strains within the phylotypes IA1, IC and II of *C. acnes*. Some strains express more DsA1 polypeptide than DsA2 polypeptide and other strains express more DsA2 polypeptide than DsA1 polypeptide. Providing both a *C. acnes* DsA1 polypeptide and a *C. acnes* DsA2 polypeptide may be advantageous as this allows to target a wider range of *C. acnes* strains. It is possible that a DsA1 polypeptide and a DsA2 polypeptide can take over each other's function if they are targeted individually. Providing both DsA1 and DsA2 polypeptides may thus decrease the chance of immune defence evasion. Providing both DsA1 and DsA2 polypeptides may elicit an immune (e.g. antibody) response against a greater number of *C. acnes* strains (e.g. may elicit an antibody response against *C. acnes* strains expressing lower levels of one of the two polypeptides) e.g. compared to use of either DsA1 or DsA2 polypeptide alone. Providing both DsA1 and DsA2 polypeptides may thus increase immunogenicity. Provision of a chimeric *C. acnes* DsA1/DsA2 polypeptide as a single molecule, rather than provision of a DsA1 polypeptide and a DsA2 polypeptide as individual polypeptides, may facilitate manufacture of polypeptide and/or nucleic acids for use in the present invention.

Chimeric *C. acnes* DsA1/DsA2 polypeptides of the invention may be used to elicit an immune response against a *C. acnes* infection. Antibodies induced by chimeric *C. acnes* DsA1/DsA2 polypeptides were shown to bind to the surface of *C. acnes* bacteria. Antibodies induced by chimeric *C. acnes* DsA1/DsA2 polypeptides were shown to elicit opsonophagocytic killing in vitro. These antibodies may have superior cross-reactivity relative to antibodies elicited by individual (non-chimeric) *C. acnes* DsA1 polypeptides or *C. acnes* DsA2 polypeptides. Chimeric *C. acnes* DsA1/DsA2 polypeptides may elicit antibodies which specifically bind to both full length *C. acnes* DsA1 polypeptide and *C. acnes* DsA2 polypeptide, e.g. as determined in an ELISA assay. The antibodies elicited by DsA1 or DsA2 polypeptides may be cross-reactive against various *C. acnes* phylotypes. Furthermore, the antibodies elicited by chimeric DsA1/DsA2 polypeptides may be cross-reactive against various *C. acnes* phylotypes. The inventors have demonstrated that chimeric *C. acnes* DsA1/DsA2 polypeptides elicited an antibody (e.g. IgG) response when delivered as a mRNA encoding the antigen as well as in the form of recombinant protein.

Accordingly, in one aspect, the invention provides a nucleic acid that comprises a nucleotide sequence encoding a chimeric *C. acnes* DsA1/DsA2 polypeptide, wherein the chimeric *C. acnes* DsA1/DsA2 polypeptide comprises: (i) (a) a CSD2 of a *C. acnes* DsA1 polypeptide and (b) a CSD1 and/or a CSD3 of a *C. acnes* DsA2 polypeptide: or (ii) (a) a CSD2 of a *C. acnes* DsA2 polypeptide and (b) a CSD1 and/or a CSD3 of a *C. acnes* DsA1 polypeptide. The nucleic acid may be a messenger RNA (mRNA). In a further aspect, the invention provides a chimeric *C. acnes* DsA1/DsA2 polypeptide having an amino acid sequence comprising: (i) (a) a CSD2 of a *C. acnes* DsA1 polypeptide and (b) a CSD1 and/or a CSD3 of a *C. acnes* DsA2 polypeptide; or (ii) (a) a CSD2 of a *C. acnes* DsA2 polypeptide and (b) a CSD1 and/or a CSD3 of a *C. acnes* DsA1 polypeptide. A chimeric *C. acnes* DsA1/DsA2 polypeptide for use in the present invention, e.g. delivered as a mRNA or as a recombinant protein, may elicit an immune response (e.g. antibody response) in a subject. Such antibodies may be cross-reactive antibodies which specifically bind to both a native *C. acnes* DsA1 polypeptide and a native *C. acnes* DsA2 polypeptide. Such antibody response may be cross-reactive against various *C. acnes* phylotypes (e.g. phylotypes IA1, IA2, IB IC, II and III).

In some embodiments, a chimeric *C. acnes* DsA1/DsA2 polypeptide comprises:

(i) a NSR of a *C. acnes* DsA1 polypeptide or a NSR of a *C. acnes* DsA2 polypeptide (e.g. of a *C. acnes* DsA1 polypeptide), (ii) a CSD1 of a *C. acnes* DsA1 polypeptide or a CSD1 of a *C. acnes* DsA2 polypeptide (e.g. of a *C. acnes* DsA1 polypeptide), (iii) optionally a SR1 of a *C. acnes* DsA1 polypeptide (or a portion thereof) and/or a SR1 of a *C. acnes* DsA2 polypeptide (or a portion thereof), (iv) a CSD2 of a *C. acnes* DsA1 polypeptide or a CSD2 of a *C. acnes* DsA2 polypeptide (e.g. of a *C. acnes* DsA2 polypeptide), (v) optionally a SR2 of a *C. acnes* DsA1 polypeptide (or a portion thereof) and/or a SR2 of a *C. acnes* DsA2 polypeptide (or a portion thereof), and (vi) a CSD3 of a *C. acnes* DsA1 polypeptide or a CSD3 of a *C. acnes* DsA2 polypeptide (e.g. of a *C. acnes* DsA1 polypeptide).

As described in WO2021/165543, the SRs within *C. acnes* DsA1 polypeptides and *C. acnes* DsA2 polypeptides are typically regions which are enriched in intrinsically disordered polypeptide sequences (i.e., they are largely unstructured). The SRs share the property of linking ("spacing") two structural domains, such as the CSDs (such as CSD1, CSD2 and CSD3). Therefore, the CSDs from a *C. acnes DsA*1 polypeptide and a *C. acnes* DsA2 polypeptide may be combined by appropriately engineering the SRs such that their length (number of amino acid residues) is conserved. Advantageously, this design strategy may retain the structural integrity of the individual structured domains (e.g., the CSDs) in the resulting chimeric DsA1/DsA2 polypeptides.

In some embodiments, a chimeric *C. acnes* DsA1/DsA2 polypeptide of the invention comprises (e.g. from N terminus to C terminus) amino acid residues 21-102 of SEQ ID NO: 204, the amino acid residues 121-240 of SEQ ID NO: 205 and the amino acid residues 250-295 of SEQ ID NO: 204.

In some embodiments, the chimeric *C. acnes* DsA1/DsA2 polypeptide comprises a sequence according to any one of SEQ ID NO: 28-30, SEQ ID NO: 39 or SEQ ID NO: 70-72 or SEQ ID NO: 81 or a sequence having at least 90%, at least 91%, at least 92%, at least 93%, at least 94%, at least 95%, at least 96%, at least 97%, at least 98%, or at least 99% identity thereto. In some embodiments, the chimeric *C. acnes* DsA1/DsA2 polypeptide comprises a sequence having at least 95% identity to any one of SEQ ID NO: 28-30, SEQ ID NO: 39 or SEQ ID NO: 70-72 or SEQ ID NO: 81. Preferably, the chimeric *C. acnes* DsA1/DsA2 polypeptide comprises an amino acid sequence according to SEQ ID NO: 70 or a sequence that has at least 90%, at least 91%, at least 92%, at least 93%, at least 94%, at least 95%, at least 96%, at least 97%, at least 98%, or at least 99% identity thereto.

In some embodiments, the chimeric *C. acnes* DsA1/DsA2 polypeptide comprises, consists of or consists essentially of (e.g. comprises) an amino acid sequence according to SEQ ID NO: 70.

In some embodiments, a nucleic acid comprising a nucleotide sequence encoding the chimeric *C. acnes* DsA1/DsA2 polypeptide comprises a nucleotide sequence according to SEQ ID NO: 113-114, SEQ ID NO: 179, SEQ ID NO: 123 or SEQ ID NO: 190 (e.g., SEQ ID NO: 179) or a sequence that has at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, a nucleic acid comprising a nucleotide sequence encoding the chimeric *C. acnes* DsA1/DsA2 polypeptide comprises a nucleotide sequence that is least 85% identical to SEQ ID NO: 113-114, SEQ ID NO: 179, SEQ ID NO: 123 or SEQ ID NO: 190 (e.g., SEQ ID NO: 179). In some embodiments, a nucleic acid comprising a nucleotide sequence encoding the chimeric *C. acnes* DsA1/DsA2 polypeptide comprises or consists of a nucleotide sequence encoding a secretion signal peptide sequence (e.g., a viral secretion signal peptide sequence described herein) and a nucleotide sequence according to SEQ ID NO: 179. In some embodiments, a nucleic acid comprising a nucleotide sequence encoding the chimeric *C. acnes* DsA1/DsA2 polypeptide comprises or consists of a nucleotide sequence according to SEQ ID NO: 113.

In one embodiment, the nucleic acid of the invention is a mRNA comprising or consisting of (e.g. consisting of) the following structural elements:

(i) a 5' cap with the following structure:

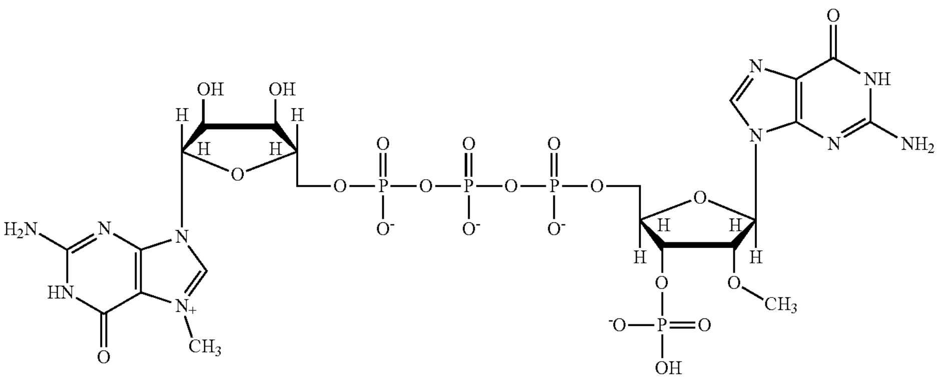

(ii) a 5' untranslated region (5' UTR) having the nucleic acid sequence according to SEQ ID NO: 265;

(iii) a protein coding region having the nucleic acid sequence according to SEQ ID NO: 113;

(iv) a 3' untranslated region (3' UTR) having the nucleic acid sequence according to SEQ ID NO: 266; and (v) a poly A tail, optionally wherein the poly A tail comprises at least 75 adenosine nucleotides (such as about 80 adenosine nucleotides) or at least 100 adenosine nucleotides (such as about 115 adenosine nucleotides), e.g., wherein the poly A tail comprises at least 100 adenosine nucleotides.

In some embodiments, the mRNA is chemically modified and the chemical modification comprises N1-methylpseudouridine in place of every uridine. The mRNA may be encapsulated in a LNP.

Chimeric DsA1/DsA2/PITP

Chimeric *C. acnes* DsA1/DsA2/PITP polypeptides have been described previously (WO2021/165543).

DsA1 polypeptides and DsA2 polypeptides may be expressed on *C. acnes* phylotypes IA1, IA2, IC and II. Antibodies induced by DsA1 polypeptides and DsA2 polypeptides may be unable to bind to *C. acnes* MLST phylotypes IB and III. Antibodies against *C. acnes* PITP polypeptides on the other hand may be able to bind to *C. acnes* type IB and *C. acnes* Type III. Therefore, PITP may be an antigen that can complement the immune response induced by other *C. acnes* antigens, e.g. DsA1 and/or DsA2. The combination of a *C. acnes* PITP polypeptide and a chimeric *C. acnes* DsA1/DsA2 polypeptide (delivered as a mRNA or in the form of a recombinant protein) may elicit an immune response against a greater number of *C. acnes* strains or phylotypes compared to use of individual antigens. A combination of DsA1 and/or DsA2 with PITP, delivered as a mRNA or in the form of a recombinant protein may provide an immune response (e.g. an antibody response) that is cross-reactive against a greater number of strains or phylotypes of *C. acnes* relative to using only DsA1 and/or DsA2. A *C. acnes* PITP polypeptide may be provided as a separate polypeptide molecule (delivered as a mRNA or in the form of a recombinant protein) or as part of a chimeric *C. acnes* DsA1/DsA2/PITP polypeptide (delivered as a mRNA or in the form of a recombinant protein).

Chimeric *C. acnes* DsA1/DsA2/PITP polypeptides of the invention (delivered as a mRNA or in the form of a recombinant protein) may be used to elicit an immune response against a *C. acnes* infection. A chimeric *C. acnes* DsA1/DsA2/PITP polypeptide (delivered as a mRNA or in the form of a recombinant protein) may elicit an immune response against a greater number of *C. acnes* strains compared to use of individual antigens (e.g. DsA1, DsA2 or PITP), e.g. a cross-reactive immune response. Provision of a chimeric *C. acnes* DsA1/DsA2/PITP polypeptide, rather than provision of a *C. acnes* DsA1 polypeptide, a *C. acnes* DsA2 polypeptide and a *C. acnes* PITP polypeptide as individual polypeptides (or a chimeric *C. acnes* DsA1/DsA2 polypeptide and a *C. acnes* PITP polypeptide), may facilitate manufacture of polypeptide and/or nucleic acids for use in the present invention.

Chimeric *C. acnes* DsA1/DsA2/PITP polypeptides may elicit an antibody response which is cross-reactive against various *C. acnes* phylotypes. The inventors have demonstrated that chimeric *C. acnes* DsA1/DsA2/PITP polypeptides elicited an antibody (e.g. IgG) response when delivered as a mRNA encoding the antigen as well as in the form of recombinant protein. Antibodies induced by chimeric *C. acnes* DsA1/DsA2/PITP polypeptides were shown to bind to the surface of *C. acnes* bacteria.

Accordingly, in one aspect, the invention provides a nucleic acid that comprises a nucleotide sequence encoding a chimeric *C. acnes* DsA1/DsA2/PITP polypeptide, wherein the chimeric *C. acnes* DsA1/DsA2/PITP polypeptide comprises a ENFD of a *C. acnes* PITP polypeptide and:

(i) (a) a CSD2 of a *C. acnes* DsA1 polypeptide and (b) a CSD1 and/or a CSD3 of a *C. acnes* DsA2 polypeptide; or (ii) (a) a CSD2 of a *C. acnes* DsA2 polypeptide and (b) a CSD1 and/or a CSD3 of a *C. acnes* DsA1 polypeptide.

The nucleic acid may be a messenger RNA (mRNA).

In a further aspect, the invention provides a chimeric *C. acnes* DsA1/DsA2/PITP polypeptide comprising a ENFD of a *C. acnes* PITP polypeptide and:

(i) (a) a CSD2 of a *C. acnes* DsA1 polypeptide and (b) a CSD1 and/or a CSD3 of a *C. acnes* DsA2 polypeptide; or (ii) (a) a CSD2 of a *C. acnes* DsA2 polypeptide and (b) a CSD1 and/or a CSD3 of a *C. acnes* DsA1 polypeptide.

A *C. acnes* DsA1/DsA2/PITP polypeptide for use in the present invention, e.g. delivered as a mRNA or as a recombinant protein, may elicit an immune response (e.g. antibodies) in a subject. Such antibodies may include antibodies which specifically bind to a native *C. acnes* DsA1 polypeptide, antibodies which specifically bind to a native *C. acnes* DsA2 polypeptide and/or antibodies which specifically bind to a native *C. acnes* PITP polypeptide. Such antibodies may be cross-reactive against various *C. acnes* phylotypes (e.g. phylotypes IA1, IA2, IB IC, II and III).).

In some embodiments, a chimeric *C. acnes* DsA1/DsA2 polypeptide comprises a CSD2 of a *C. acnes* DsA2 polypeptide, a CSD1 of a *C. acnes* DsA1 polypeptide, a CSD3 of a *C. acnes* DsA1 polypeptide and a ENFD of a *C. acnes* PITP polypeptide. In some embodiments, a chimeric *C. acnes* DsA1/DsA2/PITP polypeptide comprises:

(a) (i) a NSR of a *C. acnes* DsA1 polypeptide or a NSR of a *C. acnes* DsA2 polypeptide (e.g. of a *C. acnes* DsA1 polypeptide), (ii) a CSD1 of a *C. acnes* DsA1 polypeptide or a CSD1 of a *C. acnes* DsA2 polypeptide (e.g. of a *C. acnes* DsA1 polypeptide), (iii) optionally a SR1 of a *C. acnes* DsA1 polypeptide (or a portion thereof) and/or a SR1 of a *C. acnes* DsA2 polypeptide (or a portion thereof), (iv) a CSD2 of a *C. acnes* DsA1 polypeptide or a CSD2 of a *C. acnes* DsA2 polypeptide (e.g. of a *C. acnes* DsA2 polypeptide), (v) optionally a SR2 of a *C. acnes* DsA1 polypeptide (or a portion thereof) and/or a SR2 of a *C. acnes* DsA2 polypeptide (or a portion thereof), and (vi) a CSD3 of a *C. acnes* DsA1 polypeptide or a CSD3 of a *C. acnes* DsA2 polypeptide (e.g. of a *C. acnes* DsA1 polypeptide); and (b) a ENFD of a *C. acnes* PITP polypeptide.

As described in WO2021/165543, the SRs within *C. acnes* DsA1 polypeptides and *C. acnes* DsA2 polypeptides and PITP are typically regions which are enriched in intrinsically disordered polypeptide sequences (i.e., they are largely unstructured). The SRs share the property of linking ("spacing") two structural domains, such as the CSDs (such as CSD1, CSD2 and CSD3 of *C. acnes* DsA1 polypeptides and *C. acnes* DsA2 polypeptides), the ENFD of *C. acnes* PITP polypeptides or the HbD of *C. acnes* PITP polypeptides. Therefore, CSDs from a *C. acnes* DsA1 polypeptide and a *C. acnes* DsA2 polypeptide, ENFD of a *C. acnes* PITP polypeptide and/or the HbD of *C. acnes* PITP polypeptide may be combined by interspersing them with SRs of a similar length (number of amino acid residues) to that of the SRs in a native *C. acnes* polypeptide. Advantageously, this design strategy may retain the structural integrity of the individual structured domains (e.g., the CSDs, ENFD and HbD) in the resulting chimeric DsA1/DsA2/PITP polypeptides.

In some embodiments, the chimeric *C. acnes* DsA1/DsA2/PITP polypeptide comprises an amino acid sequence according to any one of SEQ ID NO: 38, SEQ ID NO: 40-41, SEQ ID NO: 80, SEQ ID NO: 82-83 or SEQ ID NO: 367-368 (e.g., SEQ ID NO: 80, 82, 83 or 368) or a sequence that has at least 90%, at least 91%, at least 92%, at least 93%, at least 94%, at least 95%, at least 96%, at least 97%, at least 98%, or at least 99% identity thereto. In some embodiments, the chimeric *C. acnes* DsA1/DsA2/PITP polypeptide comprises a sequence having at least 90% identity to any one of SEQ ID NO: 38, SEQ ID NO: 40-41, SEQ ID NO: 80, SEQ ID NO: 82-83 or SEQ ID NO: 367-368 (e.g., SEQ ID NO: 80, 82, 83 or 368). In some embodiments, the chimeric *C. acnes* DsA1/DsA2/PITP polypeptide comprises a sequence having at least 95% identity to any one of SEQ ID NO: 38, SEQ ID NO: 40-41, SEQ ID NO: 80, SEQ ID NO: 82-83 or SEQ ID NO: 367-368 (e.g., SEQ ID NO: 80, 82, 83 or 368).

In some embodiments, the chimeric *C. acnes* DsA1/DsA2/PITP polypeptide consists of an amino acid sequence according to SEQ ID NO: 80, 82, 83 or 368.

In some embodiments, a nucleic acid comprising a nucleotide sequence encoding the chimeric *C. acnes* DsA1/DsA2/PITP polypeptide comprises a nucleotide sequence according to any one of SEQ ID NO: 122, SEQ ID NO 124-125, SEQ ID NO: 189 or SEQ ID NO: 191-192 (e.g., SEQ ID NO: 189 or 192) or a sequence that has at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, a nucleic acid comprising a nucleotide sequence encoding the chimeric *C. acnes* DsA1/DsA2/PITP polypeptide comprises a nucleotide sequence that is least 85% identical to any one of SEQ ID NO: 122. SEQ ID NO 124-125. SEQ ID NO: 189 or SEQ ID NO: 191-192 (e.g., SEQ ID NO: 189 or 192).

In some embodiments, a nucleic acid comprising a nucleotide sequence encoding the chimeric *C. acnes* DsA1/DsA2 polypeptide consists of a nucleotide sequence encoding a secretion signal peptide sequence (e.g., a viral secretion signal peptide sequence described herein) and a sequence according to any one of SEQ ID NO: 189 or SEQ ID NO: 191-192.

Chimeric DsA1/DsA2/PITP/CAMP2

The inventors have designed chimeric *C. acnes* DsA1/DsA2/PITP/CAMP2 polypeptides (also referred to herein as chimeric *C. acnes* CAMP2/DsA1/DsA2/PITP polypeptides). Chimeric *C. acnes* DsA1/DsA2/PITP/CAMP2 polypeptides of the present invention may elicit an immune (e.g. antibody) response. This response may be a protective immune (e.g. antibody) response. Chimeric *C. acnes* DsA1/DsA2/PITP/CAMP2 polypeptides may elicit an immune response (e.g. antibodies) against native *C. acnes* DsA1 polypeptide, an immune response (e.g. antibodies) against native *C. acnes* DsA2 polypeptide, an immune response (e.g. antibodies) against native *C. acnes* PITP polypeptide and/or an immune response (e.g. antibodies) against native *C. acnes* CAMP2 polypeptide. Such antibodies may be cross-reactive against various *C. acnes* MLST phylotypes (e.g. phylotypes IA1, IA2, IB IC, II and III). The antibodies elicited by chimeric *C. acnes* DsA1/DsA2/PITP/CAMP2 polypeptides may neutralise biological activity of CAMP2 polypeptide, such as CAMP2 inflammatory activity. The antibodies elicited by the chimeric *C. acnes* DsA1/DsA2/PITP/CAMP2 polypeptides may opsonize *C. acnes* bacteria. Opsonization may target immune effector cells such as phagocytes to *C. acnes* bacteria. This may lead to killing of *C. acnes* bacteria by such immune effector cells (e.g. phagocytic killing). Chimeric *C. acnes* DsA1/DsA2/PITP/CAMP2 polypeptides may elicit antibodies that can neutralise biological activity of CAMP2 polypeptide, such as CAMP2 inflammatory activity. Chimeric *C. acnes* DsA1/DsA2/PITP/CAMP2 polypeptides may therefore elicit (a) antibodies that neutralise biological activity of a *C. acnes* CAMP2 polypeptide, such as inflammatory activity and (b) antibodies that opsonize *C. acnes* bacteria and recruit immune effector cells such as phagocytes. Thus, immunisation with chimeric *C. acnes* DsA1/DsA2/PITP/CAMP2 polypeptides of the invention (e.g. delivered as a mRNA or as a recombinant protein) may provide a more effective immune response (e.g. more effective killing of *C. acnes* bacteria in a subject) than immunisation with chimeric DsA1/DsA2/PITP polypeptides or individual DsA1. DsA2 or PITP antigens or a CAMP2 polypeptide on its own.

The inventors have demonstrated that chimeric *C. acnes* DsA1/DsA2/PITP/CAMP2 polypeptides elicited an antibody (e.g. IgG) response against DsA1, DsA2, PITP and CAMP2 antigens when delivered as a mRNA encoding the polypeptide. Antibodies induced by the chimeric *C. acnes* DsA1/DsA2/PITP/CAMP2 polypeptides were shown to bind to the surface of *C. acnes* bacteria. Antibodies induced by the chimeric *C. acnes* DsA1/DsA2/PITP/CAMP2 polypeptides were shown to elicit opsonophagocytic killing in vitro. The inventors have also shown that antibodies induced by the chimeric *C. acnes* DsA1/DsA2/PITP/CAMP2 polypeptides reduced the co-hemolytic activity of *C. acnes* CAMP2 polypeptide.

Combining DsA1, DsA2, PITP and CAMP2 antigens in a single chimeric polypeptide may advantageously reduce reactogenicity of a vaccine, e.g. in the context of the chimeric polypeptide being delivered in the form of a single mRNA, e.g. because a vaccine formulation of a single mRNA may use less cationic lipid or LNP than a vaccine formulation comprising several different mRNAs. Combining DsA1, DsA2, PITP and CAMP2 antigens in a single chimeric polypeptide may also facilitate the manufacturing of a vaccine as it is easier, quicker and less costly to make a single nucleic acid or polypeptide combining the four antigens rather than separate nucleic acids or polypeptides for the different antigens.

As described above herein, the design strategy may exploit the structural integrity of the individual structured domains (e.g., the CSDs of DsA1 and DsA2 and ENFD of PITP) in the resulting chimeric DsA1/DsA2/PITP/CAMP2 polypeptides. The design strategy may also exploit flexible linker domain of *C. acnes* CAMP2 polypeptide and/or a flexible linker-like sequence at the C terminus of the chimeric *C. acnes* DsA1/DsA2/PITP polypeptide.

Accordingly, in one aspect, the invention provides a nucleic acid that comprises a nucleotide sequence encoding a chimeric *C. acnes* DsA1/DsA2/PITP/CAMP2 polypeptide, wherein the chimeric *C. acnes* DsA1/DsA2/PITP/CAMP2 polypeptide comprises a *C. acnes* DsA1 or an immunogenic fragment thereof, a *C. acnes* DsA2 or an immunogenic fragment thereof, a *C. acnes* PITP polypeptide or an immunogenic fragment thereof and a *C. acnes* CAMP2 polypeptide or an immunogenic fragment thereof. Typically, the nucleic acid is a messenger RNA (mRNA).

In a further aspect, the invention provides a chimeric *C. acnes* DsA1/DsA2/PITP/CAMP2 polypeptide comprising a *C. acnes* DsA1 or an immunogenic fragment thereof, a *C. acnes* DsA2 or an immunogenic fragment thereof, a *C. acnes* PITP polypeptide or an immunogenic fragment thereof and a *C. acnes* CAMP2 polypeptide or an immunogenic fragment thereof.

In some embodiments, the immunogenic fragment of *C. acnes* DsA1 polypeptide is a CSD2 of a *C. acnes* DsA1 polypeptide. In some embodiments, the immunogenic fragment of *C. acnes* DsA2 polypeptide is a CSD2 of a *C. acnes* DsA2 polypeptide.

In some embodiments, a second conserved sub-domain ("CSD2") of *C. acnes* DsA1 polypeptide corresponds to amino acid residues 120-239 of SEQ ID NO: 204. See the section "DsA1" above for description of other domains of a *C. acnes* DsA1 polypeptide and their boundaries. As is known in the art, the positions of the CSD2 and other domains within other native *C. acnes* DsA1 polypeptides may be determined by aligning the polypeptide sequence of a given DsA1 polypeptide with that of SEQ ID NO: 204, and identifying the regions of the DsA1 polypeptide which have high sequence identity, respectively, to that of the CSD2 and other domains of SEQ ID NO: 204, respectively.

In some embodiments, a second conserved sub-domain ("CSD2") of *C. acnes* DsA2 polypeptide corresponds to amino acid residues 121-240 of SEQ ID NO: 205. See the section "DsA2" above for description of other domains of a *C. acnes* DsA2 polypeptide and their boundaries. As is known in the art, the positions of the CSD2 and other domains within other native *C. acnes* DsA2 polypeptides may be determined by aligning the polypeptide sequence of a given DsA2 polypeptide with that of SEQ ID NO: 205, and identifying the regions of the DsA2 polypeptide which have high sequence identity, respectively, to that of the CSD2 and other domains of SEQ ID NO: 205, respectively.

In some embodiments, the immunogenic fragment of a *C. acnes* PITP polypeptide comprises a ENFD of a *C. acnes* PITP polypeptide.

In some embodiments, an extended neocarzinostatin family domain ("ENFD") of *C. acnes* PITP corresponds to amino acid residues 1-133 of SEQ ID NO: 206. See the section "PITP" above for description of other domains of a *C. acnes* PITP polypeptide and their boundaries. As is known in the art, the positions of the ENFD and other domains within other native *C. acnes* PITP polypeptides may be determined by aligning the polypeptide sequence of a given PITP polypeptide with that of SEQ ID NO: 206, and identifying the regions of the PITP polypeptide which have high sequence identity, respectively, to that of the ENFD and other domains of SEQ ID NO: 206, respectively.

In some embodiments, the immunogenic fragment of *C. acnes* CAMP2 polypeptide comprises a N-terminal domain of *C. acnes* CAMP2 polypeptide. In some embodiments, the immunogenic fragment of *C. acnes* CAMP2 polypeptide comprises a N-terminal domain of *C. acnes* CAMP2 polypeptide and a linker domain of *C. acnes* CAMP2 polypeptide. In some embodiments, the immunogenic fragment of *C. acnes* CAMP2 polypeptide comprises a C-terminal domain of *C. acnes* CAMP2 polypeptide. In some embodiments, the immunogenic fragment of *C. acnes* CAMP2 polypeptide comprises a linker domain of *C. acnes* CAMP2 polypeptide and a C-terminal domain of *C. acnes* CAMP2 polypeptide.

In some embodiments, a N-terminal domain of a *C. acnes* CAMP2 polypeptide corresponds to residues 29-176 of SEQ ID NO: 202. In some embodiments, a C-terminal domain of a *C. acnes* CAMP2 polypeptide corresponds to residues 189-267 of SEQ ID NO: 202. In some embodiments, a linker domain of a *C. acnes* CAMP2 polypeptide corresponds to residues 177-188 of SEQ ID NO: 202. As is known in the art, the positions of the N-terminal domain. C-terminal domain and linker domain within other *C. acnes* CAMP2 polypeptides may be determined by aligning the polypeptide sequence of a given CAMP2 polypeptide with that of SEQ ID NO: 202, and identifying the regions of the CAMP2 polypeptide which have high sequence identity to that the sequence of the N-terminal domain. C-terminal domain and linker domain of SEQ ID NO: 202, respectively. Analysis of 430 CAMP2 polypeptide sequences from naturally occurring strains of *C. acnes* showed that there was a high degree of sequence conservation between the CAMP2 sequences (see "CAMP2" section above). FIGS. 44A-44C show an exemplary alignment of CAMP2 polypeptide sequences from naturally occurring *C. acnes* strains relative to SEQ NO: 202 (i.e., KPA171202_REF in FIGS. 44A-44C). Alignments such as the one in FIGS. 44A-44C can be used to identify the positions of the N-terminal domain. C-terminal domain and linker domain in sequences other than SEQ ID NO: 202.

In some embodiments, any two or more of (1) the *C. acnes* DsA1 polypeptide or an immunogenic fragment thereof. (2) the *C. acnes* DsA2 polypeptide or an immunogenic fragment thereof. (3) the *C. acnes* PITP polypeptide or an immunogenic fragment thereof, and (4) the *C. acnes* CAMP2 polypeptide or an immunogenic fragment thereof, are attached via linkers (such as the linkers described in section "Linkers" below). In other embodiments. (1) the *C. acnes* DsA1 polypeptide or an immunogenic fragment thereof. (2) the *C. acnes* DsA2 polypeptide or an immunogenic fragment thereof. (3) the *C. acnes* PITP polypeptide or an immunogenic fragment thereof, and (4) the *C. acnes* CAMP2 polypeptide or an immunogenic fragment thereof are directly fused to each other (i.e., there is no linker, such as an amino acid linker, connecting the DsA1, DsA2, PITP and CAMP2 polypeptides or their immunogenic fragments to each other). In some embodiments, such chimeric *C. acnes* DsA1/DsA2/PITP/CAMP2 polypeptides comprise a linker domain of *C. acnes* CAMP2 polypeptide.

In one embodiment, the chimeric *C. acnes* DsA1/DsA2/PITP/CAMP2 polypeptide comprises:

(a) a chimeric *C. acnes* DsA1/DsA2 polypeptide, e.g. as described herein;

(b) an immunogenic fragment of a *C. acnes* PITP polypeptide comprising a ENFD of a *C. acnes* PITP polypeptide; and (c) a *C. acnes* CAMP2 polypeptide or an immunogenic fragment thereof.

In some embodiments, the chimeric *C. acnes* DsA1/DsA2 polypeptide comprises (i) (1) a CSD2 of a *C. acnes* DsA1 polypeptide and (2) a CSD1 and/or a CSD3 of a *C. acnes* DsA2 polypeptide: or (ii) (1) a CSD2 of a *C. acnes* DsA2 polypeptide and (2) a CSD1 and/or a CSD3 of a *C. acnes* DsA1 polypeptide. See above and the sections "DsA1" and "DsA2" for description of domains of *C. acnes* DsA1 and DsA2 polypeptides, respectively, and their boundaries. In some embodiments, the chimeric *C. acnes* DsA1/DsA2/PITP/CAMP2 polypeptide is as defined in (ii). Typically, the chimeric *C. acnes* DsA1/DsA2/PITP/CAMP2 polypeptide comprises a CSD1 of a *C. acnes* DsA1 polypeptide, a CSD2 of a *C. acnes* DsA2 polypeptide and a CSD3 of a *C. acnes* DsA1 polypeptide.

In some embodiments, the chimeric *C. acnes* DsA1/DsA2 polypeptide of (a) comprises a sequence according to SEQ ID NO: 70, or a sequence having at least 90%, at least 91%, at least 92%, at least 93%, at least 94%, at least 95%, at least 96%, at least 97%, at least 98%, or at least 99% identity thereto.

In some embodiments, the immunogenic fragment of a *C. acnes* PITP polypeptide comprising a ENFD of a *C. acnes* PITP polypeptide in (b) comprises the sequence corresponding to amino acid residues 1-133 of SEQ ID NO: 73 or a sequence having at least 90%, at least 91%, at least 92%, at least 93%, at least 94%, at least 95%, at least 96%, at least 97%, at least 98%, or at least 99% identity to the sequence of amino acid residues 1-133 of SEQ ID NO: 73. In some embodiments, the immunogenic fragment of a *C. acnes* PITP polypeptide comprising a ENFD of a *C. acnes* PITP polypeptide in (b) comprises the sequence corresponding to amino acid residues 1-146 of SEQ ID NO: 73 or a sequence having at least 90%, at least 91%, at least 92%, at least 93%, at least 94%, at least 95%, at least 96%, at least 97%, at least 98%, or at least 99% identity to the sequence of amino acid residues 1-146 of SEQ ID NO: 73. Typically, the immunogenic fragment of a *C. acnes* PITP polypeptide comprising a ENFD of a *C. acnes* PITP polypeptide in (b) comprises the sequence corresponding to amino acid residues 1-146 of SEQ ID NO: 73.

In some embodiments, (a) and (b) comprise SEQ ID NO: 80 or a sequence having at least 90%, at least 91%, at least 92%, at least 93%, at least 94%, at least 95%, at least 96%, at least 97%, at least 98%, or at least 99% identity thereto. In some embodiments, (a) and (b) comprise SEQ ID NO: 82 or a sequence having at least 90%, at least 91%, at least 92%, at least 93%, at least 94%, at least 95%, at least 96%, at least 97%, at least 98%, or at least 99% identity thereto. In some embodiments. (a) and (b) comprise SEQ ID NO: 83 or a sequence having at least 90%, at least 91%, at least 92%, at least 93%, at least 94%, at least 95%, at least 96%, at least 97%, at least 98%, or at least 99% identity thereto. Typically. (a) and (b) comprise SEQ ID NO: 80.

In some embodiments, (c) is a *C. acnes* CAMP2 polypeptide, e.g., a full-length *C. acnes* CAMP2 polypeptide, typically a mature form of full-length CAMP2 polypeptide of *C. acnes* (without the native signal peptide sequence). In some embodiments, (c) comprises SEQ ID NO: 203 or a sequence having at least 90%, at least 91%, at least 92%, at least 93%, at least 94%, at least 95%, at least 96%, at least 97%, at least 98%, or at least 99% identity thereto. Typically, (c) comprises SEQ ID NO: 203.

In some embodiments, the immunogenic fragment of a *C. acnes* CAMP2 polypeptide in (c) comprises a N-terminal domain of a *C. acnes* CAMP2 polypeptide. In some embodiments, (c) comprises amino acid residues 29-176 of SEQ ID NO: 202 or a sequence having at least 90%, at least 91%, at least 92%, at least 93%, at least 94%, at least 95%, at least 96%, at least 97%, at least 98%, or at least 99% identity to the sequence of amino acid residues 29-176 of SEQ ID NO: 202.

In some embodiments, the immunogenic fragment of a *C. acnes* CAMP2 polypeptide in (c) comprises a N-terminal domain of a *C. acnes* CAMP2 polypeptide and a linker domain of a *C. acnes* CAMP2 polypeptide. In some embodiments. (c) comprises amino acid residues 29-188 of SEQ ID NO: 202 or a sequence having at least 90%, at least 91%, at least 92%, at least 93%, at least 94%, at least 95%, at least 96%, at least 97%, at least 98%, or at least 99% identity to the sequence of amino acid residues 29-188 of SEQ ID NO: 202.

In some embodiments, the immunogenic fragment of a *C. acnes* CAMP2 polypeptide in (c) comprises a C-terminal domain of a *C. acnes* CAMP2 polypeptide. In some embodiments, (c) comprises amino acid residues 189-267 of SEQ ID NO: 202 or a sequence having at least 90%, at least 91%, at least 92%, at least 93%, at least 94%, at least 95%, at least 96%, at least 97%, at least 98%, or at least 99% identity to the sequence of amino acid residues 189-267 of SEQ ID NO: 202.

In some embodiments, the immunogenic fragment of a *C. acnes* CAMP2 polypeptide in (c) comprises a linker domain of a *C. acnes* CAMP2 polypeptide and a C-terminal domain of a *C. acnes* CAMP2 polypeptide. In some embodiments, (c) comprises amino acid residues 177-267 of SEQ ID NO: 202 or a sequence having at least 90%, at least 91%, at least 92%, at least 93%, at least 94%, at least 95%, at least 96%, at least 97%, at least 98%, or at least 99% identity to the sequence of amino acid residues 177-267 of SEQ ID NO: 202.

In some embodiments, any two or more of (a), (b) and (c) are attached via linkers (such as the linkers described in section "Linkers" below). Typically, (a), (b) and (c) are directly fused to each other (i.e., there is no linker, such as an amino acid linker, connecting (a), (b) and (c)), e.g. in the order specified below. In some embodiments, (c) comprises a linker domain of *C. acnes* CAMP2 polypeptide.

In some embodiments, the chimeric *C. acnes* DsA1/DsA2/PITP/CAMP2 polypeptide comprises, from N-terminus to C-terminus: (a), (b) and (c). In other embodiments, the chimeric *C. acnes* DsA1/DsA2/PITP/CAMP2 polypeptide comprises, from N-terminus to C-terminus: (c), (a) and (b). Typically, the chimeric *C. acnes* DsA1/DsA2/PITP/CAMP2 polypeptide comprises, from N-terminus to C-terminus: (c), (a) and (b).

In some embodiments, the chimeric *C. acnes* DsA1/DsA2/PITP/CAMP2 polypeptide comprises a transmembrane domain (TMB) sequence, e.g. a TMB as defined herein (see the section "Heterologous transmembrane domains (TMBs)" below). In certain embodiments, the TMB sequence is positioned at the N-terminus of the chimeric *C. acnes* DsA1/DsA2/PITP/CAMP2 polypeptide. In other embodiments, the TMB sequence is positioned at the C-terminus of the chimeric *C. acnes* DsA1/DsA2/PITP/CAMP2 polypeptide. Typically, the TMB sequence is positioned at the C-terminus of the chimeric *C. acnes* DsA1/DsA2/PITP/CAMP2 polypeptide.

In some embodiments, the chimeric *C. acnes* DsA1/DsA2/PITP/CAMP2 polypeptide comprises a sequence according to any one of SEQ ID NO: 373-376 (e.g. SEQ ID NO: 373 or 374) or a sequence having at least 90%, at least 91%, at least 92%, at least 93%, at least 94%, at least 95%, at least 96%, at least 97%, at least 98%, or at least 99% identity thereto. In some embodiments, the chimeric *C. acnes* DsA1/DsA2/PITP/CAMP2 polypeptide comprises a sequence according to SEQ ID NO: 373 or a sequence having at least 90%, at least 91%, at least 92%, at least 93%, at least 94%, at least 95%, at least 96%, at least 97%, at least 98%, or at least 99% identity thereto, and a TMB sequence (e.g. a sequence according to SEQ ID NO: 84). Typically, the chimeric *C. acnes* DsA1/DsA2/PITP/CAMP2 polypeptide comprises (1) a sequence according to SEQ ID NO: 374 or a sequence having at least 90%, at least 91%, at least 92%, at least 93%, at least 94%, at least 95%, at least 96%, at least 97%, at least 98%, or at least 99% identity thereto: or (2) a sequence according to SEQ ID NO: 373, or a sequence having at least 90%, at least 91%, at least 92%, at least 93%, at least 94%, at least 95%, at least 96%, at least 97%, at least 98%, or at least 99% identity thereto, and a TMB sequence.

In some embodiments, the nucleic acid comprising a nucleotide sequence encoding the chimeric *C. acnes* DsA1/DsA2/PITP/CAMP2 polypeptide comprises a nucleotide sequence encoding a secretion signal peptide sequence as described herein (e.g. a secretion signal peptide sequence as described in the section "Secretion signal peptide (SS) sequences" below).

In some embodiments, the nucleic acid comprising a nucleotide sequence encoding the chimeric *C. acnes* DsA1/DsA2/PITP/CAMP2 polypeptide comprises a sequence according to any one of SEQ ID NO: 386-390 or SEQ ID NO: 393 (e.g. any one of SEQ ID NO: 387 or a sequence having at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, the nucleic acid comprising a nucleotide sequence encoding the chimeric *C. acnes* DsA1/DsA2/PITP/CAMP2 polypeptide comprises a sequence according to SEQ ID NO: 384 or SEQ ID NO: 385 or a sequence having at least 75%, at least 80%, at least 85%, at least 90%, at least 91%, at least 92%, at least 93%, at least 94%, at least 95%, at least 96%, at least 97%, at least 98%, or at least 99% identity thereto, and a nucleotide sequence encoding a TMB sequence (e.g. a nucleotide sequence encoding SEQ ID NO: 84). In some embodiments, the nucleotide sequence encoding SEQ ID NO: 84 is as defined in SEQ ID NO: 395 or 396. Typically, the nucleic acid comprising a nucleotide sequence encoding the chimeric *C. acnes* DsA1/DsA2/PITP/CAMP2 polypeptide comprises (1) a sequence according to SEQ ID NO: 387, or a sequence having at least 75%, at least 80%, at least 85%, at least 90%, at least 91%, at least 92%, at least 93%, at least 94%, at least 95%, at least 96%, at least 97%, at least 98%, or at least 99% identity thereto: or (2) a sequence according to SEQ ID NO: 384 or SEQ ID NO: 385, or a sequence having at least 75%, at least 80%, at least 85%, at least 90%, at least 91%, at least 92%, at least 93%, at least 94%, at least 95%, at least 96%, at least 97%, at least 98%, or at least 99% identity thereto, and a nucleotide sequence encoding a TMB sequence.

In some embodiments, the nucleic acid comprising a nucleotide sequence encoding the chimeric *C. acnes* DsA1/DsA2/PITP/CAMP2 polypeptide comprises a nucleotide sequence according to any one of SEQ ID NO: 377-383 or SEQ ID NO: 394 (e.g. any one of SEQ ID NO: 377-380) or a sequence having at least 75%, at least 80%, at least 85%, at least 90%, at least 91%, at least 92%, at least 93%, at least 94%, at least 95%, at least 96%, at least 97%, at least 98%, or at least 99% identity thereto. In some embodiments, the nucleic acid comprising a nucleotide sequence encoding the chimeric *C. acnes* DsA1/DsA2/PITP/CAMP2 polypeptide comprises a nucleotide sequence that is least 75% identical to any one of SEQ ID NO: 377-380.

In some embodiments, the chimeric *C. acnes* DsA1/DsA2/PITP/CAMP2 polypeptide comprises a sequence of a chimeric *C. acnes* DsA1/DsA2/PITP polypeptide as described herein. In some embodiments, the chimeric *C. acnes* DsA1/DsA2/PITP/CAMP2 polypeptide comprises a sequence of a chimeric *C. acnes* DsA1/DsA2 polypeptide as described herein.

Variants of the Polypeptides of the Present Invention

Mutation of Cysteine Residues

One or more cysteine residues in the polypeptides described herein may be mutated by single amino acid substitutions, e.g. to a serine residue. Cysteine residues are involved in disulphide bridge formation and thus cysteine mutations may limit polypeptide multimerisation.

In some embodiments, the *C. acnes* DsA1 polypeptide described herein comprises a single amino acid substitution at one or more (e.g. all) positions corresponding to a cysteine residue in a native *C. acnes* DsA1 polypeptide. In some embodiments, the *C. acnes* DsA1 polypeptide comprises one or more single amino acid substitutions at positions corresponding to C25 (e.g. C25S), C291 (e.g. C291S or C291M) and/or C293 (e.g. C293S or C293P) of SEQ ID NO: 204.

In some embodiments, the *C. acnes* DsA2 polypeptide described herein comprises a single amino acid substitution at one or more (e.g. all) positions corresponding to a cysteine residue in a native *C. acnes* DsA2 polypeptide. In some embodiments, the *C. acnes* DsA2 polypeptide comprises one or more single amino acid substitutions at positions corresponding to C26 (e.g. C26S) and/or C292 (e.g. C292S) of SEQ ID NO: 205.

In some embodiments, the *C. acnes* PITP polypeptide described herein comprises a single amino acid substitution at one or more (e.g. all) positions corresponding to a cysteine residue in a native *C. acnes* PITP polypeptide. In some embodiments, the *C. acnes* PITP polypeptide comprises one or more single amino acid substitutions at positions corresponding to C200 (e.g. C200S), C371 (e.g. C371S) and/or C429 (e.g. C429S) of SEQ ID NO: 206. In some embodiments, the *C. acnes* PITP polypeptide comprises a single amino acid substitution at one or both (e.g. both) positions corresponding to C200 (e.g. C200S) and C371 (e.g. C371S) of SEQ ID NO: 206. In preferred embodiments, a *C. acnes* PITP polypeptide having the sequence of SEQ ID NO: 73 comprises a serine residue at positions 200 and 371. In other embodiments, a *C. acnes* PITP polypeptide having the sequence of SEQ ID NO: 77 comprises a serine residue at positions 200 and 371.

In some embodiments, the chimeric *C. acnes* DsA1/DsA2 polypeptide described herein comprises a single amino acid substitution at one or more (e.g. all) positions corresponding to a cysteine residue in a native *C. acnes* DsA1 polypeptide and/or one or more (e.g. all) positions corresponding to a cysteine residue in a native *C. acnes* DsA2 polypeptide. In some embodiments, the chimeric *C. acnes* DsA1/DsA2 polypeptide comprises a single amino acid substitution at one or more (all) positions corresponding to C25 (e.g. C25S), C291 (e.g. C291S or C291M) and/or C293 (e.g. C293S or C293P) of SEQ ID NO: 204. In some embodiments, the chimeric *C. acnes* DsA1/DsA2 polypeptide comprises one or more (e.g. all three) amino acid substitutions selected from C25S, C291S and/or C293P wherein C25, C291 and/or C293 correspond to the residues in SEQ ID NO: 204. In preferred embodiments, a chimeric *C. acnes* DsA1/DsA2 polypeptide having the sequence of SEQ ID NO: 70 comprises a serine residue at positions 25 and 291 and a proline residue at position 293. In other embodiments, a chimeric *C. acnes* DsA1/DsA2 polypeptide having the sequence of SEQ ID NO: 72 comprises a serine residue at positions 25 and 291 and a proline residue at position 293. In other embodiments, a chimeric *C. acnes* DsA1/DsA2 polypeptide having the sequence of SEQ ID NO: 81 comprises a serine residue at position 18 and a proline residue at position 286. In other embodiments, a chimeric C *acnes* DsA1/DsA2 polypeptide having the sequence of SEQ ID NO: 81 comprises a serine residue at position 18, a methionine residue at position 284 and a proline residue at position 286, wherein the residues correspond to positions 25, 291 and 293, respectively, in SEQ ID NO: 204.

In some embodiments, the chimeric *C. acnes* DsA1/DsA2/PITP polypeptide described herein comprises a single amino acid substitution at one or more (e.g. all) positions corresponding to a cysteine residue in a native *C. acnes* DsA1 polypeptide, one or more (e.g. all) positions corresponding to a cysteine residue in a native *C. acnes* DsA2 polypeptide and/or one or more (e.g. all) positions corresponding to a cysteine residue in a native *C. acnes* PITP polypeptide. In some embodiments, the chimeric *C. acnes* DsA1/DsA2/PITP polypeptide comprises a single amino acid substitution at one or more positions corresponding to C25 (e.g. C25S), C291 (e.g. C291S or C291M) and/or C293 (e.g. C293S or C293P) of SEQ ID NO: 204. In some embodiments, the chimeric *C. acnes* DsA1/DsA2/PITP polypeptide comprises one or more (e.g. all three) amino acid substitutions selected from C25S, C291S and/or C293P wherein C25, C291 and/or C293 corresponds to the residues in SEQ ID NO: 204. In some embodiments, a chimeric *C. acnes* DsA1/DsA2/PITP polypeptide having the sequence of SEQ ID NO: 80 or of SEQ ID NO: 83 (e.g. SEQ ID NO: 83) comprises a serine residue at positions 25 and 291 and a proline residue at position 293. In other embodiments, a chimeric *C. acnes* DsA1/DsA2/PITP polypeptide having the sequence of SEQ ID NO: 82 comprises a serine residue at position 25 and a proline residue at position 293. In some embodiments, a chimeric *C. acnes* DsA1/DsA2/PITP polypeptide having the sequence of SEQ ID NO: 82 comprises a serine residue at position 25, a methionine residue at position 291 and a proline residue at position 293. In other embodiments, a chimeric *C. acnes* DsA1/DsA2/PITP polypeptide having the sequence of SEQ ID NO: 368 comprises a serine residue at position 18, a methionine residue at position 284 and a proline residue at position 286. In some embodiments, a chimeric *C. acnes* DsA1/DsA2/PITP polypeptide having the sequence of SEQ ID NO: 368 comprises a serine residue at position 18, a methionine residue at position 284 and a proline residue at position 286, wherein the residues correspond to positions 25, 291 and 293, respectively, in SEQ ID NO: 204.

In some embodiments, the chimeric *C. acnes* DsA1/DsA2/PITP/CAMP2 polypeptide described herein comprises a single amino acid substitution at one or more (e.g. all) positions corresponding to a cysteine residue in a native *C. acnes* DsA1 polypeptide, one or more (e.g. all) positions corresponding to a cysteine residue in a native *C. acnes* DsA2 polypeptide and/or one or more (e.g. all) positions corresponding to a cysteine residue in a native *C. acnes* PITP polypeptide. In some embodiments, the chimeric *C. acnes* DsA1/DsA2/PITP polypeptide comprises a single amino acid substitution at one or more positions corresponding to C25 (e.g. C25S), C291 (e.g. C291S or C291M) and/or C293 (e.g. C293S or C293P) of SEQ ID NO: 204. In some embodiments, the chimeric *C. acnes* DsA1/DsA2/PITP/CAMP2 polypeptide comprises one or more (e.g. all three) amino acid substitutions selected from C25S, C291S and/or C293P wherein C25, C291 and/or C293 corresponds to the residues in SEQ ID NO: 204. In some embodiments, a chimeric *C. acnes* DsA1/DsA2/PITP/CAMP2 polypeptide having the sequence of SEQ ID NO: 373 or of SEQ ID NO: 374 comprises a serine residue at positions 264 and 530 and a proline residue at position 532. In other embodiments, a chimeric *C. acnes* DsA1/DsA2/PITP/CAMP2 polypeptide having the sequence of SEQ ID NO: 375 comprises a serine residue at positions 185 and 451 and a proline residue at position 453. In other embodiments, a chimeric *C. acnes* DsA1/DsA2/PITP/CAMP2 polypeptide having the sequence of SEQ ID NO: 376 comprises a serine residue at positions 25 and 291 and a proline residue at position 293.

Mutation of Glycosylation Sites

Glycosylation may occur in eukaryotic cells but typically, it does not occur in prokaryotic cells. "Glycosylation" as used herein refers to the addition of a saccharide unit to a protein. In particular. N-linked glycosylation is the attachment of glycan to an amide nitrogen of an asparagine (Asn; N) residue in a protein. N-glycosylation can occur at any asparagine residue in a protein that is accessible to and recognised by glycosylating enzymes following translation of the protein, and is most common at accessible asparagines that are part of an NXS/T motif, wherein the second amino acid residue following the asparagine is a serine (Ser; S) or threonine (Thr; T). O-linked glycosylation is the attachment of a glycan to the oxygen atom of serine (Ser) or threonine (Thr) residue in a protein. The process of attachment results in a glycosylated protein. This glycan may be a polysaccharide. A non-human glycosylation pattern can render a polypeptide undesirably reactogenic when used to elicit antibodies. Additionally, glycosylation of a polypeptide that is not normally glycosylated (such as polypeptides described herein, which are polypeptides naturally found in prokaryotic cells or derived from such polypeptides) may alter its immunogenicity. For example, glycosylation can mask important immunogenic epitopes within a protein. Thus, to reduce or eliminate glycosylation, either asparagine residues or serine/threonine residues can be modified, for example, by substitution to another amino acid.

In certain embodiments, one or more of the *C. acnes* CAMP2 polypeptide, the modified *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and the chimeric *C. acnes* DsA1/DsA2/PITP/CAMP2 polypeptide as described herein comprises at least one mutated glycosylation site, preferably at least one mutated N-linked glycosylation site and/or at least one O-linked glycosylation site. In some embodiments, one or more glycosylation sites in one or more of the *C. acnes* CAMP2 polypeptide, the modified *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and the chimeric *C. acnes* DsA1/DsA2/PITP/CAMP2 polypeptide as described herein are removed. The removal of a glycosylation site may decrease glycosylation of the polypeptide. In some embodiments, one or more of the *C. acnes* CAMP2 polypeptide, the modified *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and the chimeric *C. acnes* DsA1/DsA2/PITP/CAMP2 polypeptide as described herein has decreased glycosylation relative to the respective native polypeptide. The removal of glycosylation sites may eliminate glycosylation of the polypeptide.

In certain embodiments, the modification comprises a substitution of one or more of an N, S, and T amino acid (e.g., in an NXS/T sequence motif), wherein X corresponds to any amino acid. In some embodiments, the modification comprises a substitution of one or more serine (Ser) or threonine (Thr) residue(s) in a protein. In some embodiments, an N, S, or T amino acid is substituted with a conservative amino acid substitution. Typically, an N amino acid may be substituted with a Q, S, K or A amino acid.

In some embodiments, the *C. acnes* CAMP2 polypeptide and/or the modified *C. acnes* CAMP2 polypeptide described herein comprise a single amino acid substitution at one or more (e.g. all) positions corresponding to a glycosylation site in a native *C. acnes* CAMP2 polypeptide. A N-glycosylation site in a *C. acnes* CAMP2 polypeptide and/or a modified *C. acnes* CAMP2 polypeptide may be present at a position corresponding to residue N166 of SEQ ID NO: 203. A N-glycosylation site may include N166, F167 and S168, with glycosylation at N166, relative to the residue numbering in SEQ ID NO: 203. In some embodiments, a *C. acnes* CAMP2 polypeptide and/or a modified *C. acnes* CAMP2 polypeptide of the invention comprise an amino acid substitution at position corresponding to N166 (e.g. N166S), relative to the residue numbering in SEQ ID NO: 203. A *C. acnes* CAMP2 polypeptide and/or a modified *C. acnes* CAMP2 polypeptide may comprise the sequence of SEQ ID NO: 50, 51 or 54 with serine at position 166. O-glycosylation sites in a *C. acnes* CAMP2 polypeptide and/or a modified *C. acnes* CAMP2 polypeptide may be present at positions corresponding to any S and/or T residues in SEQ ID NO: 203.

In some embodiments, the *C. acnes* DsA1 polypeptide described herein comprises a single amino acid substitution at one or more (e.g. all) positions corresponding to a glycosylation site in a native *C. acnes* DsA1 polypeptide. A N-glycosylation site in a *C. acnes* DsA1 polypeptide may be present at a position corresponding to residue N255 of SEQ ID NO: 204. A N-glycosylation site may include N255, I256 and T257, with glycosylation at N255, relative to the residue numbering in SEQ ID NO: 204. In some embodiments, a *C. acnes* DsA1 polypeptide as described herein comprises an amino acid substitution at position corresponding to N255 (e.g. N255Q or N255Q), relative to the residue numbering in SEQ ID NO: 204. O-glycosylation sites in a *C. acnes* DsA1 polypeptide as described herein may be present at positions corresponding to any S and/or T residues in SEQ ID NO: 204, such as the S292 residue.

In some embodiments, the *C. acnes* DsA2 polypeptide described herein comprises a single amino acid substitution at one or more (e.g. all) positions corresponding to a glycosylation site in a native *C. acnes* DsA2 polypeptide. A N-glycosylation site in a *C. acnes* DsA2 polypeptide may be present at a position corresponding to residue N5 of SEQ ID NO: 205. A N-glycosylation site may include N5, S6 and S7, with glycosylation at N5, relative to the residue numbering in SEQ ID NO: 205. In some embodiments, a *C. acnes* DsA2 polypeptide as described herein comprises an amino acid substitution at position corresponding to N5 (e.g. N5Q), relative to the residue numbering in SEQ ID NO: 205. A *C. acnes* DsA2 polypeptide may comprise the sequence of SEQ ID NO: 68 or 69 with glutamine at position 5. O-glycosylation sites in a *C. acnes* DsA2 polypeptide as described herein may be present at positions corresponding to any S and/or T residues in SEQ ID NO: 205.

In some embodiments, the *C. acnes* PITP polypeptide described herein comprises a single amino acid substitution at one or more (e.g. all) positions corresponding to a glycosylation site in a native *C. acnes* PITP polypeptide. N-glycosylation sites in a *C. acnes* PITP polypeptide may be present at positions corresponding to residues N230, N242, N362 and N373 of SEQ ID NO: 206. N-glycosylation sites may include (i) N230, G231 and S232 (with glycosylation at N230); (ii) N242, G243 and S244 (with glycosylation at N242); (iii) N362, L363 and T364 (with glycosylation at N362); and/or (iv) N373, V374 and T375 (with glycosylation at N373), wherein the amino acid numbering is relative to the residue numbering in SEQ ID NO: 206. In some embodiments, a *C. acnes* PITP polypeptide of the invention comprises one or more (e.g. all) amino acid substitutions at positions corresponding to N230 (e.g. N230K), S244 (e.g. S244G), N362 (e.g. N362Q) and N373 (e.g. N373S), wherein the amino acid numbering is relative to the residue numbering in SEQ ID NO: 206. In some embodiments, a *C. acnes* PITP polypeptide as described herein comprises one or more (e.g. all) amino acid substitutions at positions corresponding to N230 (e.g. N230K), N242 (e.g. N242G), N362 (e.g. N362Q) and N373 (e.g. N373S), wherein the amino acid numbering is relative to the residue numbering in SEQ ID NO: 206. O-glycosylation sites in a *C. acnes* PITP polypeptide may be present at positions corresponding to any S and/or T residues in SEQ ID NO: 206. In some embodiments, a *C. acnes* PITP polypeptide as described herein comprises the sequence of SEQ ID NO: 76, 77 or 79 with lysine at position 230, glycine at position 244, glutamine at position 362 and serine at position 373.

In some embodiments, the chimeric C *acnes* DsA1/DsA2 polypeptide described herein comprises a single amino acid substitution at one or more (e.g. all) positions corresponding to a glycosylation site in a native C *acnes* DsA1 polypeptide and/or one or more (e.g. all) positions corresponding to a glycosylation site in a native *C. acnes* DsA2 polypeptide. A N-glycosylation site in a chimeric *C. acnes* DsA1/DsA2 polypeptide may be present at a position corresponding to the residue N255 of SEQ ID NO: 70. A N-glycosylation site may include N255, 1256 and T257, with glycosylation at N255, relative to the residue numbering in SEQ ID NO: 70. In some embodiments, the chimeric *C. acnes* DsA1/DsA2 polypeptide comprises a N255Q or a N255A (e.g. N255Q) substitution in SEQ ID NO: 70. In some embodiments, a chimeric *C. acnes* DsA1/DsA2 polypeptide of the invention comprises an amino acid substitution at the position corresponding to N255 (e.g. N255Q or N255A), relative to the residue numbering in SEQ ID NO: 70. In some embodiments, the chimeric *C. acnes* DsA1/DsA2 polypeptide comprises the sequence of SEQ ID NO: 72 with glutamine at position 255. O-glycosylation sites in a chimeric *C. acnes* DsA1/DsA2 polypeptide may be present at positions corresponding to any S and/or T residues in SEQ ID NO: 70. O-glycosylation sites in a chimeric *C. acnes* DsA1/DsA2 polypeptide may be present at positions corresponding to residues S291 and/or S292 of SEQ ID NO: 70. An O-glycosylation site may include S291 and S292, with glycosylation at S291 and/or S292, relative to the residue numbering in SEQ ID NO: 70. In some embodiments, the chimeric *C. acnes* DsA1/DsA2 polypeptide comprises one or more (e.g. all three) substitutions selected from a N255A, a S291M and a S292G. In some embodiments, the chimeric *C. acnes* DsA1/DsA2 polypeptide comprises one or more (e.g. all three) amino acid substitutions at positions corresponding to N255 (e.g. N255A), S291 (e.g. S291M) and S292 (e.g. S292G), relative to the residue numbering in SEQ ID NO: 70. A chimeric *C. acnes* DsA1/DsA2 polypeptide may comprise the sequence of SEQ ID NO: 81 with alanine at position 248, methionine at position 284 and glycine at position 285. In some embodiments, the chimeric *C. acnes* DsA1/DsA2 polypeptide comprises the sequence of SEQ ID NO: 81 with alanine at position 248, methionine at position 284 and glycine at position 285, wherein the residues correspond to positions 255, 291 and 292, respectively, in SEQ ID NO: 70.

In some embodiments, the chimeric *C. acnes* DsA1/DsA2/PITP polypeptide described herein comprises a single amino acid substitution at one or more (e.g. all) positions corresponding to a glycosylation site in a native C *acnes* DsA1 polypeptide, one or more (e.g. all) positions corresponding to a glycosylation site in a native *C. acnes* DsA2 polypeptide and/or one or more (e.g. all) positions corresponding to a glycosylation site in a native *C. acnes* PITP polypeptide. A N-glycosylation site in a chimeric *C. acnes* DsA1/DsA2/PITP polypeptide may be present at a position corresponding to the residue N255, relative to the residue numbering in SEQ ID NO: 80 or 83. A N-glycosylation site may include N255, 1256 and T257, with glycosylation at N255, relative to the residue numbering in SEQ ID NO: 80 or 83. In some embodiments, the chimeric *C. acnes* DsA1/DsA2/PITP polypeptide comprises a N255Q or a N255A (e.g. N255A) substitution in SEQ ID NO: 80 or 83. In some embodiments, a chimeric *C. acnes* DsA1/DsA2/PITP polypeptide of the invention comprises an amino acid substitution at the position corresponding to N255 (e.g. N255Q or N255A), relative to the residue numbering in SEQ ID NO: 80 or 83. O-glycosylation sites in a chimeric *C. acnes* DsA1/DsA2/PITP polypeptide may be present at positions corresponding to any S and/or T residues in SEQ ID NO: 80 or 83. O-glycosylation sites in a chimeric *C. acnes* DsA1/DsA2/PITP polypeptide may be present at one or more (e.g. all) positions corresponding to residues S291, S292, T299, T301, T303, T305, T425, S428 and T436 of SEQ ID NO: 80 or 83. In some embodiments, a chimeric *C. acnes* DsA1/DsA2/PITP polypeptide as described herein comprises the substitution of the PTPTPTPT region located between positions 298 and 305 of SEQ ID NO: 80 or 83, with a GGGGG linker. In some embodiments, the chimeric *C. acnes* DsA1/DsA2/PITP polypeptide comprises one or more (e.g. all) substitutions selected from a S291M, S292G, P298G, T299G, P300G, T301G, P302G, T425G, S428G and T436G. In some embodiments, the chimeric *C. acnes* DsA1/DsA2/PITP polypeptide comprises one or more (e.g. all) substitutions selected from a S291M, S292G, T425G, S428G and T436G, relative to the residue numbering in SEQ ID NO: 80 or 83. In some embodiments, the chimeric *C. acnes* DsA1/DsA2/PITP polypeptide comprises one or more (e.g. all) amino acid substitutions at positions corresponding to S291 (e.g. S291M), S292 (e.g. S292G), T425 (e.g. T425G), S428 (e.g. S428G) and T436 (e.g. T436G), relative to the residue numbering in SEQ ID NO: 80 or 83. A chimeric *C. acnes* DsA1/DsA2/PITP polypeptide may comprise the sequence of SEQ ID NO: 82 with methionine at position 291 and glycine at positions 292, 299, 301, 422, 425 and 433. In some embodiments, the chimeric *C. acnes* DsA1/DsA2/PITP polypeptide may comprise the sequence of SEQ ID NO: 82 with methionine at position 291 and glycine at positions 292, 298, 299, 300, 301, 302, 422, 425 and 433. In some embodiments, the chimeric *C. acnes* DsA1/DsA2/PITP polypeptide may comprise the sequence of SEQ ID NO: 368 with alanine at position 248, methionine at position 284 and glycine at positions 285, 291, 292, 293, 294, 295, 415, 418 and 426.

In some embodiments, the chimeric *C. acnes* DsA1/DsA2/PITP/CAMP2 polypeptide described herein comprises a single amino acid substitution at one or more (e.g. all) positions corresponding to a glycosylation site in a native *C. acnes* DsA1 polypeptide, one or more (e.g. all) positions corresponding to a glycosylation site in a native *C. acnes* DsA2 polypeptide, one or more (e.g. all) positions corresponding to a glycosylation site in a native *C. acnes* PITP polypeptide and/or one or more (e.g. all) positions corresponding to a glycosylation site in a native *C. acnes* CAMP2 polypeptide.

As described in the section above "Chimeric DsA1 DsA2 PITP CAMP2", a chimeric *C. acnes* DsA1/DsA2/PITP/CAMP2 polypeptide may comprise a *C. acnes* CAMP2 polypeptide or immunogenic fragment thereof. A N-glycosylation site in a chimeric *C. acnes* DsA1/DsA2/PITP/CAMP2 polypeptide may be present at a position corresponding to residue N166 of SEQ ID NO: 203 (i.e. corresponding to N194 of SEQ ID NO: 202), if that residue is present in the chimeric *C. acnes* DsA1/DsA2/PITP/CAMP2 polypeptide. A N-glycosylation site in a chimeric *C. acnes* DsA1/DsA2/PITP/CAMP2 polypeptide may be present at position N166, F167 and S168, with glycosylation at N166, relative to the residue numbering in SEQ ID NO: 203 (i.e., corresponding to position N194, F195 and S196, with glycosylation at N194, relative to the residue numbering in SEQ ID NO: 202), if those residues are present in the chimeric *C. acnes* DsA1/DsA2/PITP/CAMP2 polypeptide. In some embodiments, a *C. acnes* DsA1/DsA2/PITP/CAMP2 polypeptide of the invention comprises an amino acid substitution at position corresponding to N166 (e.g. N166S), relative to the residue numbering in SEQ ID NO: 203 (i.e., corresponding to N194 (e.g. N194S), relative to the residue numbering in SEQ ID NO: 202), if present in the polypeptide. O-glycosylation sites in a *C. acnes* DsA1/DsA2/PITP/CAMP2 polypeptide may be present at positions corresponding to any S and/or T residues in SEQ ID NO: 203 (i.e., corresponding to any S and/or T residues in residues 29-267 of SEQ ID NO: 202), if present in the chimeric *C. acnes* DsA1/DsA2/PITP/CAMP2 polypeptide.

As described in the section above "Chimeric DsA1 DsA2 PITP CAMP2", a chimeric *C. acnes* DsA1/DsA2/PITP/CAMP2 polypeptide may comprise SEQ ID NO: 80, 82 or 83. A N-glycosylation site in a chimeric *C. acnes* DsA1/DsA2/PITP/CAMP2 polypeptide may be present at a position corresponding to residue N255, relative to the residue numbering in SEQ ID NO: 80 or 83. A N-glycosylation site in a chimeric *C. acnes* DsA1/DsA2/PITP/CAMP2 polypeptide may include N255, I256 and T257, with glycosylation at N255, relative to the residue numbering in SEQ ID NO: 80 or 83. In some embodiments, a chimeric *C. acnes* DsA1/DsA2/PITP/CAMP2 polypeptide of the invention comprises an amino acid substitution at the position corresponding to N255 (e.g. N255Q or N255A), relative to the residue numbering in SEQ ID NO: 80 or 83. O-glycosylation sites in a chimeric *C. acnes* DsA1/DsA2/PITP/CAMP2 polypeptide may be present at positions corresponding to any S and/or T residues in SEQ ID NO: 80 or 83. O-glycosylation sites in a chimeric *C. acnes* DsA1/DsA2/PITP/CAMP2 polypeptide may be present at one or more (e.g. all) positions corresponding to residues S291, S292, T299, T301, T303, T305, T425, S428 and T436 of SEQ ID NO: 80 or 83. In some embodiments, a chimeric *C. acnes* DsA1/DsA2/PITP/CAMP2 polypeptide as described herein comprises the substitution of the PTPTPTPT region located between positions 298 and 305 of SEQ ID NO: 80 or 83, with a GGGGG linker. In some embodiments, the chimeric *C. acnes* DsA1/DsA2/PITP/CAMP2 polypeptide comprises one or more (e.g. all) substitutions selected from a S291M, S292G, P298G, T299G, P300G, T301G, P302G, T425G, S428G and T436G. In some embodiments, the chimeric *C. acnes* DsA1/DsA2/PITP/CAMP2 polypeptide comprises one or more (e.g. all) substitutions selected from a S291M, S292G, T425G, S428G and T436G, relative to the residue numbering in SEQ ID NO: 80 or 83. In some embodiments, the chimeric *C. acnes* DsA1/DsA2/PITP/CAMP2 polypeptide comprises one or more (e.g. all) amino acid substitutions at positions corresponding to S291 (e.g. S291M), S292 (e.g. S292G), T425 (e.g. T425G), S428 (e.g. S428G) and T436 (e.g. T436G), relative to the residue numbering in SEQ ID NO: 80 or 83. A chimeric *C. acnes* DsA1/DsA2/PITP/CAMP2 polypeptide may comprise the sequence of SEQ ID NO: 82 with methionine at position 291 and glycine at positions 292, 299, 301, 422, 425 and 433. In some embodiments, the chimeric *C. acnes* DsA1/DsA2/PITP/CAMP2 polypeptide may comprise the sequence of SEQ ID NO: 82 with methionine at position 291 and glycine at positions 292, 298, 299, 300, 301, 302, 422, 425 and 433.

Secretion Signal Peptide (SS) Sequences

The *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and/or the chimeric *C. acnes* DsA1/DsA2/PITP/CAMP2 polypeptide as described herein may comprise a secretion signal peptide (SS) sequence. The secretion signal peptide may be cleaved in post-translation processing of the *C. acnes* polypeptides described herein. The mature form of the *C. acnes* polypeptide may therefore not comprise the secretion signal peptide sequence. However, a nucleotide sequence encoding a secretion signal peptide sequence may be present in nucleic acids described herein encoding the *C. acnes* polypeptides described herein.

The *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and/or the chimeric *C. acnes* DsA1/DsA2/PITP/CAMP2 polypeptide as described herein may comprise a secretion signal peptide sequence of the respective native *C. acnes* polypeptide. This may be advantageous if the *C. acnes* polypeptides are expressed in a prokaryotic cell as recombinant proteins.

In some embodiments, the *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and/or the chimeric *C. acnes* DsA1/DsA2/PITP/CAMP2 polypeptide as described herein may comprise viral or eukaryotic (e.g. human) secretion signal peptide sequences. The use of viral or eukaryotic secretion signal peptide sequences attached to a polypeptide described herein may offer numerous advantages for immunogenic compositions. When expressed from an mRNA, especially in a eukaryotic cell, a polypeptide of the invention comprising a SS sequence may have increased extracellular expression relative to the polypeptide without the SS sequence. The increased extracellular expression may promote higher immunogenicity and by extension, better vaccine efficacy.

Viral SS sequences may be found in publicly accessible databases (e.g., the NCBI or UniProt databases) which include an annotated viral polypeptide sequence and identify the start and end position of an experimentally validated SS.

In certain embodiments, the SS sequence as well as the location of the SS sequence cleavage site for a given known input polypeptide sequence may be predicted by using the SignalP algorithm. The SignalP algorithm (and more particularly SignalP v6.0) is described in further detail in Armenteros et al. (Nature Biotechnology. 37:420-423, 2019). Teufel et al. (Nature Biotechnology. 40:1023-1025. 2022), and services.healthtech.dtu.dk/services/SignalP-6.0/, each of which is incorporated herein by reference in their entirety. The strength of the prediction is assessed based on a cumulative rank score that considers the likelihood of detecting canonical features of the signal sequence (SS likelihood score) and the probability of cleavage at the cleavage site (cleavage probability score). In certain embodiments, the viral secretion signal peptide has a SignalP cleavage probability score of at least 0.8, at least 0.85, at least 0.90 or at least 0.95, as determined using SignalP 6.0. In some embodiments, the viral secretion signal peptide has a SignalP signal peptide likelihood score of at least 0.8, at least 0.85, at least 0.90 or at least 0.95, as determined using SignalP 6.0.

In certain embodiments, the SS sequence is a viral SS sequence. In certain embodiments, the viral secretion signal peptide sequence is derived from a viral sequence in a virus able to infect humans. The phrase "influenza", "SARS COV-2", "varicella-zoster virus (VZV)", "measles", "rubella", "rabies," "Ebola," and "smallpox" preceding the phrase "secretion signal peptide sequence" indicates that the secretion signal peptide was derived from the virus corresponding to that name.

In certain embodiments, the viral secretion signal peptide is derived from a viral sequence selected from the group consisting of: an influenza secretion signal peptide sequence, a SARS COV-2 secretion signal peptide sequence, a varicella-zoster virus (VZV) secretion signal peptide sequence, a measles secretion signal peptide sequence, a rubella secretion signal peptide sequence, a mumps secretion signal peptide sequence, an Ebola secretion signal peptide sequence, a rabies secretion signal peptide sequence, and a smallpox secretion signal peptide sequence. These particular signal peptides are derived from viral sequences in viruses which have been administered to humans as vaccines (live-attenuated, inactivated or mRNA), with demonstrated strong safety profiles.

In certain embodiments, the viral secretion signal peptide is selected from the group consisting of: an influenza hemagglutinin (HA) secretion signal peptide sequence, a SARS COV-2 spike secretion signal peptide sequence, a VZV gB secretion signal peptide sequence, a VZV gE secretion signal peptide sequence, a VZV gI secretion signal peptide sequence, a VZV gK secretion signal peptide sequence, a measles F-protein secretion signal peptide sequence, a rubella E1 protein secretion signal peptide sequence, a rubella E2 protein secretion signal peptide sequence, a mumps F-protein secretion signal peptide sequence, an Ebola GP protein secretion signal peptide sequence, a rabies virus glycoprotein (Rabies G) secretion signal peptide sequence, and a smallpox 6 kDa IC protein secretion signal peptide sequence.

In certain embodiments, the viral secretion signal peptide comprises an HA secretion signal peptide sequence from influenza A or influenza B, preferably from influenza A.

Exemplary viral secretion signal peptide amino acid sequences of the disclosure are shown below in Table 2. Exemplary viral secretion signal peptide amino acid sequences derived from Influenza A or B of the disclosure are shown below in Table 3.

TABLE 2

Viral Secretion Signal Peptide (SS) Amino Acid Sequences

| NAME OF THE PROTEIN | ORGANISM | STRAIN | SEQUENCE OF THE SS |
|---|---|---|---|
| HA (HIN1) | Influenza virus | A/New Caledonia/ 20/1999 | MKAKLLVLLCTFTATYA (SEQ ID NO: 210) |
| HA (H1N1pdm) | Influenza virus | A/California/ 7/2009 | MKAILVVLLYTFATANA (SEQ ID NO: 211) |
| HA (H3N2) | Influenza virus | A/Moscow/10/ 1999 | MKTIIALSYILCLVFA (SEQ ID NO: 212) |
| HAB | Influenza virus | B/Phuket/ 3073/2013 | MKAIIVLLMVVTSNA (SEQ ID NO: 213) |
| Spike | SARS COV-2 | Wuhan-1 | MFVFLVLLPLVS (SEQ ID NO: 214) |
| Spike | SARS COV-2 | Wuhan-1 (long version) | MFLLTTKRTMFVFLVLLPLVS (SEQ ID NO: 215) |
| gB | VZV | Oka strain | MSPCGYYSKWRNRDRPEYRRNLRFRRFFSSIHPNAAAGSGFNGPGVFITSVTGVWLCFLCIFSMFVTAVVS (SEQ ID NO: 216) |
| gE | VZV | Oka strain | MGTVNKPVVGVLMGFGIITGTLRITNPVRA (SEQ ID NO: 217) |
| gI | VZV | Oka strain | MFLIQCLISAVIFYIQVTNA (SEQ ID NO: 218) |
| gK | VZV | Oka strain | MQALGIKTEHFIIMCLLSGHA (SEQ ID NO: 219) |
| F | Measles | Edmonston-Zagreb strain | MGLKVNVSAIFMAVLLTLQTPTG (SEQ ID NO: 220) |
| E1 | Rubella | RA27/3 strain | MGAAAALTAVVLQGYNPPAYG (SEQ ID NO: 221) |
| E2 | Rubella | RA27/3 strain | MGAPQAFLAGLLLAAVAVGTARA (SEQ ID NO: 222) |
| F | Mumps | Miyahara strain | MKVFLVTCLGFAVFSSSVC (SEQ ID NO: 223) |
| GP | Ebola virus | Mayinga-76 strain | MGVTGILQLPRDRFKRTSFFLWVIILFQRTFS (SEQ ID NO: 224) |
| 6kDa IC | Smallpox | Germany 91-3 strain | MRSLIIFLLFPSIIYS (SEQ ID NO: 225) |
| Rabies G | Rabies | Rabies Pasteur strain | MVPQALLFVPLLVFPLCFG (SEQ ID NO: 226) |

TABLE 3

Influenza A and B Specific Viral Secretion Signal Peptide (SS) Amino Acid Sequences

| STRAIN NAME OR ID | SEQUENCE OF THE SS |
|---|---|
| A/Beijing/262/95 (HIN1)-like virus | MKAKLLVLLCTFTATYA (SEQ ID NO: 210) |
| A/Brisbane/02/2018 (H1N1)pdm09-like virus | MKAILVVLLYTFTTANA (SEQ ID NO: 227) |
| A/Brisbane/59/2007 (HIN1)-like virus | MKVKLLVLLCTFTATYA (SEQ ID NO: 228) |
| A/California/7/2009 (HIN1)-like virus | MKAILVVLLYTFATANA (SEQ ID NO: 211) |
| A/Guangdong-Maonan/SWL1536/2019 (HIN1)pdm09-like virus | MKAILVVLLYTFTTANA (SEQ ID NO: 227) |
| A/Hawaii/70/2019 (H1N1)pdm09-like virus | MKAILVVLLYTFTTANA (SEQ ID NO: 227) |
| A/Michigan/45/2015 (H1N1)pdm09-like virus | MKAILVVLLYTFTTANA (SEQ ID NO: 227) |
| A/New Caledonia/20/99 (HIN1)-like virus | MKAKLLVLLCTFTATYA (SEQ ID NO: 210) |
| A/Solomon Islands/3/2006 (HIN1)-like virus | MKVKLLVLLCTFTATYA (SEQ ID NO: 228) |
| A/Sydney/5/2021 (H1N1)pdm09-like virus | MKAILVVMLYTFTTANA (SEQ ID NO: 229) |
| A/Victoria/2570/2019 (HIN1)pdm09-like virus | MKAILVVMLYTFTTANA (SEQ ID NO: 229) |
| A/Victoria/4897/2022 (HIN1)pdm09-like virus | MKAILVVMLYTFTTANA (SEQ ID NO: 229) |
| A/Wisconsin/588/2019 (H1N1)pdm09-like virus | MKAILVVMLYTFTTANA (SEQ ID NO: 229) |
| A/Wisconsin/67/2022 (HIN1)pdm09-like virus | MKAILVVMLYTFTTANA (SEQ ID NO: 229) |
| H1N1 CONSENSUS SEQ #1 (without substitutions) | MKAILVVLLYTFTTANA (SEQ ID NO: 227) |
| A/Brisbane/10/2007 (H3N2)-like virus | MKTIIALSYILCLVFT (SEQ ID NO: 230) |
| A/California/7/2004 (H3N2)-like virus | MKTIIALSYILCLVFA (SEQ ID NO: 212) |
| A/Cambodia/e0826360/2020 (H3N2)-like virus | MKTIIALSYILCLVFA (SEQ ID NO: 212) |
| A/Darwin/6/2021 (H3N2)-like virus | MKTIIALSNILCLVFA (SEQ ID NO: 231) |
| A/Darwin/9/2021 (H3N2)-like virus | MKTIIALSNILCLVFA (SEQ ID NO: 231) |
| A/Fujian/411/2002 (H3N2)-like virus | MKTIIALSYILCLVFA (SEQ ID NO: 212) |
| A/Hong Kong/2671/2019 (H3N2)-like virus | MKAIIALSNILCLVFA (SEQ ID NO: 232) |
| A/Hong Kong/45/2019 (H3N2)-like virus | MKAIIALSNILCLVFA (SEQ ID NO: 232) |
| A/Hong Kong/4801/2014 (H3N2)-like virus | MKTIIALSYILCLVFA (SEQ ID NO: 212) |

TABLE 3-continued

Influenza A and B Specific Viral Secretion Signal Peptide (SS) Amino Acid Sequences

| STRAIN NAME OR ID | SEQUENCE OF THE SS |
|---|---|
| A/Kansas/14/2017 (H3N2)-like virus | MKTIIALSCILCLVFA (SEQ ID NO: 233) |
| A/Moscow/10/99 (H3N2)-like virus | MKTIIALSYILCLVFA (SEQ ID NO: 212) |
| A/Perth/16/2009 (H3N2)-like virus | MKTIIALSYILCLVFA (SEQ ID NO: 212) |
| A/Singapore/INFIMH-16-0019/2016 (H3N2)-like virus | MKTIIALSYILCLVFA (SEQ ID NO: 212) |
| A/South Australia/34/2019 (H3N2)-like virus | MKTIIALSYILCLVFA (SEQ ID NO: 212) |
| A/Switzerland/8060/2017 (H3N2)-like virus | MKTIIALSYILCLVFA (SEQ ID NO: 212) |
| A/Switzerland/9715293/2013 (H3N2)-like virus | MKTIIALSYILCLVFA (SEQ ID NO: 212) |
| A/Sydney/5/97 (H3N2)-like virus | MKTIIALSYILCLVFA (SEQ ID NO: 212) |
| A/Texas/50/2012 (H3N2)-like virus | MKTIIALSYILCLVFA (SEQ ID NO: 212) |
| A/Victoria/361/2011 (H3N2)-like virus | MKTIIALSHILCLVFA (SEQ ID NO: 234) |
| A/Wellington/1/2004 (H3N2)-like virus | MKTIIALSYILCLVFA (SEQ ID NO: 212) |
| A/Wisconsin/67/2005 (H3N2)-like virus | MKTIIALSYILCLVFA (SEQ ID NO: 212) |
| H3N2 CONSENSUS SEQ #1 (without substitutions) | MKTIIALSYILCLVFA (SEQ ID NO: 212) |
| B/Austria/1359417/2021 (B/Victoria lineage)-like | MKAIIVLLMVVTSNA (SEQ ID NO: 213) |
| B/Brisbane/60/2008-like virus | MKAIIVLLMVVTSNA (SEQ ID NO: 213) |
| B/Colorado/06/2017-like virus (B/Victoria/2/87 lineage) | MKAIIVLLMVVTSSA (SEQ ID NO: 235) |
| B/Hong Kong/330/2001-like virus | MKAIIVLLMVVTSNA (SEQ ID NO: 213) |
| B/Malaysia/2506/2004-like virus | MKAIVLLMVVTSNA (SEQ ID NO: 213) |
| B/Washington/02/2019 (B/Victoria lineage)-like virus | MKAIIVLLMVVTSNA (SEQ ID NO: 213) |
| B/Beijing/184/93-like virus | MKAIIVLLMVVTSNA (SEQ ID NO: 213) |
| B/Florida/4/2006-like virus | MKAIIVLLMVVTSNA (SEQ ID NO: 213) |
| B/Massachusetts/2/2012-like virus | MKAIIVLLMVVTSNA (SEQ ID NO: 213) |

TABLE 3-continued

| Influenza A and B Specific Viral Secretion Signal Peptide (SS) Amino Acid Sequences | |
|---|---|
| STRAIN NAME OR ID | SEQUENCE OF THE SS |
| B/Phuket/3073/2013-like virus | MKAIIVLLMVVTSNA (SEQ ID NO: 213) |
| B/Sichuan/379/99-like virus | MEAIIVLLMVVTSNA (SEQ ID NO: 236) |
| INFLUENZA B VICTORIA/YAMAGATA CONSENSUS SEQUENCE (without substitutions) | MKAIIVLLMVVTSNA (SEQ ID NO: 213) |
| H1N1 CONSENSUS SEQ #2 (with substitutions) | MK$X_1X_2$L$X_3$V$X_4$L$X_5$TF$X_6X_7X_8X_9$A $X_1$ is selected from A and V; $X_2$ is selected from I and K; $X_3$ is selected from V and L; $X_4$ is selected from L and M; $X_5$ is selected from Y and C; $X_6$ is selected from T and A; $X_7$ is selected from T and A; $X_8$ is selected from A and T; and $X_9$ is selected from N and Y (SEQ ID NO: 237) |
| H3N2 CONSENSUS SEQ #2 (with substitutions) | MK$X_1$IIALS$X_2$ILCLVF$X_3$ $X_1$ is selected from T and A; $X_2$ is selected from Y, N, C, and H; and $X_3$ is selected from T and A (SEQ ID NO: 238) |
| INFLUENZA B VICTORIA CONSENSUS SEQ (with substitutions) | MKAIIVLLMVVTS$X_1$A $X_1$ is selected from S and N (SEQ ID NO: 239) |
| INFLUENZA B YAMAGATA CONSENSUS SEQ (with substitutions) | M$X_1$AIIVLLMVVTSNA $X_1$ is selected from K and E (SEQ ID NO: 240) |

The secretion signal peptide sequence may be positioned at the N terminus or the C terminus (e.g. at the N terminus) of a polypeptide described herein.

In certain embodiments, the SS amino acid sequence is encoded by a codon-optimized polynucleotide sequence.

In certain embodiments, the viral secretion signal peptide is derived from a viral sequence in a virus able to infect humans.

In certain embodiments, the viral secretion signal peptide is derived from a viral sequence selected from the group consisting of: an influenza secretion signal peptide sequence, and a non-influenza secretion signal peptide sequence selected from the group consisting of a SARS COV-2 secretion signal peptide sequence, a varicella-zoster virus (VZV) secretion signal peptide sequence, a measles secretion signal peptide sequence, a rubella secretion signal peptide sequence, a mumps secretion signal peptide sequence, an Ebola secretion signal peptide sequence, a smallpox secretion signal peptide sequence, and a rabies secretion signal peptide sequence.

In certain embodiments, the viral secretion signal peptide is selected from the group consisting of: an influenza hemagglutinin (HA) secretion signal peptide sequence, a SARS COV-2 spike secretion signal peptide sequence, a VZV gB secretion signal peptide sequence, a VZV gE secretion signal peptide sequence, a VZV gI secretion signal peptide sequence, a VZV gK secretion signal peptide sequence, a measles F-protein secretion signal peptide sequence, a rubella E1 protein secretion signal peptide sequence, a rubella E2 protein secretion signal peptide sequence, a mumps F-protein secretion signal peptide sequence, an Ebola GP protein secretion signal peptide sequence, a smallpox 6 kDa IC protein secretion signal peptide sequence, and a rabies G protein secretion signal peptide sequence, preferably wherein the viral secretion signal peptide comprises an HA secretion signal peptide sequence from influenza A or influenza B, more preferably from influenza A.

In certain embodiments, the HA secretion signal peptide sequence comprises an amino acid sequence MKX1X2LX3VX4LX5TFX6X7X8X9A (SEQ ID NO: 237) wherein X1 is selected from A and V; X2 is selected from I and K; X3 is selected from V and L; X4 is selected from L and M; X5 is selected from Y and C; X6 is selected from T and A X7 is selected from T and A; X8 is selected from A and T; and X9 is selected from N and Y.

In certain embodiments, the HA secretion signal peptide sequence comprises an amino acid sequence selected from MKAKLLVLLCTFTATYA (SEQ ID NO: 210), MKAILVVLLYTFTTANA (SEQ ID NO: 227). MKVKLLVLLCTFTATYA (SEQ ID NO: 228), MKAILVVLLYTFATANA (SEQ ID NO: 211), and MKAILVVMLYTFTTANA (SEQ ID NO: 229).

In certain embodiments, the HA secretion signal peptide sequence comprises an amino acid sequence MKXIIIALSX2ILCLVFX3 (SEQ ID NO: 238) wherein X1 is selected from T and A; X2 is selected from Y, N, C, and H; and X3 is selected from T and A.

In certain embodiments, the HA secretion signal peptide sequence comprises an amino acid sequence selected from MKTIIALSYILCLVFT (SEQ ID NO: 230), MKTIIALSYILCLVFA (SEQ ID NO: 212), MKTIIALSNILCLVFA (SEQ ID NO: 231), MKAIIALSNILCLVFA (SEQ ID NO: 232), MKTIIALSCILCLVFA (SEQ ID NO: 233) and MKTIIALSHILCLVFA (SEQ ID NO: 234).

In certain embodiments, the HA secretion signal peptide sequence comprises an amino acid sequence MKAIIVLLMVVTSXIA (SEQ ID NO: 239) wherein X1 is selected from S and N.

In certain embodiments, the HA secretion signal peptide sequence comprises an amino acid sequence MX1AIIVLLMVVTSNA (SEQ ID NO: 240) wherein X1 is selected from K and E.

In certain embodiments, the HA secretion signal peptide sequence comprises an amino acid sequence selected from MKAIIVLLMVVTSNA (SEQ ID NO: 213). MKAIIVLLMVVTSSA (SEQ ID NO: 235), and MEAIIVLLMVVTSNA (SEQ ID NO: 236).

In certain embodiments, the viral secretion signal peptide comprises an amino acid sequence selected from the group consisting of: MKAKLLVLLCTFTATYA (SEQ ID NO: 210); MKAILVVLLYTFATANA (SEQ ID NO: 211); MKTIIALSYILCLVFA (SEQ ID NO: 212); MKAIIVLL- MVVTSNA (SEQ ID NO: 213); MFVFLVLLPLVS (SEQ ID NO: 214); MFLLTTKRTMFVFLVLLPLVS (SEQ ID NO: 215) MSPCGYYSKWRNRDRPEYRRNLRFRRFF-SSIHPNAAAGSGFNGPGVFITSVTGVWLCFLCIFS MFVTAVVS (SEQ ID NO: 216); MGTVNKPVVGVLMGFGIITGTLRITNPVRA (SEQ ID NO: 217); MFLIQCLISAVIFYIQVTNA (SEQ ID NO: 218); MQALGIKTEHFIIMCLLSGHA (SEQ ID NO: 219); MGLKVNVSAIFMAVLLTLQTPTG (SEQ ID NO: 220); MGAAAALTAVVLQGYNPPAYG (SEQ ID NO: 221); MGAPQAFLAGLLLAAVAVGTARA (SEQ ID NO: 222): MKVFLVTCLGFAVFSSSVC (SEQ ID NO: 223); MGVTGILQLPRDRFKRTSFFLWVIILFQRTFS (SEQ ID NO: 224); MRSLIIFLLFPSIIYS (SEQ ID NO: 225); and MVPQALLFVPLLVFPLCFG (SEQ ID NO: 226).

In certain embodiments, the viral secretion signal peptide comprises an amino acid sequence of MKAKLL-VLLCTFTATYA (SEQ ID NO: 210).

In certain embodiments, the viral secretion signal peptide is positioned at the N-terminus of a polypeptide disclosed herein.

In certain embodiments, the viral secretion signal peptide is positioned at the C-terminus of a polypeptide disclosed herein.

In certain embodiments, the viral secretion signal peptide is attached to a polypeptide disclosed herein with a linker.

Heterologous Transmembrane Domains (TMBs)

The *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and/or the chimeric *C. acnes* DsA1/DsA2/PITP/CAMP2 polypeptide as described herein may comprise a transmembrane domain (TMB), more particularly a heterologous (non-native) TMB. The inclusion of a heterologous TMB may be advantageous as this will localise the antigen to the cell membrane. This may reduce antigen intracellular localisation and further promote higher immunogenicity relative to the antigen without the TMB sequence.

The *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and/or the chimeric *C. acnes* DsA1/DsA2/PITP/CAMP2 polypeptide comprising a heterologous transmembrane domain may also comprise a secretion signal peptide sequence. Typically, a nucleic acid described herein encoding the chimeric *C. acnes* CAMP2 polypeptide that comprises a heterologous transmembrane domain also comprises a nucleotide sequence encoding a secretion signal peptide sequence. Typically, a nucleic acid described herein encoding the *C. acnes* DsA1 polypeptide that comprises a heterologous transmembrane domain also comprises a nucleotide sequence encoding a secretion signal peptide sequence. Typically, a nucleic acid described herein encoding the *C. acnes* DsA2 polypeptide that comprises a heterologous transmembrane domain also comprises a nucleotide sequence encoding a secretion signal peptide sequence. Typically, a nucleic acid described herein encoding the *C. acnes* PITP polypeptide that comprises a heterologous transmembrane domain also comprises a nucleotide sequence encoding a secretion signal peptide sequence. Typically, a nucleic acid described herein encoding the chimeric *C. acnes* DsA1/DsA2 polypeptide that comprises a heterologous transmembrane domain also comprises a nucleotide sequence encoding a secretion signal peptide sequence. Typically, a nucleic acid described herein encoding the chimeric *C. acnes* DsA1/DsA2/PITP polypeptide that comprises a heterologous transmembrane domain also comprises a nucleotide sequence encoding a secretion signal peptide sequence. Typically, a nucleic acid described herein encoding the chimeric *C. acnes* DsA1/DsA2/PITP/CAMP2 polypeptide that comprises a heterologous transmembrane domain also comprises a nucleotide sequence encoding a secretion signal peptide sequence.

The TMB may be from any known TMB in the art, including but not limited to, TMBs from eukaryotic transmembrane proteins (e.g., mammalian transmembrane proteins, such as human transmembrane proteins), TMBs from prokaryotic transmembrane proteins, and TMBs from viral transmembrane proteins. TMBs may further be identified through in silico prediction algorithms, for example, in the TMHMM prediction method described in Krogh et al. (J Mol Biol. 305 (3): 567-580. 2001) and services.healthtech.dtu.dk/services/TMHMM-2.0/, each of which is incorporated herein by reference in their entirety. Some features of TMBs are described in further detail in Albers et al. (Chapter 2-cell membrane structures and functions. Basic Neurochemistry eighth edition. Pages 26-39, 2012), incorporated herein by reference. TMBs are typically, but not exclusively, comprised predominantly of nonpolar (hydrophobic) amino acid residues and may traverse a lipid bilayer once or several times. The skilled person knows well methods to determine the hydrophobicity of an amino acid. See Simm et al. (2016), Biol Res., 49 (1):31; Wimlet and White (1996), Nat Struct Biol., 3(10): 842-848; blanco.biomol.uci.edu/hydrophobicity_scales.html; and cgl.ucsf.edu/chimera/docs/UsersGuide/midas/hydrophob.html.

The TMBs usually comprise alpha helices, each helix containing 18-21 amino acids, which is sufficient to span the lipid bilayer. Accordingly, in certain embodiments, the transmembrane domain comprises one or more alpha helices. In some embodiments, the TMB: (a) comprises or consists of 15 to 50 amino acid residues, preferably 15 to 30 amino acid residues, more preferably 18 to 25 amino acid residues; and/or (b) comprises at least 50%, at least 55%, or at least 60% of hydrophobic amino acid residues, preferably selected in the group consisting of: alanine, isoleucine, leucine, valine, phenylalanine, tryptophane and tyrosine; and/or (c) comprises at least one alpha helix.

In certain embodiments, the transmembrane domain is derived from an integral membrane protein, as further defined hereafter and in Albers et al., An "integral membrane protein" (also known as an intrinsic membrane protein) is a membrane protein that is permanently attached to the lipid membrane. In certain embodiments, the transmembrane domain is derived from an integral polytopic protein. An integral polytopic protein is one that spans the entire membrane. In certain embodiments, the transmembrane domain is derived from a single pass (trans) membrane protein, more particularly a bitopic membrane protein, e.g., of Type I or Type II. Single-pass membrane proteins cross the membrane only once (i.e., a bitopic membrane protein), while multi-pass membrane proteins weave in and out, crossing several times. Single pass transmembrane proteins can be categorized as Type I, which are positioned such that their carboxyl-terminus is towards the cytosol, or Type II, which have their amino-terminus towards the cytosol. In certain embodiments, the transmembrane domain is derived from an integral monotopic protein. An integral monotopic protein is one that is associated with the membrane from only one side and does not span the lipid bilayer completely.

In certain embodiments, the heterologous transmembrane domain is derived from a non-human sequence.

In certain embodiments, the heterologous transmembrane domain is derived from a viral sequence. The phrase "influenza", "SARS COV-2", "varicella-zoster virus (VZV)", "measles", "rubella", "rabies," "Ebola," and "smallpox" preceding the phrase "transmembrane domain sequence" indicates that the transmembrane domain sequence was derived from the virus corresponding to that name.

In certain embodiments, the heterologous transmembrane domain is derived from a viral transmembrane domain sequence selected from the group consisting of: an influenza transmembrane domain sequence, a SARS COV-2 transmembrane domain sequence, a varicella-zoster virus (VZV) transmembrane domain sequence, a measles transmembrane domain sequence, a rubella transmembrane domain sequence, a mumps transmembrane domain sequence, a rabies transmembrane domain sequence, and an Ebola transmembrane domain sequence. These particular transmembrane domains are derived from viral sequences in viruses which have been administered to humans as vaccines (live-attenuated, inactivated or mRNA), with demonstrated strong safety profiles.

In certain embodiments, the heterologous transmembrane domain is selected from the group consisting of: an influenza hemagglutinin (HA) transmembrane domain sequence, a SARS COV-2 spike transmembrane domain sequence, a VZV gB transmembrane domain sequence, a VZV gE transmembrane domain sequence, a VZV gI transmembrane domain sequence, a VZV gK transmembrane domain sequence, a measles F-protein transmembrane domain sequence, a rubella E1 protein transmembrane domain sequence, a rubella E2 protein transmembrane domain sequence, a mumps F-protein transmembrane domain sequence, a rabies virus glycoprotein (Rabies G) transmembrane domain sequence, and an Ebola GP protein transmembrane domain sequence.

In certain embodiments, the heterologous transmembrane domain comprises an HA transmembrane domain sequence from influenza A or influenza B, preferably from influenza A.

Exemplary viral transmembrane domain amino acid sequences of the disclosure are shown below in Table 4.

TABLE 4

Viral Transmembrane Domain (TMB) Signal Amino Acid Sequences

| NAME OF THE PROTEIN | ORGANISM | STRAIN | SEQUENCE OF THE TMB |
|---|---|---|---|
| HA (H1N1) | Influenza virus | A/New Caledonia/20/1999 | ILAIYSTVASSLVLLVSLGAISF (SEQ ID NO: 208) |
| HA (H1N1pdm) | Influenza virus | A/California/7/2009 | ILAIYSTVASSLVLVVSLGAISF (SEQ ID NO: 209) |
| HA (H3N2) | Influenza virus | A/Moscow/10/1999 | ILWISFAISCFLLCVVLLGFI (SEQ ID NO: 241) |
| HAB | Influenza virus | B/Phuket/3073/2013 | STAASSLAVTLMLAIFIVYMV (SEQ ID NO: 242) |
| Spike | SARS COV-2 | Wuhan-1 | WYIWLGFIAGLIAIVMVTIML (SEQ ID NO: 243) |
| gB | VZV | Oka strain | FGALAVGLLVLAGLVAAFFAY (SEQ ID NO: 244) |
| gE | VZV | Oka strain | AAWTGGLAAVVLLCLVIFLIC (SEQ ID NO: 245) |
| gI | VZV | Oka strain | IIIPIVASVMILTAMVIVIVI (SEQ ID NO: 246) |
| gK | VZV | Oka strain | YFWCVQLKMIFFAWFVYGMYL (SEQ ID NO: 247) |
| F | Measles | Edmonston-Zagreb strain | IVYILIAVCLGGLIGIPALIC (SEQ ID NO: 248) |
| E1 | Rubella | RA27/3 strain | LDHAFAAFVLLVPWVLIFMVC (SEQ ID NO: 249) |
| E2 | Rubella | RA27/3 strain | WWQLTLGAICALLLAGLLACC (SEQ ID NO: 250) |
| F | Mumps | Miyahara strain | IVAALVLSILSIIISLLFCCW (SEQ ID NO: 251) |
| GP | Ebola | Mayinga-76 strain | WIPAGIGVTGVIIAVIALFCI (SEQ ID NO: 252) |
| Rabies G | Rabies | Rabies Pasteur strain | VLLSAGALTALMLIIFLMTCW (SEQ ID NO: 253) |

In certain embodiments, the heterologous TMB sequence is positioned at the N-terminus or the C-terminus (e.g. C-terminus) of a polypeptide described herein.

In certain embodiments, the TMB amino acid sequence is encoded by a codon-optimized polynucleotide sequence.

In some embodiments, one or more of the *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and/or the chimeric *C. acnes* DsA1/DsA2/PITP/CAMP2 polypeptide comprise a heterologous transmembrane domain as described herein. In alternative embodiments, the *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, the chimeric *C. acnes* DsA1/DsA2/PITP polypeptide and/or the chimeric *C. acnes* DsA1/DsA2/PITP/CAMP2 polypeptide do not comprise a heterologous transmembrane domain. Such polypeptides may comprise a secretion signal peptide sequence. In further embodiments, the polypeptides of the invention are secreted. In some embodiments, the *C. acnes* CAMP2 polypeptide described herein is a secreted polypeptide. In some embodiments, the *C. acnes* DsA1 polypeptide described herein is a secreted polypeptide. In some embodiments, the *C. acnes* DsA2 polypeptide described herein is a secreted polypeptide. In some embodiments, the the *C. acnes* PITP polypeptide described herein is a secreted polypeptide. In some embodiments, chimeric *C. acnes* DsA1/DsA2 polypeptide described herein is a secreted polypeptide. In some embodiments, chimeric *C. acnes* DsA1/DsA2/PITP polypeptide described herein is a secreted polypeptide. In some embodiments, chimeric *C. acnes* DsA1/DsA2/PITP/CAMP2 polypeptide described herein is a secreted polypeptide. Secreted polypeptides described herein comprise a secretion signal peptide sequence.

In certain embodiments the TMB: (a) comprises or consists of 15 to 50 amino acid residues, preferably 15 to 30 amino acid residues, more preferably 18 to 25 amino acid residues; and/or (b) comprises at least 50% of hydrophobic amino acid residues, preferably selected in the group consisting of: alanine, isoleucine, leucine, valine, phenylalanine, tryptophane and tyrosine; and/or (c) comprises at least one alpha helix.

In certain embodiments the TMB is derived from an integral membrane protein, preferably from a single pass membrane protein, more preferably from a bitopic membrane protein, even more preferably from a bitopic membrane protein of Type I.

In certain embodiments the TMB is derived from a non-human sequence.

In certain embodiments, the TMB is derived from a viral sequence.

In certain embodiments, the TMB is derived from a viral transmembrane domain sequence selected from the group consisting of: an influenza transmembrane domain sequence, and a non-influenza transmembrane domain sequence selected from the group consisting of a SARS COV-2 transmembrane domain sequence, a varicella-zoster virus (VZV) transmembrane domain sequence, a measles transmembrane domain sequence, a rubella transmembrane domain sequence, a mumps transmembrane domain sequence, an Ebola transmembrane domain sequence, and a rabies transmembrane domain sequence.

In certain embodiments, the TMB is selected from the group consisting of: an influenza hemagglutinin (HA) transmembrane domain sequence, a SARS COV-2 spike transmembrane domain sequence, a VZV gB transmembrane domain sequence, a VZV gE transmembrane domain sequence, a VZV gI transmembrane domain sequence, a VZV gK transmembrane domain sequence, a measles F-protein transmembrane domain sequence, a rubella E1 protein transmembrane domain sequence, a rubella E2 protein transmembrane domain sequence, a mumps F-protein transmembrane domain sequence, an Ebola GP protein transmembrane domain sequence and a rabies G protein transmembrane domain sequence, preferably wherein the TMB comprises an HA transmembrane domain sequence from influenza A or influenza B, more preferably from influenza A.

In certain embodiments, the TMB comprises an amino acid sequence selected from the group consisting of: ILAIYSTVASSLVLLVSLGAISF (SEQ ID NO: 208); ILAIYSTVASSLVL VVSLGAISF (SEQ ID NO: 209); ILWISFAISCFLLCVVLLGFI (SEQ ID NO: 241); STAASSLAVTLMLAIFIVYMV (SEQ ID NO: 242); WYIWLGFIAGLIAIVMVTIML (SEQ ID NO: 243); FGALAVGLLVLAGLVAAFFAY (SEQ ID NO: 244); (SEQ AAWTGGLAAVVLLCLVIFLIC ID NO: 245); IIIPIVASVMILTAMVIVIVI (SEQ ID NO: 246); YFWCVQLKMIFFAWFVYGMYL (SEQ ID NO: 247); IVYILIAVCLGGLIGIPALIC (SEQ ID NO: 248); LDHAFAAFVLLVPWVLIFMVC (SEQ ID NO: 249); WWQLTLGAICALLLAGLLACC (SEQ ID NO: 250); IVAALVLSILSIIISLLFCCW (SEQ ID NO: 251); WIPAGIGVTGVIIAVIALFCI (SEQ ID NO: 252); and VLLSAGALTALMLIIFLMTCW (SEQ ID NO: 253).

In certain embodiments, the TMB comprises an amino acid sequence of ILAIYSTVASSLVLLVSLGAISF (SEQ ID NO: 208).

In certain embodiments, the TMB is attached to a polypeptide described herein with a linker.

In certain embodiments, the TMB is positioned at the N-terminus of a polypeptide described herein.

In certain embodiments, the TMB is positioned at the C-terminus of a polypeptide described herein.

Linkers

In some embodiments, the polypeptides of the invention comprise linkers. In some embodiments, the polypeptides of the invention comprise two or more antigens attached via linkers.

In certain embodiments of the disclosure, the secretion signal peptide (SS) sequence or transmembrane domain (TMB) are directly fused to a polypeptide described herein (i.e., there is no linker, such as an amino acid linker, connecting the SS sequence or TMB to the polypeptide described herein).

In other embodiments, the SS sequences and TMBs of the disclosure are optionally attached to a polypeptide described herein with a linker. In certain embodiments, the linker is an amino acid linker. In the certain embodiments, the amino acid linker is 1-10 amino acids in length (e.g., the amino acid linker has a length of 1 amino acid, 2 amino acids, 3 amino acids, 4 amino acids, 5 amino acids, 6 amino acids, 7 amino acids, 8 amino acids, 9 amino acids, or 10 amino acids).

Illustrative examples of linkers include glycine polymers (Gly)n, where n is an integer of at least one, two, three, four, five, six, seven, or eight; glycine-serine polymers (GlySer)n, where n is an integer of at least one, two, three, four, five, six, seven, or eight; glycine-alanine polymers; alanine-serine polymers; and other flexible linkers known in the art.

Glycine and glycine-serine polymers are relatively unstructured and flexible, and therefore may be able to serve as a neutral tether between the SS sequence and/or TMB and the polypeptides described herein. In certain embodiments, the linker is SGS or GSG.

Other exemplary linkers include, but are not limited to, the following amino acid sequences: GGG; DGGGS (SEQ ID NO: 254); TGEKP (SEQ ID NO: 255) (Liu et al. Proc. Natl. Acad. Sci. 94: 5525-5530. 1997); GGRR (SEQ ID NO: 256); (GGGGS)n (SEQ ID NO: 257), wherein n=1, 2, 3, 4 or 5 (Kim et al. Proc. Natl. Acad. Sci. 93: 1156-1160. 1996); EGKSSGSGSESKVD (SEQ ID NO: 258) (Chaudhary et al. Proc. Natl. Acad. Sci. 87: 1066-1070. 1990); KESGSVSSEQLAQFRSLD (SEQ ID NO: 259) (Bird et al. Science. 242:423-426. 1988), GGRRGGGS (SEQ ID NO: 260); LRQRDGERP (SEQ ID NO: 261); LRQKDGGGSERP (SEQ ID NO: 262); and GSTSGSGKPGSGEGSTKG (SEQ ID NO: 263) (Cooper et al. Blood. 101 (4); 1637-1644. 2003). Preferred linkers are shorter, e.g., consisting of 3, 4 or 5 amino acids.

Additional examples of linkers are provided in Chen et al. (Adv Drug Deliv Rev. 65 (10): 1357-1369. 2013), incorporated herein by reference.

Compositions-Nucleic Acid and Polypeptide

The invention provides a composition comprising one or more nucleic acids of the disclosure. The invention also provides a composition comprising one or more polypeptides of the disclosure. A composition of the invention may be a pharmaceutical composition, e.g. comprising a pharmaceutically acceptable carrier, excipient or diluent. In certain embodiments, the composition of the invention is an immunogenic composition. An "immunogenic composition" means a composition comprising a nucleic acid or protein that, when administered to a subject, elicits an immune response, e.g. an antigen-specific immune response. The immune response may be a humoral (antibody) immune response or a cell-mediated immune response. The composition of the invention may be a vaccine composition.

Immunogenic compositions (e.g. vaccine compositions) may elicit immunity (e.g. antibody response) against *C. acnes* infection. The antibody response may include antibodies that bind to the surface of *C. acnes* bacteria and recruit immune effector cells (e.g. effector cells of the immune system such as phagocytes). The antibodies may be capable of eliciting opsonophagocytic killing in vitro. The antibodies may be cross-reactive across a range of *C. acnes* strains. The antibodies may decrease or neutralise CAMP2-mediated inflammation.

"Protective immunity" or a "protective immune response", as used herein, refers to immunity or eliciting an immune response against an infectious agent (e.g., *C. acnes*), which is exhibited by a subject, that prevents or ameliorates an infection or reduces at least one symptom thereof. Specifically, induction of protective immunity or a protective immune response from administration of a composition of the invention is evident by elimination or reduction of the presence of one or more symptoms of the *C. acnes* infection. As used herein, the term "immune response" refers to both the humoral immune response and the cell-mediated immune response. In some embodiments, treatment with a composition of the invention as described herein provides protective immunity against infection by *C. acnes*.

Nucleic Acid Compositions

In one aspect, the invention provides a composition comprising a nucleic acid as described herein comprising a nucleotide sequence encoding a *C. acnes* CAMP2 polypeptide as described herein.

In another aspect, the invention provides a composition comprising a nucleic acid as described herein comprising a nucleotide sequence encoding a modified *C. acnes* CAMP2 polypeptide as described herein.

In another aspect, the invention provides a composition comprising a nucleic acid as described herein comprising a nucleotide sequence encoding a *C. acnes* DsA1 polypeptide as described herein.

In another aspect, the invention provides a composition comprising a nucleic acid as described herein comprising a nucleotide sequence encoding a *C. acnes* DsA2 polypeptide as described herein.

In another aspect, the invention provides a composition comprising a nucleic acid as described herein comprising a nucleotide sequence encoding a *C. acnes* PITP polypeptide as described herein.

In another aspect, the invention provides a composition comprising a nucleic acid as described herein comprising a nucleotide sequence encoding a chimeric *C. acnes* DsA1/DsA2 polypeptide as described herein.

In another aspect, the invention provides a composition comprising a nucleic acid as described herein comprising a nucleotide sequence encoding a chimeric *C. acnes* DsA1/DsA2/PITP polypeptide as described herein.

In another aspect, the invention provides a composition comprising a nucleic acid as described herein comprising a nucleotide sequence encoding a chimeric *C. acnes* DsA1/DsA2/PITP/CAMP2 polypeptide as described herein.

Any of the compositions described herein may comprise one or more nucleic acid encoding one or more antigens as described in WO2021/165543 (herein incorporated by reference).

CAMP 2 Compositions

In one aspect, the invention provides a composition comprising a nucleic acid as described herein comprising a nucleotide sequence encoding a *C. acnes* CAMP2 polypeptide as described herein.

In another aspect, the invention provides an immunogenic composition comprising a nucleic acid as described herein comprising a nucleotide sequence encoding a *C. acnes* CAMP2 polypeptide as described herein and wherein the nucleic acid is an mRNA.

In another aspect, the invention provides a composition comprising a nucleic acid as described herein comprising a nucleotide sequence encoding a *C. acnes* CAMP2 polypeptide as described herein and wherein the composition further comprises an LNP.

A composition comprising a *C. acnes* CAMP2 polypeptide for use in the present invention, e.g. delivered as a mRNA and/or in the form of a composition comprising a LNP, may elicit antibodies in a subject. Such antibodies may neutralise biological activity of CAMP2 polypeptide, such as CAMP2 inflammatory activity. Such antibodies may neutralise CAMP2 polypeptide co-hemolytic activity.

In some embodiments, any of the compositions described herein that comprise (a) a nucleic acid as described herein comprising a nucleotide sequence encoding a *C. acnes* CAMP2 polypeptide further comprise one or more of (b) (i) a nucleic acid as described herein comprising a nucleotide sequence encoding a *C. acnes* DsA1 polypeptide, (b) (ii) a nucleic acid as described herein comprising a nucleotide sequence encoding a *C. acnes* DsA2 polypeptide, (b) (iii) a nucleic acid as described herein comprising a nucleotide sequence encoding a *C. acnes* PITP polypeptide, (b) (iv) a nucleic acid as described herein comprising a nucleotide sequence encoding a chimeric *C. acnes* DsA1/DsA2 polypeptide, and (b) (v) a nucleic acid as described herein comprising a nucleotide sequence encoding a chimeric *C. acnes* DsA1/DsA2/PITP polypeptide. In some embodiments, the composition comprises the nucleic acid of (b) (i), the nucleic acid of (b) (ii) and the nucleic acid of (b) (iii). In some embodiments, the composition comprises the nucleic acid of (b) (v). In preferred embodiments, the composition comprises the nucleic acid of (b) (iii); and the nucleic acid of (b) (iv).

In some embodiments, any two or more nucleic acids in (a) and (b) (i)-(v) are located on the same nucleic acid molecule or on different nucleic acid molecules (e.g. wherein all the nucleic acids in the composition are on the same nucleic acid molecule or wherein all the nucleic acids in the composition are on individual nucleic acid molecules. In some embodiments, the nucleic acid in (a), the nucleic acid in (b) (iii) and the nucleic acid in (b) (iv) are located on the same nucleic acid molecule or separate nucleic acid molecules. In some embodiments, the nucleic acid in (a) and the nucleic acid in (b) (v) are located on the same nucleic acid molecule or separate nucleic acid molecules. In some embodiments, the composition comprises provides a nucleic acid that comprises a nucleotide sequence encoding a chimeric *C. acnes* DsA1/DsA2/PITP/CAMP2 polypeptide as described herein. Typically, the nucleic acid in (a), the nucleic acid in (b) (iii) and the nucleic acid in (b) (iv) are provided by separate nucleic acid molecules.

Modified CAMP 2 Compositions

In another aspect, the invention provides a composition comprising a nucleic acid as described herein comprising a nucleotide sequence encoding a modified *C. acnes* CAMP2 polypeptide as described herein.

In some embodiments, the composition further comprises one or more of (i) a nucleic acid as described herein comprising a nucleotide sequence encoding a *C. acnes* DsA1 polypeptide, (ii) a nucleic acid as described herein comprising a nucleotide sequence encoding a *C. acnes* DsA2 polypeptide, (iii) a nucleic acid as described herein comprising a nucleotide sequence encoding a *C. acnes* PITP polypeptide, (iv) a nucleic acid as described herein comprising a nucleotide sequence encoding a chimeric *C. acnes* DsA1/DsA2 polypeptide, and (v) a nucleic acid as described herein comprising a nucleotide sequence encoding a chimeric *C. acnes* DsA1/DsA2/PITP polypeptide.

In some embodiments, the composition comprises the nucleic acid of (i), the nucleic acid of (ii) and the nucleic acid of (iii). In some embodiment, the composition comprises the nucleic acid of (v). In preferred embodiments, the composition comprises the nucleic acid of (iii); and the nucleic acid of (iv).

DsA1, DsA2 and PITP Compositions

In another aspect, the invention provides a composition comprising a nucleic acid as described herein comprising one or more of (i) a nucleic acid as described herein comprising a nucleotide sequence encoding a *C. acnes* DsA1 polypeptide, (ii) a nucleic acid as described herein comprising a nucleotide sequence encoding a *C. acnes* DsA2 polypeptide, (iii) a nucleic acid as described herein comprising a nucleotide sequence encoding a *C. acnes* PITP polypeptide, (iv) a nucleic acid as described herein comprising a nucleotide sequence encoding a chimeric *C. acnes* DsA1/DsA2 polypeptide, (v) a nucleic acid as described herein comprising a nucleotide sequence encoding a chimeric *C. acnes* DsA1/DsA2/PITP polypeptide and (vi) a nucleic acid as described herein comprising a nucleotide sequence encoding a chimeric *C. acnes* DsA1/DsA2/PITP/CAMP2 polypeptide.

The combination of a *C. acnes* DsA1. DsA2 and PITP polypeptides may elicit an immune response against a greater number of *C. acnes* phylotypes compared to use of individual antigens. Using a combination of DsA1 and/or DsA2 with PITP may elicit a pool of antibodies that are cross-reactive with a greater number of *C. acnes* strains compared to use of individual antigens. Preferably. *C. acnes* DsA1 and DsA2 polypeptides are provided as a chimeric *C. acnes* DsA1/DsA2 polypeptide. A *C. acnes* PITP polypeptide may be provided as a separate polypeptide molecule, as part of a chimeric *C. acnes* DsA1/DsA2/PITP polypeptide or as part of a chimeric *C. acnes* DsA1/DsA2/PITP/CAMP2 polypeptide. Typically, a *C. acnes* PITP polypeptide is provided as a separate polypeptide molecule.

In some embodiments, the composition comprises the nucleic acid as described herein comprising a nucleotide sequence encoding the *C. acnes* DsA1 polypeptide, the nucleic acid as described herein comprising a nucleotide sequence encoding the *C. acnes* DsA2 polypeptide and the nucleic acid as described herein comprising a nucleotide sequence encoding the *C. acnes* PITP polypeptide.

In some embodiments, the composition comprises the nucleic acid as described herein comprising a nucleotide sequence encoding the chimeric *C. acnes* DsA1/DsA2 polypeptide as described herein and the nucleic acid as described herein comprising a nucleotide sequence encoding the *C. acnes* PITP polypeptide as described herein. Typically, the chimeric *C. acnes* DsA1/DsA2 polypeptide comprises an amino acid sequence according to SEQ ID NO: 70, or a sequence that has at least 90%, at least 91%, at least 92%, at least 93%, at least 94%, at least 95%, at least 96%, at least 97%, at least 98%, or at least 99% (e.g. at least 90% or at least 95%) identity thereto, and the *C. acnes* PITP polypeptide comprises the sequence according to SEQ ID NO: 73, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 90% or at least 95%) identity thereto. In some embodiments, the chimeric *C. acnes* DsA1/DsA2 polypeptide comprises the sequence of SEQ ID NO: 70 and the *C. acnes* PITP polypeptide comprises the sequence according to SEQ ID NO: 73. In some embodiments, the chimeric *C. acnes* DsA1/DsA2 polypeptide consists of an amino acid sequence according to SEQ ID NO: 70 and the *C. acnes* PITP polypeptide consists of an amino acid sequence according to SEQ ID NO: 73.

In some embodiments, the nucleic acid comprising a nucleotide sequence encoding the chimeric *C. acnes* DsA1/DsA2 polypeptide comprises a nucleotide sequence according to SEQ ID NO: 179, or a sequence that has at least 75%, at least 80%, at least 85%, at least 90%, at least 91%, at least 92%, at least 93%, at least 94%, at least 95%, at least 96%, at least 97%, at least 98%, or at least 99% (e.g. 85%) identity thereto, and the nucleic acid comprising a nucleotide sequence encoding the *C. acnes* PITP polypeptide comprises a nucleotide sequence according to SEQ ID NO: 182, or a sequence that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% (e.g. 75%) identity thereto.

In some embodiments, the nucleic acid comprising a nucleotide sequence encoding the chimeric *C. acnes* DsA1/DsA2 polypeptide consists of a nucleotide sequence encoding a secretion signal peptide sequence (e.g., a viral secretion signal peptide sequence described herein) and a sequence according to SEQ ID NO: 179, or a sequence that has at least 85% identity thereto, and the nucleic acid comprising a nucleotide sequence encoding the *C. acnes* PITP polypeptide consists of a nucleotide sequence encoding a secretion signal peptide sequence (e.g., a viral secretion signal peptide sequence described herein) and a sequence according to SEQ ID NO: 182, or a sequence that has at least 75% identity thereto.

Any one of the compositions of the invention may comprise a combination as described herein of the nucleic acids as described herein (e.g. they may be formulated in the same composition). The combinations as described herein of the nucleic acids as described herein may alternatively be in two or more separate compositions (e.g. as a combination of compositions for simultaneous, separate or sequential administration. (e.g. in a therapeutic or prophylactic use as described herein)).

A composition of the present disclosure comprising one or more nucleic acids of the present disclosure can also include one or more additional components such as small molecule immunopotentiators (e.g., TLR agonists). A composition of the present disclosure can also include a delivery system for a nucleic acid described herein (e.g. RNA), such as a liposome, an oil-in-water emulsion, or a microparticle. In some embodiments, the composition comprises a lipid nanoparticle (LNP). In certain embodiments, the composition comprises a nucleic acid molecule of the invention encapsulated within an LNP.

In some embodiments, a composition as described herein is in a frozen liquid form. In some embodiments, a composition as described herein is in a lyophilized form (e.g. in a lyophilized form).

Polypeptide Compositions

In one aspect, the invention provides a composition comprising a *C. acnes* CAMP2 polypeptide as described herein.

In another aspect, the invention provides a composition comprising a modified *C. acnes* CAMP2 polypeptide as described herein.

In another aspect, the invention provides a composition comprising a *C. acnes* DsA1 polypeptide as described herein.

In another aspect, the invention provides a composition comprising a *C. acnes* DsA2 polypeptide as described herein.

In another aspect, the invention provides a composition comprising a *C. acnes* PITP polypeptide as described herein.

In another aspect, the invention provides a composition comprising a chimeric *C. acnes* DsA1/DsA2 polypeptide as described herein.

In another aspect, the invention provides a composition comprising a chimeric *C. acnes* DsA1/DsA2/PITP polypeptide as described herein.

In another aspect, the invention provides a composition comprising a chimeric *C. acnes* DsA1/DsA2/PITP/CAMP2 polypeptide as described herein.

Any of the compositions described herein may comprise any of the polypeptide antigens as described in WO2021/165543.

CAMP 2 Compositions

In one aspect, the invention provides a composition comprising a *C. acnes* CAMP2 polypeptide as described herein.

In some embodiments, the composition comprising (a) a *C. acnes* CAMP2 polypeptide as described herein further comprises one or more of (b) (i) a *C. acnes* DsA1 polypeptide as described herein, (b) (ii) a *C. acnes* DsA2 polypeptide as described herein, (b) (iii) a *C. acnes* PITP polypeptide as described herein, (b) (iv) a chimeric *C. acnes* DsA1/DsA2 polypeptide as described herein, and (b) (v) a chimeric *C. acnes* DsA1/DsA2/PITP polypeptide as described herein. In some embodiments, the composition comprises the polypeptide of (b) (i), the polypeptide of (b) (ii) and the polypeptide of (b) (iii). In some embodiments, the composition comprises the polypeptide of (b) (v). In preferred embodiments, the composition comprises the polypeptide of (b) (iii); and the polypeptide of (b) (iv).

In some embodiments, the polypeptides of (a), (b) (iii) and (b) (iv) are provided as a chimeric polypeptide, e.g. a chimeric *C. acnes* DsA1/DsA2/PITP/CAMP2 polypeptide as described herein. In some embodiments, the polypeptides of (a) and (b) (v) are provided as a chimeric polypeptide, e.g. a chimeric *C. acnes* DsA1/DsA2/PITP/CAMP2 polypeptide as described herein. Typically, the polypeptides of (a), (b) (iii) and (b) (iv) are provided as separate polypeptides.

Modified CAMP 2 Compositions

In another aspect, the invention provides a composition comprising a modified *C. acnes* CAMP2 polypeptide as described herein.

In some embodiments, the composition comprising a modified *C. acnes* CAMP2 polypeptide as described herein further comprises one or more of (i) a *C. acnes* DsA1 polypeptide as described herein. (ii) a *C. acnes* DsA2 polypeptide as described herein, (iii) a *C. acnes* PITP polypeptide as described herein, (iv) a chimeric *C. acnes* DsA1/DsA2 polypeptide as described herein, and (v) a chimeric *C. acnes* DsA1/DsA2/PITP polypeptide as described herein.

In some embodiments, the composition comprises the polypeptide of (i), the polypeptide of (ii) and the polypeptide of (iii). In some embodiments, the composition comprises the polypeptide of (v). In preferred embodiments, the composition comprises the polypeptide of (iii); and the polypeptide of (iv).

DsA1, DsA2 and PITP Compositions

In another aspect, the invention provides a composition comprising one or more of (i) a *C. acnes* DsA1 polypeptide as described herein, (ii) a *C. acnes* DsA2 polypeptide as described herein, (iii) a *C. acnes* PITP polypeptide as described herein, (iv) a chimeric *C. acnes* DsA1/DsA2 polypeptide as described herein, (v) a chimeric *C. acnes* DsA1/DsA2/PITP polypeptide as described herein, and (vi) a chimeric DsA1/DsA2/PITP/CAMP2 polypeptide as described herein.

In some embodiments, the composition comprises the *C. acnes* DsA1 polypeptide as described herein, the *C. acnes* DsA2 polypeptide as described herein, and the *C. acnes* PITP polypeptide as described herein.

In some embodiments, the composition comprises the chimeric *C. acnes* DsA1/DsA2 polypeptide as described herein and the *C. acnes* PITP polypeptide as described herein. Typically, the chimeric *C. acnes* DsA1/DsA2 polypeptide comprises an amino acid sequence according to SEQ ID NO: 70, or a sequence that has at least 90%, at least 91%, at least 92%, at least 93%, at least 94%, at least 95%, at least 96%, at least 97%, at least 98%, or at least 99% (e.g. at least 90% or at least 95%) identity thereto, and the *C. acnes* PITP polypeptide comprises the sequence according to SEQ ID NO: 73, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 90% or at least 95%) identity thereto. In some embodiments, the chimeric *C. acnes* DsA1/DsA2 polypeptide comprises the sequence of SEQ ID NO: 70 and the *C. acnes* PITP polypeptide comprises the sequence according to SEQ ID NO: 73. In some embodiments, the chimeric *C. acnes* DsA1/DsA2 polypeptide consists of an amino acid sequence according to SEQ ID NO: 70 and the *C. acnes* PITP polypeptide consists of an amino acid sequence according to SEQ ID NO: 73.

Any one of the compositions of the invention may comprise a combination as described herein of the polypeptides as described herein (e.g. they may be formulated in the same composition). The combinations as described herein of the polypeptides as described herein may alternatively be in two or more separate compositions (e.g. as a combination of compositions for simultaneous, separate or sequential administration. (e.g. in a therapeutic or prophylactic use as described herein)).

A composition of the present disclosure comprising one or more polypeptides of the present disclosure may comprise an adjuvant as described herein. As used herein, an "adjuvant" refers to a substance or vehicle that enhances the immune response to an antigen. Adjuvants can include, without limitation, a suspension of minerals (e.g., alum, aluminum hydroxide, or phosphate) on which antigen is adsorbed; a water-in-oil or oil-in-water emulsion in which antigen solution is emulsified in mineral oil or in water (e.g., Freund's incomplete adjuvant). Sometimes killed mycobacteria is included (e.g., Freund's complete adjuvant) to further enhance antigenicity. Adjuvants can include squalene based oil in water emulsion adjuvants (e.g. AF03 e.g as described in WO2007006939 and U.S. Pat. No. 8,703,095; AS03, e.g. as described in WO1995017209, WO1995017210 and U.S. Pat. Nos. 6,623,739, 7,029,678 and 7,510,698; and MF59, e.g as described in WO1990014837 and U.S. Pat. Nos. 6,299,884 and 6,451, 325). Immuno-stimulatory oligonucleotides (e.g., a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants can also include biological molecules, such as Toll-Like Receptor (TLR) agonists (e.g. AS01, e.g. as described in WO2007068907 and U.S. Pat. Nos. 10,039,823 and 10,143,745; SPA14, e.g. as described in WO2022090359; and LEQ, e.g. as described in WO2023056089) and costimulatory molecules.

In some embodiments, the adjuvant is selected from the group consisting of: Aluminum based adjuvant (e.g. AlOOH), Squalene based oil in water emulsion adjuvants (e.g. AF03, AS03, MF59) and Liposome-based adjuvants comprising a saponin and a TLR4 agonist (e.g. SPA14, LEQ, AS01).

In preferred embodiments, the adjuvant is selected from the group consisting of AlOOH, AF03 and SPA14.

In some embodiments, a composition as described herein is in a frozen liquid form. In some embodiments, a composition as described herein is in a lyophilized form.

Combinations-Nucleic Acid and Polypeptide

Nucleic Acid Combinations

The invention provides combinations comprising two or more nucleic acids of the invention.

CAMP 2 Combinations

In some aspects, the invention provides a combination comprising a nucleic acid comprising a nucleotide sequence encoding a *C. acnes* CAMP2 polypeptide; and one or more of: (i) a nucleic acid comprising a nucleotide sequence encoding a *C. acnes* DsA1 polypeptide; (ii) a nucleic acid comprising a nucleotide sequence encoding a *C. acnes* DsA2 polypeptide; (iii) a nucleic acid comprising a nucleotide sequence encoding a *C. acnes* PITP polypeptide; (iv) a nucleic acid comprising a nucleotide sequence encoding a chimeric *C. acnes* DsA1/DsA2 polypeptide; and (v) a nucleic acid comprising a nucleotide sequence encoding a chimeric *C. acnes* DsA1/DsA2/PITP polypeptide.

In some embodiments, the combination comprises the nucleic acid of (i), the nucleic acid of (ii) and the nucleic acid of (iii). In some embodiments, the composition comprises the nucleic acid of (v). In preferred embodiments, the composition comprises the nucleic acid of (iii); and the nucleic acid of (iv). In some embodiments, the combination comprises the nucleic acid of (v). In preferred embodiments, the combination comprises the nucleic acid of (iii), and the nucleic acid of (iv).

In some embodiments, the combination comprises a nucleic acid comprising a nucleotide sequence encoding a *C. acnes* CAMP2 polypeptide, the nucleic acid in (iii) and the nucleic acid in (iv). In some embodiments, the combination comprises a nucleic acid comprising a nucleotide sequence encoding a *C. acnes* CAMP2 polypeptide and the nucleic acid in (v). In some embodiments, such combinations are provided as a nucleic acid that comprises a nucleotide sequence encoding a chimeric *C. acnes* DsA1/DsA2/PITP/CAMP2 polypeptide as described herein. Typically, the nucleic acid comprising a nucleotide sequence encoding a *C. acnes* CAMP2 polypeptide, the nucleic acid in (iii) and the nucleic acid in (iv) are provided by separate nucleic acid molecules.

Modified CAMP 2 Combinations

In another aspect, the invention provides a combination comprising a nucleic acid as described herein comprising a nucleotide sequence encoding a modified *C. acnes* CAMP2 polypeptide as described herein and one or more of (i) a nucleic acid as described herein comprising a nucleotide sequence encoding a *C. acnes* DsA1 polypeptide, (ii) a nucleic acid as described herein comprising a nucleotide sequence encoding a *C. acnes* DsA2 polypeptide, (iii) a nucleic acid as described herein comprising a nucleotide sequence encoding a *C. acnes* PITP polypeptide, (iv) a nucleic acid as described herein comprising a nucleotide sequence encoding a chimeric *C. acnes* DsA1/DsA2 polypeptide, and (v) a nucleic acid as described herein comprising a nucleotide sequence encoding a chimeric *C. acnes* DsA1/DsA2/PITP polypeptide.

In some embodiments, the combination comprises the nucleic acid of (i), the nucleic acid of (ii) and the nucleic acid of (iii). In some embodiment, the combination comprises the nucleic acid of (v). In preferred embodiments, the combination comprises the nucleic acid of (iii); and the nucleic acid of (iv).

DsA1, DsA2 and PITP Combinations

In one aspect, the invention provides a combination comprising one or more of: (i) a nucleic acid comprising a nucleotide sequence encoding a *C. acnes* DsA1 polypeptide; (ii) a nucleic acid comprising a nucleotide sequence encoding a *C. acnes* DsA2 polypeptide; (iii) a nucleic acid comprising a nucleotide sequence encoding a *C. acnes* PITP polypeptide; (iv) a nucleic acid comprising a nucleotide sequence encoding a chimeric *C. acnes* DsA1/DsA2 polypeptide; and (v) a nucleic acid comprising a nucleotide sequence encoding a chimeric *C. acnes* DsA1/DsA2/PITP polypeptide.

In some embodiments, the combination comprises the nucleic acid as described herein comprising a nucleotide sequence encoding the *C. acnes* DsA1 polypeptide, the nucleic acid as described herein comprising a nucleotide sequence encoding the *C. acnes* DsA2 polypeptide and the nucleic acid as described herein comprising a nucleotide sequence encoding the *C. acnes* PITP polypeptide.

In some embodiments, the combination comprises the nucleic acid as described herein comprising a nucleotide sequence encoding the chimeric *C. acnes* DsA1/DsA2 polypeptide as described herein and the nucleic acid as described herein comprising a nucleotide sequence encoding the *C. acnes* PITP polypeptide as described herein. Typically, the chimeric *C. acnes* DsA1/DsA2 polypeptide comprises an amino acid sequence according to SEQ ID NO: 70, or a sequence that has at least 90%, at least 91%, at least 92%, at least 93%, at least 94%, at least 95%, at least 96%, at least 97%, at least 98%, or at least 99% (e.g. at least 90% or at least 95%) identity thereto, and the *C. acnes* PITP polypeptide comprises the sequence according to SEQ ID NO: 73, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 90% or at least 95%) identity thereto. In some embodiments, the chimeric *C. acnes* DsA1/DsA2 polypeptide comprises the sequence of SEQ ID NO: 70 and the *C. acnes* PITP polypeptide comprises the sequence according to SEQ ID NO: 73. In some embodiments, the chimeric *C. acnes* DsA1/DsA2 polypeptide consists of an amino acid sequence according to SEQ ID NO: 70 and the *C. acnes* PITP polypeptide consists of an amino acid sequence according to SEQ ID NO: 73.

In some embodiments, the nucleic acid comprising a nucleotide sequence encoding the chimeric *C. acnes* DsA1/DsA2 polypeptide comprises a nucleotide sequence according to SEQ ID NO: 179 or a sequence that has at least 75%, at least 80%, at least 85%, at least 90%, at least 91%, at least 92%, at least 93%, at least 94%, at least 95%, at least 96%, at least 97%, at least 98%, or at least 99% (e.g. 85%) identity thereto, and the nucleic acid comprising a nucleotide sequence encoding the *C. acnes* PITP polypeptide comprises a nucleotide sequence according to any one of SEQ ID NO: 182 or a sequence that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% (e.g. 75%) identity thereto.

In some embodiments, the nucleic acid comprising a nucleotide sequence encoding the chimeric *C. acnes* DsA1/DsA2 polypeptide consists of a nucleotide sequence encoding a secretion signal peptide sequence (e.g., a viral secretion signal peptide sequence described herein) and a sequence according to SEQ ID NO: 179 or a sequence that has at least 85% identity thereto, and the nucleic acid comprising a nucleotide sequence encoding the *C. acnes* PITP polypeptide consists of a nucleotide sequence encoding a secretion signal peptide sequence (e.g., a viral secretion signal peptide sequence described herein) and a sequence according to SEQ ID NO: 182, or a sequence that has at least 75% identity thereto.

Polypeptide Combinations

The invention provides combinations comprising two or more polypeptides of the invention.

CAMP 2 Combinations

In some aspects, the invention provides a combination comprising a *C. acnes* CAMP2 polypeptide; and one or more of: (i) a *C. acnes* DsA1 polypeptide as described herein, (ii) a *C. acnes* DsA2 polypeptide as described herein, (iii) a *C. acnes* PITP polypeptide as described herein, (iv) a chimeric *C. acnes* DsA1/DsA2 polypeptide as described herein, and (v) a chimeric *C. acnes* DsA1/DsA2/PITP polypeptide as described herein.

In some embodiments, the combination comprises the polypeptide of (i), the polypeptide of (ii) and the polypeptide of (iii). In some embodiments, the combination comprises the polypeptide of (v). In preferred embodiments, the combination comprises the polypeptide of (iii); and the polypeptide of (iv). In some embodiments, such combinations are provided as a chimeric polypeptide, e.g. a chimeric *C. acnes* DsA1/DsA2/PITP/CAMP2 polypeptide as described herein. Typically, the *C. acnes* CAMP2 polypeptide, the polypeptide of (iii) and the polypeptide of (iv) are provided as separate polypeptides.

Modified CAMP 2 Combinations

In another aspect, the invention provides a combination comprising a modified *C. acnes* CAMP2 polypeptide as described herein and one or more of (i) a *C. acnes* DsA1 polypeptide as described herein. (ii) a *C. acnes* DsA2 polypeptide as described herein, (iii) a *C. acnes* PITP polypeptide as described herein, (iv) a chimeric *C. acnes* DsA1/DsA2 polypeptide as described herein, and (v) a chimeric *C. acnes* DsA1/DsA2/PITP polypeptide as described herein.

In some embodiments, the combination comprises the polypeptide of (i), the polypeptide of (ii) and the polypeptide of (iii). In some embodiments, the combination comprises the polypeptide of (v). In preferred embodiments, the combination comprises the polypeptide of (iii); and the polypeptide of (iv).

DsA1, DsA2 and PITP Compositions

In one aspect, the invention provides a combination comprising one or more of (i) a *C. acnes* DsA1 polypeptide as described herein, (ii) a *C. acnes* DsA2 polypeptide as described herein, (iii) a *C. acnes* PITP polypeptide as described herein, (iv) a chimeric *C. acnes* DsA1/DsA2 polypeptide as described herein, and (v) a chimeric *C. acnes* DsA1/DsA2/PITP polypeptide as described herein.

In some embodiments, the combination comprises the *C. acnes* DsA1 polypeptide as described herein, the *C. acnes* DsA2 polypeptide as described herein, and the *C. acnes* PITP polypeptide as described herein.

In some embodiments, the composition comprises the chimeric *C. acnes* DsA1/DsA2 polypeptide as described herein and the *C. acnes* PITP polypeptide as described herein. Typically, the chimeric *C. acnes* DsA1/DsA2 polypeptide comprises an amino acid sequence according to SEQ ID NO: 70, or a sequence that has at least 90%, at least 91%, at least 92%, at least 93%, at least 94%, at least 95%, at least 96%, at least 97%, at least 98%, or at least 99% (e.g. at least 90% or at least 95%) identity thereto, and the *C. acnes* PITP polypeptide comprises the sequence according to SEQ ID NO: 73, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 90% or at least 95%) identity thereto. In some embodiments, the chimeric *C. acnes* DsA1/DsA2 polypeptide comprises the sequence of SEQ ID NO: 70 and the *C. acnes* PITP polypeptide comprises the sequence according to SEQ ID NO: 73. In some embodiments, the chimeric *C. acnes* DsA1/DsA2 polypeptide consists of an amino acid sequence according to SEQ ID NO: 70 and the *C. acnes* PITP polypeptide consists of an amino acid sequence according to SEQ ID NO: 73.

LNPs

In certain embodiments, the composition of the invention (e.g. the composition comprising a nucleic acid of the invention) further comprises a lipid nanoparticle (LNP). In certain embodiments, the nucleic acid of the invention is encapsulated in the LNP.

The LNPs of the disclosure may comprise four categories of lipids: (i) an ionizable lipid (e.g., a cationic lipid); (ii) a PEGylated lipid; (iii) a cholesterol-based lipid, and (iv) a helper lipid.

A. Ionizable Lipids

An ionizable lipid facilitates mRNA encapsulation and may be a cationic lipid. A cationic lipid affords a positively charged environment at low pH to facilitate efficient encapsulation of the negatively charged mRNA drug substance.

In some embodiments, the cationic lipid is OF-02:

Formula (I)

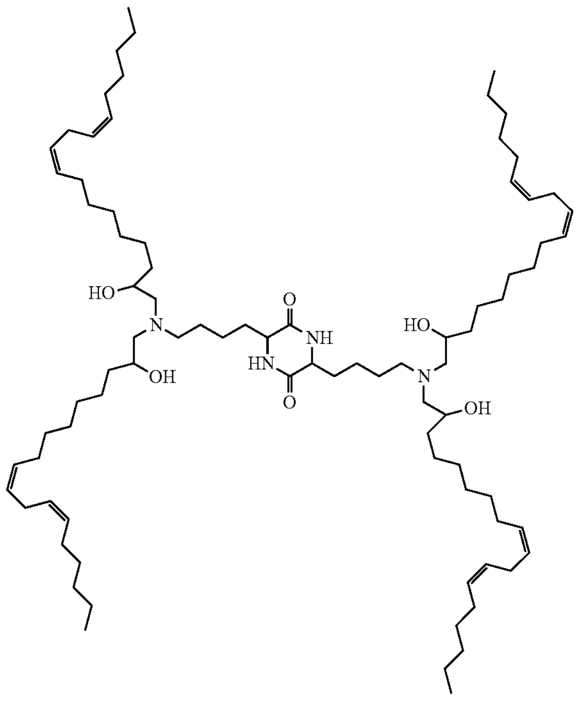

OF-O2

In some embodiments, the cationic lipid is cKK-E10 (Dong et al., PNAS (2014) 111 (11):3955-60; U.S. Pat. No. 9,512,073):

Formula (II)

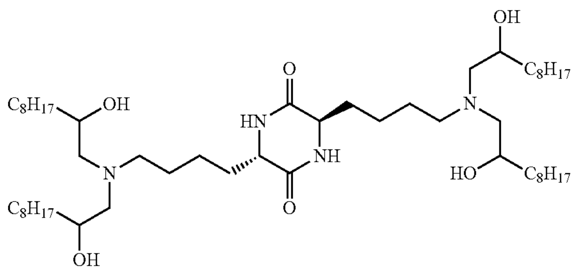

cKK-E10

An exemplary LNP formulation herein, Lipid B, contains cKK-E10.

In some embodiments, the cationic lipid is GL-HEPES-E3-E10-DS-3-E18-1 (2-(4-(2-((3-(Bis((Z)-2-hydroxyoctadec-9-en-1-yl)amino)propyl)disulfaneyl)ethyl)piperazin-1-yl)ethyl 4-(bis(2-hydroxydecyl)amino)butanoate), which is a HEPES-based disulfide cationic lipid with a piperazine core, having the Formula III:

Formula (III)

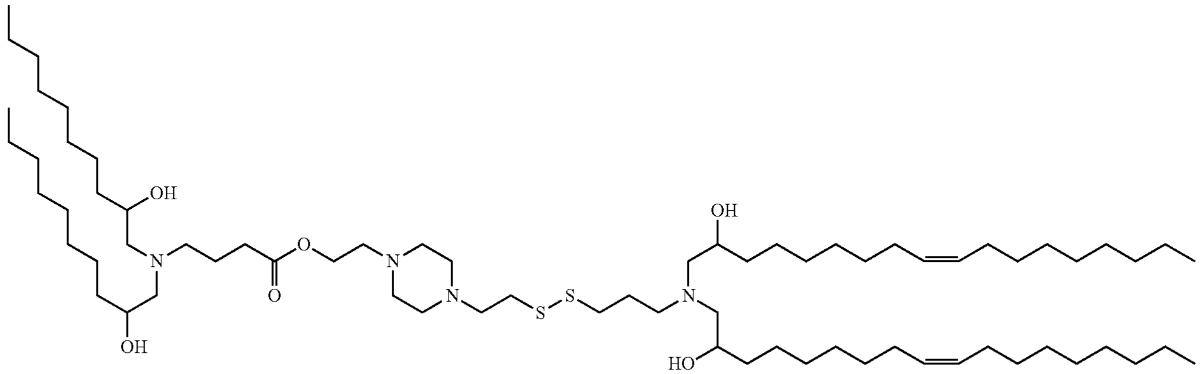

OF-02 is a non-degradable structural analog of OF-Deg-Lin. OF-Deg-Lin contains degradable ester linkages to attach the diketopiperazine core and the doubly-unsaturated tails, whereas OF-02 contains non-degradable 1,2-amino-alcohol linkages to attach the same diketopiperazine core and the doubly-unsaturated tails (Fenton et al., Adv Mater. (2016) 28:2939; U.S. Pat. No. 10,201,618). An exemplary LNP formulation herein, Lipid A, contains OF-2.

An exemplary LNP formulation herein, Lipid C, contains GL-HEPES-E3-E10-DS-3-E18-1. Lipid C has the same composition as Lipid A or Lipid B but for the difference in the cationic lipid.

Typically, the cationic lipid is GL-HEPES-E3-E12-DS-4-E10 (2-(4-(2-((3-(bis(2-hydroxydecyl)amino)butyl)disulfaneyl)ethyl)piperazin-1-yl)ethyl 4-(bis(2-hydroxydodecyl)amino)butanoate), which is a HEPES-based disulfide cationic lipid with a piperazine core, having the Formula IV:

Formula (IV)

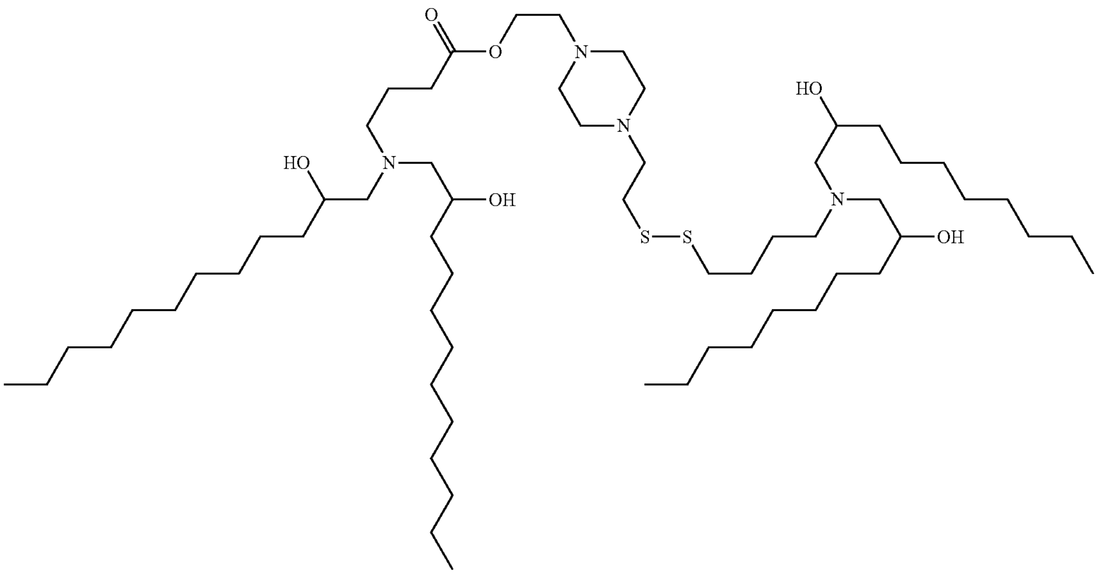

An exemplary LNP formulation herein, Lipid D, contains GL-HEPES-E3-E12-DS-4-E10. Lipid D has the same composition as Lipid A or Lipid B but for the difference in the cationic lipid.

In some embodiments, the cationic lipid is GL-HEPES-E3-E12-DS-3-E14 (2-(4-(2-((3-(Bis(2-hydroxytetradecyl)amino)propyl)disulfaneyl)ethyl)piperazin-1-yl)ethyl 4-(bis(2-hydroxydodecyl)amino)butanoate), which is a HEPES-based disulfide cationic lipid with a piperazine core, having the Formula V:

Formula (V)

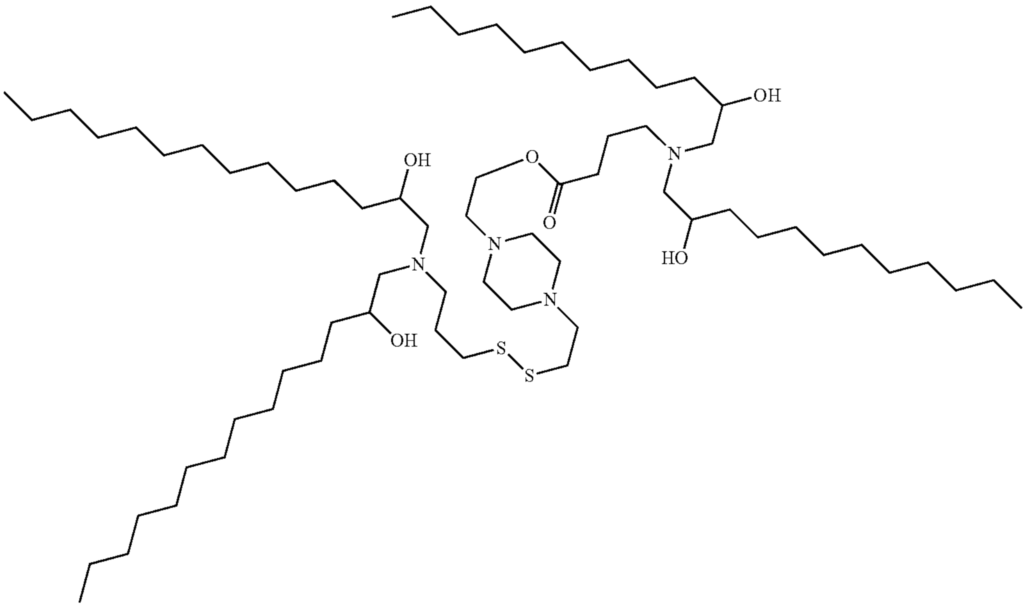

An exemplary LNP formulation herein, Lipid E, contains GL-HEPES-E3-E12-DS-3-E14. Lipid E has the same composition as Lipid A or Lipid B but for the difference in the cationic lipid.

The cationic lipids GL-HEPES-E3-E10-DS-3-E18-1 (III), GL-HEPES-E3-E12-DS-4-E10 (IV), and GL-HEPES-E3-E12-DS-3-E14 (V) can be synthesized according to the general procedure set out in Scheme 1:

Scheme 1: General Synthetic Scheme for Lipids of Formulas (III), (IV), and (V)

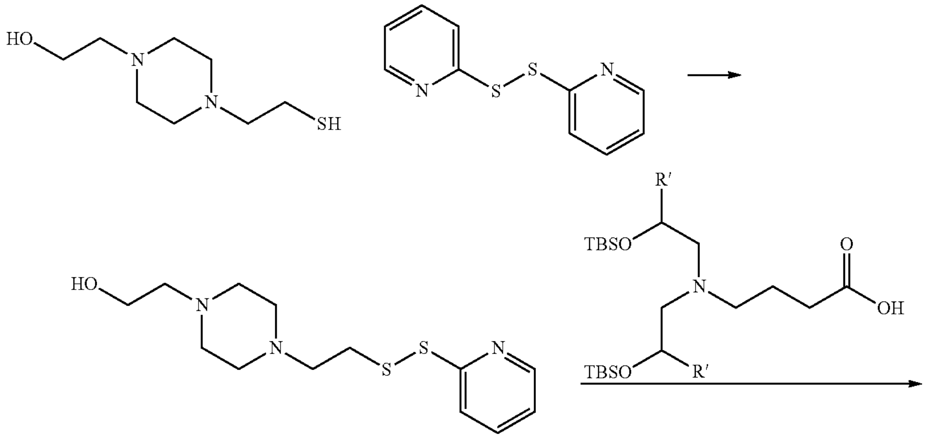

(VI)

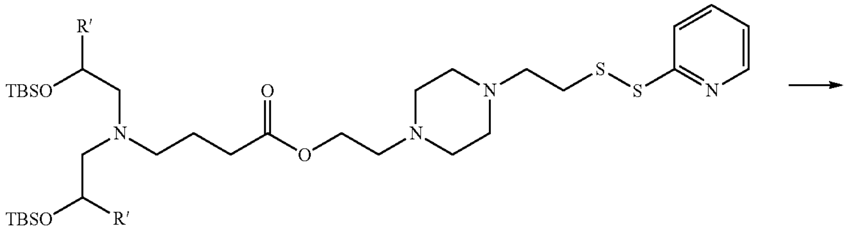

(VII)

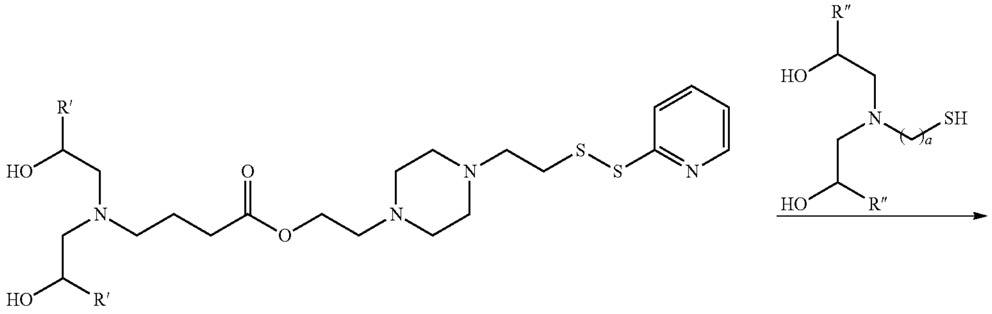

(VIII)

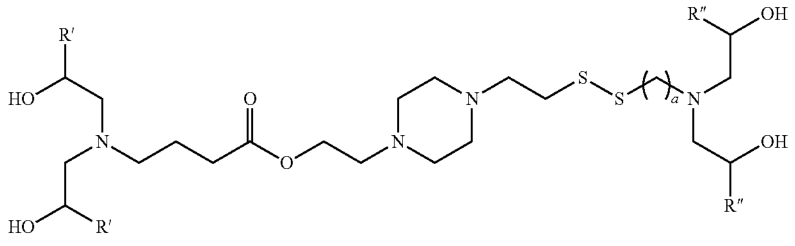

(IX)

In some embodiments, the cationic lipid is MC3, having the Formula VI:

Formula (VI)

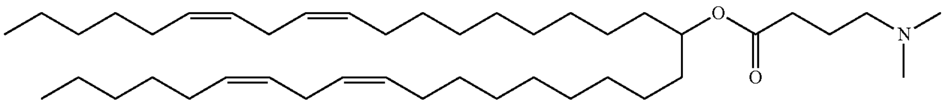

In some embodiments, the cationic lipid is SM-102 (9-heptadecanyl 8-{(2-hydroxyethyl)[6-oxo-6-(undecyloxy)hexyl]amino}octanoate), having the Formula VII:

Formula (VII)

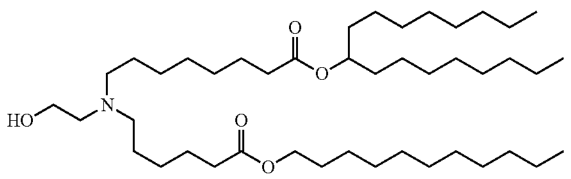

In some embodiments, the cationic lipid is ALC-0315 [(4-hydroxybutyl)azanediyl]di(hexane-6,1-diyl) bis(2-hexyldecanoate), having the Formula VIII:

Formula (VIII)

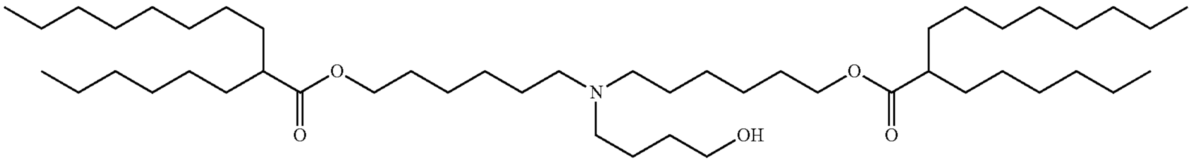

In some embodiments, the cationic lipid is cOrn-EE1, having the Formula IX:

Formula (IX)

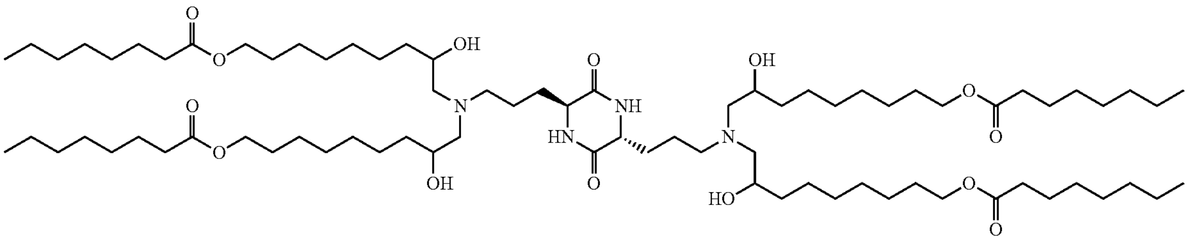

In some embodiments, the cationic lipid may be selected from the group comprising cKK-E10; OF-02; [(6Z,9Z,28Z,31Z)-heptatriaconta-6,9,28,31-tetraen-19-yl] 4-(dimethylamino)butanoate (D-Lin-MC3-DMA); 2,2-dilinoleyl-4-dimethylaminoethyl-[1,3]-dioxolane (dLin-KC2-DMA); 1,2-dilinoleyloxy-N,N-dimethyl-3-aminopropane (dLin-DMA); di((Z)-non-2-en-1-yl) 9-((4-(dimethylamino)butanoyl)oxy)heptadecanedioate (L319); 9-heptadecanyl 8-{(2-hydroxyethyl)[6-oxo-6-(undecyloxy)hexyl]amino}octanoate (SM-102); [(4-hydroxybutyl)azanediyl]di(hexane-6,1-diyl) bis(2-hexyldecanoate) (ALC-0315); [3-(dimethylamino)-2-[(Z)-octadec-9-enoyl]oxypropyl] (Z)-octadec-9-enoate (DODAP); 2,5-bis(3-aminopropylamino)-N-[2-[di(heptadecyl)amino]-2-oxoethyl]pentanamide (DOGS); [(3S,8S,9S,10R,13R,14S,17R)-10,13-dimethyl-17-[(2R)-6-methylheptan-2-yl]-2,3,4,7,8,9,11,12,14,15,16,17-dodecahydro-1H-cyclopenta[a]phenanthren-3-yl]N-[2-(dimethylamino)ethyl]carbamate (DC-Chol); tetrakis(8-methylnonyl) 3,3',3",3"'-(((methylazanediyl) bis(propane-3,1 diyl))bis(azanetriyl))tetrapropionate (306Oi10): decyl (2-(dioctylammonio)ethyl)phosphate (9A1P9); ethyl 5,5-di((Z)-heptadec-8-en-1-yl)-1-(3-(pyrrolidin-1-yl)propyl)-2,5-dihydro-1H-imidazole-2-carboxylate (A2-Iso5-2DC18); bis(2-(dodecyldisulfanyl)ethyl) 3,3'-((3-methyl-9-oxo-10-oxa-13,14-dithia-3,6-diazahexacosyl)azanediyl)dipropionate (BAME-O16B); 1,1'-((2-(4-(2-((2-(bis(2-hydroxydodecyl)amino)ethyl) (2-hydroxydodecyl)amino)ethyl) piperazin-1-yl)ethyl)azanediyl) bis(dodecan-2-ol) (C12-200); 3,6-bis(4-(bis(2-hydroxydodecyl)amino) butyl)piperazine-2,5-dione (cKK-E12); hexa(octan-3-yl) 9,9',9",9"',9"",9""'-((((benzene-1,3,5-tricarbonyl)yris(azanediyl)) tris (propane-3,1-diyl)) tris(azanetriyl))hexanonanoate (FTT5); (((3,6-dioxopiperazine-2,5-diyl)bis(butane-4,1-diyl))bis(azanetriyl))tetrakis(ethane-2,1-diyl) (9Z,9'Z,9"Z,9"'Z,12Z,12'Z,12"Z,12"'Z)-tetrakis (octadeca-9,12-dienoate) (OF-Deg-Lin): TT3; N1,N3,N5-tris(3-(didodecylamino)propyl)benzene-1,3,5-tricarboxamide: N1-[2-((1S)-1-[(3-aminopropyl)amino]-4-[di(3-aminopropyl)amino]butylcarboxamido)ethyl]-3,4-di[oleyloxy]-benzamide (MVL5); heptadecan-9-yl 8-((2-hydroxyethyl)(8-(nonyloxy)-8-oxooctyl)amino)octanoate (Lipid 5); GL-HEPES-E3-E10-DS-3-E18-1; GL-HEPES-E3-E12-DS-4-E10; GL-HEPES-E3-E12-DS-3-E14; and combinations thereof.

In some embodiments, the cationic lipid is IM-001, having the Formula X (EP23306049.0):

Formula (X)

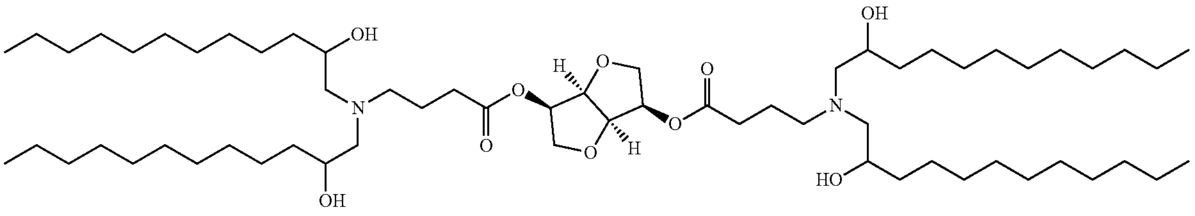

An exemplary LNP formulation herein, Lipid F, contains IM-001. Lipid F has the same composition as Lipid A or Lipid B but for the difference in the cationic lipid.

The cationic lipid IM-001 (X) can be synthesized according to the general procedure set out in Scheme 2:

Scheme 2: General Synthetic Scheme for Lipid of Formula (X)

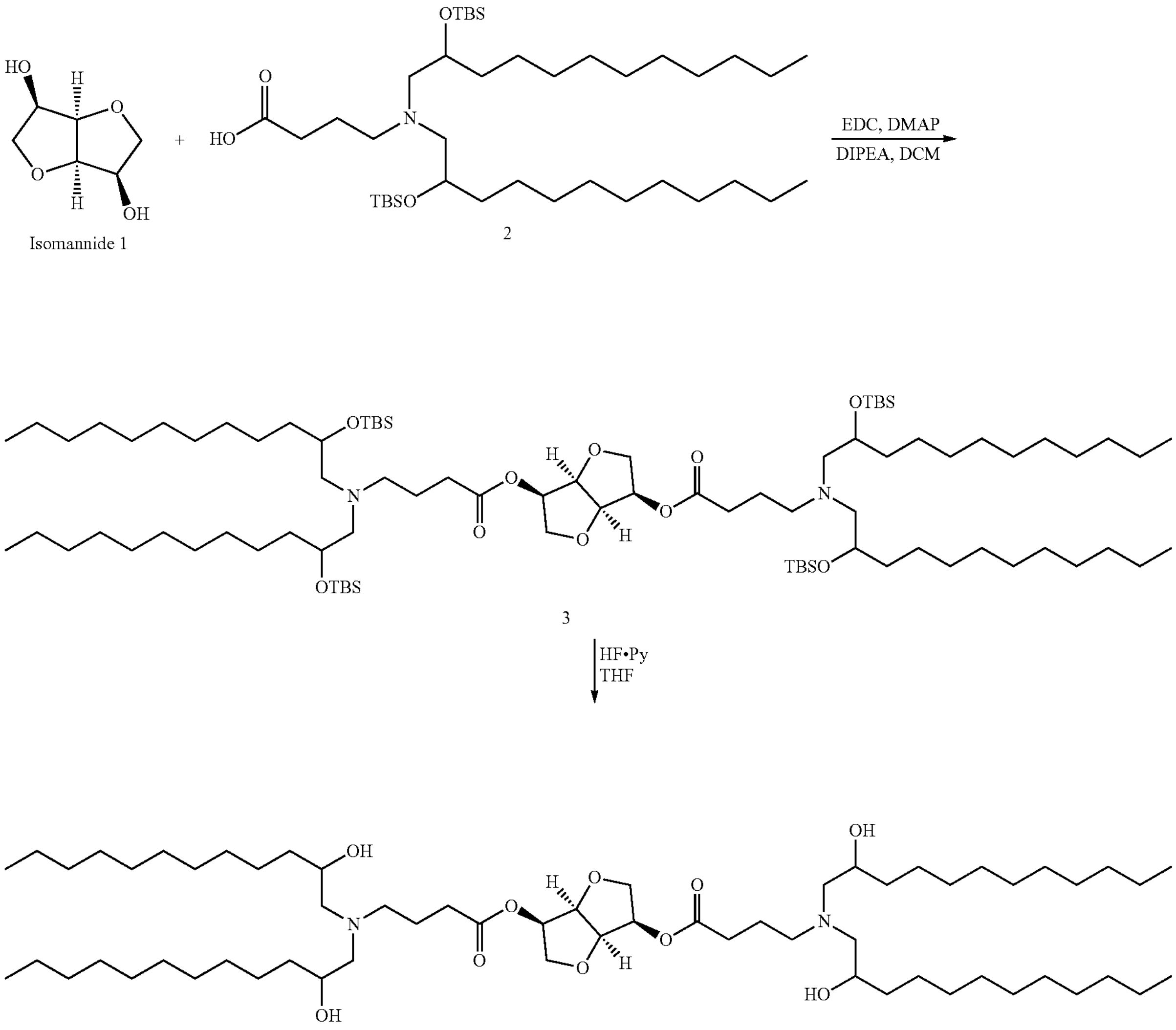

Isomannide 1

2

3

IM-001

Scheme 2 may be performed as described in Example 12.

In some embodiments, the cationic lipid is IS-001, having the Formula XI (EP23306049.0):

Mater. 28:2939. 2016); U.S. Pat. Nos. 9,512,073; and 10,201,618, each of which is incorporated herein by reference.

Formula (XI)

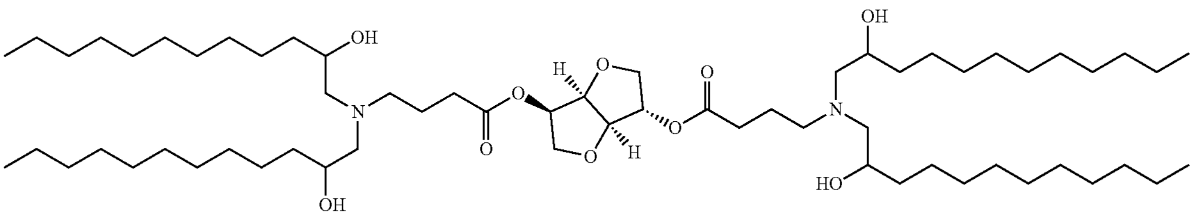

An exemplary LNP formulation herein, Lipid G, contains IS-001. Lipid G has the same composition as Lipid A or Lipid B but for the difference in the cationic lipid.

The cationic lipid IS-001 (XI) can be synthesized according to the general procedure set out in Scheme 3:

B. PEGylated Lipids

The PEGylated lipid component provides control over particle size and stability of the nanoparticle. The addition of such components may prevent complex aggregation and provide a means for increasing circulation lifetime and Scheme 3: General Synthetic Scheme for Lipid of Formula (XI)

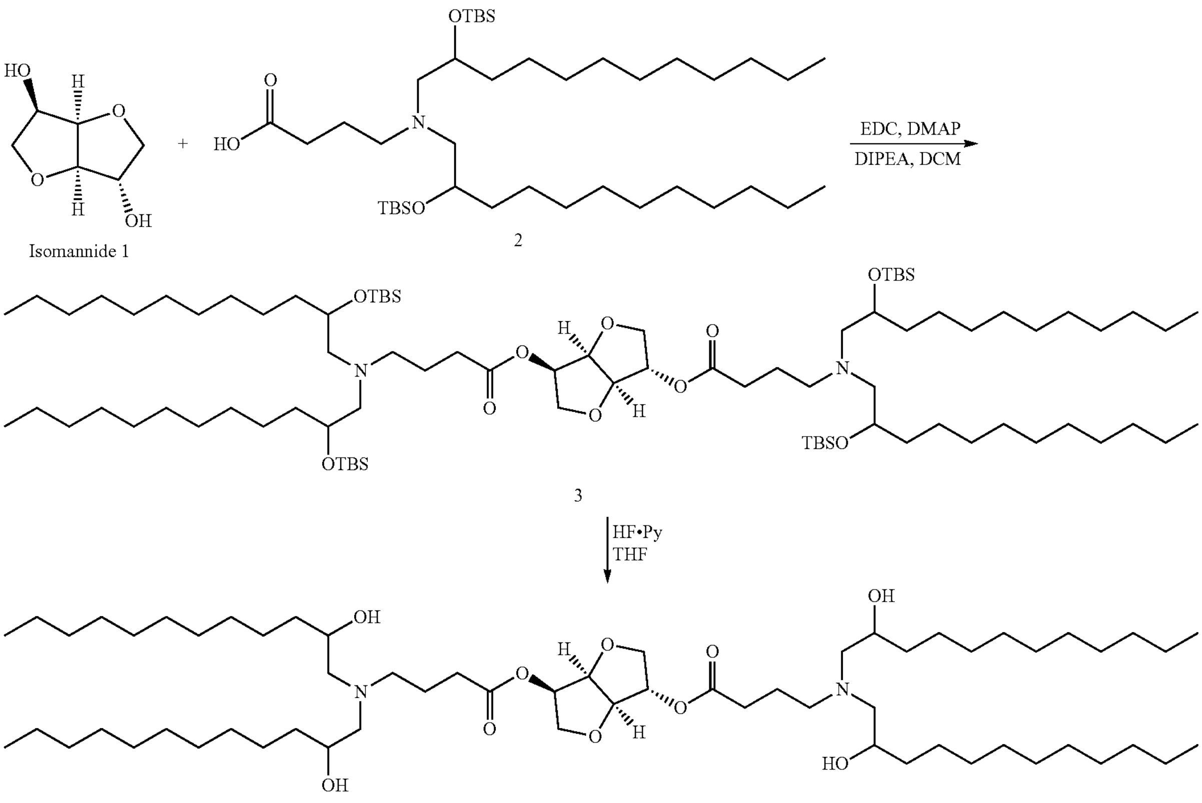

Isomannide 1

2

3

IS-001

Scheme 3 may be performed as described in Example 14.

In some embodiments, the cationic lipid is biodegradable.

In some embodiments, the cationic lipid is not biodegradable.

In some embodiments, the cationic lipid is cleavable.

In some embodiments, the cationic lipid is not cleavable.

Cationic lipids are described in further detail in Dong et al. (PNAS. 111 (11): 3955-60. 2014); Fenton et al. (Adv increasing the delivery of the lipid-nucleic acid pharmaceutical composition to target tissues (Klibanov et al. FEBS Letters 268 (1): 235-7. 1990). These components may be selected to rapidly exchange out of the pharmaceutical composition in vivo (see, e.g., U.S. Pat. No. 5,885,613).

Contemplated PEGylated lipids include, but are not limited to, a polyethylene glycol (PEG) chain of up to 5 kDa in length covalently attached to a lipid with alkyl chain(s) of $C_6$-$C_{20}$ (e.g., $C_8$, $C_{10}$, $C_{12}$, $C_{14}$, $C_{16}$, or $C_{18}$) length, such as a derivatized ceramide (e.g., N-octanoyl-sphingosine-1-[succinyl(methoxypolyethylene glycol)] (C8 PEG ceramide)). In some embodiments, the PEGylated lipid is 1,2-dimyristoyl-rac-glycero-3-methoxypolyethylene glycol (DMG-PEG); 1,2-distearoyl-sn-glycero-3-phosphoethanolamine-polyethylene glycol (DSPE-PEG); 1,2-dilauroyl-sn-glycero-3-phosphoethanolamine-polyethylene glycol (DLPE-PEG); or 1,2-distearoyl-rac-glycero-polyethelene glycol (DSG-PEG), PEG-DAG; PEG-PE; PEG-S-DAG; PEG-S-DMG; PEG-cer; a PEG-dialkyoxypropylcarbamate; 2-[(polyethylene glycol)-2000]-N,N-ditetradecylacetamide (ALC-0159); and combinations thereof.

In certain embodiments, the PEG has a high molecular weight, e.g., 2000-2400 g/mol. In certain embodiments, the PEG is PEG2000 (or PEG-2K). In certain embodiments, the PEGylated lipid herein is DMG-PEG2000, DSPE-PEG2000, DLPE-PEG2000, DSG-PEG2000, C8 PEG2000, or ALC-0159 (2-[(polyethylene glycol)-2000]-N,N-ditetradecylacetamide). In certain embodiments, the PEGylated lipid herein is DMG-PEG2000.

C. Cholesterol-Based Lipids

The cholesterol component provides stability to the lipid bilayer structure within the nanoparticle. In some embodiments, the LNPs comprise one or more cholesterol-based lipids. Suitable cholesterol-based lipids include, for example: DC-Choi (N,N-dimethyl-N-ethylcarboxamidocholesterol), 1,4-bis(3-N-oleylamino-propyl)piperazine (Gao et al., Biochem Biophys Res Comm. (1991) 179:280; Wolf et al., BioTechniques (1997) 23:139; U.S. Pat. No. 5,744,335), imidazole cholesterol ester ("ICE"; WO2011/068810), sitosterol (22,23-dihydrostigmasterol), β-sitosterol, sitostanol, fucosterol, stigmasterol (stigmasta-5,22-dien-3-ol), ergosterol; desmosterol (3β-hydroxy-5,24-cholestadiene); lanosterol (8,24-lanostadien-3b-ol); 7-dehydrocholesterol (Δ5,7-cholesterol); dihydrolanosterol (24,25-dihydrolanosterol); zymosterol (5α-cholesta-8,24-dien-3β-ol); lathosterol (5α-cholest-7-en-3β-ol); diosgenin ((3β,25R)-spirost-5-en-3-ol); campesterol (campest-5-en-3β-ol); campestanol (5α-campestan-3b-ol); 24-methylene cholesterol (5,24(28)-cholestadien-24-methylen-3β-ol); cholesteryl margarate (cholest-5-en-3β-yl heptadecanoate); cholesteryl oleate; cholesteryl stearate and other modified forms of cholesterol. In some embodiments, the cholesterol-based lipid used in the LNPs is cholesterol.

D. Helper Lipids

A helper lipid enhances the structural stability of the LNP and helps the LNP in endosome escape. It improves uptake and release of the mRNA drug payload. In some embodiments, the helper lipid is a zwitterionic lipid, which has fusogenic properties for enhancing uptake and release of the drug pay load. Examples of helper lipids are 1,2-dioleoyl-SN-glycero-3-phosphoethanolamine (DOPE); 1,2-distearoyl-sn-glycero-3-phosphocholine (DSPC); 1,2-dioleoyl-sn-glycero-3-phospho-L-serine (DOPS); 1,2-dielaidoyl-sn-glycero-3-phosphoethanolamine (DEPE); and 1,2-dioleoyl-sn-glycero-3-phosphocholine (DPOC), dipalmitoylphosphatidylcholine (DPPC), DMPC, 1,2-dilauroyl-sn-glycero-3-phosphocholine (DLPC), 1,2-Distearoylphosphatidylethanolamine (DSPE), and 1,2-dilauroyl-sn-glycero-3-phosphoethanolamine (DLPE).

Other exemplary helper lipids are dioleoylphosphatidylcholine (DOPC), dioleoylphosphatidylglycerol (DOPG), dipalmitoylphosphatidylglycerol (DPPG), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), phosphatidylserine, sphingolipids, sphingomyelins, ceramides, cerebrosides, gangliosides, 16-O-monomethyl PE, 16-O-dimethyl PE, 18-1-trans PE, 1-stearoyl-2-oleoyl-phosphatidyethanolamine (SOPE), or a combination thereof. In certain embodiments, the helper lipid is DOPE. In certain embodiments, the helper lipid is DSPC.

In various embodiments, the present LNPs comprise (i) a cationic lipid selected from OF-02, cKK-E10, GL-HEPES-E3-E10-DS-3-E18-1, GL-HEPES-E3-E12-DS-4-E10, GL-HEPES-E3-E12-DS-3-E14, IM-001 or IS-001; (ii) DMG-PEG2000; (iii) cholesterol; and (iv) DOPE.

In other embodiments, the present LNPs comprise (i) SM-102; (ii) DMG-PEG2000; (iii) cholesterol; and (iv) DSPC.

In yet other embodiments, the present LNPs comprise (i) ALC-0315; (ii) ALC-0159; (iii) cholesterol; and (iv) DSPC.

E. Molar Ratios of the Lipid Components

The molar ratios of the above components are important for the LNPs' effectiveness in delivering mRNA. The molar ratio of the cationic lipid, the PEGylated lipid, the cholesterol-based lipid, and the helper lipid is A:B:C:D, where A+B+C+D=100%. In some embodiments, the molar ratio of the cationic lipid in the LNPs relative to the total lipids (i.e., A) is 35-55%, such as 35-50% (e.g., 38-42% such as 40%, or 45-50%). In some embodiments, the molar ratio of the PEGylated lipid component relative to the total lipids (i.e., B) is 0.25-2.75% (e.g., 1-2% such as 1.5%). In some embodiments, the molar ratio of the cholesterol-based lipid relative to the total lipids (i.e., C) is 20-50% (e.g., 27-30% such as 28.5%, or 38-43%). In some embodiments, the molar ratio of the helper lipid relative to the total lipids (i.e., D) is 5-35% (e.g., 28-32% such as 30%, or 8-12%, such as 10%). In some embodiments, the (PEGylated lipid+cholesterol) components have the same molar amount as the helper lipid. In some embodiments, the LNPs contain a molar ratio of the cationic lipid to the helper lipid that is more than 1.

In certain embodiments, the LNP of the disclosure comprises:

a cationic lipid at a molar ratio of 35% to 55% or 40% to 50% (e.g., a cationic lipid at a molar ratio of 35%, 36%, 37%, 38%, 39%, 40%, 41% 42%, 43%, 44%, 45%, 46%, 47%, 48%, 49%, 50%, 51%, 52%, 53%, 54%, or 55%);

a polyethylene glycol (PEG) conjugated (PEGylated) lipid at a molar ratio of 0.25% to 2.75% or 1.00% to 2.00% (e.g., a PEGylated lipid at a molar ratio of 0.25%, 0.50%, 0.75%, 1.00%, 1.25%, 1.50%, 1.75%, 2.00%, 2.25%, 2.50%, or 2.75%);

a cholesterol-based lipid at a molar ratio of 20% to 50%, 25% to 45%, or 28.5% to 43% (e.g., a cholesterol-based lipid at a molar ratio of 20%, 21%, 22%, 23%, 24%, 25%, 26%, 27%, 28%, 29%, 30%, 31%, 32%, 33%, 34%, 35%, 36%, 37%, 38%, 39%, 40%, 41% 42%, 43%, 44%, 45%, 46%, 47%, 48%, 49%, or 50%); and a helper lipid at a molar ratio of 5% to 35%, 8% to 30%, or 10% to 30% (e.g., a helper lipid at a molar ratio of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%).

wherein all of the molar ratios are relative to the total lipid content of the LNP.

In certain embodiments, the LNP comprises: a cationic lipid at a molar ratio of 40%; a PEGylated lipid at a molar ratio of 1.5%; a cholesterol-based lipid at a molar ratio of 28.5%; and a helper lipid at a molar ratio of 30%.

In certain embodiments, the LNP of the disclosure comprises: a cationic lipid at a molar ratio of 45 to 50%; a PEGylated lipid at a molar ratio of 1.5 to 1.7%; a cholesterol-based lipid at a molar ratio of 38 to 43%; and a helper lipid at a molar ratio of 9 to 10%.

In certain embodiments, the PEGylated lipid is dimyristoyl-PEG2000 (DMG-PEG2000).

In various embodiments, the cholesterol-based lipid is cholesterol.

In some embodiments, the helper lipid is 1,2-dioleoyl-SN-glycero-3-phosphoethanolamine (DOPE).

In certain embodiments, the LNP comprises: OF-02 at a molar ratio of 35% to 55%; DMG-PEG2000 at a molar ratio of 0.25% to 2.75%; cholesterol at a molar ratio of 20% to 50%; and DOPE at a molar ratio of 5% to 35%.

In certain embodiments, the LNP comprises: cKK-E10 at a molar ratio of 35% to 55%; DMG-PEG2000 at a molar ratio of 0.25% to 2.75%; cholesterol at a molar ratio of 20% to 50%; and DOPE at a molar ratio of 5% to 35%.

In certain embodiments, the LNP comprises: GL-HEPES-E3-E10-DS-3-E18-1 at a molar ratio of 35% to 55%: DMG-PEG2000 at a molar ratio of 0.25% to 2.75%; cholesterol at a molar ratio of 20% to 50%; and DOPE at a molar ratio of 5% to 35%.

In certain embodiments, the LNP comprises: GL-HEPES-E3-E12-DS-4-E10 at a molar ratio of 35% to 55%: DMG-PEG2000 at a molar ratio of 0.25% to 2.75%; cholesterol at a molar ratio of 20% to 50%; and DOPE at a molar ratio of 5% to 35%.

In certain embodiments, the LNP comprises: GL-HEPES-E3-E12-DS-3-E14 at a molar ratio of 35% to 55%; DMG-PEG2000 at a molar ratio of 0.25% to 2.75%; cholesterol at a molar ratio of 20% to 50%; and DOPE at a molar ratio of 5% to 35%.

In certain embodiments, the LNP comprises: SM-102 at a molar ratio of 35% to 55%; DMG-PEG2000 at a molar ratio of 0.25% to 2.75%; cholesterol at a molar ratio of 20% to 50%; and DSPC at a molar ratio of 5% to 35%.

In certain embodiments, the LNP comprises: ALC-0315 at a molar ratio of 35% to 55%; ALC-0159 at a molar ratio of 0.25% to 2.75%; cholesterol at a molar ratio of 20% to 50%; and DSPC at a molar ratio of 5% to 35%.

In certain embodiments, the LNP comprises: OF-02 at a molar ratio of 40%; DMG-PEG2000 at a molar ratio of 1.5%; cholesterol at a molar ratio of 28.5%; and DOPE at a molar ratio of 30%. This LNP formulation is designated "Lipid A" herein.

In certain embodiments, the LNP comprises: cKK-E10 at a molar ratio of 40%; DMG-PEG2000 at a molar ratio of 1.5%; cholesterol at a molar ratio of 28.5%; and DOPE at a molar ratio of 30%. This LNP formulation is designated "Lipid B" herein.

In certain embodiments, the LNP comprises: GL-HEPES-E3-E10-DS-3-E18-1 at a molar ratio of 40%; DMG-PEG2000 at a molar ratio of 1.5%; cholesterol at a molar ratio of 28.5%; and DOPE at a molar ratio of 30%. This LNP formulation is designated "Lipid C" herein.

Typically, the LNP comprises: GL-HEPES-E3-E12-DS-4-E10 at a molar ratio of 40%; DMG-PEG2000 at a molar ratio of 1.5%; cholesterol at a molar ratio of 28.5%; and DOPE at a molar ratio of 30%. This LNP formulation is designated "Lipid D" herein.

In certain embodiments, the LNP comprises; GL-HEPES-E3-E12-DS-3-E14 at a molar ratio of 40%; DMG-PEG2000 at a molar ratio of 1.5%; cholesterol at a molar ratio of 28.5%; and DOPE at a molar ratio of 30%. This LNP formulation is designated "Lipid E" herein.

In certain embodiments, the LNP comprises: IM-001 at a molar ratio of 40%; DMG-PEG2000 at a molar ratio of 1.5%; cholesterol at a molar ratio of 28.5%; and DOPE at a molar ratio of 30%. This LNP formulation is designated "Lipid F" herein.

In certain embodiments, the LNP comprises: IS-001 at a molar ratio of 40%; DMG-PEG2000 at a molar ratio of 1.5%; cholesterol at a molar ratio of 28.5%; and DOPE at a molar ratio of 30%. This LNP formulation is designated "Lipid G" herein.

In certain embodiments, the LNP comprises: 9-heptadecanyl 8-{(2-hydroxyethyl) [6-oxo-6-(undecyloxy)hexyl] amino}octanoate (SM-102) at a molar ratio of 50%; 1,2-distearoyl-sn-glycero-3-phosphocholine (DSPC) at a molar ratio of 10%; cholesterol at a molar ratio of 38.5%; and 1,2-dimyristoyl-rac-glycero-3-methoxypolyethylene glycol-2000 (DMG-PEG2000) at a molar ratio of 1.5%.

In certain embodiments, the LNP comprises: (4-hydroxybutyl)azanediyl]di(hexane-6,1-diyl)bis(2-hexyldecanoate) (ALC-0315) at a molar ratio of 46.3%; 1,2-distearoyl-sn-glycero-3-phosphocholine (DSPC) at a molar ratio of 9.4%; cholesterol at a molar ratio of 42.7%; and 2-[(polyethylene glycol)-2000]-N,N-ditetradecylacetamide (ALC-0159) at a molar ratio of 1.6%.

In certain embodiments, the LNP comprises: (4-hydroxybutyl)azanediyl]di(hexane-6,1-diyl) bis(2-hexyldecanoate) (ALC-0315) at a molar ratio of 47.4%; 1,2-distearoyl-sn-glycero-3-phosphocholine (DSPC) at a molar ratio of 10%; cholesterol at a molar ratio of 40.9%; and 2-[(polyethylene glycol)-2000]-N,N-ditetradecylacetamide (ALC-0159) at a molar ratio of 1.7%.

To calculate the actual amount of each lipid to be put into an LNP formulation, the molar amount of the cationic lipid is first determined based on a desired N/P ratio, where N is the number of nitrogen atoms in the cationic lipid and P is the number of phosphate groups in the mRNA to be transported by the LNP. Next, the molar amount of each of the other lipids is calculated based on the molar amount of the cationic lipid and the molar ratio selected. These molar amounts are then converted to weights using the molecular weight of each lipid.

F. Nucleic Acids within LNPs

The LNP compositions described herein may comprise a nucleic acid (e.g., a mRNA) of the present invention.

Where desired, the LNP may be multi-valent. In some embodiments, the LNP may carry nucleic acids, such as mRNAs, that encode more than one polypeptide (antigen), such as two, three, four, five, or six polypeptides (antigens). For example, the LNP may carry multiple nucleic acids of the present invention (e.g., mRNA), each encoding a different polypeptide described herein; or carry a polycistronic mRNA that can be translated into more than one polypeptide described herein (e.g., each antigen-coding sequence is separated by a nucleotide linker encoding a self-cleaving peptide such as a 2A peptide). An LNP carrying different nucleic acids (e.g., mRNA) typically comprises (encapsulates) multiple copies of each nucleic acid. For example, an LNP carrying or encapsulating two different nucleic acids typically carries multiple copies of each of the two different nucleic acids.

Typically, two or more (e.g., two or three) nucleic acids (e.g., mRNAs) as described herein encoding different polypeptides as described herein are co-encapsulated in the same LNP. For example, the LNPs described herein may co-encapsulate a nucleic acid (e.g. mRNA) encoding a chimeric *C. acnes* DsA1/DsA2 polypeptide and a nucleic acid (e.g. mRNA) encoding a *C. acnes* PITP polypeptide. The LNPs described herein may co-encapsulate a nucleic acid (e.g. mRNA) encoding a chimeric *C. acnes* DsA1/DsA2 polypeptide and a nucleic acid (e.g. mRNA) encoding a modified *C. acnes* CAMP2 polypeptide (or a *C. acnes* CAMP2 polypeptide). The LNPs described herein may co-encapsulate a nucleic acid (e.g. mRNA) encoding a *C. acnes* PITP polypeptide and a nucleic acid (e.g. mRNA) encoding a modified *C. acnes* CAMP2 polypeptide (or a *C. acnes* CAMP2 polypeptide). Any two nucleic acids (e.g., two mRNAs) as described herein may be present in a weight ratio of 1:1.

The LNPs described herein may co-encapsulate (i) a nucleic acid (e.g. mRNA) encoding a chimeric *C. acnes* DsA1/DsA2 polypeptide as described herein, (ii) a nucleic acid (e.g. mRNA) encoding a *C. acnes* PITP polypeptide as described herein; and (iii) a nucleic acid (e.g. mRNA) encoding a modified C. *acnes* CAMP2 polypeptide as described herein (or a *C. acnes* CAMP2 polypeptide). Three nucleic acids (e.g., three mRNAs) as described herein may be present in a weight ratio of 1:1:1.

The LNP is as described herein (e.g. Lipid D).

Alternatively, any two or more (e.g., three) nucleic acids (e.g., mRNAs) encoding different polypeptides as described herein are encapsulated in separate LNPs. In some embodiments, a single LNP formulation may comprise multiple kinds (e.g., two, three, four, five, six, seven, eight, nine, ten, or more) of LNPs, each kind carrying a different nucleic acid (e.g., mRNA).

When the nucleic acid is mRNA, the mRNA may be unmodified (i.e., containing only natural ribonucleotides A, U, C, and/or G linked by phosphodiester bonds), or chemically modified (e.g., including nucleotide analogs such as pseudouridines (e.g., N-1-methyl pseudouridine), 2'-fluoro ribonucleotides, and 2'-methoxy ribonucleotides, and/or phosphorothioate bonds). The mRNA molecule may comprise a 5' cap and a poly A tail.

G. Buffer and Other Components

To stabilize the nucleic acid and/or LNPs (e.g., to prolong the shelf-life of the vaccine product), to facilitate administration of the LNP pharmaceutical composition, and/or to enhance in vivo expression of the nucleic acid, the nucleic acid and/or LNP can be formulated in combination with one or more carriers, targeting ligands, stabilizing reagents (e.g., preservatives and antioxidants), and/or other pharmaceutically acceptable excipients. Examples of such excipients are parabens, thimerosal, thiomersal, chlorobutanol, benzalkonium chloride, and chelators (e.g., EDTA).

The LNP compositions of the present disclosure can be provided as a frozen liquid form or a lyophilized form. A variety of cryoprotectants may be used, including, without limitations, sucrose, trehalose, glucose, mannitol, mannose, dextrose, and the like. The cryoprotectant may constitute 5-30% (w/v) of the LNP composition. In some embodiments, the LNP composition comprises trehalose, e.g., at 5-30% (e.g., 10%) (w/v). Once formulated with the cryoprotectant, the LNP compositions may be frozen (or lyophilized and cryopreserved) at −20° C., to −80° C.

The LNP compositions may be provided to a patient in an aqueous buffered solution-thawed if previously frozen, or if previously lyophilized, reconstituted in an aqueous buffered solution at bedside. The buffered solution preferably is isotonic and suitable for e.g., intramuscular or intradermal injection. In some embodiments, the buffered solution is a phosphate-buffered saline (PBS).

Nucleic Acids

A nucleic acid of the invention may be RNA or DNA. The nucleic acids of the invention may be single or double-stranded. In certain embodiments, the nucleic acid is RNA, e.g. mRNA.

mRNA

In some embodiments, the nucleic acids of the present invention are messenger RNAs (mRNAs). mRNAs can be modified or unmodified, mRNAs may contain one or more coding and non-coding regions. A coding region is alternatively referred to as an open reading frame (ORF). Non-coding regions in an mRNA include the 5' cap, 5' untranslated region (UTR), 3' UTR, and a poly A tail. An mRNA can be purified from natural sources, produced using recombinant expression systems (e.g., in vitro transcription) and optionally purified, or chemically synthesised.

In certain embodiments, the mRNA comprises an ORF encoding an antigen of interest. In certain embodiments, the RNA (e.g., mRNA) further comprises at least one 5' UTR, 3' UTR, a poly(A) tail, and/or a 5' cap. In some embodiments, the mRNA comprises (i) a 5' cap as defined herein; (ii) a 5' untranslated region (UTR) as defined herein; (iii) a protein coding region; (iv) a 3' UTR as defined herein; and (v) a polyA tail. Typically, the 3' end of (i) bonds directly to the 5' end of (ii) via a 3' to 5' phosphodiester linkage: the 3' end of (ii) bonds directly to the 5' end of (iii) via a 3 to 5' phosphodiester linkage; the 3' end of (iii) bonds directly to the 5' end of (iv) via a 3' to 5' phosphodiester linkage; and the 3' end of (iv) bonds directly to the 5' end of (v) via a 3' to 5' phosphodiester linkage.

In certain embodiments, the mRNA comprises at least one, at least two, at least three or more stop codon(s), wherein the stop codon(s) can be selected from UAA, UGA and UAG, and wherein the at least two, at least three or more stop codon(s) can be identical or different. Typically, the at least one stop codon comprises UAA or UGA (e.g. UAA). Typically, the at least two stop codons comprise at least two identical stop codons, such as UAA or UGA (e.g. UAAUAA or UGAUGA) or at least two different stop codons, which may in particular be selected from UAA and UGA (e.g. UGAUAA). Typically, the at least three stop codons comprise UAA, UGA and UAG (e.g. UGAUAAUAG).

An mRNA sequence is presented in the 5' to 3' direction unless otherwise indicated.

5' Cap

An mRNA 5' cap can provide resistance to nucleases found in most eukaryotic cells and promote translation efficiency. Several types of 5' caps are known. A 7-methylguanosine cap (also referred to as “m7G” or “Cap-0”), comprises a guanosine that is linked through a 5'-5'-triphosphate bond to the first transcribed nucleotide.

A 5' cap is typically added as follows: first, an RNA terminal phosphatase removes one of the terminal phosphate groups from the 5' nucleotide, leaving two terminal phosphates: guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5)ppp, (5'(A, G(5')ppp(5')A, and G(5')ppp(5')G. Additional cap structures are described in U.S. Publication No. US 2016/0032356 and U.S. Publication No. US 2018/0125989, which are incorporated herein by reference.

5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5)G (the ARCA cap); G(5')ppp (5')A; G(5')ppp(5')G; m7G(5')ppp(5')A; m7G(5')ppp(5')G; m7G(5')ppp(5')(2'oMeA)pG; m7G(5')ppp(5')(2'oMeA)pU; m7G(5')ppp(5')(2'oMeG)pG (New England BioLabs, Ipswich, MA; TriLink Biotechnologies). 5'-capping of modified RNA may be completed post-transcriptionally using a vaccinia virus capping enzyme to generate the Cap 0 structure: m7G(5')ppp(5')G. Cap 1 structure may be generated using both vaccinia virus capping enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2-O methyl-transferase. Cap 3 structure may be generated from the Cap 2 structure followed by the 2'-O-methylation of the 5'-preantepenultimate nucleotide using a 2'-O methyl-transferase.

In certain embodiments, the mRNA of the disclosure comprises a 5' cap selected from the group consisting of 3'-O-Me-m7G(5')ppp(5')G (the ARCA cap), G(5')ppp(5')A, G(5')ppp(5')G, m7G(5')ppp(5')A, m7G(5')ppp(5')G, m7G (5')ppp(5')(2'OMeA)pG, m7G(5')ppp(5')(2'OMeA)pU, and m7G(5')ppp(5')(2'OMeG)pG.

In certain embodiments, the mRNA of the disclosure comprises a 5' cap of:

tides in length, about 850 nucleotides in length, about 900 nucleotides in length, about 950 nucleotides in length, about 1,000 nucleotides in length, about 1,500 nucleotides in length, about 2,000 nucleotides in length, about 2,500 nucleotides in length, about 3,000 nucleotides in length, about 3,500 nucleotides in length, about 4,000 nucleotides in length, about 4,500 nucleotides in length or about 5,000 nucleotides in length.

In some embodiments, the mRNA disclosed herein may comprise a 3' UTR comprising one or more of a polyadenylation signal, a binding site for proteins that affect an mRNA's stability of location in a cell, or one or more binding sites for miRNAs. In some embodiments, a 3' UTR may be 50 to 5,000 nucleotides in length or longer. In some embodiments, a 3' UTR may be 50 to 1,000 nucleotides in length or longer. In some embodiments, the 3' UTR is at least about 50 nucleotides in length, about 100 nucleotides in length, about 150 nucleotides in length, about 200 nucleotides in length, about 250 nucleotides in length, about 300 nucleotides in length, about 350 nucleotides in length, about 400 nucleotides in length, about 450 nucleotides in length, about 500 nucleotides in length, about 550 nucleotides in length, about 600 nucleotides in length, about 650 nucleotides in length, about 700 nucleotides in length, about 750

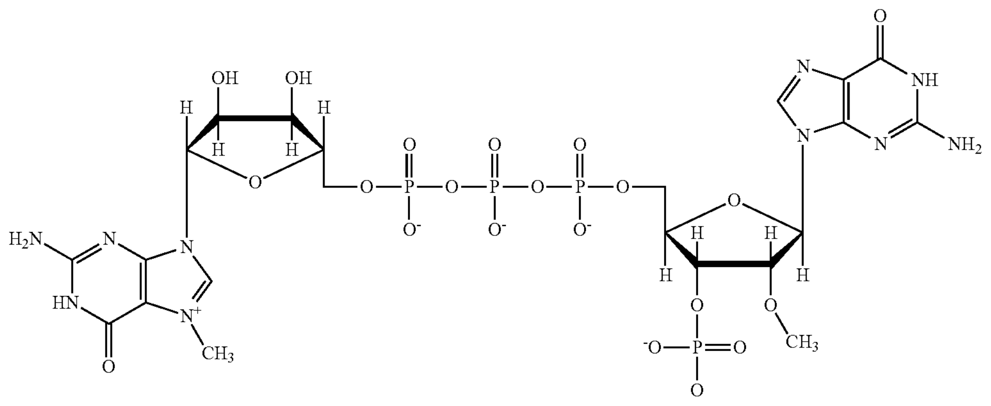

Untranslated Region (UTR)

In some embodiments, the mRNA of the invention includes a 5' and/or 3' untranslated region (UTR). In mRNA, the 5' UTR starts at the transcription start site and continues to the start codon but does not include the start codon. The 3' UTR starts immediately following the stop codon and continues until the transcriptional termination signal.

In some embodiments, the mRNA disclosed herein may comprise a 5' UTR that includes one or more elements that affect an mRNA's stability or translation. In some embodiments, a 5' UTR may be about 10 to 5,000 nucleotides in length. In some embodiments, a 5' UTR may be about 50 to 500 nucleotides in length. In some embodiments, the 5' UTR is at least about 10 nucleotides in length, about 20 nucleotides in length, about 30 nucleotides in length, about 40 nucleotides in length, about 50 nucleotides in length, about 100 nucleotides in length, about 150 nucleotides in length, about 200 nucleotides in length, about 250 nucleotides in length, about 300 nucleotides in length, about 350 nucleotides in length, about 400 nucleotides in length, about 450 nucleotides in length, about 500 nucleotides in length, about 550 nucleotides in length, about 600 nucleotides in length, about 650 nucleotides in length, about 700 nucleotides in length, about 750 nucleotides in length, about 800 nucleotides in length, about 800 nucleotides in length, about 850 nucleotides in length, about 900 nucleotides in length, about 950 nucleotides in length, about 1,000 nucleotides in length, about 1,500 nucleotides in length, about 2,000 nucleotides in length, about 2,500 nucleotides in length, about 3,000 nucleotides in length, about 3,500 nucleotides in length, about 4,000 nucleotides in length, about 4,500 nucleotides in length, or about 5,000 nucleotides in length.

In some embodiments, the mRNA disclosed herein may comprise a 5' or 3' UTR that is derived from a gene distinct from the one encoded by the mRNA transcript (i.e., the UTR is a heterologous UTR).

In certain embodiments, the 5' and/or 3' UTR sequences can be derived from mRNA which are stable (e.g., globin, actin, GAPDH, tubulin, histone, or citric acid cycle enzymes) to increase the stability of the mRNA. For example, a 5' UTR sequence may include a partial sequence of a CMV immediate-early 1 (IE1) gene, or a fragment thereof, to improve the nuclease resistance and/or improve the half-life of the mRNA. Also contemplated is the inclusion of a sequence encoding human growth hormone (hGH), or a fragment thereof, to the 3' end or untranslated region of the mRNA. Generally, these modifications improve the stability and/or pharmacokinetic properties (e.g., half-life)

of the mRNA relative to their unmodified counterparts, and include, for example, modifications made to improve such mRNA resistance to in vivo nuclease digestion.

Exemplary 5' UTRs include a sequence derived from a CMV immediate-early 1 (IE1) gene (U.S. Publication Nos. 2014/0206753 and 2015/0157565, each of which is incorporated herein by reference), or the sequence GGGAUCCUACC (SEQ ID NO: 264) (U.S. Publication No. 2016/0151409, incorporated herein by reference).

In various embodiments, the 5' UTR may be derived from the 5' UTR of a TOP gene. TOP genes are typically characterized by the presence of a 5'-terminal oligopyrimidine (TOP) tract. Furthermore, most TOP genes are characterized by growth-associated translational regulation. However, TOP genes with a tissue specific translational regulation are also known. In certain embodiments, the 5 UTR derived from the 5' UTR of a TOP gene lacks the 5' TOP motif (the oligopyrimidine tract) (e.g., U.S. Publication Nos. 2017/0029847, 2016/0304883, 2016/0235864, and 2016/0166710, each of which is incorporated herein by reference).

In certain embodiments, the 5' UTR is derived from a ribosomal protein Large 32 (L32) gene (U.S. Publication No. 2017/0029847, supra).

In certain embodiments, the 5' UTR is derived from the 5' UTR of an hydroxysteroid (17-b) dehydrogenase 4 gene (HSD17B4) (U.S. Publication No. 2016/0166710, supra).

In certain embodiments, the 5' UTR is derived from the 5' UTR of an ATP5A1 gene (U.S. Publication No. 2016/0166710, supra).

In some embodiments, an internal ribosome entry site (IRES) is used instead of a 5' UTR.

In some embodiments, the 5'UTR comprises a nucleic acid sequence set forth in SEQ ID NO: 265 and reproduced below:

```
                                    (SEQ ID NO: 265)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG.
```

In some embodiments, the 3'UTR comprises a nucleic acid sequence set forth in SEQ ID NO: 266 and reproduced below:

```
                                    (SEQ ID NO: 266)
CGGGUGGCAUCCCUGUGACCCCUCCCCAGUGCCUCUCCUGGCCCUGGAA

GUUGCCACUCCAGUGCCCACCAGCCUUGUCCUAAUAAAAUUAAGUUGCA

UC.
```

The 5' UTR and 3'UTR are described in further detail in WO2012/075040, incorporated herein by reference.

Polyadenylated Tail

As used herein, the terms "poly(A) sequence," "poly(A) tail," and "poly(A) region" refer to a sequence of adenosine nucleotides at the 3' end of the mRNA molecule. The poly(A) tail may confer stability to the mRNA and protect it from exonuclease degradation. The poly(A) tail may enhance translation. In some embodiments, the poly(A) tail is essentially homopolymeric. For example, a poly(A) tail of 100 adenosine nucleotides may have essentially a length of 100 nucleotides. In certain embodiments, the poly(A) tail may be interrupted by at least one nucleotide different from an adenosine nucleotide (e.g., a nucleotide that is not an adenosine nucleotide). For example, a poly(A) tail of 100 adenosine nucleotides may have a length of more than 100 nucleotides (comprising 100 adenosine nucleotides and at least one nucleotide, or a stretch of nucleotides, that are different from an adenosine nucleotide). In certain embodiments, the poly(A) tail comprises the sequence

```
                                    (SEQ ID NO: 267)
AAAAAAAAAAAAAAAAAAAAAAAAAAAAAAGCAUAUGACUAAAAAAAAAA

AAAAAAAAAAAAAAAAAAAAAAAAAAAAAAAAAAAAAAAAAAAAAAAAAA

AAAAAAAAAA.
```

The "poly(A) tail." as used herein, typically relates to RNA. However, in the context of the disclosure, the term likewise relates to corresponding sequences in a DNA molecule (e.g., a "poly(T) sequence").

The poly(A) tail may comprise about 10 to about 500 adenosine nucleotides, about 10 to about 200 adenosine nucleotides, about 40 to about 200 adenosine nucleotides, or about 40 to about 150 adenosine nucleotides. The length of the poly(A) tail may be at least about 10, 50, 75, 100, 150, 200, 250, 300, 350, 400, 450, or 500 adenosine nucleotides. In some embodiments, the poly A tail comprises at least 75 nucleotides (e.g. about 80 adenosine nucleotides). In some embodiments, the poly A tail comprises at least 100 adenosine nucleotides (e.g. about 115 adenosine nucleotides). Typically, the poly A tail comprises at least 100 adenosine nucleotides.

In some embodiments where the nucleic acid is an RNA, the poly(A) tail of the nucleic acid is obtained from a DNA template during RNA in vitro transcription. In certain embodiments, the poly(A) tail is obtained in vitro by common methods of chemical synthesis without being transcribed from a DNA template. In various embodiments, poly(A) tails are generated by enzymatic polyadenylation of the RNA (after RNA in vitro transcription) using commercially available polyadenylation kits and corresponding protocols, or alternatively, by using immobilized poly(A) polymerases, e.g., using methods and means as described in WO2016/174271.

The nucleic acid may comprise a poly(A) tail obtained by enzymatic polyadenylation, wherein the majority of nucleic acid molecules comprise about 100 (+/−20) to about 500 (+/−50) or about 250 (+/−20) adenosine nucleotides.

In some embodiments, the nucleic acid may comprise a poly(A) tail derived from a template DNA and may additionally comprise at least one additional poly(A) tail generated by enzymatic polyadenylation, e.g., as described in WO2016/091391.

In certain embodiments, the nucleic acid comprises at least one polyadenylation signal.

In various embodiments, the nucleic acid may comprise at least one poly(C) sequence.

The term "poly(C) sequence." as used herein, is intended to be a sequence of cytosine nucleotides of up to about 200 cytosine nucleotides. In some embodiments, the poly(C) sequence comprises about 10 to about 200 cytosine nucleotides, about 10 to about 100 cytosine nucleotides, about 20 to about 70 cytosine nucleotides, about 20 to about 60 cytosine nucleotides, or about 10 to about 40 cytosine nucleotides. In some embodiments, the poly(C) sequence comprises about 30 cytosine nucleotides.

Chemical Modification

The mRNA disclosed herein may be modified or unmodified. In some embodiments, the mRNA may comprise at least one chemical modification. In some embodiments, the mRNA disclosed herein may contain one or more modifications that typically enhance RNA stability. Exemplary modifications can include backbone modifications, sugar modifications, or base modifications. In some embodiments, the disclosed mRNA may be synthesized from naturally occurring nucleotides and/or nucleotide analogues (modified nucleotides) including, but not limited to, purines (adenine (A) and guanine (G)) or pyrimidines (thymine (T), cytosine (C), and uracil (U)). In certain embodiments, the disclosed mRNA may be synthesized from modified nucleotide analogues or derivatives of purines and pyrimidines, such as, e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine.

In some embodiments, the disclosed mRNA may comprise at least one chemical modification including, but not limited to, pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methy luridine, 5-methy luridine, 5-methoxyuridine, and 2'-O-methyl uridine.

In some embodiments, the chemical modification is selected from the group consisting of pseudouridine, N1-methylpseudouridine, 5-methylcytosine, 5-methoxyuridine, and a combination thereof.

In some embodiments, the chemical modification comprises N1-methylpseudouridine. Typically, the chemical modification comprises N1-methylpseudouridine in place of every uridine, i.e. 100% of U residues are N1-methylpseudouridine.

In some embodiments, at least 20%, at least 30%, at least 40%, at least 50%, at least 60%, at least 70%, at least 80%, at least 85%, at least 90%, at least 95%, or 100% of the uracil nucleotides in the mRNA are chemically modified.

In some embodiments, at least 20%, at least 30%, at least 40%, at least 50%, at least 60%, at least 70%, at least 80%, at least 85%, at least 90%, at least 95%, or 100% of the uracil nucleotides in the ORF are chemically modified.

The preparation of such analogues is described, e.g., in U.S. Pat. Nos. 4,373,071, 4,401,796, 4,415,732, 4,458,066, 4,500,707, 4,668,777, 4,973,679, 5,047,524, 5,132,418, 5,153,319, 5,262,530, and 5,700,642.

mRNA Synthesis

The mRNAs disclosed herein may be synthesized according to any of a variety of methods. For example, mRNAs according to the present disclosure may be synthesized via in vitro transcription (IVT). Some methods for in vitro transcription are described, e.g., in Geall et al. (2013) Semin. Immunol. 25(2): 152-159; Brunelle et al. (2013) Methods Enzymol. 530:101-14. Briefly. IVT is typically performed with a linear or circular DNA template containing a promoter, a pool of ribonucleotide triphosphates, a buffer system that may include DTT and magnesium ions, an appropriate RNA polymerase (e.g., T3, T7, or SP6 RNA polymerase), DNase I, pyrophosphatase, and/or RNase inhibitor. The exact conditions may vary according to the specific application. The presence of these reagents is generally undesirable in a final mRNA product and these reagents can be considered impurities or contaminants which can be purified or removed to provide a clean and/or homogeneous mRNA that is suitable for therapeutic use. While mRNA provided from in vitro transcription reactions may be desirable in some embodiments, other sources of mRNA can be used according to the instant disclosure including wild-type mRNA produced from bacteria, fungi, plants, and/or animals.

Processes for Making the Present LNP Vaccines

The present LNPs can be prepared by various techniques presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion that results in the formation of MLVs. Unilamellar vesicles (ULV) can then be formed by homogenization, sonication or extrusion of the multilamellar vesicles. In addition, unilamellar vesicles can be formed by detergent removal techniques.

Various methods are described in US 2011/0244026, US 2016/0038432, US 2018/0153822, US 2018/0125989, and PCT/US2020/043223 (filed Jul. 23, 2020) and can be used to practice the present disclosure. One exemplary process entails encapsulating mRNA by mixing it with a mixture of lipids, without first pre-forming the lipids into lipid nanoparticles, as described in US 2016/0038432. Another exemplary process entails encapsulating mRNA by mixing pre-formed LNPs with mRNA, as described in US 2018/0153822.

In some embodiments, the process of preparing mRNA-loaded LNPs includes a step of heating one or more of the solutions to a temperature greater than ambient temperature, the one or more solutions being the solution comprising the pre-formed lipid nanoparticles, the solution comprising the mRNA and the mixed solution comprising the LNP-encapsulated mRNA. In some embodiments, the process includes the step of heating one or both of the mRNA solution and the pre-formed LNP solution, prior to the mixing step. In some embodiments, the process includes heating one or more of the solutions comprising the pre-formed LNPs, the solution comprising the mRNA and the solution comprising the LNP-encapsulated mRNA, during the mixing step. In some embodiments, the process includes the step of heating the LNP-encapsulated mRNA, after the mixing step. In some embodiments, the temperature to which one or more of the solutions is heated is or is greater than about 30° C. 37° C. 40° C. 45° C. 50° C. 55° C. 60° C. 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature is about 65° C.

Various methods may be used to prepare an mRNA solution suitable for the present disclosure. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water or a buffer at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps. Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of, or greater than, about 60 ml/minute, 100 ml/minute, 140 ml/minute, 180 ml/minute, 220 ml/minute, 260 ml/minute, 300 ml/minute, 340 ml/minute, 380 ml/minute, 420) ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

The process of incorporation of a desired mRNA into a lipid nanoparticle is referred to as "loading." Exemplary methods are described in Lasic et al., FEBS Lett. (1992) 312:255-8. The LNP-incorporated nucleic acids may be completely or partially located in the interior space of the lipid nanoparticle, within the bilayer membrane of the lipid nanoparticle, or associated with the exterior surface of the lipid nanoparticle membrane. The incorporation of an mRNA into lipid nanoparticles is also referred to herein as "encapsulation" wherein the nucleic acid is entirely or substantially contained within the interior space of the lipid nanoparticle.

Suitable LNPs may be made in various sizes. In some embodiments, decreased size of lipid nanoparticles is associated with more efficient delivery of an mRNA. Selection of an appropriate LNP size may take into consideration the site of the target cell or tissue and to some extent the application for which the lipid nanoparticle is being made.

A variety of methods known in the art are available for sizing of a population of lipid nanoparticles. Preferred methods herein utilize Zetasizer Nano ZS (Malvern Panalytical) to measure LNP particle size. In one protocol, 10 μl of an LNP sample are mixed with 990 μl of 10% trehalose. This solution is loaded into a cuvette and then put into the Zetasizer machine. The z-average diameter (nm), or cumulants mean, is regarded as the average size for the LNPs in the sample. The Zetasizer machine can also be used to measure the polydispersity index (PDI) by using dynamic light scattering (DLS) and cumulant analysis of the autocorrelation function. Average LNP diameter may be reduced by sonication of formed LNP. Intermittent sonication cycles may be alternated with quasi-elastic light scattering (QELS) assessment to guide efficient lipid nanoparticle synthesis.

In some embodiments, the LNP has an average diameter of 30 nm to 200 nm (e.g. an average diameter of 80 nm to 150 nm).

In some embodiments, the majority of purified LNPs, i.e., greater than about 50%, 55%, 60%, 65%, 70%, 75%, 80%, 85%, 90%, 95%, 96%, 97%, 98%, or 99% of the LNPs, have a size of about 70-150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, substantially all (e.g., greater than 80 or 90%) of the purified lipid nanoparticles have a size of about 70-150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm).

In some embodiments, the LNPs in the present composition have an average size of less than 150 nm, less than 120 nm, less than 100 nm, less than 90 nm, less than 80 nm, less than 70 nm, less than 60 nm, less than 50 nm, less than 30 nm, or less than 20 nm.

In some embodiments, greater than about 70%, 75%, 80%, 85%, 90%, 95%, 96%, 97%, 98%, 99% of the LNPs in the present composition have a size ranging from about 40-90 nm (e.g., about 45-85 nm, about 50-80 nm, about 55-75 nm, about 60-70 nm) or about 50-70 nm (e.g., 55-65 nm) are particular suitable for pulmonary delivery via nebulization.

In some embodiments, the dispersity, or measure of heterogeneity in size of molecules (PDI), of LNPs in a pharmaceutical composition provided by the present disclosure is less than about 0.5. In some embodiments, an LNP has a PDI of less than about 0.5, less than about 0.4, less than about 0.3, less than about 0.28, less than about 0.25, less than about 0.23, less than about 0.20, less than about 0.18, less than about 0.16, less than about 0.14, less than about 0.12, less than about 0.10, or less than about 0.08. The PDI may be measured by a Zetasizer machine as described above.

In some embodiments, greater than about 75%, 80%, 85%, 90%, 95%, 96%, 97%, 98%, or 99% of the purified LNPs in a pharmaceutical composition provided herein encapsulate an mRNA within each individual particle. In some embodiments, substantially all (e.g., greater than 80% or 90%) of the purified lipid nanoparticles in a pharmaceutical composition encapsulate an mRNA within each individual particle. In some embodiments, a lipid nanoparticle has an encapsulation efficiency of between 50% and 99%; or greater than about 60, 65, 70, 75, 80, 85, 90, 92, 95, 98, or 99%. Typically, lipid nanoparticles for use herein have an encapsulation efficiency of at least 90% (e.g., at least 91, 92, 93, 94, or 95%).

In some embodiments, an LNP has a N/P ratio of between 1 and 10. In some embodiments, a lipid nanoparticle has a N/P ratio above 1, about 1, about 2, about 3, about 4, about 5, about 6, about 7, or about 8. In further embodiments, a typical LNP herein has an N/P ratio of 4.

In some embodiments, a pharmaceutical composition according to the present disclosure contains at least about 0.5 μg, 1 μg, 5 μg, 10 μg, 100 μg, 500 μg, or 1000 μg of encapsulated mRNA. In some embodiments, a pharmaceutical composition contains about 0.1 μg to 1000 μg, at least about 0.5 μg, at least about 0.8 μg, at least about 1 μg, at least about 5 μg, at least about 8 μg, at least about 10 μg, at least about 50 μg, at least about 100 μg, at least about 500 μg, or at least about 1000 μg of encapsulated mRNA.

In some embodiments, mRNA can be made by chemical synthesis or by in vitro transcription (IVT) of a DNA template. In this process, in an IVT process, a cDNA template is used to produce an mRNA transcript and the DNA template is degraded by a DNase. The transcript is purified by depth filtration and tangential flow filtration (TFF). The purified transcript is further modified by adding a cap and a tail, and the modified RNA is purified again by depth filtration and TFF.

The mRNA is then prepared in an aqueous buffer and mixed with an amphiphilic solution containing the lipid components of the LNPs. An amphiphilic solution for dissolving the four lipid components of the LNPs may be an alcohol solution. In some embodiments, the alcohol is ethanol. The aqueous buffer may be, for example, a citrate, phosphate, acetate, or succinate buffer and may have a pH of about 3.0-7.0, e.g., about 3.5, about 4.0, about 4.5, about 5.0, about 5.5, about 6.0, or about 6.5. The buffer may contain other components such as a salt (e.g., sodium, potassium, and/or calcium salts). In particular embodiments, the aqueous buffer has 1 mM citrate. 150 mM NaCl, pH 4.5.

The process for making a composition comprising LNPs and mRNA(s) involves mixing of a buffered mRNA solution with a solution of lipids in ethanol in a controlled homogeneous manner, where the ratio of lipids:mRNA is maintained throughout the mixing process. In this illustrative example, the mRNA is presented in an aqueous buffer containing citric acid monohydrate, tri-sodium citrate dihydrate, and sodium chloride. The mRNA solution is added to the solution (1 mM citrate buffer. 150 mM NaCl, pH 4.5). The lipid mixture of four lipids (e.g., a cationic lipid, a PEGylated lipid, a cholesterol-based lipid, and a helper lipid) is dissolved in ethanol. The aqueous mRNA solution and the ethanol lipid solution are mixed at a volume ratio of 4:1 in a "T" mixer with a near "pulseless" pump system. The resultant mixture is then subjected for downstream purification and buffer exchange. The buffer exchange may be achieved using dialysis cassettes or a TFF system. TFF may be used to concentrate and buffer-exchange the resulting nascent LNP immediately after formation via the T-mix process. The diafiltration process is a continuous operation, keeping the volume constant by adding appropriate buffer at the same rate as the permeate flow.

Vectors

In one aspect, disclosed herein are vectors comprising the mRNA compositions disclosed herein. The RNA sequences encoding a protein of interest (e.g., mRNA encoding a polypeptide disclosed herein) can be cloned into a number of types of vectors. For example, the nucleic acids can be cloned into a vector including, but not limited to, a plasmid, a phagemid, a phage derivative, an animal virus, and a cosmid. Vectors of particular interest can include expression vectors, replication vectors, probe generation vectors, sequencing vectors, and vectors optimized for in vitro transcription.

In certain embodiments, the vector can be used to express mRNA in a host cell. In various embodiments, the vector can be used as a template for IVT. The construction of optimally translated IVT mRNA suitable for therapeutic use is disclosed in detail in Sahin, et al. (2014). Nat. Rev. Drug Discov. 13, 759-780; Weissman (2015). Expert Rev. Vaccines 14, 265-281.

In some embodiments, the vectors disclosed herein can comprise at least the following, from 5' to 3': an RNA polymerase promoter; a polynucleotide sequence encoding a 5' UTR; a polynucleotide sequence encoding an ORF; a polynucleotide sequence encoding a 3' UTR; and a polynucleotide sequence encoding at least one RNA aptamer. In some embodiments, the vectors disclosed herein may comprise a polynucleotide sequence encoding a poly(A) sequence and/or a polyadenylation signal.

A variety of RNA polymerase promoters are known. In some embodiments, the promoter can be a T7 RNA polymerase promoter. Other useful promoters can include, but are not limited to. T3 and SP6 RNA polymerase promoters. Consensus nucleotide sequences for T7, T3, and SP6 promoters are known.

Also disclosed herein are host cells (e.g., mammalian cells, e.g., human cells) comprising the vectors or RNA compositions disclosed herein. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid or vector disclosed herein.

Vectors can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendorf, Hamburg, Germany), cationic liposome mediated transfection using lipofection, polymer encapsulation, peptide mediated transfection, biolistic particle delivery systems such as "gene guns" (see, for example. Nishikawa, et al. (2001). Hum Gene Ther. 12 (8):861-70, or the TransIT-RNA transfection Kit (Mirus, Madison, WI).

Chemical means for introducing a vector into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell or otherwise expose a cell to the inhibitor of the present disclosure, in order to confirm the presence of the mRNA sequence in the host cell a variety of assays may be performed.

Self-Replicating RNA, Trans-Replicating RNA and Non-Replicating RNA

Typically, the nucleic acid molecules described herein are non-replicating RNAs. However, the nucleic acid molecules described herein may alternatively be self-replicating RNAs or trans-replicating RNAs.

Self-replicating RNA

Self-replicating (or self-amplifying) RNA can be produced by using replication elements derived from, e.g., alphaviruses, and substituting the structural viral proteins with a nucleotide sequence encoding a protein of interest (e.g., a polypeptide described herein). A self-replicating RNA is typically a positive-strand molecule which can be directly translated after delivery to a cell, and this translation provides an RNA-dependent RNA polymerase which then produces both antisense and sense transcripts from the delivered RNA. Thus, the delivered RNA leads to the production of multiple daughter RNAs. These daughter RNAs, as well as collinear subgenomic transcripts, may be translated themselves to provide in situ expression of an encoded antigen, or may be transcribed to provide further transcripts with the same sense as the delivered RNA which are translated to provide in situ expression of the antigen. The overall result of this sequence of transcriptions is a large amplification in the number of the introduced replicon RNAs and so the encoded antigen becomes a major polypeptide product of the cells.

One suitable system for achieving self-replication in this manner is to use an alphavirus-based replicon. These replicons are positive stranded (positive sense-stranded) RNAs which lead to translation of a replicase (or replicase-transcriptase) after delivery to a cell. The replicase is translated as a polyprotein which auto-cleaves to provide a replication complex which creates genomic-strand copies of the positive-strand delivered RNA. These negative (−)-stranded transcripts can themselves be transcribed to give further copies of the positive-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used, e.g., the attenuated TC83 mutant of VEEV has been used in replicons, see the following reference: WO2005/113782, incorporated herein by reference.

In one embodiment, each self-replicating RNA described herein encodes (i) an RNA-dependent RNA polymerase which can transcribe RNA from the self-replicating RNA molecule and (ii) an influenza protein antigen. The polymerase can be an alphavirus replicase, e.g., comprising one or more of alphavirus proteins nsP1, nsP2, nsP3, and nsP4. Whereas natural alphavirus genomes encode structural virion proteins in addition to the non-structural replicase polyprotein, in certain embodiments, the self-replicating RNA molecules do not encode alphavirus structural proteins. Thus, the self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the present disclosure and their place is taken by gene(s) encoding the immunogen of interest, such that the subgenomic transcript encodes the immunogen rather than the structural alphavirus virion proteins. Self-replicating RNA are described in further detail in WO2011005799, incorporated herein by reference.

Trans-Replicating RNA

Trans-replicating (or trans-amplifying) RNA possess similar elements as the self-replicating RNA described above. However, with trans replicating RNA, two separate RNA molecules are used. A first RNA molecule encodes for the RNA replicase described above (e.g., the alphavirus replicase) and a second RNA molecule encodes for the protein of interest (e.g., a polypeptide described herein). The RNA replicase may replicate one or both of the first and second RNA molecule, thereby greatly increasing the copy number of RNA molecules encoding the protein of interest. Trans replicating RNA are described in further detail in WO2017162265, incorporated herein by reference.

Non-Replicating RNA

Non-replicating (or non-amplifying) RNA is an RNA without the ability to replicate itself.

Therapeutic Uses

In another aspect, the invention provides the polypeptides, nucleic acids, combinations or compositions of the present invention for use as a medicament. The invention also provides the use of the polypeptides, nucleic acids, combinations or compositions of the present invention for the manufacture of a medicament. The medicament may be used for treating or preventing a disease as described herein. The invention further provides a method of treating or preventing a disease comprising administering the polypeptides, nucleic acids, combinations or compositions of the present invention to a subject in need thereof. The polypeptides, nucleic acids, combinations or compositions of the present invention may, for example, be administered in an amount effective to treat or prevent the disease in the subject. Polypeptides, nucleic acids, combinations or compositions may thus be administered in an effective amount.

In another aspect, the invention provides the polypeptides, nucleic acids, combinations or compositions of the present invention for use in treating or preventing *C. acnes* infection in a subject (e.g. human). The invention also provides the use of the polypeptides, nucleic acids, combinations or compositions of the present invention for the manufacture of a medicament for treating or preventing *C. acnes* infection in a subject (e.g. human). The invention further provides a method of treating or preventing *C. acnes* infection in a subject (e.g. human), the method comprising administering the polypeptides, nucleic acids, combinations or compositions of the present invention to the subject. The polypeptides, nucleic acids, combinations or compositions of the present invention may, for example, be administered in an amount effective to treat or prevent *C. acnes* infection in the subject (i.e. administered in an effective amount). *C. acnes* infection may be mild, moderate or severe (e.g. moderate or severe).

The polypeptides, nucleic acids, combinations or compositions of the invention may be used for eliciting an immune response in a subject, e.g. an immune response against *C. acnes* infection.

In another aspect, the invention provides the polypeptides, nucleic acids, combinations or compositions of the present invention for use in treating or preventing acne (also known as acne vulgaris) in a subject (e.g. human). The invention also provides the use of the polypeptides, nucleic acids, combinations or compositions of the present invention for the manufacture of a medicament for treating or preventing acne in a subject (e.g. human). The invention further provides a method of treating or preventing acne in a subject (e.g. human), the method comprising administering the polypeptides, nucleic acids, combinations or compositions of the present invention to the subject. The polypeptides, nucleic acids, combinations or compositions of the present invention may, for example, be administered in an amount effective to treat or prevent acne in the subject (i.e. administered in an effective amount). Acne may be caused by *C. acnes*. Acne may be mild, moderate or severe (e.g. moderate or severe).

In some embodiments, a treatment as described herein achieves at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least a 70%, at least a 75%, at least a 80%, least a 85% or at least a 90% (e.g. at least a 50%) reduction in the number of inflammatory acne lesions relative to the number of inflammatory acne lesions prior to the treatment, e.g. at 2, 3, 4, 5, 6, 7, 8, 9, 10, 11, 12 months (e.g. 3 or 6 months) after administration of the treatment (e.g. after the last dose of the treatment). In some embodiments, the inflammatory acne lesions are on a subject's face. In some embodiments, the inflammatory acne lesions are on a subject's face and one other body area (e.g. chest or back).

In some embodiments, a treatment as described herein achieves at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least a 70%, at least a 75%, at least a 80%, least a 85% or at least a 90% (e.g. at least a 50%) reduction in the number of non-inflammatory acne lesions relative to the number of non-inflammatory acne lesions prior to the treatment, e.g. at 2, 3, 4, 5, 6, 7, 8, 9, 10, 11, 12 months (e.g. 3 or 6 months) after administration of the treatment (e.g. after the last dose of the treatment). In some embodiments, the non-inflammatory acne lesions are on a subject's face. In some embodiments, the non-inflammatory acne lesions are on a subject's face and one other body area (e.g. chest or back).

In some embodiments, a treatment as described herein achieves a reduction in the Investigator's Global Assessment (IGA) score for a subject relative to the score prior to the treatment, e.g. at 2, 3, 4, 5, 6, 7, 8, 9, 10, 11, 12 months (e.g. 3 or 6 months) after administration of the treatment (e.g. after the last dose of the treatment). In some embodiments, a treatment as described herein achieves at least a two-grade improvement in the Investigator's Global Assessment (IGA) score for a subject relative to the score prior to the treatment, e.g. at 2, 3, 4, 5, 6, 7, 8, 9, 10, 11, 12 months (e.g. 3 or 6 months) after administration of the treatment (e.g. after the last dose of the treatment). In some embodiments, the IGA score improvement results in an IGA score of 0, 1 or 2 (e.g. 0 or 1), e.g. at 2, 3, 4, 5, 6, 7, 8, 9, 10, 11, 12 months (e.g. 3 or 6 months) after administration of the treatment (e.g. after the last dose of the treatment).

The polypeptides, nucleic acids, combinations or compositions of the invention may be used for treating or preventing chronic blepharitis associated with *C. acnes* infection and/or endophthalmitis associated with *C. acnes* infection.

The invention provides the polypeptides, nucleic acids, combinations or compositions of the present invention for use in a method of providing protective immunity against a *C. acnes* infection in a subject. The invention also provides the use of the polypeptides, nucleic acids, combinations or compositions of the present invention for the manufacture of a medicament for use in a method of providing protective immunity against a *C. acnes* infection in a subject. The invention further provides a method of providing protective immunity against a *C. acnes* infection in a subject, the method comprising administering the polypeptides, nucleic acids, combinations or compositions of the present invention to the subject. The polypeptides, nucleic acids, combinations or compositions of the present invention may, for example, be administered in an amount effective to providing protective immunity against a *C. acnes* infection in the subject (i.e. administered in an effective amount). Protective immunity may be protective against development of a pathological condition induced by *C. acnes* infection (e.g. acne). Protective immunity may prevent or reduce development of a *C. acnes*-associated indication.

The polypeptides, nucleic acids, combinations or compositions of the invention may elicit antibodies (e.g. antigen-specific antibodies), such as IgG. Antibodies (DsA1, DsA2 and/or PITP-specific antigens) may bind the surface of *C. acnes* bacteria. Antibodies (DsA1, DsA2 and/or PITP-specific antigens) may opsonize *C. acnes* bacteria. This may allow recruitment of immune effector cells (e.g. phagocytes) to the bacteria. *C. acnes* bacteria may be phagocytosed by recruited immune effector cells. Within the IgG isotype, antibodies may be IgG1, IgG2, IgG3 or IgG4 subclass. The antibody may have a k or a 2 light chain. In some embodiments, the polypeptides, nucleic acids, combinations or compositions of the invention may elicit an antibody response that is cross-reactive against two or more strains or phylotypes of *C. acnes*, e.g. cross-reactive against two or more phylotypes (e.g. cross-reactive against phylotypes IA1, IA2, IB IC, II and III).

The polypeptides, nucleic acids, combinations or compositions of the invention may reduce inflammation associated with (e.g. caused by) *C. acnes* infection. The polypeptides, nucleic acids, combinations or compositions of the invention may reduce *C. acnes*-mediated tissue inflammation.

The polypeptides, nucleic acids, combinations or compositions of the invention may inhibit biofilm formation by *C. acnes*. In some embodiments, biofilm formation may be prevented. In some embodiments, biofilm formation may be reduced.

Administration of a polypeptide, nucleic acid, combination or composition of the invention to a subject may enable the subject to produce a *C. acnes* antigen-responsive memory B cell population on exposure to *C. acnes* bacteria or the *C. acnes* antigen. The polypeptides, nucleic acids, combinations or compositions of the invention may be used to induce a primary immune response and/or to boost an immune response.

The polypeptides, nucleic acids, combinations or compositions of the invention may be used in a prime-boost vaccination regime. Immunity against a *C. acnes* infection according to the invention may be provided by administering a priming vaccine, comprising a polypeptide, nucleic acid, combinations or composition of the invention, followed by a booster vaccine. The booster vaccine may be the same as the primer vaccine.

In certain embodiments, the subject is a vertebrate, e.g., a mammal, such as a human or a veterinary mammal (e.g. cat, dog, horse, cow, sheep, cattle, deer, goat, pig, rodents (e.g. mice)). In preferred embodiments, the subject is a human. The subject (e.g. the human subject) may be male or female. The subject may be a child (0-10 years old), an adolescent (10-18 years old) or an adult (over 18 years old). In some embodiments, human subjects may be 0-30, or 0-45 (e.g. 5-18, 12-45, 18-45 or 9-45) years old. For example, the subject may be 9-45, 12-45 or 18-45 (e.g. 9-45) years old.

In some embodiments, the subject has at least one of the following: (i) score of grade 3 or grade 4 on the IGA scale; (ii) at least 25 non-inflammatory lesions (e.g. open and/or closed comedones) optionally on the subject's face; (iii) at least 20 inflammatory lesions (e.g. papules and/or pustules) optionally on the subject's face; (iv) 2 or fewer nodulocystic lesions (e.g. nodules and/or cysts) optionally on the subject's face. In some embodiments, the subject has at least two of (i)-(iv). In some embodiments, the subject has at least three of (i)-(iv). Typically, the subject has all four of (i)-(iv). A subject having all four of (i)-(iv) may have moderate/severe acne.

Acne vulgaris (also referred to herein as acne) manifests in different severity grades: mild, moderate and severe. Moderate and severe acne account for more than one third of all cases and require medical treatment. In some embodiments, subjects may have mild, moderate or severe (e.g., moderate or severe acne) *C. acnes* infection. The subjects may have mild, moderate or severe acne (e.g., moderate or severe acne). In some embodiments, the subjects have mild, moderate or severe acne (e.g., moderate or severe acne).

Modes of Administration

The polypeptides, nucleic acids, combinations or compositions of the present invention can be administered parenterally (e.g., intramuscularly, intradermally, subcutaneously, intraperitoneally, intravenously, or to the interstitial space of a tissue) or by rectal, oral, vaginal, topical, transdermal, intranasal, sublingual, ocular, aural, pulmonary or other mucosal administration. In some embodiments, delivery is by mucosal administration. Typically, administration is intramuscular.

In certain embodiments, nucleic acids, polypeptides, compositions or combinations (e.g., compositions) of the invention are provided for use in intramuscular (IM) injection. The nucleic acids, polypeptides, compositions or combinations (e.g., compositions) can be administered to the thigh or the upper arm of a subject at, e.g., their deltoid muscle in the upper arm. In some embodiments, the nucleic acids, polypeptides, compositions or combinations (e.g., compositions) are provided in a pre-filled syringe or injector (e.g., single-chambered or multi-chambered). Injection may be via a needle (e.g. a hypodermic needle), but needle-free injection may alternatively be used. A typical intramuscular dose is 0.5 ml. In some embodiments, the nucleic acids, polypeptides, compositions or combinations (e.g., compositions) are provided for use in inhalation and is provided in a pre-filled pump, aerosolizer, or inhaler.

In certain embodiments, nucleic acids, polypeptides, compositions or combinations (e.g., compositions) of the invention are provided for use in skin injection, e.g. in the epidermis, the dermis or the hypodermis of the skin. In some embodiments, the nucleic acids, polypeptides, compositions or combinations of the invention (e.g. compositions) are provided in a device suitable for skin injection, such as a needle (e.g. an epidermic, dermic or hypodermic needle), a needle free device, a microneedle device or a microprojection array device. Examples of microneedle or microprojection array devices suitable for the skin injection according to the invention are described in US20230270842A1, US20220339416A1, US20210085598A1, US20200246450A1, US20220143376A1, US20180264244A1, US20180263641A1, US20110245776A1.

The nucleic acids, polypeptides, compositions or combinations (e.g., compositions) of the invention may be used to elicit systemic, cutaneous and/or mucosal immunity.

Dosage treatment can be a single dose schedule or a multiple dose schedule. Multiple doses (e.g. two or three) may be used in a primary immunisation schedule and/or in a booster immunisation schedule. A primary dose schedule may be followed by a booster dose schedule. Multiple doses (e.g., two doses or three) will typically be administered at least 1 week apart (e.g. about 2 weeks, about 3 weeks, about 4 weeks, about 6 weeks, about 8 weeks, about 10 weeks, about 12 weeks, about 16 weeks, etc.) to subjects in need thereof to achieve the desired therapeutic or prophylactic effects (e.g., two months). The doses (e.g., prime and booster doses) may be separated by an interval of e.g., 1 week. 2 weeks, 3 weeks, 4 weeks, one month, two months, three months, four months, five months, six months, one year, two years, five years, or ten years (e.g., two months). In some embodiments, a subject is administered a single dose intramuscularly. In some embodiments, the subject is administered two doses intramuscularly (e.g. two months apart).

A composition of the invention may be in the form of an extemporaneous formulation, e.g. a composition of the invention may be lyophilised. Such compositions may be reconstituted with a physiological buffer (e.g., PBS) just before use. The compositions of the invention may be provided in the form of an aqueous solution or a frozen aqueous solution and can be directly administered to subjects without reconstitution (after thawing, if previously frozen).

In some embodiments of a composition comprising one or more nucleic acids (e.g., mRNA(s)) as described herein, a single dose of the composition contains 1-300 (or 1-50) ug of a mRNA as described herein (e.g., monovalent or multivalent). For example, a single dose may contain about 2.5 μg, about 5 μg, about 7.5 μg, about 10 μg, about 12.5 μg, about 15 μg, about 30 μg, about 45 μg, about 60 μg, about 75 μg, about 90 μg, about 105 μg, about 120 μg, about 135 μg, about 150 μg, about 165 μg, about 180 μg, about 195 μg, about 210 μg, about 225 μg, about 240 μg, about 250 μg, about 260 μg, about 275 μg, or about 300 μg of the one or more nucleic acids (e.g., mRNA(s)) described herein, e.g. for intramuscular (IM) injection. In some embodiments, the composition comprises 40-50 μg (e.g., about 45 μg) of the one or more nucleic acid(s) (e.g. mRNA(s)). In some embodiments, the composition comprises 110-140 μg (e.g., about 120 μg) of the one or more nucleic acid(s) (e.g. mRNA(s)). In some embodiments, the composition comprises 200-250 μg (e.g., about 225 μg) of the one or more nucleic acid(s) (e.g. mRNA(s)).

The composition may comprise three nucleic acids (e.g., three mRNAs) as described herein encoding different polypeptides as described herein and the nucleic acids may be present in a weight ratio of 1:1:1. In some embodiments, the composition comprises a total of about 45 μg, about 120 μg or about 225 μg of the nucleic acids. The composition may therefore comprise about 15 μg, about 40 μg or about 75 μg of each of the three nucleic acids.

The composition may comprise two nucleic acids (e.g., two mRNAs) as described herein encoding different polypeptides as described herein and the nucleic acids may be present in a weight ratio of 1:1.

In further embodiments, a composition of the invention may be provided as a multi-valent single dose contains multiple (e.g., 2, 3, or 4) kinds of LNPs, each for a different antigen, and each kind of LNP has an mRNA amount of, e.g., 2.5 μg, about 5 μg, about 7.5 μg, about 10 μg, about 12.5 μg, about 15 μg, about 30 μg, about 45 μg, about 60 μg, about 75 μg, about 90 μg, about 105 μg, about 120 μg, about 135 μg, about 150 μg, about 165 μg, about 180 μg, about 195 μg, about 210 μg, about 225 μg, about 250 μg, about 275 μg, or about 300 μg.

In some embodiments, the subject is administered one or more nucleic acid compositions of the present invention. The nucleic acid compositions may comprise a nucleic acid comprising a nucleotide sequence encoding a polypeptide antigen as described herein. The nucleic acid compositions may be administered simultaneously, separately or sequentially. In some embodiments, the subject is administered a nucleic acid combination of the present invention. The nucleic acid combinations include combinations of two or more (e.g., three) nucleic acids as described herein. The nucleic acids within a combination may be administered simultaneously, separately or sequentially.

In some embodiments, the subject is administered one or more polypeptide compositions of the present invention. The polypeptide compositions may comprise a polypeptide antigen as described herein. The polypeptide compositions may be administered simultaneously, separately or sequentially. In some embodiments, the subject is administered a polypeptide combination of the present invention. The polypeptide combinations include combinations of two or more (e.g., three) polypeptides as described herein. The nucleic acids within a combination may be administered simultaneously, separately or sequentially.

In some embodiments, the subject is administered one or more nucleic acid compositions of the present invention and one or more polypeptide compositions of the invention. The nucleic acid composition and the one or more polypeptide compositions may be administered simultaneously, separately or sequentially.

Compositions administered separately or sequentially may be administered within 12 months of each other, within six months of each other, or within one month or less of each other (e.g. within 10 days). Compositions may be administered within 7 days, within 3 days, within 2 days, or within 24 hours of each other. Simultaneous administration may involve administering the compositions of the invention at the same time. Simultaneous administration may include administration of the compositions of the invention to a patient within 12 hours of each other, within 6 hours, within 3 hours, within 2 hours or within 1 hour of each other, typically within the same visit to a clinical centre.

The present invention also provides a kit comprising one or more compositions described herein in one or more containers or provides one or more composition as described herein in one or more containers and a physiological buffer for reconstitution in another container. The container(s) may contain a single-use dosage or multi-use dosage. The containers may be pre-treated glass vials or ampules. The kit may include instructions for use.

Definitions

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

As used herein, the term "effective amount" refers to an amount (e.g., of a nucleic acid, a polypeptide, a combination or a composition as described herein) sufficient to effect beneficial or desired results. An effective amount can be administered in one or more administrations, applications or dosages, and is not intended to be limited to a particular formulation or administration route. The term "effective amount" includes, e.g., therapeutically effective amount and/or prophylactically effective amount. The term "effective amount" as used herein refers to an amount (e.g., of a nucleic acid, a polypeptide, a combination or a composition as described herein) which is effective for producing some desired therapeutic or prophylactic effects in the treatment or prevention of an infection, disease, disorder and/or condition at a reasonable benefit/risk ratio applicable to any medical treatment.

The term "fragment" or "variant" when referring to the polypeptides of the present disclosure include any polypeptides which retain at least some of the properties (e.g., specific antigenic property of the polypeptide or the ability of polypeptide to contribute to the induction of antibody binding) of the reference polypeptide. Fragments of polypeptides include N-terminally and/or C-terminally truncated fragments, e.g. C-terminal fragments and N-terminal fragments, as well as deletion fragments but do not include the naturally occurring full-length polypeptide (or mature polypeptide). A deletion fragment refers to a polypeptide with one or more internal amino acids deleted from the full-length polypeptide. Variants of polypeptides include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions. Such variations (i.e. truncations and/or amino acid substitutions, deletions, or insertions) may occur either on the amino acid level or correspondingly on the nucleic acid level.

Identity with respect to a sequence is defined herein as the percentage of nucleic acid or amino acid residues in the candidate sequence that are identical with the reference amino acid sequence after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides or the nucleic acids of two polynucleotides. For example, using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. The percent identity can be calculated as: the total number of identical matches multiplied by 100 and then divided by the sum of the length of the longer sequence within the matched span and the number of gaps introduced into the shorter sequences in order to align the two sequences.

As used herein, the term "kit" refers to a packaged set of related components, such as one or more compounds or compositions and one or more related materials such as solvents, solutions, buffers, instructions, or desiccants.

The term "linked" or "attached" as used herein refers to a first amino acid sequence or nucleotide sequence covalently joined to a second amino acid sequence or nucleotide sequence, respectively (e.g., a secretion signal peptide amino acid sequence and/or a heterologous transmembrane domain amino acid sequence linked to a *C. acnes* polypeptide amino acid sequence). The first amino acid or nucleotide sequence can be directly joined to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

Acne lesions may be noninflammatory or inflammatory. Noninflammatory lesions of acne include open (blackheads) or closed (whiteheads) comedones. These lesions, especially closed comedones, may be precursors to the larger inflammatory lesions and therefore are of clinical importance. Inflammatory lesions may include papules, pustules, nodules and nodulocystic lesions, depending on the severity and location of the inflammation within the dermis. The papules and pustules may have surrounding halos of erythema allowing for their characterisation as inflammatory. Typically, nodules are erythematous and often tender and/or painful. In some embodiment, nodules are deep-seated in the skin (e.g. centred in the dermis and/or subcutis). Nodules may be greater than 5 mm in diameter.

Acne may be mild, moderate or severe, based on number and type of lesions affecting a specific skin area. Acne severity may be determined using the Investigator's Global Assessment (IGA) scale, which grades acne severity from 0 to 4. The IGA scale includes the following categories: clear (grade 0), almost clear (grade 1), mild severity (grade 2), moderate severity (grade 3), and severe (grade 4).

As used herein, the term "mild acne" refers to a severity grade of acne wherein some non-inflammatory lesions are present, with few inflammatory lesions. Typically, the subject has papules and/or pustules. e.g. the subject may have papules and/or pustules only. Typically, the subject does not have any nodulocystic lesions. Mild acne may be Grade 2 acne according to the IGA scale.

As used herein, the term "moderate acne" refers to a severity grade of acne wherein a subject has many comedones, papules and/or pustules. The subject may have a nodule, e.g. the subject may have no more than one nodule. Moderate acne typically affects more than half of a subject's face. Moderate acne may be Grade 3 acne according to the IGA scale.

As used herein, the term "severe acne" refers to a severity grade of acne wherein a subject has numerous comedones, papules and pustules. Typically the subject has one or more nodules and/or cysts. Severe acne typically affects a subject's entire face. For example, a subject's entire face may be covered with comedones, papules and pustules. Severe acne may be Grade 4 acne according to the IGA scale.

EMBODIMENTS

The invention includes at least the following numbered embodiments:

1. A nucleic acid comprising a nucleotide sequence encoding a modified *C. acnes* CAMP2 polypeptide, wherein the modified *C. acnes* CAMP2 polypeptide comprises an amino acid sequence comprising a *C. acnes* CAMP2 polypeptide sequence and a transmembrane domain sequence.
2. The nucleic acid of embodiment 1, wherein the transmembrane domain sequence is positioned at the N terminus or the C terminus (e.g. the C terminus) of the modified *C. acnes* CAMP2 polypeptide.
3. The nucleic acid of embodiment 1 or 2, wherein the transmembrane domain sequence comprises a viral transmembrane domain sequence, which is optionally selected from the group consisting of: an influenza hemagglutinin (HA) transmembrane domain sequence, a SARS COV-2 spike transmembrane domain sequence, a VZV gB transmembrane domain sequence, a VZV gE transmembrane domain sequence, a VZV gI transmembrane domain sequence, a VZV gK transmembrane domain sequence, a measles F-protein transmembrane domain sequence, a rubella E1 protein transmembrane domain sequence, a rubella E2 protein transmembrane domain sequence, a mumps F-protein transmembrane domain sequence, an Ebola GP protein transmembrane domain sequence and a rabies transmembrane domain sequence.
4. The nucleic acid of any one of embodiments 1-3, wherein the transmembrane domain sequence comprises an amino acid sequence according to any one of the sequences in Table 4.
5. The nucleic acid of any one of embodiments 1-4, wherein the transmembrane domain sequence comprises an amino acid sequence according to any one of SEQ ID NO: 208-209 (e.g., SEQ ID NO: 208).
6. The nucleic acid of any one of embodiments 1-5, wherein the modified *C. acnes* CAMP2 polypeptide comprises a non-native (e.g. viral) secretion signal peptide sequence.
7. The nucleic acid of embodiment 6, wherein the secretion signal peptide sequence is positioned at the N terminus or the C terminus (e.g. the N terminus) of the modified *C. acnes* CAMP2 polypeptide.
8. The nucleic acid of embodiment 6 or 7, wherein the secretion signal peptide sequence is a viral secretion signal peptide sequence, which optionally comprises a sequence selected from the group consisting of: an influenza hemagglutinin (HA) secretion signal peptide sequence, a SARS COV-2 spike secretion signal peptide sequence, a VZV gB secretion signal peptide sequence, a VZV gE secretion signal peptide sequence, a VZV gI secretion signal peptide sequence, a VZV gK secretion signal peptide sequence, a measles F-protein secretion signal peptide sequence, a rubella E1 protein secretion signal peptide sequence, a rubella E2 protein secretion signal peptide sequence, a mumps F-protein secretion signal peptide sequence, an Ebola GP protein secretion signal peptide sequence, and a smallpox 6 kDa IC protein secretion signal peptide sequence.
9. The nucleic acid of any one of embodiments 6-8, wherein the secretion signal peptide sequence comprises a sequence according to any one of the sequences in Table 2 or 3.
10. The nucleic acid of any one of embodiments 6-9, wherein the secretion signal peptide sequence comprises a sequence according to any one of SEQ ID NO: 210-211 (e.g., SEQ ID NO: 210).
11. The nucleic acid of any one of embodiments 1-10, wherein the modified *C. acnes* CAMP2 polypeptide comprises a mutation at one or more (e.g., all) positions corresponding to an N-glycosylation site and/or one or more (e.g., all) positions corresponding to an O-glycosylation site in a native *C. acnes* CAMP2 polypeptide, optionally wherein the mutation is a single amino acid substitution.
12. The nucleic acid of embodiment 11, wherein:
    (i) the *C. acnes* CAMP2 polypeptide comprises a mutation at position N166 relative to SEQ ID NO:

203, optionally wherein the mutation is a single amino acid substitution, e.g. N166S; and/or (ii) the *C. acnes* CAMP2 polypeptide comprises a substitution of one or more serine (Ser) and/or threonine (Thr) residue(s).

13. The nucleic acid of any one of embodiments 1-12, wherein the nucleic acid is a messenger RNA (mRNA).

14. The nucleic acid of embodiment 13, wherein the mRNA comprises a 5' cap, at least one 5' untranslated region (5' UTR), at least one 3' untranslated region (3' UTR), and/or at least one polyadenylation (poly(A)) sequence.

15. The nucleic acid of embodiments 13 or 14, wherein the mRNA is unmodified or:

(i) the mRNA comprises at least one chemical modification, optionally wherein the chemical modification is selected from the group consisting of e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxy methylaminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine (e.g., wherein the chemical modification comprises N1-methylpseudouridine); and/or (ii) the mRNA is synthesized from modified nucleotide analogues or derivatives of purines and pyrimidines, optionally wherein the modified nucleotide analogues or derivatives of purines and pyrimidines are selected from the group consisting of: 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxy methylaminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine.

16. The nucleic acid of embodiment 15, wherein the mRNA comprises at least one chemical modification (e.g., wherein at least 20%, at least 30%, at least 40%, at least 50%, at least 60%, at least 70%, at least 80%, at least 85%, at least 90%, at least 95%, or 100% of the uridines in the mRNA are chemically modified), optionally wherein the chemical modification comprises N1-methylpseudouridine e.g. in place of every uridine.

17. The nucleic acid of any one of embodiments 13-16, wherein the mRNA is a self-replicating mRNA or a non-replicating mRNA.

18. The nucleic acid of embodiment 17, wherein the mRNA is a non-replicating mRNA.

19. The nucleic acid of any one of embodiments 1-18, wherein:

(i) the modified *C. acnes* CAMP2 polypeptide comprises a sequence according to any one of SEQ ID NO: 203, SEQ ID NO: 207, SEQ ID NO: 43-58, SEQ ID NO: 1-16 or SEQ ID NO: 339-363 (e.g. SEQ ID NO: 207), or a sequence having at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 85%, 90% or 95%) identity thereto; and/or (ii) the *C. acnes* CAMP2 polypeptide comprises an amino acid substitution at one or more positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 203, e.g. wherein the *C. acnes* CAMP2 polypeptide comprises an amino acid substitution at one or more positions corresponding to residues T6 (e.g. T6I), A9 (e.g. A9T), S11 (e.g. S11A), S18 (e.g. S18N), D19 (e.g. D19E or D19Y), R21 (e.g. R21H), I24 (e.g. I24M, I24L or 124T), A29 (e.g. A29P), H30 (e.g. H30R), V37 (e.g. V37A), D48 (e.g. D48N), R61 (e.g. R61H), E65 (e.g. E65D), A68 (e.g. A68T), D76 (e.g. D76N), V87 (e.g. V87A), I91 (e.g. 191V), D92 (e.g. D92G), T98 (e.g. T98K), T100 (e.g. T100I), R106 (e.g. R106S), K118 (e.g. K118N), S128 (e.g. S128T), A138 (e.g. A138T), R143 (e.g. R143H), E145 (e.g. E145D or E145K), T154 (e.g. T154A), K169 (e.g. K169R), N177 (e.g. N177D), D179 (e.g. D179N or D179H), A189 (e.g. A189E), N207 (e.g. N207D or N207A), E221 (e.g. E221K) and/or L223 (e.g. L223F) of SEQ ID NO: 203.

20. The nucleic acid of any one of embodiments 1-19, wherein the nucleic acid comprises a nucleotide sequence according to any one of SEQ ID NO: 153-167. SEQ ID NO: 87-101, SEQ ID NO: 391-392 or SEQ ID NO: 398-399 (e.g., SEQ ID NO: 91, SEQ ID NO: 90, SEQ ID NO: 391 or SEQ ID NO: 392, such as SEQ ID NO: 91), or a sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 75%, 80% or 85%, such as 75% or 80%) identity thereto.

21. A modified *C. acnes* CAMP2 polypeptide having an amino acid sequence comprising a *C. acnes* CAMP2 polypeptide sequence and a transmembrane domain sequence.

22. The modified *C. acnes* CAMP2 polypeptide of embodiment 21, wherein the transmembrane domain sequence is positioned at the N terminus or the C-terminus (e.g. the C terminus) of the modified *C. acnes* CAMP2 polypeptide.

23. The modified *C. acnes* CAMP2 polypeptide of embodiment 21 or 22, wherein the transmembrane domain sequence comprises a viral transmembrane domain sequence, which is optionally selected from the group consisting of: an influenza hemagglutinin (HA) transmembrane domain sequence, a SARS COV-2 spike transmembrane domain sequence, a VZV gB transmembrane domain sequence, a VZV gE transmembrane domain sequence, a VZV gI transmembrane domain sequence, a VZV gK transmembrane domain sequence, a measles F-protein transmembrane domain sequence, a rubella E1 protein transmembrane domain sequence, a rubella E2 protein transmembrane domain sequence, a mumps F-protein transmembrane domain sequence, an Ebola GP protein transmembrane domain sequence and a rabies transmembrane domain sequence.
24. The modified *C. acnes* CAMP2 polypeptide of any one of embodiments 21-23, wherein the transmembrane domain sequence comprises an amino acid sequence according to any one of the sequences in Table 4.
25. The modified *C. acnes* CAMP2 polypeptide of any one of embodiments 21-24, wherein the transmembrane domain sequence comprises an amino acid sequence according to any one of SEQ ID NO: 208-209.
26. The modified *C. acnes* CAMP2 polypeptide of any one of embodiments 21-25, wherein the modified *C. acnes* CAMP2 polypeptide comprises a mutation at one or more (e.g., all) positions corresponding to an N-glycosylation site and/or one or more (e.g., all) positions corresponding to an O-glycosylation site in a native *C. acnes* CAMP2 polypeptide, optionally wherein the mutation is a single amino acid substitution.
27. The modified *C. acnes* CAMP2 polypeptide of embodiment 26, wherein the *C. acnes* CAMP2 polypeptide comprises a mutation at position N166 relative to SEQ ID NO: 203, optionally wherein:
    (i) the mutation is a single amino acid substitution, e.g. N166S; and/or
    (ii) the *C. acnes* CAMP2 polypeptide comprises a substitution of one or more serine (Ser) and/or threonine (Thr) residue(s).
28. The modified *C. acnes* CAMP2 polypeptide of any one of embodiments 21-27, wherein
    (i) the modified *C. acnes* CAMP2 polypeptide comprises a sequence according to any one of SEQ ID NO: 203, SEQ ID NO: 207, SEQ ID NO: 43-58, SEQ ID NO: 1-16 or SEQ ID NO: 339-363 (e.g. SEQ ID NO: 207), or a sequence having at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 85%, 90% or 95%) identity thereto; and/or
    (ii) the *C. acnes* CAMP2 polypeptide comprises an amino acid substitution at one or more positions corresponding to residues 6, 9, 11, 18, 19, 21, 24, 29, 30, 37, 48, 61, 65, 68, 76, 87, 91, 92, 98, 100, 106, 118, 128, 138, 143, 145, 154, 169, 177, 179, 189, 207, 221 and/or 223 of SEQ ID NO: 203, e.g. wherein the *C. acnes* CAMP2 polypeptide comprises an amino acid substitution at one or more positions corresponding to residues T6 (e.g. T6I), A9 (e.g. A9T), S11 (e.g. S11A), S18 (e.g. S18N), D19 (e.g. D19E or D19Y), R21 (e.g. R21H), I24 (e.g. I24M, I24L or I24T), A29 (e.g. A29P), H30 (e.g. H30R), V37 (e.g. V37A), D48 (e.g. D48N), R61 (e.g. R61H), E65 (e.g. E65D), A68 (e.g. A68T), D76 (e.g. D76N), V87 (e.g. V87A), I91 (e.g. 191V), D92 (e.g. D92G), T98 (e.g. T98K), T100 (e.g. T100I), R106 (e.g. R106S), K118 (e.g. K118N), S128 (e.g. S128T), A138 (e.g. A138T), R143 (e.g. R143H), E145 (e.g. E145D or E145K), T154 (e.g. T154A), K169 (e.g. K169R), N177 (e.g. N177D), D179 (e.g. D179N or D179H), A189 (e.g. A189E), N207 (e.g. N207D or N207A), E221 (e.g. E221K) and/or L223 (e.g. L223F) of SEQ ID NO: 203.
29. A composition, optionally an immunogenic composition, comprising the nucleic acid (e.g. a mRNA) of any one of embodiments 1-20.
30. An immunogenic composition comprising a nucleic acid comprising a nucleotide sequence encoding a *C. acnes* CAMP2 polypeptide, wherein the nucleic acid is a mRNA.
31. A composition, optionally an immunogenic composition, comprising a nucleic acid comprising a nucleotide sequence encoding a *C. acnes* CAMP2 polypeptide and a lipid nanoparticle (LNP), optionally wherein the nucleotide sequence encoding the *C. acnes* CAMP2 polypeptide is encapsulated in the LNP.
32. A composition, optionally an immunogenic composition, comprising:
    (a) a nucleic acid (e.g., a mRNA) comprising a nucleotide sequence encoding a *C. acnes* CAMP2 polypeptide; and
    (b) one or more of:
        (i) a nucleic acid comprising a nucleotide sequence encoding a *C. acnes* DsA1 polypeptide;
        (ii) a nucleic acid comprising a nucleotide sequence encoding a *C. acnes* DsA2 polypeptide;
        (iii) a nucleic acid comprising a nucleotide sequence encoding a *C. acnes* PITP polypeptide;
        (iv) a nucleic acid comprising a nucleotide sequence encoding a chimeric *C. acnes* DsA1/DsA2 polypeptide; and
        (v) a nucleic acid comprising a nucleotide sequence encoding a chimeric *C. acnes* DsA1/DsA2/PITP polypeptide.
33. The composition of embodiment 32, wherein the composition comprises:
    the nucleic acid in (a) and the nucleic acid in (b) (i), and optionally the nucleic acid in (b) (ii) and/or the nucleic acid in (b) (iii);
    the nucleic acid in (a) and the nucleic acid in (b) (ii), and optionally the nucleic acid in (b) (i) and/or the nucleic acid in (b) (iii);
    the nucleic acid in (a) and the nucleic acid in (b) (iii), and optionally the nucleic acid in (b) (i) and/or the nucleic acid in (b) (ii);
    the nucleic acid in (a) and the nucleic acid in (b) (iv), and optionally the nucleic acid in (b) (iii);
    the nucleic acid in (a) and the nucleic acid in (b) (v); or
    the nucleic acid in (a) and the nucleic acid in (b) (i)-(iii).
34. The composition of embodiment 32 or 33, wherein the composition comprises the nucleic acid in (a), the nucleic acid in (b) (iii) and the nucleic acid in (b) (iv), optionally wherein the nucleic acids are present in a weight ratio of 1:1:1.

35. The composition of embodiment 34, wherein
 the *C. acnes* CAMP2 polypeptide comprises a sequence according to SEQ ID NO: 203 or a sequence having at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g. at least 85%, 90% or 95%) identity thereto:
 the chimeric *C. acnes* DsA1/DsA2 polypeptide comprises a sequence according to SEQ ID NO: 70 or a sequence having at least 90%, at least 91%, at least 92%, at least 93%, at least 94%, at least 95%, at least 96%, at least 97%, at least 98%, or at least 99% (e.g., at least 90%) identity thereto; and
 the *C. acnes* PITP polypeptide comprises a sequence according to SEQ ID NO: 73 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity thereto.

36. The composition of embodiment 32 or 33, wherein the composition comprises the nucleic acid in (a) and the nucleic acid in (b) (v), optionally wherein the nucleic acid in b (v) has a nucleotide sequence according to SEQ ID NO: 80, SEQ ID NO: 82 or SEQ ID NO: 83 (e.g. SEQ ID NO: 80 or SEQ ID NO: 83).

37. The composition of any one of embodiments 32-35, wherein any two or more nucleic acids in (a) and (b) (i)-(v) are located on the same nucleic acid molecule or on different nucleic acid molecules (e.g. wherein all the nucleic acids in the composition are on the same nucleic acid molecule or wherein all the nucleic acids in the composition are on individual nucleic acid molecules).

38. The composition of embodiment 34, wherein the nucleic acid in (a), the nucleic acid in (b) (iii) and the nucleic acid in (b) (iv) are located on the same nucleic acid molecule or separate nucleic acid molecules.

39. The composition of embodiment 35, wherein the nucleic acid in (a) and the nucleic acid in (b) (v) are located on the same nucleic acid molecule or separate nucleic acid molecules.

40. The composition of any one of embodiments 29-31, wherein the composition further comprises one or more of:
 (i) a nucleic acid comprising a nucleotide sequence encoding a *C. acnes* DsA1 polypeptide;
 (ii) a nucleic acid comprising a nucleotide sequence encoding a *C. acnes* DsA2 polypeptide;
 (iii) a nucleic acid comprising a nucleotide sequence encoding a *C. acnes* PITP polypeptide;
 (iv) a nucleic acid comprising a nucleotide sequence encoding a chimeric *C. acnes* DsA1/DsA2 polypeptide; and
 (v) a nucleic acid comprising a nucleotide sequence encoding a chimeric *C. acnes* DsA1/DsA2/PITP polypeptide.

41. The composition of embodiment 40, wherein the composition comprises:
 the nucleic acid in (i), and optionally the nucleic acid in (ii) and/or the nucleic acid in (iii);
 the nucleic acid in (ii), and optionally the nucleic acid in (i) and/or the nucleic acid in (iii);
 the nucleic acid in (iii), and optionally the nucleic acid in (i) and/or the nucleic acid in (ii);
 the nucleic acid in (iv), and optionally the nucleic acid in (iii);
 the nucleic acid in (v); or
 the nucleic acid in (i)-(iii).

42. The composition of embodiment 40 or 41, wherein the composition comprises the nucleic acid in (iii) and the nucleic acid in (iv), optionally wherein the nucleic acids are present in a weight ratio of 1:1:1.

43. The composition of embodiment 42, wherein:
 (i) the *C. acnes* CAMP2 polypeptide comprises a sequence according to SEQ ID NO: 207 or a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% (e.g. at least 60%, such as at least 85%, 90% or 95%) identity thereto; the chimeric *C. acnes* DsA1/DsA2 polypeptide comprises a sequence according to SEQ ID NO: 70 or a sequence having at least 90%, at least 91%, at least 92%, at least 93%, at least 94%, at least 95%, at least 96%, at least 97%, at least 98%, or at least 99% (e.g., at least 90%) identity thereto; and the *C. acnes* PITP polypeptide comprises a sequence according to SEQ ID NO: 73 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity thereto; or
 (ii) the nucleotide sequence encoding the *C. acnes* CAMP2 polypeptide comprises a sequence according to SEQ ID NO: 91 or a sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%, 80% or 85%) identity thereto;
 the nucleotide sequence encoding the chimeric *C. acnes* DsA1/DsA2 polypeptide comprises a sequence according to SEQ ID NO: 113 or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto; and
 the nucleotide sequence encoding the *C. acnes* PITP polypeptide comprises a sequence according to SEQ ID NO: 115 or a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% (e.g., at least 50%) identity thereto.

44. The composition of embodiment 40 or 41, wherein the composition comprises the nucleic acid in (v), optionally wherein the nucleic acid in (v) comprises a nucleotide sequence according to SEQ ID NO: 80, SEQ ID NO: 82 or SEQ ID NO: 83 (e.g., SEQ ID NO: 80 or 83).

45. The composition of any one of embodiments 40-44, wherein any two or more of (a) the nucleic acid of any one of embodiments 1-20 and (b) the nucleic acids in (i)-(v) are located on the same nucleic acid molecule or on different nucleic acid molecules (e.g. on the same nucleic acid molecule).
46. The composition of embodiment 45, wherein the nucleic acid in (a), the nucleic acid in (b) (iii) and the nucleic acid in (b) (iv) are located on the same nucleic acid molecule.
47. The composition of any one of embodiments 40-44, wherein any two or more of (a) the nucleic acid comprising a nucleotide sequence encoding a *C. acnes* CAMP2 polypeptide and (b) the nucleic acids in (i)-(v) are located on the same nucleic acid molecule or on different nucleic acid molecules (e.g. on the same nucleic acid molecule).
48. The composition of embodiment 47, wherein the nucleic acid in (a) and the nucleic acid in (b) (v) are located on the same nucleic acid molecule.
49. The composition of any one of embodiments 29-30 or 32-48, wherein the composition further comprises a lipid nanoparticle (LNP), optionally wherein any one or more nucleic acids are encapsulated in the LNP, e.g. wherein the LNP has an average diameter of 30 nm to 200 nm (e.g. an average diameter of 80 nm to 150 nm).
50. The composition of embodiment 31 or 49, wherein the LNP comprises at least one cationic lipid, optionally wherein the cationic lipid:
    is biodegradable or is not biodegradable, and/or
    the cationic lipid is cleavable or is not cleavable.
51. The composition of embodiment 49 or 50, wherein the cationic lipid is selected from the group consisting of OF-02, cKK-E10, OF-Deg-Lin, GL-HEPES-E3-E10-DS-3-E18-1, GL-HEPES-E3-E12-DS-4-E10, GL-HEPES-E3-E12-DS-3-E14, SM-102, ALC-0315, IM-001 and IS-001.
52. The composition of any one of embodiments 49-51, wherein the cationic lipid is selected from the group consisting of OF-02, cKK-E10, GL-HEPES-E3-E12-DS-4-E10, IM-001 and IS-001 (e.g., wherein the cationic lipid is GL-HEPES-E3-E12-DS-4-E10).
53. The composition of any one of embodiments 31 or 49-52, wherein the LNP further comprises a polyethylene glycol (PEG) conjugated (PEGylated) lipid, a cholesterol-based lipid, and a helper lipid, optionally wherein the LNP comprises: a cationic lipid at a molar ratio of 35% to 55%; a polyethylene glycol (PEG) conjugated (PEGylated) lipid at a molar ratio of 0.25% to 2.75%; a cholesterol-based lipid at a molar ratio of 20% to 45%; and a helper lipid at a molar ratio of 5% to 35%, wherein all of the molar ratios are relative to the total lipid content of the LNP,
    e.g. wherein the LNP comprises a cationic lipid at a molar ratio of 40%, a PEGylated lipid at a molar ratio of 1.5%, a cholesterol-based lipid at a molar ratio of 28.5%, and a helper lipid at a molar ratio of 30%.
54. The composition of any one of embodiments 49-53, wherein any two or more (e.g., three) nucleic acids are co-encapsulated in a single LNP.
55. The composition of any one of embodiments 49-53, wherein any two or more (e.g., three) nucleic acids are encapsulated in separate LNPs.
56. The composition of any one of embodiments 29-55, wherein the mRNA comprises a 5' cap, at least one 5' untranslated region (5' UTR), at least one 3' untranslated region (3' UTR), and/or at least one polyadenylation (poly(A)) sequence.
57. The composition of any one of embodiments 29-56, wherein the mRNA is unmodified or:
    (i) the mRNA comprises at least one chemical modification, optionally wherein the chemical modification is selected from the group consisting of e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine (e.g., wherein the chemical modification comprises N1-methylpseudouridine); and/or
    (ii) the mRNA is synthesized from modified nucleotide analogues or derivatives of purines and pyrimidines, optionally wherein the modified nucleotide analogues or derivatives of purines and pyrimidines are selected from the group consisting of: 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethyl-aminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine.
58. The composition of any one of embodiments 29-57, wherein the mRNA comprises at least one chemical modification (e.g., wherein at least 20%, at least 30%, at least 40%, at least 50%, at least 60%, at least 70%, at least 80%, at least 85%, at least 90%, at least 95%, or 100% of the uridines in the mRNA are chemically modified), optionally wherein the chemical modification comprises N1-methylpseudouridine e.g. in place of every uridine.
59. The composition of any one of embodiments 29-58, wherein the mRNA is a self-replicating mRNA or a non-replicating mRNA, e.g. wherein the mRNA is a non-replicating mRNA.

60. The composition of any one of embodiments 29-59, wherein the composition can be in a frozen liquid form or in a lyophilized form (e.g., in a lyophilized form).
61. A composition, optionally an immunogenic composition, comprising the modified *C. acnes* CAMP2 polypeptide as defined in any one of embodiments 21-28.
62. The composition of embodiment 61, wherein the composition further comprises a *C. acnes* DsA1 polypeptide.
63. The composition of embodiment 61 or 62, wherein the composition further comprises a *C. acnes* DsA2 polypeptide.
64. The composition of any of embodiments 61-63, wherein the composition further comprises a *C. acnes* PITP polypeptide.
65. The composition of any of embodiments 61-64, wherein the composition further comprises a chimeric *C. acnes* DsA1/DsA2 polypeptide.
66. The composition of any of embodiments 61-65, wherein the composition further comprises a chimeric *C. acnes* DsA1/DsA2/PITP polypeptide.
67. The composition of embodiment 61, wherein the composition further comprises a chimeric *C. acnes* DsA1/DsA2 polypeptide and a *C. acnes* PITP polypeptide.
68. A composition, optionally an immunogenic composition, comprising:
    (a) a *C. acnes* CAMP2 polypeptide; and
    (b) one or more of:
        (i) a *C. acnes* DsA1 polypeptide,
        (ii) a *C. acnes* DsA2 polypeptide,
        (iii) a *C. acnes* PITP polypeptide,
        (iv) a chimeric *C. acnes* DsA1/DsA2 polypeptide, and
        (v) a chimeric *C. acnes* DsA1/DsA2/PITP polypeptide.
69. The composition of embodiment 68, wherein the composition comprises:
    the polypeptide in (a) and the polypeptide in (b) (i), and optionally the polypeptide in (b) (ii) and/or the polypeptide in (b) (iii);
    the polypeptide in (a) and the polypeptide in (b) (ii), and optionally the polypeptide in (b) (i) and/or the polypeptide in (b) (iii);
    the polypeptide in (a) and the polypeptide in (b) (iii), and optionally the polypeptide in (b) (i) and/or the polypeptide in (b) (ii);
    the polypeptide in (a) and the polypeptide in (b) (iv), and optionally the polypeptide in (b) (iii);
    the polypeptide in (a) and the polypeptide in (b) (v); or
    the polypeptide in (a) and the polypeptide in (b) (i)-(iii).
70. The composition of any one of embodiments 61-69, wherein the composition further comprises an adjuvant, optionally wherein the adjuvant is selected from the group consisting of: Aluminum based adjuvant (e.g. AlOOH), Squalene based oil in water emulsion adjuvants (e.g. AF03, AS03, MF59) and Liposome-based adjuvants comprising a saponin and a TLR4 agonist (e.g. SPA14, AS01, LEQ), further optionally wherein the adjuvant is selected from the group consisting of AlOOH, AF03 and SPA14.
71. The composition of any one of embodiments 29-70, wherein one or more of the *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, and the chimeric *C. acnes* DsA1/DsA2/PITP polypeptide further comprises:
    (i) a non-native transmembrane domain sequence (e.g. a viral transmembrane domain sequence; and/or
    (ii) a non-native secretion signal peptide sequence.
72. The composition of any one of embodiments 61-71, wherein the composition can be in a frozen liquid form or in a lyophilized form.
73. A combination comprising:
    (a) a nucleic acid (e.g., a mRNA) comprising a nucleotide sequence encoding a *C. acnes* CAMP2 polypeptide; and
    (b) one or more of:
        (i) a nucleic acid comprising a nucleotide sequence encoding a *C. acnes* DsA1 polypeptide;
        (ii) a nucleic acid comprising a nucleotide sequence encoding a *C. acnes* DsA2 polypeptide;
        (iii) a nucleic acid comprising a nucleotide sequence encoding a *C. acnes* PITP polypeptide;
        (iv) a nucleic acid comprising a nucleotide sequence encoding a chimeric *C. acnes* DsA1/DsA2 polypeptide; and
        (v) a nucleic acid comprising a nucleotide sequence encoding a chimeric *C. acnes* DsA1/DsA2/PITP polypeptide.
74. The combination of embodiment 73, wherein the combination comprises:
    the nucleic acid in (a) and the nucleic acid in (b) (i), and optionally the nucleic acid in (b) (ii) and/or the nucleic acid in (b) (iii);
    the nucleic acid in (a) and the nucleic acid in (b) (ii), and optionally the nucleic acid in (b) (i) and/or the nucleic acid in (b) (iii);
    the nucleic acid in (a) and the nucleic acid in (b) (iii), and optionally the nucleic acid in (b) (i) and/or the nucleic acid in (b) (ii);
    the nucleic acid in (a) and the nucleic acid in (b) (iv), and optionally the nucleic acid in (b) (iii);
    the nucleic acid in (a) and the nucleic acid in (b) (v); or
    the nucleic acid in (a) and the nucleic acid in (b) (i)-(iii).
75. The combination of embodiment 73 or 74, wherein the combination comprises the nucleic acid in (a), the nucleic acid in (b) (iii) and the nucleic acid in (b) (iv).
76. The combination of embodiment 73 or 74, wherein the combination comprises the nucleic acid in (a) and the nucleic acid in (b) (v).
77. The combination of any one of embodiments 73-76, wherein any two or more nucleic acids in (a) and (b) (i)-(v) are located on the same nucleic acid molecule or on different nucleic acid molecules (e.g. wherein all the nucleic acids in the composition are on the same nucleic acid molecule or wherein all the nucleic acids in the composition are on individual nucleic acid molecules).
78. The combination of embodiment 75, wherein the nucleic acid in (a), the nucleic acid in (b) (iii) and the nucleic acid in (b) (iv) are located on the same nucleic acid molecule or on individual nucleic acid molecules.
79. The combination of embodiment 76, wherein the nucleic acid in (a) and the nucleic acid in (b) (v) are located on the same nucleic acid molecule.

80. A combination comprising the nucleic acid (e.g. a mRNA) of any one of embodiments 1-20 and one or more of:
  (i) a nucleic acid comprising a nucleotide sequence encoding a *C. acnes* DsA1 polypeptide;
  (ii) a nucleic acid comprising a nucleotide sequence encoding a *C. acnes* DsA2 polypeptide;
  (iii) a nucleic acid comprising a nucleotide sequence encoding a *C. acnes* PITP polypeptide;
  (iv) a nucleic acid comprising a nucleotide sequence encoding a chimeric *C. acnes* DsA1/DsA2 polypeptide; and
  (v) a nucleic acid comprising a nucleotide sequence encoding a chimeric *C. acnes* DsA1/DsA2/PITP polypeptide.
81. The combination of embodiment 80, wherein the combination comprises:
  the nucleic acid in (i), and optionally the nucleic acid in (ii) and/or the nucleic acid in (iii);
  the nucleic acid in (ii), and optionally the nucleic acid in (i) and/or the nucleic acid in (iii);
  the nucleic acid in (iii), and optionally the nucleic acid in (i) and/or the nucleic acid in (ii);
  the nucleic acid in (iv), and optionally the nucleic acid in (iii);
  the nucleic acid in (v); or
  the nucleic acid in (i)-(iii).
82. The combination of embodiment 80 or 81, wherein the combination comprises the nucleic acid in (iii) and the nucleic acid in (iv).
83. The combination of embodiment 80 or 81, wherein the combination comprises the nucleic acid in (v).
84. The combination of any one of embodiments 80-83, wherein any two or more of (a) the nucleic acid of any one of embodiments 1-20 and (b) the nucleic acids in (i)-(v) are located on the same nucleic acid molecule or on different nucleic acid molecules (e.g. on the same nucleic acid molecule).
85. The combination of embodiment 84, wherein the nucleic acid in (a), the nucleic acid in (b) (iii) and the nucleic acid in (b) (iv) are located on the same nucleic acid molecule or separate nucleic acid molecules.
86. The combination of embodiment 84, wherein the nucleic acid in (a) and the nucleic acid in (b) (v) are located on the same nucleic acid molecule or separate nucleic acid molecules.
87. A combination comprising the modified *C. acnes* CAMP2 polypeptide as defined in any one of embodiments 21-28 and one or more of:
  (i) a *C. acnes* DsA1 polypeptide;
  (ii) a *C. acnes* DsA2 polypeptide;
  (iii) a *C. acnes* PITP polypeptide;
  (iv) a chimeric *C. acnes* DsA1/DsA2 polypeptide; and
  (v) a chimeric *C. acnes* DsA1/DsA2/PITP polypeptide.
88. The combination of embodiment 87, wherein the combination comprises:
  the polypeptide in (i), and optionally the polypeptide in (ii) and/or the polypeptide in (iii);
  the polypeptide in (ii), and optionally the polypeptide in (i) and/or the polypeptide in (iii);
  the polypeptide in (iii), and optionally the polypeptide in (i) and/or the polypeptide in (ii);
  the polypeptide in (iv), and optionally the polypeptide in (iii);
  the polypeptide in (v); or
  the polypeptide in (i)-(iii).
89. A combination, optionally an immunogenic combination, comprising:
  (a) a *C. acnes* CAMP2 polypeptide; and
  (b) one or more of:
    (i) a *C. acnes* DsA1 polypeptide,
    (ii) a *C. acnes* DsA2 polypeptide,
    (iii) a *C. acnes* PITP polypeptide,
    (iv) a chimeric *C. acnes* DsA1/DsA2 polypeptide, and
    (v) a chimeric *C. acnes* DsA1/DsA2/PITP polypeptide.
90. The combination of embodiment 89, wherein the combination comprises:
  the polypeptide in (a) and the polypeptide in (b) (i), and optionally the polypeptide in (b) (ii) and/or the polypeptide in (b) (iii);
  the polypeptide in (a) and the polypeptide in (b) (ii), and optionally the polypeptide in (b) (i) and/or the polypeptide in (b) (iii);
  the polypeptide in (a) and the polypeptide in (b) (iii), and optionally the polypeptide in (b) (i) and/or the polypeptide in (b) (ii);
  the polypeptide in (a) and the polypeptide in (b) (iv), and optionally the polypeptide in (b)(iii);
  the polypeptide in (a) and the polypeptide in (b) (v); or the polypeptide in (a) and the polypeptide in (b) (i)-(iii).
91. The combination of any one of embodiments 73-90, wherein the one or more of the *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, and the chimeric *C. acnes* DsA1/DsA2/PITP polypeptide further comprise a non-native transmembrane domain sequence (e.g. a viral transmembrane domain sequence).
92. The combination of any one of embodiments 73-91, wherein the one or more of the *C. acnes* CAMP2 polypeptide, the *C. acnes* DsA1 polypeptide, the *C. acnes* DsA2 polypeptide, the *C. acnes* PITP polypeptide, the chimeric *C. acnes* DsA1/DsA2 polypeptide, and the chimeric *C. acnes* DsA1/DsA2/PITP polypeptide further comprise a non-native secretion signal peptide sequence.
93. The combination of any one of embodiments 73-92, wherein the nucleic acids are present in the same composition.
94. The combination of any one of embodiments 73-92, wherein the nucleic acids are present in two or more separate compositions.
95. The combination of any one of embodiments 89-92, wherein the polypeptides are present in the same composition.
96. The combination of any one of embodiments 89-92, wherein the polypeptides are present in two or more separate compositions.
97. A nucleic acid comprising a nucleotide sequence encoding a chimeric *C. acnes* DsA1/DsA2 polypeptide, wherein the chimeric *C. acnes* DsA1/DsA2 polypeptide comprises an amino acid sequence comprising:
  (i) the sequence of SEQ ID NO: 70, or a sequence having at least 90%, at least 91%, at least 92%, at least 93%, at least 94%, at least 95%, at least 96%, at least 97%, at least 98%, or at least 99% (e.g., at least 90%) identity to SEQ ID NO: 70; and
  (ii) a secretion signal peptide sequence e.g., a non-native secretion signal peptide sequence and/or a heterologous transmembrane domain, optionally wherein the chimeric *C. acnes* DsA1/DsA2 polypeptide comprises a sequence according to SEQ ID NO: 28 or a sequence having at least 90%, at least 91%, at least 92%, at least 93%, at least 94%, at least 95%, at least 96%, at least 97%, at least 98%, or at least 99% (e.g., at least 90%) identity to SEQ ID NO: 28.

98. The nucleic acid of embodiment 97 wherein the chimeric *C. acnes* DsA1/DsA2 polypeptide comprises a non-native secretion signal peptide sequence.

99. The nucleic acid of embodiment 97 or 98, wherein the secretion signal peptide sequence is positioned at the N terminus or the C terminus (e.g. the N terminus) of the chimeric *C. acnes* DsA1/DsA2 polypeptide.

100. The nucleic acid of any one of embodiments 97-99, wherein the heterologous transmembrane domain is positioned at the N terminus or the C terminus (e.g. the C terminus) of the chimeric *C. acnes* DsA1/DsA2 polypeptide.

101. The nucleic acid of any one of embodiments 97-100, wherein the nucleic acid comprises:

(i) a sequence of SEQ ID NO: 113 or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity to SEQ ID NO: 113; or (ii) a sequence of SEQ ID NO: 179 or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity to SEQ ID NO: 179.

102. The nucleic acid of any one of embodiments 97-101, wherein the nucleic acid is a mRNA.

103. A chimeric *C. acnes* DsA1/DsA2 polypeptide comprising (i) the sequence of SEQ ID NO: 70, or a sequence having at least 90%, at least 91%, at least 92%, at least 93%, at least 94%, at least 95%, at least 96%, at least 97%, at least 98%, or at least 99% (e.g., at least 90%) identity to SEQ ID NO: 70; and (ii) a heterologous transmembrane domain.

104. The chimeric *C. acnes* DsA1/DsA2 polypeptide of embodiment 103, wherein the heterologous transmembrane domain is positioned at the N terminus or the C terminus (e.g. the C terminus) of the chimeric *C. acnes* DsA1/DsA2 polypeptide.

105. The chimeric *C. acnes* DsA1/DsA2 polypeptide of any one of embodiments 103-104, wherein the polypeptide comprises the sequence of SEQ ID NO: 28 or a sequence having at least 90%, at least 91%, at least 92%, at least 93%, at least 94%, at least 95%, at least 96%, at least 97%, at least 98%, or at least 99% (e.g., at least 90%) identity to SEQ ID NO: 28.

106. A nucleic acid comprising a nucleotide sequence encoding a *C. acnes* PITP polypeptide, wherein the *C. acnes* PITP polypeptide comprises an amino acid sequence comprising:

(i) the sequence of SEQ ID NO: 73, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity thereto; and (ii) a secretion signal peptide sequence, e.g., a non-native secretion signal peptide sequence, and/or a heterologous transmembrane domain, optionally wherein the *C. acnes* PITP polypeptide comprises an amino acid sequence according to SEQ ID NO: 31 or an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity to SEQ ID NO: 31.

107. The nucleic acid of embodiment 106, wherein the *C. acnes* PITP polypeptide comprises a non-native secretion signal peptide sequence.

108. The nucleic acid of embodiment 106 or 107, wherein the heterologous transmembrane domain is positioned at the at the N terminus or the C terminus (e.g. the C terminus) of the *C. acnes* PITP polypeptide.

109. The nucleic acid of any one of embodiments 106-108, wherein the secretion signal peptide sequence is positioned at the N terminus or the C terminus (e.g. the N terminus) of the *C. acnes* PITP polypeptide.

110. The nucleic acid of any one of embodiments 106-109, wherein the nucleic acid comprises a sequence of SEQ ID NO: 115 or a sequence of SEQ ID NO: 182 or a sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity to SEQ ID NO: 115 or SEQ ID NO: 182.

111. The nucleic acid of any one of embodiments 106-110, wherein the nucleic acid is mRNA.

112. A *C. acnes* PITP polypeptide comprising (i) the sequence of SEQ ID NO: 73, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity to SEQ ID NO: 73, and (ii) a heterologous transmembrane domain.

113. The *C. acnes* PITP polypeptide of embodiment 112, wherein the heterologous transmembrane domain is positioned at the N terminus or the C terminus (e.g. the C terminus) of the *C. acnes* PITP polypeptide.

114. The *C. acnes* PITP polypeptide of any one of embodiments 112-113, wherein the polypeptide comprises a sequence of SEQ ID NO: 31 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity to SEQ ID NO: 31.

115. A nucleic acid comprising a nucleotide sequence encoding a chimeric *C. acnes* DsA1/DsA2/PITP polypeptide, wherein the chimeric *C. acnes* DsA1/DsA2/PITP polypeptide comprises an amino acid sequence comprising:

(i) a chimeric *C. acnes* DsA1/DsA2 polypeptide sequence which comprises the sequence of SEQ ID NO: 70, or a sequence having at least 90%, at least 91%, at least 92%, at least 93%, at least 94%, at least 95%, at least 96%, at least 97%, at least 98%, or at least 99% (e.g., at least 90%) identity to SEQ ID NO: 70; and (ii) a *C. acnes* PITP polypeptide sequence;

and wherein (i) and (ii) are encoded on the same nucleic acid molecule.

116. The nucleic acid of embodiment 115, wherein the *C. acnes* PITP polypeptide sequence comprises an amino acid sequence corresponding to residues 1 to 133 of SEQ ID NO: 206 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity thereto.

117. The nucleic acid of embodiment 116, wherein the *C. acnes* PITP polypeptide sequence consists of an amino acid sequence corresponding to residues 1 to 133 of SEQ ID NO: 206 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity thereto.

118. The nucleic acid of embodiment 115 or 116, wherein the *C. acnes* PITP polypeptide sequence comprises an amino acid sequence corresponding to residues 1 to 146 of SEQ ID NO: 206 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity thereto.

119. The nucleic acid of embodiment 115 or 116, wherein the *C. acnes* PITP polypeptide sequence consists of an amino acid sequence corresponding to residues 1 to 146 of SEQ ID NO: 206 or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity thereto.

120. The nucleic acid of any one of embodiments 115-119, wherein the nucleic acid comprises a sequence of any one of SEQ ID NO: 189 or 192 or a sequence having at least 50%, at least 75%, at least 80%, at least 85%, at least 90%, at least 91%, at least 92%, at least 93%, at least 94%, at least 95%, at least 96%, at least 97%, at least 98%, or at least 99% (e.g. at least 85%) identity to any one of SEQ ID NO: 189 or 192.

121. The nucleic acid of any one of embodiments 115-120, wherein the chimeric *C. acnes* DsA1/DsA2/PITP polypeptide further comprises a secretion signal peptide sequence (e.g., a viral a secretion signal peptide sequence).

122. The nucleic acid of any one of embodiments 115-121, wherein the chimeric *C. acnes* DsA1/DsA2/PITP polypeptide further comprises a heterologous transmembrane domain sequence.

123. A chimeric DsA1/DsA2/PITP polypeptide comprising an amino acid sequence comprising:

(i) a chimeric *C. acnes* DsA1/DsA2 polypeptide sequence comprising the sequence of SEQ ID NO: 70, or a sequence having at least 90%, at least 91%, at least 92%, at least 93%, at least 94%, at least 95%, at least 96%, at least 97%, at least 98%, or at least 99% (e.g., at least 90%) identity to SEQ ID NO: 70; and (ii) a *C. acnes* PITP polypeptide sequence.

124 The chimeric DsA1/DsA2/PITP polypeptide of embodiment 123, wherein the *C. acnes* PITP polypeptide sequence comprises an amino acid sequence corresponding to residues 1 to 133 of SEQ ID NO: 206.

125. The chimeric DsA1/DsA2/PITP polypeptide of embodiment 123, wherein the *C. acnes* PITP polypeptide sequence consists of an amino acid sequence corresponding to residues 1 to 133 of SEQ ID NO: 206.

126. The chimeric DsA1/DsA2/PITP polypeptide of embodiment 123, wherein the *C. acnes* PITP polypeptide sequence comprises an amino acid sequence corresponding to residues 1 to 146 of SEQ ID NO: 206.

127. The chimeric DsA1/DsA2/PITP polypeptide of embodiment 123, wherein the *C. acnes* PITP polypeptide sequence consists of an amino acid sequence corresponding to residues 1 to 146 of SEQ ID NO: 206.

128. The chimeric DsA1/DsA2/PITP polypeptide of any one of embodiments 123-127, wherein the chimeric *C. acnes* DsA1/DsA2/PITP polypeptide comprises an amino acid sequence according to any one of SEQ ID NO: 80, 82 or 83 (e.g., SEQ ID NO: 80 or 83) or a sequence having at least 75%, at least 90%, at least 91%, at least 92%, at least 93%, at least 94%, at least 95%, at least 96%, at least 97%, at least 98%, or at least 99% (e.g., at least 95%) identity to any one of SEQ ID NO: 80, 82 or 83 (e.g., SEQ ID NO: 80 or 83).

129 The chimeric DsA1/DsA2/PITP polypeptide of any one of embodiments 123-128 wherein the chimeric *C. acnes* DsA1/DsA2/PITP polypeptide further comprises a heterologous transmembrane domain sequence.

130. The chimeric DsA1/DsA2/PITP polypeptide any one of embodiments 123-129, wherein (i) is a chimeric *C. acnes* DsA1/DsA2 polypeptide, optionally comprising the sequence of SEQ ID NO: 70, or a sequence having at least 90%, at least 91%, at least 92%, at least 93%, at least 94%, at least 95%, at least 96%, at least 97%, at least 98%, or at least 99% (e.g., at least 90%) identity to SEQ ID NO: 70.

131. The chimeric DsA1/DsA2/PITP polypeptide of any one of embodiments 123-130, wherein the polypeptide comprises a sequence of SEQ ID NO: 80, 82 or 83 (e.g., SEQ ID NO: 80 or 83) or a sequence having at least 50%, at least 90%, at least 91%, at least 92%, at least 93%, at least 94%, at least 95%, at least 96%, at least 97%, at least 98%, or at least 99% (e.g., at least 95%) identity thereto.

132 A composition comprising:

(i) a nucleic acid comprising a nucleotide sequence encoding a *C. acnes* DsA1 polypeptide;

(ii) a nucleic acid comprising a nucleotide sequence encoding a *C. acnes* DsA2 polypeptide; and (iii) a nucleic acid comprising a nucleotide sequence encoding a *C. acnes* PITP polypeptide.

133 A composition comprising (i) a nucleic acid comprising a nucleotide sequence encoding a chimeric *C. acnes* DsA1/DsA2 polypeptide and (ii) a nucleic acid comprising a nucleotide sequence encoding a *C. acnes* PITP polypeptide, optionally wherein the nucleic acids are present in a weight ratio of 1:1.

134 A composition comprising a nucleic acid comprising a nucleotide sequence encoding a chimeric *C. acnes* DsA1/DsA2/PITP polypeptide.

135 The composition of any one of embodiments 133-134, wherein any two or more nucleic acids are located on the same nucleic acid molecule.

136 The composition of any one of embodiments 133-134, wherein any two or more nucleic acids are located on different nucleic acid molecules.

137. The composition of any one of embodiments 133-136, wherein the composition further comprises a lipid nanoparticle (LNP), optionally wherein any one or more nucleic acids are encapsulated in the LNP, e.g. wherein the LNP has an average diameter of 30 nm to 200 nm (e.g. an average diameter of 80 nm to 150 nm).

138 The composition of any one of embodiment 137, wherein the LNP comprises at least one cationic lipid, optionally wherein the cationic lipid
is biodegradable or is not biodegradable, and/or
the cationic lipid is cleavable or is not cleavable.

139. The composition of any one of embodiments 137-138, wherein the cationic lipid is selected from the group consisting of OF-02, cKK-E10, OF-Deg-Lin, GL-HEPES-E3-E10-DS-3-E18-1, GL-HEPES-E3-E12-DS-4-E10, GL-HEPES-E3-E12-DS-3-E14, SM-102, ALC-0315, IM-001 and IS-001.

140 The composition of any one of embodiments 137-139, wherein the cationic lipid is selected from the group consisting of OF-02, cKK-E10, GL-HEPES-E3-E12-DS-4-E10, IM-001 and IS-001 (e.g. wherein the cationic lipid is GL-HEPES-E3-E12-DS-4-E10).

141. The composition of any one of embodiments 137-140, wherein the LNP further comprises a polyethylene glycol (PEG) conjugated (PEGylated) lipid, a cholesterol-based lipid, and a helper lipid, optionally wherein the LNP comprises: a cationic lipid at a molar ratio of 35% to 55%; a polyethylene glycol (PEG) conjugated (PEGylated) lipid at a molar ratio of 0.25% to 2.75%; a cholesterol-based lipid at a molar ratio of 20% to 45%; and a helper lipid at a molar ratio of 5% to 35%, wherein all of the molar ratios are relative to the total lipid content of the LNP,
   e.g. wherein the LNP comprises a cationic lipid at a molar ratio of 40%, a PEGylated lipid at a molar ratio of 1.5%, a cholesterol-based lipid at a molar ratio of 28.5%, and a helper lipid at a molar ratio of 30%.

142. The composition of embodiment 137-141, wherein any two or more nucleic acids are co-encapsulated in a single LNP.

143 The composition of any one of embodiments 137-142, wherein any two or more nucleic acids are encapsulated in separate LNPs.

144. The composition of any one of embodiments 133-143, wherein any one or more nucleic acids is a mRNA, optionally wherein each of the nucleic acids is a mRNA.

145. The composition of any one of embodiments 133-144, wherein the composition can be in a frozen liquid form or in a lyophilized form (e.g., in a lyophilized form).

146. A composition comprising:
   (i) a *C. acnes* DsA1 polypeptide;
   (ii) a *C. acnes* DsA2 polypeptide; and
   (iii) a *C. acnes* PITP polypeptide.

147. A composition comprising a chimeric *C. acnes* DsA1/DsA2 polypeptide, and a *C. acnes* PITP polypeptide.

148. A composition comprising a chimeric *C. acnes* DsA1/DsA2/PITP polypeptide.

149. The composition of any one of embodiments 146-148, wherein the composition is an immunogenic composition.

150. The composition of any one of embodiments 146-149, wherein the composition further comprises an adjuvant.

151. The composition of embodiment 150, wherein the adjuvant is selected from the group consisting of: Aluminum based adjuvant (e.g. AlOOH). Squalene based oil in water emulsion adjuvants (e.g. AF03, AS03, MF59) and Liposome-based adjuvants comprising a saponin and a TLR4 agonist (e.g. SPA14, AS01, LEQ), e.g., wherein the adjuvant is selected from the group consisting of AIOOH, AF03 and SPA14.

152. The composition according to any one of embodiments 148-151, wherein the composition can be in a frozen liquid form or in a lyophilized form (e.g., in a lyophilized form).

153. The composition of any one of embodiments 133-152, wherein the *C. acnes* DsA1 polypeptide further comprises a secretion signal peptide sequence (e.g., a viral a secretion signal peptide sequence).

154. The composition of any one of embodiment 133-153, wherein the *C. acnes* DsA2 polypeptide further comprises a secretion signal peptide sequence (e.g., a viral a secretion signal peptide sequence).

155. The composition of any one of embodiment 133-154, wherein the *C. acnes* PITP polypeptide further comprises a secretion signal peptide sequence (e.g., a viral a secretion signal peptide sequence).

156. The composition any one of embodiments 133-155, wherein the *C. acnes* chimeric DsA1/DsA2 polypeptide further comprises a secretion signal peptide sequence (e.g., a viral a secretion signal peptide sequence).

157. The composition of any one of embodiments 133-153, wherein the *C. acnes* chimeric DsA1/DsA2/PITP polypeptide further comprises a secretion signal peptide sequence (e.g., a viral a secretion signal peptide sequence).

158. The composition of any one of embodiment 133-157, wherein the *C. acnes* DsA1 polypeptide further comprises a heterologous transmembrane domain sequence.

159 The composition of any one of embodiment 133-158, wherein the *C. acnes* DsA2 polypeptide further comprises a heterologous transmembrane domain sequence.

160. The composition of any one of embodiment 133-159, wherein the *C. acnes* PITP polypeptide further comprises a heterologous transmembrane domain sequence.

161. The composition of any one of embodiment 133-160, wherein the chimeric *C. acnes* DsA1/DsA2 polypeptide further comprises a heterologous transmembrane domain sequence.

162 The composition of any one of embodiment 133-161, wherein the chimeric *C. acnes* DsA1/DsA2/PITP polypeptide further comprises a heterologous transmembrane domain sequence.

163. A combination comprising:
   (i) a nucleic acid comprising a nucleotide sequence encoding a *C. acnes* DsA1 polypeptide;
   (ii) a nucleic acid comprising a nucleotide sequence encoding a *C. acnes* DsA2 polypeptide; and
   (iii) a nucleic acid comprising a nucleotide sequence encoding a *C. acnes* PITP polypeptide.

164. A combination comprising (i) a nucleic acid comprising a nucleotide sequence encoding a chimeric *C. acnes* DsA1/DsA2 polypeptide and (ii) a nucleic acid comprising a nucleotide sequence encoding a *C. acnes* PITP polypeptide.
165. The combination of any one of embodiments 163 or 164, wherein any two or more nucleic acids are located on the same nucleic acid molecule.
166. The combination of any one of embodiments 163-164, wherein any two or more nucleic acids are located on different nucleic acid molecules.
167. The combination of any one of embodiments 163-166, wherein any one or more nucleic acids is a mRNA.
168. The combination of any one of embodiments 163-167, wherein each of the nucleic acids is a mRNA.
169. A combination comprising:
(i) a *C. acnes* DsA1 polypeptide;
(ii) a *C. acnes* DsA2 polypeptide; and
(iii) a *C. acnes* PITP polypeptide.
170. A combination comprising a chimeric *C. acnes* DsA1/DsA2 polypeptide, and a *C. acnes* PITP polypeptide.
171. The combination of embodiment 169 or 170 wherein the *C. acnes* DsA1 polypeptide further comprises a secretion signal peptide sequence (e.g., a viral a secretion signal peptide sequence).
172. The combination of any one of embodiments 169-171, wherein the *C. acnes* DsA2 polypeptide further comprises a secretion signal peptide sequence (e.g., a viral a secretion signal peptide sequence).
173. The combination of any one of embodiments 169-172, wherein the *C. acnes* PITP polypeptide further comprises a secretion signal peptide sequence (e.g., a viral a secretion signal peptide sequence).
174. The combination of any one of embodiments 169-173, wherein the *C. acnes* chimeric DsA1/DsA2 polypeptide further comprises a secretion signal peptide sequence (e.g., a viral a secretion signal peptide sequence).
175. The combination of any one of embodiments 169-174, wherein the *C. acnes* DsA1 polypeptide further comprises a heterologous transmembrane domain sequence.
176. The combination of any one of embodiments 169-175, wherein the *C. acnes* DsA2 polypeptide further comprises a heterologous transmembrane domain sequence.
177. The combination of embodiment any one of embodiments 169-176, wherein the *C. acnes* PITP polypeptide further comprises a heterologous transmembrane domain sequence.
178. The combination of any one of embodiments 169-177, wherein the chimeric *C. acnes* DsA1/DsA2 polypeptide further comprises a heterologous transmembrane domain sequence.
179. The combination of any one of embodiments 169-178, wherein the nucleic acids are present in the same composition.
180. The combination of any one of embodiments 169-178, wherein the nucleic acids are present in two or more separate compositions.
181. The combination of any one of embodiments 169-177, wherein the polypeptides are present in the same composition.
182. The combination of any one of embodiments 169-177, wherein the polypeptides are present in two or more separate compositions.
183. The nucleic acid of any one of the preceding embodiments, the composition of any one of the preceding embodiments or the combination of any one of the preceding embodiments, wherein the secretion signal peptide sequence comprises a sequence selected from the group consisting of: an influenza hemagglutinin (HA) secretion signal peptide sequence, a SARS COV-2 spike secretion signal peptide sequence, a VZV gB secretion signal peptide sequence, a VZV gE secretion signal peptide sequence, a VZV gI secretion signal peptide sequence, a VZV gK secretion signal peptide sequence, a measles F-protein secretion signal peptide sequence, a rubella E1 protein secretion signal peptide sequence, a rubella E2 protein secretion signal peptide sequence, a mumps F-protein secretion signal peptide sequence, an Ebola GP protein secretion signal peptide sequence, a smallpox 6 kDa IC protein secretion signal peptide sequence and a rabies G protein secretion signal peptide sequence.
184. The nucleic acid of any one of the preceding embodiments, the composition of any one of the preceding embodiments or the combination of any one of the preceding embodiments wherein the nucleotide sequence encoding the secretion signal peptide sequence comprises a sequence according to any one of the sequences in Table 2 or Table 3.
185. The nucleic acid of any one of the preceding embodiments, the composition of any one of the preceding embodiments or the combination of any one of the preceding embodiments, wherein the secretion signal peptide sequence comprises an amino acid sequence according to any one of SEQ ID NO: 210-211.
186. The nucleic acid of any one of the preceding embodiments, the polypeptide of any one of the preceding embodiments, the composition of any one of the preceding embodiments or the combination of any one of the preceding embodiments, wherein the heterologous transmembrane domain comprises a viral transmembrane domain sequence, optionally wherein the viral transmembrane domain sequence is selected from the group consisting of: an influenza hemagglutinin (HA) transmembrane domain sequence, a SARS COV-2 spike transmembrane domain sequence, a VZV gB transmembrane domain sequence, a VZV gE transmembrane domain sequence, a VZV gI transmembrane domain sequence, a VZV gK transmembrane domain sequence, a measles F-protein transmembrane domain sequence, a rubella E1 protein transmembrane domain sequence, a rubella E2 protein transmembrane domain sequence, a mumps F-protein transmembrane domain sequence, an Ebola GP protein transmembrane domain sequence and a rabies transmembrane domain sequence.
187. The nucleic acid of any one of the preceding embodiments, the polypeptide of any one of the preceding embodiments, the composition of any one of the preceding embodiments or the combination of any one of the preceding embodiments, wherein the transmembrane domain comprises an amino acid sequence according to any one of the sequences in Table 4.
188. The nucleic acid of any one of the preceding embodiments, the polypeptide of any one of the preceding embodiments, the composition of any one of the preceding embodiments or the combination of any one of the preceding embodiments, wherein the transmembrane domain sequence comprises an amino acid sequence according to any one of SEQ ID NO: 208-209.

189. The nucleic acid of any one of the preceding embodiments or the composition of any one of the preceding embodiments, wherein the mRNA comprises a 5' cap, at least one 5' untranslated region (5' UTR), at least one 3' untranslated region (3' UTR), and/or at least one polyadenylation (poly(A)) sequence.

190. The nucleic acid of any one of the preceding embodiments or the composition of any one of the preceding embodiments, wherein the mRNA is unmodified.

191. The nucleic acid of any one of the preceding embodiments or the composition of any one of the preceding embodiments, wherein:

(i) the mRNA comprises at least one chemical modification, optionally wherein the chemical modification is selected from the group consisting of e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine. 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil. N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine (e.g., wherein the chemical modification comprises N1-methylpseudouridine), optionally wherein at least 20%, at least 30%, at least 40%, at least 50%, at least 60%, at least 70%, at least 80%, at least 85%, at least 90%, at least 95%, or 100% of the uridines in the mRNA are chemically modified); and/or (ii) the mRNA is synthesized from modified nucleotide analogues or derivatives of purines and pyrimidines, optionally wherein the modified nucleotide analogues or derivatives of purines and pyrimidines are selected from the group consisting of: 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine. 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethyl-aminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil. N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine.

192. The nucleic acid or the composition embodiment 191, wherein the chemical modification of the mRNA comprises N1-methylpseudouridine e.g. in place of every uridine.

193. The nucleic acid of any one of the preceding embodiments or the composition of any one of the preceding embodiments, wherein the mRNA is a self-replicating mRNA.

194. The nucleic acid of any one of the preceding embodiments or the composition of any one of the preceding embodiments, wherein the mRNA is a non-replicating mRNA.

195. The nucleic acid of any one of the preceding embodiments, the polypeptide of any one of the preceding embodiments, the composition of any one of the preceding embodiments, or the combination of any one of the preceding embodiments, wherein the *C. acnes* DsA1 polypeptide comprises a mutation at one or more (e.g., all) positions corresponding to an N-glycosylation site and/or a mutation at one or more (e.g., all) positions corresponding to an O-glycosylation site in the native *C. acnes* DsA1 polypeptide, optionally wherein the mutation is a single amino acid substitution.

196 The nucleic acid of any one of the preceding embodiments, the polypeptide of any one of the preceding embodiments, the composition of any one of the preceding embodiments, or the combination of any one of the preceding embodiments, wherein the *C. acnes* DsA1 polypeptide comprises a single amino acid substitution at one or more (e.g., all) positions corresponding to a cysteine residue in the native *C. acnes* DsA1 polypeptide, optionally wherein the single amino acid substitution is a substitution of cysteine with serine.

197 The nucleic acid of any one of the preceding embodiments, the polypeptide of any one of the preceding embodiments, the composition of any one of the preceding embodiments, or the combination of any one of the preceding embodiments, wherein the *C. acnes* DsA2 polypeptide comprises a mutation at one or more (e.g., all) positions corresponding to an N-glycosylation site and/or a mutation at one or more (e.g., all) positions corresponding to an O-glycosylation site in the native *C. acnes* DsA2 polypeptide, optionally wherein the mutation is a single amino acid substitution.

198. The nucleic acid of any one of the preceding embodiments, the polypeptide of any one of the preceding embodiments, the composition of any one of the preceding embodiments, or the combination of any one of the preceding embodiments, wherein the *C. acnes* DsA2 polypeptide comprises a single amino acid substitution at one or more (e.g., all) positions corresponding to a cysteine residue in the native *C. acnes* DsA2 polypeptide, optionally wherein the single amino acid substitution is a substitution of cysteine with serine.

199 The nucleic acid of any one of the preceding embodiments, the polypeptide of any one of the preceding embodiments, the composition of any one of the preceding embodiments, or the combination of any one of the preceding embodiments, wherein the *C. acnes* PITP polypeptide comprises a mutation at one or more (e.g., all) positions corresponding to an N-glycosylation site and/or a mutation at one or more (e.g., all) positions corresponding to an O-glycosylation site in the native *C. acnes* PITP polypeptide, optionally wherein the mutation is a single amino acid substitution.

200. The nucleic acid of any one of the preceding embodiments, the polypeptide of any one of the preceding embodiments, the composition of any one of the preceding embodiments, or the combination of any one of the preceding embodiments, wherein the *C. acnes* PITP polypeptide comprises a single amino acid substitution at one or more (e.g., all) positions corresponding to a cysteine residue in the native *C. acnes* PITP polypeptide, optionally wherein the single amino acid substitution is a substitution of cysteine with serine.

201 The nucleic acid of any one of the preceding embodiments, the polypeptide of any one of the preceding embodiments, the composition of any one of the preceding embodiments, or the combination of any one of the preceding embodiments, wherein the chimeric *C. acnes* DsA1/DsA2 polypeptide comprises a mutation at one or more (e.g., all) positions corresponding to an N-glycosylation site and/or a mutation at one or more (e.g., all) positions corresponding to an O-glycosylation site in the respective native *C. acnes* DsA1 polypeptide and/or in the respective native *C. acnes* DsA2 polypeptide, optionally wherein the mutation is a single amino acid substitution.

202. The nucleic acid of any one of the preceding embodiments, the polypeptide of any one of the preceding embodiments, the composition of any one of the preceding embodiments, or the combination of any one of the preceding embodiments, wherein the chimeric *C. acnes* DsA1/DsA2 polypeptide comprises a single amino acid substitution at one or more (e.g., all) positions corresponding to a cysteine residue in the respective native *C. acnes* DsA1 polypeptide and/or in in the respective native *C. acnes* DsA2 polypeptide, optionally wherein the single amino acid substitution is a substitution of cysteine with serine.

203. The nucleic acid of any one of the preceding embodiments, the polypeptide of any one of the preceding embodiments, the composition of any one of the preceding embodiments, or the combination of any one of the preceding embodiments, wherein the chimeric *C. acnes* DsA1/DsA2/PITP polypeptide comprises a mutation at one or more (e.g., all) positions corresponding to an N-glycosylation site and/or a mutation at one or more (e.g., all) positions corresponding to an O-glycosylation site in the respective native *C. acnes* DsA1 polypeptide, in the respective native *C. acnes* DsA2 polypeptide and/or in the respective native *C. acnes* PITP polypeptide, optionally wherein the mutation is a single amino acid substitution.

204. The nucleic acid of any one of the preceding embodiments, the polypeptide of any one of the preceding embodiments, the composition of any one of the preceding embodiments, or the combination of any one of the preceding embodiments, wherein the chimeric *C. acnes* DsA1/DsA2/PITP polypeptide comprises a single amino acid substitution at one or more (e.g., all) positions corresponding to a cysteine residue in the respective native *C. acnes* DsA1 polypeptide, in the respective native *C. acnes* DsA2 polypeptide and/or in the respective native *C. acnes* PITP polypeptide, optionally wherein the single amino acid substitution is a substitution of cysteine with serine.

205 The nucleic acid of any one of the preceding embodiments, the polypeptide of any one of the preceding embodiments, the composition of any one of the preceding embodiments, or the combination of any one of the preceding embodiments, wherein the *C. acnes* CAMP2 polypeptide comprises a mutation at one or more (e.g., all) positions corresponding to an N-glycosylation site and/or a mutation at one or more (e.g., all) positions corresponding to an O-glycosylation site in the respective native *C. acnes* CAMP2 polypeptide, optionally wherein the mutation is a single amino acid substitution.

206. The nucleic acid of any one of the preceding embodiments, the polypeptide of any one of the preceding embodiments, the composition of any one of the preceding embodiments, or the combination of any one of the preceding embodiments, wherein the *C. acnes* CAMP2 polypeptide comprises a single amino acid substitution at one or more (e.g., all) positions corresponding to a cysteine residue in the respective native *C. acnes* CAMP2 polypeptide, optionally wherein the single amino acid substitution is a substitution of cysteine with serine.

207. The composition of any one of the preceding embodiments or the combination of any one of the preceding embodiments, wherein the *C. acnes* DsA1 polypeptide comprises the sequence of any one of SEQ ID NO: 204, SEQ ID NO: 17-19 or SEQ ID NO: 59-61, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity to any one of SEQ ID NO: 204, SEQ ID NO: 17-19 or SEQ ID NO: 59-61.

208. The composition of any one of the preceding embodiments or the combination of any one of the preceding embodiments, wherein the *C. acnes* DsA2 polypeptide comprises the sequence of any one of SEQ ID NO: 205, SEQ ID NO: 20-27 or SEQ ID NO: 62-69, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%)

identity to any one of SEQ ID NO: 205, SEQ ID NO: 20-27 or SEQ ID NO: 62-69.

209. The composition of any one of the preceding embodiments or the combination of any one of the preceding embodiments, wherein the *C. acnes* PITP polypeptide comprises the sequence according to any one of SEQ ID NO: 206. SEQ ID NO: 31-37 or SEQ ID NO: 73-79, or a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 75%) identity to any one of SEQ ID NO: 206, SEQ ID NO: 31-37 or SEQ ID NO: 73-79.

210. The composition of any one of the preceding embodiments or the combination of any one of the preceding embodiments, wherein the chimeric *C. acnes* DsA1/DsA2 polypeptide comprises the sequence of SEQ ID NO: 28-30, SEQ ID NO: 39 or SEQ ID NO: 70-72 or SEQ ID NO: 81 (e.g., SEQ ID NO: 70), or a sequence having at least 90%, at least 91%, at least 92%, at least 93%, at least 94%, at least 95%, at least 96%, at least 97%, at least 98%, or at least 99% (e.g., at least 90%) identity to any one of SEQ ID NO: 28-30, SEQ ID NO: 39 or SEQ ID NO: 70-72 or SEQ ID NO: 81.

211. The composition of any one of the preceding embodiments or the combination of any one of the preceding embodiments, wherein the chimeric *C. acnes* DsA1/DsA2/PITP polypeptide comprises the sequence of SEQ ID NO: 80, 82 or 83 (e.g., SEQ ID NO: 80 or 83), or a sequence having at least 90%, at least 91%, at least 92%, at least 93%, at least 94%, at least 95%, at least 96%, at least 97%, at least 98%, or at least 99% (e.g., at least 75%) identity to SEQ ID NO: 80, 82 or 83 (e.g., SEQ ID NO: 80 or 83).

212. The composition of any one of the preceding embodiments or the combination of any one of the preceding embodiments, wherein the *C. acnes* CAMP2 polypeptide comprises the sequence of SEQ ID NO: 203, or a sequence having at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% (e.g., at least 60%, such as at least 85%) identity to SEQ ID NO: 203.

213. An mRNA comprising or consisting of (e.g. consisting of) the following structural elements:

(i) a 5' cap with the following structure:

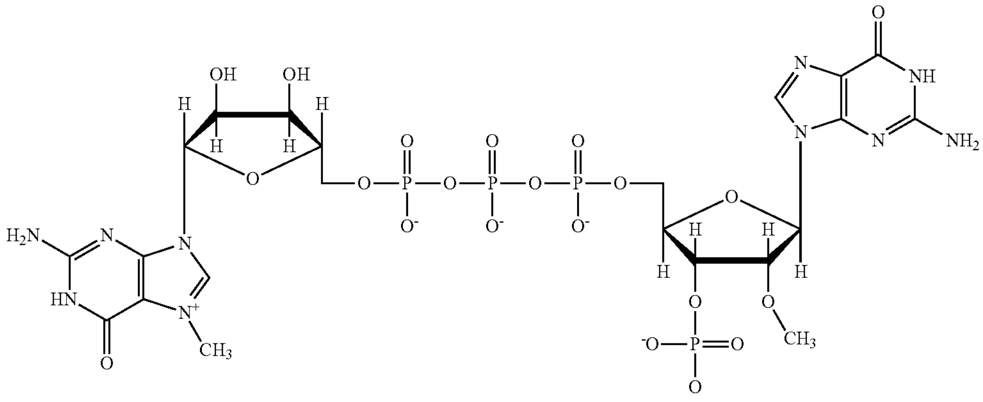

(ii) a 5' untranslated region (5' UTR) having the nucleic acid sequence according to SEQ ID NO: 265;

(iii) a protein coding region having the nucleic acid sequence according to any one of SEQ ID NO: 90-91, or SEQ ID NO: 391-392 (e.g., SEQ ID NO: 91);

(iv) a 3' untranslated region (3' UTR) having the nucleic acid sequence according to SEQ ID NO: 266; and (v) a poly A tail, optionally wherein the poly A tail comprises at least 75 adenosine nucleotides (such as about 80 adenosine nucleotides) or at least 100 adenosine nucleotides (such as about 115 adenosine nucleotides), e.g., wherein the polyA tail comprises at least 100 adenosine nucleotides.

214. The mRNA of embodiment 213, wherein the mRNA is chemically modified and wherein the chemical modification comprises or consist of (e.g. consists of) N1-methylpseudouridine in place of every uridine.

215. The mRNA of embodiments 213 or 214, wherein the 3' end of (i) bonds directly to the 5' end of (ii) via a 3' to 5' phosphodiester linkage; the 3' end of (ii) bonds directly to the 5' end of (iii) via a 3' to 5' phosphodiester linkage; the 3' end of (iii) bonds directly to the 5' end of (iv) via a 3' to 5' phosphodiester linkage; and the 3' end of (iv) bonds directly to the 5' end of (v) via a 3' to 5' phosphodiester linkage.

216. An mRNA comprising or consisting of (e.g. consisting of) the following structural elements:

(i) a 5' cap with the following structure:

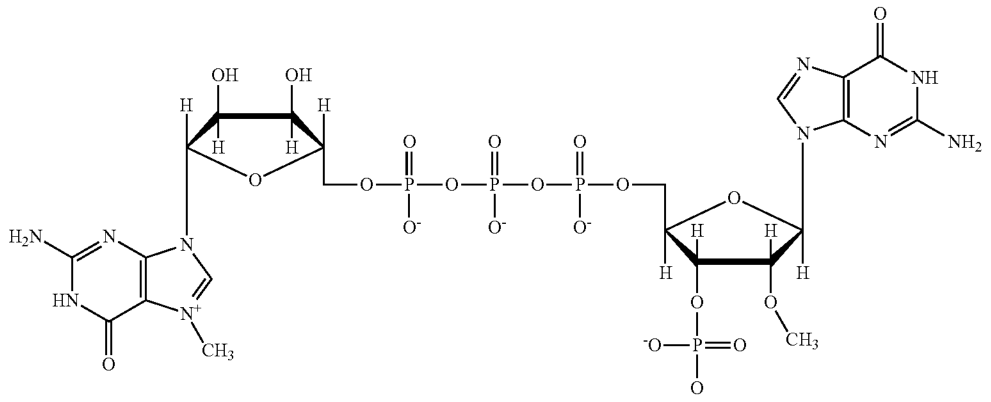

(ii) a 5' untranslated region (5' UTR) having the nucleic acid sequence according to SEQ ID NO: 265;

(iii) a protein coding region having the nucleic acid sequence according to SEQ ID NO: 113;

(iv) a 3' untranslated region (3' UTR) having the nucleic acid sequence according to SEQ ID NO: 266; and (v) a poly A tail, optionally wherein the poly A tail comprises at least 75 adenosine nucleotides (such as about 80 adenosine nucleotides) or at least 100 adenosine nucleotides (such as about 115 adenosine nucleotides), e.g., wherein the poly A tail comprises at least 100 adenosine nucleotides.

217. The mRNA of embodiment 216, wherein the mRNA is chemically modified and wherein the chemical modification comprises or consist of (e.g. consists of) N1-methylpseudouridine in place of every uridine.

218. The mRNA of embodiment 216 or 217, wherein the 3' end of (i) bonds directly to the 5' end of (ii) via a 3' to 5' phosphodiester linkage; the 3' end of (ii) bonds directly to the 5' end of (iii) via a 3' to 5' phosphodiester linkage; the 3' end of (iii) bonds directly to the 5' end of (iv) via a 3' to 5' phosphodiester linkage; and the 3' end of (iv) bonds directly to the 5' end of (v) via a 3' to 5' phosphodiester linkage.

219. An mRNA comprising or consisting of (e.g. consisting of) the following structural elements:

(i) a 5' cap with the following structure:

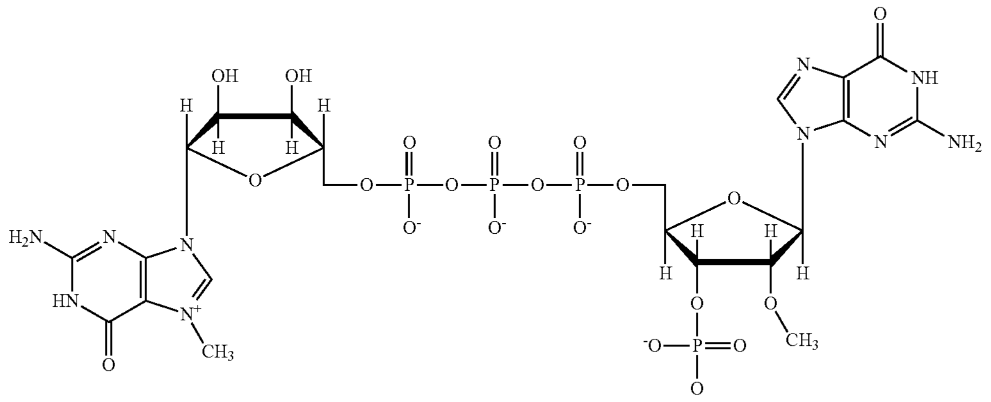

(ii) a 5' untranslated region (5' UTR) having the nucleic acid sequence according to SEQ ID NO: 265;

(iii) a protein coding region having the nucleic acid sequence according to SEQ ID NO: 115;

(iv) a 3' untranslated region (3' UTR) having the nucleic acid sequence according to SEQ ID NO: 266; and (v) a poly A tail, optionally wherein the poly A tail comprises at least 75 adenosine nucleotides (such as about 80 adenosine nucleotides) or at least 100 adenosine nucleotides (such as about 115 adenosine nucleotides), e.g., wherein the polyA tail comprises at least 100 adenosine nucleotides.

220. The mRNA of embodiment 219, wherein the mRNA is chemically modified and wherein the chemical modification comprises or consist of (e.g. consists of) N1-methylpseudouridine in place of every uridine.

221. The mRNA of embodiment 219 or 220, wherein the 3' end of (i) bonds directly to the 5' end of (ii) via a 3' to 5' phosphodiester linkage; the 3' end of (ii) bonds directly to the 5' end of (iii) via a 3' to 5' phosphodiester linkage; the 3' end of (iii) bonds directly to the 5' end of (iv) via a 3' to 5' phosphodiester linkage; and the 3' end of (iv) bonds directly to the 5' end of (v) via a 3' to 5' phosphodiester linkage.

222. A LNP encapsulating the mRNA of any one of embodiments 213-215.

223. A LNP encapsulating the mRNA of any one of embodiments 216-218.
224. A LNP encapsulating the mRNA of any one of embodiment 219-221.
225. A LNP encapsulating the mRNA of any one of embodiments 213-215 and the mRNA of any one of embodiments 216-218, optionally wherein the mRNAs are present in a weight ratio of 1:1.
226. A LNP encapsulating the mRNA of any one of embodiments 213-215 and the mRNA of any one of embodiments 219-221, optionally wherein the mRNAs are present in a weight ratio of 1:1.
227. A LNP encapsulating the mRNA of any one of embodiments 216-218 and the mRNA of any one of embodiments 219-221, optionally wherein the mRNAs are present in a weight ratio of 1:1.
228. A LNP encapsulating the mRNA of any one of embodiments 213-215, the mRNA of any one of embodiments 216-218 and the mRNA of any one of embodiments 219-221, optionally wherein the mRNAs are present in a weight ratio of 1:1:1.
229. A composition (e.g. an immunogenic composition) comprising the mRNA according to any one of embodiments 213-221.
230. The composition of embodiment 229, wherein the composition comprises:
   (i) the mRNA of any one of embodiments 213-215 and the mRNA of any one of embodiments 216-218, optionally wherein the mRNAs are present in a weight ratio of 1:1, further optionally wherein the mRNAs are co-encapsulated in the same LNP;
   (ii) the mRNA of any one of embodiments 216-218 and the mRNA of any one of embodiments 219-221, optionally wherein the mRNAs are present in a weight ratio of 1:1, further optionally wherein the mRNAs are co-encapsulated in the same LNP;
   (iii) the mRNA of any one of embodiments 213-215 and the mRNA of any one of embodiments 219-221, optionally wherein the mRNAs are present in a weight ratio of 1:1, further optionally wherein the mRNAs are co-encapsulated in the same LNP; or
   (iv) the mRNA of any one of embodiments 213-215, the mRNA of any one of embodiments 216-218 and the mRNA of any one of embodiments 219-221, optionally wherein the mRNAs are present in a weight ratio of 1:1:1, further optionally wherein the mRNAs are co-encapsulated in the same LNP.
231. The composition of embodiment 229 or 230, wherein the composition comprises the mRNA of embodiment 213 and the mRNA of embodiment 216, optionally wherein each mRNA comprises at least one chemical modification (e.g., wherein at least 20%, at least 30%, at least 40%, at least 50%, at least 60%, at least 70%, at least 80%, at least 85%, at least 90%, at least 95%, or 100% of the uridines in the mRNA are chemically modified), e.g. wherein the chemical modification comprises N1-methylpseudouridine, preferably wherein all uridines are substituted with N1-methylpseudouridine.
232. The composition of embodiment 229 or 230, wherein the composition comprises the mRNA of embodiment 213 and the mRNA of embodiment 219, optionally wherein each mRNA comprises at least one chemical modification (e.g., wherein at least 20%, at least 30%, at least 40%, at least 50%, at least 60%, at least 70%, at least 80%, at least 85%, at least 90%, at least 95%, or 100% of the uridines in the mRNA are chemically modified), e.g. wherein the chemical modification comprises N1-methylpseudouridine, preferably wherein all uridines are substituted with N1-methylpseudouridine.
233. The composition of embodiment 229 or 230, wherein the composition comprises the mRNA of embodiment 216 and the mRNA of embodiment 219, optionally wherein each mRNA comprises at least one chemical modification (e.g., wherein at least 20%, at least 30%, at least 40%, at least 50%, at least 60%, at least 70%, at least 80%, at least 85%, at least 90%, at least 95%, or 100% of the uridines in the mRNA are chemically modified), e.g. wherein the chemical modification comprises N1-methylpseudouridine, preferably wherein all uridines are substituted with N1-methylpseudouridine.
234. A composition (e.g. an immunogenic composition) comprising the LNPs according to any one of embodiments 222-228.
235. The composition of embodiment 229 or 230 or the LNP of any one of embodiments 222-228, wherein:
   (i) the LNP comprises at least one cationic lipid, optionally wherein the cationic lipid
   is biodegradable or is not biodegradable, and/or
   the cationic lipid is cleavable or is not cleavable; and
   (ii) the cationic lipid is selected from the group consisting of OF-02, cKK-E10, GL-HEPES-E3-E12-DS-4-E10, IM-001 and IS-001, optionally wherein the cationic lipid is GL-HEPES-E3-E12-DS-4-E10.
236 The composition or the LNP of embodiment 235, wherein the LNP comprises GL-HEPES-E3-E12-DS-4-E10 at a molar ratio of 40%. DMG-PEG2000 at a molar ratio of 1.5%, cholesterol at a molar ratio of 28.5% and DOPE at a molar ratio of 30%.
237. The composition according to any one of embodiments 29-60, 132-145, 183-212 or 229-236, wherein the composition comprises 1-300 μg of the one or more nucleic acid(s) (e.g. mRNA(s)), such as about 2.5 μg, about 5 μg, about 7.5 μg, about 10 μg, about 12.5 μg, about 15 μg, about 30 μg, about 45 μg, about 60 μg, about 75 μg, about 90 μg, about 105 μg, about 120 μg, about 135 μg, about 150 μg, about 165 μg, about 180 μg, about 195 μg, about 210 μg, or about 225 μg of the one or more nucleic acid(s) (e.g., mRNA(s)).
238 The composition according to embodiment 237, wherein the composition comprises 40-50 μg (e.g., about 45 μg) of the one or more nucleic acid(s) (e.g. mRNA(s)).
239 The composition according to embodiment 237, wherein the composition comprises 110-140 μg (e.g., about 120 μg) of the one or more nucleic acid(s) (e.g. mRNA(s)).
240. The composition according to embodiment 237, wherein the composition comprises 200-250 μg (e.g., about 225 μg) of the one or more nucleic acids of mRNA(s)).
241. A vaccine composition comprising the nucleic acid (e.g. mRNA) of any one of the preceding embodiments, the polypeptide of any one of the preceding embodiments or the combination of any one of the preceding embodiments.
242. The nucleic acid (e.g. mRNA) of any one of the preceding embodiments, the polypeptide of any one of the preceding embodiments, the composition of any one of the preceding embodiments, or the combination of any one of the preceding embodiments for use as a medicament.
243. The use of the nucleic acid (e.g. mRNA) of any one of the preceding embodiments, the polypeptide of any one of the preceding embodiments, the composition of any one of the preceding embodiments, or the combination of any one of the preceding embodiments for the manufacture of a medicament.

244. A method of treating or preventing a disease comprising administering the nucleic acid (e.g. mRNA) of any one of the preceding embodiments, the polypeptide of any one of the preceding embodiments, the composition of any one of the preceding embodiments, or the combination of any one of the preceding embodiments to a subject in need thereof.

245. The nucleic acid (e.g. mRNA) of any one of the preceding embodiments, the polypeptide of any one of the preceding embodiments, the composition of any one of the preceding embodiments, or the combination of any one of the preceding embodiments for use in a method of treating or preventing *C. acnes* infection (e.g. a moderate or severe *C. acnes* infection) in a subject (e.g. human).

246 The use of the nucleic acid (e.g. mRNA) of any one of the preceding embodiments, the polypeptide of any one of the preceding embodiments, the composition of any one of the preceding embodiments, or the combination of any one of the preceding embodiments for the manufacture of a medicament for treating or preventing *C. acnes* infection (e.g. a moderate or severe *C. acnes* infection) in a subject (e.g. human).

247. A method of treating or preventing a *C. acnes* infection (e.g. a moderate or severe *C. acnes* infection) comprising administering the nucleic acid (e.g. mRNA) of any one of the preceding embodiments, the polypeptide of any one of the preceding embodiments, the composition of any one of the preceding embodiments, or the combination of any one of the preceding embodiments to a subject (e.g. human) in need thereof.

248. The nucleic acid (e.g. mRNA) of any one of the preceding embodiments, the polypeptide of any one of the preceding embodiments, the composition of any one of the preceding embodiments, or the combination of any one of the preceding embodiments for use in a method of treating or preventing acne (e.g. mild, moderate or severe acne) in a subject (e.g. human).

249. The use of the nucleic acid (e.g. mRNA) of any one of the preceding embodiments, the polypeptide of any one of the preceding embodiments, the composition of any one of the preceding embodiments, or the combination of any one of the preceding embodiments for the manufacture of a medicament for treating or preventing acne (e.g. mild, moderate or severe acne) in a subject (e.g. human).

250. A method of treating or preventing acne (e.g. mild, moderate or severe acne) comprising administering nucleic acid (e.g. mRNA) of any one of the preceding embodiments, the polypeptide of any one of the preceding embodiments, the composition of any one of the preceding embodiments, or the combination of any one of the preceding embodiments to a subject (e.g. human) in need thereof.

251. The nucleic acid (e.g. mRNA) of any one of the preceding embodiments, the polypeptide of any one of the preceding embodiments, the composition of any one of the preceding embodiments, or the combination of any one of the preceding embodiments for use in a method of eliciting an immune response in a subject, optionally wherein the subject is a human subject.

252. The use of nucleic acid (e.g. mRNA) of any one of the preceding embodiments, the polypeptide of any one of the preceding embodiments, the composition of any one of the preceding embodiments, or the combination of any one of the preceding embodiments for the manufacture of a medicament for eliciting an immune response in a subject, optionally wherein the subject is a human subject.

253. A method of eliciting an immune response in a subject comprising administering nucleic acid (e.g. mRNA) of any one of the preceding embodiments, the polypeptide of any one of the preceding embodiments, the composition of any one of the preceding embodiments, or the combination of any one of the preceding embodiments to the subject.

254. The method of any one of embodiments 244, 247, 250 or 253, wherein the method comprises:
   (i) administering one dose of the nucleic acid, the polypeptide, the composition, or the combination; or
   (ii) administering two doses of the nucleic acid, the polypeptide, the composition, or the combination, optionally wherein the two doses are administered two months apart e.g. wherein the administration is according to (ii).

255. The nucleic acid, the polypeptide, the composition, or the combination for use according to any one of embodiments 242, 245, 248 or 251, wherein the method comprises:
   (i) administering one dose of the nucleic acid, the polypeptide, the composition, or the combination: or
   (ii) administering two doses of the nucleic acid, the polypeptide, the composition, or the combination, optionally wherein the two doses are administered two months apart.

256. The use of the nucleic acid, the polypeptide, the composition, or the combination according to any one of embodiments 243, 246, 249, or 252, wherein the treating or preventing comprises:
   (i) administering one dose of the nucleic acid, the polypeptide, the composition, or the combination; or
   (ii) administering two doses of the nucleic acid, the polypeptide, the composition, or the combination, optionally wherein the two doses are administered two months apart.

257. The method of any one of embodiments 244, 247, 250, 253 or 254, the nucleic acid, the polypeptide, the composition, or the combination for use according to any one of embodiments 242, 245, 248, 251 or 255, or the use of the nucleic acid, the polypeptide, the composition, or the combination of any one of embodiments 243, 246, 249, 252 or 256, wherein the method comprises administering the polypeptide, nucleic acid, composition or combination
   (i) intramuscularly; or
   (ii) through skin injection (e.g. in the epidermis, the dermis or the hypodermis of the skin), such as intradermally, optionally with a device suitable for skin injection, such as a needle (e.g. an epidermic, dermic or hypodermic needle), a needle free device, a microneedle device or a microprojection array device.

258. The method of any one of embodiments 244, 247, 250, 253, 254 or 257, the nucleic acid, the polypeptide, the composition, or the combination for use according to any one of embodiments 242, 245, 248, 251, 255 or 257, or the use of the nucleic acid, the polypeptide, the composition, or the combination of any one of embodiments 243, 246, 249, 252, 256 or 257, wherein the subject is a human subject and wherein the subject is between 9 and 45 years old or between 12 and 45 years old (e.g. between 18 and 45 years old).

259. An mRNA comprising or consisting of (e.g. consisting of) the following structural elements:

(i) a 5' cap with the following structure:

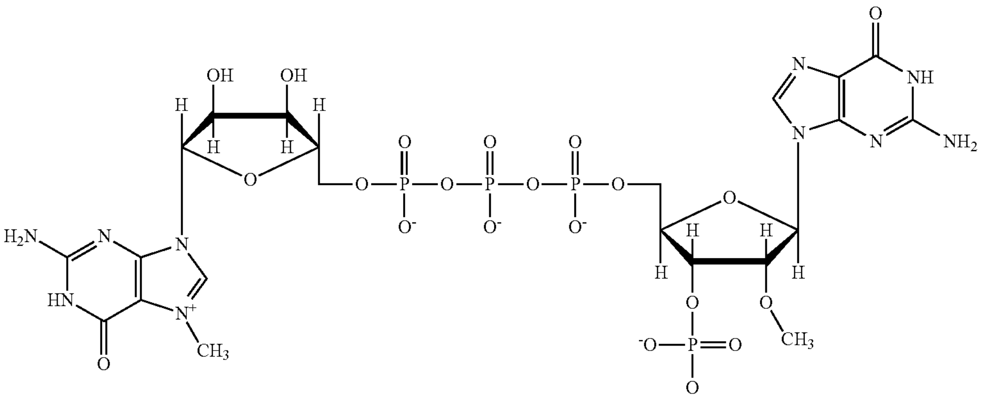

(ii) a 5' untranslated region (5' UTR) having the nucleic acid sequence according to SEQ ID NO: 265;

(iii) a protein coding region having the nucleic acid sequence according to any one of SEQ ID NO: 87-89;

(iv) a 3' untranslated region (3' UTR) having the nucleic acid sequence according to SEQ ID NO: 266; and (v) a poly A tail.

260. The mRNA of embodiment 259, wherein the mRNA is chemically modified and wherein the chemical modification comprises or consist of (e.g. consists of) N1-methylpseudouridine in place of every uridine.

261. The mRNA of embodiment 259 or 260, wherein the 3' end of (i) bonds directly to the 5' end of (ii) via a 3' to 5' phosphodiester linkage; the 3' end of (ii) bonds directly to the 5' end of (iii) via a 3' to 5' phosphodiester linkage; the 3' end of (iii) bonds directly to the 5' end of (iv) via a 3' to 5' phosphodiester linkage; and the 3' end of (iv) bonds directly to the 5' end of (v) via a 3' to 5' phosphodiester linkage.

262. A LNP encapsulating the mRNA of embodiments 259-261.

263. A nucleic acid comprising a nucleotide sequence encoding a chimeric *C. acnes* DsA1/DsA2/PITP/CAMP2 polypeptide, wherein the chimeric *C. acnes* DsA1/DsA2/PITP/CAMP2 polypeptide comprises:

(a) a chimeric *C. acnes* DsA1/DsA2 polypeptide, e.g., as described in any one of embodiments 97-105;

(b) an immunogenic fragment of a *C. acnes* PITP polypeptide, optionally wherein the immunogenic fragment comprises a ENFD of a *C. acnes* PITP polypeptide; and (c) a *C. acnes* CAMP2 polypeptide or an immunogenic fragment thereof.

264. The nucleic acid of embodiment 263, wherein the chimeric *C. acnes* DsA1/DsA2 polypeptide comprises:

(A) (1) a CSD2 of a *C. acnes* DsA1 polypeptide and (2) a CSD1 and/or a CSD3 of a *C. acnes* DsA2 polypeptide; or (B) (1) a CSD2 of a *C. acnes* DsA2 polypeptide and (2) a CSD1 and/or a CSD3 of a *C. acnes* DsA1 polypeptide 265. The nucleic acid of embodiment 264, wherein the chimeric *C. acnes* DsA1/DsA2/PITP/CAMP2 polypeptide is as defined in (B).

266. The nucleic acid of any one of embodiments 263-265, wherein the chimeric *C. acnes* DsA1/DsA2/PITP/CAMP2 polypeptide comprises a CSD1 of a *C. acnes* DsA1 polypeptide, a CSD2 of a *C. acnes* DsA2 polypeptide and a CSD3 of a *C. acnes* DsA1 polypeptide.

267. The nucleic acid of any one of embodiments 263-266, wherein the chimeric *C. acnes* DsA1/DsA2 polypeptide of (a) comprises a sequence according to SEQ ID NO: 70, or a sequence having at least 90%, at least 91%, at least 92%, at least 93%, at least 94%, at least 95%, at least 96%, at least 97%, at least 98%, or at least 99% (e.g., at least 90%) identity thereto.

268. The nucleic acid of any one of embodiments 263-267, wherein the immunogenic fragment of a *C. acnes* PITP polypeptide comprising a ENFD of a *C. acnes* PITP polypeptide in (b) comprises the sequence corresponding to amino acid residues 1-133 of SEQ ID NO: 73 or a sequence having at least 90%, at least 91%, at least 92%, at least 93%, at least 94%, at least 95%, at least 96%, at least 97%, at least 98%, or at least 99% (e.g., at least 90%) identity thereto.

269. The nucleic acid of embodiment 268, wherein the immunogenic fragment of a *C. acnes* PITP polypeptide comprising a ENFD of a *C. acnes* PITP polypeptide in (b) comprises the sequence corresponding to amino acid residues 1-146 of SEQ ID NO: 73 or a sequence having at least 90%, at least 91%, at least 92%, at least 93%, at least 94%, at least 95%, at least 96%, at least 97%, at least 98%, or at least 99% (e.g., at least 90%) identity thereto.

270. The nucleic acid of any one of embodiments 263-269, wherein (a) and (b) comprise SEQ ID NO: 80, 82 or 83 or a sequence having at least 90%, at least 91%, at least 92%, at least 93%, at least 94%, at least 95%, at least 96%, at least 97%, at least 98%, or at least 99% (e.g., at least 90%) identity thereto.

271. The nucleic acid of embodiment 270, wherein (a) and (b) comprise SEQ ID NO: 80 or a sequence having at least 90%, at least 91%, at least 92%, at least 93%, at least 94%, at least 95%, at least 96%, at least 97%, at least 98%, or at least 99% (e.g., at least 90%) identity thereto.

272. The nucleic acid of any one of embodiments 263-269, wherein (c) is a *C. acnes* CAMP2 polypeptide, optionally wherein (c) comprises SEQ ID NO: 203 or a sequence having at least 90%, at least 91%, at least 92%, at least 93%, at least 94%, at least 95%, at least 96%, at least 97%, at least 98%, or at least 99% (e.g., at least 90%) identity thereto.

273. The nucleic acid of embodiment 272, wherein:
(i) the chimeric *C. acnes* DsA1/DsA2/PITP/CAMP2 polypeptide comprises a sequence according to SEQ ID NO: 373 or 374 or a sequence having at least 90%, at least 91%, at least 92%, at least 93%, at least 94%, at least 95%, at least 96%, at least 97%, at least 98%, or at least 99% (e.g., at least 90%) identity thereto; and/or
(ii) the nucleotide sequence encoding the chimeric *C. acnes* DsA1/DsA2/PITP/CAMP2 polypeptide comprises a sequence according to any one of SEQ ID NO: 384-387 (e.g., SEQ ID NO: 385 or 387) or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto; and/or
(iii) the nucleotide sequence encoding the chimeric *C. acnes DsA*1/DsA2/PITP/CAMP2 polypeptide comprises a sequence according to any one of SEQ ID NO: 377-380 (e.g., SEQ ID NO: 378 or 380) or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto.

274. The nucleic acid of any one of embodiments 263-269, wherein the immunogenic fragment of a *C. acnes* CAMP2 polypeptide in (c) comprises a N-terminal domain of a *C. acnes* CAMP2 polypeptide, e.g. wherein the immunogenic fragment of a *C. acnes* CAMP2 polypeptide in (c) comprises amino acid residues 29-176 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity to the sequence of amino acid residues 29-176 of SEQ ID NO: 202.

275. The nucleic acid of any one of embodiments 263-269, wherein the immunogenic fragment of a *C. acnes* CAMP2 polypeptide in (c) comprises a N-terminal domain of a *C. acnes* CAMP2 polypeptide and a linker domain of a *C. acnes* CAMP2 polypeptide.

276. The nucleic acid of embodiment 275, wherein the immunogenic fragment of a *C. acnes* CAMP2 polypeptide in (c) comprises amino acid residues 29-188 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity thereto.

277. The nucleic acid of embodiment 276, wherein:
(i) the chimeric *C. acnes* DsA1/DsA2/PITP/CAMP2 polypeptide comprises a sequence according to SEQ ID NO: 375 or a sequence having at least 90%, at least 91%, at least 92%, at least 93%, at least 94%, at least 95%, at least 96%, at least 97%, at least 98%, or at least 99% (e.g., at least 90%) identity thereto; and/or
(ii) the nucleotide sequence encoding the chimeric *C. acnes DsA*1/DsA2/PITP/CAMP2 polypeptide comprises a sequence according to any one of SEQ ID NO: 388-389 (e.g., SEQ ID NO: 389) or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto; and/or
(iii) the nucleotide sequence encoding the chimeric *C. acnes DsA*1/DsA2/PITP/CAMP2 polypeptide comprises a sequence according to any one of SEQ ID NO: 381-382 (e.g., SEQ ID NO: 382) or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto.

278. The nucleic acid of any one of embodiments 263-269, wherein the immunogenic fragment of a *C. acnes* CAMP2 polypeptide in (c) comprises a C-terminal domain of a *C. acnes* CAMP2 polypeptide.

279. The nucleic acid of embodiment 278, wherein the immunogenic fragment of a *C. acnes* CAMP2 polypeptide in (c) comprises amino acid residues 189-267 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity thereto.

280. The nucleic acid of embodiment 279, wherein:
(i) the chimeric *C. acnes* DsA1/DsA2/PITP/CAMP2 polypeptide comprises a sequence according to SEQ ID NO: 376 or a sequence having at least 90%, at least 91%, at least 92%, at least 93%, at least 94%, at least 95%, at least 96%, at least 97%, at least 98%, or at least 99% (e.g., at least 90%) identity thereto; and/or
(ii) the nucleotide sequence encoding the chimeric *C. acnes DsA*1/DsA2/PITP/CAMP2 polypeptide comprises a sequence according to any one of SEQ ID NO: 390 or 393 (e.g., SEQ ID NO: 390) or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto; and/or
(iii) the nucleotide sequence encoding the chimeric *C. acnes DsA*1/DsA2/PITP/CAMP2 polypeptide comprises a sequence according to any one of SEQ ID NO: 383 or 394 (e.g., SEQ ID NO: 383) or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto.

281. The nucleic acid of any one of embodiments 263-269, wherein the immunogenic fragment of a *C. acnes* CAMP2 polypeptide in (c) comprises a linker domain of a *C. acnes* CAMP2 polypeptide and a C-terminal domain of a *C. acnes* CAMP2 polypeptide, e.g. wherein the immunogenic fragment of a *C. acnes* CAMP2 polypeptide in (c) comprises amino acid residues 177-267 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity to the sequence of amino acid residues 177-267 of SEQ ID NO: 202.

282. The nucleic acid of any one of embodiments 263-281, wherein any two or more of (a), (b) and (c) are attached via linkers or are directly fused to each other (e.g., wherein any two or more of (a), (b) and (c) are directly fused to each other).

283. The nucleic acid of any one of embodiments 263-282, wherein the chimeric *C. acnes* DsA1/DsA2/PITP/CAMP2 polypeptide comprises, from N-terminus to C-terminus:
 (a), (b) and (c); or
 (c), (a) and (b),
 e.g., wherein wherein the chimeric *C. acnes* DsA1/DsA2/PITP/CAMP2 polypeptide comprises, from N-terminus to C-terminus: (c), (a) and (b).

284. The nucleic acid of any one of embodiments 263-283, wherein the chimeric *C. acnes* DsA1/DsA2/PITP/CAMP2 polypeptide comprises a transmembrane domain sequence.

285. The nucleic acid of embodiment 284, wherein the transmembrane sequence is positioned at the N terminus or the C terminus (e.g. the C terminus) of the chimeric *C. acnes* DsA1/DsA2/PITP/CAMP2 polypeptide.

286. The nucleic acid of embodiment 285, wherein the transmembrane domain sequence comprises an amino acid sequence according to any one of the sequences in Table 4 or SEQ ID NO: 84 (e.g., SEQ ID NO: 208 or 84).

287. The nucleic acid of embodiment 286, wherein:
 (i) the chimeric *C. acnes* DsA1/DsA2/PITP/CAMP2 polypeptide comprises a sequence according to SEQ ID NO: 373 or a sequence having at least 90%, at least 91%, at least 92%, at least 93%, at least 94%, at least 95%, at least 96%, at least 97%, at least 98%, or at least 99% (e.g., at least 90%) identity thereto and a transmembrane domain sequence (e.g., SEQ ID NO: 84); and/or
 (ii) the nucleotide sequence encoding the chimeric *C. acnes* DsA1/DsA2/PITP/CAMP2 polypeptide comprises a sequence according to SEQ ID NO: 384, or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto, and a nucleotide sequence encoding a transmembrane domain sequence (e.g., a sequence according to SEQ ID NO: 395), or
 the nucleotide sequence encoding the chimeric *C. acnes* DsA1/DsA2/PITP/CAMP2 polypeptide comprises a sequence according to SEQ ID NO: 385, or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto, and a nucleotide sequence encoding a transmembrane domain sequence (e.g., a sequence according to SEQ ID NO: 396),
 e.g., wherein the nucleotide sequence encoding the chimeric *C. acnes* DsA1/DsA2/PITP/CAMP2 polypeptide comprises a sequence according to SEQ ID NO: 385 and a sequence according to SEQ ID NO: 396; and/or
 (iii) the nucleotide sequence encoding the chimeric *C. acnes DsA*1/DsA2/PITP/CAMP2 polypeptide comprises a sequence according to SEQ ID NO: 377 or 378 or a sequence having at least 75%, at least 80%, at least 85%, at least 90%, at least 91%, at least 92%, at least 93%, at least 94%, at least 95%, at least 96%, at least 97%, at least 98%, or at least 99% (e.g., at least 75%) identity thereto (e.g., the chimeric *C. acnes* DsA1/DsA2/PITP/CAMP2 polypeptide comprises a sequence according to SEQ ID NO: 378).

288. The nucleic acid of any one of embodiments 263-287, wherein the chimeric *C. acnes* DsA1/DsA2/PITP/CAMP2 polypeptide comprises a non-native (e.g. viral) secretion signal peptide sequence.

289. The nucleic acid of embodiment 288, wherein the secretion signal peptide sequence is positioned at the N-terminus or the C-terminus (e.g. the N-terminus) of the chimeric *C. acnes* DsA1/DsA2/PITP/CAMP2 polypeptide.

290. The nucleic acid of embodiment 288 or 289, wherein the secretion signal peptide sequence is a viral secretion signal peptide sequence, which optionally comprises a sequence selected from the group consisting of: an influenza hemagglutinin (HA) secretion signal peptide sequence, a SARS COV-2 spike secretion signal peptide sequence, a VZV gB secretion signal peptide sequence, a VZV gE secretion signal peptide sequence, a VZV gI secretion signal peptide sequence, a VZV gK secretion signal peptide sequence, a measles F-protein secretion signal peptide sequence, a rubella E1 protein secretion signal peptide sequence, a rubella E2 protein secretion signal peptide sequence, a mumps F-protein secretion signal peptide sequence, an Ebola GP protein secretion signal peptide sequence, and a smallpox 6 kDa IC protein secretion signal peptide sequence.

291. The nucleic acid of any one of embodiments 288-290, wherein the secretion signal peptide sequence comprises a sequence according to any one of the sequences in Table 2 or 3.

292. The nucleic acid of any one of embodiments 288-291, wherein the secretion signal peptide sequence comprises a sequence according to any one of SEQ ID NO: 210-211 (e.g., SEQ ID NO: 210).

293. The nucleic acid of any one of embodiments 263-287, wherein the nucleic acid is mRNA.

294. A chimeric *C. acnes* DsA1/DsA2/PITP/CAMP2 polypeptide comprising:
 (a) a chimeric *C. acnes* DsA1/DsA2 polypeptide, e.g., as described in any one of embodiments 97-105;
 (b) an immunogenic fragment of a *C. acnes* PITP polypeptide, optionally wherein the immunogenic fragment comprises a ENFD of a *C. acnes* PITP polypeptide; and
 (c) a *C. acnes* CAMP2 polypeptide or an immunogenic fragment thereof.

295. The chimeric *C. acnes* DsA1/DsA2/PITP/CAMP2 polypeptide of embodiment 294, wherein the chimeric *C. acnes* DsA1/DsA2 polypeptide comprises:
 (A) (1) a CSD2 of a *C. acnes* DsA1 polypeptide and (2) a CSD1 and/or a CSD3 of a *C. acnes* DsA2 polypeptide: or
 (B) (1) a CSD2 of a *C. acnes* DsA2 polypeptide and (2) a CSD1 and/or a CSD3 of a *C. acnes* DsA1 polypeptide 296. The chimeric *C. acnes* DsA1/DsA2/PITP/CAMP2 polypeptide of embodiment 295, wherein the chimeric *C. acnes* DsA1/DsA2/PITP/CAMP2 polypeptide is as defined in (B).

297. The chimeric *C. acnes* DsA1/DsA2/PITP/CAMP2 polypeptide of any one of embodiments 294-296, wherein the chimeric *C. acnes* DsA1/DsA2/PITP/CAMP2 polypeptide comprises a CSD1 of a *C. acnes* DsA1 polypeptide, a CSD2 of a *C. acnes* DsA2 polypeptide and a CSD3 of a *C. acnes* DsA1 polypeptide.

298. The chimeric *C. acnes* DsA1/DsA2/PITP/CAMP2 polypeptide of any one of embodiments 294-297, wherein the chimeric *C. acnes* DsA1/DsA2 polypeptide of (a) comprises a sequence according to SEQ ID NO: 70, or a sequence having at least 90%, at least 91%, at least 92%, at least 93%, at least 94%, at least 95%, at least 96%, at least 97%, at least 98%, or at least 99% (e.g., at least 90%) identity thereto.

299. The chimeric *C. acnes* DsA1/DsA2/PITP/CAMP2 polypeptide of any one of embodiments 294-298, wherein the immunogenic fragment of a *C. acnes* PITP polypeptide comprising a ENFD of a *C. acnes* PITP polypeptide in (b) comprises the sequence corresponding to amino acid residues 1-133 of SEQ ID NO: 73 or a sequence having at least 90%, at least 91%, at least 92%, at least 93%, at least 94%, at least 95%, at least 96%, at least 97%, at least 98%, or at least 99% (e.g., at least 90%) identity thereto.

300 The chimeric *C. acnes* DsA1/DsA2/PITP/CAMP2 polypeptide of embodiment 299, wherein the immunogenic fragment of a *C. acnes* PITP polypeptide comprising a ENFD of a *C. acnes* PITP polypeptide in (b) comprises the sequence corresponding to amino acid residues 1-146 of SEQ ID NO: 73 or a sequence having at least 90%, at least 91%, at least 92%, at least 93%, at least 94%, at least 95%, at least 96%, at least 97%, at least 98%, or at least 99% (e.g., at least 90%) identity thereto.

301. The chimeric *C. acnes* DsA1/DsA2/PITP/CAMP2 polypeptide of any one of embodiments 294-300, wherein (a) and (b) comprise SEQ ID NO: 80, 82 or 83 or a sequence having at least 90%, at least 91%, at least 92%, at least 93%, at least 94%, at least 95%, at least 96%, at least 97%, at least 98%, or at least 99% (e.g., at least 90%) identity thereto.

302. The chimeric *C. acnes* DsA1/DsA2/PITP/CAMP2 polypeptide of embodiment 301, wherein (a) and (b) comprise SEQ ID NO: 80 or a sequence having at least 90%, at least 91%, at least 92%, at least 93%, at least 94%, at least 95%, at least 96%, at least 97%, at least 98%, or at least 99% (e.g., at least 90%) identity thereto.

303. The chimeric *C. acnes* DsA1/DsA2/PITP/CAMP2 polypeptide of any one of embodiments 294-302, wherein (c) is a *C. acnes* CAMP2 polypeptide, optionally wherein (c) comprises SEQ ID NO: 203 or a sequence having at least 90%, at least 91%, at least 92%, at least 93%, at least 94%, at least 95%, at least 96%, at least 97%, at least 98%, or at least 99% (e.g., at least 90%) identity thereto.

304. The chimeric *C. acnes* DsA1/DsA2/PITP/CAMP2 polypeptide of embodiment 303, wherein the chimeric *C. acnes* DsA1/DsA2/PITP/CAMP2 polypeptide comprises a sequence according to SEQ ID NO: 373 or 374 or a sequence having at least 90%, at least 91%, at least 92%, at least 93%, at least 94%, at least 95%, at least 96%, at least 97%, at least 98%, or at least 99% (e.g., at least 90%) identity thereto.

305. The chimeric *C. acnes* DsA1/DsA2/PITP/CAMP2 polypeptide of any one of embodiments 294-302, wherein the immunogenic fragment of a *C. acnes* CAMP2 polypeptide in (c) comprises a N-terminal domain of a *C. acnes* CAMP2 polypeptide, e.g. wherein the immunogenic fragment of a *C. acnes* CAMP2 polypeptide in (c) comprises amino acid residues 29-176 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity to the sequence of amino acid residues 29-176 of SEQ ID NO: 202.

306. The chimeric *C. acnes* DsA1/DsA2/PITP/CAMP2 polypeptide of any one of embodiments 294-302, wherein the immunogenic fragment of a *C. acnes* CAMP2 polypeptide in (c) comprises a N-terminal domain of a *C. acnes* CAMP2 polypeptide and a linker domain of a *C. acnes* CAMP2 polypeptide.

307. The chimeric *C. acnes* DsA1/DsA2/PITP/CAMP2 polypeptide of embodiment 306, wherein the immunogenic fragment of a *C. acnes* CAMP2 polypeptide in (c) comprises amino acid residues 29-188 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity thereto.

308. The chimeric *C. acnes* DsA1/DsA2/PITP/CAMP2 polypeptide of embodiment 307, wherein the chimeric *C. acnes* DsA1/DsA2/PITP/CAMP2 polypeptide comprises a sequence according to SEQ ID NO: 375 or a sequence having at least 90%, at least 91%, at least 92%, at least 93%, at least 94%, at least 95%, at least 96%, at least 97%, at least 98%, or at least 99% (e.g., at least 90%) identity thereto.

309. The chimeric *C. acnes* DsA1/DsA2/PITP/CAMP2 polypeptide of any one of embodiments 294-302, wherein the immunogenic fragment of a *C. acnes* CAMP2 polypeptide in (c) comprises a C-terminal domain of a *C. acnes* CAMP2 polypeptide.

310. The chimeric *C. acnes* DsA1/DsA2/PITP/CAMP2 polypeptide of embodiment 309, wherein the immunogenic fragment of a *C. acnes* CAMP2 polypeptide in (c) comprises amino acid residues 189-267 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity thereto.

311. The chimeric *C. acnes* DsA1/DsA2/PITP/CAMP2 polypeptide of embodiment 310, wherein the chimeric *C. acnes* DsA1/DsA2/PITP/CAMP2 polypeptide comprises a sequence according to SEQ ID NO: 376 or a sequence having at least 90%, at least 91%, at least 92%, at least 93%, at least 94%, at least 95%, at least 96%, at least 97%, at least 98%, or at least 99% (e.g., at least 90%) identity thereto.

312. The chimeric *C. acnes* DsA1/DsA2/PITP/CAMP2 polypeptide of any one of embodiments 294-302, wherein the immunogenic fragment of a *C. acnes* CAMP2 polypeptide in (c) comprises a linker domain of a *C. acnes* CAMP2 polypeptide and a C-terminal domain of a *C. acnes* CAMP2 polypeptide, e.g. wherein the immunogenic fragment of a *C. acnes* CAMP2 polypeptide in (c) comprises amino acid residues 177-267 of SEQ ID NO: 202 or a sequence having at least 90%, at least 91%, at least 92%, at least 93%, at least 94%, at least 95%, at least 96%, at least 97%, at least 98%, or at least 99% (e.g., at least 90%) identity to the sequence of amino acid residues 177-267 of SEQ ID NO: 202.

313 The chimeric *C. acnes* DsA1/DsA2/PITP/CAMP2 polypeptide of any one of embodiments 294-312, wherein any two or more of (a), (b) and (c) are attached via linkers or are directly fused to each other (e.g., wherein any two or more of (a), (b) and (c) are directly fused to each other).

314. The chimeric *C. acnes* DsA1/DsA2/PITP/CAMP2 polypeptide of any one of embodiments 294-313, wherein the chimeric *C. acnes* DsA1/DsA2/PITP/CAMP2 polypeptide comprises, from N-terminus to C-terminus:
(a), (b) and (c); or
(c), (a) and (b),
e.g., wherein wherein the chimeric *C. acnes* DsA1/DsA2/PITP/CAMP2 polypeptide comprises, from N-terminus to C-terminus: (c), (a) and (b).
315. The chimeric *C. acnes* DsA1/DsA2/PITP/CAMP2 polypeptide of any one of embodiments 294-314, wherein the chimeric *C. acnes* DsA1/DsA2/PITP/CAMP2 polypeptide comprises a transmembrane domain sequence.
316. The chimeric *C. acnes* DsA1/DsA2/PITP/CAMP2 polypeptide of embodiment 315, wherein the transmembrane sequence is positioned at the N terminus or the C terminus (e.g. the C terminus) of the chimeric *C. acnes* DsA1/DsA2/PITP/CAMP2 polypeptide.
317. The chimeric *C. acnes* DsA1/DsA2/PITP/CAMP2 polypeptide of embodiment 316, wherein the transmembrane domain sequence comprises an amino acid sequence according to any one of the sequences in Table 4 or SEQ ID NO: 84 (e.g., SEQ ID NO: 84).
318. The chimeric *C. acnes* DsA1/DsA2/PITP/CAMP2 polypeptide of embodiment 317, wherein the chimeric *C. acnes* DsA1/DsA2/PITP/CAMP2 polypeptide comprises a sequence according to SEQ ID NO: 373 or a sequence having at least 90%, at least 91%, at least 92%, at least 93%, at least 94%, at least 95%, at least 96%, at least 97%, at least 98%, or at least 99% (e.g., at least 90%) identity thereto and a transmembrane domain sequence (e.g., SEQ ID NO: 84).
319. A LNP encapsulating the mRNA of embodiment 293, optionally wherein the LNP has an average diameter of 30 nm to 200 nm (e.g. an average diameter of 80 nm to 150 nm).
320. A composition, optionally an immunogenic composition, comprising the nucleic acid (e.g., a mRNA) according to any one of embodiments 263-293.
321. The composition of embodiments 320, wherein the composition further comprises a lipid nanoparticle (LNP), optionally wherein the nucleic acid is encapsulated in the LNP, optionally wherein the LNP has an average diameter of 30 nm to 200 nm (e.g. an average diameter of 80 nm to 150 nm).
322 The composition of any one of embodiment 319 or 321, wherein the LNP comprises at least one cationic lipid, optionally wherein the cationic lipid
is biodegradable or is not biodegradable, and/or
the cationic lipid is cleavable or is not cleavable.
323. The composition of embodiment 322, wherein the cationic lipid is selected from the group consisting of OF-02, cKK-E10, OF-Deg-Lin, GL-HEPES-E3-E10-DS-3-E18-1, GL-HEPES-E3-E12-DS-4-E10, GL-HEPES-E3-E12-DS-3-E14, SM-102, ALC-0315, IS-001 and IM-001.
324. The composition of embodiment 323, wherein the cationic lipid is selected from the group consisting of OF-02, cKK-E10, GL-HEPES-E3-E12-DS-4-E10, IS-001 and IM-001 (e.g. wherein the cationic lipid is GL-HEPES-E3-E12-DS-4-E10).
325. The composition of any one of embodiments 319 or 321-324, wherein the LNP further comprises a polyethylene glycol (PEG) conjugated (PEGylated) lipid, a cholesterol-based lipid, and a helper lipid, optionally wherein the LNP comprises: a cationic lipid at a molar ratio of 35% to 55%; a polyethylene glycol (PEG) conjugated (PEGylated) lipid at a molar ratio of 0.25% to 2.75%: a cholesterol-based lipid at a molar ratio of 20% to 45%; and a helper lipid at a molar ratio of 5% to 35%, wherein all of the molar ratios are relative to the total lipid content of the LNP,
e.g. wherein the LNP comprises a cationic lipid at a molar ratio of 40%, a PEGylated lipid at a molar ratio of 1.5%, a cholesterol-based lipid at a molar ratio of 28.5%, and a helper lipid at a molar ratio of 30%.
326. The composition of any one of embodiments 320-325, wherein the nucleic acid is mRNA.
327. The composition of any one of embodiments 326, wherein the mRNA comprises a 5' cap, at least one 5' untranslated region (5' UTR), at least one 3' untranslated region (3' UTR), and/or at least one polyadenylation (poly(A)) sequence.
328. The composition of any one of embodiments 326-327, wherein the mRNA is unmodified or:
(i) the mRNA comprises at least one chemical modification, optionally wherein the chemical modification is selected from the group consisting of e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine. 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine (e.g., wherein the chemical modification comprises N1-methylpseudouridine); and/or
(ii) the mRNA is synthesized from modified nucleotide analogues or derivatives of purines and pyrimidines, optionally wherein the modified nucleotide analogues or derivatives of purines and pyrimidines are selected from the group consisting of: 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxy hydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine.

329. The composition of any one of embodiments 326-328, wherein the mRNA comprises at least one chemical modification (e.g., wherein at least 20%, at least 30%, at least 40%, at least 50%, at least 60%, at least 70%, at least 80%, at least 85%, at least 90%, at least 95%, or 100% of the uridines in the mRNA are chemically modified), optionally wherein the chemical modification comprises N1-methylpseudouridine e.g. in place of every uridine.

330. The composition of any one of embodiments 326-329, wherein the mRNA is a self-replicating mRNA or a non-replicating mRNA, e.g. wherein the mRNA is a non-replicating mRNA.

331. The composition of any one of embodiments 326-330, wherein the composition can be in a frozen liquid form or in a lyophilized form (e.g., in a lyophilized form).

332. A composition, optionally an immunogenic composition, comprising the chimeric *C. acnes* DsA1/DsA2/PITP/CAMP2 polypeptide as defined in any one of embodiments 294-318, optionally wherein the composition can be in a frozen liquid form or in a lyophilized form (e.g., in a lyophilized form).

333. The composition of embodiment 332, wherein the composition further comprises an adjuvant, optionally wherein the adjuvant is selected from the group consisting of: Aluminum based adjuvant (e.g. AlOOH), Squalene based oil in water emulsion adjuvants (e.g. AF03, AS03, MF59) and Liposome-based adjuvants comprising a saponin and a TLR4 agonist (e.g. SPA14, AS01, LEQ).

334. A vaccine composition comprising the nucleic acid (e.g. mRNA) of any one of embodiments 263-293 or the polypeptide of any one of embodiments 294-318.

335. The nucleic acid (e.g. mRNA) of any one of embodiments 263-293, the polypeptide of any one of embodiments 294-318, the LNP of embodiment 319 or the composition of any one of embodiments 320-333 for use as a medicament.

336. The use of the nucleic acid (e.g. mRNA) of any one of embodiments 263-293, the polypeptide of any one of embodiments 294-318, the LNP of embodiment 319 or the composition of any one of embodiments 320-333 for the manufacture of a medicament.

337. A method of treating or preventing a disease comprising administering the nucleic acid (e.g. mRNA) of any one of embodiments 263-293, the polypeptide of any one of embodiments 294-318, the LNP of embodiment 319 or the composition of any one of embodiments 320-333 to a subject in need thereof.

338 The nucleic acid (e.g. mRNA) of any one of embodiments 263-293, the polypeptide of any one of embodiments 294-318, the LNP of embodiment 319 or the composition of any one of embodiments 320-333 for use in a method of treating or preventing *C. acnes* infection (e.g. a moderate or severe *C. acnes* infection) in a subject (e.g. human).

339. The use of the nucleic acid (e.g. mRNA) of any one of embodiments 263-293, the polypeptide of any one of embodiments 294-318, the LNP of embodiment 319 or the composition of any one of embodiments 320-333 for the manufacture of a medicament for treating or preventing *C. acnes* infection (e.g. a moderate or severe *C. acnes* infection) in a subject (e.g. human).

340. A method of treating or preventing a *C. acnes* infection (e.g. a moderate or severe *C. acnes* infection) comprising administering the nucleic acid (e.g. mRNA) of any one of embodiments 263-293, the polypeptide of any one of embodiments 294-318, the LNP of embodiment 319 or the composition of any one of embodiments 320-333 to a subject (e.g. human) in need thereof.

341. The nucleic acid (e.g. mRNA) of any one of embodiments 263-293, the polypeptide of any one of embodiments 294-318, the LNP of embodiment 319 or the composition of any one of embodiments 320-333 for use in a method of treating or preventing acne (e.g. mild, moderate or severe acne) in a subject (e.g. human).

342. The use of the nucleic acid (e.g. mRNA) of any one of embodiments 263-293, the polypeptide of any one of embodiments 294-318, the LNP of embodiment 319 or the composition of any one of embodiments 320-333 for the manufacture of a medicament for treating or preventing acne (e.g. mild, moderate or severe acne) in a subject (e.g. human).

343. A method of treating or preventing acne (e.g. mild, moderate or severe acne) comprising administering nucleic acid (e.g. mRNA) of any one of embodiments 263-293, the polypeptide of any one of embodiments 294-318, the LNP of embodiment 319 or the composition of any one of embodiments 320-333 to a subject (e.g. human) in need thereof.

344. The nucleic acid (e.g. mRNA) of any one of embodiments 263-293, the polypeptide of any one of embodiments 294-318, the LNP of embodiment 319 or the composition of any one of embodiments 320-333 for use in a method of eliciting an immune response in a subject, optionally wherein the subject is a human subject.

345. The use of nucleic acid (e.g. mRNA) of any one of embodiments 263-293, the polypeptide of any one of embodiments 294-318, the LNP of embodiment 319 or the composition of any one of embodiments 320-333 for the manufacture of a medicament for eliciting an immune response in a subject, optionally wherein the subject is a human subject.

346. A method of eliciting an immune response in a subject comprising administering nucleic acid (e.g. mRNA) of any one of embodiments 263-293, the polypeptide of any one of embodiments 294-318, the LNP of embodiment 319 or the composition of any one of embodiments 320-333 to the subject.

347. The method of any one of embodiments 337, 340, 343 or 346, wherein the method comprises:
(i) administering one dose of the nucleic acid, the polypeptide or the composition; or
(ii) administering two doses of the nucleic acid, the polypeptide or the composition, optionally wherein the two doses are administered two months apart e.g. wherein the administration is according to (ii).

348. The nucleic acid, the polypeptide or the composition for use according to any one of embodiments 335, 338, 341 or 344, wherein the method comprises:
(i) administering one dose of the nucleic acid, the polypeptide or the composition; or
(ii) administering two doses of the nucleic acid, the polypeptide or the composition, optionally wherein the two doses are administered two months apart.

349. The use of the nucleic acid, the polypeptide or the composition according to any one of embodiments 336, 339, 342 or 345, wherein the treating or preventing comprises:
   (i) administering one dose of the nucleic acid, the polypeptide or the composition; or
   (ii) administering two doses of the nucleic acid, the polypeptide or the composition, optionally wherein the two doses are administered two months apart.
350. The method of any one of embodiments 337, 340, 343, 346 or 347, the nucleic acid, the polypeptide or the composition for use according to any one of embodiments 335, 338, 341, 344 or 348, or the use of the nucleic acid, the polypeptide or the composition of any one of embodiments 336, 339, 342, 345 or 349, wherein the method comprises administering the polypeptide, nucleic acid or the composition intramuscularly.
351. The method of any one of embodiments 337, 340, 343, 346 or 347, the nucleic acid, the polypeptide or the composition for use according to any one of embodiments 335, 338, 341, 344 or 348, or the use of the nucleic acid, the polypeptide or the composition of any one of embodiments 336, 339, 342, 345 or 349, wherein the method comprises administering the polypeptide, nucleic acid or the composition through skin injection (e.g. in the epidermis, the dermis or the hypodermis of the skin), such as intradermally, optionally with a device suitable for skin injection, such as a needle (e.g. an epidermic, dermic or hypodermic needle), a needle free device, a microneedle device or a microprojection array device.
352. The method of any one of embodiments 337, 340, 343, 346, 347, 350 or 351, the nucleic acid, the polypeptide, the composition, or the combination for use according to any one of embodiments 335, 338, 341, 344, 348, 350 or 351, or the use of the nucleic acid, the polypeptide, the composition, or the combination of any one of embodiments 336, 339, 342, 345 or 349-351, wherein the subject is a human subject and wherein the subject is between 9 and 45 years old or between 12 and 45 years old (e.g. between 18 and 45 years old).

BRIEF DESCRIPTION OF THE DRAWINGS

FIG. 5 shows characterization data of proteins expressed in HEK cells after in vitro cell transfection with mRNA constructs encoding *C. acnes* CAMP2 polypeptides (construct design shown in FIG. 4).

FIG. 43 shows a table summarizing the Western blot analysis of protein expression and localization from CAMP2 and PITP mRNA constructs containing a SS from glycoprotein derived from Influenza (subtypes A or B). Rabies. Varicella (VZV), or Ebola viruses, with or without their respective glycoprotein TMB domain post transfection in HEK Expi293F cells.

FIGS. 44*a, b* and *c* display different (overlapping) segments of the alignment: residues 1-101 (a). 99-201 (b) and 199-267 (c)—residue numbering including the secretion signal peptide sequence.

MODES FOR CARRYING OUT THE INVENTION

Example 1—Main Methods

Enzyme-Linked Immunosorbent Assays (ELISA)

Figure 1:
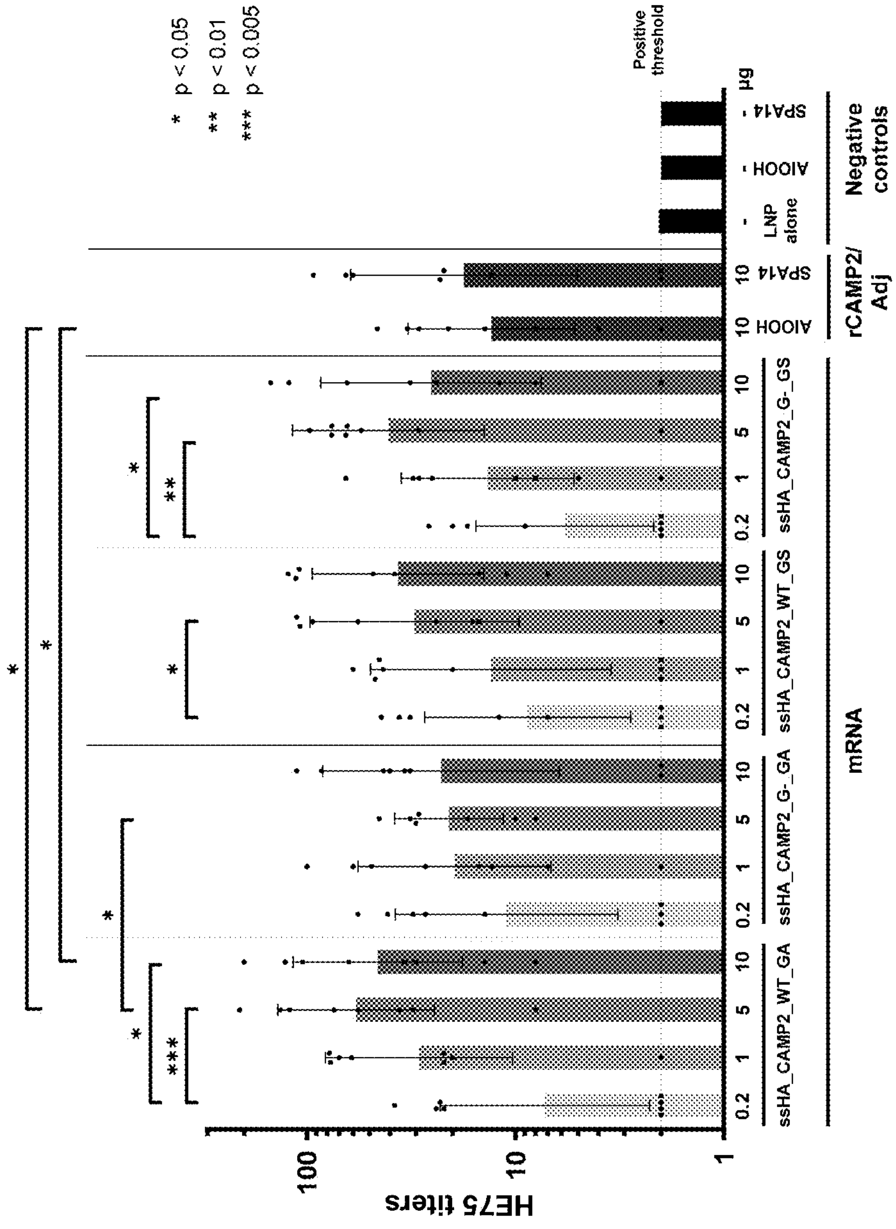
FIG. 1 shows co-hemolytic neutralizing titers of IgG purified from sera of mice immunized twice at 3 weeks interval with different mRNA constructs encoding *C. acnes* CAMP2 polypeptides (encapsulated in a LNP comprising ckk-E10 as cationic lipid) or a recombinant *C. acnes* CAMP2 polypeptides (formulated in either AlOOH or SPA14 adjuvants). LNP alone, and adjuvants alone (AlOOH and SPA14) served as negative controls.

An ELISA method was used to detect and quantify the IgG immune response elicited by various antigens (e.g. various constructs based on DsA1, DsA2, PITP or CAMP2) following administration in mice.

The specific IgG titers were measured from individual sera using an ELISA method in a 384-well plate on a Hamilton automated platform, or manually. Briefly, 384-well micro-plates were coated with the recombinant protein of interest (e.g. DsA1, DsA2, PITP, CAMP2), at protein concentrations ranging from 0.25 to 2 μg/mL in PBS 1X, and kept overnight at +4° C. Coating solution was removed and washed with buffer 1 (PBS 1X/Tween20 0.1%). Unspecific binding was prevented by incubating the coated plates with a saturation buffer containing either 2% BSA or 1% skimmed milk in PBSIX during 90 min at room temperature (RT). Plates were emptied, then a 2-fold serial dilution of the serum samples (containing the specific IgG antibodies to be measured) were added to the plates. The plates were incubated for 90 min at RT and then washed with buffer 1. The formed antigen-antibodies complexes were subsequently revealed by adding an anti-species secondary antibody (Goat Anti-Mouse IgG; JACKSON; 115-036-062 or Goat Anti-Rabbit IgG; SIGMA; A0545) conjugated with horse radish peroxidase (HRP). After 90 min incubation at RT, the plates were washed with buffer 1. The reaction was developed by adding a substrate of peroxidase (H2O2) combined with a chromogen (TMB solution), inducing the hydrolysis of the substrate and developing a yellow coloration. The hydrolysis reaction was chemically stopped after 30 min at RT by the addition of HCl(1N (normality)), and Optical Density (OD) was measured at 450-650 nm on a spectrophotometer (Synergy HTX. Biotek). The difference between the OD at 450 nm and the OD at 650 nm is directly proportional to the amount of specific IgG antibodies bound to the recombinant protein of interest (antigen). The IgG titers of a serum sample were calculated either directly by expressing a titer that is the inverse of the dilution corresponding to an OD equal to 1, or relative to a reference serum of the same animal species applied to each plate. The IgG titers (Arbitrary units) were calculated using Softmax Pro software.

Surface Binding Assays (SBA)

Following administration of various antigens (e.g. various constructs based on DsA1, DsA2, PITP or CAMP2) in mice. Surface Binding Assays (SBA) using a fluorescence cytometer were used to determine the binding efficiency of serum antibodies to the cell surface of live Cutibacterium *acnes* (*C. acnes*) bacteria. In particular, the ability to bind the cell surface of *C. acnes* strains from different genetic types was used to assess cross-reactivity of the serum antibodies.

Briefly, bacterial suspensions of *C. acnes* strains (e.g. *C. acnes* types IA1 (NCTC737) and IB (KPA171202)) were precultured in *Brucella* Blood Agar with Hemin and Vitamin K1 (BD) for 48- to 72-hours anaerobically and inoculated in Thioglycollate broth at OD600 nm of 0.15 for 16- to 18-hours at 37° C., in anaerobic atmosphere. The precultures were then diluted in Thioglycollate with or without the addition of 750 μg/mL deferoxamine at OD600 nm of 0.15 and incubated 24-hours at 37° C. under anaerobic conditions.

Bacteria were washed and resuspended in HBSS buffer containing 2% Bovine Serum Albumin (BSA) to a final concentration of $4\times10^6$ Colony Forming Units (CFU)/mL. Heat inactivated serum samples and the assay control serum were brought to RT and diluted in HBSS 2% BSA. 50 μL of a 2-fold serial dilution of the serum samples and 50 μL of bacteria suspension were deposited in a 96-deepwell plate, and incubated for 30 min at RT. To reveal antibodies (contained in the serum) bound to bacteria, reaction plates were washed twice and 100 μL of secondary anti-mouse/rabbit IgG antibody conjugated to Alexa Fluor 488 (Alexa Fluor 488 F(ab')2 fragment of goat anti mouse IgG/life technology #A1101) (diluted 1:500 in HBSS containing 0.5% BSA) were added, and incubated for 30 min at RT. 50 μL of SYTO60 (diluted 1:500 in HBSS) were added to the reaction and incubated for 15 min at RT, in order to stain bacteria. Reaction plates were washed twice and bacteria were resuspended in 150 μL HBSS for the acquisition of median fluorescence intensity (MFI) with a flow cytometer (NovoCyte, Agilent). The MFI is a correlate of the amount of surface-bound antibodies.

Opsonophagocytic Killing (OPK) Assays

Opsonophagocytic killing (OPK) assays may be used to determine the ability of antibodies to induce opsonisation of *C. acnes* bacteria by mobilizing immune cells against the bacteria, leading to a reduction in the bacterial cell numbers. OPK assays were used to test serum antibodies elicited by various antigens (e.g. various constructs based on DsA1, DsA2, PITP or CAMP2) following their administration in mice.

The OPK assay involves co-culture of HL-60 cell line (a human promyelocytic leukemia cell line), differentiated into granulocyte-like human cells with live *C. acnes* bacteria pre-incubated with serum antibodies.

Briefly, HL-60 cells (at a concentration of $5\times10^5$ cells/mL) were differentiated in cell differentiation medium containing dimethylformamide (DMF, Sigma), i.e. RPMI medium (RPMI medium 1640) 1x+Glutamax (Gibco)) containing 10% heat inactivated FCS and 0.8% DMF, for 3 days at 37° C. After washing, the cell number was adjusted to a final concentration of $5.28\times10^6$ cells/ml in RPMI medium containing 10% FCS and 20 mM glucose.

Bacterial suspensions of *C. acnes* strains (e.g. *C. acnes* multilocus sequence types IA1 (NCTC737) and IB (KPA171202)) were cultured in thioglycolate broth at 37° C., in anaerobic atmosphere to reach an OD600 nm in the range 0.3 to 1.7. Bacteria were washed and resuspended in HBSS buffer containing 2% BSA, to a final concentration of $6\times10^4$ CFU/mL (corresponding to a final number of 1500 bacteria per well during the reaction) and incubated at room temperature for at least 30 minutes as saturation step.

Heat inactivated serum samples and the assay control serum were brought to RT. If required, predilution was performed in RPMI medium containing 10% FCS and 20 mM glucose. 50 μL of a 2-fold serial dilution of the serum samples were deposited in a 96-well reaction plate.

HL-60 cells were mixed with the bacteria at a dilution of 1:6 (in order to have a ratio a 440 HLA-60 cells for 1 bacterium), and 150 μL of the HL-60 cells/bacteria suspension were added in the wells containing the diluted serum samples. After a two-day reaction, 100 μL of each reaction were plated on *Brucella* blood agar at three different dilutions. E.g., 40 μL of diluted reaction mix (1/50 for the NCTC737 strain and 1/200 for the KPA171202 strain) were deposited on BBA. After anaerobic incubation of the plates at 37° C. for a minimum of 70 hours, the colonies on the plates were counted with a colony counter (AES Laboratories); a picture of the agar plate with a microcamera, and image analysis using the Cybel software was performed to count colonies. The number of CFU in experimental conditions (with differentiated HL-60) was compared to the CFU of the corresponding negative controls. The OPK activity was expressed as the titer corresponding to the reciprocal serum dilution that induces 50% decrease in the viable bacterial counts (CFU) in comparison with negative control sera (K50 titer), as determined using a four-parameter logistic regression model.

Co-Hemolysis Neutralisation Assay

This assay was used to measure serological titres of neutralizing recombinant *C. acnes* CAMP2 polypeptide (rCAMP2)-specific antibodies.

Briefly, IgG from mouse sera were purified with Protein G High Performance Spintrap kit (Cytiva), according to manufacturer's instructions.

Sheep red blood cells (SRBC) were prepared from whole blood suspended in Alsever anticoagulant (50% v/v), washed three times with cold PBS and resuspended in PBS by adding a volume equivalent to 10 times that of the pellet. SRBC were subsequently treated with sphingomyelinase (0.025U/mL final concentration) for 30 minutes at 37° C., then washed three times with PBS at RT. SRBC concentration was adjusted to $8.10^7$ cells/mL.

25 μL of a 2-fold serial dilution of purified IgG and 25 μL of rCAMP2 at 10 μg/mL were deposited in a 96-well reaction plate, which were incubated at 37° C. for 1 hour. Then, 50 μL of SRBC were added, and the final reaction was incubated for 2 hours at 37° C. The pellet area in each well were recorded using a Multimode Imagine plate reader.

The presence of antibodies that neutralize rCAMP2 biological activity resulted in co-hemolysis inhibition and therefore allowed the deposition of intact red blood cells at the bottom of the well, forming a pellet. Neutralising titers were defined as the reciprocal dilution that corresponds to 75% of the treated negative control pellet area, referred to Hemolysis Effect 75 (HE75). The determination of the titer corresponding to HE75 was based on a four-parameter logistic regression model.

Example 2—Comparison of mRNA Platform Versus Protein Platform, for CAMP2, H4-V3 and P028-V7 Antigens The aim of this example was to compare formulations containing mRNA encoding *C. acnes* antigens relative to formulations containing *C. acnes* polypeptides for their ability to induce a functional immune response. The tested antigens included *C. acnes* CAMP2 polypeptides, a chimeric *C. acnes* DsA1/DsA2 polypeptide (H4-V3) and *C. acnes* PITP polypeptide (P028-V7).

Preparation of mRNA-LNPs

```
Each mRNA comprised a cap1, a 5'UTR from CMV given
by the sequence:
                                     (SEQ ID NO: 265)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACG,

a 3' UTR from hGH given by the sequence:
                                     (SEQ ID NO : 266)
CGGGUGGCAUCCCUGUGACCCCUCCCCAGUGCCUCUCCUGGCCCUGGAAG
UUGCCACUCCAGUGCCCACCAGCCUUGUCCUAAUAAAAUUAAGUUGCAUC,
```

and a poly A tail. Each mRNA was encapsulated in lipid nanoparticles (LNPs) composed of four lipids: ionizable (cationic) lipid/DOPE/cholesterol/DMG-PEG, at the molar ratio of 40:30:28.5:1.5. In this example, ckk-E10 was used as the ionizable lipid for mRNAs encoding *C. acnes* CAMP2 polypeptides and GL-HEPES-E3-E12-DS-4-E10 was used as the ionizable lipid for mRNA encoding H4-V3 and mRNA encoding P028-V7.

LNPs were prepared using a T-mix process. Briefly, lipids were dissolved in ethanol (EtOH) at a final concentration of 9.331 mg/ml and mRNA solution was prepared in Citrate Buffer Saline (CBS at 1 mM citrate pH 4.5 and 150 mM sodium chloride). 3 mL of the lipid solution and 12 mL of the mRNA solution were loaded respectively in a 5 mL and 20 ml syringe. Using a T-mix system 3⁄32" and pumps, mRNA solution and lipids were mixed at a total flow rate of 250 mL/min (flow rate at 50m L/min for the lipids and flow rate of 200 mL/min for the mRNA). The mixture was then treated by buffer exchange. First, a dialysis in water: EtOH 80:20 was performed 2h at room temperature (RT), then a second dialysis in water was performed overnight at +4° C. The last step was a concentration to 1 mg/mL mRNA and a buffer exchange in Amicon at +4° C. with trehalose 10%. LNPs were then sterile filtered and stored at −80° C.

Immunisation of Mice

OF-1 outbred mice (6-week old at day 0) were immunized with the mRNA or protein antigen (at doses ranging between 0.2 and 10 μg for mRNA CAMP2, and at 1 and 5 μg doses for mRNAs H4-V3 and P028-V7, and at 10 μg for all proteins), twice. 3 or 4 weeks apart, through intra-muscular (IM) route (50 μL in quadriceps muscle hind leg, with alternance of the right and left leg between both injections). LNP alone served as negative controls for the mRNA immunisations. A final bleeding was performed 7 or 14 days after the last injection, and the sera obtained were tested in a co-hemolysis neutralisation assay (as described in Example 1), in a Surface Binding assay (as described in Example 1) and/or in an OPK assay (as described in Example 1).

Immunisation with C. *Acnes* CAMP2 Antigens Elicits Antibodies which Decrease the Co-Hemolytic Activity of CAMP 2

*C. acnes* CAMP2 antigens were evaluated for their ability to elicit antibodies which reduce the inflammatory activity of *C. acnes* CAMP2, using a co-hemolysis neutralisation assay.

The following antigens were tested:

- Two different codon-optimized mRNAs, both encoding a wild-type *C. acnes* CAMP2 polypeptide with a N-terminal HA SS (SEQ ID NO: 2): "ssHA-CAMP2_WT_GA" (SEQ ID NO: 87) and "ssHA-CAMP2_WT_GS" (SEQ ID NO: 88)
- Two different codon-optimized mRNAs, both encoding a *C. acnes* CAMP2 polypeptide with mutations at N-Glycosylation sites and with a N-terminal HA SS (SEQ ID NO: 10): "ssHA-CAMP2_G-_GA" (SEQ ID NO: 95) and "ssHA-CAMP2_G-_GS" (SEQ ID NO: 96)
- Recombinant *C. acnes* CAMP2 polypeptide of SEQ ID NO: 1 mRNA sequences were designed for coding secreted form of CAMP2. Each mRNA sequence was optimized using two different algorithms, and mRNA synthesis was performed using unmodified nucleotides. Each mRNA antigen construct (encapsulated in a LNP using ckk-E10 as the ionizable lipid) was tested at doses ranging from 0.2 to 10 μg per mouse. Recombinant *C. acnes* CAMP2 polypeptide of SEQ ID NO: 1 was formulated in either aluminium hydroxide (AlOOH) or SPA14 and tested at 10 μg per mouse. Mice were immunized twice at 3 weeks interval. The sera were obtained at day 35 following the first immunization and IgG were purified from the sera. As shown in FIG. 1, all mRNAs containing formulations induced neutralizing titers equivalent or superior to formulations with recombinant CAMP2. The optimal dose for mRNA containing formulation was 5 μg.

Evaluation of Chimeric *C. acnes* DsA1 DsA2 Antigens

Figure 2:
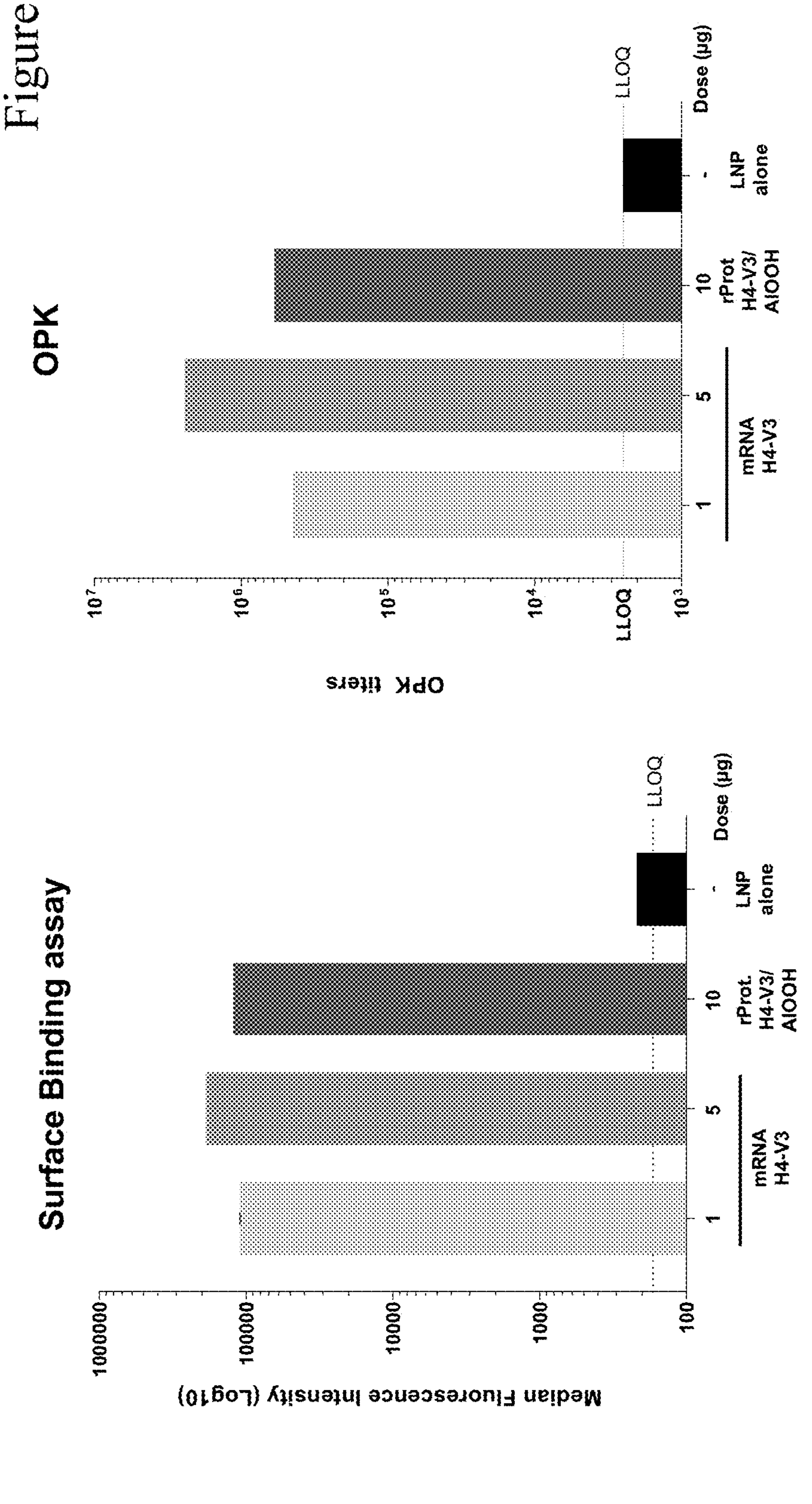
FIG. 2 shows Surface Binding (SB) and Opsonophagocytic Killing (OPK) titers from either individual sera (SB) or pool of sera (OPK), performed on NCTC737 *C. acnes* strain, of mice immunized twice at 4 weeks interval. Experimental formulations contained either H4-V3 mRNA antigen construct (encapsulated in an LNP comprising GL-HEPES-E3-E12-DS-4-E10 as cationic lipid) or H4-V3 recombinant protein (formulated in AlOOH). LNP alone served as a negative control. LLOQ=lowest limit of quantification.
Figure 3A:
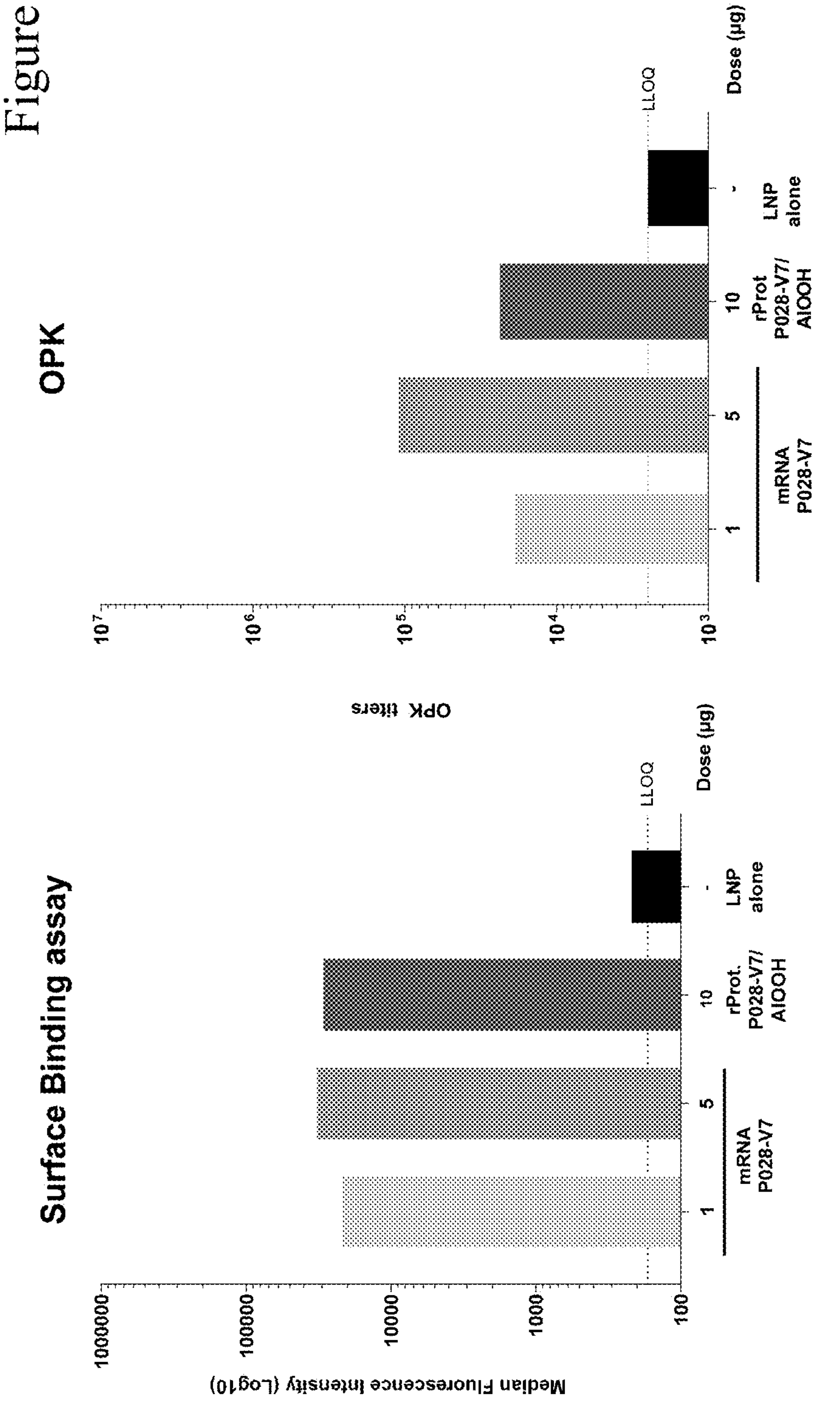
FIGS. 3A-3B show Surface Binding (SB) and Opsonophagocytic Killing (OPK) titers from either individual sera (SB) or pool of sera (OPK), performed on NCTC737 (FIG. 3*a*) and KPA171202 (FIG. 3*b*) *C. acnes* strains, of mice immunized twice at 4 weeks interval. Experimental formulations contained either P028-V7 mRNA antigen construct (encapsulated in an LNP comprising GL-HEPES-E3-E12-DS-4-E10 as cationic lipid) or P028-V7 recombinant protein (formulated in AlOOH). LNP alone served as a negative control. LLOQ=lowest limit of quantification.
Figure 3B:
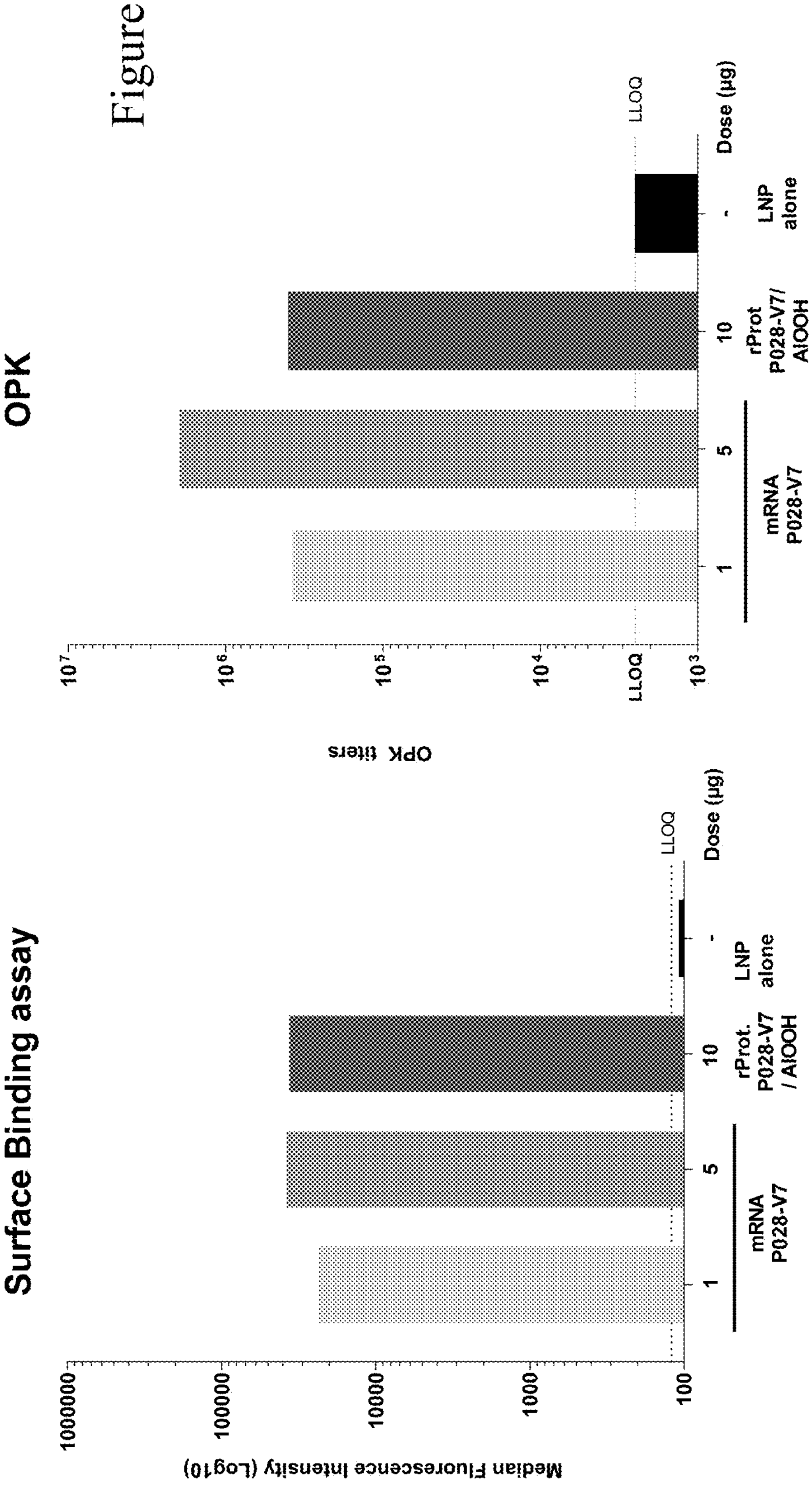

An mRNA encoding a chimeric *C. acnes* DsA1/DsA2 polypeptide, H4-V3 (SEQ ID NO: 28, having a nucleotide sequence corresponding to SEQ ID NO: 113) was tested for its ability to elicit opsonising antibodies, mRNA sequences were designed for coding secreted form of H4-V3. The mRNA was synthesised using modified nucleotides (in which all uridine nucleosides were replaced with 1-methyl pseudo uridine). The mRNA (encapsulated in a LNP using GL-HEPES-E3-E12-DS-4-E10 as the ionizable lipid) was tested at a dose of 1 and 5 μg per mouse. Recombinant H4-V3 polypeptide of SEQ ID NO: 29 (formulated in AlOOH adjuvant) was tested at 10 μg per mouse. Mice were immunized twice at 4 weeks interval. The sera were obtained at day 42 following the first immunization, and Surface Binding (SB) and Opsonophagocytic Killing (OPK) were performed from pools of sera (OPK) on NCTC737 *C. acnes* strain (IA1, RT1). This strain expressed DsA1, DsA2 and PITP. As shown in FIG. 2, the mRNA platform performed at least as well as the protein platform when a DsA1/DsA2 chimera (H4-V3) was used as antigen, as evidenced by a surface binding assay and an OPK assay.

Evaluation of *C. acnes* PITP Antigens

An mRNA encoding a *C. acnes* PITP polypeptide, P028-V7 (SEQ ID NO: 31, having a nucleotide sequence corresponding to SEQ ID NO: 115) was tested for its ability to elicit opsonising antibodies. mRNA sequences were designed for coding secreted form of P028-V7. The mRNA was synthesised using modified nucleotides (in which all uridine nucleosides were replaced with 1-methyl pseudo uridine). The mRNA (encapsulated in a LNP using GL-HEPES-E3-E12-DS-4-E10 as the ionizable lipid) was tested at a dose of 1 and 5 μg per mouse. Recombinant P028-V7 polypeptide of SEQ ID NO: 32 (formulated in AlOOH adjuvant) was tested at 10 μg per mouse. Mice were immunized twice at 4 weeks interval. The sera were obtained at day 42 following the first immunization, and Surface Binding (SB) and Opsonophagocytic Killing (OPK) experiments were performed from pools of sera on NCTC737 and KPA171202 *C. acnes* strains. The mRNA platform performed at least as well as the protein platform when a PITP variant (P028-V7) was used as antigen, as evidenced by a surface binding assay and an OPK assay, using a NCTC737 strain of *C. acnes* (IA1, RT1), or a KPA171202 strain of *C. acnes*, as shown in FIGS. **3*a* and 3*b*** respectively. The NCTC737 strain expressed DsA1, DsA2 and PITP. The KPA171202 strain expressed PITP, but not DsA1 or DsA2.

Example 3—Evaluation of CAMP2 mRNA Antigens

The aim of this example was to assess a range of *C. acnes* CAMP2 antigen constructs for their ability to induce a functional immune response, as assessed using co-hemolytic neutralising assays and ELISA assays.

Design of C. *Acnes* CAMP 2 Polypeptide Constructs

All *C. acnes* CAMP2 polypeptide sequences were derived from the *C. acnes* strain KPA171202 CAMP2 polypeptide sequence lacking a native signal sequence.

Figure 4:
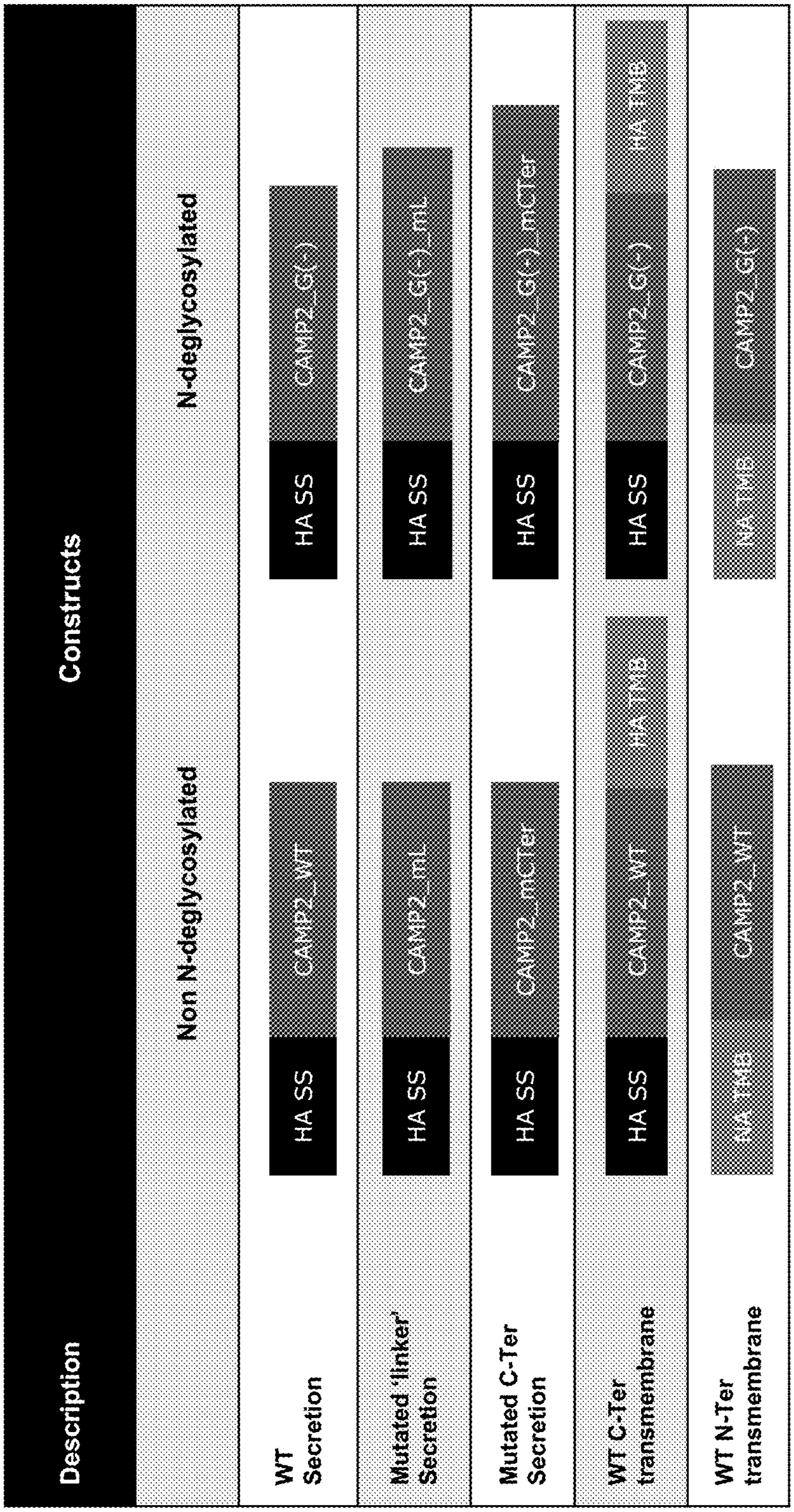
FIG. 4 shows a schematic visualization of CAMP2 mRNA constructs that have been designed and synthesized.

Six mRNA constructs encoding secreted *C. acnes* CAMP2 polypeptide constructs were designed as depicted in the top three lines in the Table of FIG. 4. Each construct comprised a N-terminal secretion peptide signal sequence of Influenza Hemagglutinin (HA, H1N1 A/Caledonia/20/1999) (HA SS) in order to target the encoded protein for secretion. The non-N-deglycosylated constructs (LHS) include:

- a native *C. acnes* CAMP2 polypeptide ("HA SS CAMP2_WT") (mRNA according to SEQ ID NO: 89),
- a *C. acnes* CAMP2 polypeptide with amino acid mutations in the linker moiety ("HA SS CAMP2_mL") (mRNA according to SEQ ID NO: 98)
- a *C. acnes* CAMP2 polypeptide with amino acid mutations within its C-terminal domain ("HA SS CAMP2_mCTer") (mRNA according to SEQ ID NO: 100)

For each of the three non-N-deglycosylated constructs, a N-deglycosylated counterpart construct was designed with mutations in a N-glycosylation site (a substitution of Asn166 by Ser) (RHS):

- a *C. acnes* CAMP2 polypeptide with a N166S mutation ("HA SS CAMP2_G(−)") (mRNA according to SEQ ID NO: 97)
- a *C. acnes* CAMP2 polypeptide with amino acid mutations in the linker moiety and with a N166S mutation ("HA SS CAMP2_G(−)_mL") (mRNA according to SEQ ID NO: 99)
- a *C. acnes* CAMP2 polypeptide with amino acid mutations within its C-terminal domain and with a N166S mutation ("HA SS CAMP2_G(−) mCTer") (mRNA according to SEQ ID NO: 101)

Additionally, four mRNA constructs encoding membrane-anchored *C. acnes* CAMP2 polypeptide constructs were designed as depicted in the two bottom lines in the Table of FIG. 4. The non-N-deglycosylated constructs (LHS) include:

- a native *C. acnes* CAMP2 polypeptide targeted to the membrane via a C-terminal transmembrane domain sequence (HA TMB) of Influenza Hemagglutinin (HA, H1N1 A/Caledonia/20/1999) ("HA SS CAMP2_WT HA TMB") (mRNA according to SEQ ID NO: 90)
- a native *C. acnes* CAMP2 polypeptide targeted to the membrane via a N-terminal transmembrane domain sequence (NA TMB) of Neuraminidase (HA, H1N1 A/Caledonia/20/1999) ("NA TMB CAMP2_WT") (mRNA according to SEQ ID NO: 92)

For each of the two Non-N-deglycosylated constructs, a N-deglycosylated counterpart construct was designed with a mutation in a N-glycosylation site (a substitution of Asn166 by Ser) (RHS):

- a *C. acnes* CAMP2 polypeptide with a N166S mutation targeted to the membrane via a C-terminal transmembrane domain sequence (HA TMB) of Influenza Hemagglutinin (HA, H1N1 A/Caledonia/20/1999) ("HA SS CAMP2_G(−) HA TMB") (mRNA according to SEQ ID NO: 94)
- a *C. acnes* CAMP2 polypeptide with a N166S mutation targeted to the membrane via a N-terminal transmembrane domain sequence (NA TMB) of Neuraminidase (HA, H1N1 A/Caledonia/20/1999) ("NA TMB CAMP2_G(−)") (mRNA according to SEQ ID NO: 93)

Generation of Polyclonal Antibodies

The anti-CAMP2 rabbit polyclonal antibodies used in this example were provided in the form of a pool of 3 rabbit polyclonal sera. Female KBL NZ white rabbit received three immunizations of recombinant *C. acnes* CAMP2 polypeptide (SEQ ID NO: 1) formulated in SPA14 and given by the IM route at week, week 3 and week 6. The final bleedings were performed on day 56. The sera were obtained by collecting the supernatant after clotting and centrifugation of the blood. Aliquots of the sera were stored at ≤−20° C.

Generation of Monoclonal Antibodies

The monoclonal antibodies G05, G03 and D07 were identified by phage display using a humanized synthetic VHH library. Phages were selected against recombinant *C. acnes* CAMP2 polypeptide (SEQ ID NO: 1) expressed in a *E. coli*-based cell free expression system. After an ELISA screening, selected clones were sequenced, reformatted into minibodies (VHH-human Fc), produced in mammalian cell and purified. Then, minibodies were characterized by BLI to verify and characterise the affinity and the epitope within recombinant *C. acnes* CAMP2 polypeptide. The functional activity was characterised using a co-hemolysis neutralisation assay (as described in Example 1). G05, G03 and D07 clones were selected as the best-performing clones. G05, D07 and G03 (which targets the same epitope as D07) were found to be functional mAbs, since they were shown to decrease the co-hemolytic activity of CAMP2.

Characterisation of the Expression Products of C. *Acnes* CAMP2 Constructs in HEK Cells Next, the mRNA constructs encoding *C. acnes* CAMP2 polypeptide depicted in FIG. 4 were transfected into HEK cells (in vitro cell transfection). Protein expression was monitored in the cell compartment where expression was expected (i.e., in the cell supernatant for constructs designed to be secreted and in the membrane for constructs designed to be membrane-anchored). The expression compartment of *C. acnes* CAMP2 polypeptides were tested by Western-Blot using anti-CAMP2 rabbit polyclonal antibodies (pAb) and monoclonal antibodies (G05 and D07 mAbs). As shown in FIG. 5, the *C. acnes* CAMP2 polypeptides designed to be secreted were detected in the supernatant for all constructs as expected. The *C. acnes* CAMP2 polypeptides designed to be membrane-anchored using a C-terminal HA TMB were detected at the cell membrane for all constructs as expected. In contrast. CAMP2 *C. acnes* CAMP2 polypeptides designed to be membrane-anchored using a N-terminal NA TMB were detected in the supernatant, indicating that this construct did not localise to the membrane.

Next, the expression products of the mRNA constructs encoding *C. acnes* CAMP2 polypeptides depicted in FIG. 4 were evaluated for their co-hemolytic activity, with the aim of further identifying assessing whether anchoring the protein into the membrane and mutations in *C. acnes* CAMP2 polypeptides affect the co-hemolytic activity of the proteins. As shown in the Table in FIG. 5, HA SS CAMP2_WT ("WT G(+)") and its N-deglycosylated counterpart HA SS CAMP2_G(−) ("WT G(−)") showed strong co-hemolytic activity. *C. acnes* CAMP2 polypeptide successfully anchored at the membrane. HA SS CAMP2_WT HA TMB ("WT C-Ter (HA) TMB G(+)") and HA SS CAMP2_G(−) HA TMB ("WT C-Ter (HA) TMB G(−)") showed a reduced or abolished co-hemolytic activity. Mutations in the C-Terminal helix ("Mutated C-ter Helix" constructs) or the linker ("Mutated Linker" constructs) either reduced or abolished the co-hemolytic activity of CAMP2. The NA TMB CAMP2_WT and NA TMB CAMP2_G(−) ("WT N-Ter (NA) TMB") constructs (which were designed to be anchored at the membrane but were instead detected in the supernatant), gave rise to co-hemolytic activity in the supernatant. Collectively, these observations indicated that the linker and C-terminal helix contained or contributed to functional domains of the protein.

The expression products of the mRNA constructs encoding *C. acnes* CAMP2 polypeptides were then further probed using monoclonal antibodies for the presence of functional epitopes. As shown in FIGS. 5, G05 and D07 are functional mAbs, as they are able to decrease the co-hemolytic activity of CAMP2. Therefore, detection of a given *C. acnes* CAMP2 polypeptide with these mAbs was interpreted as an indication that the polypeptide contained functional epitopes. All mAbs detected HA SS CAMP2_WT and its N-deglycosylated counterpart HA SS CAMP2_G(−). However, detection with mAb G05 was abolished with CAMP2 constructs with a mutated linker, while mAb D07 was abolished with CAMP2 constructs with mutated C-terminal helix. Collectively, these observations indicated that the linker and C-terminal helix contained functional epitopes.

Immunisation with C. *Acnes* CAMP2 Antigens Elicits Antibodies that Decrease the Co-Hemolytic Activity of CAMP2

Figure 6:
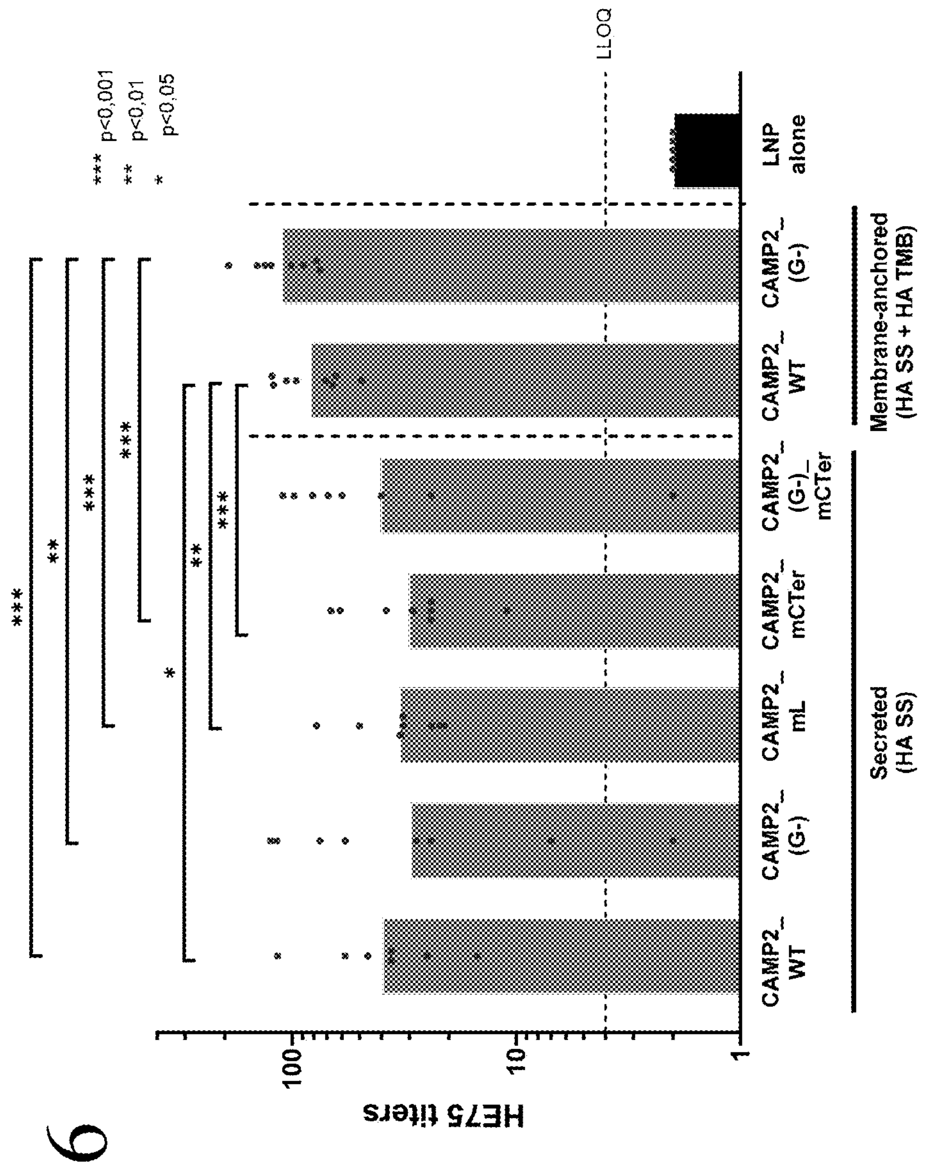
FIG. 6 shows co-hemolytic neutralizing titers of IgG purified from sera of mice immunized twice at 4 weeks interval with mRNA constructs encoding *C. acnes* CAMP2 polypeptides (construct design shown in FIG. 4). LNP alone served as a negative control. LLOQ=lowest limit of quantification.

Seven mRNA constructs encoding *C. acnes* CAMP2 polypeptides over the 10 constructs described in FIG. 4 were synthesised using modified nucleotides (in which all uridine nucleosides were replaced with 1-methyl pseudo uridine) and encapsulated in an LNP comprising GL-HEPES-E3-E12-DS-4-E10 as cationic lipid. LNP alone served as a negative control. These formulations were used to immunise mice twice at 4 weeks interval, each time at a dose of 5 µg per mouse. Mice were immunized twice at 4 weeks interval. The sera were obtained at day 42 following the first immunization, and IgG was purified from the sera. As shown in FIG. 6, membrane-anchored *C. acnes* CAMP2 polypeptides ("HA SS CAMP2_WT HA TMB" and "HA SS CAMP2_G (−) HA TMB") both showed significantly higher homogenous neutralizing titers relative to the other tested constructs. "HA SS CAMP2_WT HA TMB" and "HA SS CAMP2_G(−) HA TMB" performed comparably.

Immunisation with *C. acnes* CAMP2 antigens elicits an anti-CAMP2 IgG response mRNA constructs encoding *C. acnes* CAMP2 polypeptides (as described in FIG. 4) were synthesised using modified nucleotides (in which all uridine nucleosides were replaced with 1-methyl pseudo uridine) and encapsulated in an LNP comprising GL-HEPES-E3-E12-DS-4-E10 as cationic lipid. LNP alone served as a negative control. These formulations were used to immunise mice twice at 4 weeks interval, each time at a dose of 5 µg per mice. The sera were obtained at day 42 following the first immunization, and IgG was purified from the sera.

Figure 7:
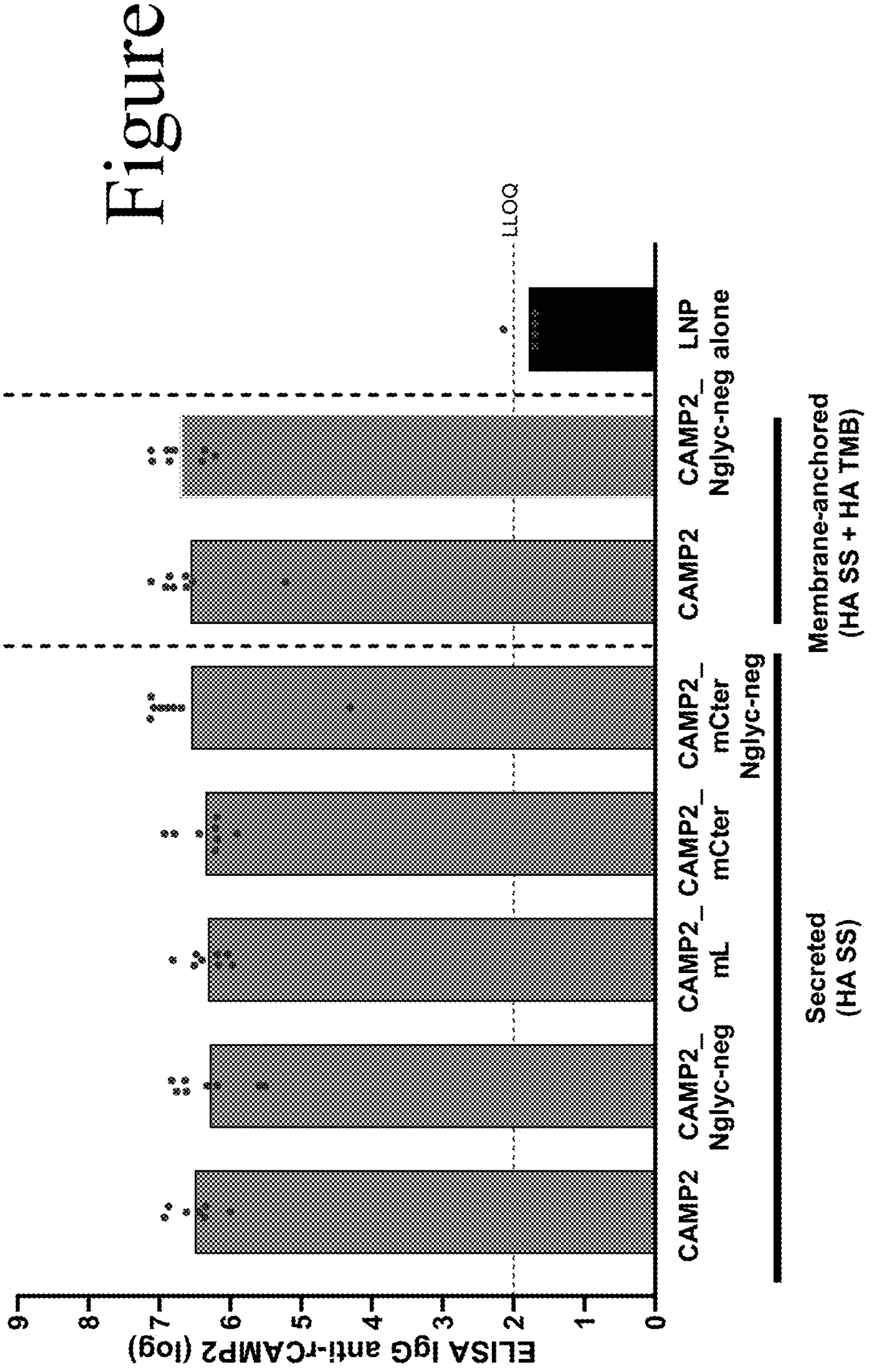
FIG. 7 shows ELISA anti-CAMP2 IgG titers of sera of mice immunized twice at 4 weeks interval with mRNA constructs encoding *C. acnes* CAMP2 polypeptides (construct design shown in FIG. 4). LNP alone served as a negative control. LLOQ=lowest limit of quantification.

The titers of anti *C. acnes* CAMP2 IgG as measured by ELISA are shown in FIG. 7. All mRNA constructs (list of constructs) elicited high, comparable and homogenous anti-CAMP2 IgG titers.

Analysis of C. *Acnes* CAMP 2 Polypeptide Glycosylation in HEK Cells

Native *C. acnes* CAMP2 polypeptide (SEQ ID NO: 203) contains one N-glycosylation site. Its sequence also has 15 serine and 28 threonine residues.

A Western blot using anti-CAMP2 mAb G05 was performed for recombinant *C. acnes* CAMP2 polypeptide (rCAMP2) and *C. acnes* CAMP2 polypeptides expressed in HEK cells transfected either with mRNA coding for secreted unmutated CAMP2 (CAMP2 Native) or secreted CAMP2 with mutated glycosylation site (CAMP2 Nglyc-neg). *C. acnes* CAMP2 polypeptides expressed by HEK cells displayed higher apparent molecular weight relative to rCAMP2 on SDS PAGE, indicating that the *C. acnes* CAMP2 polypeptides undergo glycosylation in HEK cells (data not shown). As expected, the molecular weight of CAMP2 Nglyc-neg was lower than unmutated CAMP2 indicating that unmutated CAMP2 underwent both N- and O-glycosylation. The protein was further shown to be highly and heterogeneously O-glycosylated as demonstrated by mass spectrometry.

Bio-layer interferometry (BLI) analyses showed that glycosylated CAMP2 was recognized by functional mAbs G05 and D07 as well as unglycosylated protein with similar binding kinetics parameters (Table 9).

TABLE 9

Affinity data mAbs and *C. acnes* CAMP2 polypeptides as obtained by BLI analysis

| | KD (M) | |
|---|---|---|
| mAb | Unglycosylated rCAMP2 #1 (*E. coli*) | Glycosylated rCAMP2-His #1 (HEK) |
| mAb G05 | 1.5E−9 | 1.6E−9 |
| mAb D07 | 6.2E−9 | 4.1E−9 |

Example 4—Evaluation of Specific DsA1, DsA2 and PITP mRNA Antigens

Example 4a: Evaluation of Specific DsA1, DsA2 and Chimeric DsA1/DsA2 mRNA Antigens Constructs encoding *C. acnes* DsA1 polypeptide, *C. acnes* DsA2 polypeptide and chimeric *C. acnes* DsA1/DsA2 polypeptide were tested for their ability to elicit functional antibodies in mice:

- a mRNA construct coding for the secreted form of DSAI ("HA SS_DSAI_WT_trunc") (SEQ ID NO: 103)
- a mRNA construct coding for the secreted form of DSA2 ("HA SS_DSA2_WT_trunc") (SEQ ID NO: 107)
- a mRNA construct coding for the secreted form of DSA2 mutH (i.e. with a mutation aiming to avoid putative human cross-reactivity) ("HA SS_DSA2 mutH") (SEQ ID NO: 108)
- a mRNA construct coding for the secreted form of H4-V3 (SEQ ID NO: 113)
- a mRNA construct coding for the membrane-anchored form of DSAI ("HA SS_DSAI_HA TMB") (SEQ ID NO: 102)
- a mRNA construct coding for the membrane-anchored form of DSAI (with a Ser-Gly-Ser linker between the antigen and the HA-TMB) ("HA SS_DSA1_HA TMB-sgs linker") (SEQ ID NO: 104)

- a mRNA construct coding for the membrane-anchored form of DSA2 (“HA SS_DSA2_HA TMB”) (SEQ ID NO: 105)
- a mRNA construct coding for the membrane-anchored form of DsA2 (with a Ser-Gly-Ser linker between the antigen and the HA-TMB) (“HA SS_DSA2_HA TMB-sgs linker”) (SEQ ID NO: 106)
- a mRNA construct coding for the membrane-anchored form of DSA2 mutH (“HA SS_DSA2-mutH_HA TMB”) (SEQ ID NO: 109)
- a mRNA construct coding for the membrane-anchored form of DsA2 mutH (with a Ser-Gly-Ser linker between the antigen and the HA-TMB) (SEQ ID NO: 110)
- a mRNA construct coding for the membrane-anchored form of DsA2 with N-glycosylation mutations (“DSA2 Nglyc-neg sgs linker”) (SEQ ID NO: 111)
- a mRNA construct coding for the membrane-anchored form of DsA2 with N-glycosylation mutations (“DSA2 Nglyc-neg”) (SEQ ID NO: 112)
- A formulation containing 10 μg of H4-V3 recombinant protein formulated in AlOOH (SEQ ID NO: 29)

mRNA synthesis was performed using modified nucleotides (in which all uridine nucleosides were replaced with 1-methyl pseudo uridine). The mRNA constructs were encapsulated in an LNP comprising GL-HEPES-E3-E12-DS-4-E10 as cationic lipid. LNP alone served as a negative control. Mice were immunized twice at 4 weeks interval. The mRNA content in tested formulation was of 1 μg and 5 μg per dose. The sera were obtained at day 42 following the first immunization.

DsA1, DsA2 and Chimeric DsA1 DsA2 mRNA Antigens Elicit an Anti-DsA1 IgG Response Constructs encoding *C. acnes* DsA1 polypeptide, *C. acnes* DsA2 polypeptide and chimeric *C. acnes* DsA1/DsA2 polypeptide were tested for their ability to elicit an anti-DsA1 IgG response.

Figure 8A:
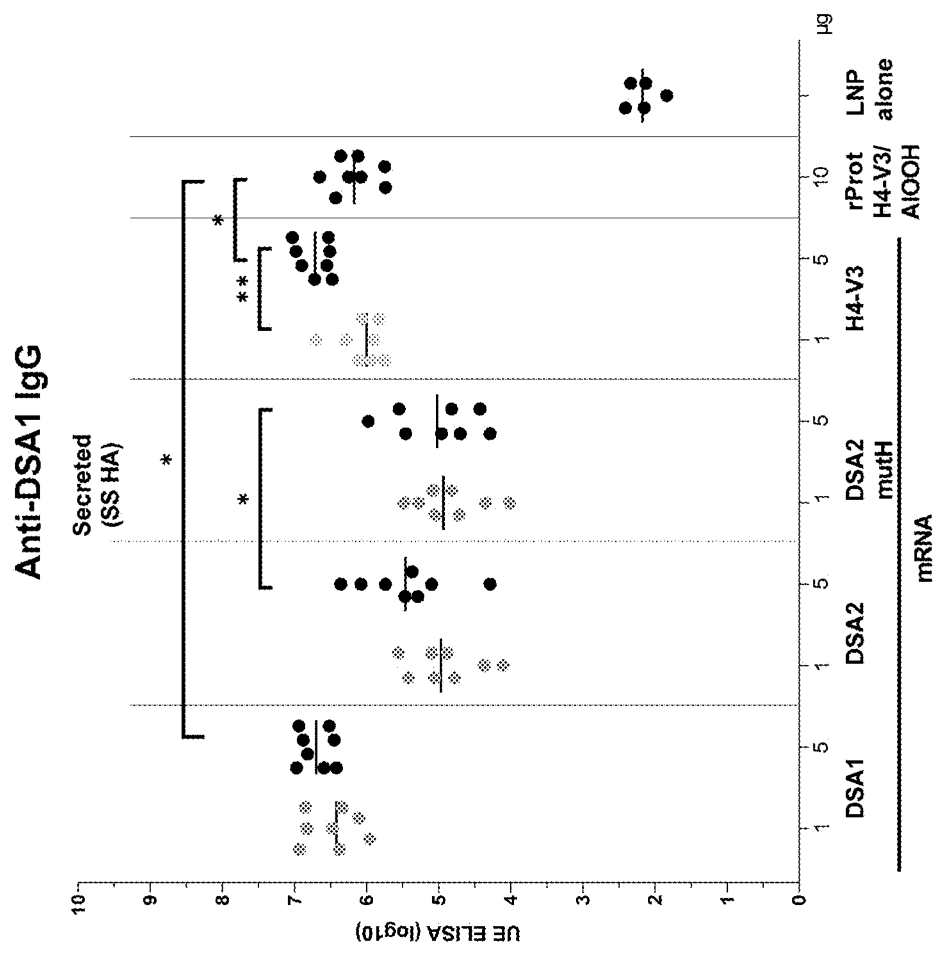
FIGS. 8A-8B show ELISA anti-DSA1 IgG titers from individual sera of mice immunized twice at 4 weeks interval with a range of mRNA constructs encoding *C. acnes* DsA1 polypeptides, *C. acnes* DsA2 polypeptides and chimeric *C. acnes* DsA1/DsA2 polypeptides, and containing either a secretion signal (FIG. 8*a*) or both a secretion signal and a transmembrane domain (FIG. 8*b*), and encapsulated in an LNP comprising GL-HEPES-E3-E12-DS-4-E10 as cationic lipid. LNP alone served as a negative control. A formulation containing 10 μg of H4-V3 recombinant protein formulated in AlOOH was used as a benchmark.
Figure 8B:
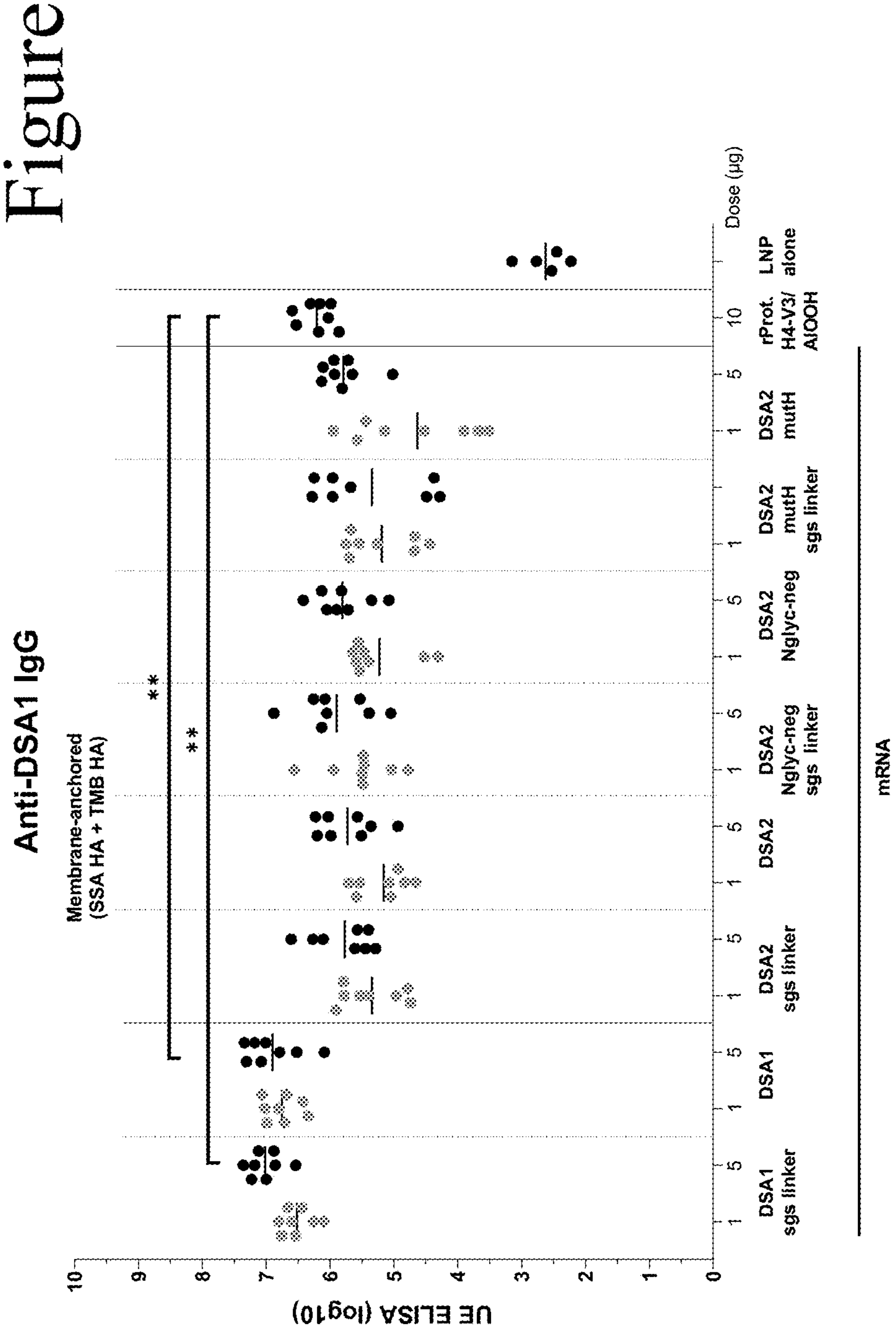

As shown in FIGS. 8A-8B, all tested formulations containing 5 μg of mRNA induced either comparable or superior ELISA IgG anti DSA1 titers relative to formulations containing 1 μg of mRNA. All mRNA formulations containing the same mRNA quantity induced comparable ELISA IgG anti DSA1 titers which were either superior (5 μg of mRNA per dose) or equivalent (1 μg of mRNA per dose) relative to recombinant protein formulations.

DsA1, DsA2 and Chimeric DsA1 DsA2 mRNA Antigens Elicit an Anti-DsA2 IgG Response Constructs encoding *C. acnes* DsA1 polypeptide. *C. acnes* DsA2 polypeptide and chimeric *C. acnes* DsA1/DsA2 polypeptide were tested for their ability to elicit an anti-DsA2 IgG response.

Figure 9A:
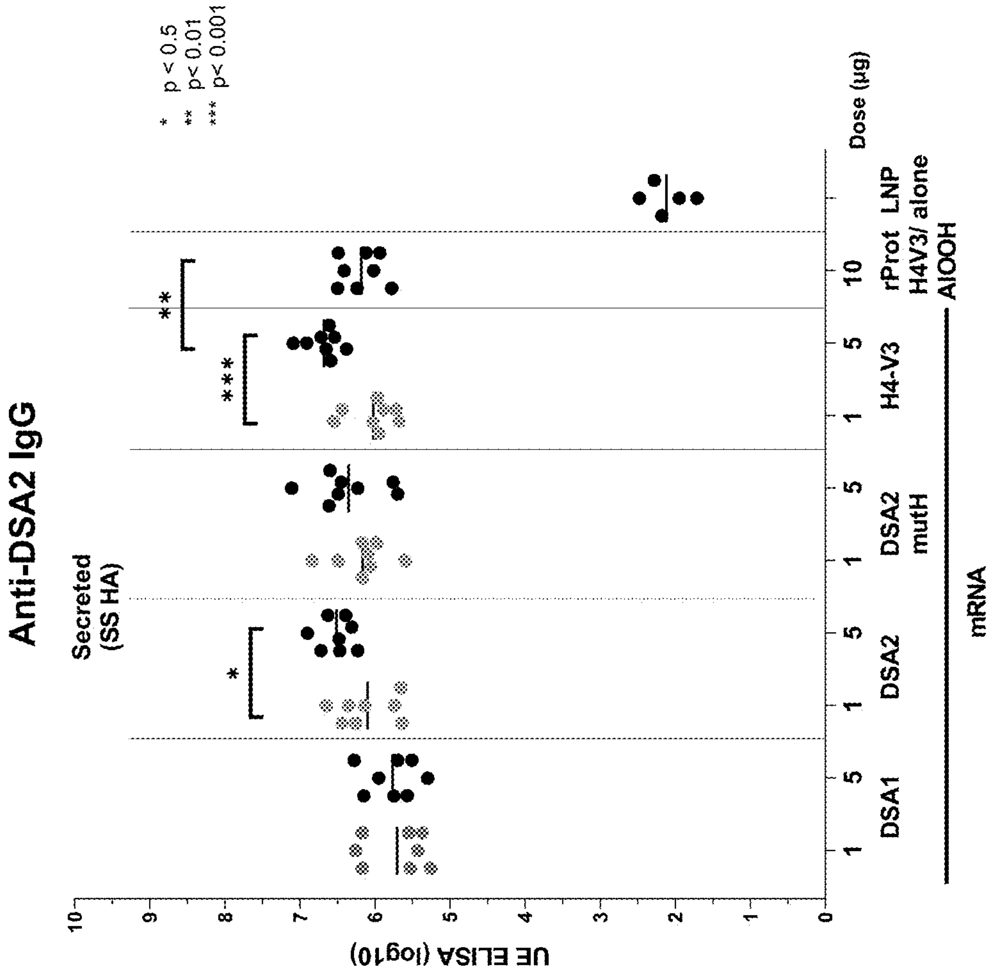
FIGS. 9A-9B show ELISA anti-DSA2 IgG titers from individual sera of mice immunized twice at 4 weeks interval with the same mRNA antigens as described in FIGS. 8A-8B, containing either a secretion signal (FIG. 9*a*) or both a secretion signal and a transmembrane domain (FIG. 9*b*), and encapsulated in the same LNP. LNP alone served as a negative control. A formulation containing 10 μg of H4-V3 recombinant protein formulated in AlOOH was used as a benchmark.
Figure 9B:
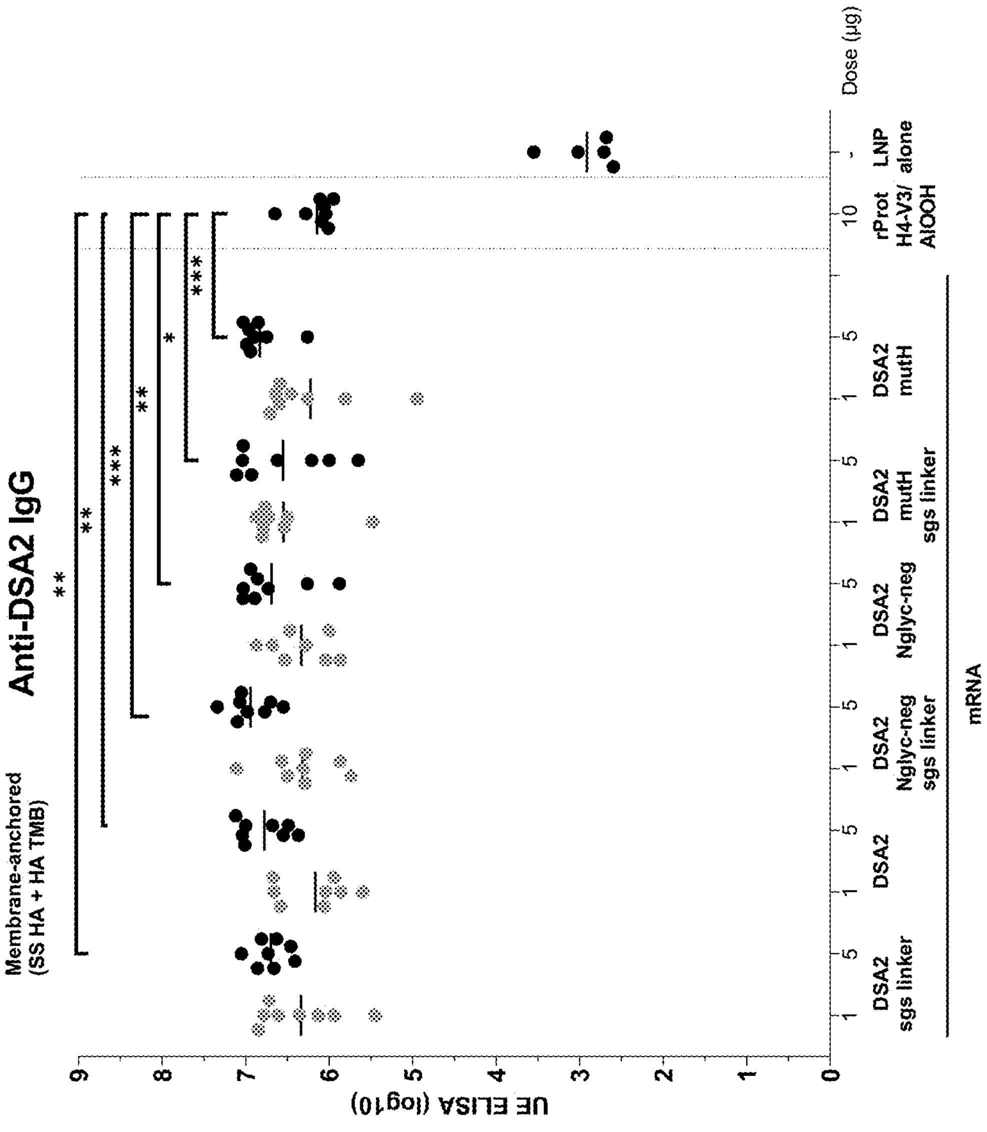

As shown in FIGS. 9A-9B, all tested formulations containing 5 μg of mRNA induced either comparable or superior ELISA IgG anti DSA2 titers than formulations containing 1 μg of mRNA. All mRNA formulations containing the same mRNA quantity induced comparable ELISA IgG anti DSA2 titers which were either superior (5 μg of mRNA per dose) or equivalent (1 μg of mRNA per dose) to recombinant protein formulations.

DsA1, DsA2 and Chimeric DsA1 DsA2 mRNA Antigens Elicit Antibodies which Bind to the Surface of *C. acnes*

Figure 10A:
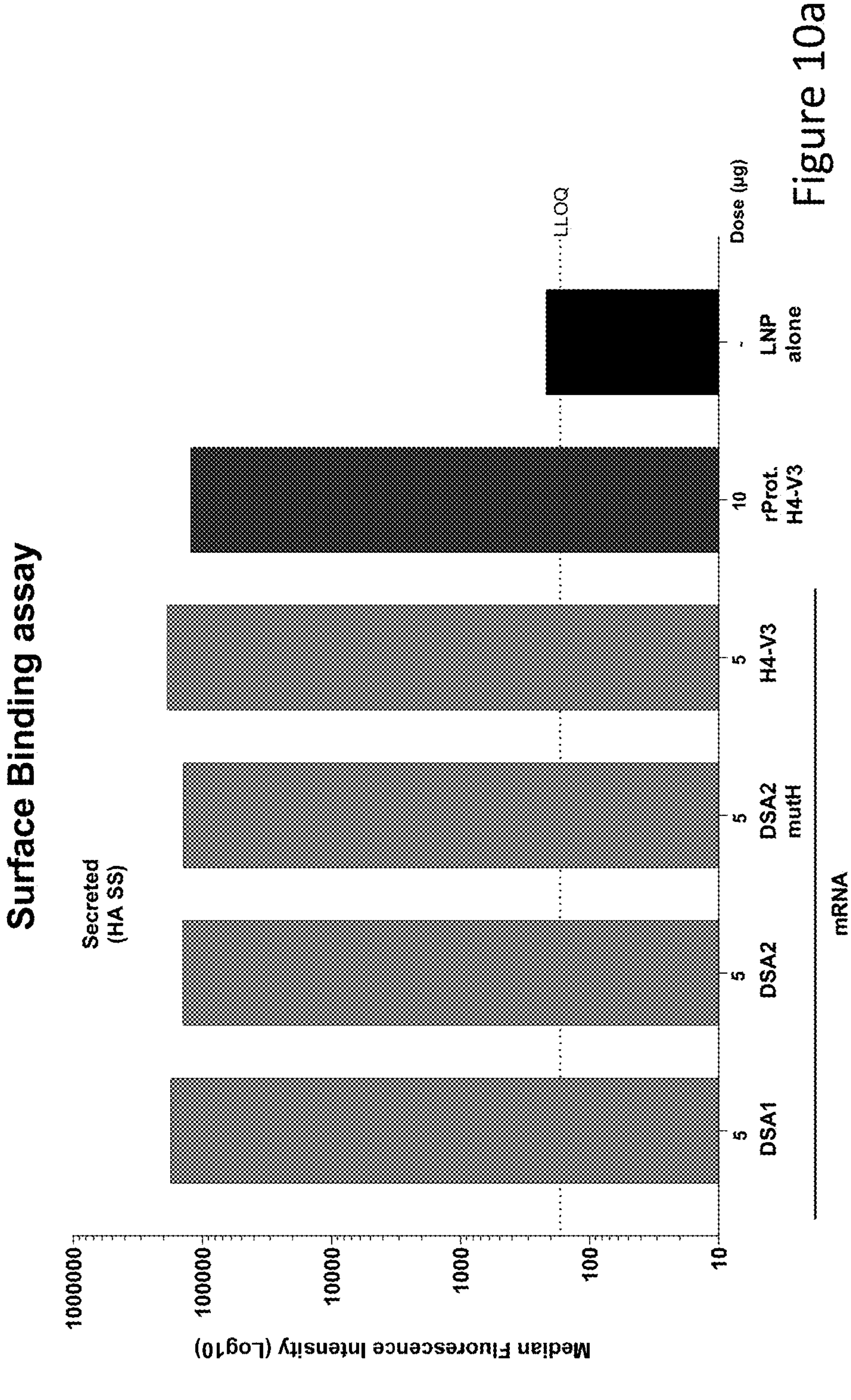
FIGS. 10A-10B show Surface Binding (SB) titers from pools of sera of mice immunized twice at 4 weeks interval with the same mRNA antigens as described in FIG. 8A-8B, containing either a secretion signal (FIG. 10*a*) or both a secretion signal and a transmembrane domain, except for the H4-V3 construct (FIG. 10*b*), and encapsulated in the same LNP. LNP alone served as a negative control. A formulation containing 10 μg of H4-V3 recombinant protein formulated in AlOOH was used as a benchmark. The SB assay was performed on NCTC737 *C. acnes* strain. LLOQ=lowest limit of quantification.
Figure 10B:
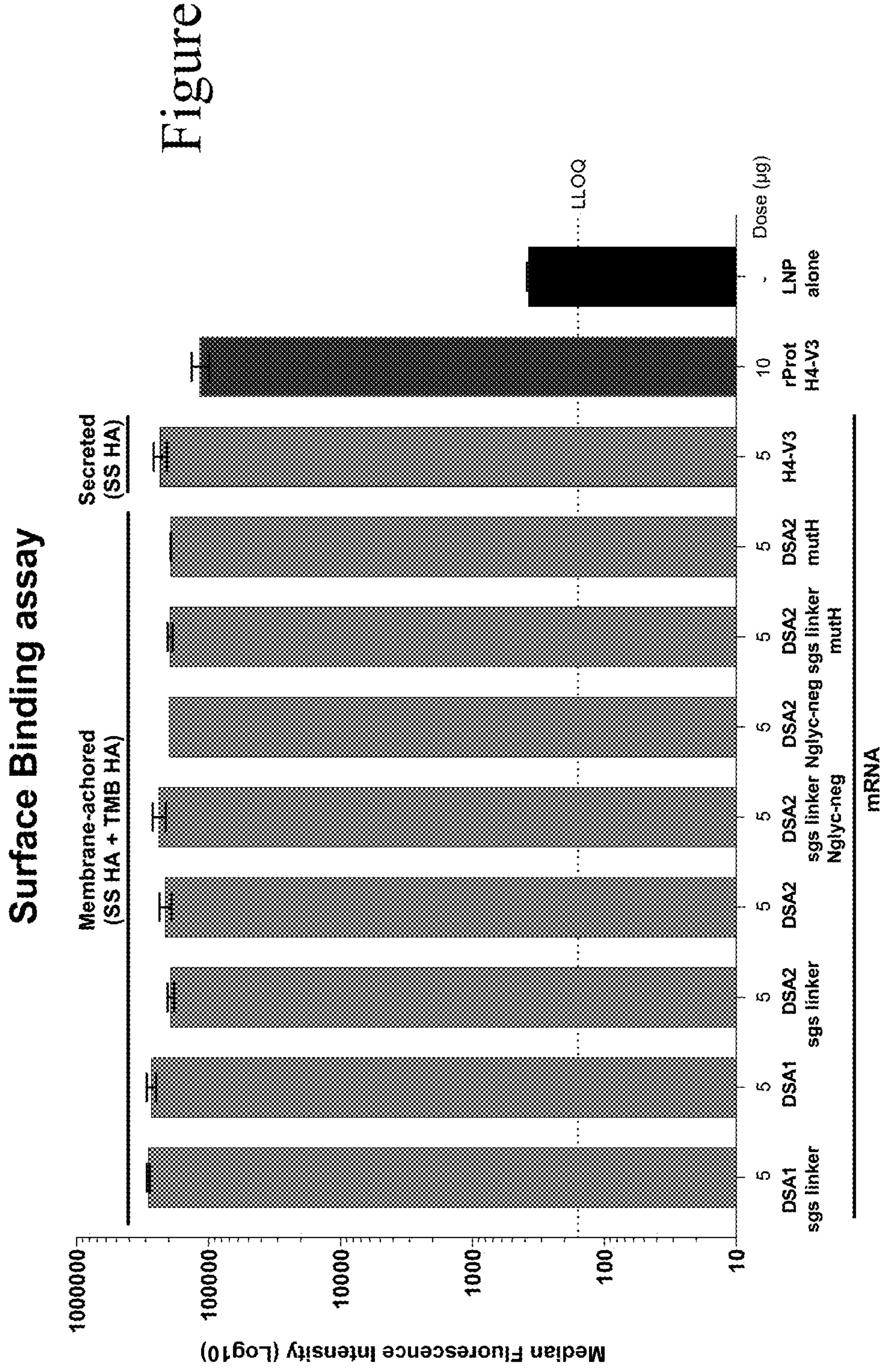

Surface Binding (SB) assays were performed on NCTC737 *C. acnes* strain from pools of sera generated at 5 μg dose. Results with the membrane-anchored constructs illustrate the means of 2 independent experiments. As shown in FIGS. 10A-10B, all mRNA formulations induced comparable SB titers.

Figure 11A:
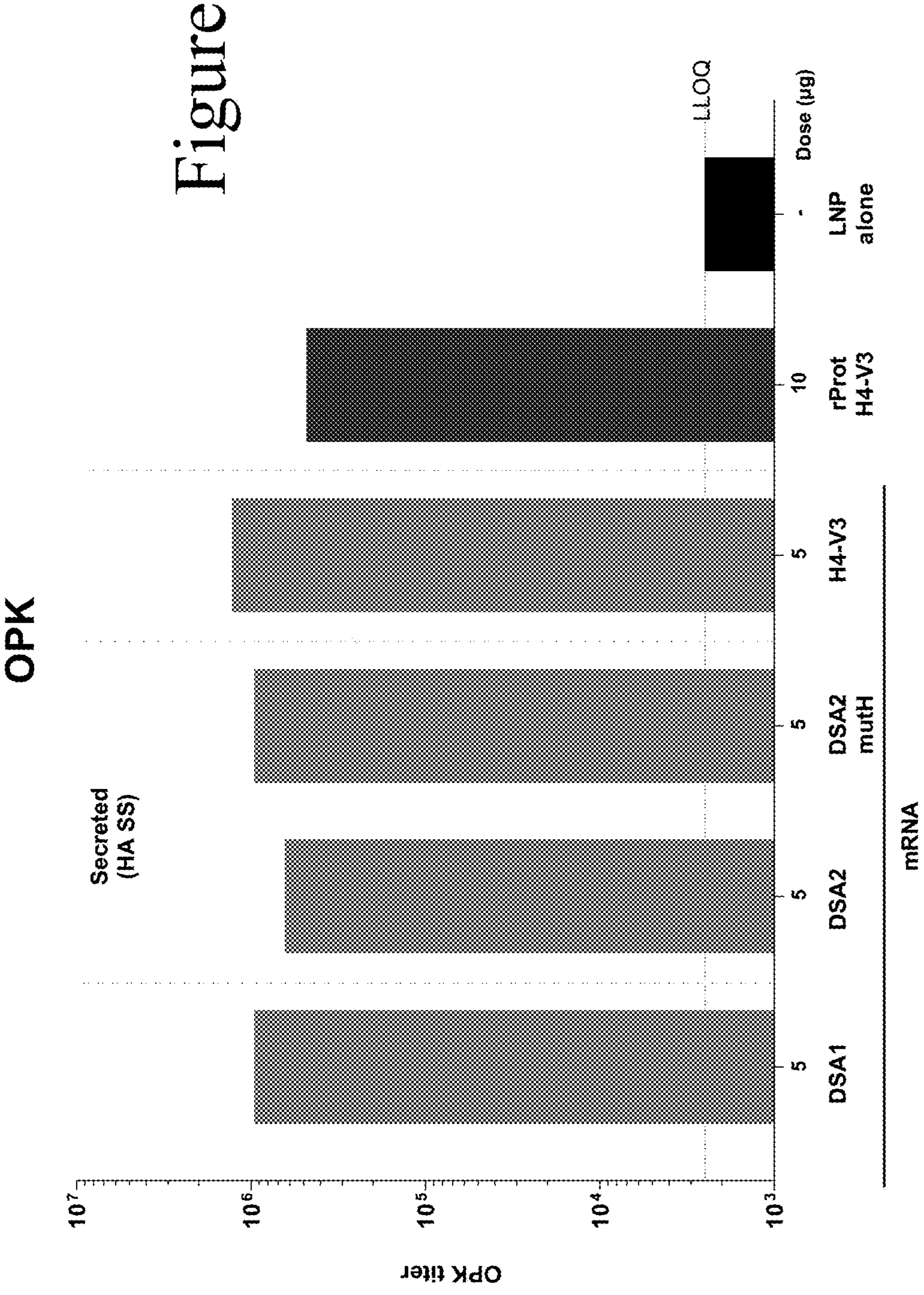
FIGS. 11A-11B show Opsonophagocytic Killing (OPK) titers from pools of sera of mice immunized twice at 4 weeks interval with the same mRNA antigens as described in FIGS. 8A-8B, containing either a secretion signal (FIG. 11*a*) or both a secretion signal and a transmembrane domain, except for the H4-V3 construct (FIG. 11*b*), and encapsulated in the same LNP. LNP alone served as a negative control. A formulation containing 10 μg of H4-V3 recombinant protein formulated in AlOOH was used as a benchmark. The OPK assay was performed on NCTC737 *C. acnes* strains. LLOQ=lowest limit of quantification.
Figure 11B:
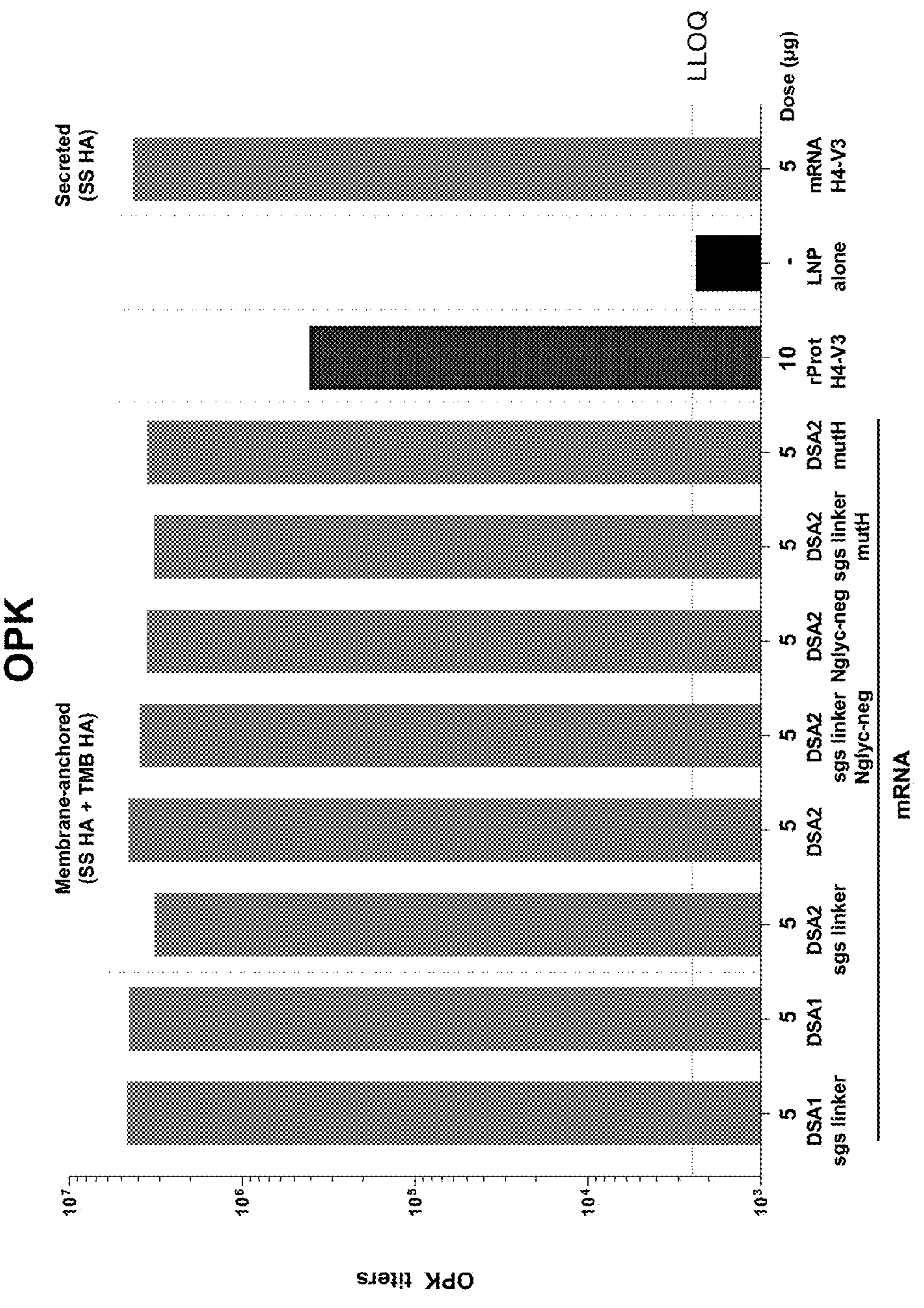

DsA1, DsA2 and Chimeric DsA1 DsA2 mRNA Antigens Elicit Antibodies with Opsonophagocytic Activity Constructs encoding *C. acnes* DsA1 polypeptide, *C. acnes* DsA2 polypeptide and chimeric *C. acnes* DsA1/DsA2 polypeptide were tested for their ability to elicit antibodies with opsonophagocytic activity. OPK assays were performed on NCTC737 *C. acnes* strains from pools of sera generated at 5 μg dose. Results illustrate the means of 2 (secreted constructs) or 3 (membrane-anchored constructs) independent experiments. As shown in FIGS. 11A-11B, all mRNA formulations induced comparable OPK titers.

mRNA Encoding Chimeric DsA1 DsA2 Polypeptide does not Undergo N-Glycosylation

A Western blot was performed for recombinant protein H4-V3 (SEQ ID NO: 29) and protein expressed by HEK cells transfected either with mRNA coding for secreted unmutated H4-V3 (SEQ ID NO: 113) or H4-V3 with mutated glycosylation site (H4-V3 Nglyc-neg) (SEQ ID NO: 114). Proteins expressed by HEK displayed higher molecular weight than recombinant protein H4-V3 indicating that the proteins undergo glycosylation in HEK cells (data not shown). The molecular weight of protein from H4-V3 Nglyc-neg construct appeared the same as unmutated H4-V3 construct suggesting that the protein did not undergo N-glycosylation. H4-V3 underwent only O-glycosylation.

Example 4B: Evaluation of Specific PITP mRNA Antigens

The following mRNA constructs encoding *C. acnes* PITP polypeptide were tested for their ability to elicit functional antibodies in mice:

- mRNA encoding secreted, native PITP (“ssHA_PITP_WT_trunc”) (SEQ ID NO: 117)
- mRNA encoding secreted PITP with mutations at N-Glycosylation sites (PITP Nglyc-neg) (SEQ ID NO: 118)
- mRNA encoding secreted P028-V7 (SEQ ID NO: 115)
- mRNA encoding secreted P028-V7 with mutations at N-Glycosylation sites (P028-V7 Nglyc-neg) (SEQ ID NO: 119)
- mRNA encoding membrane-anchored native PITP (SEQ ID NO: 120)
- mRNA encoding membrane-anchored PITP with mutations at N-Glycosylation sites (PITP Nglyc-neg) (SEQ ID NO: 121)
- P028-V7 recombinant protein (SEQ ID NO: 32)

mRNA synthesis was performed using modified nucleotides (in which all uridine nucleosides were replaced with 1-methyl pseudo uridine). The mRNA constructs were encapsulated in an LNP comprising GL-HEPES-E3-E12-DS-4-E10 as cationic lipid. LNP alone was used as negative control. Mice were immunized twice at 4 weeks interval. The mRNA content in tested formulation was of 5 μg per dose. A formulation containing 10 μg of P028-V7 recombinant protein formulated in AlOOH was used as a benchmark. The sera were obtained at day 42 following the first immunization.

PITP mRNA Antigens Elicit an Anti-PITP IgG Response

Figure 12A:
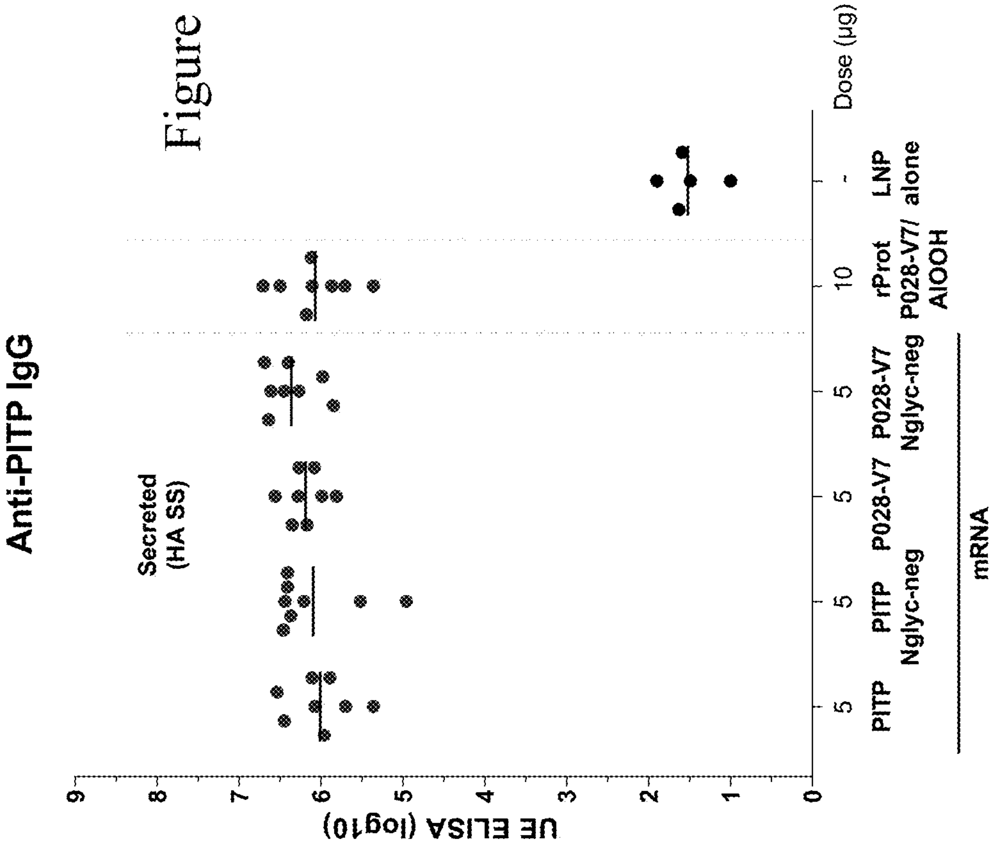
FIGS. 12A-12B show ELISA anti-PITP IgG titers from individual sera of mice immunized twice at 4 weeks interval, with a range of mRNA constructs encoding *C. acnes* PITP antigens, and containing either a secretion signal (FIG. 12*a*) or both a secretion signal and a transmembrane domain (FIG. 12*b*), encapsulated in an LNP comprising GL-HEPES-E3-E12-DS-4-E10 as cationic lipid. LNP alone was used as negative control. A formulation containing 10 μg of P028-V7 recombinant protein formulated in AlOOH was used as a benchmark.
Figure 12B:
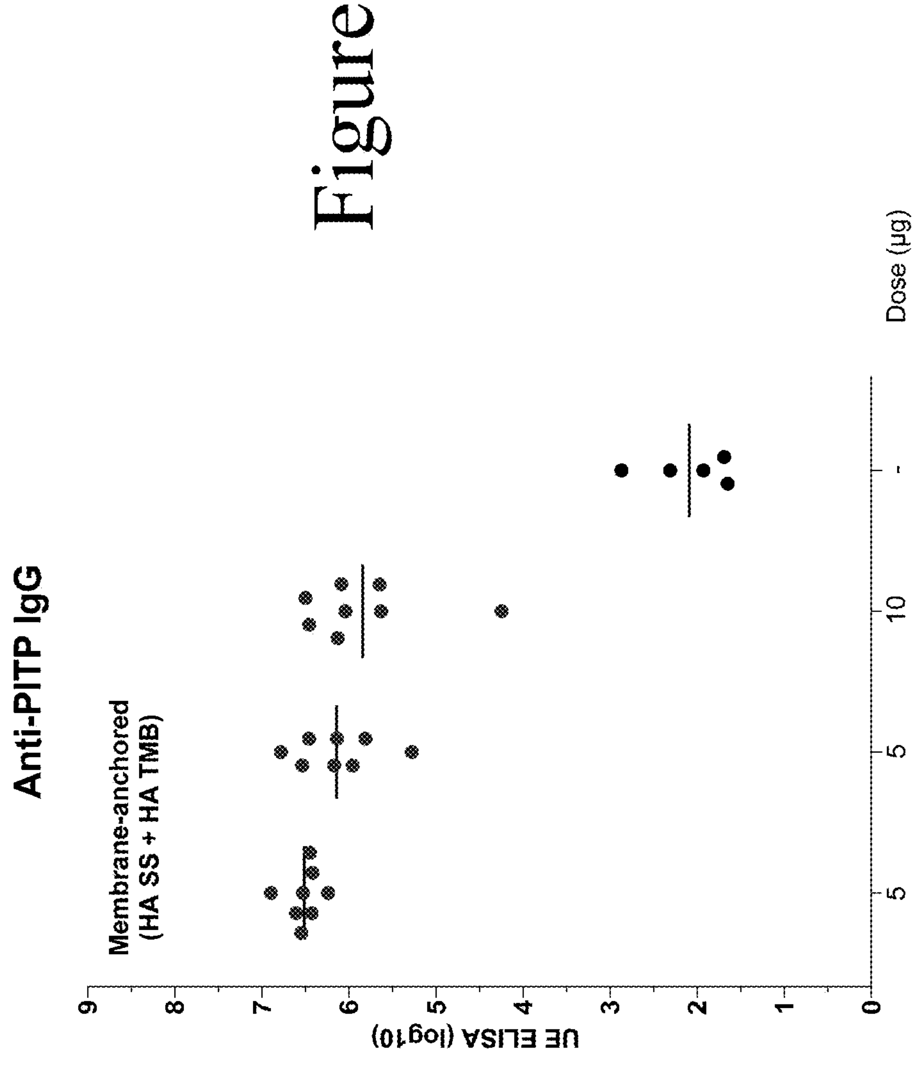

IgG anti PITP titers were measured from individual sera of mice. As shown in FIGS. 12A-12B, the membrane anchored PITP elicited superior anti-PITP titers relative to those elicited by the protein formulation. All other mRNA formulations induced IgG anti-PITP titers which were comparable to the protein formulation.

PITP mRNA Antigens Elicit Antibodies which Bind to the Surface of C. *Acnes*

Figure 13A:
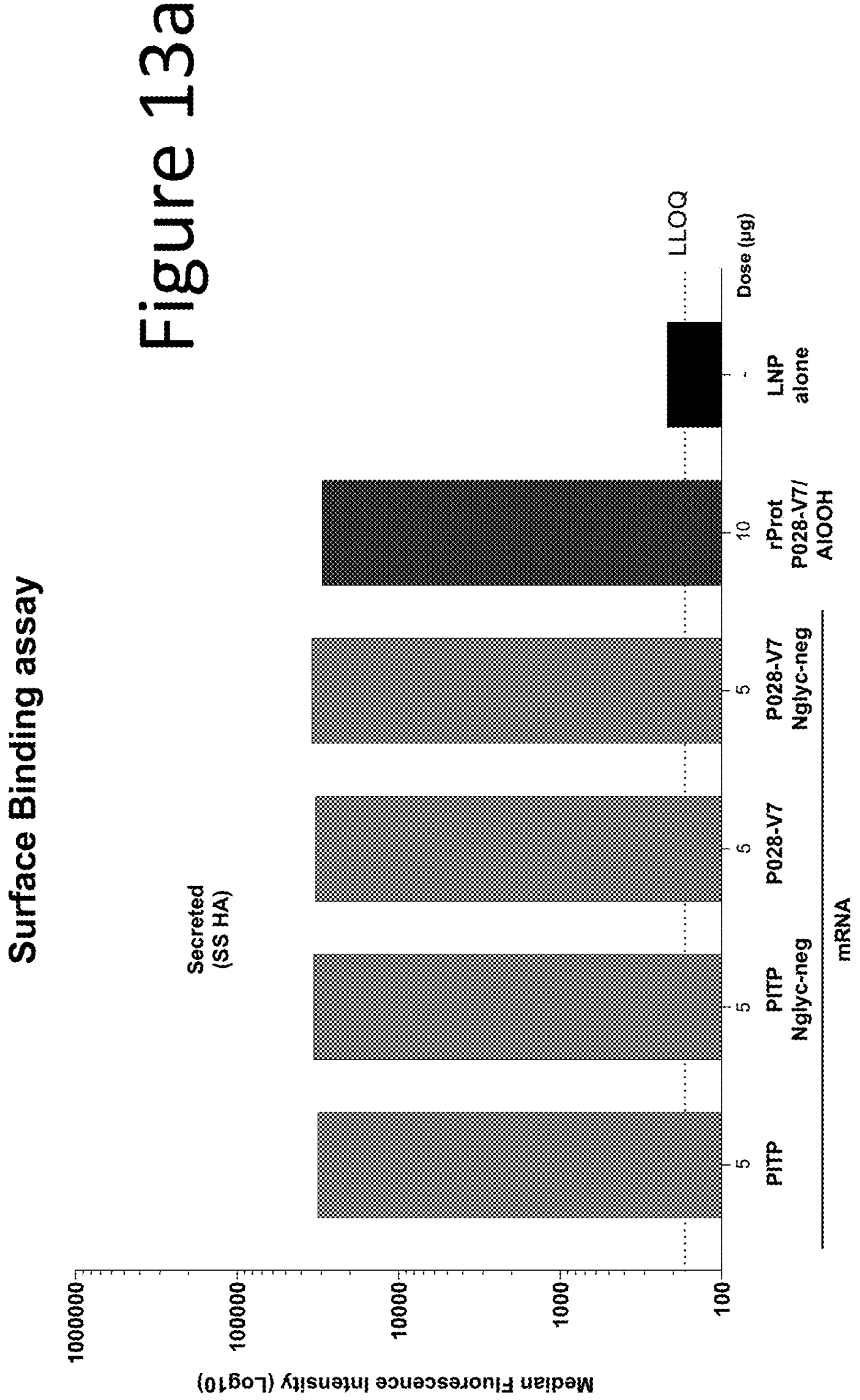
FIGS. 13A-13B show Surface Binding (SB) titers from pools of sera of mice immunized twice at 4 weeks interval, with the same mRNA antigens as described in FIGS. 12A-12B, containing either a secretion signal (FIG. 13*a*) or both a secretion signal and a transmembrane domain, except for the P028-V7 construct (FIG. 13*b*), encapsulated in the same LNP. LNP alone was used as negative control. A formulation containing 10 μg of P028-V7 recombinant protein formulated in AlOOH was used as benchmark. The SB assay was performed on a NCTC737 *C. acnes* strain. LLOQ=lowest limit of quantification.
Figure 13B:
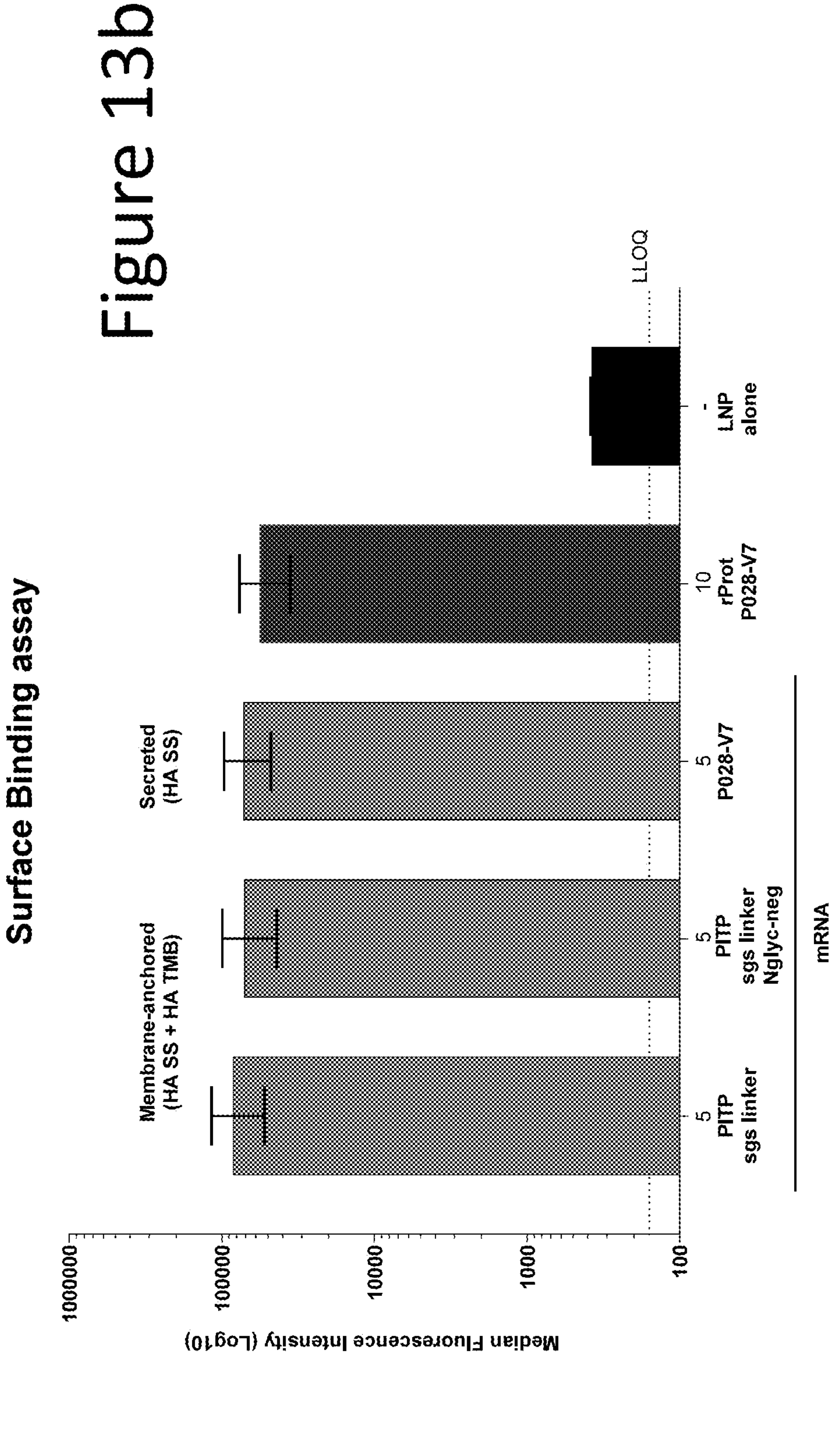

Surface Binding (SB) titers were measured on pools of sera and performed on NCTC737*C. acnes* strain. As shown in FIGS. 13A-13B, all mRNA formulations induced comparable SB titers which are also comparable to the protein formulation.

Figure 14A:
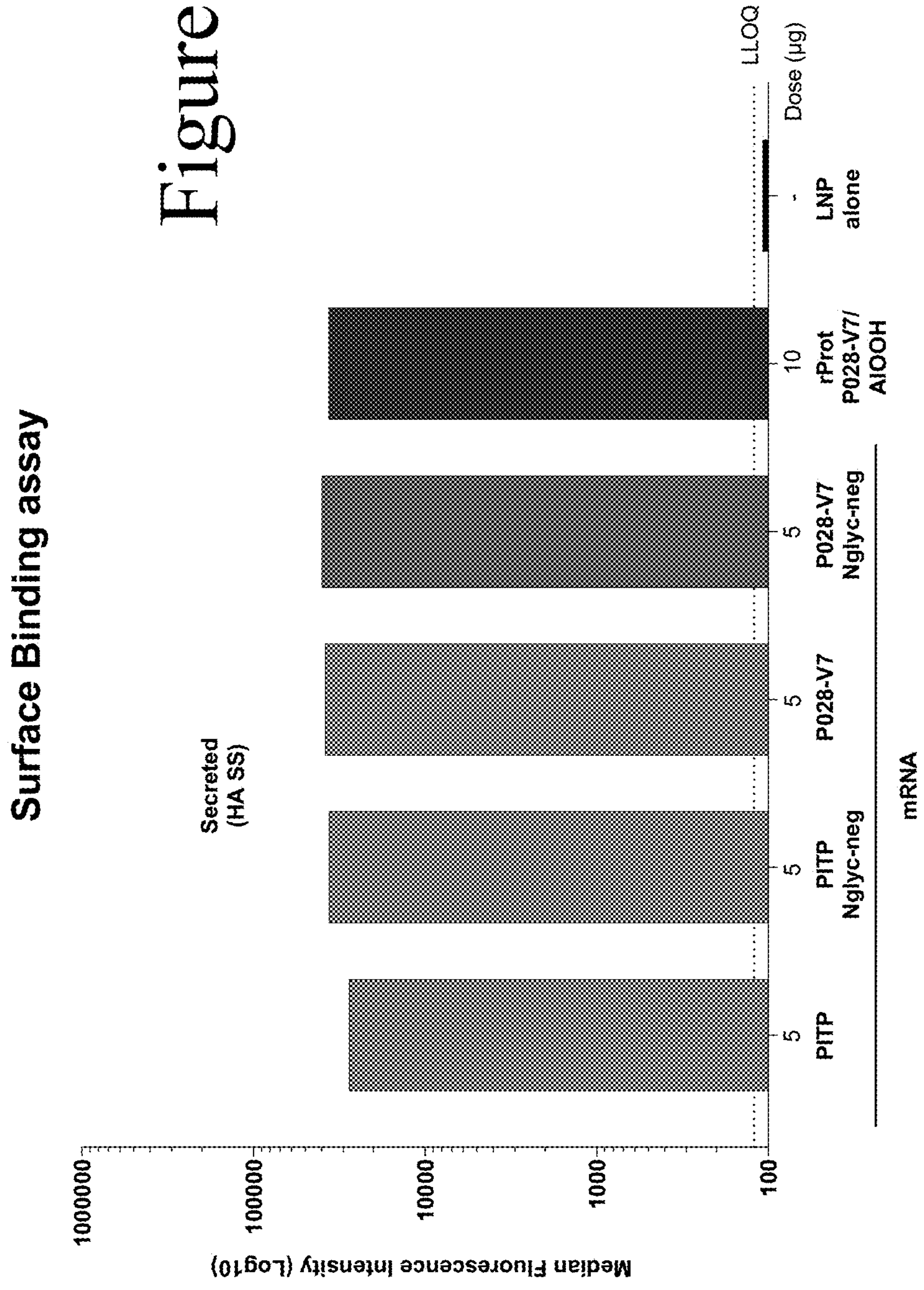
FIGS. 14A-14B show Surface Binding (SB) titers from pools of sera of mice immunized twice at 4 weeks interval, with the same mRNA antigens as described in FIGS. 12A-12B, containing either a secretion signal (FIG. 14*a*) or both a secretion signal and a transmembrane domain, except for the P028-V7 construct (FIG. 14*b*), and encapsulated in the same LNP. LNP alone was used as negative control. A formulation containing 10 μg of P028-V7 recombinant protein formulated in AlOOH was used as a benchmark. The SB assay was performed on KPA171202 *C. acnes* strain. LLOQ=lowest limit of quantification.
Figure 14B:
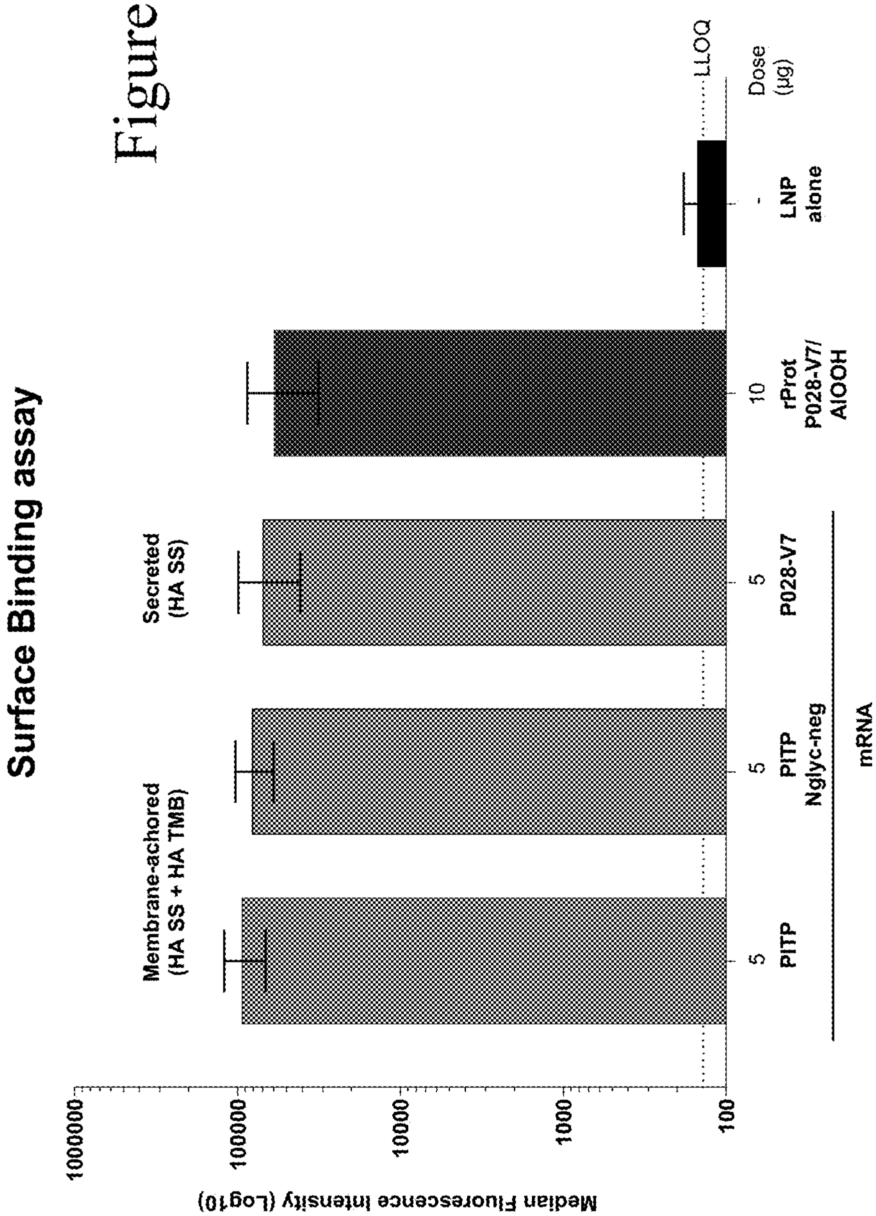

The same experiment was performed on KPA171202 *C. acnes* strain. As shown in FIGS. 14A-14B. all mRNA formulations induced comparable SB titers which are also comparable to the protein formulation.

PITP mRNA Antigens Elicit Antibodies with Opsonophagocytic Activity

Figure 15A:
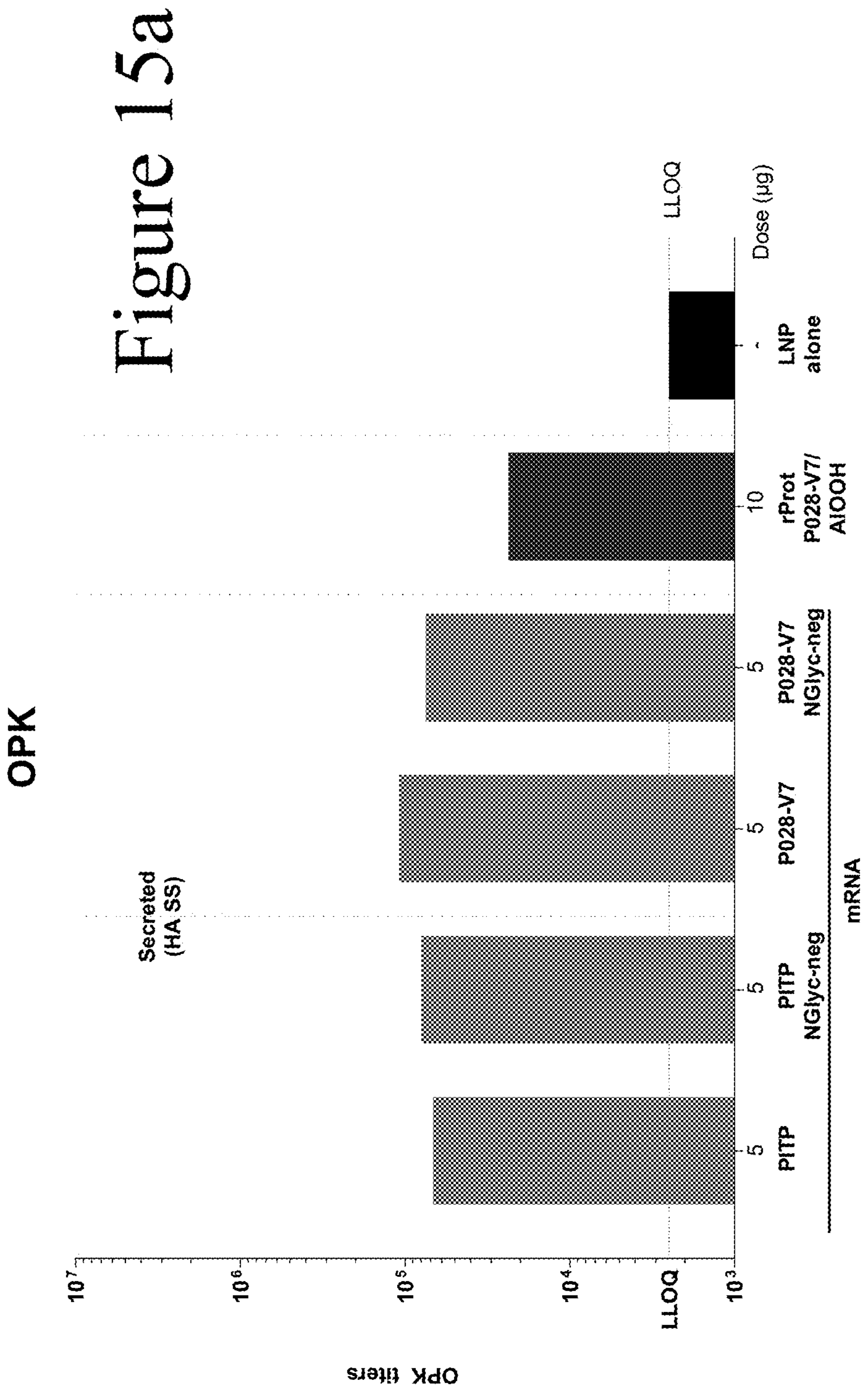
FIGS. 15A-15B show Opsonophagocytic Killing (OPK) titers from pool of sera of mice immunized twice at 4 weeks interval, with the same mRNA antigens as described in FIGS. 12A-12B, containing either a secretion signal (FIG. 15*a*) or both a secretion signal and a transmembrane domain, except for the P028-V7 construct (FIG. 15*b*), and encapsulated in the same LNP. LNP alone was used as negative control. A formulation containing 10 μg of P028-V7 recombinant protein formulated in AlOOH was used as a benchmark. The OPK assay was performed on NCTC737 *C. acnes* strain. LLOQ=lowest limit of quantification.
Figure 15B:
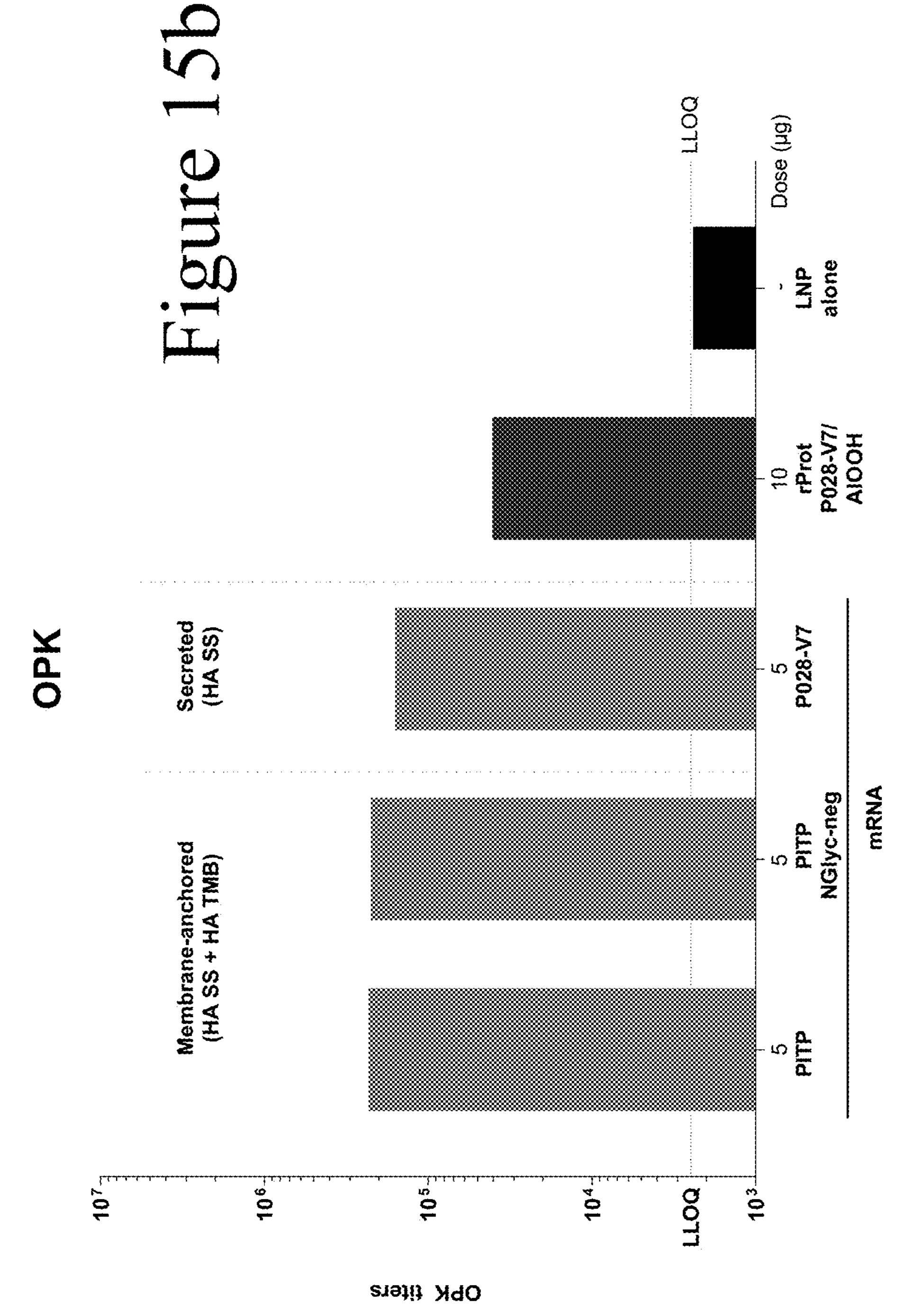

Opsonophagocytic Killing (OPK) titers were measured on NCTC737 *C. acnes* strains, from pools of sera of mice. Results with the membrane-anchored constructs illustrate the means of 3 independent experiments. As shown in FIGS. 15A-15B, all mRNA formulations induced comparable OPK titers which seemed measurably superior to the protein formulation.

Figure 16A:
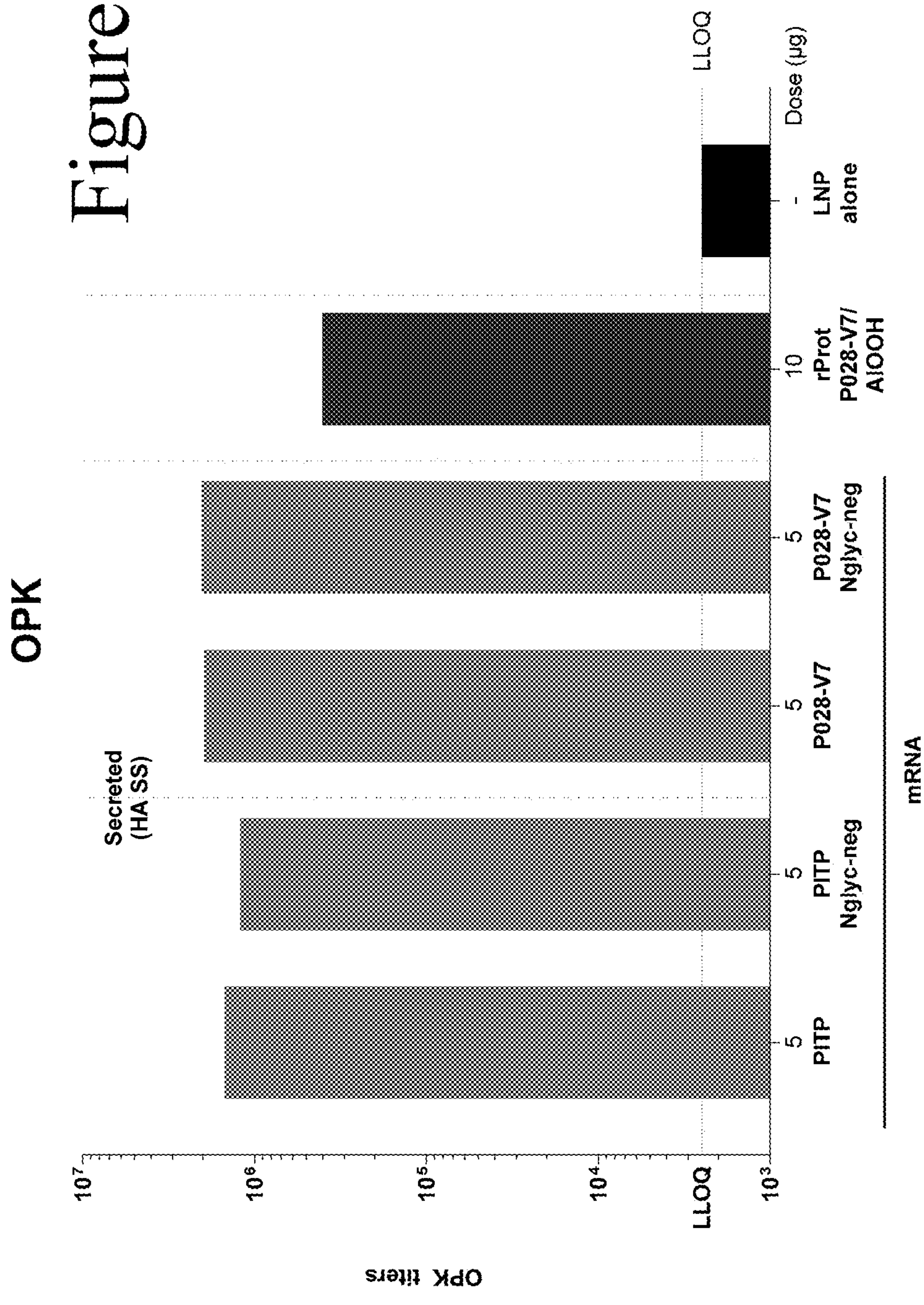
FIGS. 16A-16B show Opsonophagocytic Killing (OPK) titers from pool of sera of mice immunized twice at 4 weeks interval, with the same mRNA antigens as described in FIGS. 12A-12B, containing either a secretion signal (FIG. 16*a*) or both a secretion signal and a transmembrane domain, except for the P028-V7 construct (FIG. 16*b*), and encapsulated in the same LNP. LNP alone was used as negative control. A formulation containing 10 μg of P028-V7 recombinant protein formulated in AlOOH was used as a benchmark. The OPK assay was performed on KPA171202 *C. acnes* strain. LLOQ=lowest limit of quantification.
Figure 16B:
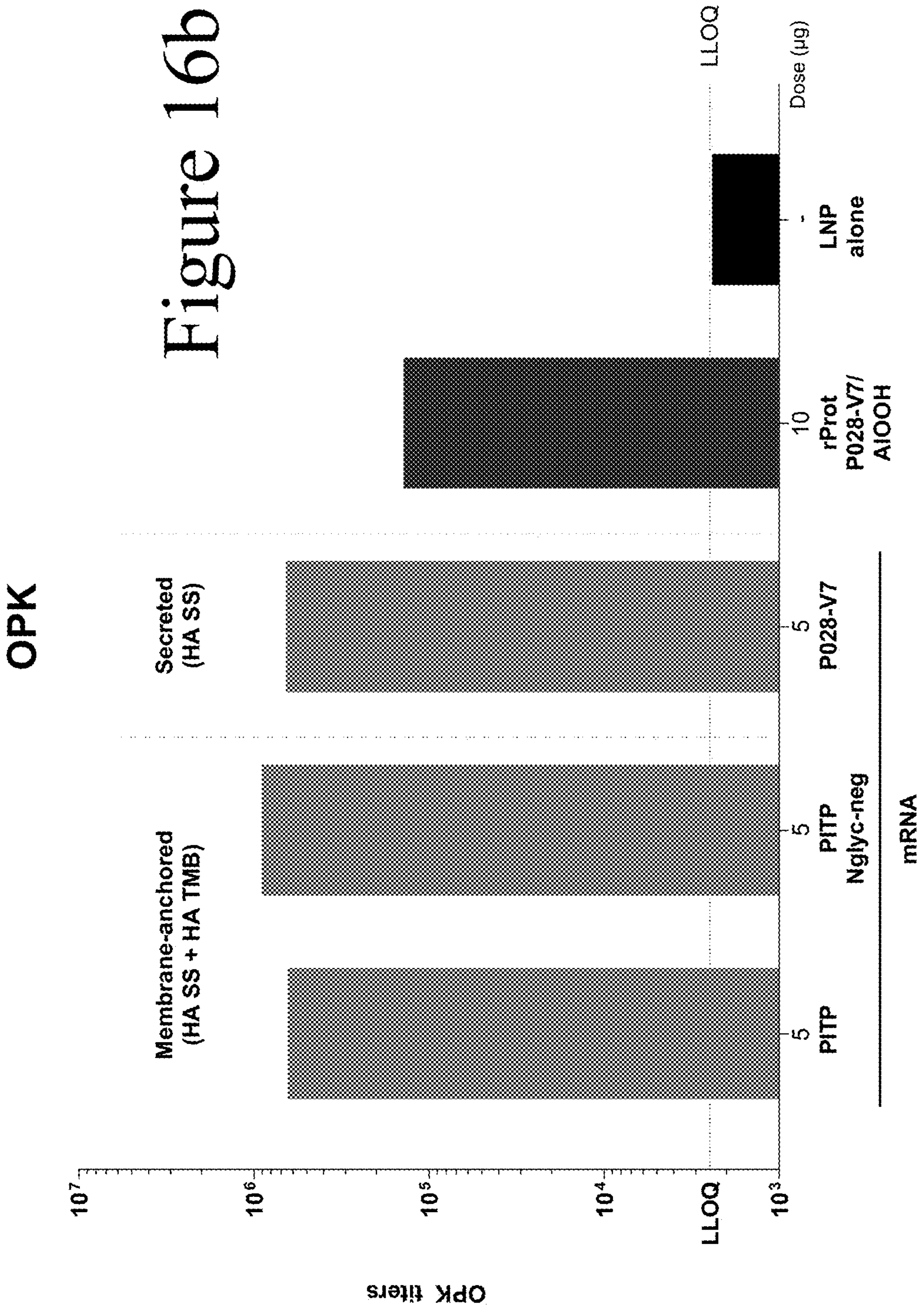

The same experiment was performed with KPA171202 *C. acnes* strain, except that results with the membrane-anchored constructs illustrate the means of 2 independent experiments. As shown in FIGS. 16A-16B, all mRNA formulations induced comparable OPK titers which seemed measurably superior to the protein formulation.

Example 5—Immunisation with mRNA H4-V3 and mRNA P28-V7 Gives Rise to Antibody Responses which Recognise a Range of C. *Acnes* Strains (Cross-Reactivity)

mRNA synthesis was performed using modified nucleotides (in which all uridine nucleosides were replaced with 1-methyl pseudo uridine). The mRNA constructs were encapsulated in an LNP comprising GL-HEPES-E3-E12-DS-4-E10 as cationic lipid. LNP alone served as a negative control. Mice were immunized twice at 4 weeks interval with the same mRNA antigens as described in Example 4 as illustrated in FIGS. 10*a*, 11*a* (DsA1 & DsA2 constructs respectively) and 16*a* (PITP constructs). The mRNA content in tested formulation was of 1 μg and 5 μg per dose. The sera were obtained at day 42 following the first immunization.

Figure 17:
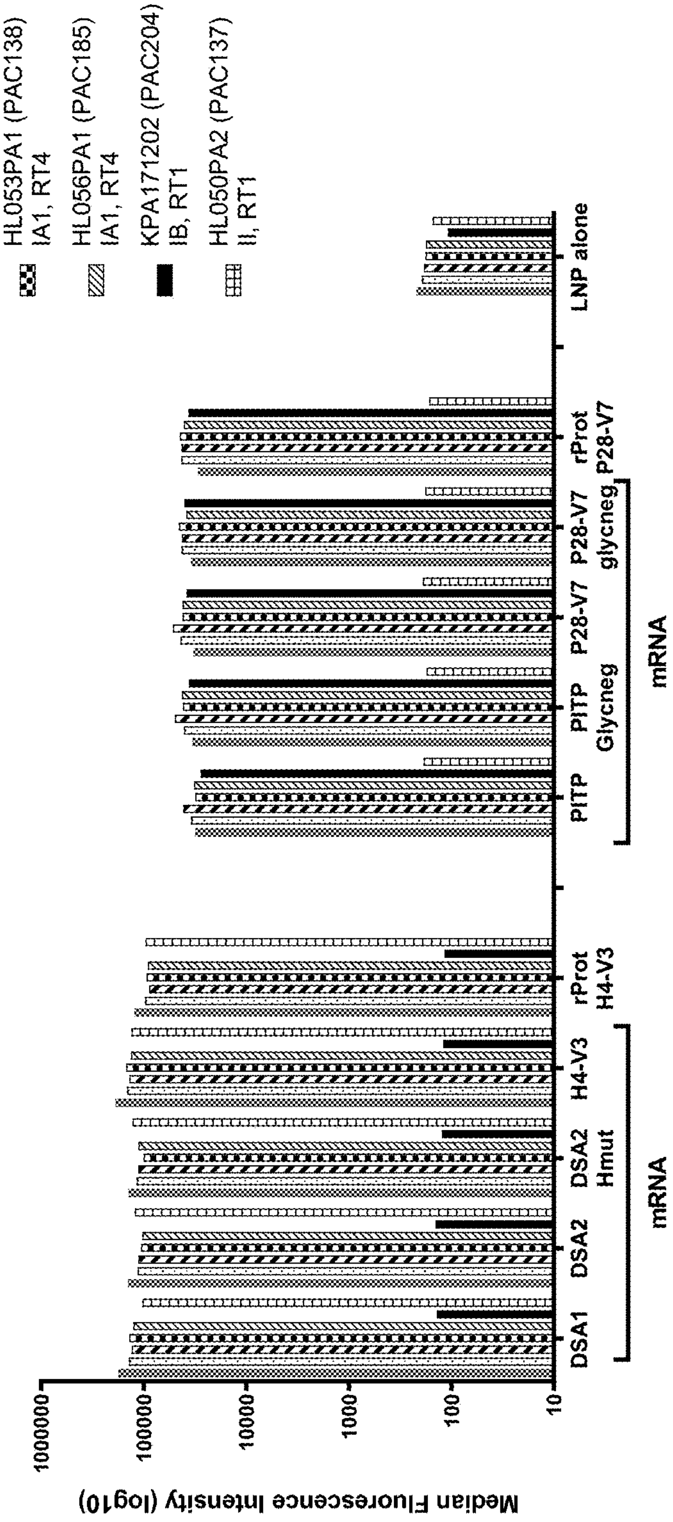
FIG. 17 shows Surface Binding (SB) titers from pool of sera, performed on *C. acnes* strains NCTC737 and KPA171202, complemented by five other strains (as listed in Table 10) to better reflect phylotype proportion found in Acne and based on i) the level of antigen expression and ii) ribotype.

Surface Binding (SB) titers performed on *C. acnes* strains NCTC737, KPA171202 and five other strains (as listed in Table 10), were evaluated from pools of sera. The strains were selected to reflect the phylotype proportion found in acne vulgaris and based on i) the level of antigen expression and ii) ribotype. The results for the 5 μg dosage are shown in FIG. 17, mRNA encoding secreted H4-V3 and mRNA encoding secreted P028-V7 performed at least as well as other mRNA constructs encoding secreted DsA1, DsA2 or PITP antigens or their recombinant protein counterparts, against a range of *C. acnes* strains.

TABLE 10

Strain collection used in Example 5

| Strain | Alternative strain name | Phylotype | Ribotype (RT) | Source | Reference for phylogenic analysis |
|---|---|---|---|---|---|
| NCTC737 | PAC205 | IA1 | 1 | NCTC | Liu et al. 2014 |
| HL043PA1 | PAC134 | IA1 | 5 | BEI Ressources | McDowell et al. 2012 Tomida et al. 2013 |
| HL043PA2 | PAC135 | IA1 | 5 | BEI Ressources | McDowell et al. 2012 Tomida et al. 2013 |
| HL053PA1 | PAC138 | IA1 | 4 | BEI Ressources | McDowell et al. 2012 Tomida et al. 2013 |
| HL056PA1 | PAC185 | IA1 | 4 | BEI Ressources | McDowell et al. 2012 Tomida et al. 2013 |
| KPA171202 | PAC204 | IB | 1 | DSMZ | Bruggeman et al. 2004 Brzuszkiewicz et al. 2011 Tomida et al. 2013 |
| HL050PA2 | PAC137 | II | 1 | BEI Ressources | Tomida et al. 2013 |

REFERENCES

Bruggemann, H., Henne, A., Hoster, F., Liesegang, H., Wiezer, A., Strittmatter, A., Hujer, S., Durre, P., and Gottschalk, G. "The complete genome sequence of *Propionibacterium acnes*, a commensal of human skin." Science (2004) 305:671-673.

Brzuszkiewicz, E.; Weiner, J.; Wollherr, A.; Thürmer, A.; Hüpeden, J.; Lomholt, H. B.; Kilian, M.; Gottschalk, G.; Daniel, R.; Mollenkopf, H. J.; et al. Comparative genomics and transcriptomics of *Propionibacterium acnes*. PLOS One (2011), 6: e21581

Liu J, Cheng A, Bangayan N J, Barnard E, Curd E, Craft N, Li H. Draft Genome Sequences of *Propionibacterium acnes* Type Strain ATCC6919 and Antibiotic-Resistant Strain HL411PA1. Genome Announc. (2014) 2: e00740-14.

McDowell A, Barnard E, Nagy I, Gao A, Tomida S, Li H, Eady A, Cove J, Nord C E, Patrick S. An expanded multilocus sequence typing scheme for *Propionibacterium acnes*: investigation of 'pathogenic', 'commensal' and antibiotic resistant strains. PLOS One. (2012) 7: e41480

Tomida S, Nguyen L, Chiu B H, Liu J, Sodergren E, Weinstock G M, Li H. Pan-genome and comparative genome analyses of *Propionibacterium acnes* reveal its genomic diversity in the healthy and diseased human skin microbiome, mBio. (2013) 4: e00003-13.

Example 6—CAMP2 mRNA Construct Synthesis and Reproducibility

Synthesis and Characterisation of mRNA Encoding C. *Acnes* CAMP 2 Polypeptide mRNA size, tail size, % of tailed population and % cap 1 were evaluated for 4 different batches of mRNA encoding *C. acnes* CAMP2 (polypeptide sequence according to SEQ ID NO: 5) produced from 2 different optimized plasmid sequences (mRNA #1 CAMP2 (SEQ ID NO: 90) and mRNA #2 CAMP2 (SEQ ID NO: 91), respectively) (2 batches/plasmid sequence: batch 1 and batch 2), mRNA synthesis was performed using modified nucleotides (in which all uridine nucleosides were replaced with 1-methyl pseudo uridine). With respect to mRNA size, tail size, % of tailed population and cap1%, all mRNAs met the targeted specifications. Sequencing analyses confirmed that the expected mRNA sequences were generated.

Characterisation of mRNA-LNP Formulation

LNP size, % encapsulation (% EE) and mRNA integrity were measured for the 4 batches of mRNA produced from mRNA #1 CAMP2 (SEQ ID NO: 90) and mRNA #2 CAMP2 (SEQ ID NO: 91) (corresponding to two different codon optimizations). Each mRNA antigen was encapsulated in an LNP comprising GL-HEPES-E3-E12-DS-4-E10 as cationic lipid. With respect to LNP size and % of encapsulation (% EE), all LNPs fell into the expected size range and the targeted % EE.

Mouse Immunisation

The 4 batches of CAMP2 mRNA were tested for their ability to elicit functional antibodies in mice:

Mice were immunized twice at 4 weeks interval, with either mRNA #1 CAMP2 (batch 1), mRNA #1 CAMP2 (batch 2), mRNA #2 CAMP2 (batch 1) or mRNA #2 CAMP2 (batch 2) encapsulated in LNP. The mRNA content in tested formulation was of 1 μg per dose. A formulation containing 10 μg of CAMP2 recombinant protein formulated in AlOOH was implemented as a benchmark. The sera were obtained at day 42 following the first immunization. LNP alone was used as negative control.

The weight gain over time of mice immunized with mRNA encoding *C. acnes* CAMP2 polypeptide was assessed. No swelling was observed at the site of injection and regular weight gain was monitored over the study period for all experimental groups (hence no local reaction and no impact on body weight).

Immunisation with C. *Acnes* CAMP2 Antigens Elicits an Anti-CAMP2 IgG Response

Figure 18:
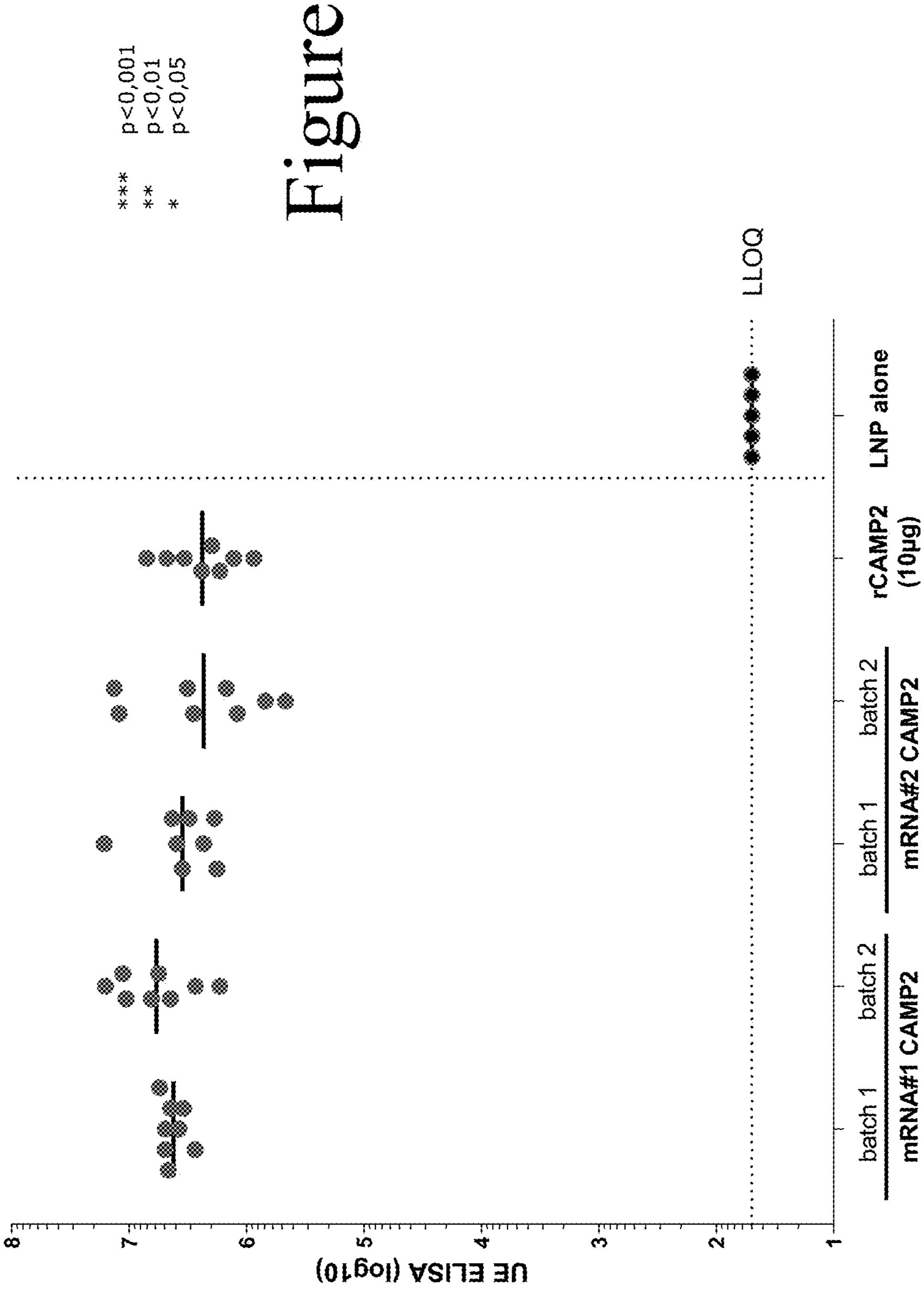
FIG. 18 shows ELISA anti-CAMP2 IgG titers from individual sera of mice immunized twice at 4 weeks interval, with CAMP2 mRNA antigens encapsulated in an LNP. A formulation containing 10 μg of CAMP2 recombinant protein formulated in AlOOH was used as a benchmark. The sera were obtained at day 42 following the first immunization. LNP alone was used as negative control, mRNA synthesis was performed using modified nucleotides. The mRNA content in tested formulation was of 1 μg per dose. LLOQ=lowest limit of quantification.

IgG anti CAMP2 titers were measured from individual sera of mice at day 42 following the first immunization and evaluated by ELISA. As shown in FIG. 18, all mRNA formulations induced comparable IgG anti CAMP2 titers, which were also comparable to those elicited by the protein formulation.

mRNA Encoding C. *Acnes* CAMP2 Polypeptides Decreases the Co-Hemolytic Activity of CAMP2

Figure 19:
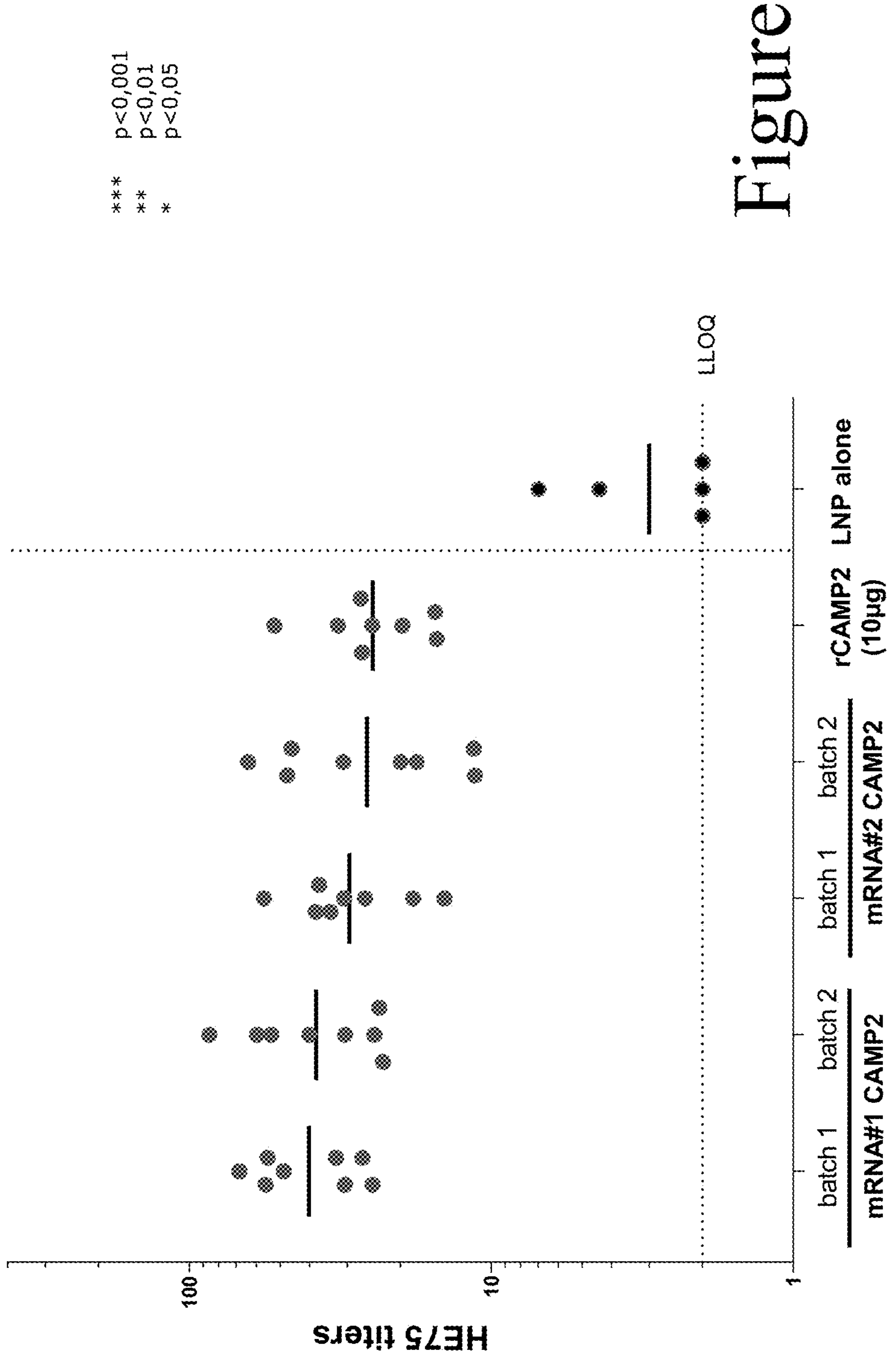
FIG. 19 shows co-hemolytic neutralizing titers of IgG purified from individual sera of mice immunized twice at 4 weeks interval, with the same mRNA antigens as described in FIGS. 18, and encapsulated in the same LNP. A formulation containing 10 μg of CAMP2 recombinant protein formulated in AlOOH was used as a benchmark. The sera were obtained at day 42 following the first immunization. LNP alone was used as negative control, mRNA synthesis was performed using modified nucleotides. The mRNA content in tested formulation was of 1 μg per dose. LLOQ=lowest limit of quantification.

Co-hemolytic neutralizing titers were measured for IgG purified from individual sera of mice. As shown in FIG. 19, all mRNA formulations induced comparable neutralizing titers which were also comparable to the protein formulation. Correlation between ELISA IgG anti CAMP2 titers and co-hemolytic neutralizing titers was good (R=0.76).

Example 7—Combinations of mRNA

Design of C. *Acnes* Antigen Constructs

Figure 20:
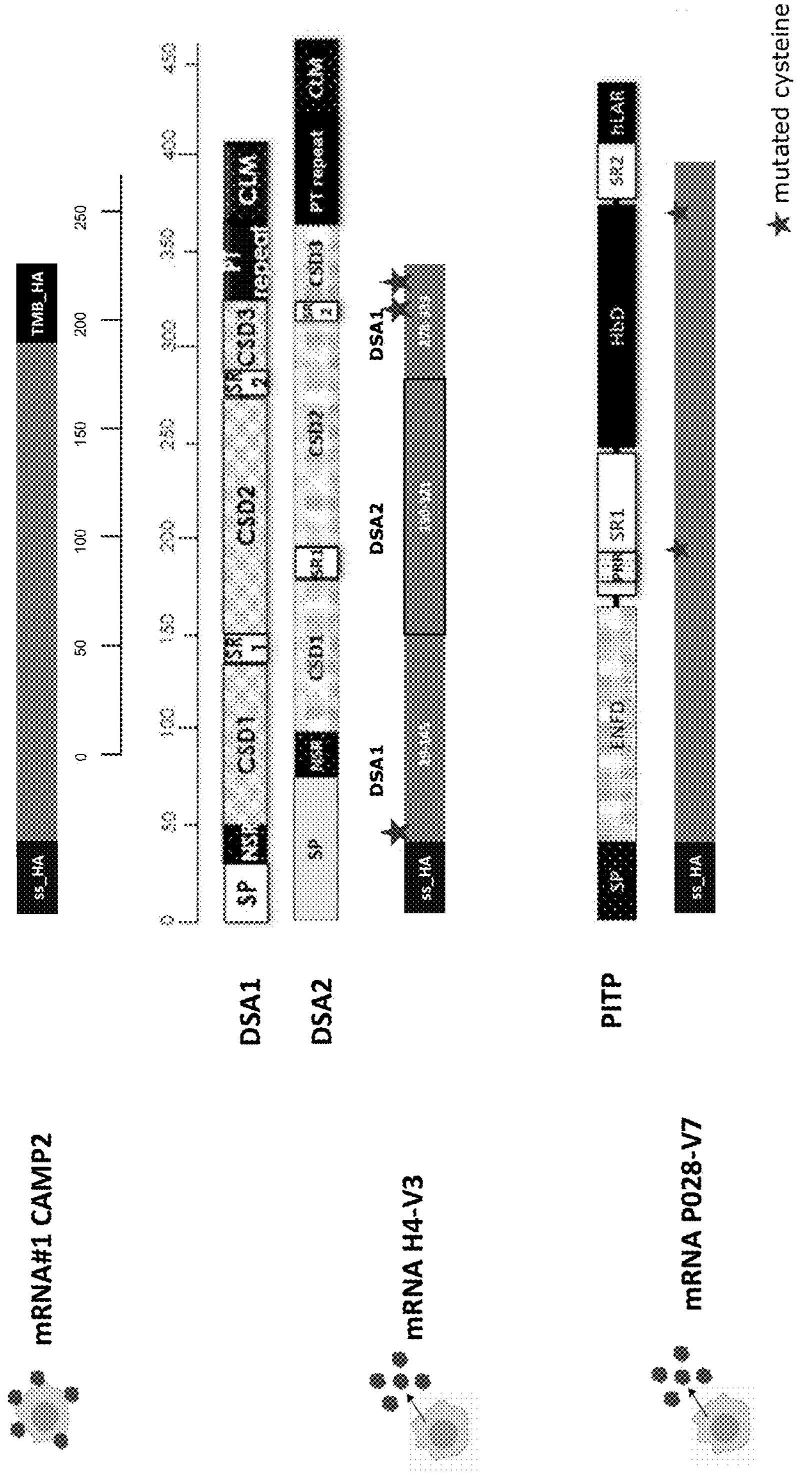
FIG. 20 shows a schematic visualization of the protein domains of DSA1, DSA2 and PITP, and the mRNA constructs that have been synthesized based on these proteins: mRNA H4-V3 (a chimera of DSA1 and DSA2) and mRNA P028-V7 (derived from PITP) as well as the mRNA construct of mRNA #1 CAMP2. The CAMP2 mRNA #1 construct comprised an unmutated CAMP2 sequence, the signal sequence (HA SS) and the transmembrane domain sequence (HA TMB) of Influenza Hemagglutinin (HA, H1N1 A/Caledonia/20/1999) at N-terminus and C-terminus respectively. The H4-V3 and P028-V7 mRNA constructs comprised the signal sequence (HA SS) of Influenza Hemagglutinin (HA, H1N1 A/Caledonia/20/1999) at N-terminus of the protein coding sequence. CAMP2, H4-V3 and P028-V7 sequences were derived from the protein sequence of *C. acnes* strain KPA171202. All protein sequences did not contain the native signal sequence of the proteins.

The schematic visualization of the protein domains of DSA1, DSA2 and PITP, and the mRNA constructs that have been synthesized based on these proteins: mRNA H4-V3 (a chimera of DSA1 and DSA2) and mRNA P028-V7 (derived from PITP) as well as the mRNA construct of mRNA #1 CAMP2. is provided in FIG. 20.

The schematic visualization of FIG. 20 provides details on protein domains of DSA1, DSA2 and PITP, and the 2 mRNA constructs that have been synthesized based on these proteins: mRNA H4-V3 (a chimeric *C. acnes* DsA1/DsA2 construct) (SEQ ID NO: 113) and mRNA P028-V7 (derived from PITP) (SEQ ID NO: 115), as well as the mRNA construct coding for CAMP2, mRNA #1 CAMP2 (SEQ ID NO: 90). The CAMP2 mRNA #1 construct comprised an unmutated CAMP2 sequence, the signal sequence (HA SS) and the transmembrane domain sequence (HA TMB) of Influenza Hemagglutinin (HA, HINI A/Caledonia/20/1999) at the N-terminus and C-terminus, respectively. The H4-V3 and P028-V7 mRNA constructs comprised the protein sequence and the signal sequence (HA SS) of Influenza Hemagglutinin (HA, H1N1 A/Caledonia/20/1999) at the N-terminus. CAMP2, H4-V3 and P028-V7 sequences were derived from the protein sequence of *C. acnes* strain KPA171202. None of the protein sequences contained the native signal sequence of the proteins.

Synthesis and Characterisation of mRNA Encoding C. *Acnes* Polypeptides mRNA synthesis was performed using modified nucleotides (in which all uridine nucleosides were replaced with 1-methyl pseudo uridine), mRNA size, tail size. % of tailed population and % cap1 were evaluated for the synthesized mRNA constructs described in FIG. 20: mRNA H4-V3 (SEQ ID NO: 113), mRNA P028-V7 (SEQ ID NO: 115) and mRNA #1 CAMP2 (SEQ ID NO: 90). With respect to mRNA size, tail size, % of tailed population and cap1%, all mRNAs met the targeted specifications. Sequencing analyses confirmed that the expected mRNA sequences were generated (data not shown).

In Vitro Expression of mRNA Encoding C. *Acnes* Polypeptides in HEK Cells

Western blots were run for in vitro expression products in HEK cells of synthesized mRNA H4-V3, mRNA P028-V7 and mRNA #1 CAMP2 (constructs described in FIG. 20), 48h after transfection. The proteins were detected in the expected compartment, namely in the membrane fraction for CAMP2 and in the supernatant for H4-V3 and P028-V7.

Characterisation of mRNA-LNP Formulation

LNP size, % encapsulation (% EE) and mRNA integrity were evaluated for mRNA H4-V3, mRNA P028-V7 and mRNA #1 CAMP2 (constructs described in FIG. 20) individually encapsulated or co-encapsulated in an LNP. The LNP comprised OF-02, cKK-E10 or GL-HEPES-E3-E12-DS-4-E10, as cationic lipid. With respect to LNP size and % of encapsulation (% EE), all LNPs fell into the expected size range and the targeted % EE, mRNA integrity in all LNPs was as expected.

Example 7A: Evaluation of mRNA Combinations in Different Lipid Formulations

The following constructs were used throughout Example 7A: mRNA constructs coding for the membrane-anchored form of CAMP2 (SEQ ID NO: 90) and the secreted forms of H4-V3 (SEQ ID NO: 113) and P028-V7 (SEQ ID NO: 115) were tested either alone or in combination: [H4-V3 plus P028-V7] or [H4-V3 plus P028-V7 plus CAMP2]. A co-mix formulation with GL-HEPES-E3-E12-DS-4-E10 LNP and the three mRNA constructs (i.e. wherein the three mRNA constructs were encapsulated separately in the LNPs) was also tested. GL-HEPES-E3-E12-DS-4-E10 LNP alone was used as negative control.

Immunisation of Mice with Formulations Containing mRNA Combinations, and Monitoring of Mice Mice were monitored for changes in body weight and temperature after immunization twice at 4 weeks interval, with either of the following mRNA constructs, encapsulated (one mRNA construct) or co-encapsulated (two or three mRNA constructs) in LNPs comprising OF-02, cKK-E10 or GL-HEPES-E3-E12-DS-4-E10 as cationic lipid, mRNA constructs coding for the membrane-anchored form of CAMP2 and the secreted forms of H4-V3 and P028-V7 were tested either alone or in combination: [H4-V3 plus P028-V7] or [H4-V3 plus P028-V7 plus CAMP2]. A co-mix formulation with GL-HEPES-E3-E12-DS-4-E10 LNP and the three mRNA constructs (i.e. wherein the three mRNA constructs were encapsulated separately in the LNPs) was also tested. GL-HEPES-E3-E12-DS-4-E10 LNP alone was used as negative control, mRNA synthesis was performed using modified nucleotides (in which all uridine nucleosides were replaced with 1-methyl pseudo uridine). The mRNA content for each construct in tested formulations was of 1 μg per dose. All tested formulations showed no impact on weight gain nor changes in body temperatures.

Mice were also monitored for swelling at the injection site. We documented higher frequencies of mice with swelling after boosting than after priming. Bi- or tri-valent formulation provoked higher swelling frequency than monovalent formulations. Overall, the OF-02 containing formulations were shown to be more reactogenic than cKK-E10 and GL-HEPES-E3-E12-DS-4-E10-containing ones, which were comparable.

Formulations Containing mRNA Encoding C. *Acnes* CAMP 2 in Combination with mRNAs Encoding Other *C. acnes* Antigens Decrease the Co-Hemolytic Activity of CAMP 2

Figure 21:
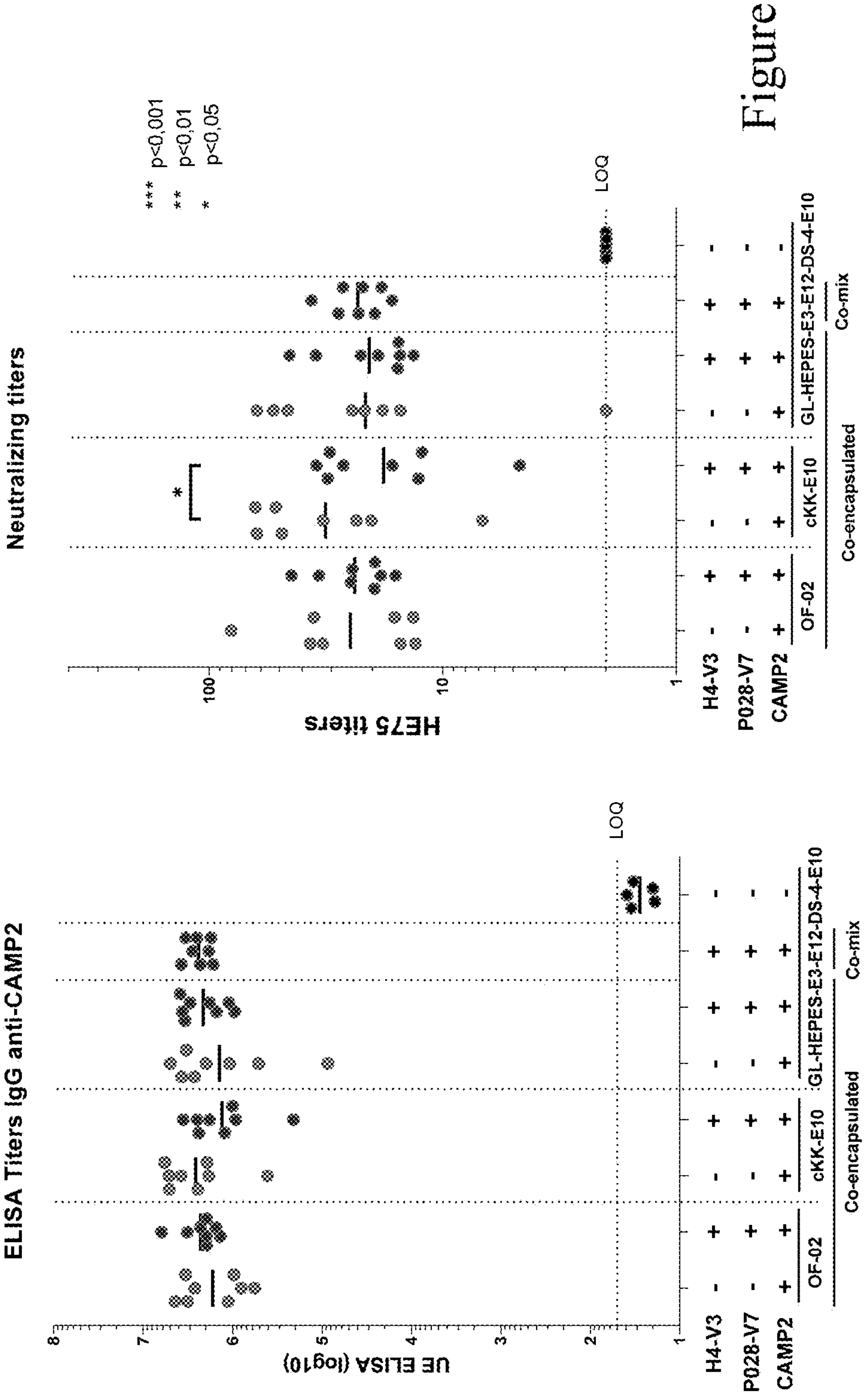
FIG. 21 shows ELISA IgG anti CAMP2 titers and co-hemolytic neutralizing titers of IgG purified from individual sera of mice immunized twice at 4 weeks interval, with the CAMP2 mRNA antigens encapsulated alone or co-encapsulated with the 2 other mRNA antigens (H4-V3 and P028-V7 as described in FIG. 20) in LNPs comprising OF-02, cKK-E10 or GL-HEPES-E3-E12-DS-4-E10 as cationic lipid. A co-mix formulation with the three mRNA antigens separately encapsulated in GL-HEPES-E3-E12-DS-4-E10 LNP was also tested. LOQ=Limit Of Quantification.

FIG. 21 shows ELISA IgG anti CAMP2 titers and co-hemolytic neutralizing titers of IgG purified from individual sera of mice immunized twice at 4 weeks interval, with the mRNA antigens as described above. As shown in FIG. 21, no interferences were monitored as CAMP2 mRNA responses were comparable between co-encapsulated mRNA and CAMP2 mRNA on its own. Co-encapsulated and co-mixed formulations also showed comparable responses for both assays.

Figure 22A:
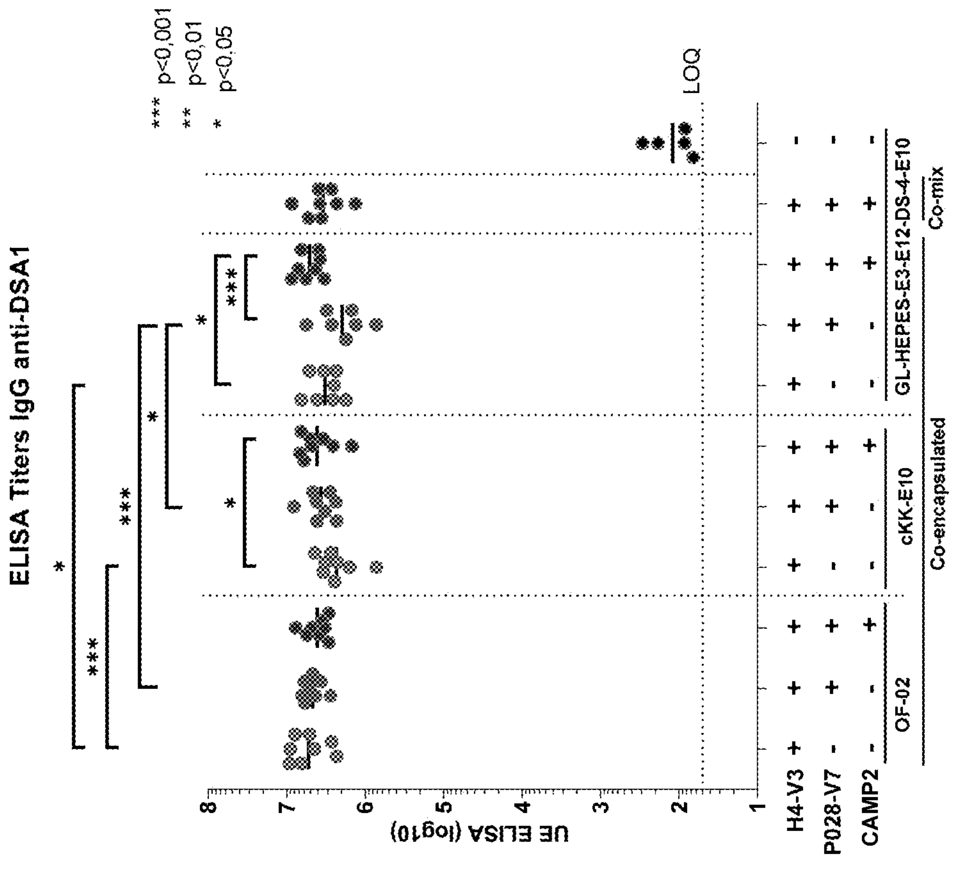
FIGS. 22A-22C show ELISA IgG anti-DSA1 (FIG. 22*a*), anti-DSA2 (FIG. 22*b*) and anti-PITP (FIG. 22*c*) titers from individual sera of mice immunized twice at 4 weeks interval with the same mRNA antigens as described in FIG. 20 and encapsulated in the same LNPs as described in FIG. 21.
Figure 22B:
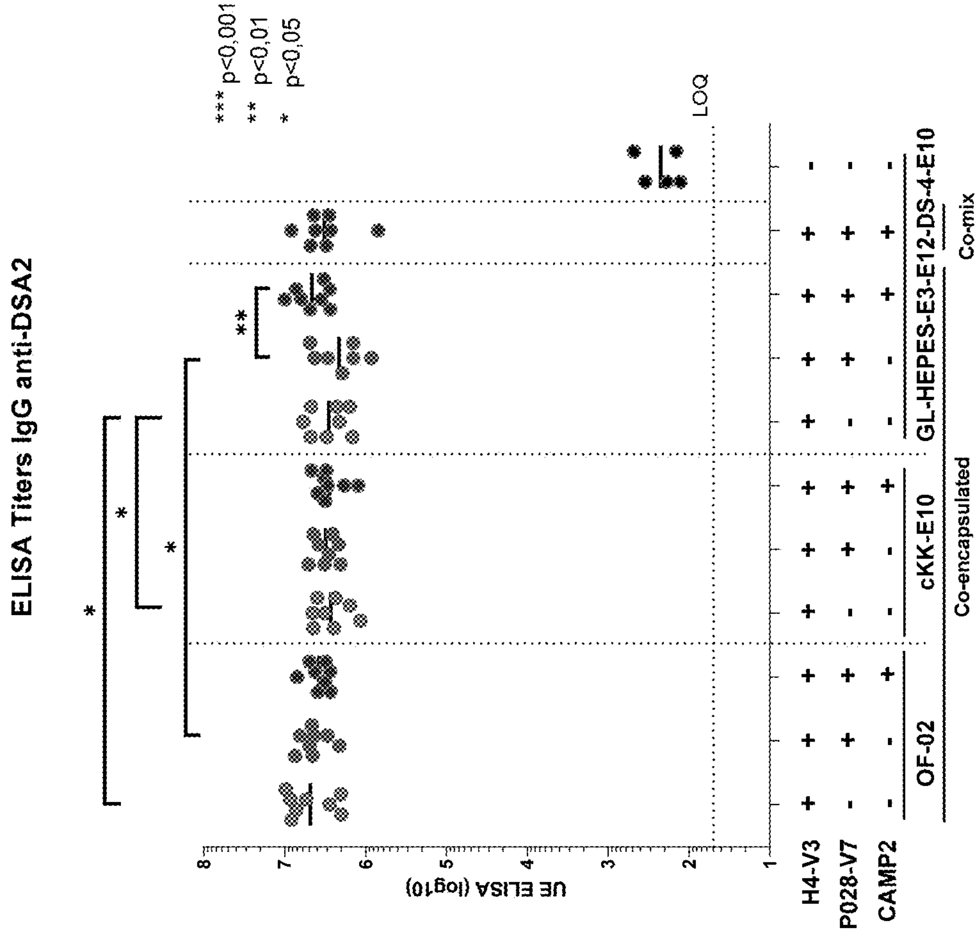
Figure 22C:
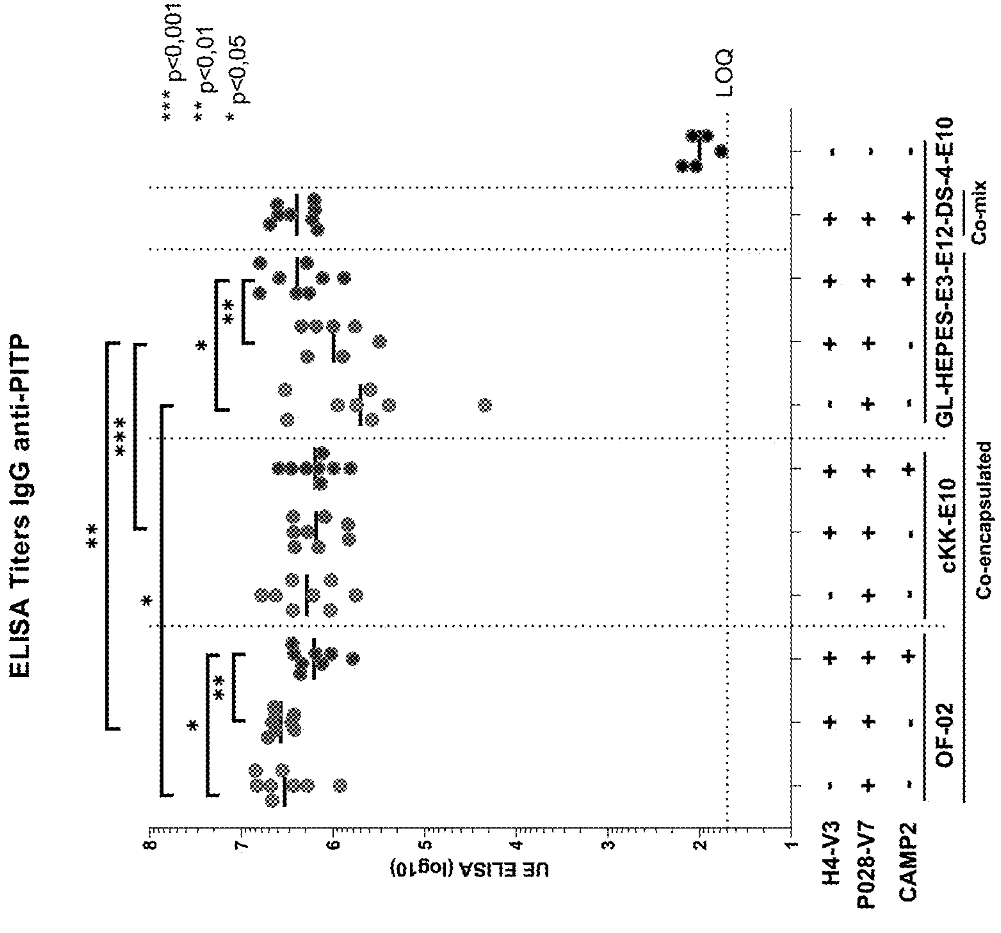

Formulations Containing Combinations of mRNAs Encoding *C. acnes* Antigens Give Rise to IgG Responses IgG anti-DSA1, -DSA2 and -PITP titers from individual sera of mice immunized twice at 4 weeks interval with the mRNA antigens as described above, were tested. As shown in FIGS. 22A-22C. ELISA IgG showed that the anti -DSA1, -DSA2 and -PITP titers were largely comparable when the three mRNAs were co-encapsulated or co-mixed (tri-valent combinations). No overall interference was detected compared to correspondent mono-valent formulation, whatever the cationic lipid in the LNP. Little interferences were observed when each mRNA was formulated either alone or in a bi-valent combination, with OF-02 LNP significantly more potent at inducing anti-DSA1, -DSA2 and -PITP titers compared to cKK-E10 & GL-HEPES-E3-E12-DS-4-E10 which were comparable.

Figure 23A:
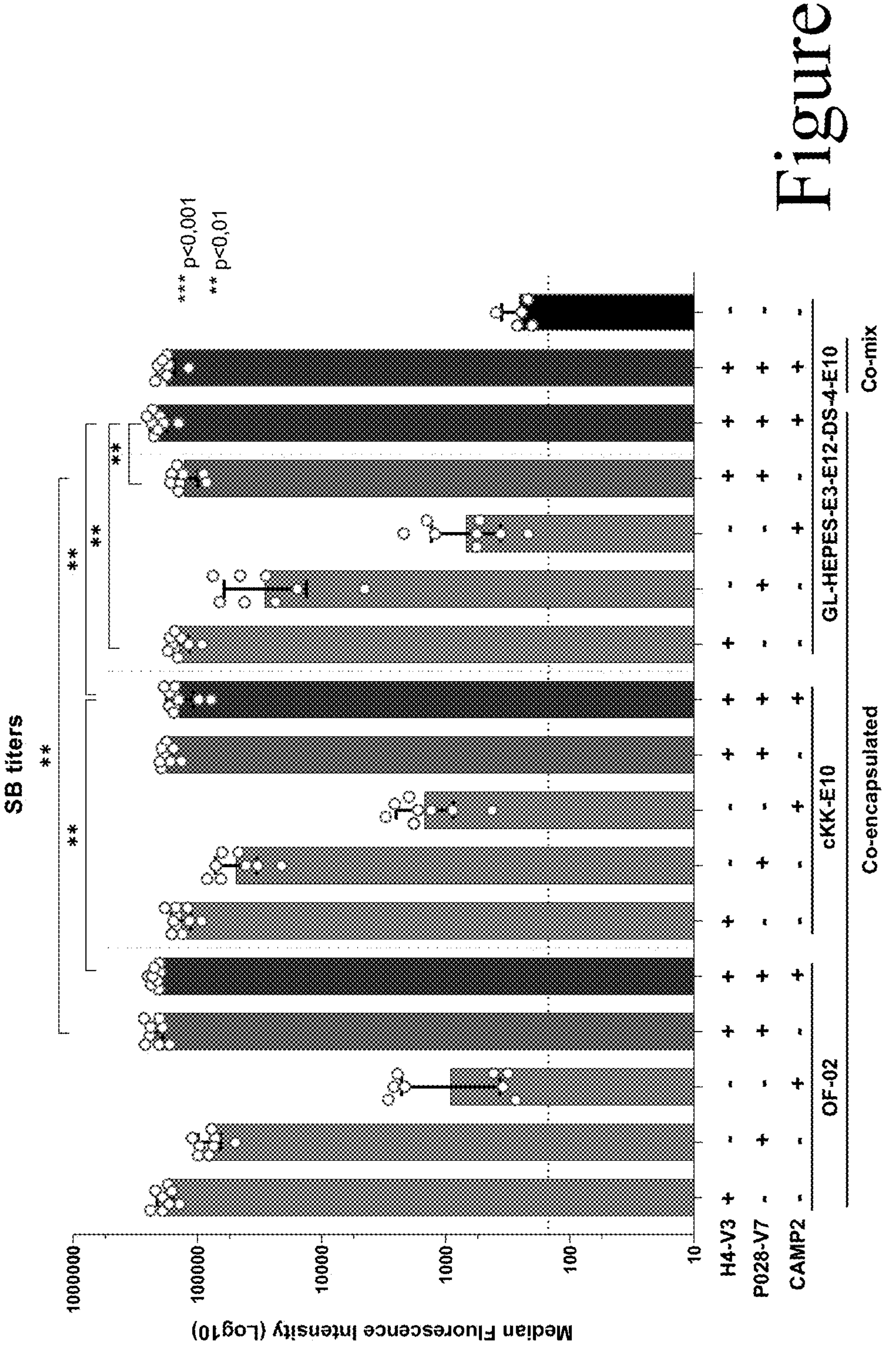
FIGS. 23A-23B show Surface Binding (SB) titers (FIG. 23*a*) and Opsonophagocytic Killing (OPK) titers (FIG. 23*b*), both performed on NCTC737 *C. acnes* strains, from individual sera of mice immunized twice at 4 weeks interval with the same mRNA antigens as described in FIG. 20 and encapsulated in the same LNPs as described in FIG. 21.
Figure 23B:
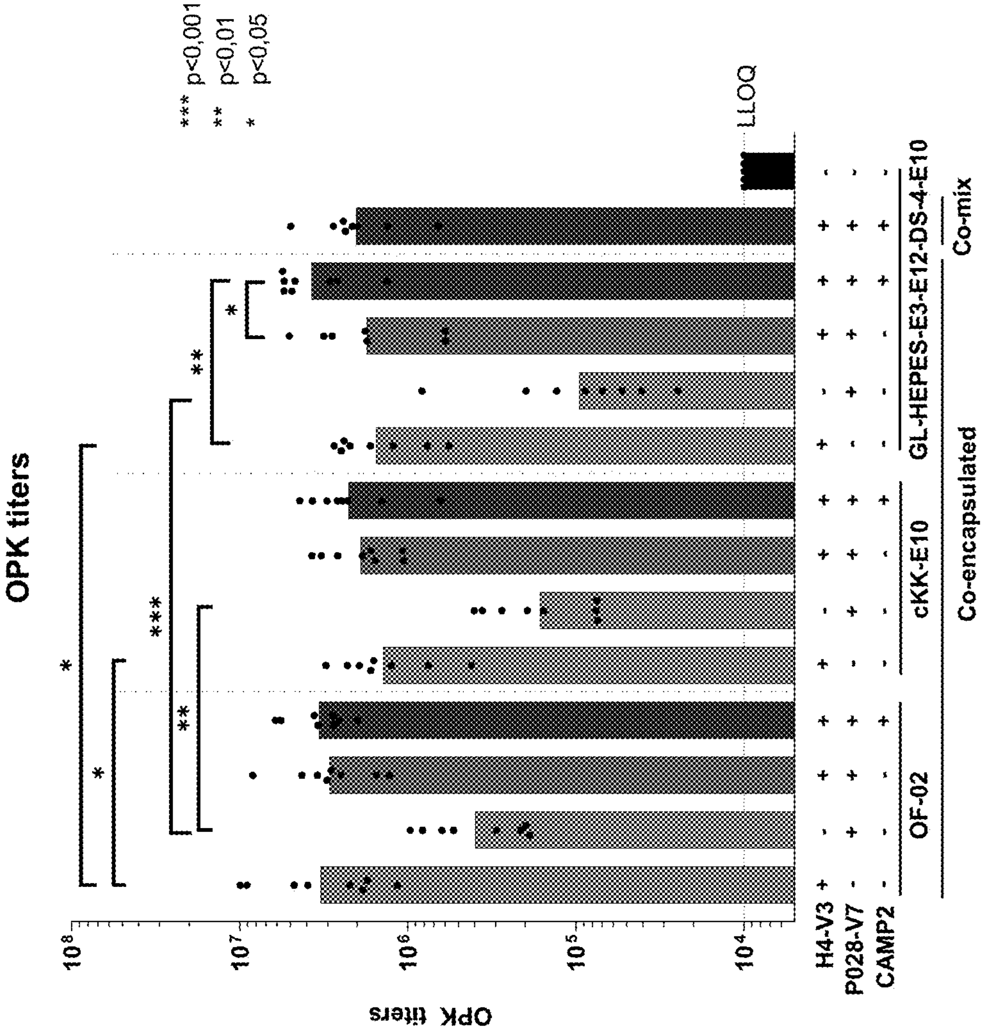

Formulations Containing Combinations of mRNAs Encoding *C. acnes* Antigens Give Rise to Antibodies which Bind to the Surface of *C. acnes*, and with Opsonophagocytic Activity Opsonophagocytic Killing (OPK) titers and Surface Binding (SB) titers, were both performed on NCTC737 *C. acnes* strains, from individual sera of mice immunized twice at 4 weeks interval with the mRNA antigens as described above. As shown in FIGS. 23A-23B, both assays documented comparable or superior titers when the three mRNAs were co-encapsulated or co-mixed (tri-valent combinations). No overall interference was detected compared to correspondent mono-valent formulation, whatever the cationic lipid in the LNP. No interferences were observed when each mRNA was formulated either alone or in a bi-valent combination, however the functional responses were dominated by H4-V3 antigen. OF-02 LNP was significantly more potent at inducing OPK titers compared to cKK-E10 & GL-HEPES-E3-E12-DS-4-E10 which were comparable.

Figure 24A:
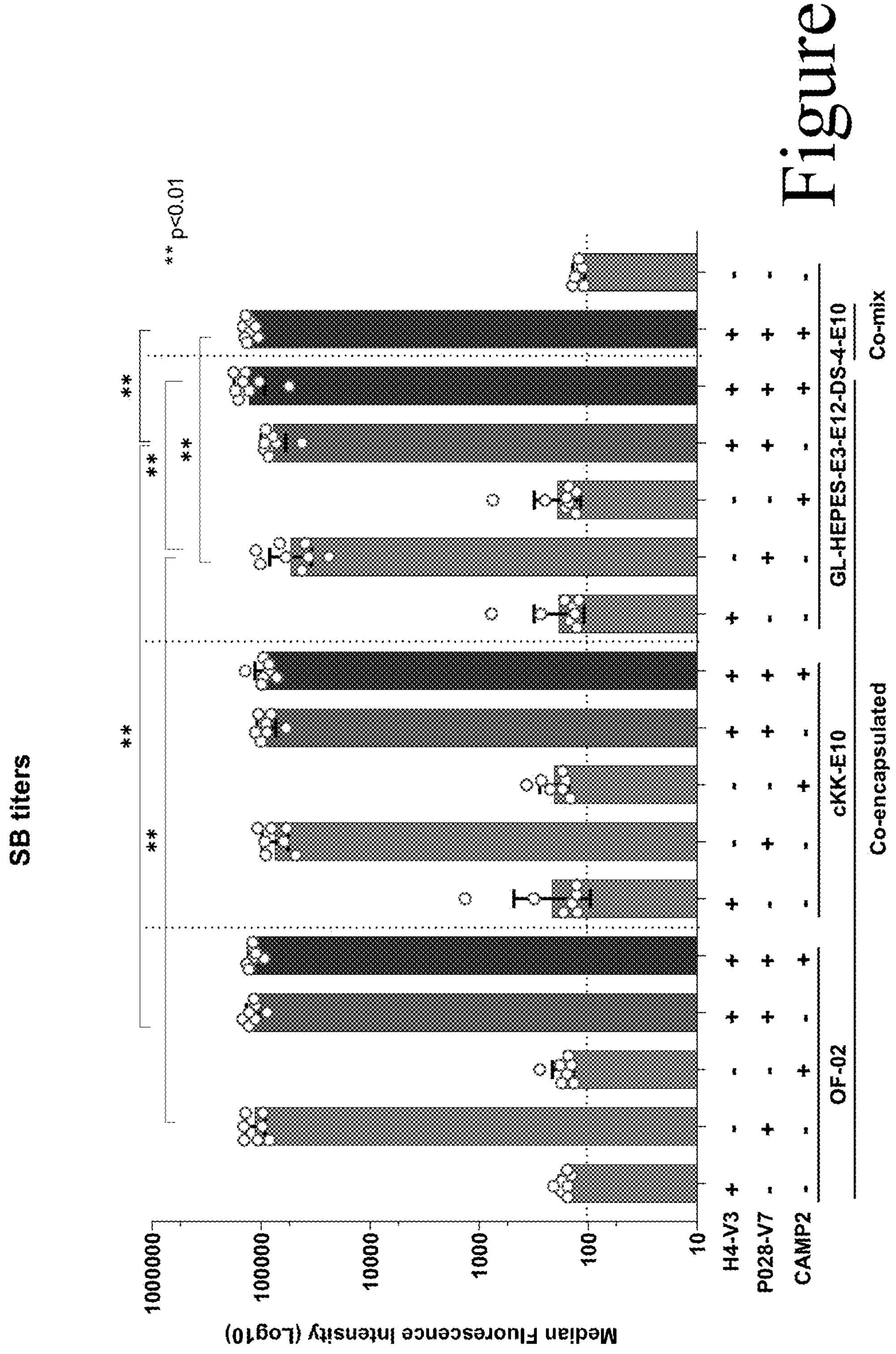
FIGS. 24A-24B show Surface Binding (SB) titers (FIG. 24*a*) and Opsonophagocytic Killing (OPK) titers (FIG. 24*b*), both performed on KPA171202 *C. acnes* strains, from individual sera (SB) or pool of sera (OPK) of mice immunized twice at 4 weeks interval with the same mRNA antigens as described in FIG. 20 and encapsulated in the same LNPs as described in FIG. 21.
Figure 24B:
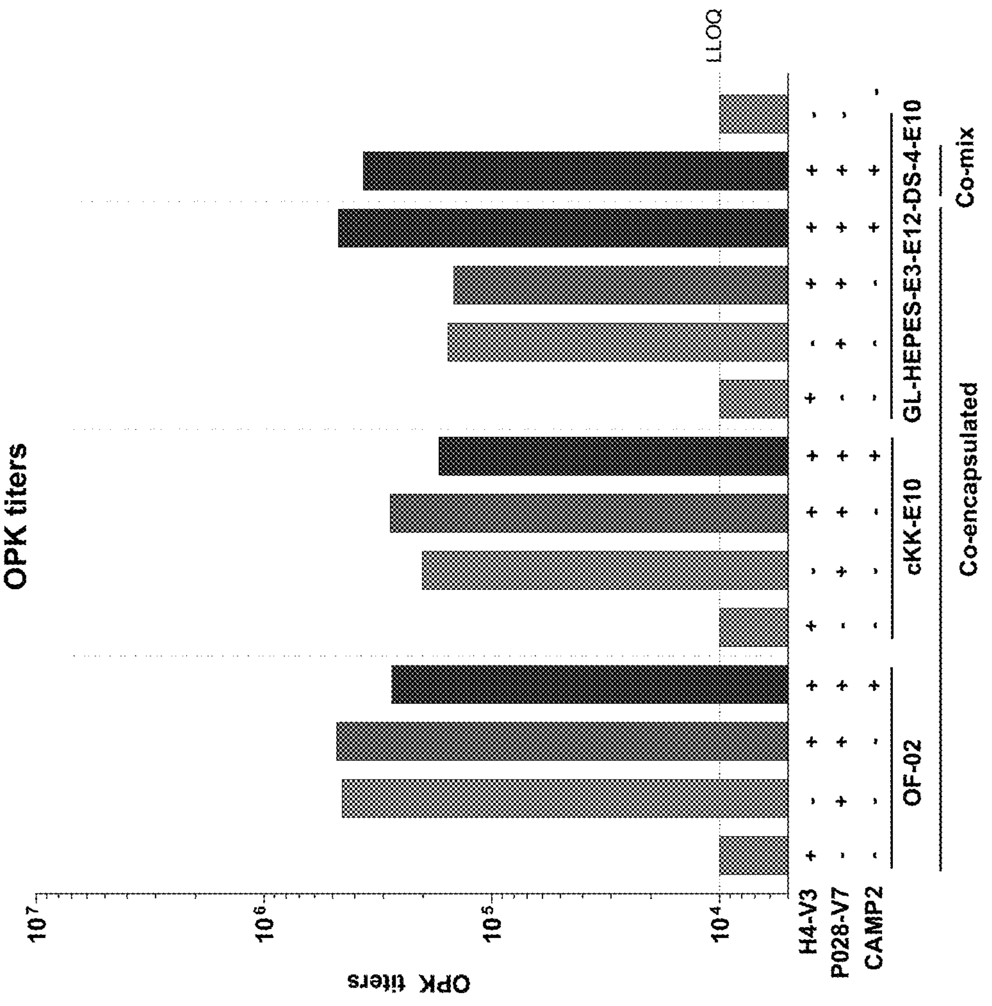

The same experiment was repeated with KPA171202 *C. acnes* strains, with individual sera of mice (for the SB assay) or pool of sera (for the OPK assay). As shown in FIGS. 24A-24B, both assays documented comparable or superior titers when the three mRNAs were co-encapsulated or co-mixed (tri-valent combinations). No overall interference was detected compared to correspondent mono-valent formulation, whatever the cationic lipid in the LNP. No interferences were observed when each mRNA was formulated either alone or in a bi-valent combination, however the functional responses were dominated by H4-V3 antigen. OF-02 LNP significantly more potent at inducing OPK titers compared to cKK-E10 & GL-HEPES-E3-E12-DS-4-E10 which were comparable

Example 7B: Mode of Action of the Combination Vaccine

Figure 25A:
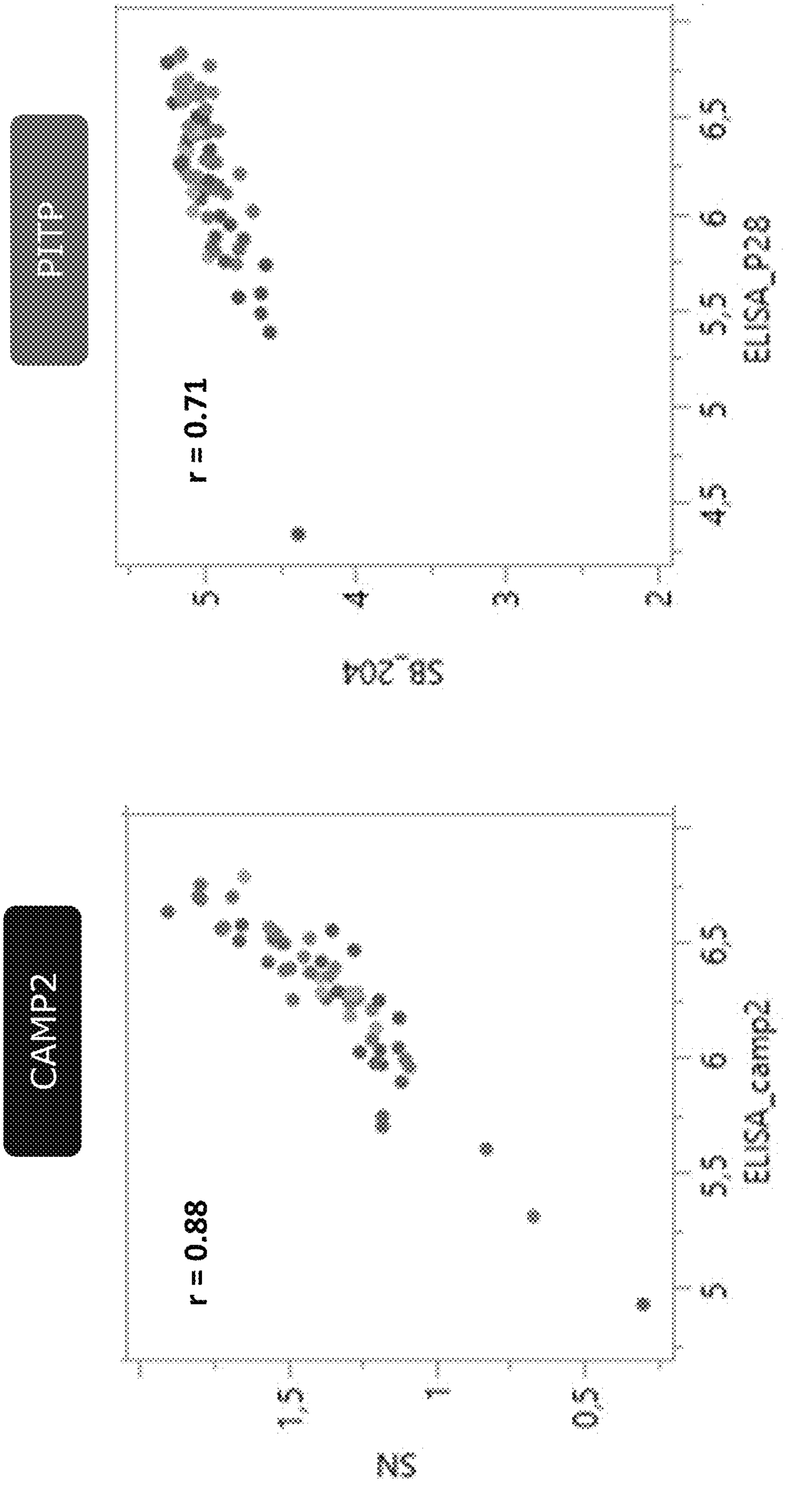
FIGS. 25A-25B show Pearson correlations between ELISA IgG anti-DSA1, -DSA2, -PITP, and -CAMP2 titers and co-hemolytic neutralizing titers (CAMP2) or Surface Binding titers (PITP, DSA1 and DSA2), or Opsonophagocytic Killing titers (DSA1 and DSA2) both performed on either KPA171202 (PITP) or NCTC737 (DSAI/DSA2) *C. acnes* strains, from individual sera of mice immunized twice at 4 weeks interval with the same mRNA antigens as described in FIG. 20 and encapsulated in the same LNPs. r=Pearson correlation factor calculated between each variable.
Figure 25B:
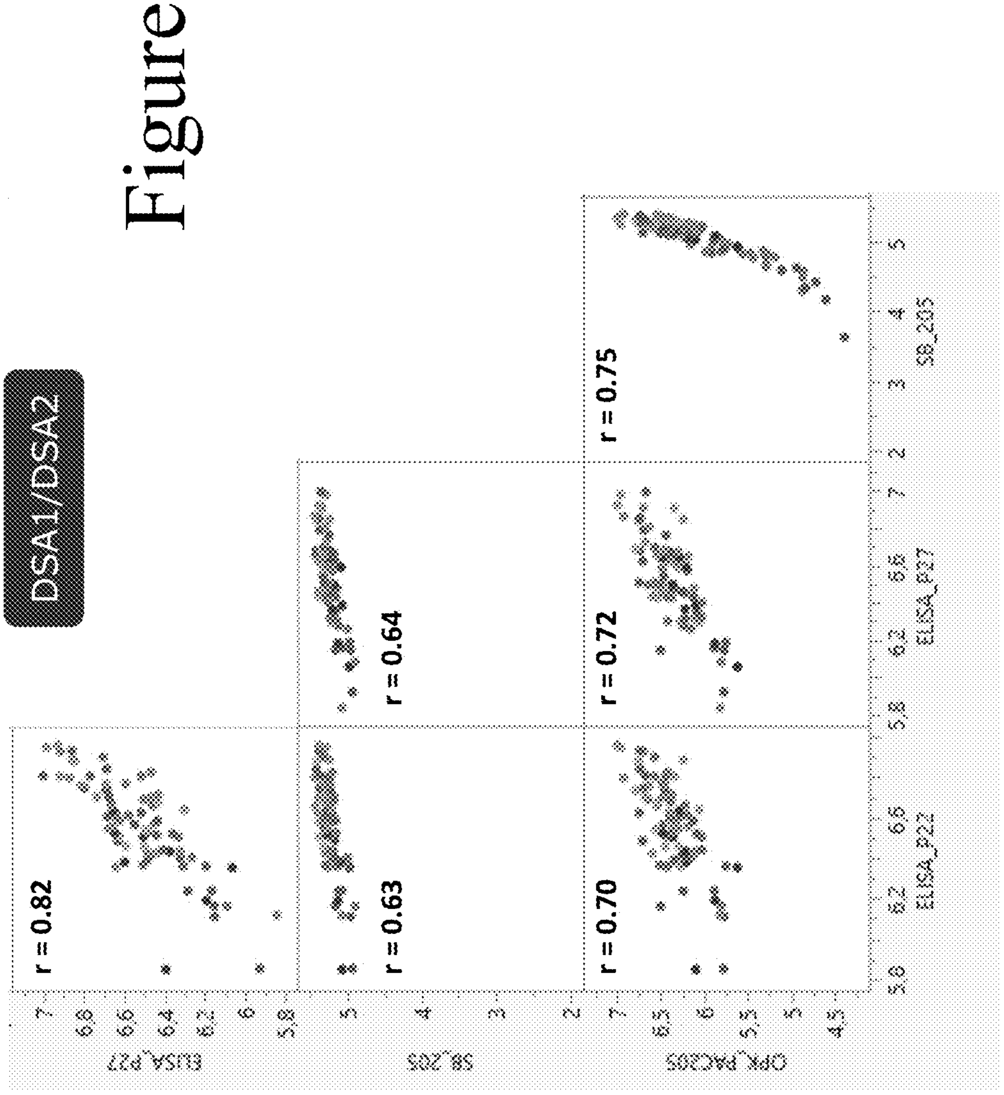
Figure 32:
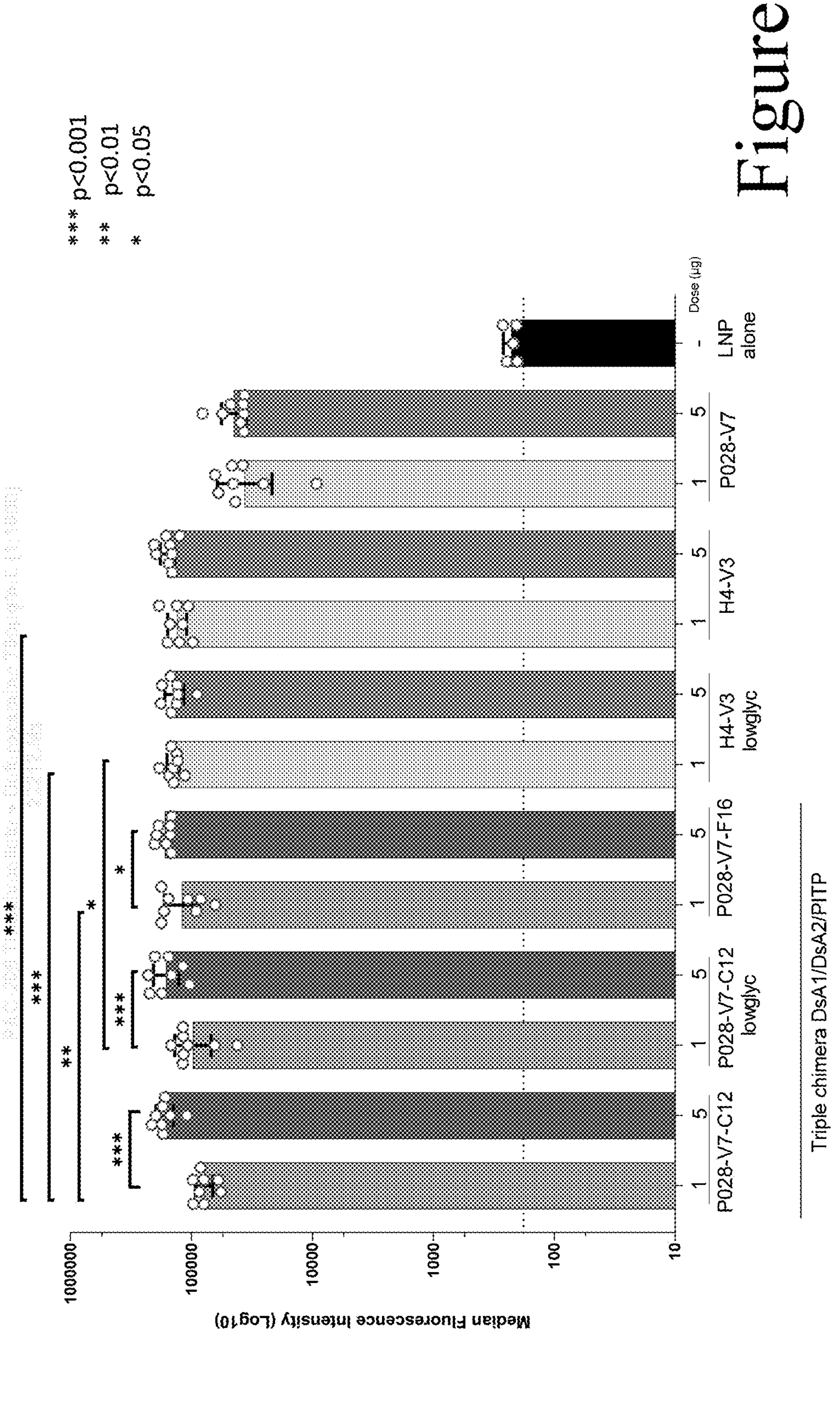
FIG. 32 shows Surface Binding (SB) titers performed on NCTC737 *C. acnes* strain, from individual sera of mice immunized twice at 4 weeks interval with the mRNA antigens described in FIG. 31 ("H4-V3", "H4-V3-lowglyc", "P028-V7-F16", "P028-V7-C12" and "P028-V7-C12lowglyc") and with the mRNA constructs coding for P028-V7. These mRNA constructs were encapsulated in the LNP GL-HEPES-E3-E12-DS-4-E10. The sera were obtained at day 42 following the first immunization. LNP alone was used as negative control, mRNA synthesis was performed using modified nucleotides. The mRNA content in tested formulation was of 1 μg and 5 μg per dose.

Correlations Between Antibody Responses Elicited by H4-V3, P28-V7 and CAMP 2 mRNAs The Pearson correlations between ELISA IgG anti-DSA1, -DSA2, -PITP, and -CAMP2 titers and co-hemolytic neutralizing titers (CAMP2) or Surface Binding titers (PITP, DSA1 and DSA2), or Opsonophagocytic Killing titers (DSA1 and DSA2)) both performed on either KPA 171202 (PITP) or NCTC737 (DSA1/DSA2) *C. acnes* strains, from individual sera of mice immunized twice at 4 weeks interval with the same mRNA antigens as described in FIG. 32 and encapsulated in the same LNPs, were analysed. The results are shown in FIGS. 25A-25B. r=Pearson correlation factor calculated between each variable. All correlated assays exhibited good r values.

Example 8—Protein-Based Vaccines and Choice of Adjuvants

Throughout Example 8, the following recombinant proteins were tested: H4-V3 (SEQ ID NO: 29). P028-V7 (SEQ ID NO: 32) and CAMP2 (SEQ ID NO: 1).

Figure 26:
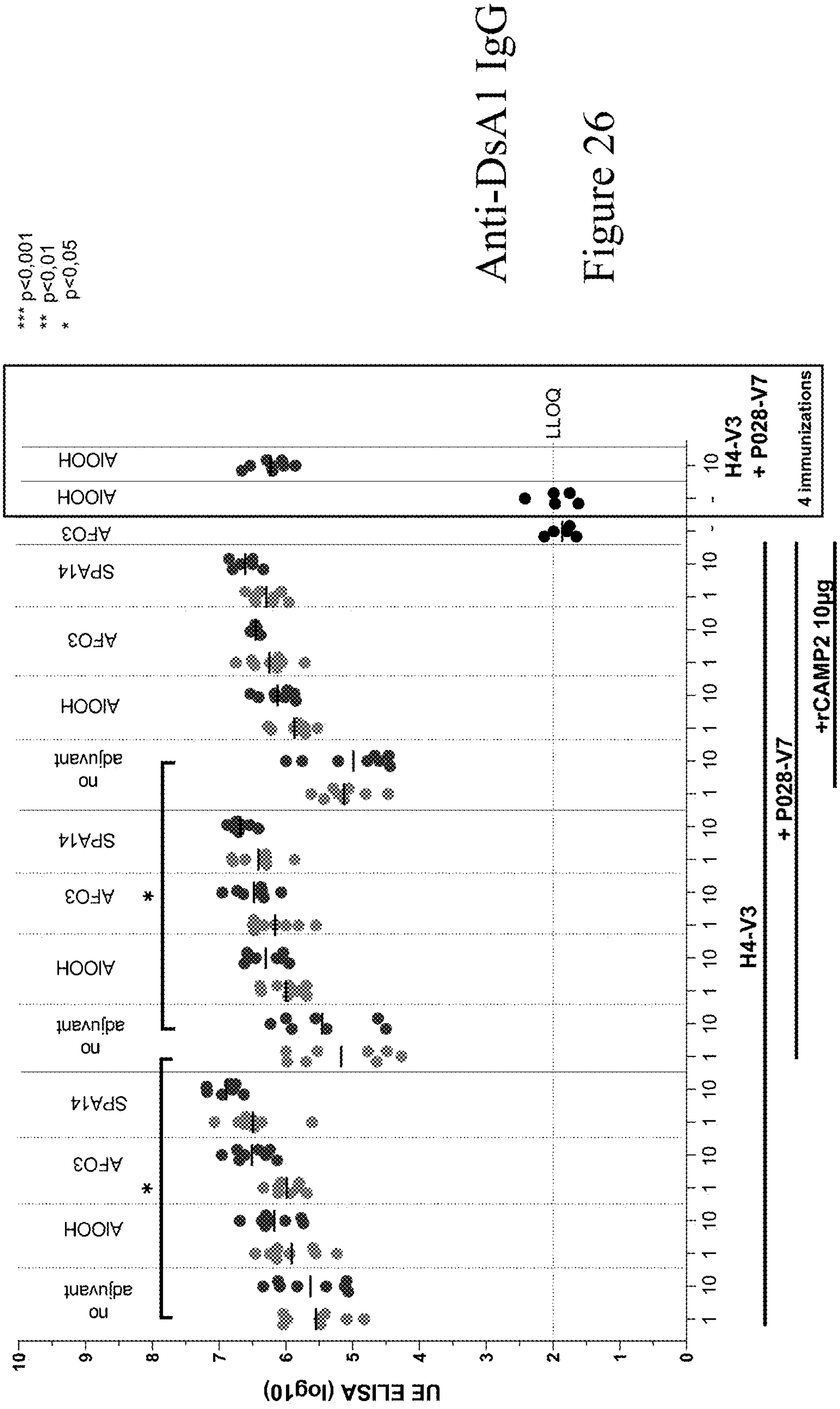
FIG. 26 shows ELISA IgG anti DSA1 titers from individual sera of mice immunized twice at 4 weeks interval with H4-V3, P028-V7 and CAMP2 recombinant proteins, formulated either alone or in combination [H4-V3 plus P028-V7] or [H4-V3 plus P028-V7 plus CAMP2]. These formulations were done with AlOOH, AF03, SPA14 adjuvants or with no adjuvant. An additional group of mice received 4 immunizations of the bivalent vaccine [H4-V3 plus P028-V7] in AlOOH at 2 weeks interval. The sera were obtained at day 42 following the first immunization. AlOOH and AF03 alone were used as negative control. The H4-V3 and P028-V7 recombinant protein content in tested formulation was of 1 μg or 10 μg of each per dose (in mono-, bi- and tri-valent). The CAMP2 recombinant protein content in tested formulation was 10 μg per dose (in mono- and tri-valent).

Formulations Containing Combinations of C. *Acnes* Proteins Give Rise to IgG Responses ELISA IgG anti DSA1 titers were measured on individual sera of mice immunized twice at 4 weeks interval with H4-V3 (SEQ ID NO: 29), P028-V7 (SEQ ID NO: 32) and CAMP2 (SEQ ID NO: 1) recombinant proteins, formulated either alone or in combination [H4-V3 plus P028-V7] or [H4-V3 plus P028-V7 plus CAMP2]. These formulations were done with AlOOH, AF03, SPA14 adjuvants or with no adjuvant. An additional group of mice received 4 immunizations of the bivalent vaccine [H4-V3 plus P028-V7] in AlOOH at 2 weeks interval. The sera were obtained at day 42 following the first immunization. AlOOH and AF03 alone were used as negative control. The H4-V3 and P028-V7 recombinant protein content in tested formulation was of 1 μg or 10 μg of each per dose (in mono-, bi- and tri-valent). The CAMP2 recombinant protein content in tested formulation was 10 μg per dose (in mono- and tri-valent). As shown in FIG. 26, ELISA IgG showed that the anti-DSA1 titers were largely comparable when the three recombinant proteins were co-formulated (bi- and tri-valent combinations). No overall interference was detected compared to correspondent mono-valent formulation, whatever the adjuvant. Little interferences were observed at 1 μg in experimental group with no adjuvant. Among adjuvanted groups, SPA14- and AlOOH-containing formulations elicited the highest and the lowest ELISA IgG anti DSA1 titers, respectively. The ELISA IgG anti DSA1 titers were comparable between groups which received 2 and 4 immunisations. 4 and 2 weeks apart respectively. Anti-DSA2 IgG response pattern was similar (data not shown).

Figure 27:
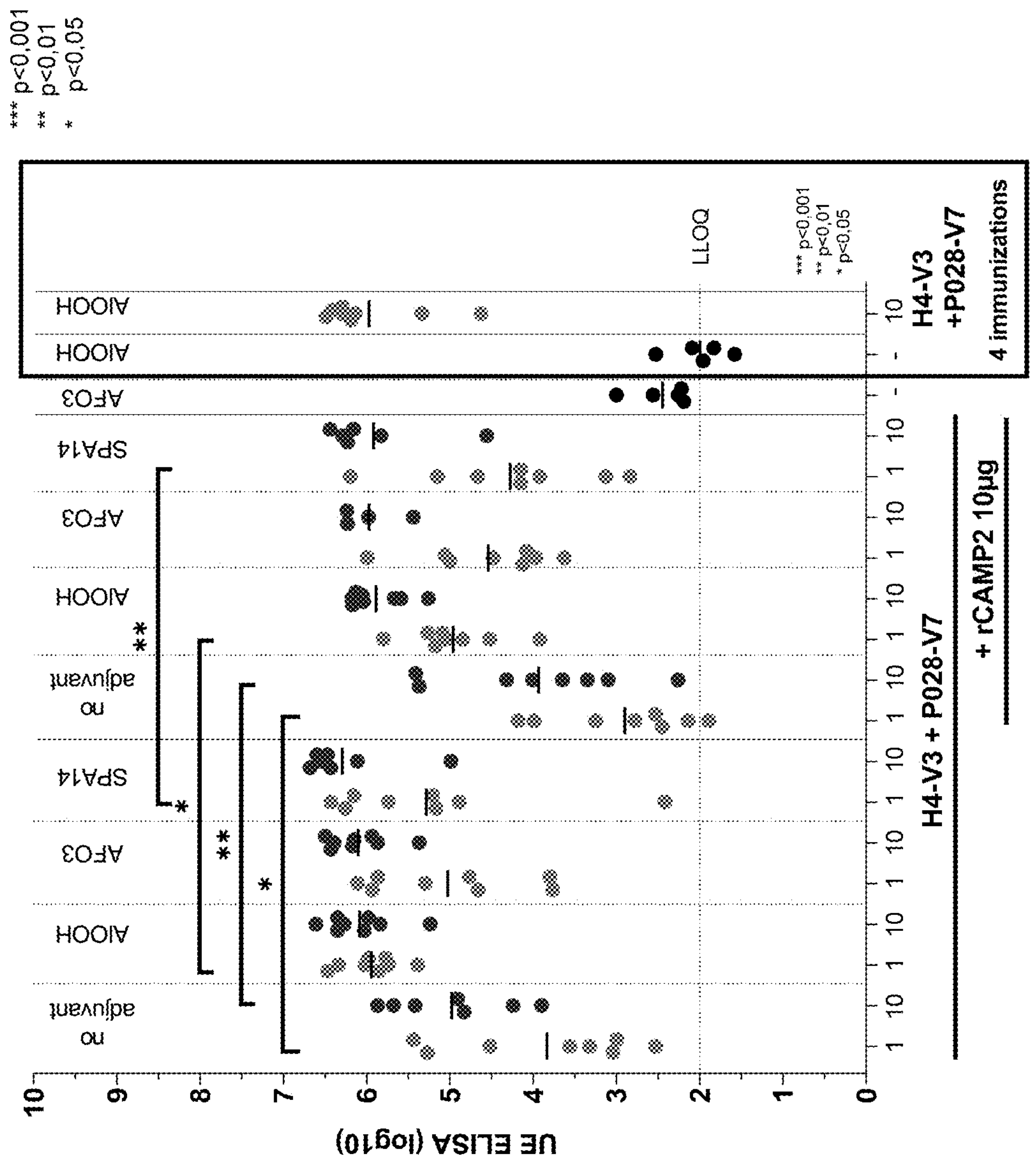
FIG. 27 shows ELISA IgG anti PITP titers from individual sera of mice immunized twice at 4 weeks interval with the same recombinant protein antigens as described in FIG. 26 and formulated in the same adjuvants.

ELISA IgG anti PITP titers from individual sera of mice immunized twice at 4 weeks interval with the same recombinant protein antigens as described in FIG. 26 and formulated in the same adjuvants. As shown in FIG. 27, ELISA IgG showed that the anti-PITP titers were largely comparable when the three recombinant proteins were co-formulated at 10 μg of each recombinant protein per dose (bivalent and tri-valent formulations). At this 10 μg per antigen dose, no overall interference was observed whatever the adjuvant which elicited comparable titers. Low and heterogenous ELISA IgG anti PITP titers were documented at 1 μg of each recombinant protein per dose, excepted in bivalent formulation at 1 μg formulated in AlOOH. The ELISA IgG anti PITP titers were comparable between groups which received 2 and 4 immunisations. 4 and 2 weeks apart respectively.

Formulations Containing Combinations of C. *Acnes* Proteins Including C. *Acnes* CAMP 2 Give Rise to IgG Responses and Decrease the Co-Hemolytic Activity of CAMP2

Figure 28A:
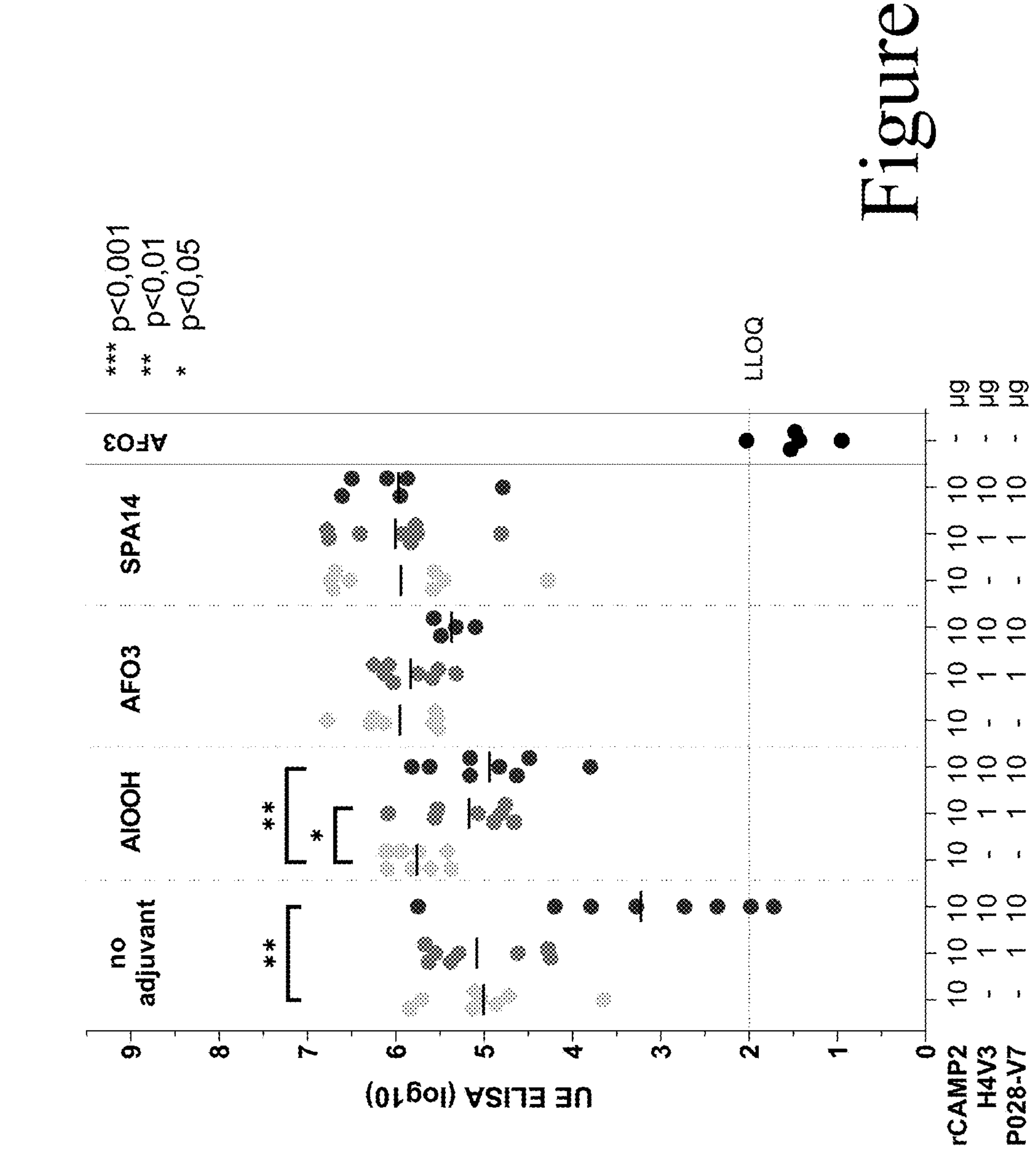
FIGS. 28A-28B show ELISA IgG anti CAMP2 titers from individual sera (FIG. 28*a*) and co-hemolytic neutralizing titers of IgG purified from individual sera (FIG. 28*b*) of mice immunized twice at 4 weeks interval with the same recombinant protein antigens as described in FIG. 26 and formulated in the same adjuvants.
Figure 28B:
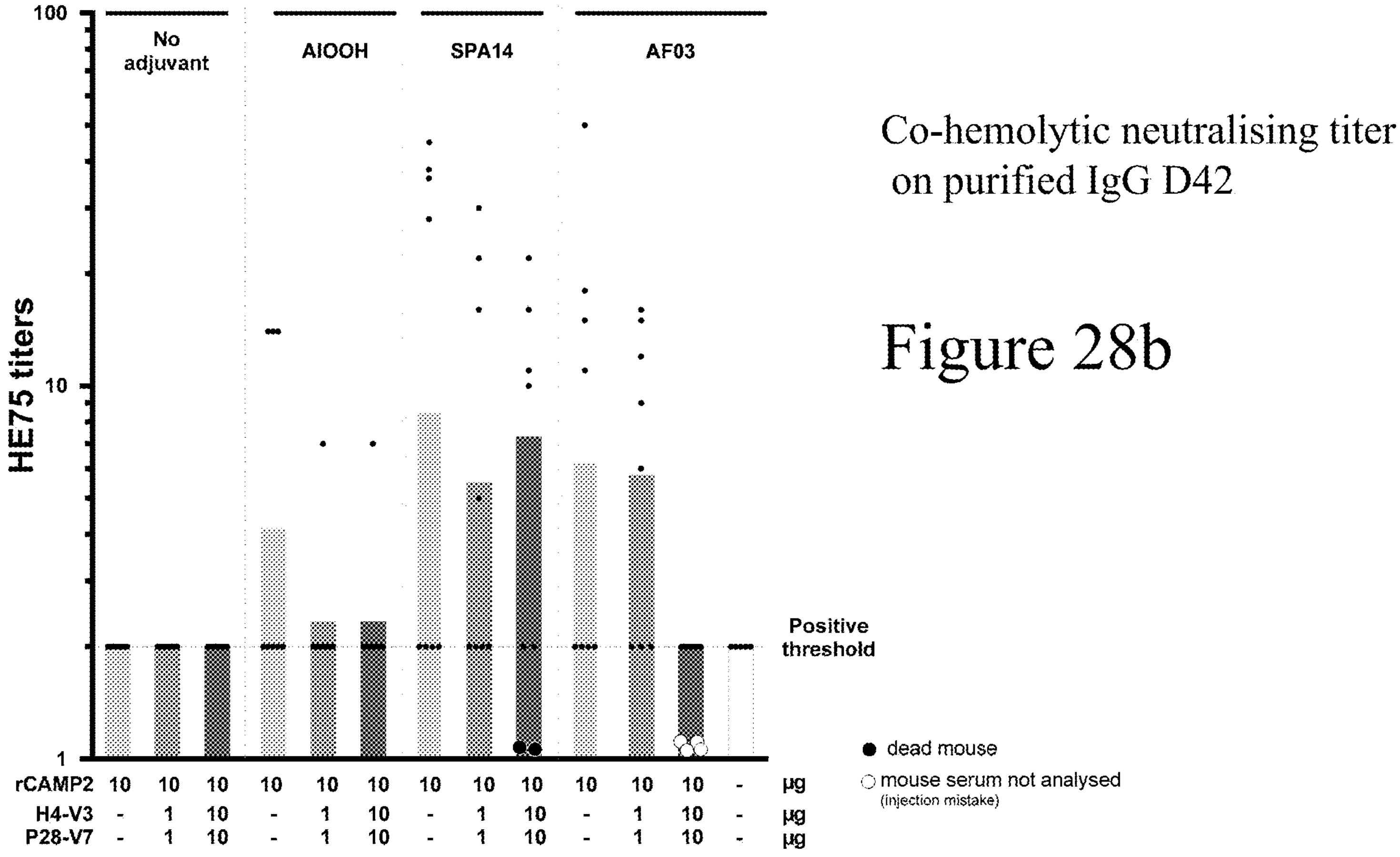

ELISA IgG anti CAMP2 titers from individual sera and co-hemolytic neutralizing titers of IgG purified from individual sera of mice immunized twice at 4 weeks interval with the same recombinant protein antigens as described in FIG. 26 and formulated in the same adjuvants. As shown in FIGS. 28A-28B, interferences were observed for ELISA IgG anti CAMP2 and neutralization titers when H4-V3 and P028-V7 were formulated at 10 μg per dose, both without adjuvant and with AF03. This was also measured at 1 μg and 10 μg doses of H4-V3 and P028-V7 formulated in AlOOH. SPA14 adjuvantation obviated interferences observed in other formulations.

Figure 29A:
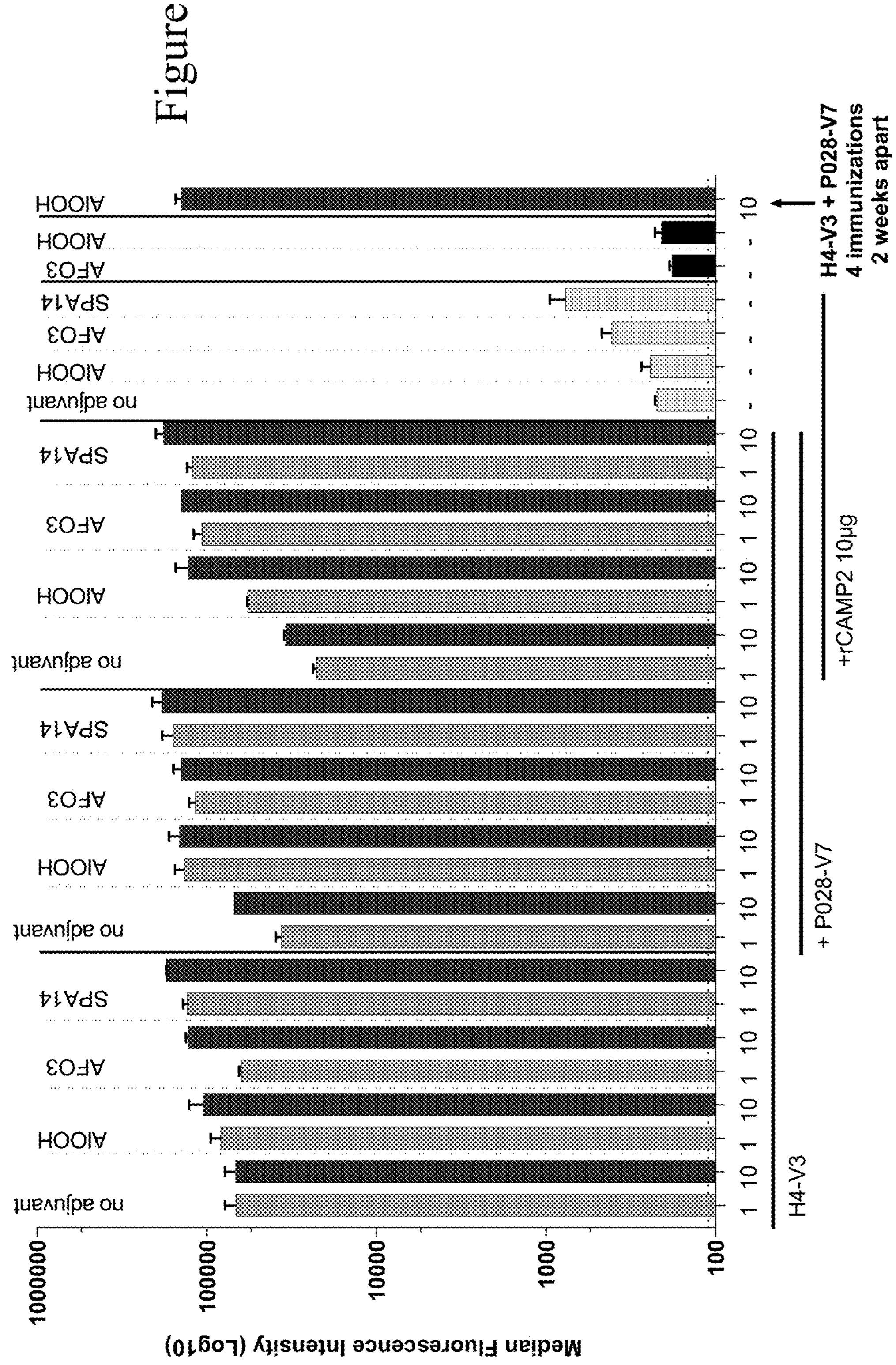
FIGS. 29A-29B show Surface Binding (SB) titers (FIG. 29*a*) and Opsonophagocytic Killing (OPK) titers (FIG. 29*b*), both performed on NCTC737 *C. acnes* strains, from pool of sera of mice immunized twice at 4 weeks interval with the same recombinant protein antigens as described in FIG. 26 and formulated in the same adjuvants.
Figure 29B:
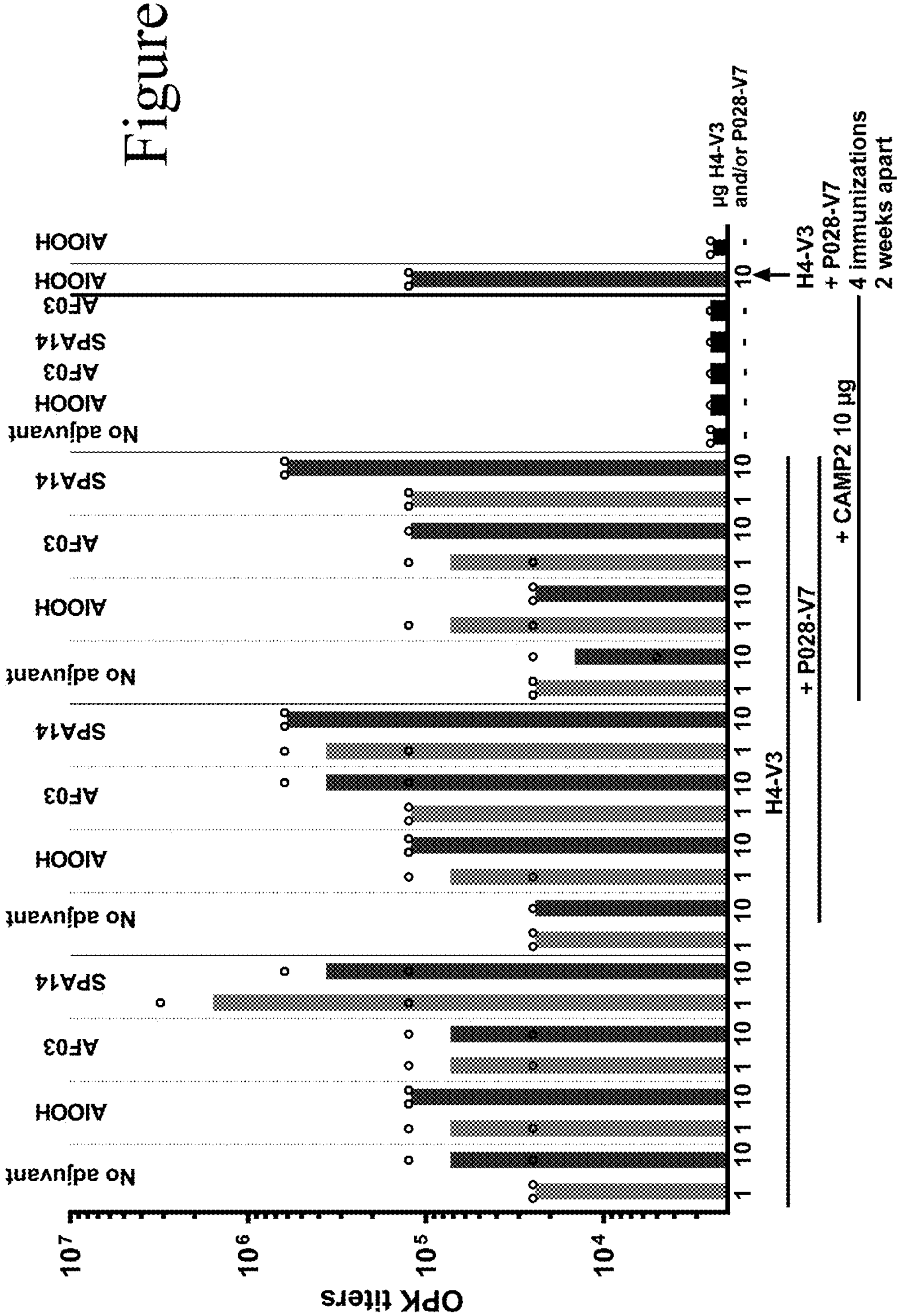

Formulations Containing Combinations of *C. acnes* Proteins Including Chimeric *C. acnes* DsA1 DsA2 Polypeptide Give Rise Antibodies which Bind to the Surface of *C. acnes*, and with Opsonophagocytic Activity Opsonophagocytic Killing (OPK) titers and Surface Binding (SB) titers were performed on NCTC737 *C. acnes* strains, from individual sera (SB) and pool of sera (OPK) of mice immunized twice at 4 weeks interval with the same recombinant protein antigens as described in FIG. 26 and formulated in the same adjuvants. As shown in FIGS. 29A-29B, both assays documented comparable or superior titers when the three recombinant proteins were co-formulated at 10 μg of each recombinant protein per dose (bivalent and tri-valent formulations). At this 10 μg per antigen dose, no overall interference was observed whatever the adjuvant which elicited comparable titers. Lower titers were documented at 1 μg of each recombinant protein per dose, excepted in bivalent formulation at 1 μg formulated in AlOOH. The titers were comparable between groups which received 2 and 4 immunisations, 4 and 2 weeks apart respectively.

Figure 30A:
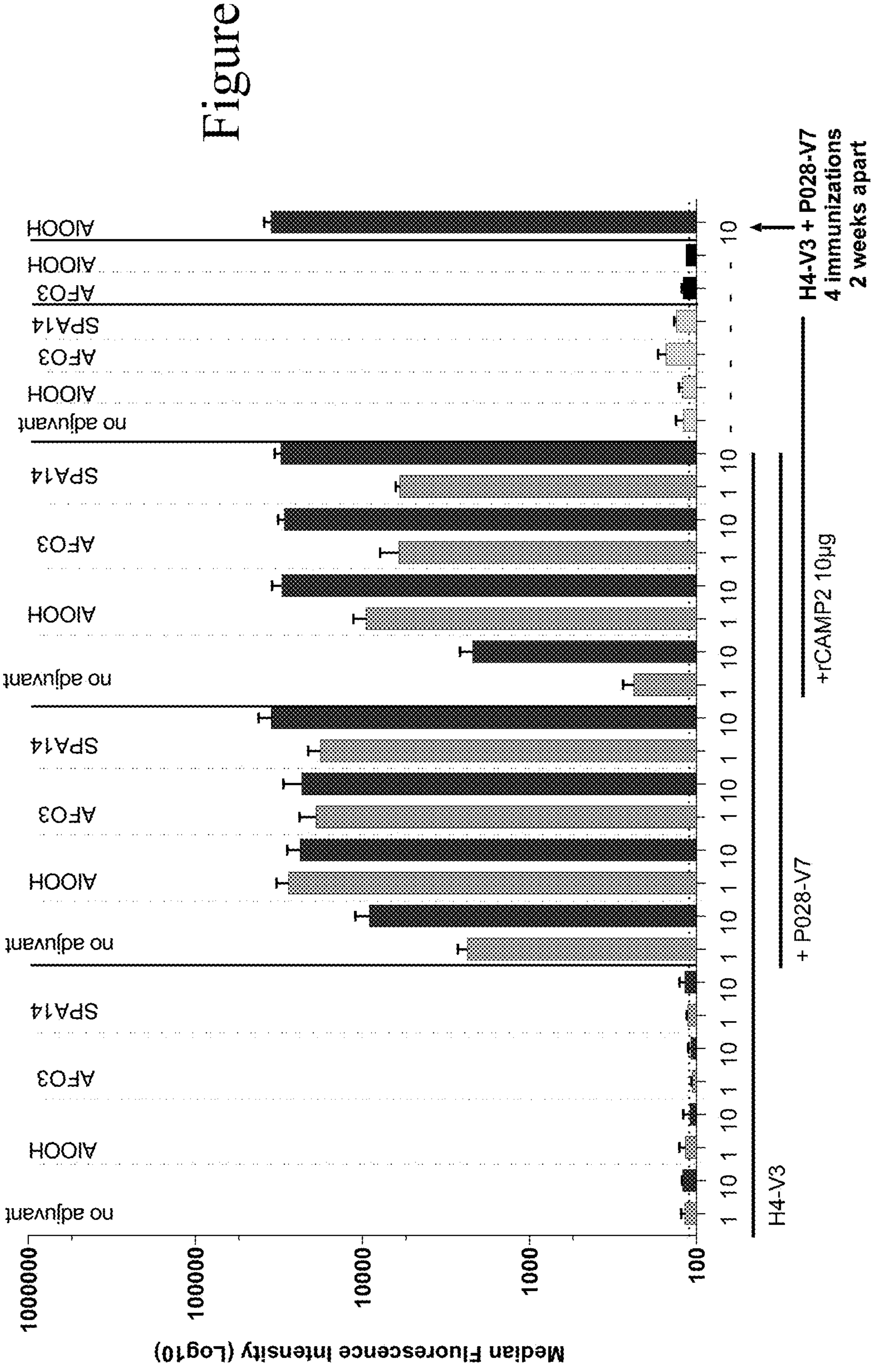
FIGS. 30A-30B show Surface Binding (SB) titers (FIG. 30*a*) and Opsonophagocytic Killing (OPK) titers (FIG. 30*b*), both performed on KPA171202 *C. acnes* strains, from individual sera (SB) and pool of sera (OPK) of mice immunized twice at 4 weeks interval with the same recombinant protein antigens as described in FIG. 26 and formulated in the same adjuvants.
Figure 30B:
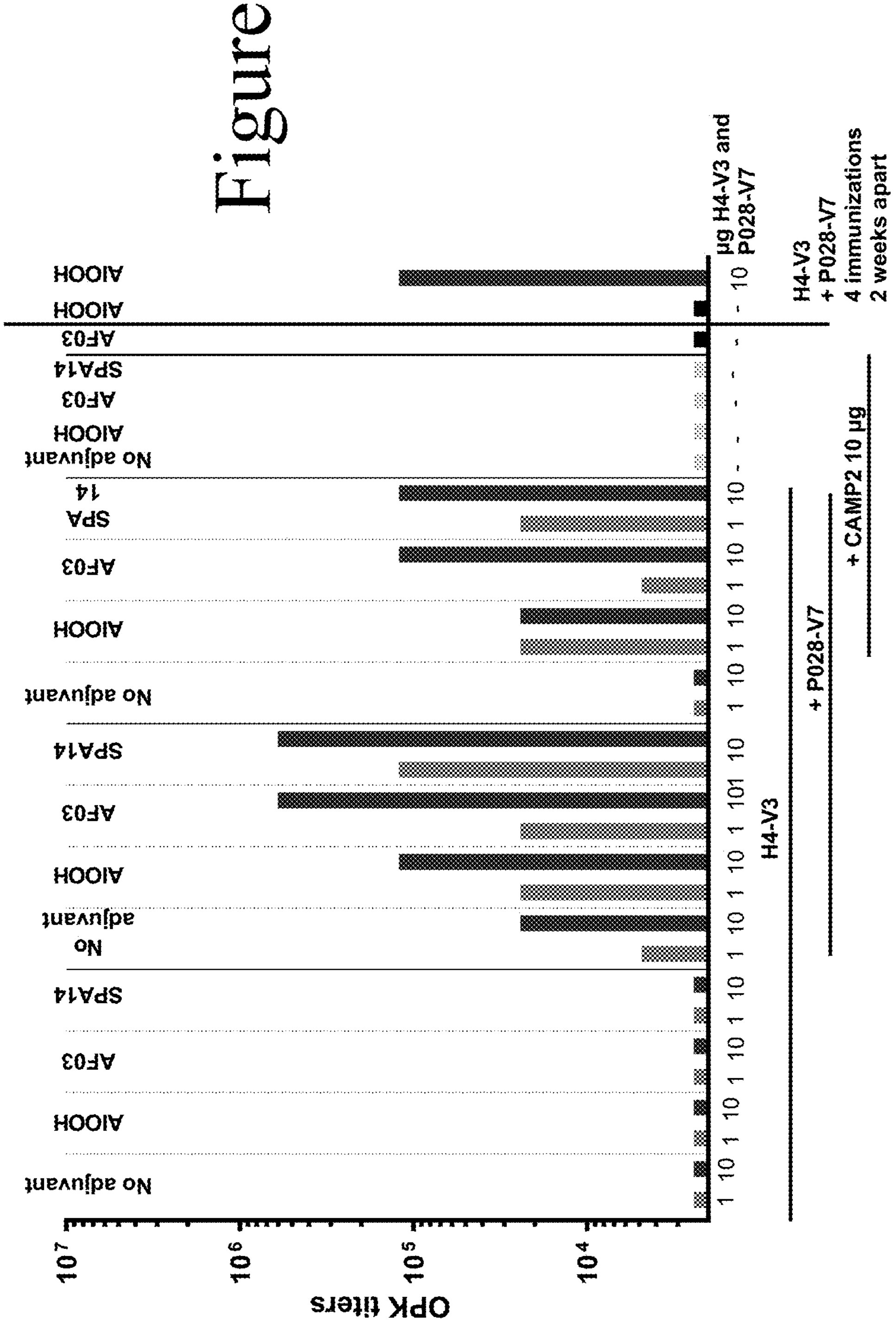

The same experiment was repeated on KPA171202 *C. acnes* strains, from individual sera (SB) and pool of sera (OPK) of mice. As shown in FIGS. 30A-30B, both assays documented comparable or superior titers when the three recombinant proteins were co-formulated at 10 μg of each recombinant protein per dose (bi-valent and tri-valent formulations). At this 10 μg per antigen dose, no overall interference was observed whatever the adjuvant which elicited comparable titers. Lower titers were documented at lug of each recombinant protein per dose, excepted in bivalent formulation at 1 μg formulated in AlOOH. The titers were comparable between groups which received 2 and 4 immunisations. 4 and 2 weeks apart respectively.

Example 9—Chimeric *C. acnes* Antigens

Construct Design of Chimeric *C. acnes* Antigens

Figure 31:
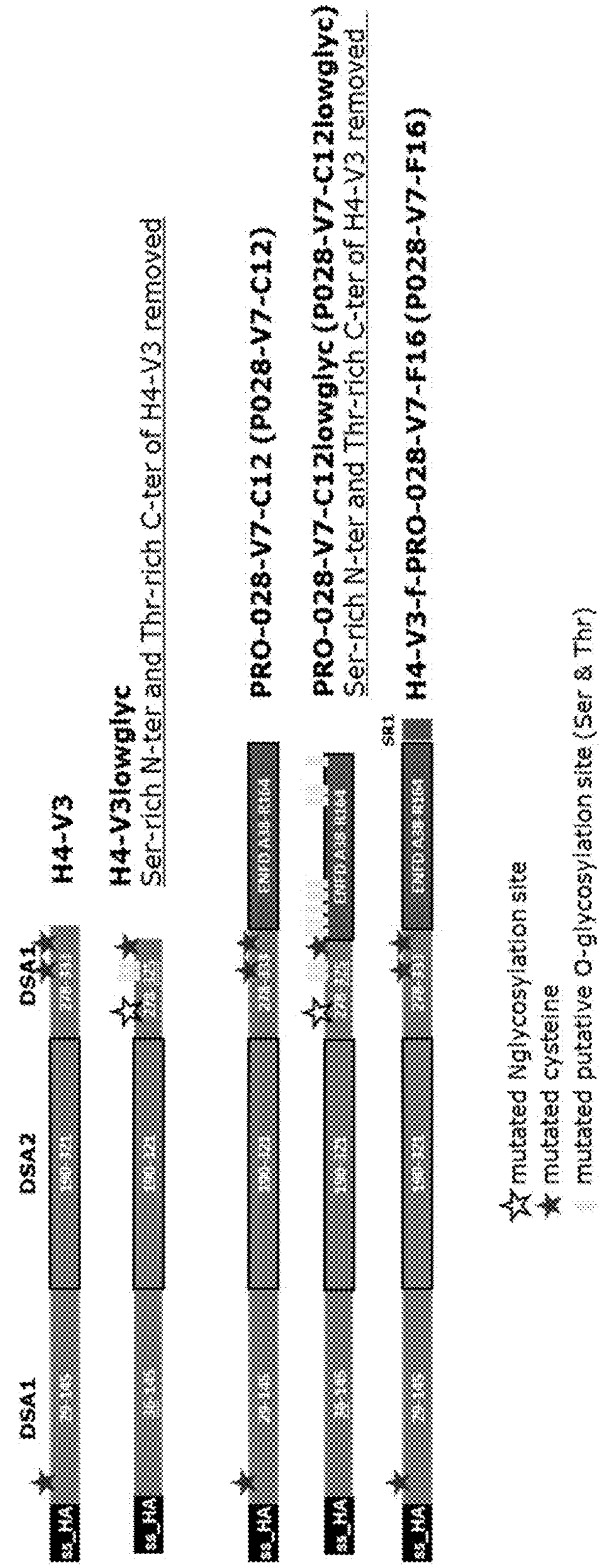
FIG. 31 shows a schematic visualization of mRNA constructs coding for chimera proteins that have been designed and synthesized.

FIG. 31 shows the mRNA constructs coding for chimera proteins that have been designed and synthesized:

Two constructs comprised either an unmutated H4-V3 sequence (SEQ ID NO: 113) or a modified H4-V3 sequence: H4-V3-lowglyc (SEQ ID NO: 123). The latter one was designed to get the lowest probability of glycosylation. H4-V3-lowglyc comprises H4-V3 sequence where the first 7 residues on the N-terminus were deleted. This modified sequence comprised a mutated N-glycosylation site, a truncation of the C-terminal PT-repeat to one copy only, and two additional mutations: S291M and S292G. Western-Blot showed that proteins expressed by HEK cells transfected with H4-V3-lowglyc construct displayed lower molecular weight than H4-V3 indicating that sequence modifications were effective to reduce the level of protein glycosylation.

Three other constructs were designed encoding a triple chimera: Fragments of P028-V7 were fused to H4-V3: either fragment P028-V7-C12 corresponding to ENFD domain (resulting in the chimera of amino acid sequence according to SEQ ID NO: SEQ ID NO: 41) or fragment P028-V7-F16 comprising ENFD domain and part of SR1 domain (resulting in the chimera of amino acid sequence according to SEQ ID NO: SEQ ID NO: 38) (see FIG. 20 for schematic visualization of P028 domains). For the triple chimera comprising P028-V7-C12 (the triple chimera has an amino acid sequence corresponding to SEQ ID NO: 41), a counterpart triple chimera construct was designed to get the lowest probability of glycosylation: P028-V7-C12lowglyc (SEQ ID NO: 40). This construct comprised H4-V3-lowglyc, and a GGGGG flexible linker (instead of a PT-repeat) connected to a mutated form of fragment P028-V7-C12. Three of five possible O-glycosylation sites of P028-V7-C12 were mutated to Glycine (Gly). Fragment P028-V7-C12 lacks predicted N-glycosylation sites. Western-Blot showed that proteins expressed by HEK cells transfected with P028-V7-C12lowglyc construct displayed lower molecular weight than P028-V7-C12 indicating that sequence modifications were effective to reduce the level of protein glycosylation.

All these constructs comprised the signal sequence of Influenza Hemagglutinin (HA. HINI A/Caledonia/20/1999) (HA SS) at N-ter to address the protein for secretion.

All sequences were derived from the protein sequence of *C. acnes* strain KPA171202.

Chimeric *C. acnes* Antigens Elicit Antibodies which Bind the Surface of *C. acnes*

FIG. 32 shows Surface Binding (SB) titers performed on NCTC737 *C. acnes* strain, from individual sera of mice immunized twice at 4 weeks interval with the mRNA antigens described in FIG. 31 ("H4-V3" (SEQ ID NO: 113). "H4-V3-lowglyc" (SEQ ID NO: 123). "P028-V7-F16" (SEQ ID NO: 122). "P028-V7-C12" (SEQ ID NO: 125) and "P028-V7-C12lowglyc" (SEQ ID NO: 124)) and with the mRNA constructs coding for P028-V7 (SEQ ID NO: 115). These mRNA constructs were encapsulated in the LNP GL-HEPES-E3-E12-DS-4-E10. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg and 5 μg per dose. P028-V7 construct elicited significantly lower SB titer than all others, which induced comparable SB titers at 5 μg dose. At 1 μg dose H4-V3 and H4-V3-lowglyc mRNA induced comparable SB titers which were significantly higher that the triple chimera.

Figure 33:
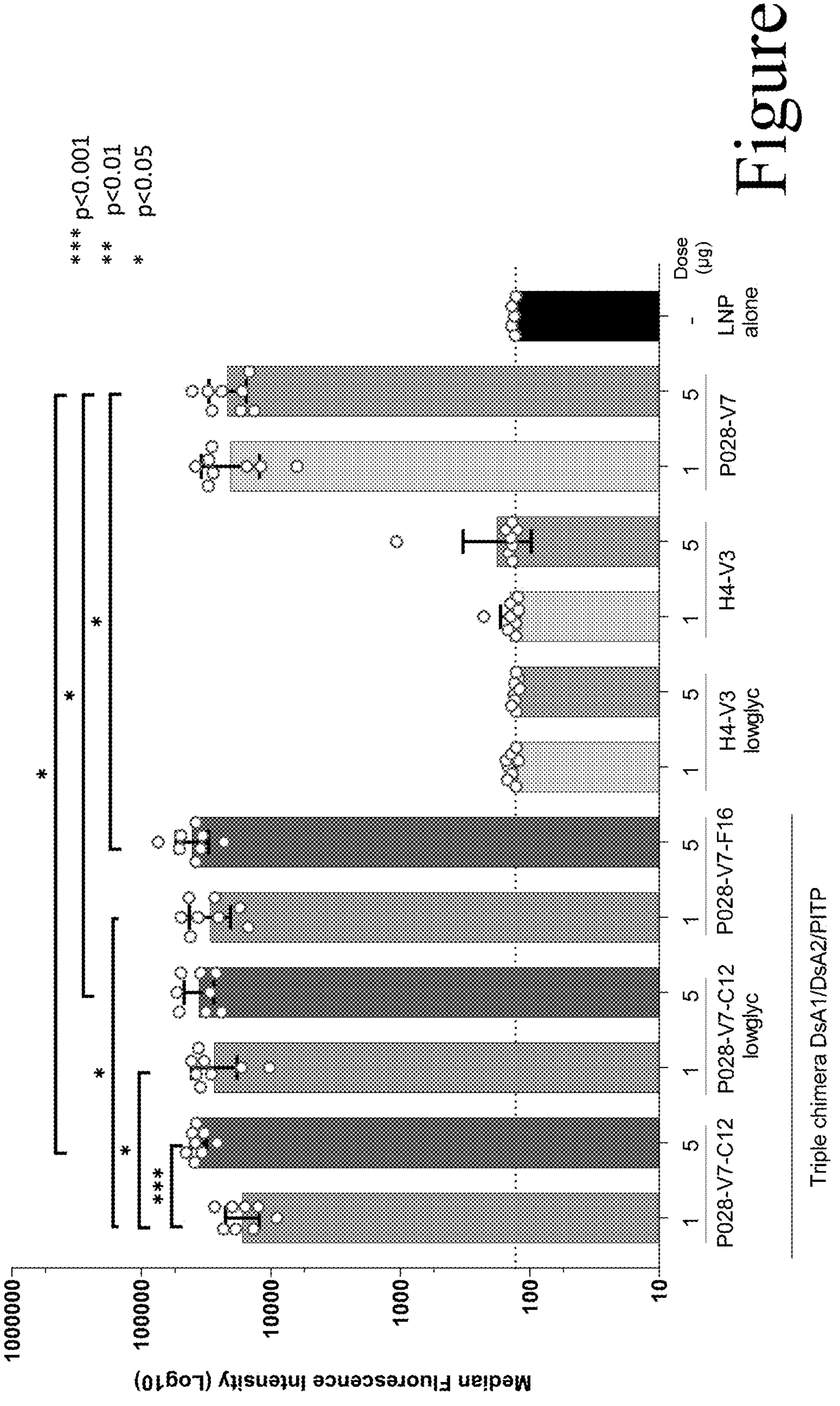
FIG. 33 shows Surface Binding (SB) titers performed on KPA171202 *C. acnes* strain, from individual sera of mice immunized twice at 4 weeks interval with the same mRNA antigens as described in FIG. 32, and encapsulated in the same LNP. The sera were obtained at day 42 following the first immunization. LNP alone was used as negative control, mRNA synthesis was performed using modified nucleotides. The mRNA content in tested formulation was of 1 μg and 5 μg per dose.

FIG. 33 shows Surface Binding (SB) titers performed on KPA171202 *C. acnes* strain, from individual sera of mice immunized twice at 4 weeks interval with the same mRNA antigens as described in FIG. 31, and encapsulated in the same LNP. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg and 5 μg per dose. All triple chimera constructs were superior to P028-V7 construct at 5 μg mRNA dose. No significant difference could be observed between all triple chimera at 5 μg dose. At lug dose mRNA SB titers were comparable between P028-V7-C12lowglyc and P028-V7-F16, which were significant superior to P028-V7-C12.

Evaluation of Mice after Immunisation with Chimeric *C. acnes* Antigens

The weight gain with time and the percentage of mice exhibiting swelling at injection site of mice immunized twice at 4 weeks interval with the same mRNA antigens as described in FIG. 31, and encapsulated in the same LNP, was measured. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg and 5 μg per dose. Limited and transient local swelling was observed at the site of injection and no swelling observed after the second injection. Regular weight gain was monitored over the study period for all experimental groups (hence no local reaction and no impact on body weight).

Figure 34A:
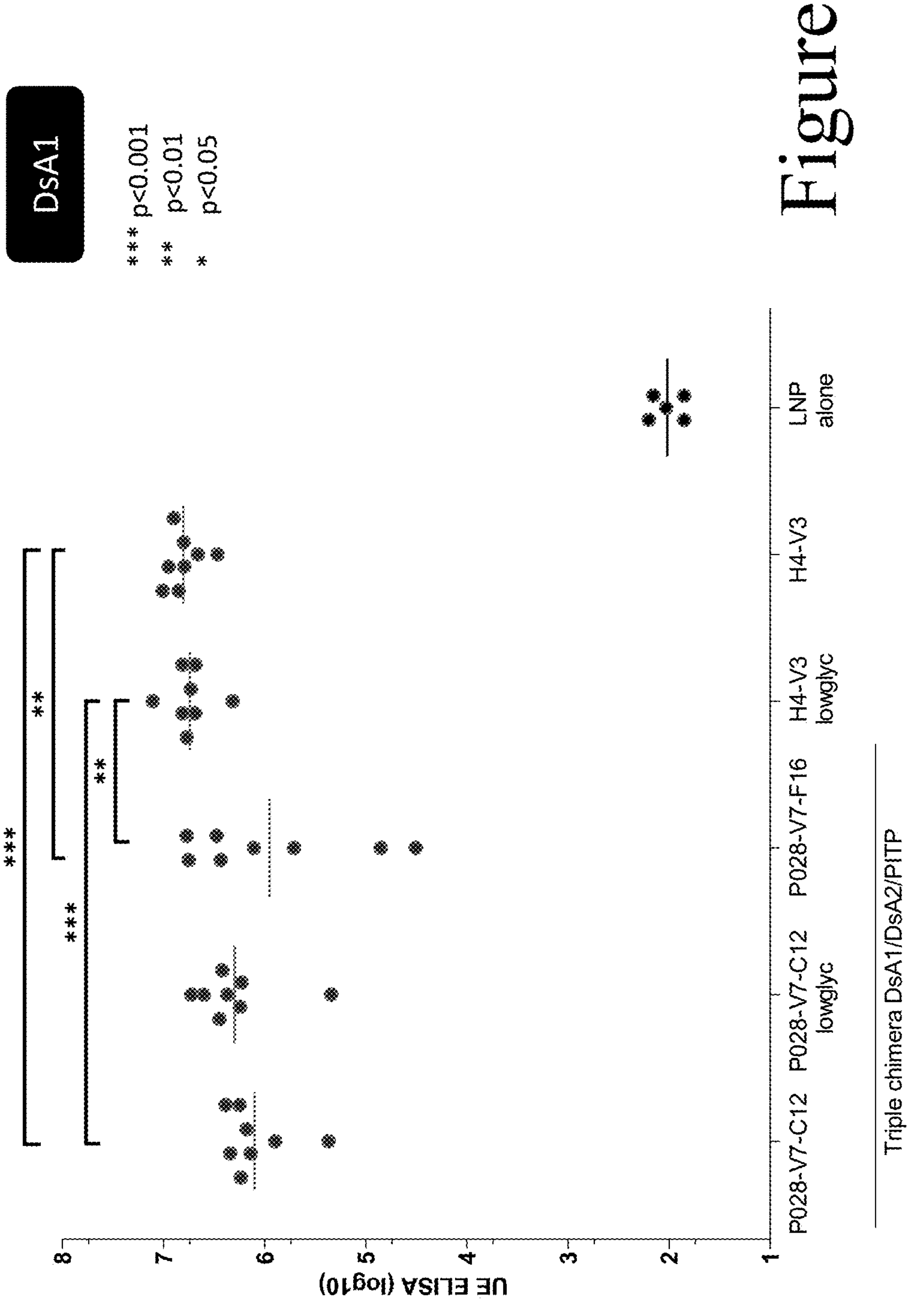
FIGS. 34A-34C show ELISA IgG anti-DSA1 (FIG. 34*a*), anti-DSA2 (FIG. 34*b*) and anti-PITP (FIG. 34*c*) titers from individual sera of mice immunized twice at 4 weeks interval with the same mRNA antigens as described in FIG. 32 and encapsulated in the same LNPs. The sera were obtained at day 42 following the first immunization. LNP alone was used as negative control, mRNA synthesis was performed using modified nucleotides. The mRNA content in tested formulation was of 1 μg per dose.
Figure 34B:
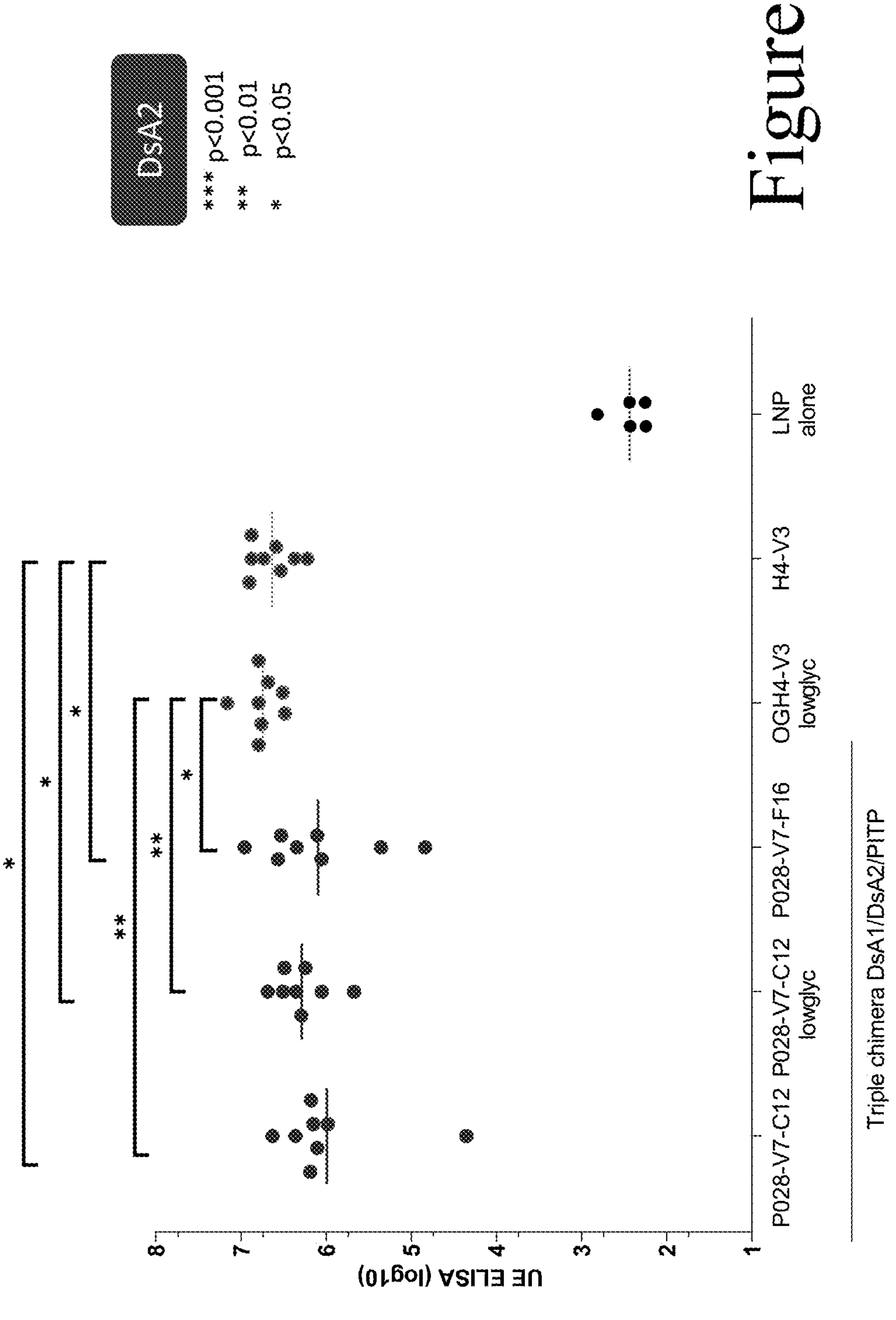
Figure 34C:
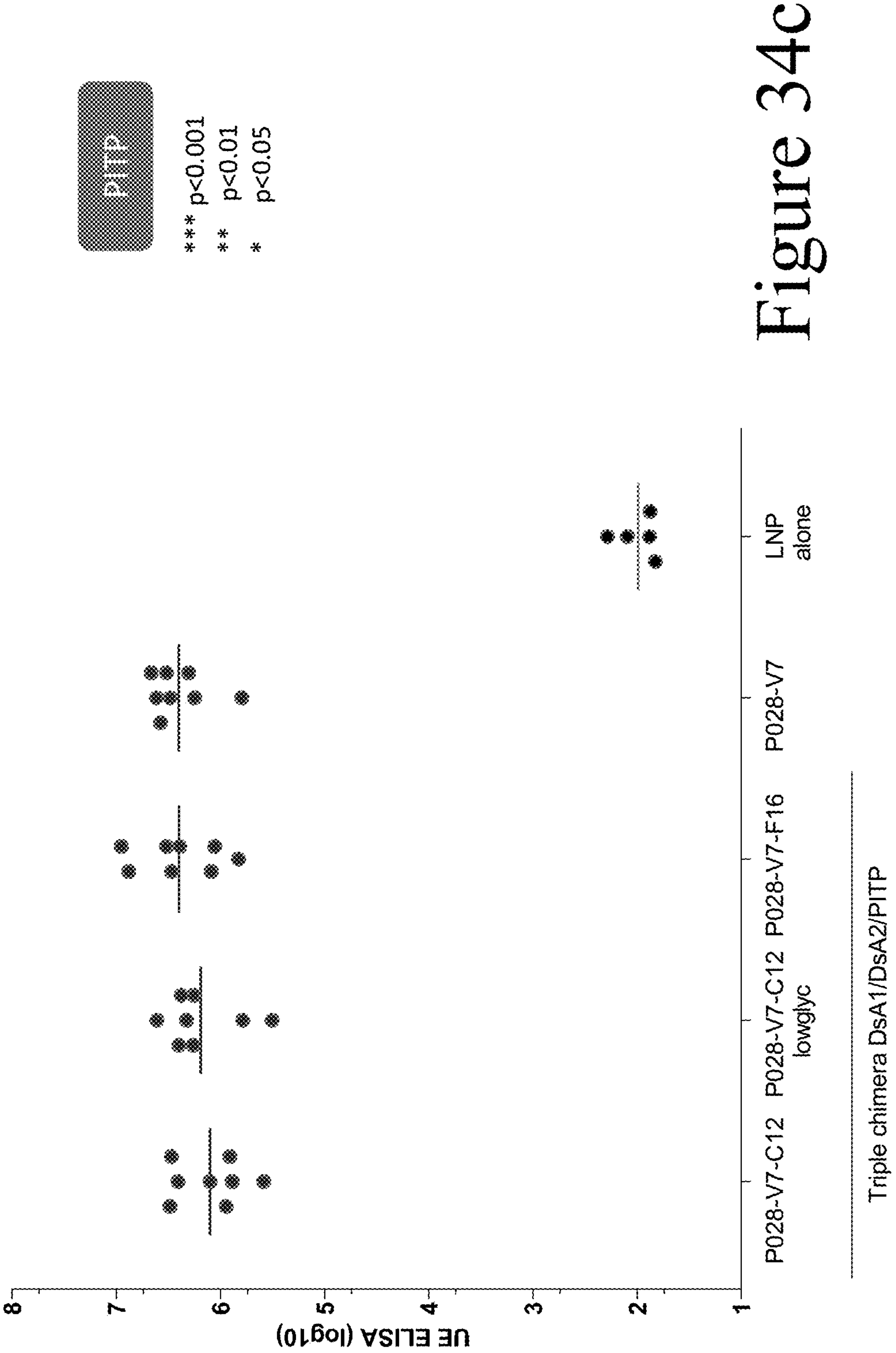

Chimeric *C. acnes* Antigens Elicit Antibodies which Give Rise to an Anti-DsA1, -DsA2 and -PITP IgG Response FIGS. 34A-34C show ELISA IgG anti-DsA1, -DsA2 and -PITP titers from individual sera of mice immunized twice at 4 weeks interval with the same mRNA antigens as described in FIG. 31 and encapsulated in the same LNPs. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg per dose. The triple chimeras induced lower ELISA IgG anti-DsA1 and -DsA2 titers than the two double chimera H4-V3 and H4-V3-lowglyc. These two double chimeras induced comparable titers. The triple chimeras induced comparable ELISA IgG anti-PITP titers relative to the P028-V7.

Figure 35A:
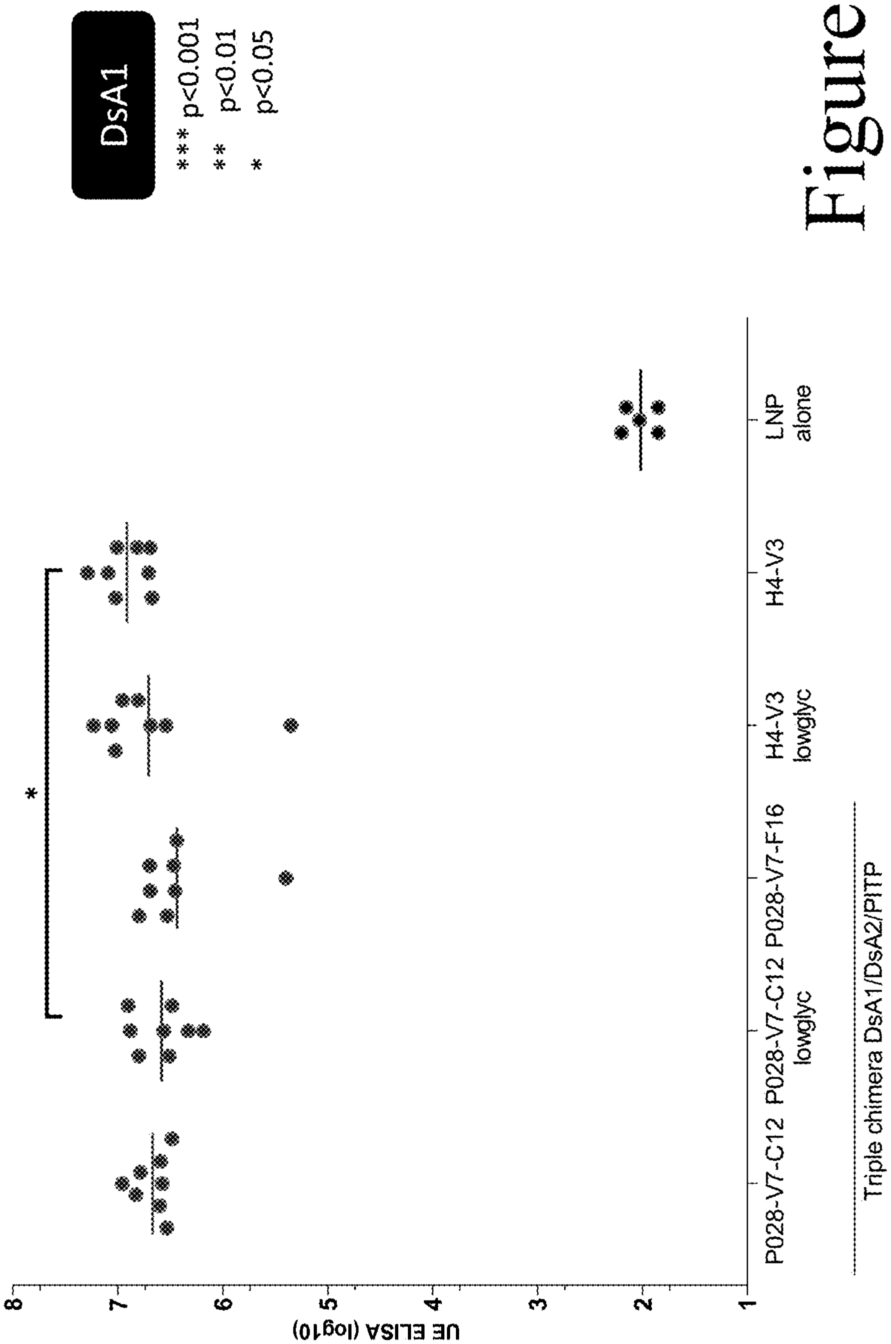
FIGS. 35A-35C show ELISA IgG anti-DSA1 (FIG. 35*a*), anti-DSA2 (FIG. 35*b*) and anti-PITP (FIG. 35*c*) titers from individual sera of mice immunized twice at 4 weeks interval with the same mRNA antigens as described in FIG. 32 and encapsulated in the same LNPs. The sera were obtained at day 42 following the first immunization. LNP alone was used as negative control, mRNA synthesis was performed using modified nucleotides. The mRNA content in tested formulation was of 5 μg per dose.
Figure 35B:
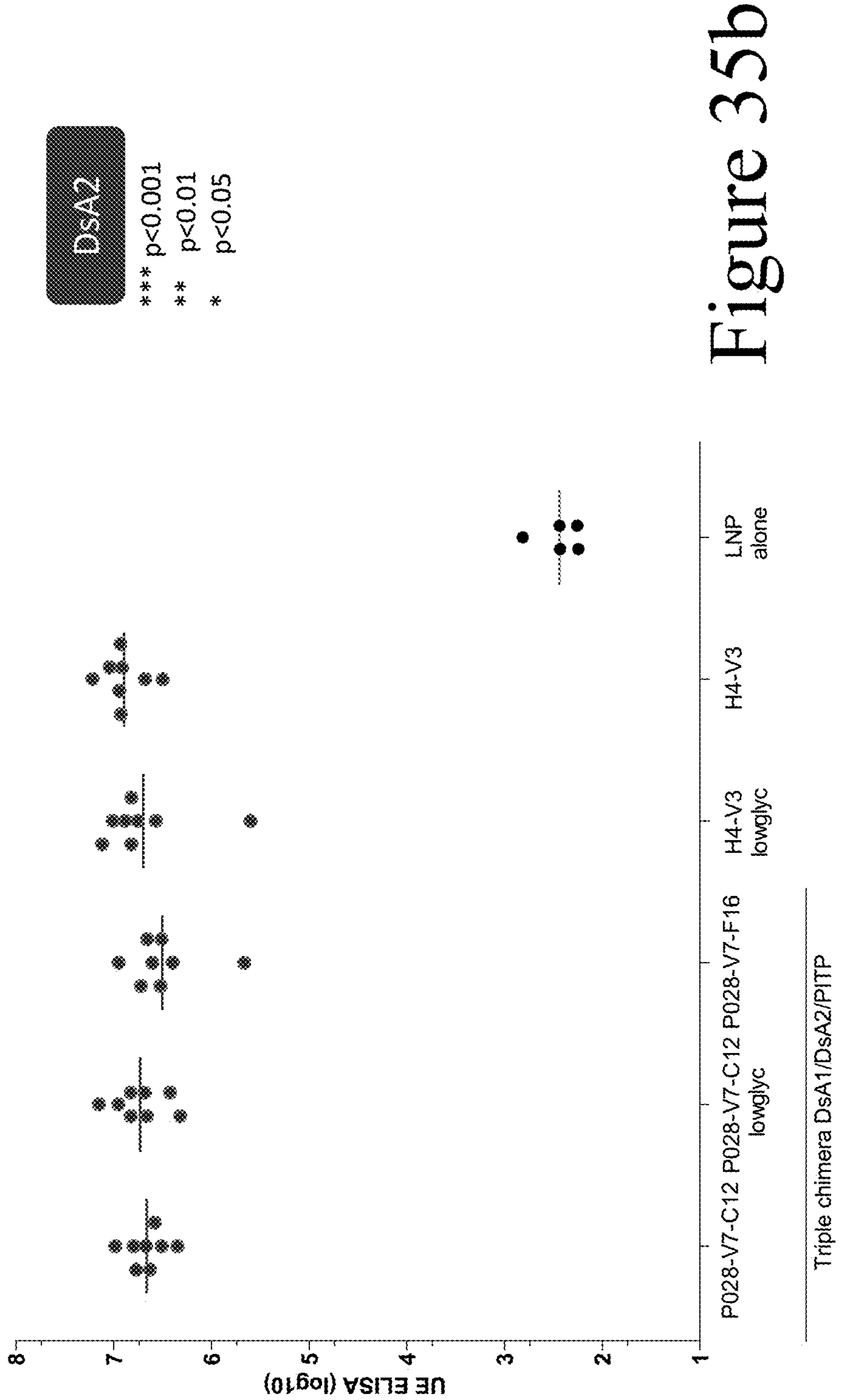
Figure 35C:
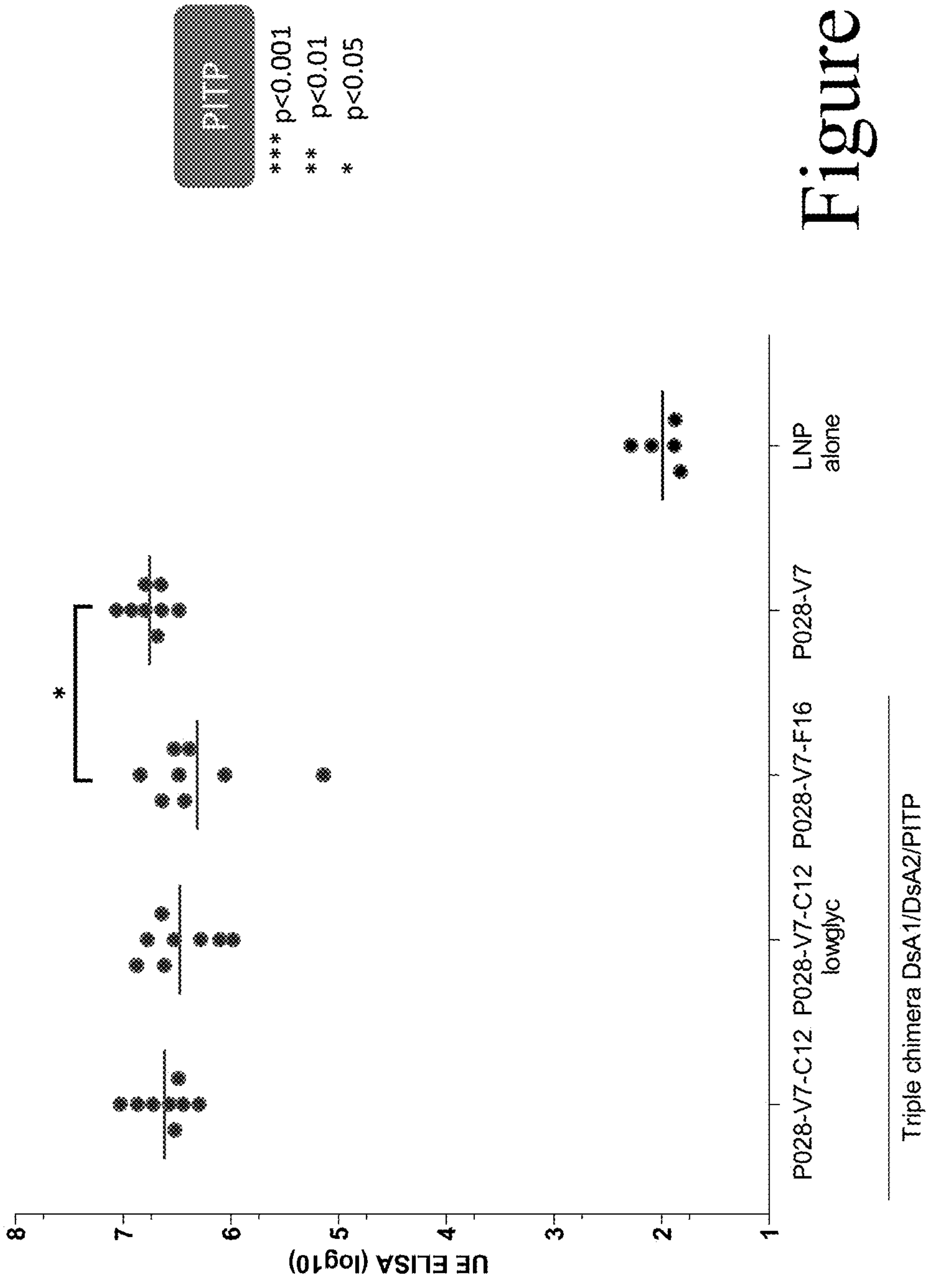

FIGS. 35A-35C show ELISA IgG anti-DSA1, -DSA2 and -PITP titers from individual sera of mice immunized twice at 4 weeks interval with the same mRNA antigens as described in FIG. 31 and encapsulated in the same LNPs. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 5 μg per dose. All mRNA constructs elicited comparable ELISA IgG anti-DsA1 and -DsA2 titers with exception of H4-V3 mRNA construct which elicited superior response to P028-V7-C12lowglyc one. All mRNA constructs elicited comparable ELISA IgG anti-PITP titers with exception of P028-V7 mRNA construct which elicited superior response to P028-V7-F16 one.

Figure 36:
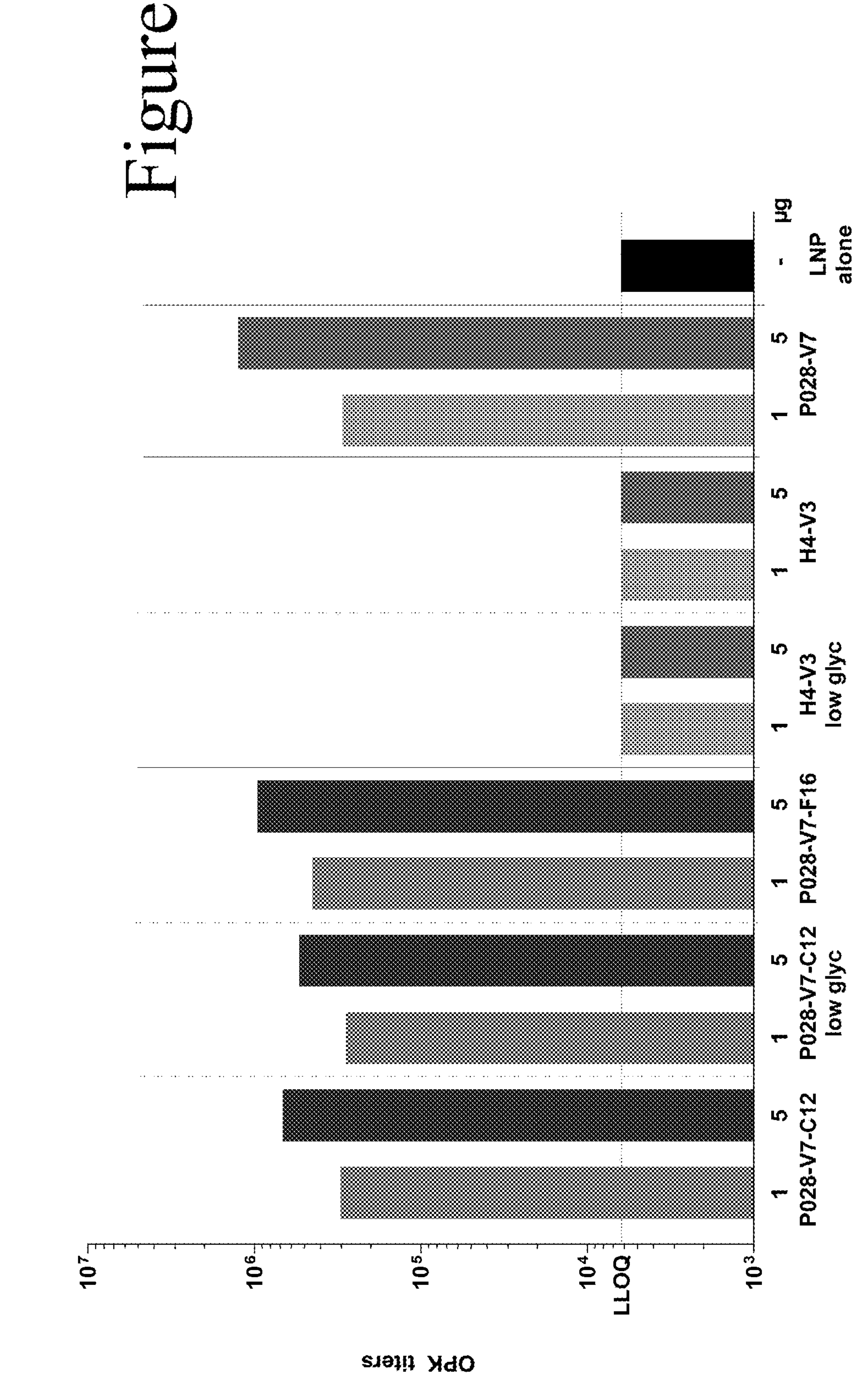
FIG. 36 shows Opsonophagocytic Killing (OPK) titers performed on KPA171202 *C. acnes* strain, from serum pools of mice immunized twice at 4 weeks interval with the same mRNA antigens as described in FIG. 32, and encapsulated in the same LNP. The sera were obtained at day 42 following the first immunization. LNP alone was used as negative control, mRNA synthesis was performed using modified nucleotides. The mRNA content in tested formulation was of 1 μg and 5 μg per dose. Results illustrate the means of 2 independent experiments. LLOQ=lowest limit of quantification.

Chimeric *C. acnes* Antigens Elicit Antibodies which have Opsonophagocytic Activity FIG. 36 shows Opsonophagocytic Killing (OPK) titers performed on KPA171202 *C. acnes* strain, from serum pools of mice immunized twice at 4 weeks interval with the same mRNA antigens as described in FIG. 31, and encapsulated in the same LNP. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg and 5 μg per dose. Results illustrate the means of 2 independent experiments. At equivalent dose, tested mRNA constructs elicited comparable OPK titers.

Figure 37:
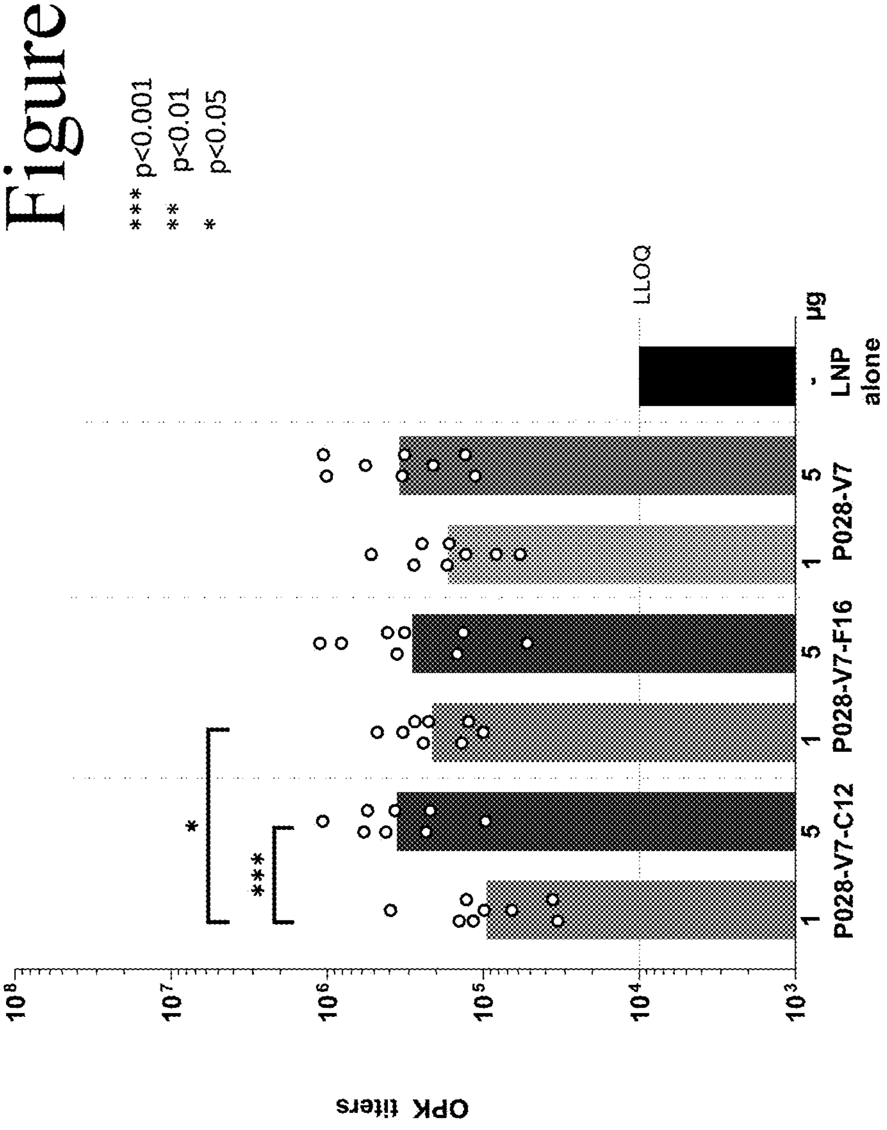
FIG. 37 shows Opsonophagocytic Killing (OPK) titers performed on KPA171202 *C. acnes* strain, from individual sera of mice immunized twice at 4 weeks interval with the same mRNA antigens as described in FIG. 32, and encapsulated in the same LNP. The graph illustrated the results for P028-V7-F16, P028-V7-C12 and P028-V7 mRNA constructs. The sera were obtained at day 42 following the first immunization. LNP alone was used as negative control, mRNA synthesis was performed using modified nucleotides. The mRNA content in tested formulation was of 1 μg and 5 μg per dose. LLOQ=lowest limit of quantification.

FIG. 37 shows Opsonophagocytic Killing (OPK) titers performed on KPA171202 *C. acnes* strain, from individual sera of mice immunized twice at 4 weeks interval with the same mRNA antigens as described in FIG. 31, and encapsulated in the same LNP. The graph illustrates the results for P028-V7-F16, P028-V7-C12 and P028-V7 mRNA constructs. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg and 5 μg per dose. At equivalent dose, tested mRNA constructs elicited comparable OPK titers.

Figure 38:
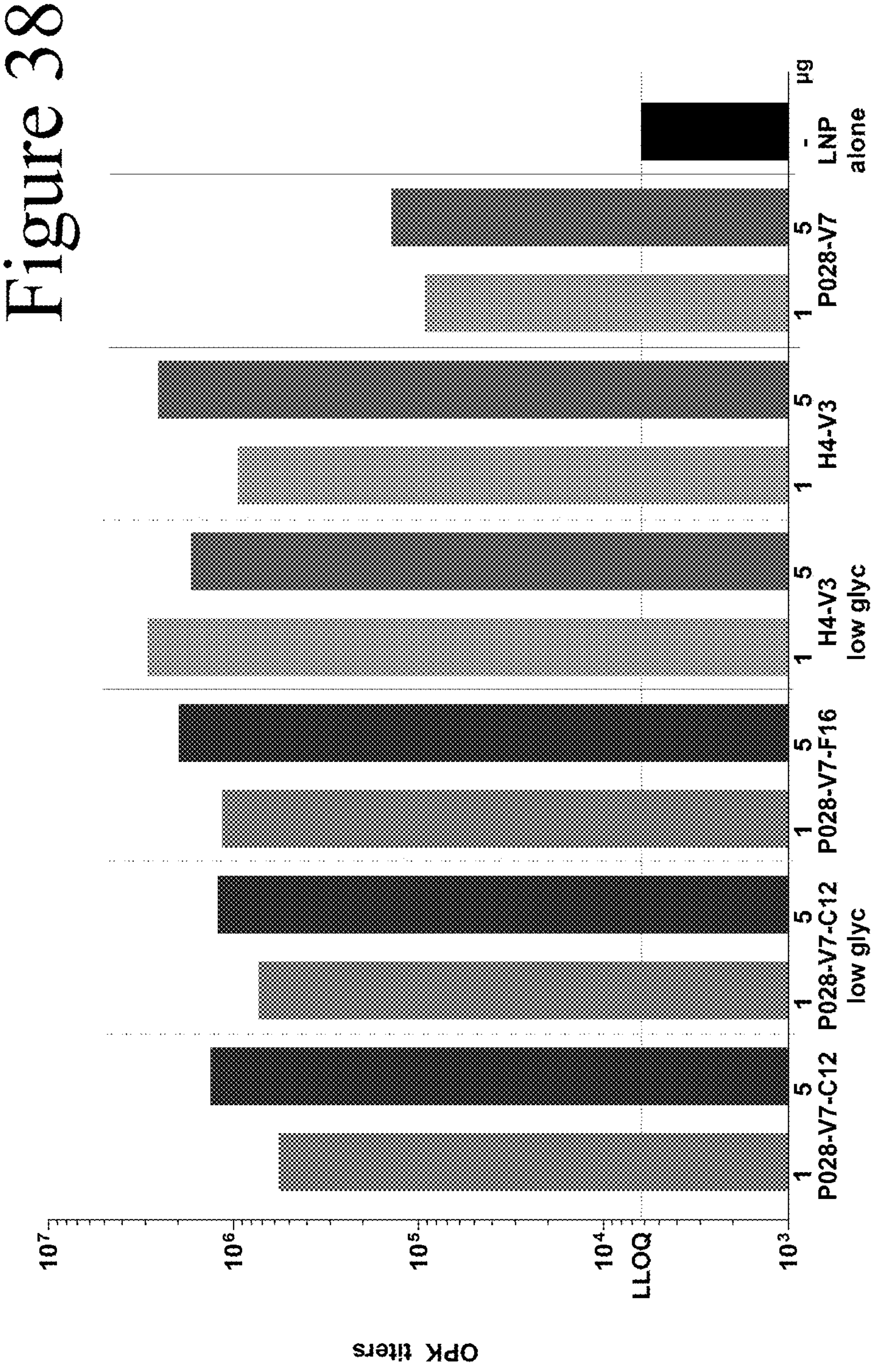
FIG. 38 shows Opsonophagocytic Killing (OPK) titers performed on NCTC737 *C. acnes* strain, from serum pools of mice immunized twice at 4 weeks interval with the same mRNA antigens as described in FIG. 32, and encapsulated in the same LNP. The sera were obtained at day 42 following the first immunization. LNP alone was used as negative control, mRNA synthesis was performed using modified nucleotides. The mRNA content in tested formulation was of 1 μg and 5 μg per dose. Results illustrate the means of 2 independent experiments. LLOQ=lowest limit of quantification.

FIG. 38 shows Opsonophagocytic Killing (OPK) titers performed on NCTC737 *C. acnes* strain, from serum pools of mice immunized twice at 4 weeks interval with the same mRNA antigens as described in FIG. 31, and encapsulated in the same LNP. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg and 5 μg per dose. Results illustrate the means of 2 independent experiments. P028-V7 construct elicited significantly lower OPK titer than all others, which induced comparable SB titers at equivalent dose with the exception of H4-V3-lowglyc mRNA construct which seem to induce higher OPK titer than other construct at 1 μg dose.

Figure 39:
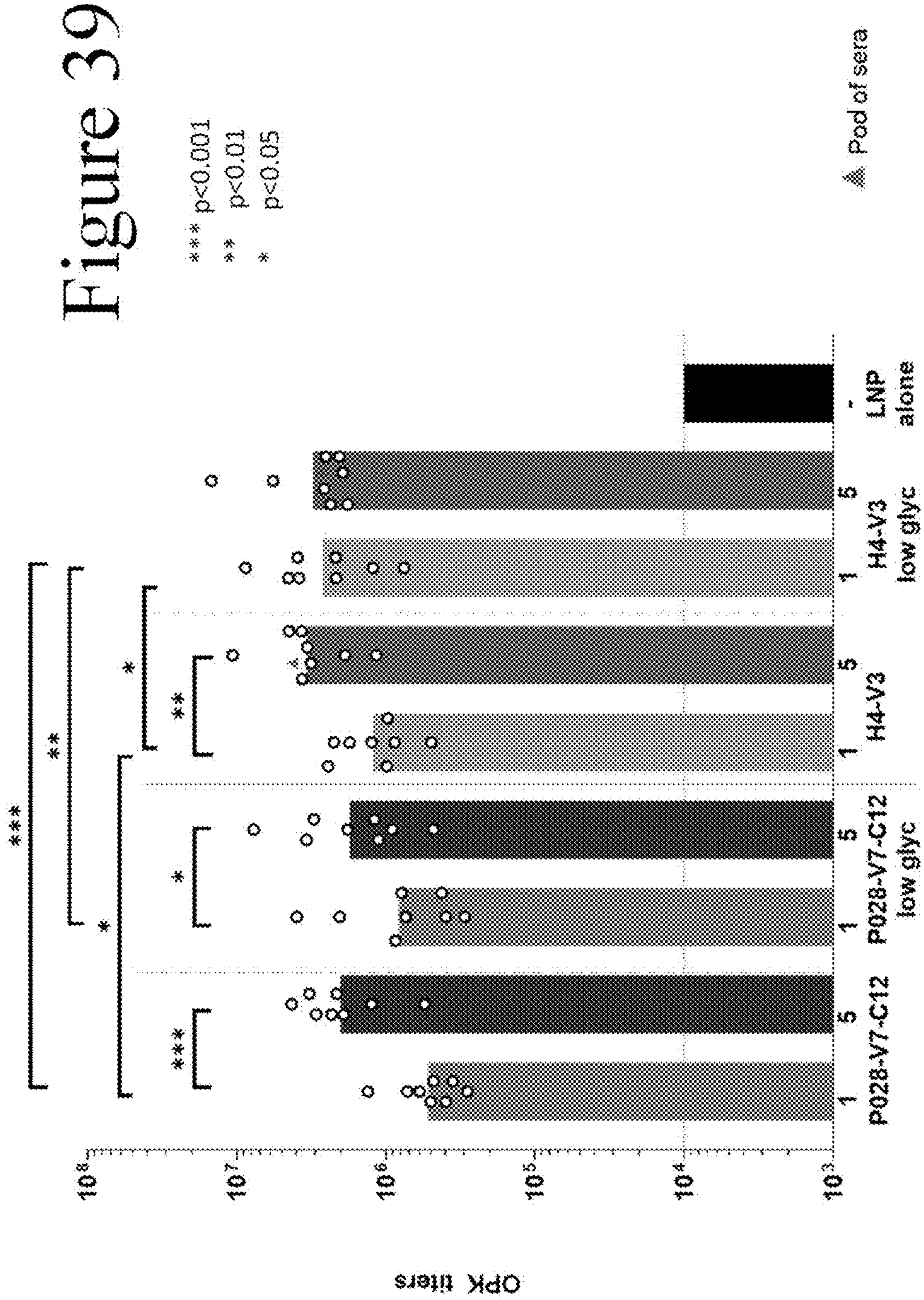
FIG. 39 shows Opsonophagocytic Killing (OPK) titers performed on NCTC737 *C. acnes* strain, from individual sera of mice immunized twice at 4 weeks interval with the same mRNA antigens as described in FIG. 32, and encapsulated in the same LNP. The graph illustrated the results for P028-V7-C12, P028-V7-C12-lowglyc, H4-V3 and H4-V3-lowglyc mRNA constructs. The sera were obtained at day 42 following the first immunization. LNP alone was used as negative control, mRNA synthesis was performed using modified nucleotides. The mRNA content in tested formulation was of 1 μg and 5 μg per dose.

FIG. 39 shows Opsonophagocytic Killing (OPK) titers performed on NCTC737 *C. acnes* strain, from individual sera of mice immunized twice at 4 weeks interval with the same mRNA antigens as described in FIG. 31, and encapsulated in the same LNP. The graph illustrated the results for P028-V7-C12, P028-V7-C12-lowglyc, H4-V3 and H4-V3-lowglyc mRNA constructs. The sera were obtained at day 42 following the first immunization. LNP alone was used as negative control, mRNA synthesis was performed using modified nucleotides (in which all uridine nucleosides were replaced with 1-methyl pseudo uridine). The mRNA content in tested formulation was of 1 μg and 5 μg per dose. At 5 μg dose, tested mRNA constructs elicited comparable OPK titers. At 1 μg dose, H4-V3-lowglyc mRNA construct elicited higher OPK titers than both P028-V7-C12 and P028-

V7-C12-lowglyc, and H4-V3 mRNA construct elicited higher OPK titers than P028-V7-C12.

Example 10—Comparison of a Chimeric *C. acnes* DsA1/DsA2/PITP mRNA Antigen Relative to a Combination of a Chimeric *C. acnes* DsA1/DsA2 mRNA Antigen and of a *C. acnes* PITP mRNA Antigen The aim of this example was to compare a 'triple chimera' formulation containing an mRNA coding for a chimeric *C. acnes* DsA1/DsA2/PITP protein (P028-V7-C12), wherein a fragment of P028-V7 corresponding to the ENFD domain, was fused to H4-V3 (as described in Example 9 and FIG. 31), relative to a 'bivalent combination' formulation containing a combination of two mRNAs, coding for the H4-V3 and P028-V7 proteins, encapsulated in a LNP, for their ability to induce a functional immune response.

Synthesis and Characterisation of the mRNAs and mRNA-LNP Formulations mRNA synthesis was performed using modified nucleotides (in which all uridine nucleosides were replaced with 1-methyl pseudo uridine). For the 'triple chimera' formulation, an mRNA of SEQ ID NO: 125 coding for the chimera protein P028-V7-C12 of SEQ ID NO: 41, was used. For the 'bivalent combination' formulation, a combination of two mRNAs of SEQ ID NO:113 and SEQ ID NO: 115, coding for the proteins H4-V3 of SEQ ID NO: 28 and P028-V7 of SEQ ID NO: 31, respectively, were used. All mRNAs comprised a cap1, a 5'UTR from CMV of SEQ ID NO: 265, a 3' UTR from hGH of SEQ ID NO: 266, and a poly A tail, and were encapsulated in a LNP containing GL-HEPES-E3-E12-DS-4-E10 as cationic lipid, as described previously. For the 'bivalent combination' formulation, the two mRNAs were co-encapsulated in the LNP.

With respect to mRNA size, tail size, % of tailed population and cap1%, all mRNAs met the targeted specifications. Sequencing analyses confirmed that the expected mRNA sequences were generated. With respect to LNP size and % of encapsulation (% EE), all LNPs fell into the expected size range (between 50 and 150 nm) and the targeted % EE (superior to 80%).

Mouse Immunisations

OF-1 outbred mice (6-week old at day 0) were immunised with the 'triple chimera' formulation (at doses ranging between 0.04 μg and 5 μg of mRNA: 8 mice per group) or with the 'bivalent combination' formulation (at doses ranging between 0.04 μg and 5 μg for each of the two mRNAs: 8 mice per group), twice. 4 weeks apart (i.e. at day 0 and day 28), through intra-muscular (IM) route (50 μL in quadriceps muscle hind leg, with alternance of the right and left leg between both injections). LNP alone (5 mice per group) was used as negative control. A final bleeding was performed 14 days after the last immunisation (i.e. at day 42 following the first immunisation), and the sera obtained were tested in a total IgG ELISA assay (as described in Example 1), in a Surface Binding assay (as described in Example 1) and/or in an OPK assay (as described in Example 1).

Immunised mice of each experimental group were clinically monitored for local signs, over the study period. There was no impact of the immunisations on body weight or on body temperature. Only a very limited and transient local swelling at the site of injection was observed, with no other clinical reaction.

Figure 40A:
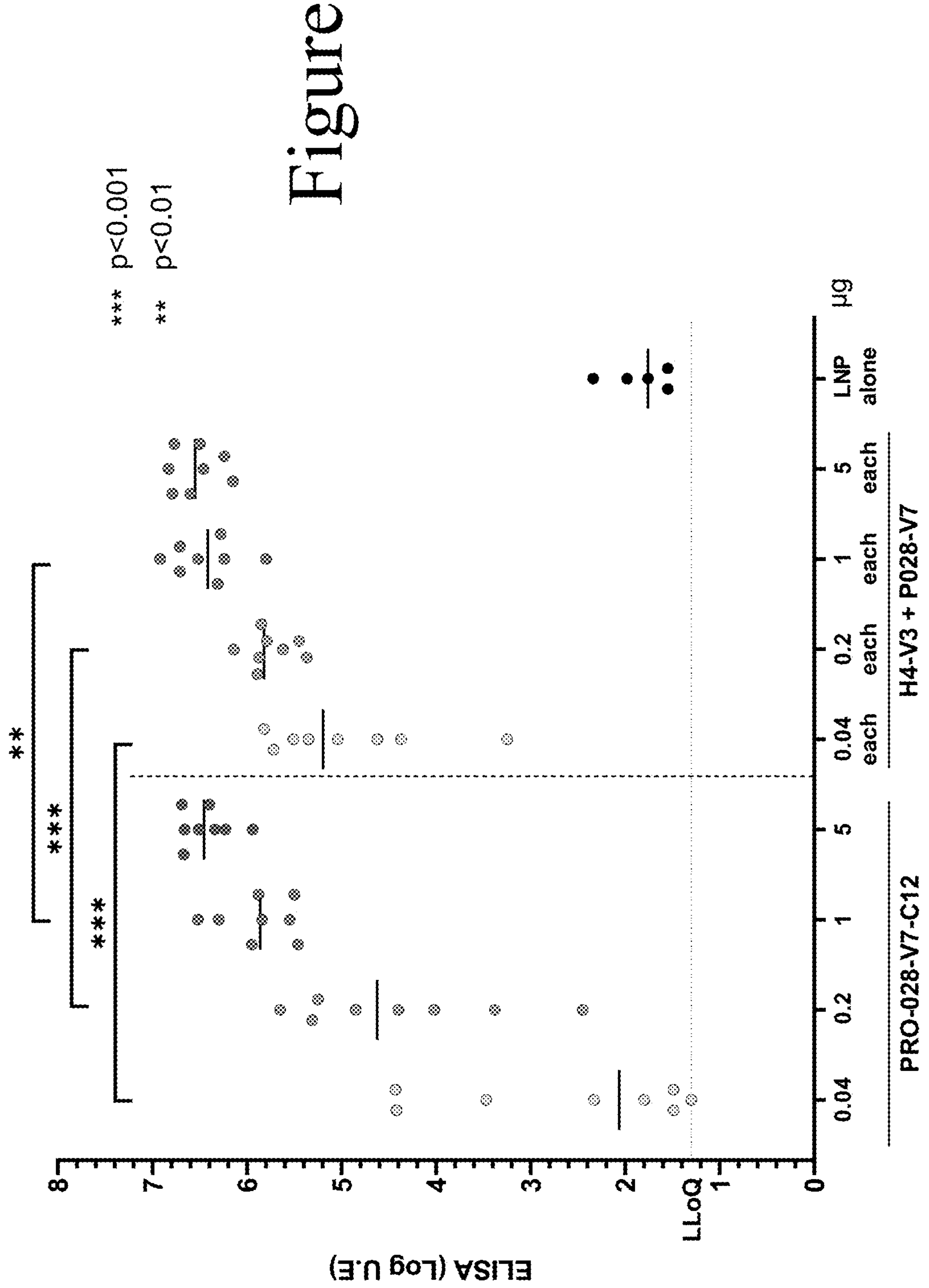
FIGS. 40A-40C show ELISA anti-DsA1 (FIG. 40*a*), anti-DsA2 (FIG. 40*b*) and anti-PITP (FIG. 40*c*) IgG titers of individual sera (day 42) of mice immunised twice at 4 weeks interval with an mRNA construct encoding a chimeric DsA1/DsA2/PITP protein or a combination of two mRNAs encoding H4-V3 and P028-V7 proteins, respectively, at various doses, and encapsulated in a LNP containing GL-HEPES-E3-E12-DS-4-E10 as cationic lipid. LNP alone served as a negative control. LLoQ=lowest limit of quantification.
Figure 40B:
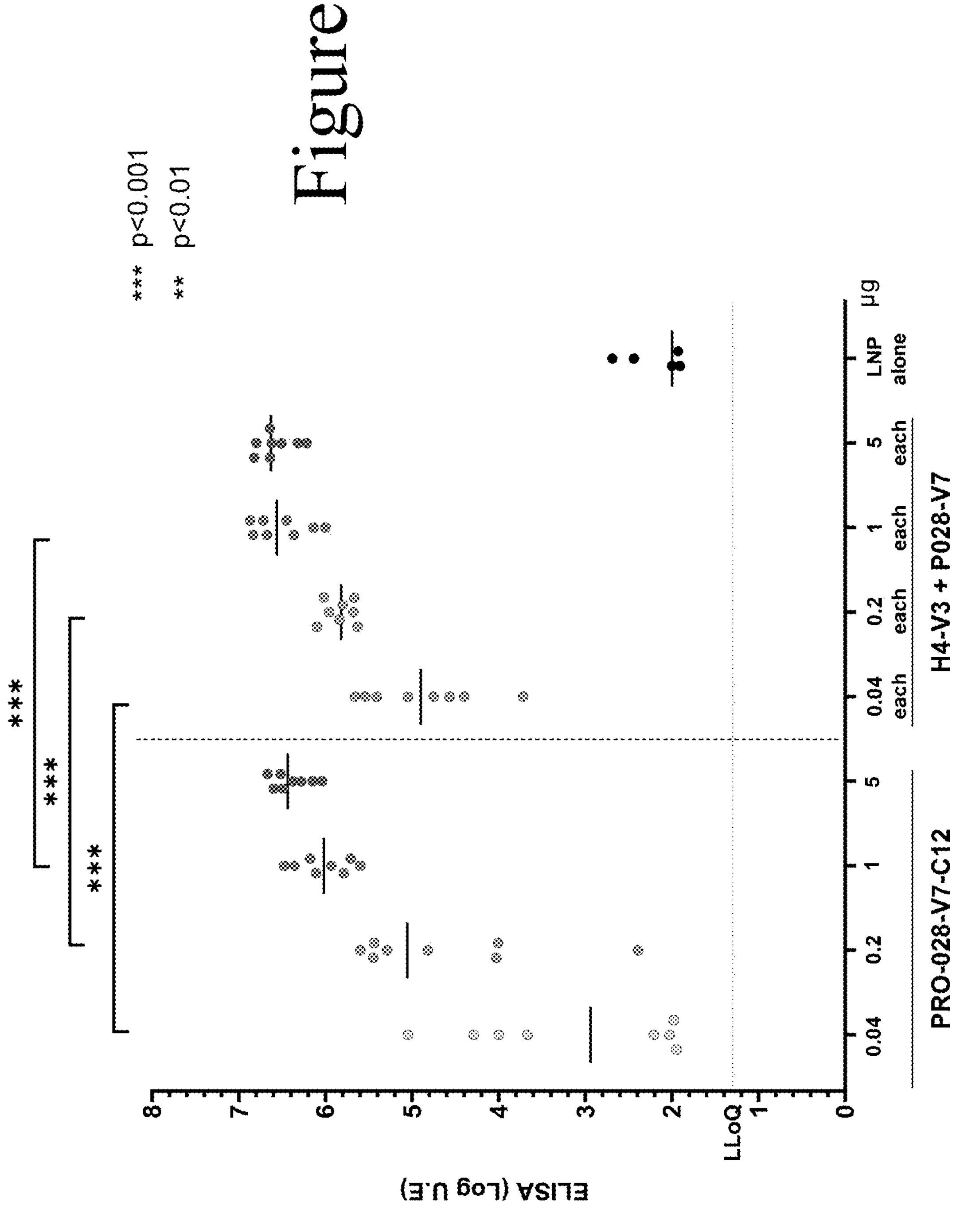
Figure 40C:
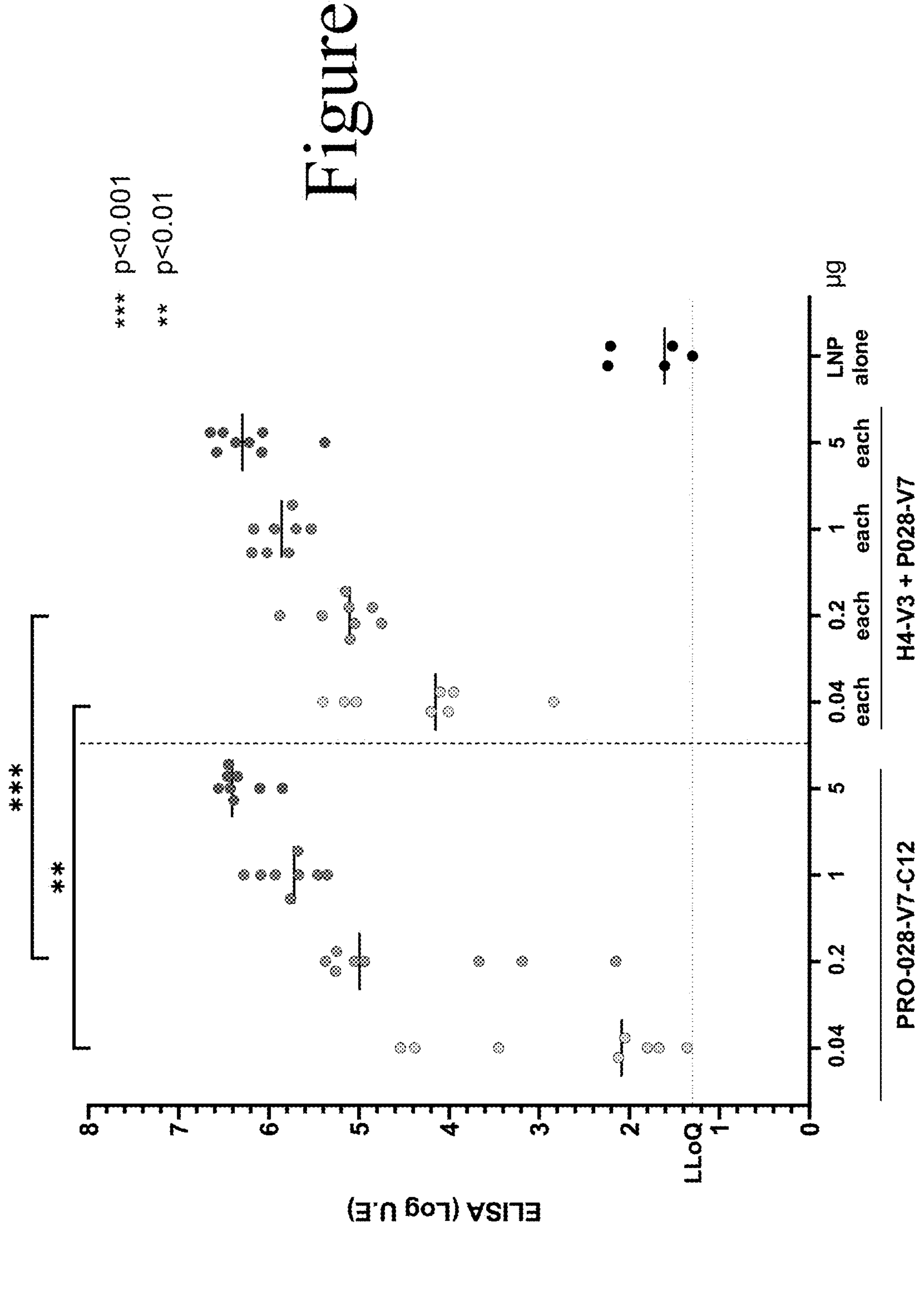

Chimeric *C. acnes* DsA1 DsA2 PITP mRNA Antigen and a Combination of a Chimeric *C. acnes* DsA1 DsA2 mRNA Antigen and a PITP mRNA Antigen Elicit Anti-DsA1, Anti-DsA2 and Anti-PITP IgG Responses Both the 'triple chimera' formulation and the 'bivalent combination' formulation elicited anti-DsA1, anti-DsA2 and anti-PITP IgG titers, as measured with an ELISA assay and as shown in FIGS. 40A-40C. At low doses, the 'triple chimera' formulation induced lower IgG titers than the 'bivalent combination' formulation. A significant dose effect was observed for both formulations. At optimal doses, the 'triple chimera' formulation induced similar IgG titers as the 'bivalent combination formulation.

Chimeric *C. acnes* DsA1 DsA2 PITP mRNA Antigen and a Combination of a Chimeric *C. acnes* DsA1 DsA2 mRNA Antigen and a PITP mRNA Antigen Elicit Antibodies which Bind to the Surface of *C. acnes*

Figure 41A:
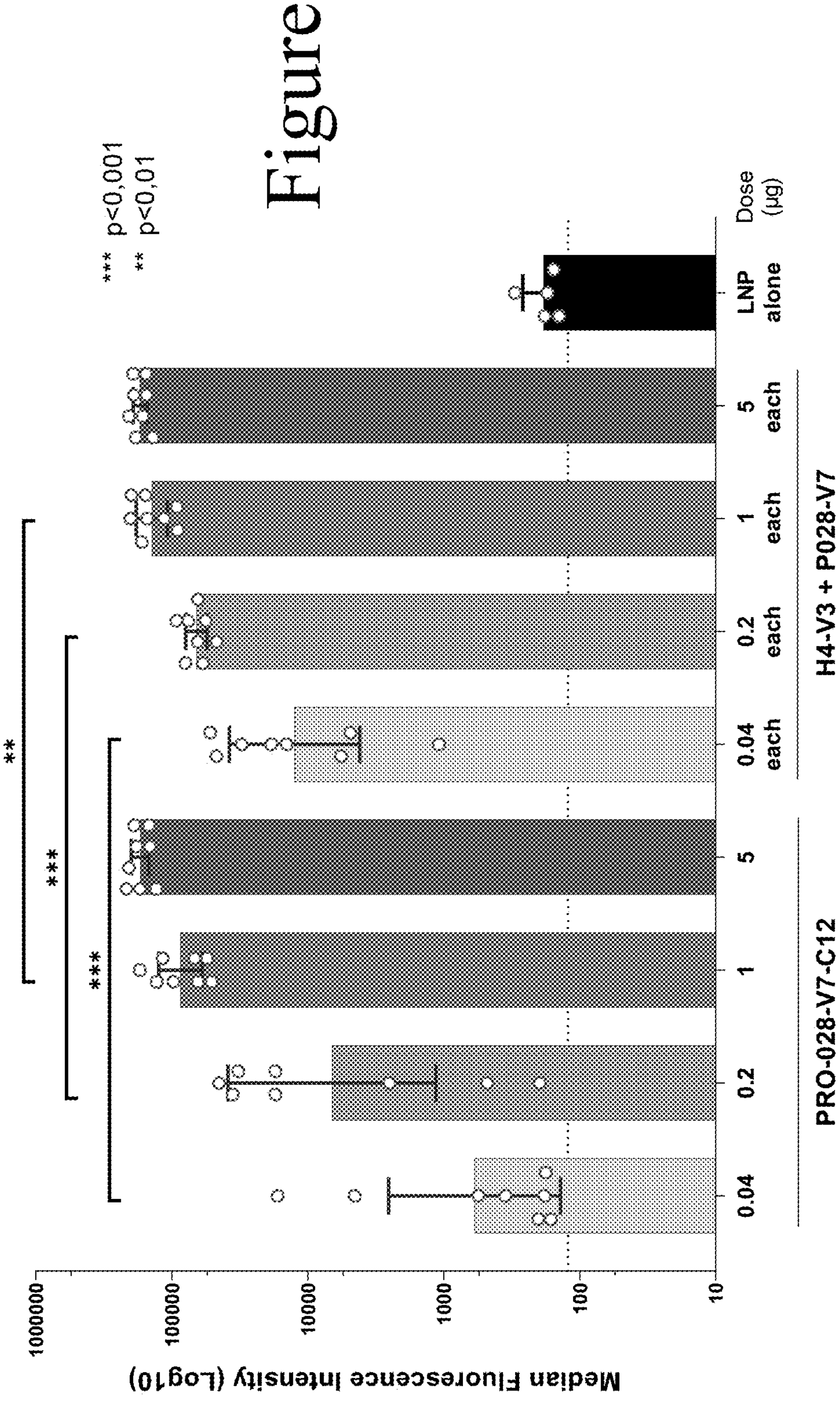
FIGS. 41A-41B show Surface Binding (SB) titers from individual sera (day 42) of mice immunised twice at 4 weeks interval with the same mRNA antigens as described in FIGS. 40A-40C and encapsulated in the same LNP. LNP alone served as a negative control. The SB assay was performed on NCTC737 *C. acnes* strain (FIG. 41*a*) or KPA171202 *C. acnes* strain (FIG. 41*b*).
Figure 41B:
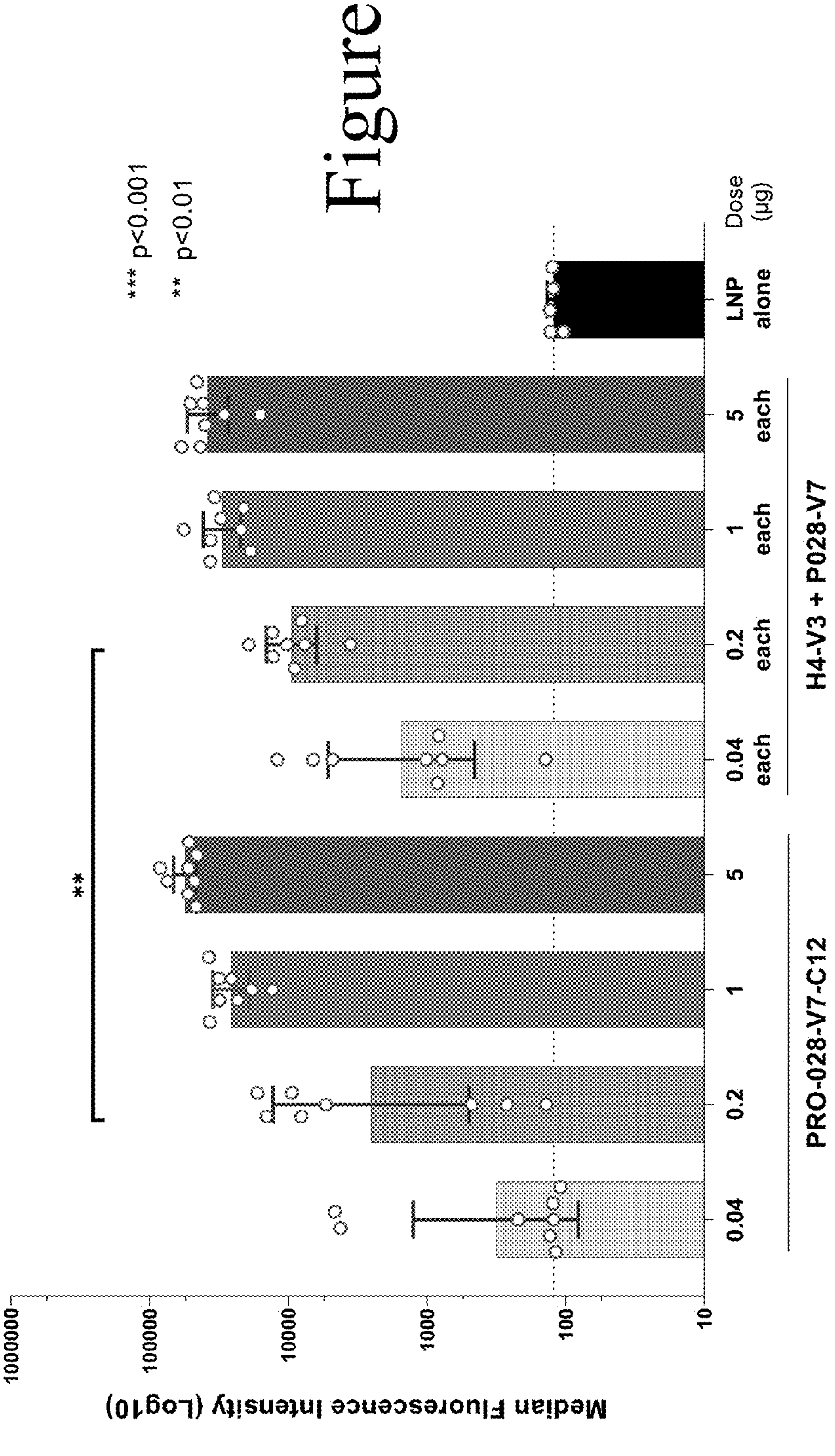

Both the 'triple chimera' formulation and the 'bivalent combination' formulation elicited SB titers, as measured with a Surface Binding (SB) assay and as shown in FIGS. 41A-41B. At low doses, the 'triple chimera' formulation induced lower SB titers than the 'bivalent combination' formulation. A significant dose effect was observed for both formulations. At optimal doses, the 'triple chimera' formulation induced similar SB titers as the 'bivalent combination' formulation.

Figure 42A:
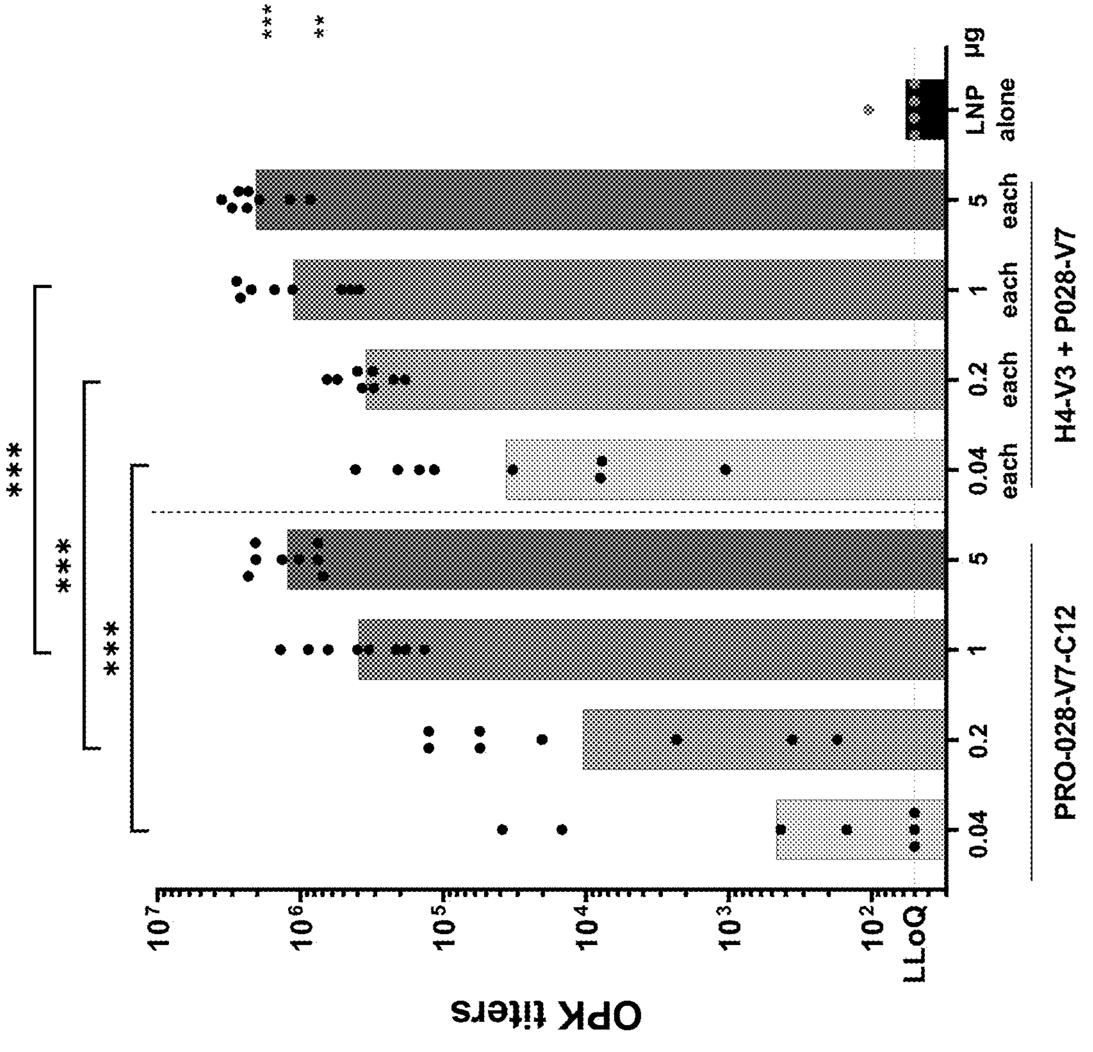
FIGS. 42A-42B show Opsonophagocytic Killing (OPK) titers from individual sera (day 42) of mice immunised twice at 4 weeks interval with the same mRNA antigens as described in FIGS. 40A-40C and encapsulated in the same LNP. LNP alone served as a negative control. The OPK assay was performed on NCTC737 *C. acnes* strain (FIG. 42*a*) or KPA171202 *C. acnes* strain (FIG. 42*b*).
Figure 42B:
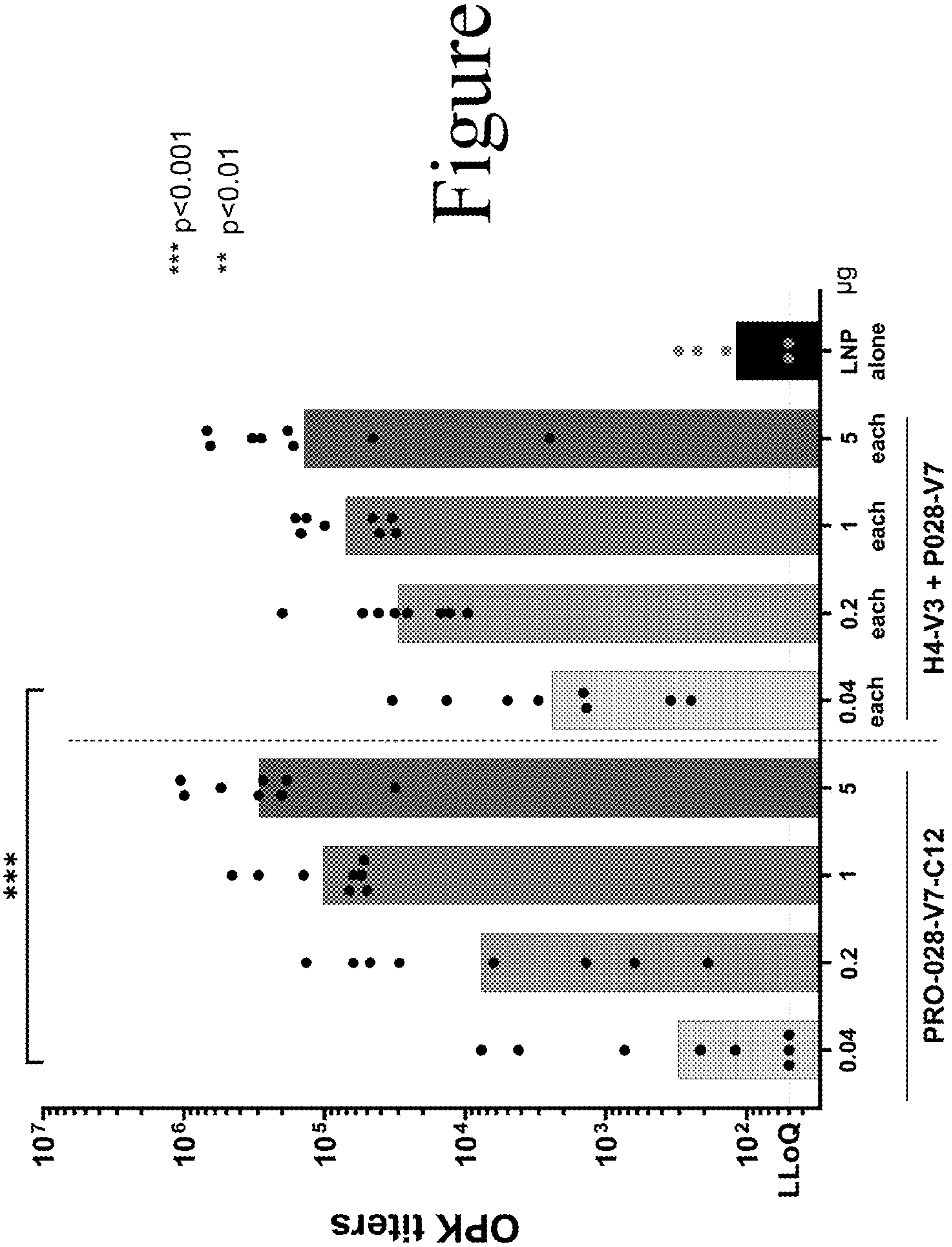
Figure 44A:
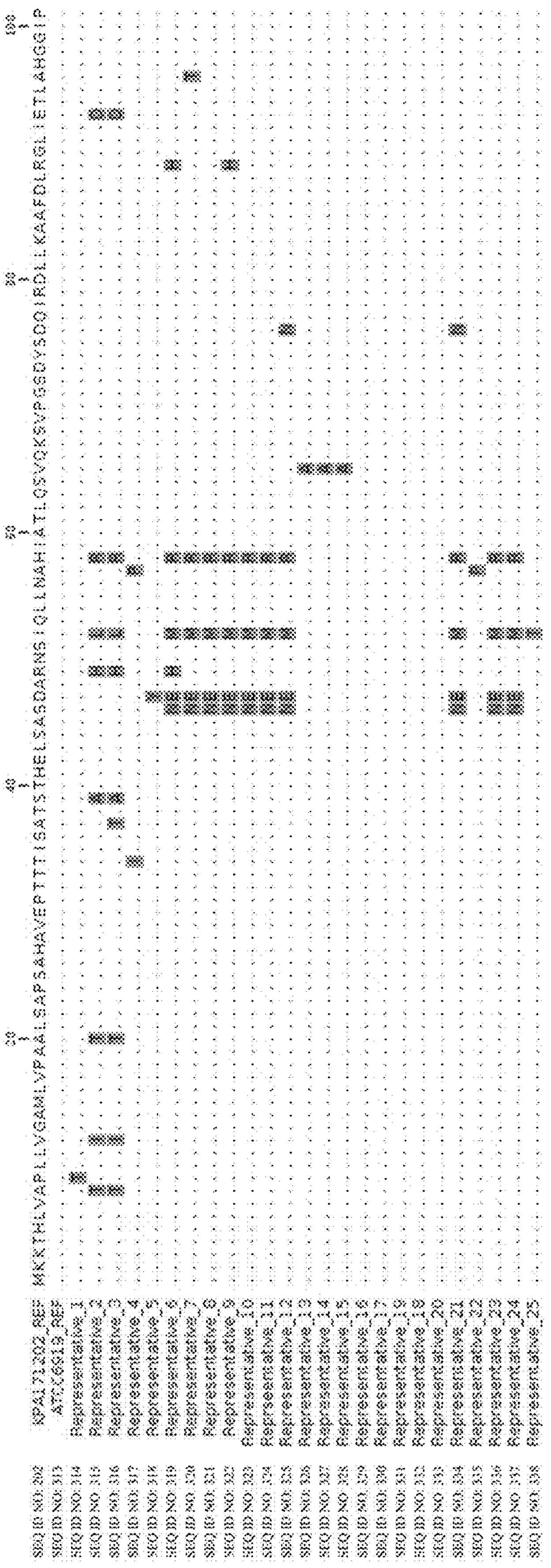
FIGS. 44A-44C show alignment of 27 different CAMP2 polypeptide sequences identified from the analysis of 430 sequences of CAMP2 from naturally occurring *C. acnes* strains (including KPA171202 and ATCC6919). Sequence variation between those CAMP2 polypeptides is concentrated at 34 residues identified across the 239 amino acid-long sequence (excluding the secretion signal peptide sequence).
Figure 44B:
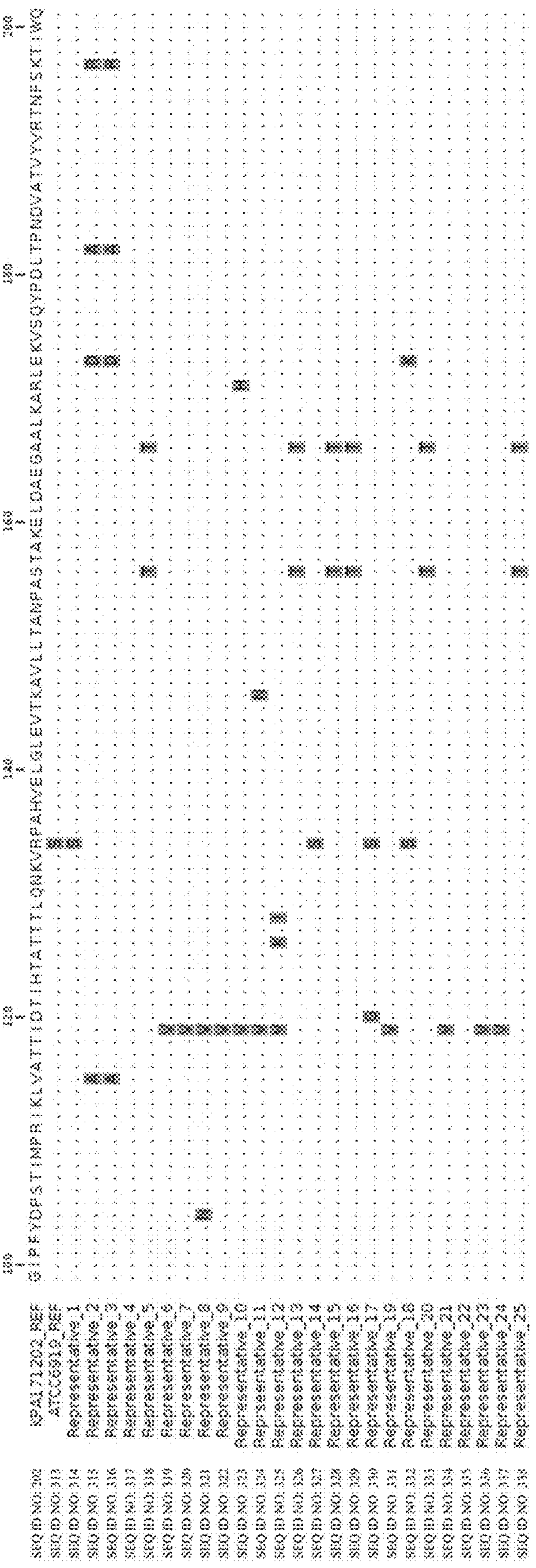
Figure 44C:
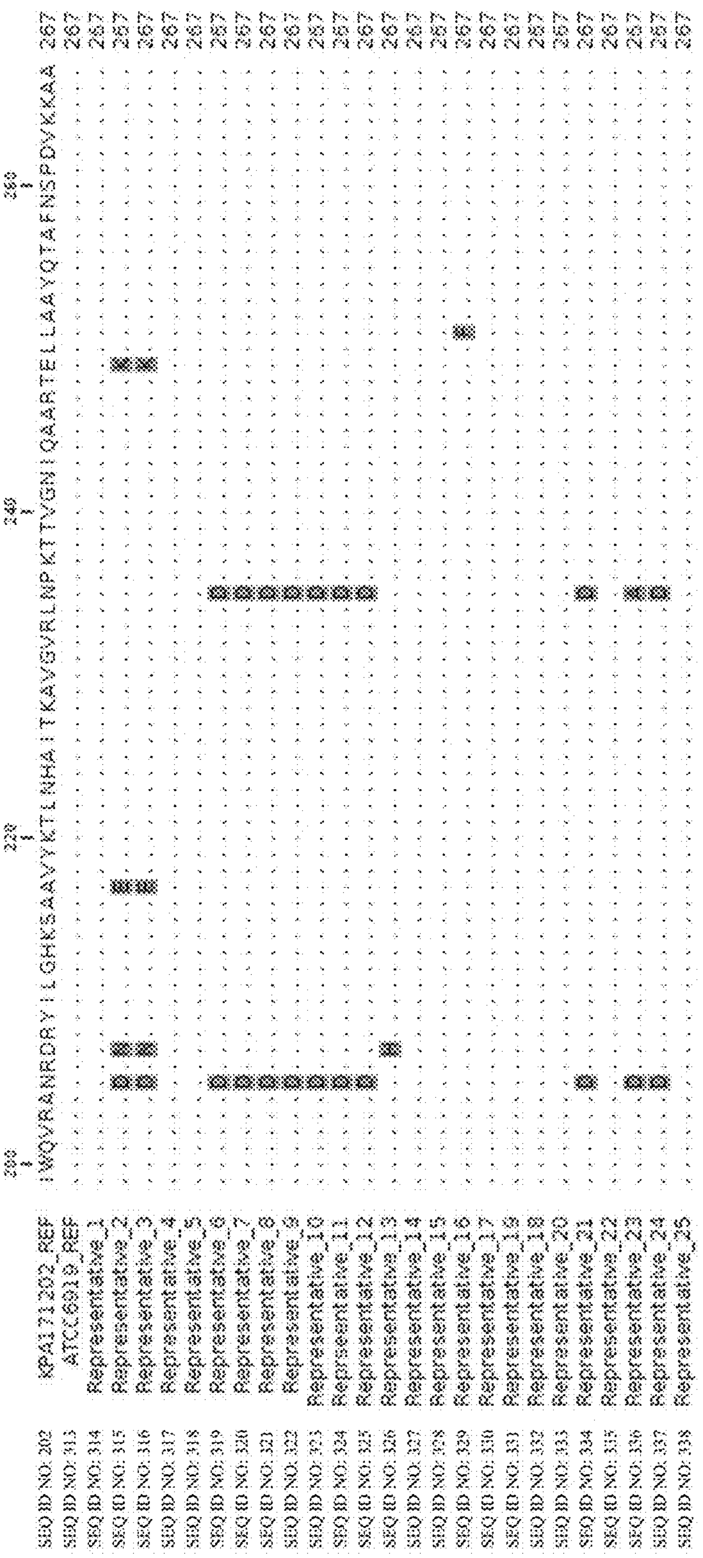

Chimeric *C. acnes* DsA1 DsA2 PITP mRNA Antigen and a Combination of a Chimeric *C. acnes* DsA1 DsA2 mRNA Antigen and a PITP mRNA Antigen Elicit Antibodies with Opsonophagocytic Activity Both the 'triple chimera' formulation and the 'bivalent combination' formulation elicited antibodies with opsonophagocytic activity, as measured with an Opsonophagocytic Killing (OPK) assay and as shown in FIGS. 42A-42B. At low doses, the 'triple chimera' formulation induced lower OPK titers than the 'bivalent combination' formulation. A significant dose effect was observed for both formulations. At optimal doses, the 'triple chimera' formulation induced similar OPK titers as the 'bivalent combination' formulation.

Correlations Between Antibody Responses Elicited by Chimeric *C. acnes* DsA1 DsA2 PITP mRNA Antigen and a Combination of a Chimeric *C. acnes* DsA1 DsA2 mRNA Antigen and a PITP mRNA Antigen The Pearson correlations between ELISA anti-DSA1 and -DSA2 IgG titers. Surface Binding titers and Opsonophagocytic Killing titers performed on NCTC737 *C. acnes* strain, on one hand, and the Pearson correlations between ELISA anti-PITP IgG titers. Surface Binding titers and Opsonophagocytic Killing titers performed on KPA171202 *C. acnes* strain, on the other hand, were analysed. All correlated assays exhibited good r values (r=Pearson correlation factor calculated between each variable), and p-values<0.001.

Example 11—Localisation of Expression Products of *C. acnes* Antigens with Various Secretion Signal Peptide Sequences and Heterologous Transmembrane Domains in HEK Expi293F Cells This Example outlines the analysis of cell viability, protein expression, and localization following the transfection of mRNA encoding *C. acnes* CAMP2 and mRNA encoding *C. acnes* PITP (see constructs in Table 11) into HEK Expi293F cells.

Transfection and Western Blot Analysis

For the transfection of cells, HEK Expi293F cells in suspension (5 mL at $2\times10^6$ cells/mL—shaker 125 mL) were transfected with 5 μg naked mRNA at 1 μg/μL mixed with equal volume of TransIT-mRNA Reagent and mRNA Boost Reagent—TransIT-mRNA Transfection Kit Mirus (Ref MIR 2250) for 2-5 minutes. The mixture was added to the cells drop-wise and incubated at 37° C. 100 rpm. 8% CO2 for 48 to 72 hours.

HEK Expi293F cell counts and cell percent viability resulting from two expression tests with the mRNA construct panel post-transfection were measured. All cell viability values exceeded 80% at 24 and 48 hours post transfection, indicating that the conditions were normal and that none of the mRNA constructs produced off-target cell cytotoxicity.

Next, mRNA-transfected cells were analysed by Western blot: After transfection, cells and medium were collected and centrifuged (500×g) to collect supernatants. The cell pellets were lysed using Lysozyme (Ready-Lyse Lysozyme Solution-Lucigen ref R1804M)+Benzonase (Sigma-ref E1014)+ Protease inhibitor cocktail (Sigma-ref P8340) for 10 min at 20° C. under 800 rpm. The cell pellet lysis was then centrifuged (11,000× g) to collect supernatants and crude extracts.

Extracts from mRNA-transfected HEK293T cells were analyzed by denaturing (95° C.) PAGE using 4-12% Bis-Tris/MES gel (Invitrogen) and Western Blot. Transfer to a nitrocellulose membrane (Bio-Rad) was performed using a semi-dry transfer system (Trans-Blot Turbo Transfer System, Bio-Rad). Blotted proteins were detected with polyclonal antibodies that recognize CAMP2 (rabbit polyclonal antibody, generated in-house, at a 1:1500 dilution) or PITP (mouse polyclonal antibody, generated in house, at a 1:1000 dilution), respectively, and a secondary antibody (anti-rabbit IgG Goat Antibody DyLight 800—Rockland, ref 611-145-002, or anti-mouse IgG). Blots were imaged with Odyssey Infrared Imager—LICOR.

CAMP2

In vitro expression of CAMP2 fused to signal sequences (labeled "SS" on gels) derived from Influenza A. Influenza B, Rabies, VZV, and Ebola glycoproteins with or without their respective transmembrane domains ("TMB") was achieved at 48-hours post-transfection in HEK Expi293F cells. CAMP2 (expected size about 26-32 kDa) was detected using a rabbit polyclonal antibody to CAMP2 (generated in-house) at a 1:1500 dilution. Controls included a CAMP2 construct without any SS as well as recombinant CAMP2. With respect to testing CAMP2 localization, samples were collected from crude extracts (total lysate), cell supernatants, and fractionated cell samples containing either intracellular or transmembrane compartments. These results demonstrate that adding a transmembrane domain induces localization of CAMP2 at the cell membrane and reduces secretion and intracellular localization. The Western blot analysis demonstrated that CAMP2 is well expressed and localizes in the expected fractions depending on the presence of a secretion signal peptide or a transmembrane domain.

PITP

In vitro expression of PITP fused to signal sequences (labeled "SS" on gels) derived from Influenza A, Influenza B, Rabies, VZV, and Ebola glycoproteins with or without their respective transmembrane domains ("TMB") was achieved at 48-hours post-transfection in HEK Expi293F cells. PITP (expected size about 42-48 kDa) was detected using a mouse polyclonal to PITP (generated in-house) at a 1:1000 dilution. Controls included an PITP construct without any SS or any TMB as well as recombinant PITP. With respect to testing PITP localization, samples were collected from crude extracts (total lysate), cell supernatants, and fractionated cell samples containing either intracellular or transmembrane compartments. Like the CAMP2 antigen localization analysis, these results demonstrate that adding a transmembrane domain induces localization of PITP at the cell membrane and reduces secretion and intracellular localization. Notwithstanding. PITP transmembrane containing constructs did show some escape into the supernatant fraction.

This Western blot analysis demonstrated that PITP is well expressed and localizes in the expected fractions depending on the presence of a secretion signal peptide or a transmembrane domain.

SUMMARY

To compare the Western blot analysis for the CAMP2 and PITP, the protein expression and localization results were tabulated as shown in FIG. 43. In general, CAMP2 or PITP containing constructs were expressed in their expected locations but with varying degrees of expression and displayed some escape to the supernatant at varying degrees when the transmembrane domain was introduced.

TABLE 11

Amino Acid Sequence Designs of CAMP2 and PITP Constructs

| Description/SEQ ID NO | Construct Name FIG. 43 | Encoded by nucleotide sequence according to SEQ ID NO: |
|---|---|---|
| Camp2 SEQ ID NO: 1 | CAMP2 No SS-TMB | SEQ ID NO: 289 |
| Camp2__SS__Flu-HA__A/California/7/2009 SEQ ID NO: 268 | CAMP2 SS Flu HA-A | SEQ ID NO: 290 |
| Camp2__SS__Flu-HA__B/Phuket/3073/2013 SEQ ID NO: 269 | CAMP2 SS Flu HA-B | SEQ ID NO: 291 |
| Camp2__SS__Rabies-G__Pasteur-vaccins SEQ ID NO: 270 | CAMP2 SS Rabies-G | SEQ ID NO: 292 |
| Camp2__SS__VZV-gI__Oka-vaccine SEQ ID NO: 271 | CAMP2 SS VZV-gI | SEQ ID NO: 293 |
| Camp2__SS__Ebola-GP__Mayinga-76 SEQ ID NO: 272 | CAMP2 SS Ebola-GP | SEQ ID NO: 294 |
| Camp2__SS__Flu-HA__A/California/7/2009__TMB SEQ ID NO: 273 | CAMP2 SS-TMB Flu HA-A | SEQ ID NO: 295 |
| Camp2__SS__Flu-HA__B/Phuket/3073/2013__TMB SEQ ID NO: 274 | CAMP2 SS-TMB Flu HA-B | SEQ ID NO: 296 |
| Camp2__SS__Rabies-G__Pasteur-vaccins__TMB SEQ ID NO: 275 | CAMP2 SS-TMB Rabies-G | SEQ ID NO: 297 |
| Camp2__SS__VZV-gI__Oka-vaccine__TMB SEQ ID NO: 276 | CAMP2 SS-TMB VZV-gI | SEQ ID NO: 298 |
| Camp2__SS__Ebola-GP__Mayinga-76__TMB SEQ ID NO: 277 | CAMP2 SS-TMB Ebola-GP | SEQ ID NO: 299 |
| PITP SEQ ID NO: 278 | PITP No SS-TMB | SEQ ID NO: 300 |
| PITP__SS__Flu-HA__A/California/7/2009 SEQ ID NO: 279 | PITP SS Flu HA-A | SEQ ID NO: 301 |
| PITP__SS__Flu-HA__B/Phuket/3073/2013 SEQ ID NO: 280 | PITP SS Flu HA-B | SEQ ID NO: 302 |

TABLE 11-continued

Amino Acid Sequence Designs of CAMP2 and PITP Constructs

| Description/SEQ ID NO | Construct Name FIG. 43 | Encoded by nucleotide sequence according to SEQ ID NO: |
|---|---|---|
| PITP__SS__Rabies-G__Pasteur-vaccins SEQ ID NO: 281 | PITP SS Rabies-G | SEQ ID NO: 303 |
| PITP__SS__VZV-gI__Oka-vaccine SEQ ID NO: 282 | PITP SS VZV-gI | SEQ ID NO: 304 |
| PITP__SS__Ebola-GP__Mayinga-76 SEQ ID NO: 283 | PITP SS Ebola-GP | SEQ ID NO: 305 |
| PITP__SS__Flu-HA__A/California/7/2009__TMB SEQ ID NO: 284 | PITP SS-TMB Flu HA-A | SEQ ID NO: 306 |

TABLE 11-continued

Amino Acid Sequence Designs of CAMP2 and PITP Constructs

| Description/SEQ ID NO | Construct Name FIG. 43 | Encoded by nucleotide sequence according to SEQ ID NO: |
|---|---|---|
| PITP__SS__Rabies-G__Pasteur-vaccins__TMB SEQ ID NO: 286 | PITP SS-TMB Rabies-G | SEQ ID NO: 308 |
| PITP__SS__VZV-gI__Oka-vaccine__TMB SEQ ID NO: 287 | PITP SS-TMB VZV-gI | SEQ ID NO: 309 |
| PITP__SS__Ebola-GP__Mayinga-76__TMB SEQ ID NO: 288 | PITP SS-TMB Ebola-GP | SEQ ID NO: 310 |

Example 12—Synthesis of IM-001 According to Scheme 2

Scheme 2: General Synthetic Scheme for Lipid of Formula (X)

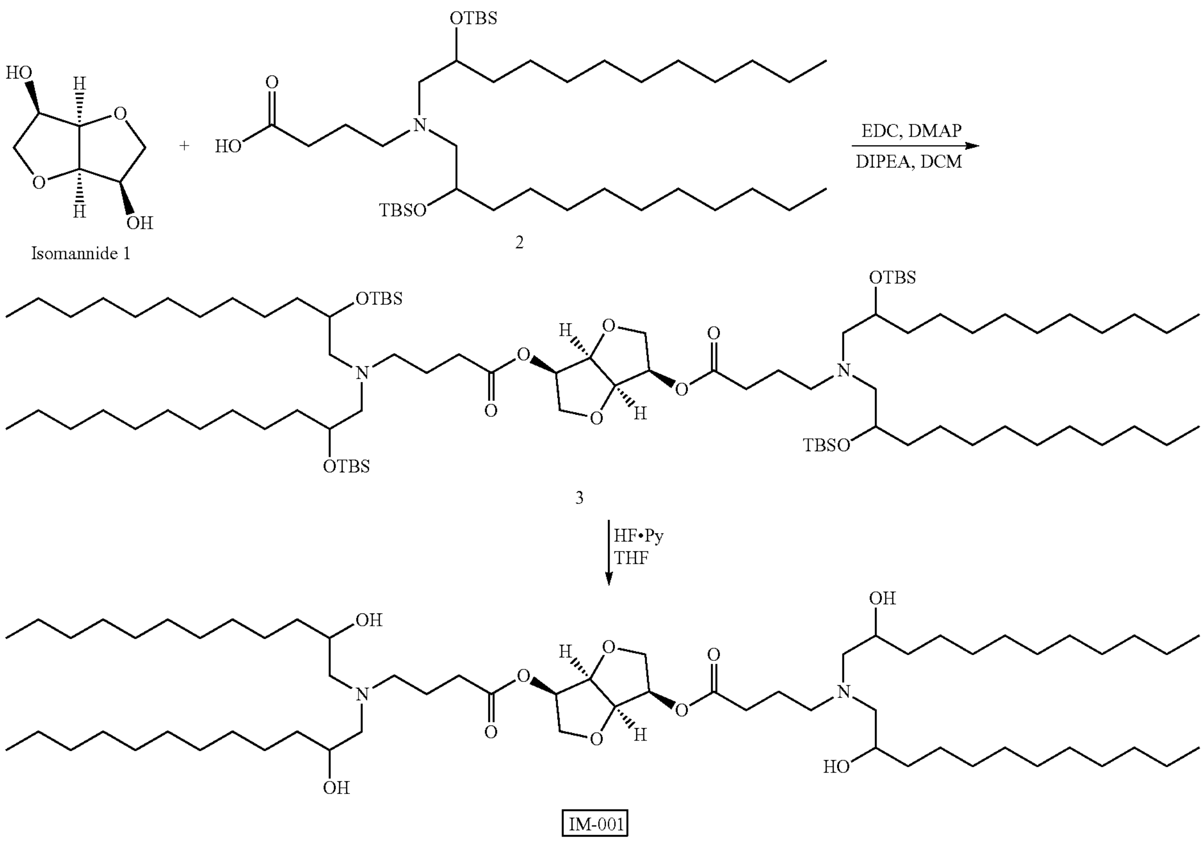

Isomannide 1

2

3

IM-001

TABLE 11-continued

Amino Acid Sequence Designs of CAMP2 and PITP Constructs

| Description/SEQ ID NO | Construct Name FIG. 43 | Encoded by nucleotide sequence according to SEQ ID NO: |
|---|---|---|
| PITP__SS__Flu-HA__B/Phuket/3073/2013__TMB SEQ ID NO: 285 | PITP SS-TMB Flu HA-B | SEQ ID NO: 307 |

Abbreviations

DCM: Dichloromethane
DIPEA: N,N-Diisopropylethylamine
DMAP: 4-Dimethylaminopyridine
EDC: 1-Ethyl-3-(3-dimethylaminopropyl)carbodiimide
EtOAc: Ethyl acetate
NaHCO3: Sodium hydrogencarbonate
Py: Pyridine
$Na_2SO4$: Sodium Sulfate
TEA: Triethylamine
TFA: Trifluoroacetic Acid MS: Mass spectrometry ESI-MS: Electrospray ionization mass spectrometry TLC: Thin Layer Chromatography Step 1: Synthesis of Intermediate (3)

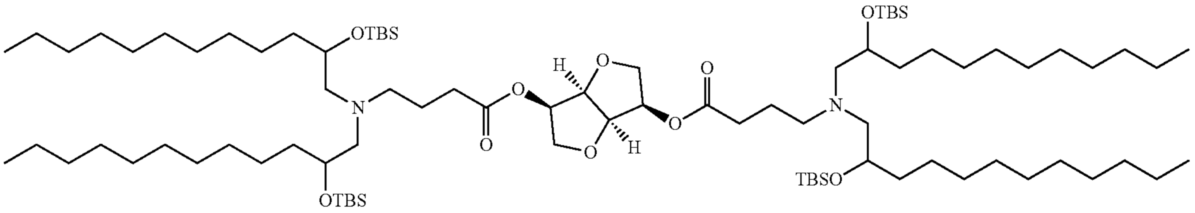 [SMILES: CCCCCCCCCCC(CN(CCCC(=O)O[C@@H]1CO[C@H]2[C@@H]1OC[C@H]2OC(=O)CCCN(CC(CCCCCCCCCC)O[Si](C)(C)C(C)(C)C)CC(CCCCCCCCCC)O[Si](C)(C)C(C)(C)C)CC(CCCCCCCCCC)O[Si](C)(C)C(C)(C)C)O[Si](C)(C)C(C)(C)C]

As depicted in Scheme 2: To a solution of acid (2) (4.58 g, 6.55 mmol) and isomannide (1) (0.38 g, 2.62 mmol) in dichloromethane (40 mL) were added DIPEA (3.65 mL, 20.96 mmol), DMAP (0.32 g, 2.62 mmol) and EDC (1.5 g, 7.86 mmol). The resulting mixture was stirred at room temperature for overnight. After 16 h. MS and TLC (30% EtOAc in hexanes) analysis indicated completion of the reaction. The reaction mixture was diluted with dichloromethane and washed with saturated $NaHCO_3$ solution, water and brine solution. The organic layer was dried over anhydrous $Na_2SO_4$ and concentrated. The crude residue was purified, and the desired product was eluted at 6% EtOAc in hexanes. The product containing fractions were concentrated to obtain 2.58 g (65%) of pure product.

Results:

ESI-MS: Calculated $C_{86}H_{177}N_2O_{10}Si_4$, $[M+H^+]$=1510.25, Observed=1510.3

Step 2: Synthesis of IM-001

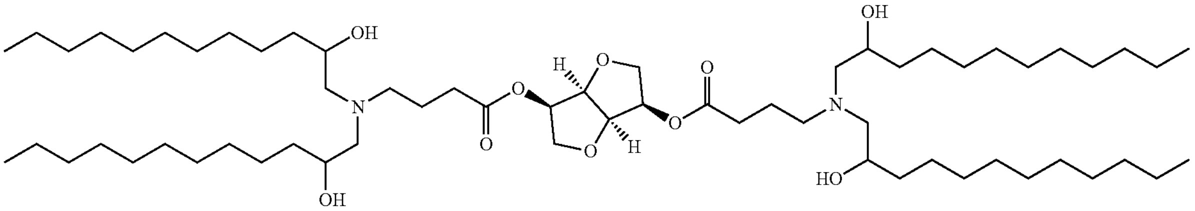 [SMILES: CCCCCCCCCCC(O)CN(CCCC(=O)O[C@@H]1CO[C@H]2[C@@H]1OC[C@H]2OC(=O)CCCN(CC(O)CCCCCCCCCC)CC(O)CCCCCCCCCC)CC(O)CCCCCCCCCC]

As depicted in Scheme 2: To a solution of Intermediate (3) (2.58 g, 1.70 mmol) in tetrahydrofuran (14 mL) was added hydrogen fluoride (70% HF.py complex, 7 mL, 51.23 mmol) at 0° C., and stirred at the same temperature for 5 minutes. Then reaction mixture was warmed to room temperature and stirred for 16 h. MS analysis indicated completion of the reaction. The reaction mixture was diluted with ethyl acetate, quenched by slow addition of solid $NaHCO_3$ at 0° C., followed by saturated $NaHCO_3$ solution. The organic layer was washed with sat. $NaHCO_3$ solution, water and brine. Then dried over anhydrous $Na_2SO_4$ and concentrated. The crude residue was purified, and the desired product was eluted at 67% EtOAc in hexanes. The purest fractions were concentrated to obtain 1.1 g (61%) of pure product.

Results:

$^1H$ NMR (400 MHZ, $CDCl_3$) δ 5.13-5.03 (m, 2H), 4.73-4.65 (m, 2H), 4.29-3.83 (m, 8H), 3.52-2.98 (m, 12H), 2.69-2.49 (m, 4H), 2.32-2.09 (m, 4H), 1.73-1.12 (m, 72H), 0.88 (t, J=6.6 Hz, 12H).

ESI-MS: Calculated $C_{62}H_{121}N_2O_{10}$, $[M+H^+]$=1053.90, Observed=1053.2 and 527.2 $[M/2+H^+]$.

Example 13—Chimeric *C. acnes* DsA1/DsA2/PITP/CAMP2 mRNA Antigens

The aim of this example was to assess formulations containing chimeric *C. acnes* DsA1/DsA2/PITP/CAMP2 mRNA constructs (i.e. wherein the four antigens are located on the same mRNA molecule) for their ability to induce a functional immune response, and to compare them with formulations containing a 'bivalent combination of a CAMP2 mRNA construct and a chimeric *C. acnes* DsA1/DsA2/PITP mRNA construct.

Design of Chimeric *C. acnes* DsA1 DsA2 PITP CAMP 2 Constructs

Figure 45:
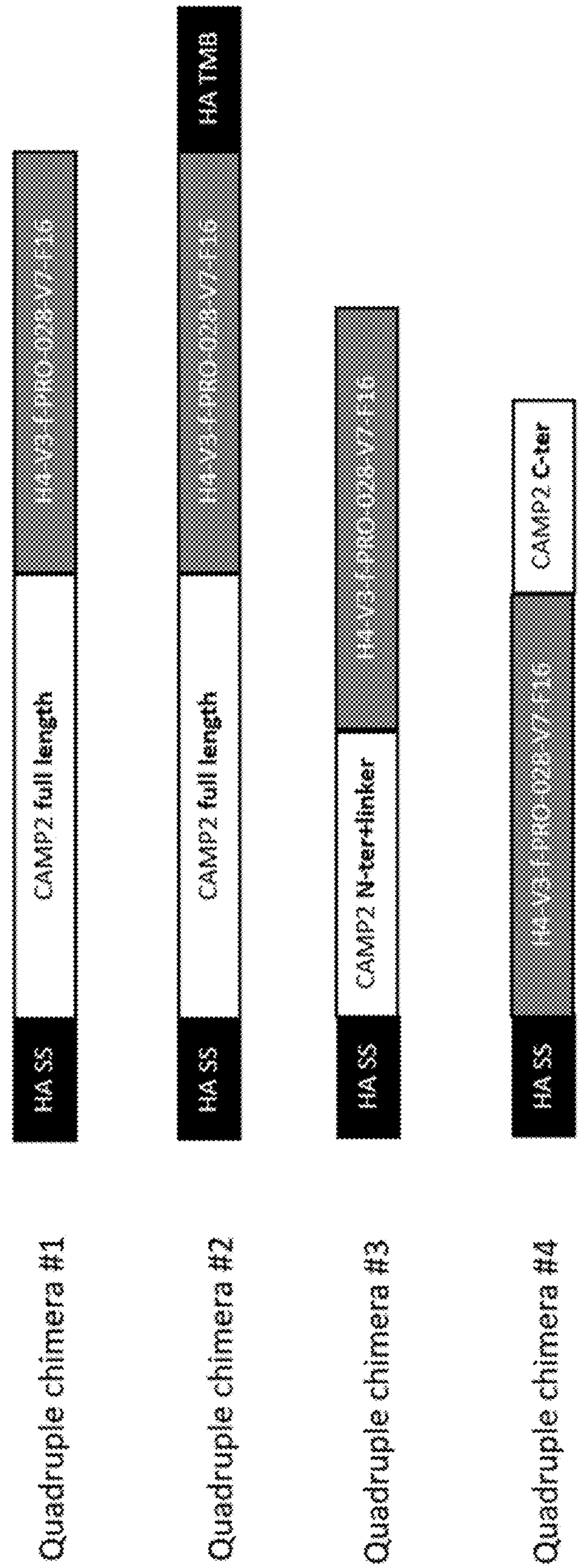
FIG. 45 shows a schematic visualization of the "quadruple chimera" mRNA constructs that have been designed, synthesized and assessed experimentally.

FIG. 45 shows the 'quadruple chimera' *C. acnes* DsA1/DsA2/PITP/CAMP2 constructs which have been designed and tested in the following experiments:

- A quadruple chimera ('Quadruple chimera #1'), comprising a full length CAMP2 at N-ter of triple chimera H4-V3-f-PRO-028-V7-F16, with a signal sequence of Influenza Hemagglutinin (HA, H1N1 A/Caledonia/20/1999) (HA SS) at N-ter of the quadruple chimera to address the protein for secretion.
- A quadruple chimera ('Quadruple chimera #2'), comprising a full length CAMP2 at N-ter of triple chimera H4-V3-f-PRO-028-V7-F16, with a HA SS at N-ter and a transmembrane domain of Influenza Hemagglutinin (HA. HINI A/Caledonia/20/1999) (HA TMB) at C-ter of the quadruple chimera to anchor the protein at the cell membrane.
- A quadruple chimera ('Quadruple chimera #3'), comprising the N-ter and linker portions of CAMP2 at N-ter of triple chimera H4-V3-f-PRO-028-V7-F16, with a HA SS at N-ter of the quadruple chimera to address the protein for secretion.

A quadruple chimera ('Quadruple chimera #4') comprising the C-ter portion of CAMP2 at C-ter of triple chimera H4-V3-f-PRO-028-V7-F16, with a HA SS at N-ter of the quadruple chimera to address the protein for secretion.

Characterization of the Expression and Localization of Chimeric *C. acnes* DsA1 DsA2 PITP CAMP 2 mRNA Constructs in HEK Cells For this experiment, the mRNAs used were as follows:

- Two codon-optimized mRNAs encoding a quadruple chimera comprising SEQ ID NO: 374 (Quadruple chimera #1):
  - Quadruple chimera #1 (CO1) of SEQ ID NO: 379 and
  - Quadruple chimera #1 (CO2) of SEQ ID NO: 380 encoding the quadruple chimera of SEQ ID NO: 370
- Two codon-optimized mRNAs encoding the quadruple chimera of SEQ ID NO: 369 (Quadruple chimera #2): Quadruple chimera #2 (CO1) of SEQ ID NO: 377 and Quadruple chimera #2 (CO2) of SEQ ID NO: 378
- Two codon-optimized mRNAs encoding the quadruple chimera of SEQ ID NO: 371 (Quadruple chimera #3): Quadruple chimera #3 (CO1) of SEQ ID NO: 381 and Quadruple chimera #3 (CO2) of SEQ ID NO: 382
- One codon-optimized mRNA encoding the quadruple chimera of SEQ ID NO: 372 (Quadruple chimera #4): Quadruple chimera #4 (CO2) of SEQ ID NO: 383
- As controls: one mRNA of SEQ ID NO: 113 encoding H4-V3, one mRNA of SEQ ID NO: 115 encoding P028-V7, one mRNA of SEQ ID NO: 91 encoding CAMP2-TMB and one mRNA of SEQ ID NO: 125 encoding the PRO-028-V7-C12 triple chimera.

Each mRNA comprised a cap1, a 5'UTR from CMV of SEQ ID NO: 265, a 3' UTR from hGH of SEQ ID NO: 266, and a polyA tail, mRNA synthesis was performed using modified nucleotides (in which all uridine nucleosides were replaced with 1-methyl pseudo uridine), and the mRNA constructs were transfected into HEK cells (in vitro cell transfection).

Figure 46A:
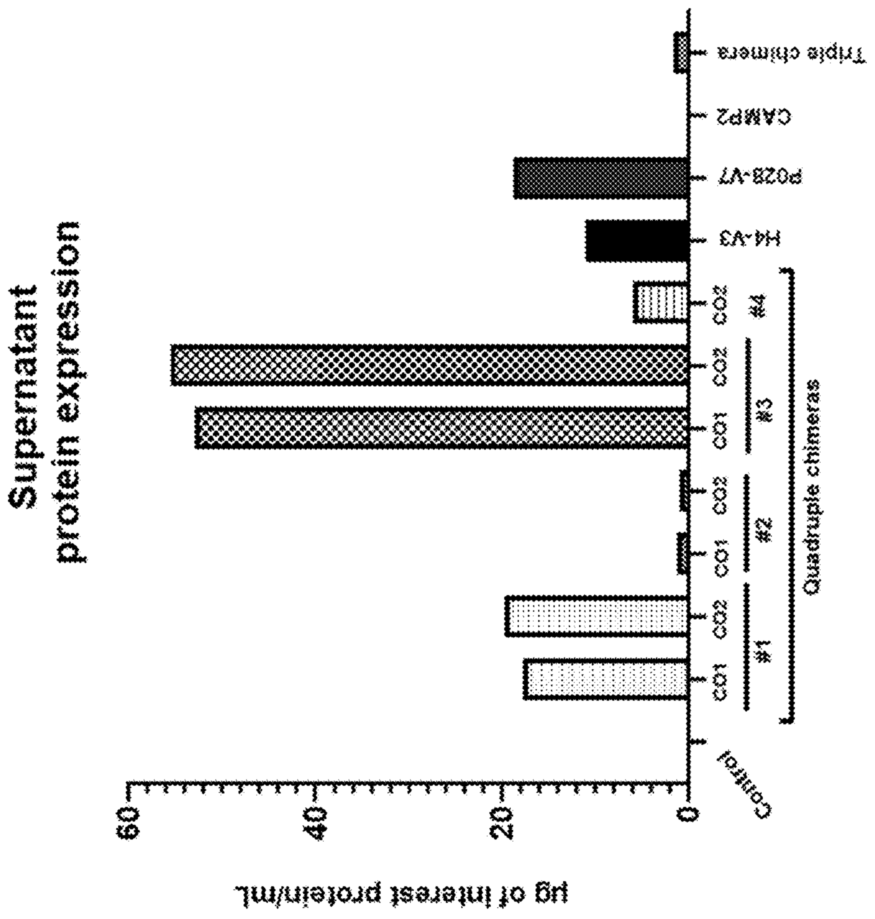
FIGS. 46A-46B shows levels of protein expression in supernatant (FIG. 46*a*) and cell lysate (FIG. 46*b*), as measured by HPLC-MS, after in vitro cell transfection of HEK Expi293F cells with "quadruple chimera" mRNA constructs (construct designs shown in FIG. 45) and other mRNA constructs used as controls.
Figure 46B:
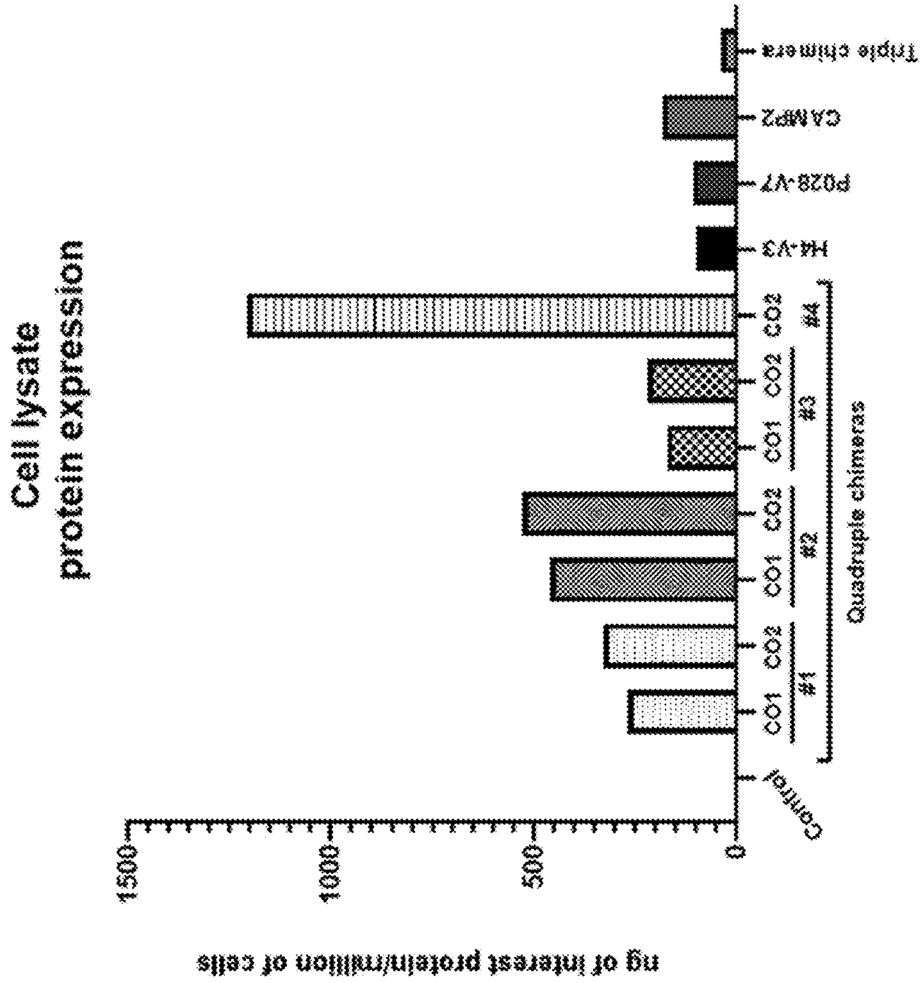

Protein expression was then assessed and measured in the supernatant and in the total cell lysate by HPLC-MS. As shown in FIGS. 46A-46B, all constructs were expressed in their expected compartments. In particular, the quadruple chimera #2 with a transmembrane domain was found in the total cell lysate, but not in the supernatant. The three other quadruple chimeras, designed to be secreted, were found both in the supernatant and in the total cell lysate. The quadruple chimera #3 with CAMP2 N-ter and linker portions was found to be the most highly secreted. The quadruple chimera #4 with a CAMP2 C-ter portion was found to be secreted at the lowest levels.

Similar results were obtained by Western blot (using as primary antibodies: an anti-CAMP2 rabbit polyclonal antibody, an anti-DsA2 mouse monoclonal antibody or an anti-PITP mouse monoclonal antibody), with all quadruple chimera proteins being expressed in their expected compartment (cell lysate and/or supernatant).

Immunization of Mice

Constructs were then tested for their ability to elicit functional antibodies in mice. In these experiments, the following mRNA constructs were used:

- One mRNA of SEQ ID NO: 380 encoding the Quadruple chimera #1
- One mRNA of SEQ ID NO: 378 encoding the Quadruple chimera #2
- One mRNA of SEQ ID NO: 382 encoding the Quadruple chimera #3
- One mRNA of SEQ ID NO: 383 encoding the Quadruple chimera #4
- For comparison: a "bivalent combination" of one mRNA of SEQ ID NO: 91 encoding a CAMP2-TMB and one mRNA of SEQ ID NO: 122 encoding the H4-V3-f-PRO-028-V7-F16 triple chimera.

Each mRNA comprised a cap1, a 5'UTR from CMV of SEQ ID NO: 265, a 3' UTR from hGH of SEQ ID NO: 266, and a polyA tail, mRNA synthesis was performed using modified nucleotides (in which all uridine nucleosides were replaced with 1-methyl pseudo uridine). The mRNA constructs were encapsulated in an LNP composed of four lipids: GL-HEPES-E3-E12-DS-4-E10 (as the ionizable lipid)/DOPE/cholesterol/DMG-PEG, at the molar ratio of 40:30:28.5:1.5. LNP alone served as a negative control.

OF-1 outbred mice (6-week old at day 0) were immunized twice at 4 weeks interval through intra-muscular (IM) route (50 μL in quadriceps muscle hind leg, with alternance of the right and left leg between both injections). The mRNA content in tested formulation was of 1 μg or 5 μg per dose (for the quadruple chimeras) and of [1 μg+1 μg] or [5 μg+5 μg] per dose (for the combination of CAMP2-TMB and triple chimera).

Mice were monitored for clinical signs. Only a limited and transient local swelling was observed at the site of injection following the second injection in all experimental groups, with no other clinical reaction (such as straight hair, loss of mobility, apathy . . . ). Moreover, regular weight gain was monitored over the study period for all experimental groups. Overall, there was no significant impact of the injections of the different formulations on clinical signs.

The sera were obtained at day 42 following the first immunization, and tested for total IgG by ELISA, in an OPK assay, in a Surface Binding assay and in a co-hemolysis neutralization assay (as described in Example 1). Results are presented below.

Chimeric *C. acnes* DsA1 DsA2 PITP CAMP2 mRNA Constructs and a Bivalent Combination of a CAMP 2-TMB mRNA Construct and a DsA1 DsA2 PITP mRNA Construct Elicit Anti-DsA1, Anti-DsA2, Anti-PITP and Anti-CAMP 2 1gG Responses Both the "quadruple chimera" formulations and the "bivalent combination" formulation elicited anti-DsA1, anti-DsA2, anti-PITP and anti-CAMP2 IgG responses, as shown in FIGS. 47A-47D.

At equivalent dose, all quadruple chimeras elicited comparable anti-DsA1 (FIG. 47*a*) and anti-DsA2 (FIG. 47*b*) IgG titers. At 1 μg dose, anti-DsA1 and anti-DsA2 Ig titers were significantly lower than the bivalent combination. At 5 μg dose all quadruple chimeras induced similar IgG titers as the bivalent combination. There was a significant difference between the 1 μg and 5 μg doses for all groups, except for the quadruple chimera #1 and the bivalent combination.

Figure 47A:
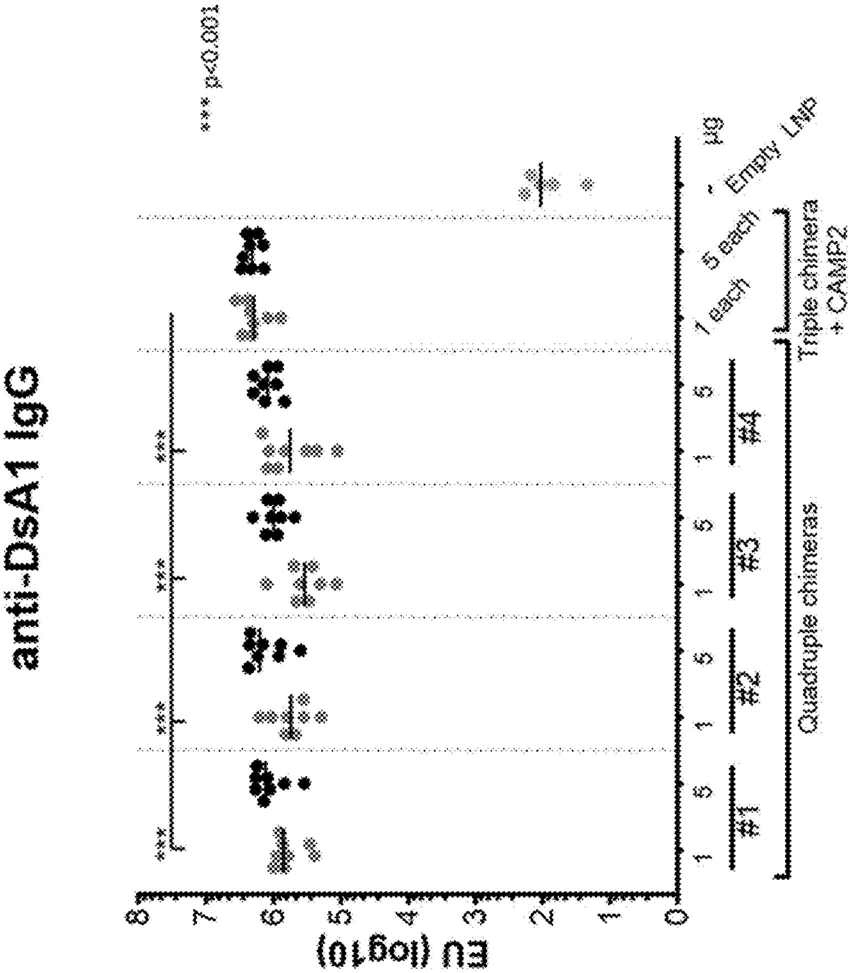
FIGS. 47A-47D show ELISA anti-DsA1 (FIG. 47*a*), anti-DsA2 (FIG. 47*b*), anti-PITP (FIG. 47*c*) and anti-CAMP2 (FIG. 47*d*) IgG titers of sera (day 42 after first immunization) of mice immunized twice at 4 weeks interval with "quadruple chimera" mRNA constructs (construct designs shown in FIG. 45), in comparison with a combination of an mRNA construct encoding CAMP2 expressed at the cell membrane and an mRNA construct encoding the H4-V3-f-PRO-028-V7-F16 triple chimera. Two doses were assessed (1 μg and 5 μg), mRNA constructs were encapsulated in an LNP comprising GL-HEPES-E3-E12-DS-4-E10 as cationic lipid. LNP alone served as a negative control. EU=ELISA unit.
Figure 47B:
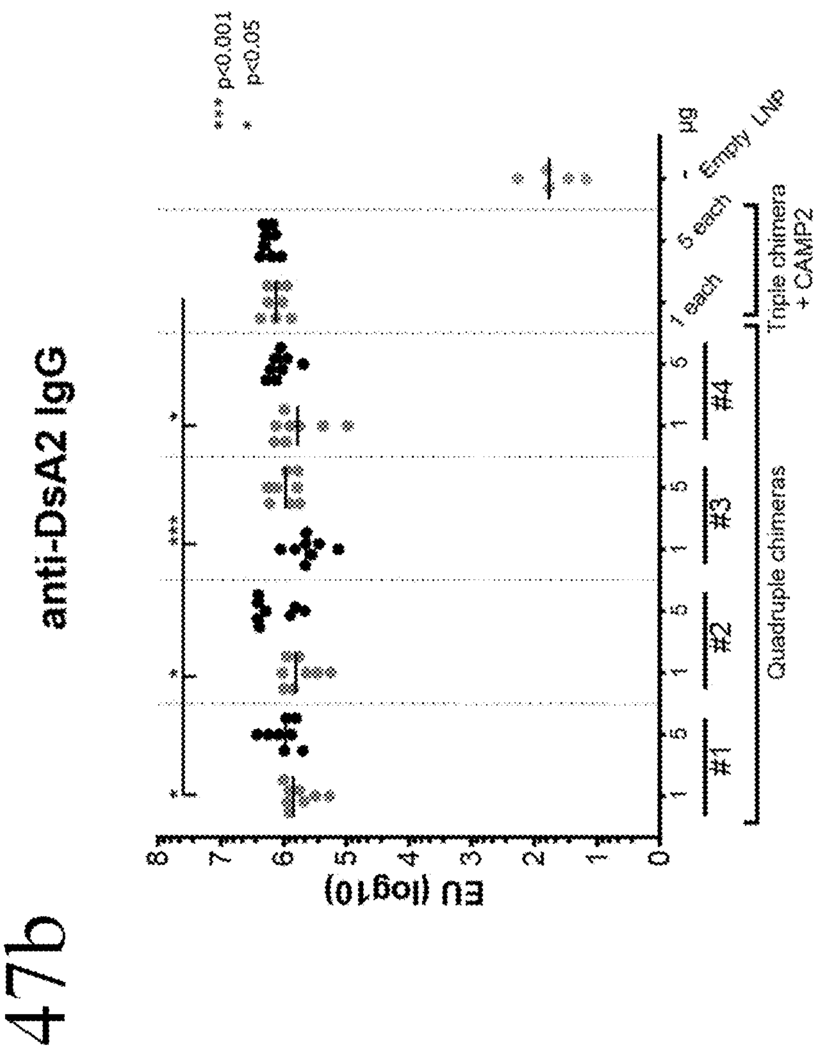
Figure 47C:
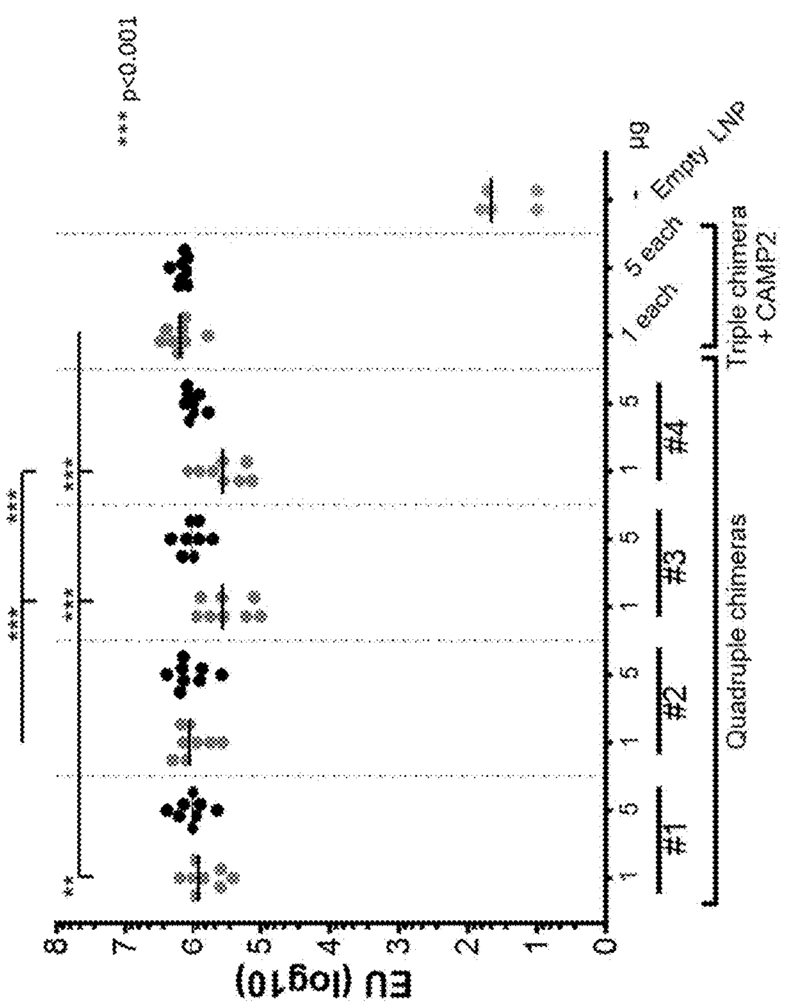

As shown in FIG. 47*c*, at 1 μg dose, anti-PITP Ig titers induced by quadruple chimeras were significantly lower than the bivalent combination, except for the quadruple chimera #2. At this lug dose, the quadruple chimera #2 elicited an anti-PITP IgG titer equivalent to the quadruple chimera #1 and significantly superior to the quadruple chimeras #3 and #4. At 5 μg dose, all quadruple chimeras elicited equivalent anti-PITP IgG titers compared to the bivalent combination.

Figure 47D:
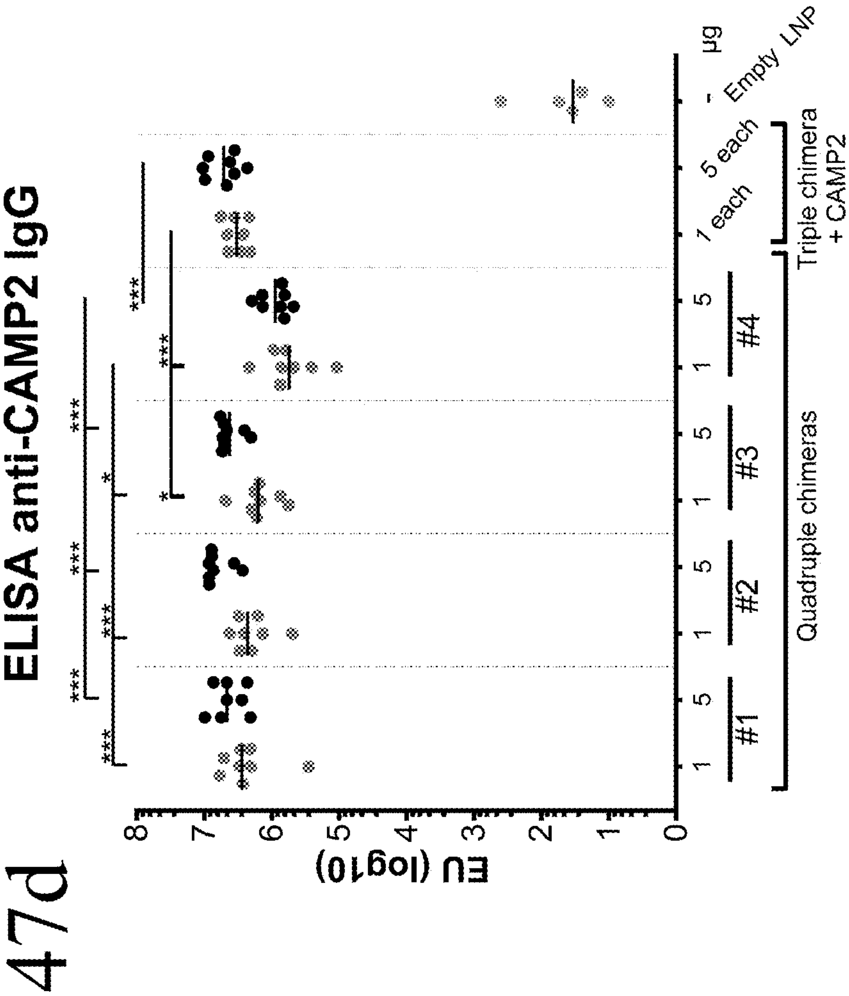

As shown in FIG. 47*d*, at 1 μg dose, the bivalent combination elicited anti-CAMP2 Ig titers comparable to the ones elicited by quadruple chimeras #1 and #2 and significantly higher than the ones elicited by quadruple chimeras #3 and #4. At 1 μg, the anti-CAMP2 Ig titer elicited by the quadruple chimera #4 was significantly lower than all tested formulations. At 5 μg dose, all quadruple chimeras elicited comparable anti-CAMP2 IgG titers to the bivalent combination, except the quadruple chimera #4 for which IgG titers were lower.

Figure 48A:
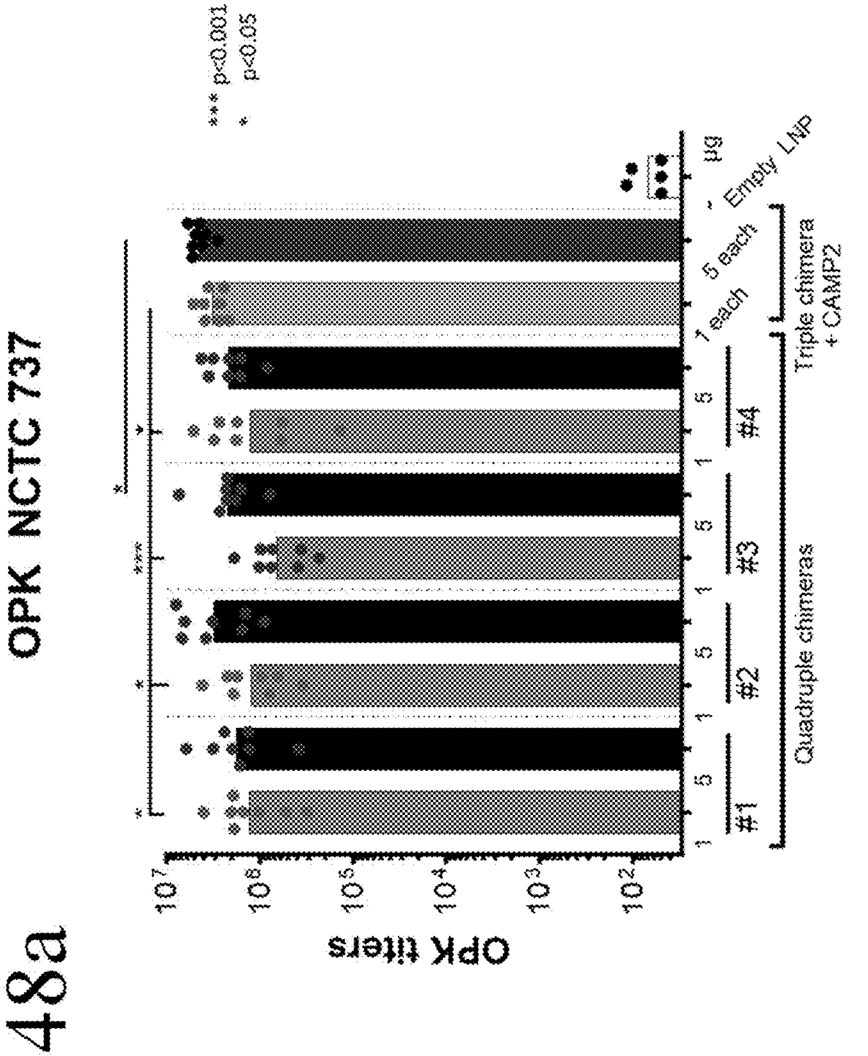
FIGS. 48A-48B show Opsonophagocytic Killing (OPK) titers from individual sera (day 42 after first immunization) of mice immunized twice at 4 weeks interval with the same mRNA constructs, at the same doses and encapsulated in the same LNP, as described in FIGS. 47A-47D. LNP alone served as a negative control. The OPK assay was performed on *C. acnes* strain NCTC737 (FIG. 48*a*) or *C. acnes* strain KPA171202 (FIG. 48*b*).
Figure 48B:
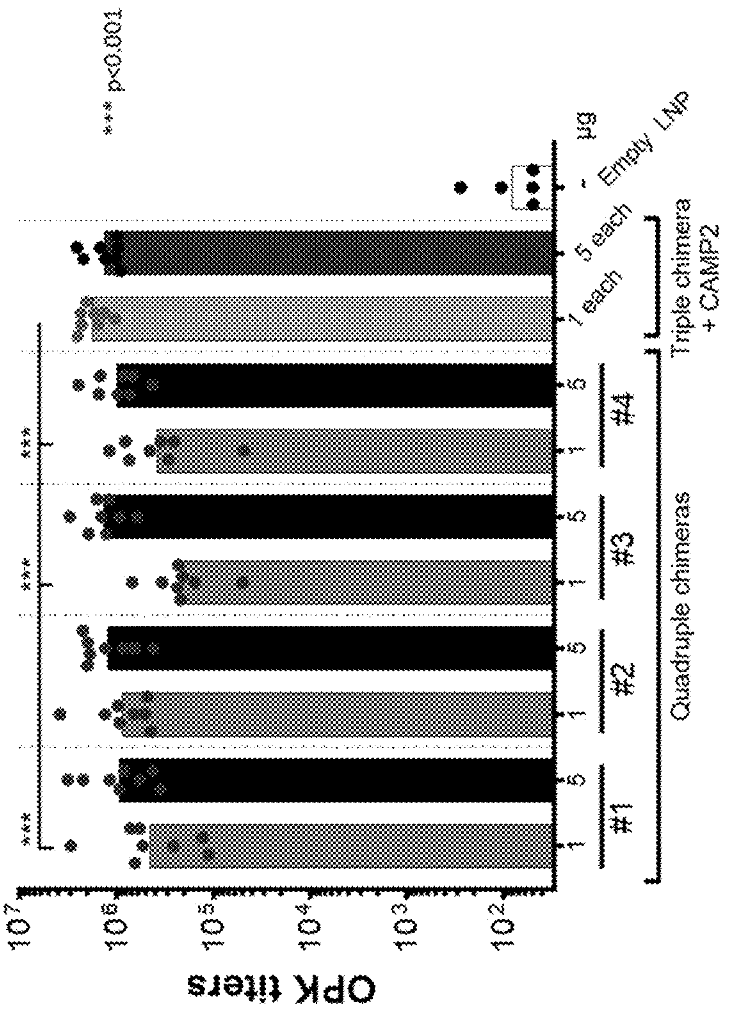

Chimeric *C. acnes* DsA1 DsA2 PITP CAMP2 mRNA Constructs and a Bivalent Combination of a CAMP 2-TMB mRNA Construct and a DsA1 DsA2 PITP mRNA Construct Elicit Antibodies which have Opsonophagocytic Activity Both the "quadruple chimera" formulations and the "bivalent combination" formulation elicited antibodies with opsonophagocytic activity, as measured with an Opsonophagocytic Killing (OPK) assay and as shown in FIGS. 48A-48B.

All four quadruple chimeras performed similarly in the OPK assay on *C. acnes* strain NCTC737 (FIG. 48*a*). There was a significant difference between the 1 μg and 5 μg doses for all groups, except for the quadruple chimera #1 and the bivalent combination. At the 1 μg dose, all quadruple chimeras induced comparable OPK titers, which were lower than the ones with the bivalent combination. At the 5 μg dose, all quadruple chimeras (except quadruple chimera #3) induced similar OPK titers as the bivalent combination.

All four quadruple chimeras performed similarly in the OPK assay on *C. acnes* strain KPA171202 (FIG. 48*b*). There was a significant difference between the 1 μg and 5 μg doses for quadruple chimera #3 and #4. At the 1 μg dose, the quadruple chimeras induced lower OPK titers than the bivalent combination, except quadruple chimera #2 for which OPK titers were equivalent. At the 5 μg dose, all quadruple chimeras induced similar OPK titers as the bivalent combination.

Chimeric *C. acnes* DsA1 DsA2 PITP CAMP2 mRNA Constructs and a Bivalent Combination of a CAMP 2-TMB mRNA Construct and a DsA1 DsA2 PITP mRNA Construct Elicit Antibodies which Bind to the Surface of *C. acnes*

Figure 49A:
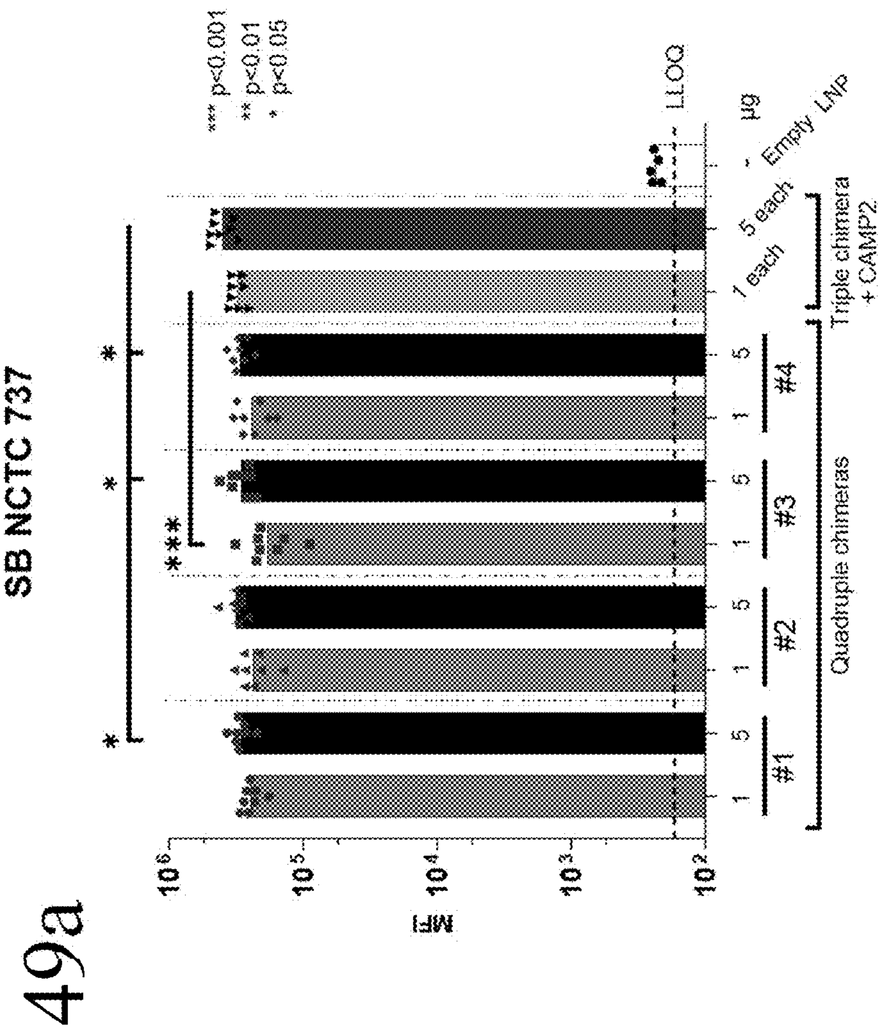
FIGS. 49A-49B show Surface Binding (SB) titers from individual sera (day 42 after first immunization) of mice immunized twice at 4 weeks interval with the same mRNA constructs, at the same doses and encapsulated in the same LNP, as described in FIGS. 47A-47D. LNP alone served as a negative control. The SB assay was performed on *C. acnes* strain NCTC737 (FIG. 49*a*) or *C. acnes* strain KPA171202 (FIG. 49*b*). LLOQ=lowest limit of quantification
Figure 49B:
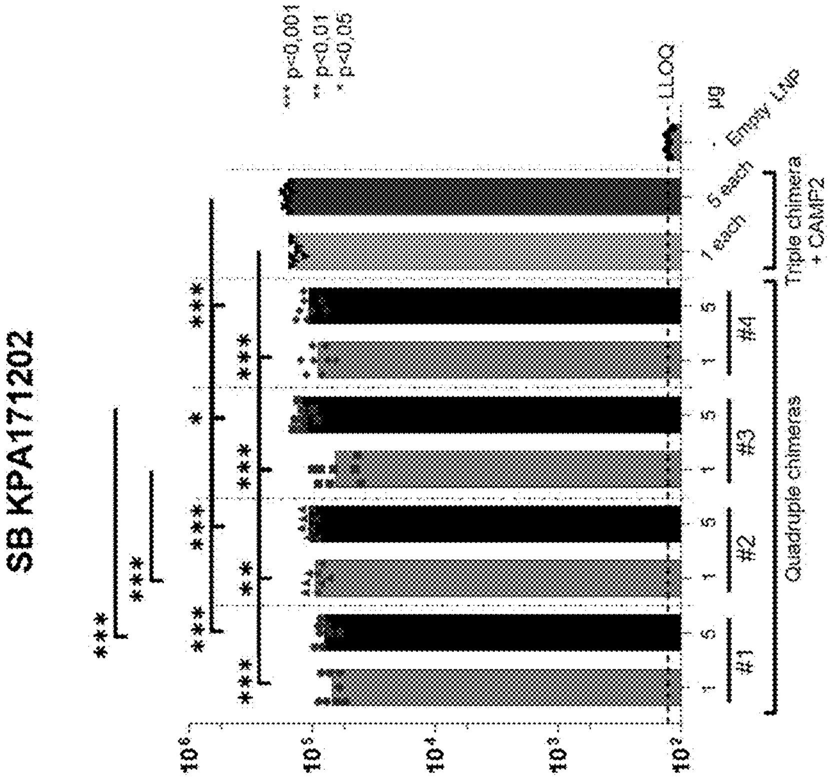

Both the "quadruple chimera" formulations and the "bivalent combination" formulation elicited SB titers, as measured with a Surface Binding (SB) assay and as shown in FIG. 49A-49B.

At the 1 μg dose, all quadruple chimeras (except quadruple chimera #3) induced similar SB value as the bivalent combination, in the SB assay on *C. acnes* strain NCTC737 (FIG. 49*a*). At the 5 μg dose, all four quadruple chimeras performed similarly. At this 5 μg dose, all quadruple chimeras (except quadruple chimera #2) induced lower SB values than the bivalent combination.

In the SB assay on *C. acnes* strain KPA171202 (FIG. 49*b*), at both the 1 μg and 5 μg doses, all quadruple chimeras induced lower SB value than the bivalent combination. The quadruple chimera #3 induced a higher SB value than the quadruple chimera #1 at 5 μg dose, and the quadruple chimera #2 induced a higher SB value than the quadruple chimera #3 at 1 μg dose.

Chimeric *C. acnes* DsA1 DsA2 PITP CAMP2 mRNA Constructs and a Bivalent Combination of a CAMP2-TMB mRNA Construct and a DsA1 DsA2 PITP mRNA Construct Elicit Antibodies which Neutralize the Co-Hemolytic Activity of CAMP2

Figure 50:
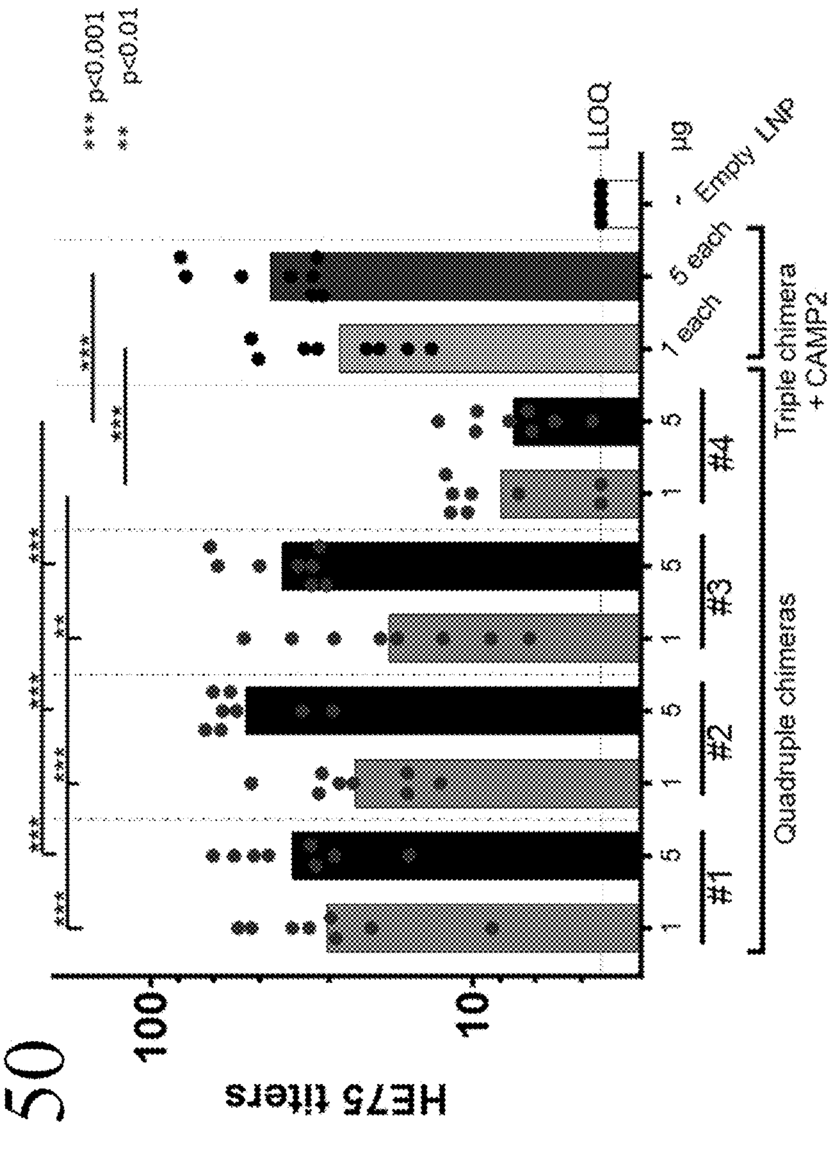
FIG. 50 shows co-hemolytic neutralizing titers of IgG purified from individual sera (day 42 after first immunization) of mice immunized twice at 4 weeks interval with the same mRNA constructs, at the same doses and encapsulated in the same LNP, as described in FIGS. 47A-47D. LNP alone served as a negative control. LLOQ=lowest limit of quantification

Both the "quadruple chimera" formulations and the "bivalent combination" formulation elicited antibodies which neutralize the co-hemolytic activity of CAMP2, as measured with a CAMP2 co-hemolytic neutralization assay (FIG. 50).

At equivalent dose, all quadruple chimeras (except quadruple chimera #4) and the bivalent combination elicited comparable co-hemolytic activity neutralization HE75 titers.

Correlations Between Antibody Responses Elicited by Chimeric *C. acnes* DsA1 DsA2 PITP CAMP2 mRNA Constructs and a Bivalent Combination of a CAMP2-TMB mRNA Construct and a DsA1 DsA2 PITP mRNA Construct Good and significant Pearson correlations (r values ranging from 0.8 to 0.9 and all p-values below 0.001) were demonstrated between ELISA anti-DsA1 and -DsA2 IgG titers. Surface Binding titers and Opsonophagocytic Killing titers performed on NCTC737 *C. acnes* strain.

Good and significant Pearson correlations (r values ranging from 0.69 to 0.77 and all p-values below 0.001) were also demonstrated between ELISA anti-PITP IgG titers. Surface Binding titers and Opsonophagocytic Killing titers on KPA171202 *C. acnes* strain.

Finally, a good and significant Pearson correlation (r value of 0.82 with a p-value below 0.001) was demonstrated between ELISA anti-CAMP2 IgG titers and the neutralization titer of CAMP2 co-hemolytic activity.

Conclusion

Overall, all quadruple chimeras induced functional antibody responses, which were comparable to the ones induced by the bivalent combination for the higher dose of 5 μg, except for the quadruple chimera #4 comprising the C-ter portion of CAMP2, relatively to the CAMP2 response. The high correlation of results between all readouts consolidates the conclusions of this study, and quadruple chimeras appear to be of interest for use as acne antigens. Compared to the bivalent combination, the quadruple chimeras could offer advantages as they may help limiting reactogenicity (by allowing to use a lower amount of cationic lipid/LNP per dose) and may allow an easier, faster and less expensive manufacturing process.

Example 14—Synthesis of IS-001 According to Scheme 3

Scheme 3: General Synthetic Scheme for Lipid of Formula (XI)

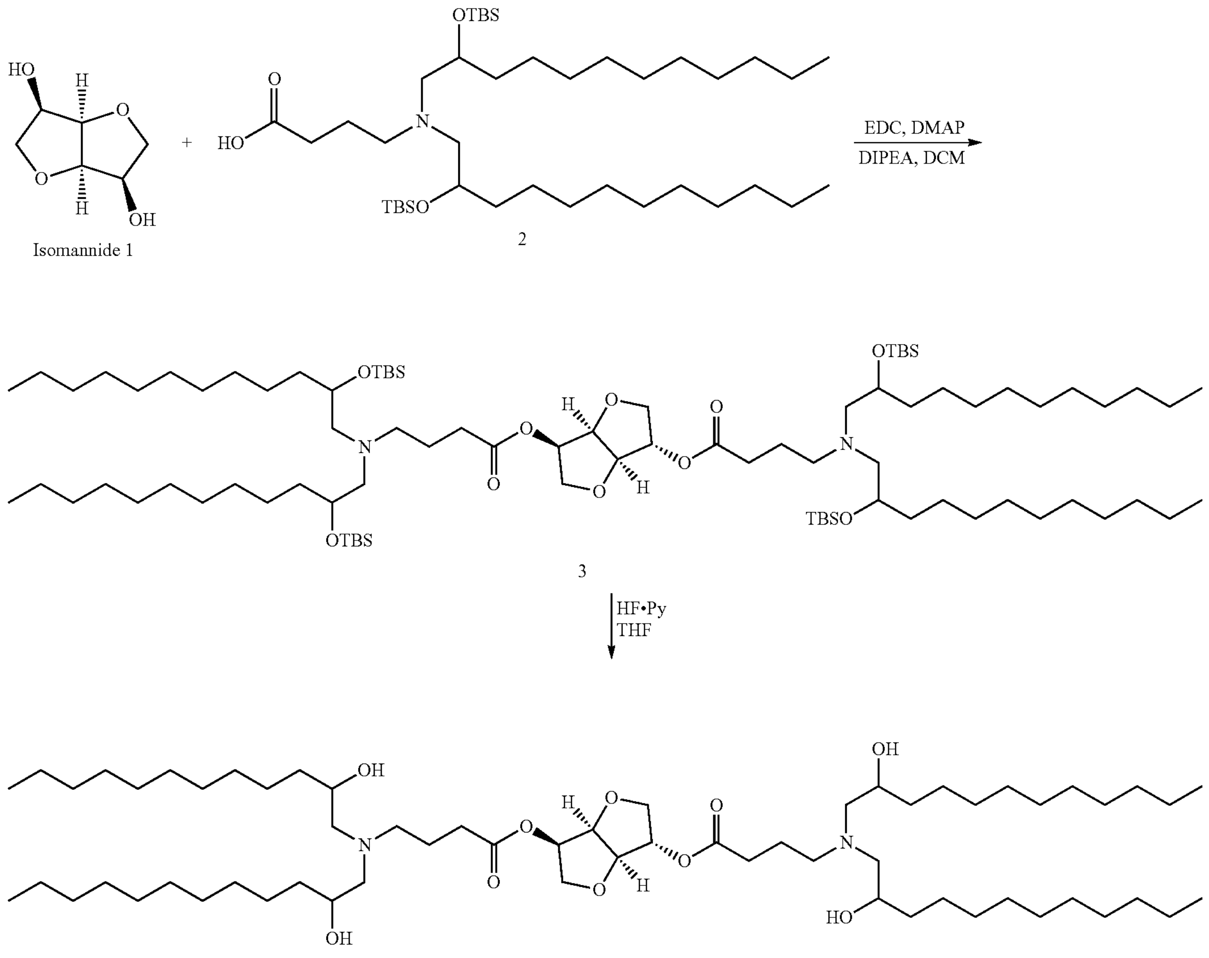

Isomannide 1

2

3

IS-001

Abbreviations:
- DCM: Dichloromethane
- DIPEA: N,N-Diisopropylethylamine
- DMAP: 4-Dimethylaminopyridine
- EDC: 1-Ethyl-3-(3-dimethylaminopropyl) carbodiimide
- EtOAc: Ethyl acetate
- NaHCO3: Sodium hydrogencarbonate
- Py: Pyridine
- $Na_2SO4$: Sodium Sulfate
- TEA: Triethylamine
- TFA: Trifluoroacetic Acid
- MS: Mass spectrometry
- ESI-MS: Electrospray ionization mass spectrometry
- TLC: Thin Layer Chromatography Step 1: Synthesis of Intermediate (3)

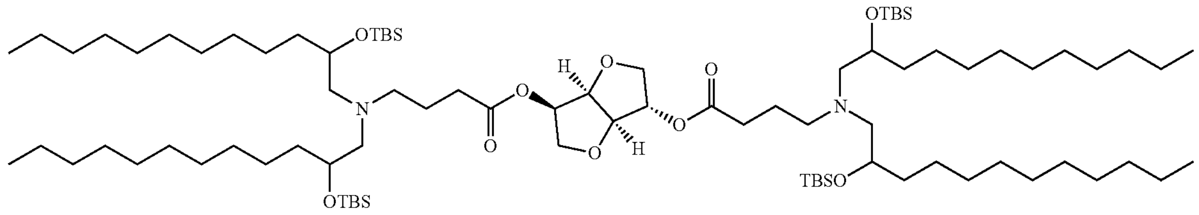 [SMILES: CCCCCCCCCCC(CN(CCCC(=O)O[C@H]1CO[C@H]2[C@@H]1OC[C@H]2OC(=O)CCCN(CC(CCCCCCCCCC)O[Si](C)(C)C(C)(C)C)CC(CCCCCCCCCC)O[Si](C)(C)C(C)(C)C)CC(CCCCCCCCCC)O[Si](C)(C)C(C)(C)C)O[Si](C)(C)C(C)(C)C]

As depicted in Scheme 3: To a solution of acid (2) (1.2 g, 1.71 mmol) and isosorbide (1) (0.100 g, 0.68 mmol) in dichloromethane (10 mL) were added DIPEA (0.95 mL, 5.47 mmol), DMAP (0.084 g, 0.68 mmol) and EDC (0.393 g, 2.05 mmol). The resulting mixture was stirred at room temperature for overnight. After 16 h, MS and TLC (30% EtOAc in hexanes) analysis indicated completion of the reaction. The reaction mixture was diluted with dichloromethane and washed with saturated $NaHCO_3$ solution, water and brine solution. The organic layer was dried over anhydrous $Na_2SO4$ and concentrated. The crude residue was purified, and the desired product was eluted at 6% EtOAc in hexanes. The product containing fractions were concentrated to obtain 0.72 g (69%) of pure product.

Results:

ESI-MS: Calculated $C_{86}H_{177}N_2O_{10}Si_4$, $[M+H^+]$=1510.25, Observed=1510.3 and 755.4 $[M/2+H^+]$ Step 2: Synthesis of IS-001

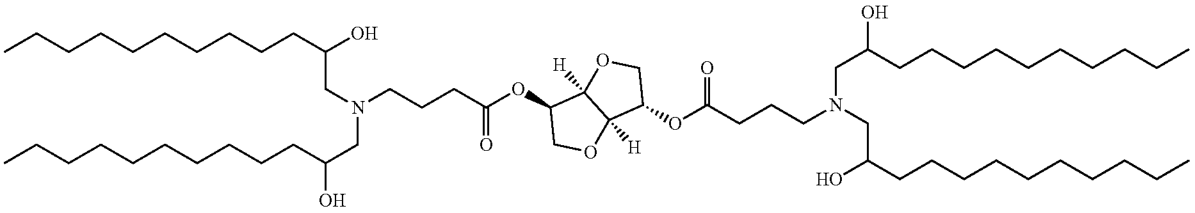 [SMILES: CCCCCCCCCCC(O)CN(CCCC(=O)O[C@H]1CO[C@H]2[C@@H]1OC[C@H]2OC(=O)CCCN(CC(O)CCCCCCCCCC)CC(O)CCCCCCCCCC)CC(O)CCCCCCCCCC]

As depicted in Scheme 3: To a solution of Intermediate (3) (0.72 g, 0.476 mmol) in tetrahydrofuran (4 mL) was added hydrogen fluoride (70% HF.py complex, 2 mL, 14.298 mmol) at 0° C., and stirred at the same temperature for 5 minutes. Then reaction mixture was warmed to room temperature and stirred for 16 h. MS analysis indicated completion of the reaction. The reaction mixture was diluted with ethyl acetate, quenched by slow addition of solid $NaHCO_3$ at 0° C. followed by saturated $NaHCO_3$ solution. The organic layer was washed with sat. $NaHCO_3$ solution, water and brine. Then dried over anhydrous $Na_2SO4$ and concentrated. The crude residue was purified, and the desired product was eluted at 65% EtOAc in hexanes. The purest fractions were concentrated to obtain 0.120 g (24%) of pure product.

Results:

$^1H$ NMR (400 MHZ, $CDCl_3$) δ 5.30-5.00 (m, 2H), 4.97-4.68 (m, 2H), 4.55-3.71 (m, 8H), 3.57-2.92 (m, 8H), 2.84-2.04 (m, 8H), 1.99-1.01 (m, 76H), 0.88 (t, J=6.8 Hz, 12H).

ESI-MS: Calculated $C_{62}H_{121}N_2O_{10}$, $[M+H^+]$=1053.90, Observed=1053.2 and 527.3 $[M/2+H^+]$

Example 15—Synthesis and Characterisation of Modified CAMP2 mRNA Constructs

Plasmids with a DNA sequence encoding a modified CAMP2 polypeptide (a CAMP2 sequence, a signal sequence (HA SS) and a transmembrane domain sequence (HA TMB) of Influenza Hemagglutinin (HA, H1N1 A/Caledonia/20/1999; SEQ ID NO: 84) at N-terminus and C-terminus respectively) operably linked to RNA polymerase promoter were linearized with a restriction enzyme and purified, mRNA transcripts were synthesized using modified nucleotides (in which all uridine nucleosides were replaced with 1-methyl pseudo uridine) by in vitro transcription using SP6 RNA Polymerase from the purified and linearized plasmid as described in US20230407358. The purified mRNA from the in vitro transcription step was capped and tailed as described in US20230407358.

Four mRNA constructs were generated from different plasmid sequences:

mRNA #1 comprising SEQ ID NO: 90 mRNA #2 comprising SEQ ID NO: 91 mRNA #3 comprising SEQ ID NO: 391 mRNA #4 comprising SEQ ID NO: 392.

```
                                          (SEQ ID NO: 265)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG,
```

-continued

```
a 3' UTR from hGH given by the sequence:
                                          (SEQ ID NO : 266)
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAU

C,
and

a poly A tail.
```

and a poly A tail.

With respect to mRNA size, tail size, % of tailed population and cap1%, all mRNAs met the targeted specifications (see Table 12). Tailing of the mRNA transcripts was assessed by capillary electrophoresis as described in US20230407358. The length of the mRNA tail was measured using capillary electrophoresis on a Fragment Analyzer instrument (Advanced Analytical). Capping of the mRNA transcripts was assessed by liquid chromatography mass spectrometry (LC/MS) as described in US20230407358.

TABLE 12

Characterisation of HA SS_CAMP2_WT_HA TMB mRNAs

| Construct sequence | Tail Length (nt) | % Tailing | Cap1 % |
|---|---|---|---|
| SEQ ID NO: 90 | 455 | 95.5% | 91% |
| SEQ ID NO: 91 | 430 | 97% | 97% |
| SEQ ID NO: 391 | 481 | 86% | 88% |
| SEQ ID NO: 392 | 423 | 95% | 95% |

mRNAs comprising the sequence according to SEQ ID NO: 90, 91 or 392 showed higher % of tailed/capped product. Higher % of tailed/capped product should result in better translation efficiency.

Polypeptide Sequences

TABLE 5

| SEQ ID NO | protein sequence | name | Alternative name | contains a secretion signal peptide sequence according to SEQ ID NO | contains a *C. acnes* antigen according to SEQ ID NO | contains a TMB sequence according to SEQ ID NO | Encoded, for example, by the nucleotide sequence according to SEQ ID NO |
|---|---|---|---|---|---|---|---|
| 1 | | | rProt CAMP2 | | 43 | | 289 |
| 2 | | ssHA_CAMP2_ WT_GA | mRNA/ssHA_CAMP2_ WT_GA | 42 | 44 | | 87 |
| 3 | | ssHA_CAMP2_ WT_GS | mRNA/ssHA_CAMP2_ WT_GS | 42 | 45 | | 88 |
| 4 | | ssHA_CAMP2_ WT_G+ | mRNA/HA SS_CAMP2_ WT | 42 | 46 | | 89 |
| 5 | | CAMP2_WT_HA TMB | mRNA/HA SS_CAMP2_ WT_HA TMB #1 | 42 | 47 | 84 | 90 |
| 6 | MKAKLLVLLCTFTATYAVEPT TTISATSTHELSASDARNSIQ LLNAHIATLQSVQKSVPGSDY SDQIRDLLKAAFDLRGLIETL AHGGIPFYDPSTIMPRIKLVA TTIDTIHTATTTLQNKVRPAH VELGLEVTKAVLLTANPASTA KELDAEGAALKARLEKVSQYP DLTPNDVATVYVRTNFSKTIW QVRANRDRYILGHKSAAVYKT LNHAITKAVGVRLNPKTTVGN IQAARTELLAAYQTAFNSPDV KKAAsgsILAIYSTVASSLVL LVSLGAISFgsg | CAMP2_WT_HA TMB | mRNA/HA SS_CAMP2_ WT_HA TMB #2 | 42 | 48 | 84 | 91 |
| 7 | | | mRNA/NA TMB_ CAMP2_WT | | 49 | | 92 |
| 8 | | | mRNA/NA TMB_ CAMP2_Nglyc-neg | | 50 | | 93 |
| 9 | | CAMP2_G-_HA TMB | mRNA/HA SS_CAMP2_ Nglyc-neg_HA TMB | 42 | 51 | 84 | 94 |
| 10 | | | mRNA/ssHA CAMP2_ G-GA | 42 | 52 | | 95 |
| 11 | | | mRNA/ssHA CAMP2_ G-GS | 42 | 53 | | 96 |
| 12 | | ssHA_CAMP2_ WT_G- | mRNA/HA SS_CAMP2_ Nglyc-neg | 42 | 54 | | 97 |
| 13 | | ssHA_CAMP2_ mL | mRNA/HA SS_CAMP2_ mL | 42 | 55 | | 98 |
| 14 | | ssHA_CAMP2_ G(-)_mL | mRNA/HA SS_CAMP2_ Nglyc-neg_mL | 42 | 56 | | 99 |
| 15 | | ssHA CAMP2 mCter | mRNA/HA SS_CAMP2_ mCter | 42 | 57 | | 100 |
| 16 | | ssHA_CAMP2_ G-_mCter | mRNA/HA SS_CAMP2_ Nglyc-neg_mCter | 42 | 58 | | 101 |
| 17 | | ssHA_DSA1_ Native_TMB_ WT_trunc | mRNA/HA SS_DSA1_ HA TMB | 42 | 59 | 85 | 102 |
| 18 | | ssHA_DSA1_ WT_trunc | mRNA/HA SS_DSA1_ WT trunc | 42 | 60 | | 103 |

TABLE 5-continued

| | | | | | | | |
|---|---|---|---|---|---|---|---|
| 19 | | ssHA_DSA1_SGS_TMB_WT_trunc | mRNA/HA SS_DSA1_HA TMB-sgs linker | 42 | 61 | 84 | 104 |
| 20 | | ssHA_DSA2_Native_TMB_WT_trunc | mRNA/HA SS_DSA2_HA TMB | 42 | 62 | 85 | 105 |
| 21 | | ssHA_DSA2_SGS_TMB_WT_trunc | mRNA/HA SS_DSA2_HA TMB-sgs linker | 42 | 63 | 84 | 106 |
| 22 | | ssHA_DSA2_WT_trunc | mRNA/HA SS_DSA2_WT trunc | 42 | 64 | | 107 |
| 23 | | ssHA_DSA2_WT_trunc_mutH | mRNA/HA SS_DSA2_mutH | 42 | 65 | | 108 |
| 24 | | ssHA_DSA2_Native_TMB_WT_trunc_mut | mRNA/HA SS_DSA2-mutH_HA TMB | 42 | 66 | 85 | 109 |
| 25 | | ssHA_DSA2_SGS_TMB_WT_trunc_mut | mRNA/HA SS_DSA2-mutH_HA TMB-sgs linker | 42 | 67 | 84 | 110 |
| 26 | | | mRNA/HA SS_DSA2-Nglyc-neg_HA TMB-sgs linker | 42 | 68 | 84 | 111 |
| 27 | | | mRNA/HA SS_DSA2-Nglyc-neg_HA TMB | 42 | 69 | 86 | 112 |
| 28 | MKAKLLVLLCTFTATYASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPT | ssHA_H4_V3 | mRNA/ssHA H4-V3 | 42 | 70 | | 113 |
| 29 | | | rProt H4-V3 | | 71 | | |
| 30 | | | mRNA/ssHA H4-V3 Nglyc-neg | 42 | 72 | | 114 |
| 31 | MKAKLLVLLCTFTATYAAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKTDHSDDTRTPVTYREATPAPTGPKTPIAPSKQPSKQAAPSKQVKPSKQAGPNKQSTTPQQKTAEHRSQTPAAHRTMTKQVSTIGASKVTSGSLTWGIRTSFTSYLRGPIANGSWKLSGGANWNGSAFTFPLTSGSFDPATKSGSLKYSGSVHMTGHHGILDMTLAEPSLQIKGSTGHLYLDVKSSSMDGKKTNYGRVDFATFGVSVSGNAAIKGSPVKLTATGAKAFAGFYRAGEPMNPLSTNLTLSAEKVSHNVTVDAVTGKVIGDDSGKGAGRGLPVT | ssHA_P028_V7 | mRNA/P28-V7 | 42 | 73 | | 115 |

TABLE 5-continued

| | | | | | | | |
|---|---|---|---|---|---|---|---|
| 32 | | | rProt P28-V7 | | 74 | | |
| 33 | | ssHA_PITP_ WT_trunc | mRNA/ssHA PITP_ WT_trunc | 42 | 75 | | 117 |
| 34 | | | mRNA/ssHA PITP_ Nglyc-neg | 42 | 76 | | 118 |
| 35 | | P028_V7_ Glyneg | mRNA/ssHA_P28-V7_ Nglyc-neg | 42 | 77 | | 119 |
| 36 | | ssHA_PITP_ SGS_TMB_HA_ WT_trunc | mRNA/ssHA PITP_ WT_HA TMB-sgs linker | 42 | 78 | 84 | 120 |
| 37 | | | mRNA/ssHA_PITP_ Nglyc-neg_HA TMB-sgs linker | 42 | 79 | 84 | 121 |
| 38 | MKAKLLVLLCTFTATYASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPTAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKTDHSDDTRTPVTYREATPAPTGPKTPI | nCO-ssHA_H4-V3-f-PRO-028-V7-F16 | H4-V3-f-PRO-028-V7-F16, triple chimera P22/P27/P28 | 42 | 80 | | 122 |
| 39 | | nCO-ssHA PRO-H4-V3-lowglyc | H4-V3 low glyc | 42 | 81 | | 123 |
| 40 | MKAKLLVLLCTFTATYASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKAMGPPKPTGGGGGAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKGDHGDDTRTPVGYR | gc.CO-ssHA PRO-028-V7-C12-lowglyc | PRO-028-V7-C12 low glyc | 42 | 82 | | 124 |
| 41 | MKAKLLVLLCTFTATYASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATA | nCO-ssHA PRO-028-V7-C12 | PRO-028-V7-C12, triple chimera P22/P27/P28 | 42 | 83 | | 125 |

TABLE 5-continued

| | | |
|---|---|---|
| | LNPALGPIAKFELIKAEIAAQ<br>AALLIRRGVHLQKAAIEHVIG<br>RAFDAAVATAIISSPILSARI<br>VTHLVRAGIDKSIAISLAPHI<br>VKRLAKEPLLAFNTAKLMKNI<br>TRQIVDVITADKAIKTAEQLE<br>KELPALDDLVKKASSPPKPTP<br>TPTPTPTAGPTVTVIPVGREG<br>GDITISGKGFSTTGFGVYVAV<br>APASVPEFYGNSDKFYGYDPS<br>KDTTESPSTIWVYTPSQKAIG<br>SRFAQGRPMNNDGSFTITMKA<br>PPFEQGKDFVVLTTKAHGVGK<br>TDHSDDTRTPVTYR | |
| 313 | *C. acnes* CAMP2 from strain ATCC6919 | 339 |

| SEQ ID NO | contains a *C. acnes* antigen according to SEQ ID NO |
|---|---|
| 314 | 339 |
| 315 | 340 |
| 316 | 341 |
| 317 | 342 |
| 318 | 343 |
| 319 | 344 |
| 320 | 345 |
| 321 | 346 |
| 322 | 347 |
| 323 | 348 |
| 324 | 349 |
| 325 | 350 |
| 326 | 351 |
| 327 | 352 |
| 328 | 353 |
| 329 | 354 |
| 330 | 355 |
| 331 | 356 |
| 332 | 357 |
| 333 | 358 |
| 334 | 359 |
| 335 | 360 |
| 336 | 361 |
| 337 | 362 |
| 338 | 363 |

TABLE 5-continued

| SEQ ID NO | Protein sequence | name | Alternative name | contains a secretion signal peptide sequence according to SEQ ID NO | contains a *C. acnes* antigen according to SEQ ID NO | contains a TMB sequence according to SEQ ID NO | Encoded, for example, by the nucleotide sequence according to SEQ ID NO |
|---|---|---|---|---|---|---|---|
| 367 | | P028 V7 C12 lowglyc V2 | | 42 | 368 | | |
| 369 | MKAKLLVLLCTFTATYAVEPTTTISATSTHELSASDARNSIQLLNAHIATLQSVQKSVPGSDYSDQIRDLLKAAFDLRGLIETLAHGGIPFYDPSTIMPRIKLVATTIDTIHTATTITTLQNKVRPAHVELGLEVTKAVLLTANPASTAKELDAEGAALKARLEKVSQYPDLTPNDVATVYVRTNFSKTIWQVRANRDRYILGHKSAAVYKTLNHAITKAVGVRLNPKTTVGNIQAARTELLAAYQTAFNSPDVEKKAASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPTAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKTDHSDDTRTPVTYREATPAPTGPKTPISGSILAIYSTVASSLVLLVSLGAISFGSG | Quad CAMP2 H4V3 f PRO 028 V7 F16_sgs HA TM_gsg_ssHA | | | 373 | | 377, 378 |
| 370 | MKAKLLVLLCTFTATYAVEPTTTISATSTHELSASDARNSIQLLNAHIATLQSVQKSVPGSDYSDQIRDLLKAAFDLRGLIETLAHGGIPFYDPSTIMPRIKLVATTIDTIHTATTTLQNKVRPAHVELGLEVTKAVLLTANPASTAKELDAEGAALKARLEKVSQYPDLTPNDVATVYVRTNFSKTIWQVRANRDRYILGHKSAAVYKTLNHAITKAVGVRLNPKTTVGNIQAARTELLAAYQTAFNSPDVKKAASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPTAGPTVTVIPVGREGGDITISGKGFSTTGFGVYVAVAPASVPEFYGNSD | Quad-CAMP2-H4V3-f-PRO-028-V7-F16_ssHA | | | 374 | | 380 |

TABLE 5-continued

| | | | | |
|---|---|---|---|---|
| | KFYGYDPSKDTTESPSTIWVY TPSQKAIGSRFAQGRPMNNDG SFTITMKAPPFEQGKDFVVLT TKAHGVGKTDHSDDTRTPVTY REATPAPTGPKTPI | | | |
| 371 | MKAKLLVLLCTFTATYAVEPT TTISATSTHELSASDARNSIQ LLNAHIATLQSVQKSVPGSDY SDQIRDLLKAAFDLRGLIETL AHGGIPFYDPSTIMPRIKLVA TTIDTIHTATTTLQNKVRPAH VELGLEVTKAVLLTANPASTA KELDAEGAALKARLEKVSQYP DLTPNDVATSSNRPRSVAQAA IATDGKGIIDKDSRDAVINDA KLRAAIAGALVKAGFSSADAV ALAPRIAKEMAKEGVLLINHH KLKALIGAQLGLLTDAKIQRA AAAVDLGIKATLAATIIPNAL GSAAFKNAVIANLVAAGIDKH LARATAVAIVATALNPALGPI AKFELIKAEIAAQAALLIRRG VHLQKAAIEHVIGRAFDAAVA TAIISSPILSARIVTHLVRAG IDKSIAISLAPHIVKRLAKEP LLAFNTAKLMKNITRQIVDVI TADKAIKTAEQLEKELPALDD LVKKASSPPKPTPTPTPTPTA GPTVTVIPVGREGGDITISGK GFSTTGFGVYVAVAPASVPEF YGNSDKFYGYDPSKDTTESPS TIWVYTPSQKAIGSRFAQGRP MNNDGSFTITMKAPPFEQGKD FVVLTTKAHGVGKTDHSDDTR TPVTYREATPAPTGPKTPI | Quad-CAMP2-Nter-link-H4V3-f-PRO-028-V7-F16_ssHA | 375 | 381, 382 |
| 372 | MKAKLLVLLCTFTATYASSNR PRSVAQAAIATDGKGIIDKDS RDAVINDAKLRAAIAGALVKA GFSSADAVALAPRIAKEMAKE GVLLINHHKLKALIGAQLGLL TDAKIQRAAAAVDLGIKATLA ATIIPNALGSAAFKNAVIANL VAAGIDKHLARATAVAIVATA LNPALGPIAKFELIKAEIAAQ AALLIRRGVHLQKAAIEHVIG RAFDAAVATAIISSPILSARI VTHLVRAGIDKSIAISLAPHI VKRLAKEPLLAFNTAKLMKNI TRQIVDVITADKAIKTAEQLE KELPALDDLVKKASSPPKPTP TPTPTPTAGPTVTVIPVGREG GDITISGKGFSTTGFGVYVAV APASVPEFYGNSDKFYGYDPS KDTTESPSTIWVYTPSQKAIG SRFAQGRPMNNDGSFTITMKA PPFEQGKDFVVLTTKAHGVGK TDHSDDTRTPVTYREATPAPT GPKTPIVYVRTNFSKTIWQVR ANRDRYILGHKSAAVYKTLNH AITKAVGVRLNPKTTVGNIQA ARTELLAAYQTAFNSPDVKKA A | Quad-H4V3-f-PRO-028-V7-F16-nolink-Cter-CAMP2_ssHA | 376 | 383, 394 |

TABLE 6

| SEQ ID NO | Encoded, for example, by the nucleotide sequence according to SEQ ID NO |
|---|---|
| 42 | any one of 126-152, 311 |
| 44 | 153 |
| 45 | 154 |

TABLE 6-continued

| | |
|---|---|
| 46 | 155 |
| 47 | 156 |
| 48 | 157 |
| 49 | 158 |
| 50 | 159 |
| 51 | 160 |
| 52 | 161 |
| 53 | 162 |
| 54 | 163 |
| 55 | 164 |
| 56 | 165 |
| 57 | 166 |
| 58 | 167 |
| 59 | 168 |
| 60 | 169 |
| 61 | 170 |
| 62 | 171 |
| 63 | 172 |
| 64 | 173 |
| 65 | 174 |
| 66 | 175 |
| 67 | 176 |
| 68 | 177 |

| SEQ ID NO | Amino acid sequence | Encoded, for example, by the nucleotide sequence according to SEQ ID NO |
|---|---|---|
| 70 | SSNRPRSVAQAAIATDGKGIIDKDSRDAVINDAKLRAAIAGALVKAGFSSADAVALAPRIAKEMAKEGVLLINHHKLK ALIGAQLGLLTDAKIQRAAAAVDLGIKATLAATIIPNALGSAAFKNAVIANLVAAGIDKHLARATAVAIVATALNPAL GPIAKFELIKAEIAAQAALLIRRGVHLQKAAIEHVIGRAFDAAVATAIISSPILSARIVTHLVRAGIDKSIAISLAPH IVKRLAKEPLLAFNTAKLMKNITRQIVDVITADKAIKTAEQLEKELPALDDLVKKASSPPKPTPTPTPTPT | 179 |
| 71 | MSSNRPRSVAQAAIATDGKGIIDKDSRDAVINDAKLRAAIAGALVKAGFSSADAVALAPRIAKEMAKEGVLLINHHKL KALIGAQLGLLTDAKIQRAAAAVDLGIKATLAATIIPNALGSAAFKNAVIANLVAAGIDKHLARATAVAIVATALNPA LGPIAKFELIKAEIAAQAALLIRRGVHLQKAAIEHVIGRAFDAAVATAIISSPILSARIVTHLVRAGIDKSIAISLAP HIVKRLAKEPLLAFNTAKLMKNITRQIVDVITADKAIKTAEQLEKELPALDDLVKKASSPPKPTPTPTPTPT | 180 |
| 72 | SSNRPRSVAQAAIATDGKGIIDKDSRDAVINDAKLRAAIAGALVKAGFSSADAVALAPRIAKEMAKEGVLLINHHKLK ALIGAQLGLLTDAKIQRAAAAVDLGIKATLAATIIPNALGSAAFKNAVIANLVAAGIDKHLARATAVAIVATALNPAL GPIAKFELIKAEIAAQAALLIRRGVHLQKAAIEHVIGRAFDAAVATAIISSPILSARIVTHLVRAGIDKSIAISLAPH IVKRLAKEPLLAFNTAKLMKQITRQIVDVITADKAIKTAEQLEKELPALDDLVKKASSPPKPTPTPTPTPT | 181 |
| 73 | AGPTVTVIPVGREGGDITISGKGFSTTGFGVYVAVAPASVPEFYGNSDKFYGYDPSKDTTESPSTIWVYTPSQKAIGS RFAQGRPMNNDGSFTITMKAPPFEQGKDFVVLTTKAHGVGKTDHSDDTRTPVTYREATPAPTGPKTPIAPSKQPSKQA APSKQVKPSKQAGPNKQSTTPQQKTAEHRSQTPAAHRTMTKQVSTIGASKVTSGSLTWGIRTSFTSYLRGPIANGSWK LSGGANWNGSAFTFPLTSGSFDPATKSGSLKYSGSVHMTGHHGILDMTLAEPSLQIKGSTGHLYLDVKSSSMDGKKTN YGRVDFATFGVSVSGNAAIKGSPVKLTATGAKAFAGFYRAGEPMNPLSTNLTLSAEKVSHNVTVDAVTGKVIGDDSGK GAGRGLPVT | 182 |

TABLE 6-continued

| | | |
|---|---|---|
| 74 | | 183 |
| 75 | | 184 |
| 76 | | 185 |
| 77 | | 186 |
| 78 | | 187 |
| 79 | | 188 |
| 80 | SSNRPRSVAQAAIATDGKGIIDKDSRDAVINDAKLRAAIAGALVKAGFSSADAVALAPRIAKEMAKEGVLLINHHKLK ALIGAQLGLLTDAKIQRAAAAVDLGIKATLAATIIPNALGSAAFKNAVIANLVAAGIDKHLARATAVAIVATALNPAL AKEPLLAFNTAKLMKNITRQIVDVITADKAIKTAEQLEKELPALDDLVKKASSPPKPTPTPTPTPTAGPTVTVIPVGR EGGDITISGKGFSTTGFGVYVAVAPASVPEFYGNSDKFYGYDPSKDTTESPSTIWVYTPSQKAIGSRFAQGRPMNNDG SFTITMKAPPFEQGKDFVVLTTKAHGVGKTDHSDDTRTPVTYREATPAPTGPKTPI | 189 |
| 81 | | 190 |
| 82 | SSNRPRSVAQAAIATDGKGIIDKDSRDAVINDAKLRAAIAGALVKAGFSSADAVALAPRIAKEMAKEGVLLINHHKLK ALIGAQLGLLTDAKIQRAAAAVDLGIKATLAATIIPNALGSAAFKNAVIANLVAAGIDKHLARATAVAIVATALNPAL GPIAKFELIKAEIAAQAALLIRRGVHLQKAAIEHVIGRAFDAAVATAIISSPILSARIVTHLVRAGIDKSIAISLAPH IVKRLAKEPLLAFNTAKLMKNITRQIVDVITADKAIKTAEQLEKELPALDDLVKKAMGPPKPTGGGGGAGPTVTVIPV GREGGDITISGKGFSTTGFGVYVAVAPASVPEFYGNSDKFYGYDPSKDTTESPSTIWVYTPSQKAIGSRFAQGRPMNN DGSFTITMKAPPFEQGKDFVVLTTKAHGVGKGDHGDDTRTPVGYR | 191 |
| 83 | SSNRPRSVAQAAIATDGKGIIDKDSRDAVINDAKLRAAIAGALVKAGFSSADAVALAPRIAKEMAKEGVLLINHHKLK ALIGAQLGLLTDAKIQRAAAAVDLGIKATLAATIIPNALGSAAFKNAVIANLVAAGIDKHLARATAVAIVATALNPAL GPIAKFELIKAEIAAQAALLIRRGVHLQKAAIEHVIGRAFDAAVATAIISSPILSARIVTHLVRAGIDKSIAISLAPH IVKRLAKEPLLAFNTAKLMKNITRQIVDVITADKAIKTAEQLEKELPALDDLVKKASSPPKPTPTPTPTPTAGPTVTV IPVGREGGDITISGKGFSTTGFGVYVAVAPASVPEFYGNSDKFYGYDPSKDTTESPSTIWVYTPSQKAIGSRFAQGRP MNNDGSFTITMKAPPFEQGKDFVVLTTKAHGVGKTDHSDDTRTPVTYR | 192 |
| 84 | sgsILAIYSTVASSLVLLVSLGAISFgsg | 193, 194, 195, 197, 198, 200, 201, 395 or 396 |
| 85 | | 196 or 199 or 312 |
| 86 | | 196 or 199 or 312 |
| 203 | **VEPTTTISATSTHELSASDARNSIQLLNAHIATLQSVQKSVPGSDYSDQIRDLLKAAFDLRGLIETLAHGGIPFYDPS TIMPRIKLVATTIDTIHTATTTLQNKVRPAHVELGLEVTKAVLLTANPASTAKELDAEGAALKARLEKVS**QYPDLTPN DVATVYVRTNFSKTIWQVRANRDRYILGHKSAAVYKTLNHAITKAVGVRLNPKTTVGNIQAARTELLAAYQTAFNSPD VKKAA | |
| 207 | **VEPTTTISATSTHELSASDARNSIQLLNAHIATLQSVQKSVPGSDYSDQIRDLLKAAFDLRGLIETLAHGGIPFYDPS TIMPRIKLVATTIDTIHTATTTLQNKVRPAHVELGLEVTKAVLLTANPASTAKELDAEGAALKARLEKVS**QYPDLTPN DVATVYVRTNFSKTIWQVRANRDRYILGHKSAAVYKTLNHAITKAVGVRLNPKTTVGNIQAARTELLAAYQTAFNSPD VKKAAsgsILAIYSTVASSLVLLVSLGAISFgsg | |

| SEQ ID NO | Encoded, for example, by the nucleotide sequence according to SEQ ID NO |
|---|---|
| 268 | 290 |
| 269 | 291 |
| 270 | 292 |
| 271 | 293 |
| 272 | 294 |
| 273 | 295 |
| 274 | 296 |
| 275 | 297 |
| 276 | 298 |

TABLE 6-continued

| | |
|---|---|
| 277 | 299 |
| 278 | 300 |
| 279 | 301 |
| 280 | 302 |
| 281 | 303 |
| 282 | 304 |
| 283 | 305 |
| 284 | 306 |
| 285 | 307 |
| 286 | 308 |
| 287 | 309 |
| 288 | 310 |

| SEQ ID NO | Amino acid sequence | Encoded, for example, by the nucleotide sequence according to SEQ ID NO |
|---|---|---|
| 368 | VAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIHIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKAITRQIVDVITADKAIKTAEQLEKELPALDDLVKKAMGPPKPTGGGGGAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKGDHGDDTRTPVGYR | |
| 373 | VEPTTTISATSTHELSASDARNSIQLLNAHIATLQSVQKSVPGSDYSDQIRDLLKAAFDLRGLIETLAHGGIPFYDPSTIMPRIKLVATTIDTIHTATTTLQNKVRPAHVELGLEVTKAVLLTANPASTAKELDAEGAALKARLEKVSQYPDLTPNDVATVYVRTNFSKTIWQVRANRDRYILGHKSAAVYKTLNHAITKAVGVRLNPKTTVGNIQAARTELLAAYQTAFNSPDVEKKAASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPTAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKTDHSDDTRTPVTYREATPAPTGPKTPI | 384, 383 |
| 374 | VEPTTTISATSTHELSASDARNSIQLLNAHIATLQSVQKSVPGSDYSDQIRDLLKAAFDLRGLIETLAHGGIPFYDPSTIMPRIKLVATTIDTIHTATTTLQNKVRPAHVELGLEVTKAVLLTANPASTAKELDAEGAALKARLEKVSQYPDLTPNDVATVYVRTNFSKTIWQVRANRDRYILGHKSAAVYKTLNHAITKAVGVRLNPKTTVGNIQAARTELLAAYQTAFNSPDVKKAASSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPTAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKTDHSDDTRTPVTYREATPAPTGPKTPI | 386, 387 |
| 375 | VEPTTTISATSTHELSASDARNSIQLLNAHIATLQSVQKSVPGSDYSDQIRDLLKAAFDLRGLIETLAHGGIPFYDPSTIMPRIKLVATTIDTIHTATTTLQNKVRPAHVELGLEVTKAVLLTANPASTAKELDAEGAALKARLEKVSQYPDLTPNDVATSSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPTAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKTDHSDDTRTPVTYREATPAPTGPKTPI | 388, 389 |
| 376 | SSNRPRSVAQAAIATDGKGIIDKDSRDAVINDAKLRAAIAGALVKAGFSSADAVALAPRIAKEMAKEGVLLINHHKLKALIGAQLGLLTDAKIQRAAAAVDLGIKATLAATIIPNALGSAAFKNAVIANLVAAGIDKHLARATAVAIVATALNPALGPIAKFELIKAEIAAQAALLIRRGVHLQKAAIEHVIGRAFDAAVATAIISSPILSARIVTHLVRAGIDKSIAISLAPHIVKRLAKEPLLAFNTAKLMKNITRQIVDVITADKAIKTAEQLEKELPALDDLVKKASSPPKPTPTPTPTPTAGPTVTVIPVGREGGDITISGKGFSTTGFGVYVAVAPASVPEFYGNSDKFYGYDPSKDTTESPSTIWVYTPSQKAIGSRFAQGRPMNNDGSFTITMKAPPFEQGKDFVVLTTKAHGVGKTDHSDDTRTPVTYREATPAPTGPKTPIVYVRTNFSKTIWQVRANRDRYILGHKSAAVYKTLNHAITKAVGVRLNPKTTVGNIQAARTELLAAYQTAFNSPDVKKAA | 390, 393 |

Nucleotide Sequences

TABLE 7

| SEQ ID NO | mRNA sequence | Name | Alter-native name | secretion signal peptide sequence according to SEQ ID NO | nucleo-tide sequence encoding a *C. acnes* antigen is according to SEQ ID NO: | contains a TMB sequence according to SEQ ID NO | Encodes the poly-peptide according to SEQ ID NO |
|---|---|---|---|---|---|---|---|
| 87 | | ssHA CAMP2_ WT_GA | mRNA/ ssHA_ CAMP2_ WT_GA | 126 | 153 | | 2 |
| 88 | | ssHA CAMP2_ WT_GS | mRNA/ ssHA_ CAMP2_ WT_GS | 127 | 154 | | 3 |
| 89 | | ssHA CAMP2_ WT_G+ | mRNA/ HASS_ CAMP2_ WT | 128 | 155 | | 4 |
| 90 | AUGAAGGCCAAGCUGCUGGUGCUGCUGUGCACC<br>UUCACCGCCACCUAUGCCGUCGAGCCCACCACC<br>ACCAUCUCCGCCACAUCCACACACGAACUGUCC<br>GCAAGCGACGCCAGAAACAGCAUCCAGCUGCUG<br>AACGCCCACAUCGCCACCCUCCAGAGCGUGCAG<br>AAGAGUGUGCCCGGCAGCGAUUAUAGCGACCAG<br>AUCCGGGACCUGCUCAAGGCCGCAUUCGACCUG<br>CGCGGCCUGAUCGAGACACUGGCUCAUGGCGGG<br>AUCCCCUUCUAUGAUCCCAGCACCAUCAUGCCC<br>AGGAUCAAGCUGGUCGCCACUACCAUCGACACC<br>AUCCACACCGCCACCACCACCCUGCAGAACAAA<br>GUGCGCCCCGCCCACGUGGAGCUGGGGCUGGAG<br>GUGACCAAAGCGGUGCUGCUGACAGCCAACCCU<br>GCAUCCACCGCCAAGGAGCUGGACGCAGAGGGC<br>GCUGCACUGAAGGCCCGGCUCGAGAAGGUGUCC<br>CAGUAUCCCGACCUGACCCCCAACGACGUGGCC<br>ACUGUGUACGUGCGGACCAACUUCAGCAAGACC<br>AUUUGGCAGGUCAGGGCCAAUAGAGACAGAUAC<br>AUCCUGGGGCACAAAAGCGCCGCCGUGUACAAG<br>ACCCUGAACCACGCCAUCACCAAGGCCGUGGGA<br>GUGCGGCUGAAUCCAAAGACCACCGUGGGCAAC<br>AUUCAGGCCGCCAGAACCGAGCUGCUGGCCGCC<br>UACCAGACAGCUUUCAAUAGCCCCGACGUGAAG<br>AAGGCCGCCUCCGGCAGCAUCCUGGCCAUCUAC<br>UCCACCGUGGCCUCCAGCCUGGUGCUGCUGGUG<br>AGCCUGGGCGCUAUCUCCUUCGGGUCUGGGUAA | CAMP2_WT_ HA TMB | mRNA/ HASS_ CAMP2_ WT_HA TMB #1 | 129 | 156 | 193 | 5 |
| 91 | aUgaaagccaagcUgcUggUgcUgcUcUgcacU<br>UUUaccgccaccUacgccgUggagcccaccaca<br>acaaUcagcgccacaUccacccacgaacUgagc<br>gccUccgacgccagaaaUUccaUccagcUgcUg<br>aacgcccacaUcgccacccUgcagagcgUgcag<br>aaaagcgUgcccggcUcUgaUUacagcgaccag<br>aUccgggaccUgcUgaaggccgccUUUgaccUg<br>agaggccUgaUcgagacacUggcccacggaggc<br>aUcccUUUcUacgaUccUagcaccaUcaUgccU<br>cggaUcaagcUggUggccacaacaaUcgacacc<br>aUccacaccgccaccaccacacUgcagaacaaa<br>gUgcggccUgcccaUgUggaacUgggccUggaa<br>gUgaccaaggccgUgcUgcUgacagccaaUccU<br>gcUagcacagccaaggaacUggaUgccgaggga<br>gccgcccUgaaggcUagacUggagaaggUgagc<br>cagUaccccgaccUgacccccaaUgacgUggca<br>accgUgUacgUgagaaccaaUUUcagcaagacc<br>aUcUggcaggUgcgggccaaUcgggacagaUac<br>aUccUgggccacaagagcgccgccgUgUacaag<br>acccUgaaUcacgccaUcaccaaggccgUgggc<br>gUgcggcUgaaUccUaagaccaccgUgggcaaU<br>aUccaggccgcccggacagaacUgcUggccgcc<br>UaccagacagccUUUaaUagcccUgaUgUgaag<br>aaggccgccagcgggagcaUUcUggccaUcUac | CAMP2_WT_ HA TMB | mRNA/ HASS_ CAMP2_ WT_HA TMB #2 | 130 | 157 | 194 | 6 |

TABLE 7-continued

| | | | | | | |
|---|---|---|---|---|---|---|
| | UcUaccgUggccUcUagccUggUgcUgcUggUg UcUcUgggagccaUUagcUUcggaUcUggcUga Uaa | | | | | |
| 92 | | mRNA/ NATMB_ CAMP2_ WT | | 158 | | 7 |
| 93 | | mRNA/ NATMB_ CAMP2_ Nglyc-neg | | 159 | | 8 |
| 94 | CAMP2_G-_HA TMB | mRNA/ HASS_ CAMP2_ Nglyc-neg_HA TMB | 131 | 160 | 195 | 9 |
| 95 | | mRNA/ ssHA_ CAMP2_ G-GA | | 161 | | 10 |
| 96 | | mRNA/ ssHA_ CAMP2_ G-GS | | 162 | | 11 |
| 97 | ssHA CAMP2_ WT_G- | mRNA/ HASS_ CAMP2_ Nglyc-neg | 132 | 163 | | 12 |
| 98 | ssHA CAMP2_ mL | mRNA/ HASS_ CAMP2_ mL | 133 | 164 | | 13 |
| 99 | ssHA CAMP2_ G(-)_mL | mRNA/ HASS_ CAMP2_ Nglyc-neg_mL | 311 | 165 | | 14 |
| 100 | ssHA CAMP2_ mCter | mRNA/ HASS_ CAMP2_ mCter | 134 | 166 | | 15 |
| 101 | ssHA CAMP2_ G-_mCter | mRNA/ HASS_ CAMP2_ Nglyc-neg_ mCter | 135 | 167 | | 16 |
| 102 | ssHA_DSA1_ Native_TMB_ WT_trunc | mRNA/ HASS_ DSAI_ HA TMB | 136 | 168 | 196 | 17 |
| 103 | ssHA_DSA1_ WT_trunc | mRNA/ HASS_ DSAI_ WT_ trunc | 137 | 169 | | 18 |
| 104 | ssHA_DSA1_ SGS_TMB_ WT_trunc | mRNA/ HASS_ DSAI_ HA TMB-sgs linker | 138 | 170 | 197 | 19 |

TABLE 7-continued

| | | | | | | | |
|---|---|---|---|---|---|---|---|
| 105 | | ssHA_DSA2_ Native_TMB_ WT_trunc | mRNA/ HASS_ DSA2_HA TMB | | 171 | | 20 |
| 106 | | ssHA_DSA2_ SGS_TMB_ WT_trunc | mRNA/ HASS_ DSA2_HA TMB-sgs linker | 139 | 172 | 198 | 21 |
| 107 | | ssHA_DSA2_ WT_trunc | mRNA/ HASS_ DSA2_WT trunc | 140 | 173 | | 22 |
| 108 | | ssHA_DSA2_ WT_trunc_ mutH | mRNA/ HASS_ DSA2_ mutH | 141 | 174 | | 23 |
| 109 | | ssHA_DSA2_ Native_TMB_ WT_trunc_ mut | mRNA/ HASS_ DSA2- mutH_ HA_TMB | 142 | 175 | 199 | 24 |
| 110 | | ssHA_DSA2_ SGS_TMB_ WT_trunc_ mut | mRNA/ HASS_ DSA2- mutH_ HA TMB- sgs linker | 143 | 176 | 200 | 25 |
| 111 | | | mRNA/ HASS_ DSA2- Nglyc- neg_HA TMB-sgs linker | 137 | 177 | 200 | 26 |
| 112 | | | mRNA/ HASS_ DSA2- Nglyc- neg_HA TMB | 137 | 178 | 312 | 27 |
| 113 | AUGAAGGCCAAGCUGCUGGUGCUGCUGUGCACA UUCACAGCAACCUAUGCAUCAUCCAACAGGCCU CGCUCCGUGGCCCAGGCUGCUAUUGCUACCGAC GGCAAGGGAAUCAUCGAUAAAGACUCCAGGGAU GCCGUGAUCAACGAUGCCAAGCUCCGGGCCGCA AUUGCCGGAGCCCUGGUGAAAGCCGGGUUCAGC UCCGCCGAUGCUGUGGCUCUGGCUCCAAGGAUU GCUAAGGAGAUGGCCAAAGAGGGGGUGCUGCUG AUUAACCACCACAAGCUGAAGGCACUGAUCGGA GCACAGCUGGGACUGCUGACUGACGCCAAAAUC CAGCGCGCCGCUGCAGCAGUCGACCUGGGCAUC AAGGCCACACUGGCUGCUACCAUCAUUCCUAAC GCUCUGGGCAGCGCAGCCUUUAAGAAUGCCGUU AUCGCCAAUCUCGUGGCUGCUGGAAUUGAUAAG CACCUGGCCAGAGCCACAGCUGUGGCCAUCGUG GCCACUGCCCUGAACCCAGCAUUGGGCCCUAUC GCUAAGUUUGAGCUGAUUAAGGCCGAGAUCGCC GCUCAGGCUGCCCUGCUGAUUCGCAGGGGAGUG CACCUGCAGAAGGCUGCCAUCGAGCACGUCAUC GGCAGAGCAUUCGACGCCGCUGUCGCCACUGCU AUCAUCUCUAGCCCAAUCCUGAGCGCCAGGAUC GUCACUCACCUGGUGAGAGCUGGGAUUGACAAA UCCAUCGCUAUCAGCCUGGCCCCUCACAUCGUG AAGAGGCUGGCUAAGGAACCACUGCUGGCUUUU AACACUGCUAAGCUGAUGAAGAAUAUUACAAGA CAGAUCGUGGACGUCAUCACCGCCGACAAAGCC AUCAAGACAGCCGAGCAGCUCGAGAAGGAGCUG CCUGCCCUGGAUGACCUGGUGAAGAAGGCAUCC | ssHA_H4_V3 | mRNA/ ssHAH4- V3 | 144 | 179 | | 28 |

TABLE 7-continued

| | | | | | | | |
|---|---|---|---|---|---|---|---|
| | UCCCCCCCUAAGCCAACCCCUACCCCAACCCCU<br>ACACCUACUUAA | | | | | | |
| 114 | | | mRNA/<br>ssHA_H4-<br>V3<br>Nglyc-<br>neg | 137 | 181 | | 30 |
| 115 | AUGAAGGCAAAGCUGCUGGUGCUGCUGUGCACA<br>UUUACUGCCACUUACGCAGCAGGCCCUACCGUC<br>ACAGUGAUCCCUGUGGGCAGAGAAGGUGGCGAC<br>AUCACCAUCAGCGGCAAGGGCUUCAGCACCACA<br>GGCUUUGGCGUGUACGUGGCCGUGGCACCUGCU<br>AGCGUGCCCGAAUUCUACGGCAAUAGCGACAAG<br>UUCUACGGCUACGACCCCAGCAAGGACACCACC<br>GAGAGCCCUAGCACCAUCUGGGUGUACACCCCU<br>AGCCAGAAGGCCAUCGGCUCUCGGUUCGCCCAG<br>GGCAGACCCAUGAACAAUGACGGCAGCUUCACA<br>AUCACCAUGAAGGCCCCCCCUUUCGAGCAGGGC<br>AAAGACUUCGUGGUGCUGACCACAAAGGCCCAU<br>GGCGUGGGCAAAACCGAUCACAGCGACGACACA<br>CGGACACCUGUCACCUACAGAGAGGCUACCCCU<br>GCCCCUACAGGCCCUAAGACACCCAUCGCCCCU<br>AGCAAGCAGCCUAGCAAGCAGGCCGCCCCUAGC<br>AAGCAGGUGAAGCCUUCUAAGCAGGCCGGCCCC<br>AACAAGCAGUCCACCACACCUCAGCAGAAGACA<br>GCCGAGCACAGAAGCCAGACCCCUGCCGCCCAC<br>CGGACCAUGACAAAGCAGGUGAGCACCAUCGGC<br>GCCAGCAAGGUGACAAGCGGCUCUCUGACCUGG<br>GGCAUCAGAACCUCUUUUACCUCCUACCUGAGA<br>GGCCCUAUCGCCAACGGCUCUUGGAAGCUGAGC<br>GGAGGCGCCAAUUGGAAUGGCUCCGCCUUCACC<br>UUCCCUCUGACCAGCGGCAGCUUCGACCCAGCC<br>ACCAAGUCCGGAAGCCUGAAGUACAGCGGCAGC<br>GUGCACAUGACAGGCCACCACGGCAUCCUGGAC<br>AUGACCCUGGCCGAGCCAAGCCUGCAGAUCAAG<br>GGAAGCACCGGCCACCUGUAUCUGGACGUGAAA<br>AGCAGCAGCAUGGACGGCAAGAAGACCAAUUAC<br>GGCAGAGUGGACUUCGCCACCUUCGGAGUGAGC<br>GUGUCUGGCAACGCCGCCAUCAAGGGCAGCCCU<br>GUGAAGCUGACCGCCACAGGCGCUAAGGCUUUU<br>GCCGGCUUCUACAGAGCCGGCGAGCCUAUGAAC<br>CCUCUGAGCACCAAUCUGACCCUGAGCGCCGAG<br>AAGGUGUCCCACAACGUGACCGUGGACGCAGUG<br>ACAGGCAAGGUGAUCGGCGACGACUCUGGCAAG<br>GGAGCCGGCCGGGGCCUGCCCGUGACAUAA | ssHA_P028_<br>V7 | mRNA/<br>P28-V7 | 145 | 182 | | 31 |
| 117 | | ssHA_PITP_<br>WT_trunc | mRNA/<br>ssHA_<br>PITP_<br>WT_<br>trunc | 146 | 184 | | 33 |
| 118 | | | mRNA/<br>ssHA_<br>PITP_<br>Nglyc-<br>neg | 137 | 185 | | 34 |
| 119 | | P028_V7_Gly<br>neg | mRNA/<br>ssHA_<br>P28-V7_<br>Nglyc-<br>neg | 147 | 186 | | 35 |
| 120 | | ssHA_PITP_<br>SGS_TMB_HA_<br>WT_trunc | mRNA/<br>ssHA_<br>PITP_<br>WT_HA<br>TMB-sgs<br>linker | 148 | 187 | 201 | 36 |
| 121 | | | mRNA/<br>ssHA_<br>PITP_<br>Nglyc-<br>neg_HA<br>TMB-sgs<br>linker | 137 | 188 | 200 | 37 |

TABLE 7-continued

| | | | | | | |
|---|---|---|---|---|---|---|
| 122 | aUgaaggccaaacUgcUggUgcUgcUgUgUaccUUUacagccacaUaUgccUccUcUaaUagaccaagaUccgUggcUcaggccgccaUcgcUacagaUgggaaaggaaUcaUcgaUaaggaUagUcgggaUgcagUgaUcaacgacgccaaacUccgagcUgccaUcgccggcgcccUggUgaaggcUgggUUUUccagcgccgacgcagUggcccUggcaccUagaaUcgccaaggagaUggcaaaggagggcgUccUgcUgaUUaaUcaccacaagcUgaaagcUcUgaUUggggcUcagcUcggacUgcUgacUgacgccaagaUccagagggccgcagcUgccgUggaUcUggggaUcaaggccacUcUggccgcUacUaUUaUUccUaacgcUcUggggUcUgccgccUUcaagaaUgcUgUcaUUgccaaccUggUggcUgcUggcaUcgacaaacaccUcgccagggcUaccgcUgUggccaUcgUUgccacagcccUgaaUccUgcccUgggcccaaUcgcUaaaUUUgagcUgaUUaaggcUgagaUcgccgcccaggccgcacUgcUgaUcagaaggggggUccaUcUgcagaaggccgcUaUUgaacaUgUgaUcggccgcgcaUUcgacgcUgccgUggccaccgcUaUcaUUUccUcUccaaUccUgagcgcacggaUUgUgacccaccUggUgagggcUggaaUUgaUaaaagcaUcgcUaUcUcccUggcUccUcaUaUcgUgaagcgccUggccaaggagccccUgcUggcUUUcaacaccgccaagcUgaUgaagaaUaUUacaagacagaUcgUUgacgUgaUcacagccgaUaaagccaUcaaaacagcUgagcagcUggaaaaggagcUccccgcccUggacgaccUggUcaaaaaagcUagcUccccUccUaagccUacccccacaccUacUccaacccccaccgccgggcccaccgUgacagUgaUccccgUgggaagggagggggggcgacaUUaccaUUagcggaaaagggUUcUccacaaccgggUUcggcgUcUacgUggccgUggcUccUgccUcUgUgccagagUUcUaUggcaaUagcgacaagUUcUaUgggUacgaUccaUcUaaggacaccaccgaaagUcccagcaccaUcUgggUgUaUacaccaUcccagaaagcaaUcggcagcagaUUcgcccaaggcaggcccaUgaaUaaUgaUggcUcUUUcaccaUUacaaUgaaggccccUccUUUcgagcagggaaaggaUUUcgUggUgcUgaccaccaaagcacaUggcgUUggaaagaccgaccacagcgacgaUacUcggaccccUgUgacUUacagagaggccaccccUgcUccaaccggcccUaaaacUcccaUcUgaUaa | nCO-ssHA H4-V3-f-PRO-028-V7-F16 | H4-V3-f-PRO-028-V7-F16, triple chimera P22/P27P28 | 149 | 189 | 38 |
| 123 | | nCO-ssHA PRO-H4-V3-lowglyc | H4-V3 low_glyc | 150 | 190 | 39 |
| 124 | aUgaaggccaagcUgcUggUgcUgcUgUgcaccUUcaccgccaccUacgccUccagcaaccggccUagaagcgUggcccaggccgccaUcgccaccgacggcaagggcaUcaUcgacaaggaUUcccgggacgccgUgaUcaaUgacgccaagcUgagagccgccaUcgccggcgcccUggUgaaggccggcUUcagcagcgccgacgccgUggcccUggcccccagaaUcgccaaggagaUggccaaggaaggcgUgcUgcUgaUcaaUcaccacaagcUgaaggcccUgaUcggcgcccagcUgggccUgcUgacagaUgccaagaUccagagagccgcUgccgccgUggaccUgggcaUcaaggccacccUggccgccaccaUcaUcccUaacgcccUgggcagcgcUgccUUcaagaaUgccgUgaUcgccaaccUggUggccgccggcaUcgacaagcaccUggccagagccacagccgUggccaUcgUggccaccgcccUgaaUccUgcccUgggccccaUcgccaagUUcgagcUgaUcaaggccgagaUcgccgcccaggccgcccUgcUgaUccggggggcgUgcaccUgcagaaggccgccaUcgaacacgUgaUcggcagagccUUcgaUgccgccgUggccaccgccaUcaUcagcUcccccaUccUgagcgccagaaUcgUgacccaccUggUgcgggccggcaUcgacaagUccaUcgccaUUagccUggccccUcacaUcgUgaagcgccUggccaaggagccccUgcUggccUUcaaUaccgccaagcUgaUgaagaaUaUcaccagacagaUcgUggaUgUgaUcaccgccgaUaaggccaUcaagaccgccgagcagcUggagaaagagcUgcccgcccUggacgaccUggUgaaaaaggccaUgggcccccUaagccUacaggcggcggcggaggcgcUggaccUaccgUgaccgUgaUccccgUgggca | gc.CO-ssHA_PRO-028-V12-lowglyc | PRO-028-V7-C12 low glyc | 151 | 191 | 40 |

TABLE 7-continued

| | | | | | | | |
|---|---|---|---|---|---|---|---|
| | gagagggcggcgaUaUcaccaUcagcggcaagg<br>gcUUcagcaccaccggcUUcggcgUgUacgUgg<br>ccgUggccccUgccagcgUgcccgagUUcUacg<br>gcaaUagcgacaagUUcUacggcUacgacccca<br>gcaaggacaccacagaaUcUcccagcaccaUcU<br>gggUgUacacccccagccagaaggccaUUggca<br>gccggUUcgcccagggccggccUaUgaacaaUg<br>aUggcagcUUcacaaUcaccaUgaaggccccac<br>ccUUcgagcagggcaaggacUUcgUggUgcUga<br>ccaccaaggcccacggagUgggcaagggcgacc<br>acggcgacgacacacggacccccgUgggcUaca<br>gaUgaUaa | | | | | | |
| 125 | aUgaaagccaagcUgcUggUgcUgcUgUgUacU<br>UUUacUgcaaccUacgccagcagcaaccgccca<br>aggUcUgUcgcacaggcUgcUaUcgccacagaU<br>ggcaagggaaUcaUUgaUaaggacagcagggaU<br>gcUgUgaUcaacgacgcaaaacUgagagccgcc<br>aUcgccggcgcacUggUgaaagccggcUUUUcU<br>UccgccgacgcagUggcUcUggcUcccagaaUc<br>gcUaaggaaaUggccaaggagggagUgcUgcUg<br>aUcaaUcaccacaaacUgaaggcUcUgaUcggg<br>gcUcagcUgggccUgcUgacUgacgcUaagaUU<br>cagagagcagcagcagcUgUcgaccUgggaaUc<br>aaggcaacccUggcagccacUaUcaUUccaaaU<br>gcUcUgggcUcUgccgccUUcaaaaacgccgUg<br>aUUgccaaUcUcgUggcagcUggaaUcgaUaag<br>caccUggcacgggccaccgccgUggcUaUcgUg<br>gccaccgcUcUgaaUcccgcccUgggcccUaUU<br>gccaagUUUgaacUgaUcaaagccgagaUcgcU<br>gcacaggccgcccUgcUcaUccgcagggggg Uc<br>caccUgcagaaagcagccaUcgagcacgUgaUc<br>ggcagggccUUUgaUgcagccgUcgccacUgcc<br>aUcaUcagcUcUccaaUccUgUcUgcccggaUU<br>gUgacUcaccUggUgcgcgccggcaUcgaUaag<br>UccaUcgcaaUcUcUcUggccccacacaUcgUg<br>aagagacUggccaaagaaccacUccUggcUUUc<br>aaUaccgccaaacUcaUgaaaaacaUcacccgg<br>cagaUcgUcgaUgUgaUUaccgccgacaaggcU<br>aUcaagaccgccgagcagcUcgaaaaggagcUg<br>ccUgcccUggacgaccUggUgaagaaagccUcc<br>UcUccacccaaacccaccccaacUccaacUcca<br>accccUacagcUggccccaccgUgaccgUcaUc<br>ccagUgggaagggaaggaggagacaUcacaaUc<br>UcUggaaaggggUUUagcacaaccggaUUUgga<br>gUgUacgUcgccgUggcccccgcaUccgUgcca<br>gaaUUcUacggcaaUUccgaUaaaUUcUacggg<br>UacgaccccUccaaggacacUacagagagcccc<br>UcUacaaUUUgggUgUacaccccaagccagaag<br>gccaUcggaagcagaUUUgcUcagggccggcca<br>aUgaacaacgacggaUccUUcacaaUcacaaUg<br>aaagcaccUcccUUUgagcagggcaaggaUUUU<br>gUggUgcUgaccaccaaggcUcacggggUcgga<br>aagaccgaUcacagcgacgaUacaagaacccccc<br>gUgacaUaccggUgaUaa | nCO-<br>ssHA_PRO-<br>028-V7-C12 | PRO-028-<br>V7-C12,<br>triple<br>chimera<br>P22/P27/<br>P28 | 152 | 192 | | 41 |

| SEQ ID NO | mRNA sequence | Name | the nucleo-tide sequence encoding a *C. acnes* antigen is according to SEQ ID NO: | contains a TMB sequence according to SEQ ID NO | Encodes the poly-peptide according to SEQ ID NO |
|---|---|---|---|---|---|
| 377 | AUGAAGGCCAAGCUGCUGGUGCUGCUGUGUACCUUCACUGCAACAUAUGCUG<br>UGGAGCCCACAACCACAAUCUCUGCCACAAGCACCCACGAGCUGUCUGCCAG<br>CGACGCCAGAAACUCCAUCCAGCUGCUGAAUGCCCACAUCGCCACACUGCAG<br>AGCGUGCAGAAAUCCGUGCCUGGCAGCGAUUACAGCGACCAGAUCCGGGACC<br>UGCUGAAGGCCGCCUUUGAUCUGAGAGGCCUGAUCGAAACCCUGGCCCACGG<br>CGGCAUUCCCUUCUAUGACCCCUCCACCAUCAUGCCCAGAAUCAAGCUGGUG<br>GCCACCACCAUCGACACCAUCCACACAGCUACAACCACCCUGCAGAACAAGG<br>UGCGGCCAGCCCAUGUGGAACUGGGCCUGGAGGUGACAAAGGCCGUGCUGCU<br>GACCGCCAAUCCUGCCAGCACAGCAAAAGAACUGGACGCCGAGGGAGCUGCU<br>CUGAAGGCCAGACUGGAAAAGGUGAGCCAGUACCCCGACCUGACACCUAAUG<br>AUGUGGCCACAGUGUACGUGAGAACCAAUUUCAGCAAGACCAUCUGGCAGGU | Quad-CAMP2-<br>H4V3-f-PRO-<br>028-V7-<br>F16_sgs_HA-<br>TM_gsg_ssHA<br>codon<br>optimization<br>#1 | 384 | 395 | 369 |

TABLE 7-continued

| | | | | |
|---|---|---|---|---|
| | GAGAGCCAACAGAGAUCGGUACAUCCUGGGCCACAAGUCCGCCGCCGUGUAC<br>AAGACCCUGAAUCACGCCAUCACCAAGGCCGUGGGCGUGCGGCUGAAUCCUA<br>AGACCACCGUGGGCAACAUCCAGGCCGCCAGAACCGAACUGCUGGCCGCCUA<br>CCAGACCGCCUUCAACAGCCCCGAUGUGAAGAAGGCCGCUAGCUCCAAUAGA<br>CCCAGAUCCGUGGCCCAGGCCGCCAUCGCCACAGAUGGCAAGGGGAUCAUCG<br>ACAAGGAUUCCAGAGACGCUGUGAUCAACGACGCAAAGCUGAGAGCCGCCAU<br>CGCCGGAGCUCUGGUGAAGGCCGGCUUUAGCAGCGCCGACGCCGUGGCACUG<br>GCCCCCAGAAUUGCAAAGGAGAUGGCAAAGGAGGGCGUGCUGCUGAUCAAUC<br>ACCACAAGCUGAAGGCCCUGAUCGGCGCACAGCUGGGCCUGCUGACCGACGC<br>AAAGAUUCAGAGAGCCGCCGCAGCCGUGGACCUGGGCAUCAAGGCCACCCUG<br>GCUGCCACCAUCAUCCCUAACGCCCUGGGCAGCGCCGCCUUCAAGAAUGCAG<br>UGAUCGCCAACCUGGUGGCCGCCGGAAUCGACAAGCACCUGGCCAGAGCCAC<br>AGCCGUCGCUAUCGUGGCCACAGCCCUGAAUCCCGCCCUGGGCCCCAUCGCC<br>AAAUUUGAACUGAUCAAGGCAGAAAUCGCUGCCCAGGCCGCCCUGCUCAUCA<br>GAAGAGGCGUCCAUCUGCAGAAGGCCGCCAUCGAGCACGUGAUUGGCAGAGC<br>CUUCGACGCCGCCGUGGCCACAGCUAUCAUUUCUUCCCCUAUCCUGUCUGCC<br>AGAAUCGUGACACACCUGGUGAGAGCCGGAAUCGACAAGUCCAUCGCCAUCU<br>CCCUGGCCCCCCACAUCGUGAAGAGACUGGCUAAGGAGCCUCUGCUGGCCUU<br>CAAUACAGCCAAGCUGAUGAAGAACAUCACAAGACAGAUCGUGGACGUGAUC<br>ACCGCCGACAAGGCCAUCAAGACAGCCGAGCAGCUGGAGAAGGAACUGCCAG<br>CCCUGGACGACCUGGUGAAGAAGGCCAGCAGCCCUCCCAAGCCUACCCCUAC<br>CCCAACCCCUACACCUACAGCCGGACCUACCGUGACCGUGAUCCCUGUGGGC<br>AGAGAGGGCGGCGACAUCACCAUCAGCGGCAAGGGCUUCAGCACAACAGGCU<br>UUGGCGUGUACGUGGCCGUGGCCCCAGCCAGCGUGCCUGAGUUUUACGGCAA<br>UAGCGACAAGUUCUACGGCUACGACCCCUCCAAGGACACCACCGAGAGCCCA<br>AGCACCAUCUGGGUGUACACACCUAGCCAGAAGGCCAUCGGCAGCAGAUUUG<br>CCCAGGGCAGGCCUAUGAAUAAUGACGGCAGCUUCACAAUCACAAUGAAGGC<br>CCCCCCCUUUGAGCAGGGCAAGGACUUCGUGGUGCUGACCACCAAGGCCCAC<br>GGCGUGGGCAAGACAGAUCACAGCGACGACACCCGGACCCCCGUGACCUACA<br>GAGAAGCAACACCUGCCCCUACCGGGCCUAAGACACCCAUCAGCGGCAGCAU<br>CCUGGCUAUCUACAGCACAGUGGCUUCUAGCCUGGUGCUGCUGGUGUCUCUG<br>GGCGCCAUCAGCUUUGGCAGCGGCUGAUAA | | | | |
| 378 | AUGAAGGCUAAGCUGCUGGUGCUGCUGUGCACAUUCACAGCCACCUACGCCG<br>UGGAGCCUACCACCACAAUCAGCGCCACCAGCACCCACGAGCUGAGCGCCAG<br>CGAUGCCAGAAAUAGCAUCCAGCUGCUGAAUGCCCACAUCGCCACCCUGCAG<br>UCCGUGCAGAAAAGCGUGCCUGGAAGCGAUUACAGCGAUCAGAUCAGGGACC<br>UGCUGAAGGCCGCCUUCGAUCUGAGAGGCCUGAUCGAGACACUGGCCCACGG<br>CGGCAUCCCUUUCUACGACCCCAGCACCAUCAUGCCUAGAAUCAAACUGGUG<br>GCCACCACCAUCGACACCAUCCACACCGCAACAACAACCCUGCAGAAUAAGG<br>UGCGGCCUGCCCACGUGGAACUGGGACUGGAAGUGACAAAGGCCGUGCUGCU<br>GACCGCUAAUCCCGCCUCCACCGCCAAGGAGCUGGAUGCCGAAGGAGCUGCC<br>CUGAAAGCCAGACUGGAGAAGGUGAGCCAGUACCCUGAUCUGACCCCUAACG<br>ACGUGGCCACCGUGUACGUGAGAACCAAUUUCAGCAAGACCAUCUGGCAGGU<br>GAGAGCCAAUCGGGACAGAUACAUCCUGGGCCACAAGUCUGCCGCCGUGUAU<br>AAAACCCUGAAUCACGCCAUCACCAAGGCCGUGGGCGUGAGACUGAACCCUA<br>AGACAACCGUGGGCAACAUCCAGGCCGCCAGAACAGAGCUGCUGGCCGCCUA<br>CCAGACAGCCUUCAAUAGCCCCGACGUGAAGAAGGCCGCUUCCAGCAAUAGA<br>CCCCGGAGCGUGGCACAGGCUGCUAUUGCCACCGACGGAAAGGGCAUCAUCG<br>AUAAAGACAGCCGGGAUGCCGUGAUCAAUGACGCCAAGCUGAGAGCAGCAAU<br>CGCCGGCGCUCUGGUGAAGGCAGGCUUCAGCAGCGCCGACGCCGUGGCUCUG<br>GCCCCUAGAAUCGCUAAGGAGAUGGCCAAGGAGGGCGUGCUGCUGAUCAAUC<br>ACCACAAGCUGAAGGCCCUGAUCGGCGCCCAGCUGGGACUGCUGACAGAUGC<br>CAAGAUCCAGAGAGCCGCUGCAGCCGUGGAUCUGGGCAUCAAGGCCACACUG<br>GCCGCCACCAUCAUCCCAAACGCCCUGGGCAGCGCCGCCUUCAAAAAUGCCG<br>UGAUUGCCAACCUGGUGGCCGCCGGCAUCGAUAAGCACCUGGCCAGAGCCAC<br>AGCCGUGGCCAUCGUGGCCACAGCCCUGAAUCCCGCACUGGGACCUAUUGCC<br>AAGUUCGAACUCAUUAAGGCCGAAAUCGCAGCCCAAGCCGCCCUGCUGAUUC<br>GGCGGGGCGUGCACCUGCAGAAAGCCGCCAUUGAGCACGUGAUCGGCAGAGC<br>CUUCGAUGCCGCUGUGGCCACCGCCAUCAUCUCCUCUCCUAUCCUGUCUGCU<br>AGAAUCGUGACCCACCUGGUCAGAGCCGGAAUCGACAAGUCUAUCGCUAUCA<br>GCCUGGCCCCCCACAUCGUGAAGAGACUGGCCAAAGAGCCCCUGCUGGCCUU<br>CAACACAGCCAAGCUCAUGAAGAAUAUCACCAGACAGAUCGUGGACGUGAUC<br>ACCGCCGACAAGGCCAUCAAAACCGCUGAGCAGCUGGAGAAGGAGCUGCCCG<br>CCCUGGAUGACCUGGUGAAGAAGGCCAGCAGCCCCCCCAAGCCUACACCUAC<br>ACCUACCCCAACCCCUACAGCCGGCCCUACAGUGACCGUGAUUCCUGUGGGC<br>AGAGAAGGAGGCGACAUCACCAUCAGCGGAAAGGGCUUCUCUACCACAGGCU<br>UCGGCGUGUACGUGGCCGUGGCCCCUGCCUCCGUGCCCGAAUUCUACGGCAA<br>CAGCGACAAGUUCUACGGCUACGACCCCAGCAAAGACACCACAGAGAGCCCU<br>UCCACCAUCUGGGUGUACACCCCUUCCCAGAAGGCCAUCGGCAGCAGAUUCG<br>CUCAGGGCAGACCUAUGAAUAACGACGGCUCUUUCACCAUCACAAUGAAGGC<br>CCCCCCCUUCGAGCAGGGCAAAGACUUCGUGGUGCUGACAACCAAGGCCCAC<br>GGCGUGGGCAAGACAGAUCACUCCGACGACACCCGGACCCCUGUGACCUACA<br>GAGAGGCAACACCUGCUCCCACCGGGCCAAAGACCCCUAUCAGCGGAAGCAU<br>CCUGGCCAUCUAUAGCACCGUGGCUAGCUCUCUGGUGCUGCUGGUGAGCCUG<br>GGAGCUAUCAGCUUUGGGAGCGGCUGAUAA | Quad-CAMP2-<br>H4V3-f-PRO-<br>028-V7-<br>F16_sgs_HA-<br>TM_gsg_ssHA<br>codon<br>optimization<br>#2 | 385 | 396 | 369 |

TABLE 7-continued

| | | | | |
|---|---|---|---|---|
| 379 | AUGAAGGCCAAGCUGCUGGUGCUGCUGUGUACCUUCACUGCAACAUAUGCUA<br>UGGUGGAGCCCACAACCACAAUCUCUGCCACAAGCACCCACGAGCUGUCUGC<br>CAGCGACGCCAGAAACUCCAUCCAGCUGCUGAAUGCCCACAUCGCCACACUG<br>CAGAGCGUGCAGAAAUCCGUGCCUGGCAGCGAUUACAGCGACCAGAUCCGGG<br>ACCUGCUGAAGGCCGCCUUUGAUCUGAGAGGCCUGAUCGAAACCCUGGCCCA<br>CGGCGGCAUUCCCUUCUAUGACCCCUCCACCAUCAUGCCCAGAAUCAAGCUG<br>GUGGCCACCACCAUCGACACCAUCCACACAGCUACAACCACCCUGCAGAACA<br>AGGUGCGGCCAGCCCAUGUGGAACUGGGCCUGGAGGUGACAAAGGCCGUGCU<br>GCUGACCGCCAAUCCUGCCAGCACAGCAAAAGAACUGGACGCCGAGGGAGCU<br>GCUCUGAAGGCCAGACUGGAAAAGGUGAGCCAGUACCCCGACCUGACACCUA<br>AUGAUGUGGCCACAGUGUACGUGAGAACCAAUUUCAGCAAGACCAUCUGGCA<br>GGUGAGAGCCAACAGAGAUCGGUACAUCCUGGGCCACAAGUCCGCCGCCGUG<br>UACAAGACCCUGAAUCACGCCAUCACCAAGGCCGUGGGCGUGCGGCUGAAUC<br>CUAAGACCACCGUGGGCAACAUCCAGGCCGCCAGAACCGAACUGCUGGCCGC<br>CUACCAGACCGCCUUCAACAGCCCCGAUGUGAAGAAGGCCGCUAGCUCCAAU<br>AGACCCAGAUCCGUGGCCCAGGCCGCCAUCGCCACAGAUGGCAAGGGGAUCA<br>UCGACAAGGAUUCCAGAGACGCUGUGAUCAACGACGCAAAGCUGAGAGCCGC<br>CAUCGCCGGAGCUCUGGUGAAGGCCGGCUUUAGCAGCGCCGACGCCGUGGCA<br>CUGGCCCCCAGAAUUGCAAAGGAGAUGGCAAAGGAGGGCGUGCUGCUGAUCA<br>AUCACCACAAGCUGAAGGCCCUGAUCGGCGCACAGCUGGGCCUGCUGACCGA<br>CGCAAAGAUUCAGAGAGCCGCCGCAGCCGUGGACCUGGGCAUCAAGGCCACC<br>CUGGCUGCCACCAUCAUCCCUAACGCCCUGGGCAGCGCCGCCUUCAAGAAUG<br>CAGUGAUCGCCAACCUGGUGGCCGCCGGAAUCGACAAGCACCUGGCCAGAGC<br>CACAGCCGUCGCUAUCGUGGCCACAGCCCUGAAUCCCGCCCUGGGCCCCAUC<br>GCCAAAUUUGAACUGAUCAAGGCAGAAAUCGCUGCCCAGGCCGCCCUGCUCA<br>UCAGAAGAGGCGUCCAUCUGCAGAAGGCCGCCAUCGAGCACGUGAUUGGCAG<br>AGCCUUCGACGCCGCCGUGGCCACAGCUAUCAUUUCUUCCCCUAUCCUGUCU<br>GCCAGAAUCGUGACACACCUGGUGAGAGCCGGAAUCGACAAGUCCAUCGCCA<br>UCUCCCUGGCCCCCCACAUCGUGAAGAGACUGGCUAAGGAGCCUCUGCUGGC<br>CUUCAAUACAGCCAAGCUGAUGAAGAACAUCACAAGACAGAUCGUGGACGUG<br>AUCACCGCCGACAAGGCCAUCAAGACAGCCGAGCAGCUGGAGAAGGAACUGC<br>CAGCCCUGGACGACCUGGUGAAGAAGGCCAGCAGCCCUCCCAAGCCUACCCC<br>UACCCCAACCCCUACACCUACAGCCGGACCUACCGUGACCGUGAUCCCUGUG<br>GGCAGAGAGGGCGGCGACAUCACCAUCAGCGGCAAGGGCUUCAGCACAACAG<br>GCUUUGGCGUGUACGUGGCCGUGGCCCAGCCAGCGUGCCUGAGUUUUACGG<br>CAAUAGCGACAAGUUCUACGGCUACGACCCCUCCAAGGACACCACCGAGAGC<br>CCAAGCACCAUCUGGGUGUACACACCUAGCCAGAAGGCCAUCGGCAGCAGAU<br>UUGCCCAGGGCAGGCCUAUGAAUAAUGACGGCAGCUUCACAAUCACAAUGAA<br>GGCCCCCCCCUUUGAGCAGGGCAAGGACUUCGUGGUGCUGACCACCAAGGCC<br>CACGGCGUGGGCAAGACAGAUCACAGCGACGACACCCGGACCCCCGUGACCU<br>ACAGAGAAGCAACACCUGCCCCUACCGGGCCUAAGACACCCAUCUGAUAA | Quad-CAMP2-<br>H4V3-f-PRO-<br>028-V7-<br>F16_ssHA<br>codon<br>optimization<br>#1 | 386 | |
| 380 | AUGAAGGCUAAGCUGCUGGUGCUGCUGUGCACAUUCACAGCCACCUACGCCG<br>UGGAGCCUACCACCACAAUCAGCGCCACCAGCACCCACGAGCUGAGCGCCAG<br>CGAUGCCAGAAAUAGCAUCCAGCUGCUGAAUGCCCACAUCGCCACCCUGCAG<br>UCCGUGCAGAAAAGCGUGCCUGGAAGCGAUUACAGCGAUCAGAUCAGGGACC<br>UGCUGAAGGCCGCCUUCGAUCUGAGAGGCCUGAUCGAGACACUGGCCCACGG<br>CGGCAUCCCUUUCUACGACCCCAGCACCAUCAUGCCUAGAAUCAAACUGGUG<br>GCCACCACCAUCGACACCAUCCACACCGCAACAACAACCCUGCAGAAUAAGG<br>UGCGGCCUGCCCACGUGGAACUGGGACUGGAAGUGACAAAGGCCGUGCUGCU<br>GACCGCUAAUCCCGCCUCCACCGCCAAGGAGCUGGAUGCCGAAGGAGCUGCC<br>CUGAAAGCCAGACUGGAGAAGGUGAGCCAGUACCCUGAUCUGACCCCUAACG<br>ACGUGGCCACCGUGUACGUGAGAACCAAUUUCAGCAAGACCAUCUGGCAGGU<br>GAGAGCCAAUCGGGACAGAUACAUCCUGGGCCACAAGUCUGCCGCCGUGUAU<br>AAAACCCUGAAUCACGCCAUCACCAAGGCCGUGGGCGUGAGACUGAACCCUA<br>AGACAACCGUGGGCAACAUCCAGGCCGCCAGAACAGAGCUGCUGGCCGCCUA<br>CCAGACAGCCUUCAAUAGCCCCGACGUGAAGAAGGCCGCUUCCAGCAAUAGA<br>CCCCGGAGCGUGGCACAGGCUGCUAUUGCCACCGACGGAAAGGGCAUCAUCG<br>AUAAAGACAGCCGGGAUGCCGUGAUCAAUGACGCCAAGCUGAGAGCAGCAAU<br>CGCCGGCGCUCUGGUGAAGGCAGGCUUCAGCAGCGCCGACGCCGUGGCUCUG<br>GCCCCUAGAAUCGCUAAGGAGAUGGCCAAGGAGGGCGUGCUGCUGAUCAAUC<br>ACCACAAGCUGAAGGCCCUGAUCGGCGCCCAGCUGGGACUGCUGACAGAUGC<br>CAAGAUCCAGAGAGCCGCUGCAGCCGUGGAUCUGGGCAUCAAGGCCACACUG<br>GCCGCCACCAUCAUCCCAAACGCCCUGGGCAGCGCCGCCUUCAAAAAUGCCG<br>UGAUUGCCAACCUGGUGGCCGCCGGCAUCGAUAAGCACCUGGCCAGAGCCAC<br>AGCCGUGGCCAUCGUGGCCACAGCCCUGAAUCCCGCACUGGGACCUAUUGCC<br>AAGUUCGAACUCAUUAAGGCCGAAAUCGCAGCCCAAGCCGCCCUGCUGAUUC<br>GGCGGGGCGUGCACCUGCAGAAAGCCGCCAUUGAGCACGUGAUCGGCAGAGC<br>CUUCGAUGCCGCUGUGGCCACCGCCAUCAUCUCCUCUCCUAUCCUGUCUGCU<br>AGAAUCGUGACCCACCUGGUCAGAGCCGGAAUCGACAAGUCUAUCGCUAUCA<br>GCCUGGCCCCCCACAUCGUGAAGAGACUGGCCAAAGAGCCCCUGCUGGCCUU<br>CAACACAGCCAAGCUCAUGAAGAAUAUCACCAGACAGAUCGUGGACGUGAUC<br>ACCGCCGACAAGGCCAUCAAAACCGCUGAGCAGCUGGAGAAGGAGCUGCCCG<br>CCCUGGAUGACCUGGUGAAGAAGGCCAGCAGCCCCCCCAAGCCUACACCUAC<br>ACCUACCCCAACCCCUACAGCCGGCCCUACAGUGACCGUGAUUCCUGUGGGC<br>AGAGAAGGAGGCGACAUCACCAUCAGCGGAAAGGGCUUCUCUACCACAGGCU<br>UCGGCGUGUACGUGGCCGUGGCCCCUGCCUCCGUGCCCGAAUUCUACGGCAA<br>CAGCGACAAGUUCUACGGCUACGACCCCAGCAAAGACACCACAGAGAGCCCU<br>UCCACCAUCUGGGUGUACACCCCUUCCCAGAAGGCCAUCGGCAGCAGAUUCG | Quad-CAMP2-<br>H4V3-f-PRO-<br>028-V7-<br>F16_ssHA<br>codon<br>optimization<br>#2 | 387 | 370 |

TABLE 7-continued

| | | | | |
|---|---|---|---|---|
| | CUCAGGGCAGACCUAUGAAUAACGACGGCUCUUUCACCAUCACAAUGAAGGC<br>CCCCCCCUUCGAGCAGGGCAAAGACUUCGUGGUGCUGACAACCAAGGCCCAC<br>GGCGUGGGCAAGACAGAUCACUCCGACGACACCCGGACCCCUGUGACCUACA<br>GAGAGGCAACACCUGCUCCCACCGGGCCAAAGACCCCUAUCUGAUAA | | | |
| 381 | AUGAAGGCCAAGCUGCUGGUGCUGCUGUGUACCUUCACUGCAACAUAUGCUG<br>UGGAGCCCACAACCACAAUCUCUGCCACAAGCACCCACGAGCUGUCUGCCAG<br>CGACGCCAGAAACUCCAUCCAGCUGCUGAAUGCCCACAUCGCCACACUGCAG<br>AGCGUGCAGAAAUCCGUGCCUGGCAGCGAUUACAGCGACCAGAUCCGGGACC<br>UGCUGAAGGCCGCCUUUGAUCUGAGAGGCCUGAUCGAAACCCUGGCCCACGG<br>CGGCAUUCCCUUCUAUGACCCCUCCACCAUCAUGCCCAGAAUCAAGCUGGUG<br>GCCACCACCAUCGACACCAUCCACACAGCUACAACCACCCUGCAGAACAAGG<br>UGCGGCCAGCCCAUGUGGAACUGGGCCUGGAGGUGACAAAGGCCGUGCUGCU<br>GACCGCCAAUCCUGCCAGCACAGCAAAAGAACUGGACGCCGAGGGAGCUGCU<br>CUGAAGGCCAGACUGGAAAAGGUGAGCCAGUACCCCGACCUGACACCUAAUG<br>AUGUGGCCACAAGCUCCAAUAGACCCAGAUCCGUGGCCCAGGCCGCCAUCGC<br>CACAGAUGGCAAGGGGAUCAUCGACAAGGAUUCCAGAGACGCUGUGAUCAAC<br>GACGCAAAGCUGAGAGCCGCCAUCGCCGGAGCUCUGGUGAAGGCCGGCUUUA<br>GCAGCGCCGACGCCGUGGCACUGGCCCCCAGAAUUGCAAAGGAGAUGGCAAA<br>GGAGGGCGUGCUGCUGAUCAAUCACCACAAGCUGAAGGCCCUGAUCGGCGCA<br>CAGCUGGGCCUGCUGACCGACGCAAAGAUUCAGAGAGCCGCCGCAGCCGUGG<br>ACCUGGGCAUCAAGGCCACCCUGGCUGCCACCAUCAUCCCUAACGCCCUGGG<br>CAGCGCCGCCUUCAAGAAUGCAGUGAUCGCCAACCUGGUGGCCGCCGGAAUC<br>GACAAGCACCUGGCCAGAGCCACAGCCGUCGCUAUCGUGGCCACAGCCCUGA<br>AUCCCGCCCUGGGCCCCAUCGCCAAAUUUGAACUGAUCAAGGCAGAAAUCGC<br>UGCCCAGGCCGCCCUGCUCAUCAGAAGAGGCGUCCAUCUGCAGAAGGCCGCC<br>AUCGAGCACGUGAUUGGCAGAGCCUUCGACGCCGCCGUGGCCACAGCUAUCA<br>UUUCUUCCCCUAUCCUGUCUGCCAGAAUCGUGACACACCUGGUGAGAGCCGG<br>AAUCGACAAGUCCAUCGCCAUCUCCCUGGCCCCCACAUCGUGAAGAGACUG<br>GCUAAGGAGCCUCUGCUGGCCUUCAAUACAGCCAAGCUGAUGAAGAACAUCA<br>CAAGACAGAUCGUGGACGUGAUCACCGCCGACAAGGCCAUCAAGACAGCCGA<br>GCAGCUGGAGAAGGAACUGCCAGCCCUGGACGACCUGGUGAAGAAGGCCAGC<br>AGCCCUCCCAAGCCUACCCCUACCCCAACCCCUACACCUACAGCCGGACCUA<br>CCGUGACCGUGAUCCCUGUGGGCAGAGAGGGCGGCGACAUCACCAUCAGCGG<br>CAAGGGCUUCAGCACAACAGGCUUUGGCGUGUACGUGGCCGUGGCCCCAGCC<br>AGCGUGCCUGAGUUUUACGGCAAUAGCGACAAGUUCUACGGCUACGACCCCU<br>CCAAGGACACCACCGAGAGCCCAAGCACCAUCUGGGUGUACACACCUAGCCA<br>GAAGGCCAUCGGCAGCAGAUUUGCCCAGGGCAGGCCUAUGAAUAAUGACGGC<br>AGCUUCACAAUCACAAUGAAGGCCCCCCCUUUGAGCAGGGCAAGGACUUCG<br>UGGUGCUGACCACCAAGGCCCACGGCGUGGGCAAGACAGAUCACAGCGACGA<br>CACCCGGACCCCCGUGACCUACAGAGAAGCAACACCUGCCCCUACCGGGCCU<br>AAGACACCCAUCUGAUAA | Quad-CAMP2-<br>Nter-link-<br>H4V3-f-PRO-<br>028-V7-<br>F16_ssHA<br>codon<br>optimization<br>#1 | 388 | 371 |
| 382 | AUGAAGGCUAAGCUGCUGGUGCUGCUGUGCACAUUCACAGCCACCUACGCCG<br>UGGAGCCUACCACCACAAUCAGCGCCACCAGCACCCACGAGCUGAGCGCCAG<br>CGAUGCCAGAAAUAGCAUCCAGCUGCUGAAUGCCCACAUCGCCACCCUGCAG<br>UCCGUGCAGAAAAGCGUGCCUGGAAGCGAUUACAGCGAUCAGAUCAGGGACC<br>UGCUGAAGGCCGCCUUCGAUCUGAGAGGCCUGAUCGAGACACUGGCCCACGG<br>CGGCAUCCCUUUCUACGACCCCAGCACCAUCAUGCCUAGAAUCAAACUGGUG<br>GCCACCACCAUCGACACCAUCCACACCGCAACAACAACCCUGCAGAAUAAGG<br>UGCGGCCUGCCCACGUGGAACUGGGACUGGAAGUGACAAAGGCCGUGCUGCU<br>GACCGCUAAUCCCGCCUCCACCGCCAAGGAGCUGGAUGCCGAAGGAGCUGCC<br>CUGAAAGCCAGACUGGAGAAGGUGAGCCAGUACCCUGAUCUGACCCCUAACG<br>ACGUGGCCACCUCCAGCAAUAGACCCCGGAGCGUGGCACAGGCUGCUAUUGC<br>CACCGACGGAAAGGGCAUCAUCGAUAAAGACAGCCGGGAUGCCGUGAUCAAU<br>GACGCCAAGCUGAGAGCAGCAAUCGCCGGCGCUCUGGUGAAGGCAGGCUUCA<br>GCAGCGCCGACGCCGUGGCUCUGGCCCCUAGAAUCGCUAAGGAGAUGGCCAA<br>GGAGGGCGUGCUGCUGAUCAAUCACCACAAGCUGAAGGCCCUGAUCGGCGCC<br>CAGCUGGGACUGCUGACAGAUGCCAAGAUCCAGAGAGCCGCUGCAGCCGUGG<br>AUCUGGGCAUCAAGGCCACACUGGCCGCCACCAUCAUCCCAAACGCCCUGGG<br>CAGCGCCGCCUUCAAAAAUGCCGUGAUUGCCAACCUGGUGGCCGCCGGCAUC<br>GAUAAGCACCUGGCCAGAGCCACAGCCGUGGCCAUCGUGGCCACAGCCCUGA<br>AUCCCGCACUGGGACCUAUUGCCAAGUUCGAACUCAUUAAGGCCGAAAUCGC<br>AGCCCAAGCCGCCCUGCUGAUUCGGCGGGGCGUGCACCUGCAGAAAGCCGCC<br>AUUGAGCACGUGAUCGGCAGAGCCUUCGAUGCCGCUGUGGCCACCGCCAUCA<br>UCUCCUCUCCUAUCCUGUCUGCUAGAAUCGUGACCCACCUGGUCAGAGCCGG<br>AAUCGACAAGUCUAUCGCUAUCAGCCUGGCCCCCCACAUCGUGAAGAGACUG<br>GCCAAAGAGCCCCUGCUGGCCUUCAACACAGCCAAGCUCAUGAAGAAUAUCA<br>CCAGACAGAUCGUGGACGUGAUCACCGCCGACAAGGCCAUCAAAACCGCUGA<br>GCAGCUGGAGAAGGAGCUGCCCGCCCUGGAUGACCUGGUGAAGAAGGCCAGC<br>AGCCCCCCCAAGCCUACACCUACACCUACCCCAACCCCUACAGCCGGCCCUA<br>CAGUGACCGUGAUUCCUGUGGGCAGAGAAGGAGGCGACAUCACCAUCAGCGG<br>AAAGGGCUUCUCUACCACAGGCUUCGGCGUGUACGUGGCCGUGGCCCCUGCC<br>UCCGUGCCCGAAUUCUACGGCAACAGCGACAAGUUCUACGGCUACGACCCCA<br>GCAAAGACACCACAGAGAGCCCUUCCACCAUCUGGGUGUACACCCCUUCCCA<br>GAAGGCCAUCGGCAGCAGAUUCGCUCAGGGCAGACCUAUGAAUAACGACGGC<br>UCUUUCACCAUCACAAUGAAGGCCCCCCCUUCGAGCAGGGCAAAGACUUCG<br>UGGUGCUGACAACCAAGGCCCACGGCGUGGGCAAGACAGAUCACUCCGACGA<br>CACCCGGACCCCUGUGACCUACAGAGAGGCAACACCUGCUCCCACCGGGCCA<br>AAGACCCCUAUCUGAUAA | Quad-CAMP2-<br>Nter-link-<br>H4V3-f-PRO-<br>028-V7-<br>F16_ssHA<br>codon<br>optimization<br>#2 | 389 | 371 |

TABLE 7-continued

| | | | |
|---|---|---|---|
| 383 AUGAAGGCUAAGCUGCUGGUGCUGCUGUGCACAUUCACAGCCACCUACGCCU<br>CCAGCAAUAGACCCCGGAGCGUGGCACAGGCUGCUAUUGCCACCGACGGAAA<br>GGGCAUCAUCGAUAAAGACAGCCGGGAUGCCGUGAUCAAUGACGCCAAGCUG<br>AGAGCAGCAAUCGCCGGCGCUCUGGUGAAGGCAGGCUUCAGCAGCGCCGACG<br>CCGUGGCUCUGGCCCCUAGAAUCGCUAAGGAGAUGGCCAAGGAGGGCGUGCU<br>GCUGAUCAAUCACCACAAGCUGAAGGCCCUGAUCGGCGCCCAGCUGGGACUG<br>CUGACAGAUGCCAAGAUCCAGAGAGCCGCUGCAGCCGUGGAUCUGGGCAUCA<br>AGGCCACACUGGCCGCCACCAUCAUCCCAAACGCCCUGGGCAGCGCCGCCUU<br>CAAAAAUGCCGUGAUUGCCAACCUGGUGGCCGCCGGCAUCGAUAAGCACCUG<br>GCCAGAGCCACAGCCGUGGCCAUCGUGGCCACAGCCCUGAAUCCCGCACUGG<br>GACCUAUUGCCAAGUUCGAACUCAUUAAGGCCGAAAUCGCAGCCCAAGCCGC<br>CCUGCUGAUUCGGCGGGGCGUGCACCUGCAGAAAGCCGCCAUUGAGCACGUG<br>AUCGGCAGAGCCUUCGAUGCCGCUGUGGCCACCGCCAUCAUCUCCUCUCCUA<br>UCCUGUCUGCUAGAAUCGUGACCCACCUGGUCAGAGCCGGAAUCGACAAGUC<br>UAUCGCUAUCAGCCUGGCCCCCCACAUCGUGAAGAGACUGGCCAAAGAGCCC<br>CUGCUGGCCUUCAACACAGCCAAGCUCAUGAAGAAUAUCACCAGACAGAUCG<br>UGGACGUGAUCACCGCCGACAAGGCCAUCAAAACCGCUGAGCAGCUGGAGAA<br>GGAGCUGCCCGCCCUGGAUGACCUGGUGAAGAAGGCCAGCAGCCCCCCCAAG<br>CCUACACCUACACCUACCCCAACCCCUACAGCCGGCCCUACAGUGACCGUGA<br>UUCCUGUGGGCAGAGAAGGAGGCGACAUCACCAUCAGCGGAAAGGGCUUCUC<br>UACCACAGGCUUCGGCGUGUACGUGGCCGUGGCCCCUGCCUCCGUGCCCGAA<br>UUCUACGGCAACAGCGACAAGUUCUACGGCUACGACCCCAGCAAAGACACCA<br>CAGAGAGCCCUUCCACCAUCUGGGUGUACACCCCUUCCCAGAAGGCCAUCGG<br>CAGCAGAUUCGCUCAGGGCAGACCUAUGAAUAACGACGGCUCUUUCACCAUC<br>ACAAUGAAGGCCCCCCCUUCGAGCAGGGCAAAGACUUCGUGGUGCUGACAA<br>CCAAGGCCCACGGCGUGGGCAAGACAGAUCACUCCGACGACACCCGGACCCC<br>UGUGACCUACAGAGAGGCAACACCUGCUCCCACCGGGCCAAAGACCCCUAUC<br>GUGUACGUGAGAACCAAUUUCAGCAAGACCAUCUGGCAGGUGAGAGCCAAUC<br>GGGACAGAUACAUCCUGGGCCACAAGUCUGCCGCCGUGUAUAAAACCCUGAA<br>UCACGCCAUCACCAAGGCCGUGGGCGUGAGACUGAACCCUAAGACAACCGUG<br>GGCAACAUCCAGGCCGCCAGAACAGAGCUGCUGGCCGCCUACCAGACAGCCU<br>UCAAUAGCCCCGACGUGAAGAAGGCCGCUUGAUAA | Quad-H4V3-f-<br>PRO-028-V7-<br>F16-nolink-<br>Cter-<br>CAMP2_ssHA<br>codon<br>optimization<br>#2 | 390 | 372 |
| 394 AUGAAGGCCAAGCUGCUGGUGCUGCUGUGUACCUUCACUGCAACAUAUGCUA<br>GCUCCAAUAGACCCAGAUCCGUGGCCCAGGCCGCCAUCGCCACAGAUGGCAA<br>GGGGAUCAUCGACAAGGAUUCCAGAGACGCUGUGAUCAACGACGCAAAGCUG<br>AGAGCCGCCAUCGCCGGAGCUCUGGUGAAGGCCGGCUUUAGCAGCGCCGACG<br>CCGUGGCACUGGCCCCCAGAAUUGCAAAGGAGAUGGCAAAGGAGGGCGUGCU<br>GCUGAUCAAUCACCACAAGCUGAAGGCCCUGAUCGGCGCACAGCUGGGCCUG<br>CUGACCGACGCAAAGAUUCAGAGAGCCGCCGCAGCCGUGGACCUGGGCAUCA<br>AGGCCACCCUGGCUGCCACCAUCAUCCCUAACGCCCUGGGCAGCGCCGCCUU<br>CAAGAAUGCAGUGAUCGCCAACCUGGUGGCCGCCGGAAUCGACAAGCACCUG<br>GCCAGAGCCACAGCCGUCGCUAUCGUGGCCACAGCCCUGAAUCCCGCCCUGG<br>GCCCCAUCGCCAAAUUUGAACUGAUCAAGGCAGAAAUCGCUGCCCAGGCCGC<br>CCUGCUCAUCAGAAGAGGCGUCCAUCUGCAGAAGGCCGCCAUCGAGCACGUG<br>AUUGGCAGAGCCUUCGACGCCGCCGUGGCCACAGCUAUCAUUUCUUCCCCUA<br>UCCUGUCUGCCAGAAUCGUGACACACCUGGUGAGAGCCGGAAUCGACAAGUC<br>CAUCGCCAUCUCCCUGGCCCCCCACAUCGUGAAGAGACUGGCUAAGGAGCCU<br>CUGCUGGCCUUCAAUACAGCCAAGCUGAUGAAGAACAUCACAAGACAGAUCG<br>UGGACGUGAUCACCGCCGACAAGGCCAUCAAGACAGCCGAGCAGCUGGAGAA<br>GGAACUGCCAGCCCUGGACGACCUGGUGAAGAAGGCCAGCAGCCCUCCCAAG<br>CCUACCCCUACCCCAACCCCUACACCUACAGCCGGACCUACCGUGACCGUGA<br>UCCCUGUGGGCAGAGAGGGCGGCGACAUCACCAUCAGCGGCAAGGGCUUCAG<br>CACAACAGGCUUUGGCGUGUACGUGGCCGUGGCCCCAGCCAGCGUGCCUGAG<br>UUUUACGGCAAUAGCGACAAGUUCUACGGCUACGACCCCUCCAAGGACACCA<br>CCGAGAGCCCAAGCACCAUCUGGGUGUACACACCUAGCCAGAAGGCCAUCGG<br>CAGCAGAUUUGCCCAGGGCAGGCCUAUGAAUAAUGACGGCAGCUUCACAAUC<br>ACAAUGAAGGCCCCCCCUUUGAGCAGGGCAAGGACUUCGUGGUGCUGACCA<br>CCAAGGCCCACGGCGUGGGCAAGACAGAUCACAGCGACGACACCCGGACCCC<br>CGUGACCUACAGAGAAGCAACACCUGCCCCUACCGGGCCUAAGACACCCAUC<br>GUGUACGUGAGAACCAAUUUCAGCAAGACCAUCUGGCAGGUGAGAGCCAACA<br>GAGAUCGGUACAUCCUGGGCCACAAGUCCGCCGCCGUGUACAAGACCCUGAA<br>UCACGCCAUCACCAAGGCCGUGGGCGUGCGGCUGAAUCCUAAGACCACCGUG<br>GGCAACAUCCAGGCCGCCAGAACCGAACUGCUGGCCGCCUACCAGACCGCCU<br>UCAACAGCCCCGAUGUGAAGAAGGCCGCUUGAUAA | Quad-H4V3-f-<br>PRO-028-V7-<br>F16-nolink-<br>Cter-<br>CAMP2_ssHA<br>codon<br>optimization<br>#1 | 393 | 372 |
| 391 AUGAAGGCCAAGCUGCUGGUGCUGCUGUGCACCUUCACCGCCACCUACGCUG<br>UGGAGCCCACCACCACCAUCAGCGCAACCUCCACCCACGAACUGUCCGCCUC<br>CGAUGCUAGGAACUCAAUCCAGCUGCUGAACGCCCACAUCGCCACACUGCAG<br>AGCGUCCAGAAAUCAGUGCCCGGCAGCGACUACUCCGACCAGAUCCGGGAUC<br>UCCUGAAGGCUGCAUUCGACCUGCGCGGCCUCAUCGAAACACUGGCCCACGG<br>AGGCAUCCCCUUCUAUGACCCAUCCACCAUCAUGCCCCGGAUCAAGCUGGUG<br>GCCACCACAAUCGACACCAUCCACACCGCCACCACCACCCUGCAGAACAAGG<br>UGAGGCCCGCACACGUGGAGCUGGGGCUGGAGGUGACUAAGGCCGUGCUGCU<br>GACAGCAAACCCCGCCUCAACCGCGAAGGAGUUGGAUGCCGAGGGCGCCGCA<br>CUGAAGGCCCGCCUGGAGAAGGUGAGCCAGUAUCCCGAUCUGACCCCCAACG<br>ACGUGGCCACCGUGUAUGUGAGGACCAAUUUCUCCAAGACCAUCUGGCAGGU<br>CAGAGCCAACAGAGACAGGUAUAUCCUGGGCCACAAGAGCGCUGCCGUGUAC<br>AAGACCCUGAACCACGCCAUCACCAAGGCCGUGGGGGUGCGGCUGAACCCUA | CAMP2_WT_<br>HA TMB | | |

TABLE 7-continued

| | | |
|---|---|---|
| | AGACCACCGUGGGGAACAUCCAGGCUGCCAGAACCGAGCUGCUGGCCGCCUA<br>UCAGACCGCAUUCAAUUCCCCCGAUGUGAAGAAGGCCGCCAGCGGCUCCAUC<br>CUGGCCAUCUACUCCACCGUGGCUAGUAGCCUGGUGCUGCUGGUGUCCCUGG<br>GAGCCAUCAGCUUCGGGAGCGGCUAA | |
| 392 | AUGAAAGCCAAGCUGCUCGUGCUGCUGUGUACCUUCACCGCCACCUACGCCG<br>UGGAACCCACCACCACAAUCUCCGCCACCUCCACCCACGAGCUGAGCGCCAG<br>CGACGCCAGAAACAGCAUUCAGCUGCUGAAUGCCCACAUCGCCACCCUGCAG<br>AGCGUGCAGAAGUCCGUGCCUGGCAGCGACUACAGCGACCAGAUCCGGGACC<br>UGCUGAAGGCCGCCUUCGACCUGAGAGGCCUGAUUGAGACACUGGCCCACGG<br>CGGCAUUCCUUUCUACGAUCCUUCUACCAUCAUGCCUAGAAUCAAGCUGGUG<br>GCCACCACCAUCGAUACCAUCCACACAGCCACCACCACACUGCAGAACAAGG<br>UGCGGCCUGCUCACGUGGAACUGGGCCUGGAAGUGACCAAGGCCGUGCUGCU<br>GACCGCCAAUCCUGCCUCCACCGCCAAGGAGCUGGACGCAGAAGGCGCUGCC<br>CUGAAGGCCAGACUGGAGAAGGUGAGCCAGUAUCCCGACCUGACCCCAAACG<br>AUGUGGCCACCGUGUACGUGCGGACAAACUUCAGCAAGACCAUCUGGCAGGU<br>GAGAGCCAACCGGGACAGAUACAUCCUGGGCCACAAGAGCGCCGCCGUGUAU<br>AAGACCCUGAACCACGCCAUCACAAAGGCCGUGGGCGUGAGACUGAACCCCA<br>AGACCACAGUGGGCAACAUCCAGGCCGCCAGGACCGAACUGCUGGCCGCCUA<br>CCAGACCGCCUUCAAUUCCCCUGACGUGAAGAAGGCCGCCUCUGGCAGCAUC<br>CUGGCCAUCUACAGCACCGUGGCCAGCUCUCUGGUGCUGCUGGUGUCUCUGG<br>GCGCCAUCAGCUUCGGCAGCGGCUGA | CAMP2_WT_<br>HA TMB |

TABLE 8

| SEQ ID NO | Nucleotide sequence | Encodes polypeptide sequence according to SEQ ID NO |
|---|---|---|
| 179 | UCAUCCAACAGGCCUCGCUCCGUGGCCCAGGCUGCUAUUGCUACCGACGGCAAGGGAAUCAUCGAUAAAGACUCCAGGG<br>AUGCCGUGAUCAACGAUGCCAAGCUCCGGGCCGCAAUUGCCGGAGCCCUGGUGAAAGCCGGGUUCAGCUCCGCCGAUGC<br>UGUGGCUCUGGCUCCAAGGAUUGCUAAGGAGAUGGCCAAAGAGGGGGUGCUGCUGAUUAACCACCACAAGCUGAAGGCA<br>CUGAUCGGAGCACAGCUGGGACUGCUGACUGACGCCAAAAUCCAGCGCGCCGCUGCAGCAGUCGACCUGGGCAUCAAGG<br>CCACACUGGCUGCUACCAUCAUUCCUAACGCUCUGGGCAGCGCAGCCUUUAAGAAUGCCGUUAUCGCCAAUCUCGUGGC<br>UGCUGGAAUUGAUAAGCACCUGGCCAGAGCCACAGCUGUGGCCAUCGUGGCCACUGCCCUGAACCCAGCAUUGGGCCCU<br>AUCGCUAAGUUUGAGCUGAUUAAGGCCGAGAUCGCCGCUCAGGCUGCCCUGCUGAUUCGCAGGGGAGUGCACCUGCAGA<br>AGGCUGCCAUCGAGCACGUCAUCGGCAGAGCAUUCGACGCCGCUGUCGCCACUGCUAUCAUCUCUAGCCCAAUCCUGAG<br>CGCCAGGAUCGUCACUCACCUGGUGAGAGCUGGGAUUGACAAAUCCAUCGCUAUCAGCCUGGCCCCUCACAUCGUGAAG<br>AGGCUGGCUAAGGAACCACUGCUGGCUUUUAACACUGCUAAGCUGAUGAAGAAUAUUACAAGACAGAUCGUGGACGUCA<br>UCACCGCCGACAAAGCCAUCAAGACAGCCGAGCAGCUCGAGAAGGAGCUGCCUGCCCUGGAUGACCUGGUGAAGAAGGC<br>AUCCUCCCCCCCUAAGCCAACCCCUACCCCAACCCCUACACCUACUUAA | 70 |
| 181 | UCAUCCAACAGGCCUCGCUCCGUGGCCCAGGCUGCUAUUGCUACCGACGGCAAGGGAAUCAUCGAUAAAGACUCCAGGG<br>AUGCCGUGAUCAACGAUGCCAAGCUCCGGGCCGCAAUUGCCGGAGCCCUGGUGAAAGCCGGGUUCAGCUCCGCCGAUGC<br>UGUGGCUCUGGCUCCAAGGAUUGCUAAGGAGAUGGCCAAAGAGGGGGUGCUGCUGAUUAACCACCACAAGCUGAAGGCA<br>CUGAUCGGAGCACAGCUGGGACUGCUGACUGACGCCAAAAUCCAGCGCGCCGCUGCAGCAGUCGACCUGGGCAUCAAGG<br>CCACACUGGCUGCUACCAUCAUUCCUAACGCUCUGGGCAGCGCAGCCUUUAAGAAUGCCGUUAUCGCCAAUCUCGUGGC<br>UGCUGGAAUUGAUAAGCACCUGGCCAGAGCCACAGCUGUGGCCAUCGUGGCCACUGCCCUGAACCCAGCAUUGGGCCCU<br>AUCGCUAAGUUUGAGCUGAUUAAGGCCGAGAUCGCCGCUCAGGCUGCCCUGCUGAUUCGCAGGGGAGUGCACCUGCAGA<br>AGGCUGCCAUCGAGCACGUCAUCGGCAGAGCAUUCGACGCCGCUGUCGCCACUGCUAUCAUCUCUAGCCCAAUCCUGAG<br>CGCCAGGAUCGUCACUCACCUGGUGAGAGCUGGGAUUGACAAAUCCAUCGCUAUCAGCCUGGCCCCUCACAUCGUGAAG<br>AGGCUGGCUAAGGAACCACUGCUGGCUUUUAACACUGCUAAGCUGAUGAAGCAGAUUACAAGACAGAUCGUGGACGUCA<br>UCACCGCCGACAAAGCCAUCAAGACAGCCGAGCAGCUCGAGAAGGAGCUGCCUGCCCUGGAUGACCUGGUGAAGAAGGC<br>AUCCUCCCCCCCUAAGCCAACCCCUACCCCAACCCCUACACCUACUUAA | 72 |
| 182 | GCAGGCCCUACCGUCACAGUGAUCCCUGUGGGCAGAGAAGGUGGCGACAUCACCAUCAGCGGCAAGGGCUUCAGCACCA<br>CAGGCUUUGGCGUGUACGUGGCCGUGGCACCUGCUAGCGUGCCCGAAUUCUACGGCAAUAGCGACAAGUUCUACGGCUA<br>CGACCCCAGCAAGGACACCACCGAGAGCCCUAGCACCAUCUGGGUGUACACCCCUAGCCAGAAGGCCAUCGGCUCUCGG<br>UUCGCCCAGGGCAGACCCAUGAACAAUGACGGCAGCUUCACAAUCACCAUGAAGGCCCCCCCUUUCGAGCAGGGCAAAG<br>ACUUCGUGGUGCUGACCACAAAGGCCCAUGGCGUGGGCAAAACCGAUCACAGCGACGACACACGGACACCUGUCACCUA<br>CAGAGAGGCUACCCCUGCCCCUACAGGCCCUAAGACACCCAUCGCCCCUAGCAAGCAGCCUAGCAAGCAGGCCGCCCCU<br>AGCAAGCAGGUGAAGCCUUCUAAGCAGGCCGGCCCCAACAAGCAGUCCACCACACCUCAGCAGAAGACAGCCGAGCACA<br>GAAGCCAGACCCCUGCCGCCCACCGGACCAUGACAAAGCAGGUGAGCACCAUCGGCGCCAGCAAGGUGACAAGCGGCUC<br>UCUGACCUGGGGCAUCAGAACCUCUUUUACCUCCUACCUGAGAGGCCCUAUCGCCAACGGCUCUUGGAAGCUGAGCGGA<br>GGCGCCAAUUGGAAUGGCUCCGCCUUCACCUUCCCUCUGACCAGCGGCAGCUUCGACCCAGCCACCAAGUCCGGAAGCC<br>UGAAGUACAGCGGCAGCGUGCACAUGACAGGCCACCACGGCAUCCUGGACAUGACCCUGGCCGAGCCAAGCCUGCAGAU<br>CAAGGGAAGCACCGGCCACCUGUAUCUGGACGUGAAAAGCAGCAGCAUGGACGGCAAGAAGACCAAUUACGGCAGAGUG<br>GACUUCGCCACCUUCGGAGUGAGCGUGUCUGGCAACGCCGCCAUCAAGGGCAGCCCUGUGAAGCUGACCGCCACAGGCG<br>CUAAGGCUUUUGCCGGCUUCUACAGAGCCGGCGAGCCUAUGAACCCUCUGAGCACCAAUCUGACCCUGAGCGCCGAGAA<br>GGUGUCCCACAACGUGACCGUGGACGCAGUGACAGGCAAGGUGAUCGGCGACGACUCUGGCAAGGGAGCCGGCCGGGGC<br>CUGCCCGUGACAUAA | 73 |
| 189 | UCCUCUAAUAGACCAAGAUCCGUGGCUCAGGCCGCCAUCGCUACAGAUGGGAAAGGAAUCAUCGAUAAGGAUAGUCGGG<br>AUGCAGUGAUCAACGACGCCAAACUCCGAGCUGCCAUCGCCGGCGCCCUGGUGAAGGCUGGGUUUUCCAGCGCCGACGC<br>AGUGGCCCUGGCACCUAGAAUCGCCAAGGAGAUGGCAAAGGAGGGCGUCCUGCUGAUUAAUCACCACAAGCUGAAAGCU | 80 |

TABLE 8-continued

| SEQ ID NO | Nucleotide sequence | Encodes polypeptide sequence according to SEQ ID NO |
|---|---|---|
| | CUGAUUGGGGCUCAGCUCGGACUGCUGACUGACGCCAAGAUCCAGAGGGCCGCAGCUGCCGUGGAUCUGGGGAUCAAGG<br>CCACUCUGGCCGCUACUAUUAUUCCUAACGCUCUGGGGUCUGCCGCCUUCAAGAAUGCUGUCAUUGCCAACCUGGUGGC<br>UGCUGGCAUCGACAAACACCUCGCCAGGGCUACCGCUGUGGCCAUCGUUGCCACAGCCCUGAAUCCUGCCCUGGGCCCA<br>AUCGCUAAAUUUGAGCUGAUUAAGGCUGAGAUCGCCGCCCAGGCCGCACUGCUGAUCAGAAGGGGGGUCCAUCUGCAGA<br>AGGCCGCUAUUGAACAUGUGAUCGGCCGCGCAUUCGACGCUGCCGUGGCCACCGCUAUCAUUUCCUCUCCAAUCCUGAG<br>CGCACGGAUUGUGACCCACCUGGUGAGGGCUGGAAUUGAUAAAAGCAUCGCUAUCUCCCUGGCUCCUCAUAUCGUGAAG<br>CGCCUGGCCAAGGAGCCCCUGCUGGCUUUCAACACCGCCAAGCUGAUGAAGAAUAUUACAAGACAGAUCGUUGACGUGA<br>UCACAGCCGAUAAAGCCAUCAAAACAGCUGAGCAGCUGGAAAAGGAGCUCCCCGCCCUGGACGACCUGGUCAAAAAAGC<br>UAGCUCCCCUCCUAAGCCUACCCCCACACCUACUCCAACCCCCACCGCCGGGCCCACCGUGACAGUGAUCCCCGUGGGA<br>AGGGAGGGGGGCGACAUUACCAUUAGCGGAAAAGGGUUCUCCACAACCGGGUUCGGCGUCUACGUGGCCGUGGCUCCUG<br>CCUCUGUGCCAGAGUUCUAUGGCAAUAGCGACAAGUUCUAUGGGUACGAUCCAUCUAAGGACACCACCGAAAGUCCCAG<br>CACCAUCUGGGUGUAUACACCAUCCCAGAAAGCAAUCGGCAGCAGAUUCGCCCAAGGCAGGCCCAUGAAUAAUGAUGGC<br>UCUUUCACCAUUACAAUGAAGGCCCCUCCUUUCGAGCAGGGAAAGGAUUUCGUGGUGCUGACCACCAAAGCACAUGGCG<br>UUGGAAAGACCGACCACAGCGACGAUACUCGGACCCCUGUGACUUACAGAGAGGCCACCCCUGCUCCAACCGGCCCUAA<br>AACUCCCAUCUGAUAA | |
| 191 | UCCAGCAACCGGCCUAGAAGCGUGGCCCAGGCCGCCAUCGCCACCGACGGCAAGGGCAUCAUCGACAAGGAUUCCCGGG<br>ACGCCGUGAUCAAUGACGCCAAGCUGAGAGCCGCCAUCGCCGGCGCCCUGGUGAAGGCCGGCUUCAGCAGCGCCGACGC<br>CGUGGCCCUGGCCCCCAGAAUCGCCAAGGAGAUGGCCAAGGAAGGCGUGCUGCUGAUCAAUCACCACAAGCUGAAGGCC<br>CUGAUCGGCGCCCAGCUGGGCCUGCUGACAGAUGCCAAGAUCCAGAGAGCCGCUGCCGCCGUGGACCUGGGCAUCAAGG<br>CCACCCUGGCCGCCACCAUCAUCCCUAACGCCCUGGGCAGCGCUGCCUUCAAGAAUGCCGUGAUCGCCAACCUGGUGGC<br>CGCCGGCAUCGACAAGCACCUGGCCAGAGCCACAGCCGUGGCCAUCGUGGCCACCGCCCUGAAUCCUGCCCUGGGCCCC<br>AUCGCCAAGUUCGAGCUGAUCAAGGCCGAGAUCGCCGCCCAGGCCGCCCUGCUGAUCCGGCGGGGCGUGCACCUGCAGA<br>AGGCCGCCAUCGAACACGUGAUCGGCAGAGCCUUCGAUGCCGCCGUGGCCACCGCCAUCAUCAGCUCCCCCAUCCUGAG<br>CGCCAGAAUCGUGACCCACCUGGUGCGGGCCGGCAUCGACAAGUCCAUCGCCAUUAGCCUGGCCCCUCACAUCGUGAAG<br>CGCCUGGCCAAGGAGCCCCUGCUGGCCUUCAAUACCGCCAAGCUGAUGAAGAAUAUCACCAGACAGAUCGUGGAUGUGA<br>UCACCGCCGAUAAGGCCAUCAAGACCGCCGAGCAGCUGGAGAAAGAGCUGCCCGCCCUGGACGACCUGGUGAAAAAGGC<br>CAUGGGCCCCCUAAGCCUACAGGCGGCGGAGGCGCUGGACCUACCGUGACCGUGAUCCCCGUGGGCAGAGAGGGC<br>GGCGAUAUCACCAUCAGCGGCAAGGGCUUCAGCACCACCGGCUUCGGCGUGUACGUGGCCGUGGCCCCUGCCAGCGUGC<br>CCGAGUUCUACGGCAAUAGCGACAAGUUCUACGGCUACGACCCCAGCAAGGACACCACAGAAUCUCCCAGCACCAUCUG<br>GGUGUACACCCCCAGCCAGAAGGCCAUUGGCAGCCGGUUCGCCCAGGGCCGGCCUAUGAACAAUGAUGGCAGCUUCACA<br>AUCACCAUGAAGGCCCCACCCUUCGAGCAGGGCAAGGACUUCGUGGUGCUGACCACCAAGGCCCACGGAGUGGGCAAGG<br>GCGACCACGGCGACGACACACGGACCCCCGUGGGCUACAGAUGA | 82 |
| 192 | AGCAGCAACCGCCCAAGGUCUGUCGCACAGGCUGCUAUCGCCACAGAUGGCAAGGGAAUCAUUGAUAAGGACAGCAGGG<br>AUGCUGUGAUCAACGACGCAAAACUGAGAGCCGCCAUCGCCGGCGCACUGGUGAAAGCCGGCUUUUCUUCCGCCGACGC<br>AGUGGCUCUGGCUCCCAGAAUCGCUAAGGAAAUGGCCAAGGAGGGAGUGCUGCUGAUCAAUCACCACAAACUGAAGGCU<br>CUGAUCGGGGCUCAGCUGGGCCUGCUGACUGACGCUAAGAUUCAGAGAGCAGCAGCAGCUGUCGACCUGGGAAUCAAGG<br>CAACCCUGGCAGCCACUAUCAUUCCAAAUGCUCUGGGCUCUGCCGCCUUCAAAAACGCCGUGAUUGCCAAUCUCGUGGC<br>AGCUGGAAUCGAUAAGCACCUGGCACGGGCCACCGCCGUGGCUAUCGUGGCCACCGCUCUGAAUCCCGCCCUGGGCCCU<br>AUUGCCAAGUUUGAACUGAUCAAAGCCGAGAUCGCUGCACAGGCCGCCCUGCUCAUCCGCAGGGGGGUCCACCUGCAGA<br>AAGCAGCCAUCGAGCACGUGAUCGGCAGGGCCUUUGAUGCAGCCGUCGCCACUGCCAUCAUCAGCUCUCCAAUCCUGUC<br>UGCCCGGAUUGUGACUCACCUGGUGCGCGCCGGCAUCGAUAAGUCCAUCGCAAUCUCUCUGGCCCCACACAUCGUGAAG<br>AGACUGGCCAAAGAACCACUCCUGGCUUUCAAUACCGCCAAACUCAUGAAAAACAUCACCCGGCAGAUCGUCGAUGUGA<br>UUACCGCCGACAAGGCUAUCAAGACCGCCGAGCAGCUCGAAAAGGAGCUGCCUGCCCUGGACGACCUGGUGAAGAAAGC<br>CUCCUCUCCACCCAAACCCACCCCAACUCCAACUCCAACCCCUACAGCUGGCCCCACCGUGACCGUCAUCCCAGUGGGA<br>AGGGAAGGAGGAGACAUCACAAUCUCUGGAAAGGGGUUUAGCACAACCGGAUUUGGAGUGUACGUCGCCGUGGCCCCCG<br>CAUCCGUGCCAGAAUUCUACGGCAAUUCCGAUAAAUUCUACGGGUACGACCCCUCCAAGGACACUACAGAGAGCCCCUC<br>UACAAUUUGGGUGUACACCCCAAGCCAGAAGGCCAUCGGAAGCAGAUUUGCUCAGGGCCGGCCAAUGAACAACGACGGA<br>UCCUUCACAAUCACAAUGAAAGCACCUCCCUUUGAGCAGGGCAAGGAUUUUGUGGUGCUGACCACCAAGGCUCACGGGG<br>UCGGAAAGACCGAUCACAGCGACGAUACAAGAACCCCCGUGACAUACCGGUGAUAA | 83 |
| 311 | | 42 |
| 312 | | 86 |
| 384 | GUGGAGCCCACAACCACAAUCUCUGCCACAAGCACCCACGAGCUGUCUGCCAGCGACGCCAGAAACUCCAUCCAGCUGC<br>UGAAUGCCCACAUCGCCACACUGCAGAGCGUGCAGAAAUCCGUGCCUGGCAGCGAUUACAGCGACCAGAUCCGGGACCU<br>GCUGAAGGCCGCCUUUGAUCUGAGAGGCCUGAUCGAAACCCUGGCCCACGGCGGCAUUCCCUUCUAUGACCCCUCCACC<br>AUCAUGCCCAGAAUCAAGCUGGUGGCCACCACCAUCGACACCAUCCACACAGCUACAACCACCCUGCAGAACAAGGUGC<br>GGCCAGCCCAUGUGGAACUGGGCCUGGAGGUGACAAAGGCCGUGCUGCUGACCGCCAAUCCUGCCAGCACAGCAAAAGA<br>ACUGGACGCCGAGGGAGCUGCUCUGAAGGCCAGACUGGAAAAGGUGAGCCAGUACCCCGACCUGACACCUAAUGAUGUG<br>GCCACAGUGUACGUGAGAACCAAUUUCAGCAAGACCAUCUGGCAGGUGAGAGCCAACAGAGAUCGGUACAUCCUGGGCC<br>ACAAGUCCGCCGCCGUGUACAAGACCCUGAAUCACGCCAUCACCAAGGCCGUGGGCGUGCGGCUGAAUCCUAAGACCAC<br>CGUGGGCAACAUCCAGGCCGCCAGAACCGAACUGCUGGCCGCCUACCAGACCGCCUUCAACAGCCCCGAUGUGAAGAAG<br>GCCGCUAGCUCCAAUAGACCCAGAUCCGUGGCCCAGGCCGCCAUCGCCACAGAUGGCAAGGGGAUCAUCGACAAGGAUU<br>CCAGAGACGCUGUGAUCAACGACGCAAAGCUGAGAGCCGCCAUCGCCGGAGCUCUGGUGAAGGCCGGCUUUAGCAGCGC<br>CGACGCCGUGGCACUGGCCCCCAGAAUUGCAAAGGAGAUGGCAAAGGAGGGCGUGCUGCUGAUCAAUCACCACAAGCUG<br>AAGGCCCUGAUCGGCGCACAGCUGGGCCUGCUGACCGACGCAAAGAUUCAGAGAGCCGCCGCAGCCGUGGACCUGGGCA<br>UCAAGGCCACCCUGGCUGCCACCAUCAUCCCUAACGCCCUGGGCAGCGCCGCCUUCAAGAAUGCAGUGAUCGCCAACCU<br>GGUGGCCGCCGGAAUCGACAAGCACCUGGCCAGAGCCACAGCCGUCGCUAUCGUGGCCACAGCCCUGAAUCCCGCCCUG<br>GGCCCCAUCGCCAAAUUUGAACUGAUCAAGGCAGAAAUCGCUGCCCAGGCCGCCCUGCUCAUCAGAAGAGGCGUCCAUC<br>UGCAGAAGGCCGCCAUCGAGCACGUGAUUGGCAGAGCCUUCGACGCCGCCGUGGCCACAGCUAUCAUUUCUUCCCCUAU<br>CCUGUCUGCCAGAAUCGUGACACACCUGGUGAGAGCCGGAAUCGACAAGUCCAUCGCCAUCUCCCUGGCCCCCCACAUC | 373 |

TABLE 8-continued

| SEQ ID NO | Nucleotide sequence | Encodes polypeptide sequence according to SEQ ID NO |
|---|---|---|
| | GUGAAGAGACUGGCUAAGGAGCCUCUGCUGGCCUUCAAUACAGCCAAGCUGAUGAAGAACAUCACAAGACAGAUCGUGG<br>ACGUGAUCACCGCCGACAAGGCCAUCAAGACAGCCGAGCAGCUGGAGAAGGAACUGCCAGCCCUGGACGACCUGGUGAA<br>GAAGGCCAGCAGCCCUCCCAAGCCUACCCCUACCCCAACCCCUACACCUACAGCCGGACCUACCGUGACCGUGAUCCCU<br>GUGGGCAGAGAGGGCGGCGACAUCACCAUCAGCGGCAAGGGCUUCAGCACAACAGGCUUUGGCGUGUACGUGGCCGUGG<br>CCCCAGCCAGCGUGCCUGAGUUUUACGGCAAUAGCGACAAGUUCUACGGCUACGACCCCUCCAAGGACACCACCGAGAG<br>CCCAAGCACCAUCUGGGUGUACACACCUAGCCAGAAGGCCAUCGGCAGCAGAUUUGCCCAGGGCAGGCCUAUGAAUAAU<br>GACGGCAGCUUCACAAUCACAAUGAAGGCCCCCCCUUUGAGCAGGGCAAGGACUUCGUGGUGCUGACCACCAAGGCCC<br>ACGGCGUGGGCAAGACAGAUCACAGCGACGACACCCGGACCCCCGUGACCUACAGAGAAGCAACACCUGCCCCUACCGG<br>GCCUAAGACACCCAUC | |
| 385 | GUGGAGCCUACCACCACAAUCAGCGCCACCAGCACCCACGAGCUGAGCGCCAGCGAUGCCAGAAAUAGCAUCCAGCUGC<br>UGAAUGCCCACAUCGCCACCCUGCAGUCCGUGCAGAAAAGCGUGCCUGGAAGCGAUUACAGCGAUCAGAUCAGGGACCU<br>GCUGAAGGCCGCCUUCGAUCUGAGAGGCCUGAUCGAGACACUGGCCCACGGCGGCAUCCCUUUCUACGACCCCAGCACC<br>AUCAUGCCUAGAAUCAAACUGGUGGCCACCACCAUCGACACCAUCCACACCGCAACAACAACCCUGCAGAAUAAGGUGC<br>GGCCUGCCCACGUGGAACUGGGACUGGAAGUGACAAAGGCCGUGCUGCUGACCGCUAAUCCCGCCUCCACCGCCAAGGA<br>GCUGGAUGCCGAAGGAGCUGCCCUGAAAGCCAGACUGGAGAAGGUGAGCCAGUACCCUGAUCUGACCCCUAACGACGUG<br>GCCACCGUGUACGUGAGAACCAAUUUCAGCAAGACCAUCUGGCAGGUGAGAGCCAAUCGGGACAGAUACAUCCUGGGCC<br>ACAAGUCUGCCGCCGUGUAUAAAACCCUGAAUCACGCCAUCACCAAGGCCGUGGGCGUGAGACUGAACCCUAAGACAAC<br>CGUGGGCAACAUCCAGGCCGCCAGAACAGAGCUGCUGGCCGCCUACCAGACAGCCUUCAAUAGCCCCGACGUGAAGAAG<br>GCCGCUUCCAGCAAUAGACCCCGGAGCGUGGCACAGGCUGCUAUUGCCACCGACGGAAAGGGCAUCAUCGAUAAAGACA<br>GCCGGGAUGCCGUGAUCAAUGACGCCAAGCUGAGAGCAGCAAUCGCCGGCGCUCUGGUGAAGGCAGGCUUCAGCAGCGC<br>CGACGCCGUGGCUCUGGCCCCUAGAAUCGCUAAGGAGAUGGCCAAGGAGGGCGUGCUGCUGAUCAAUCACCACAAGCUG<br>AAGGCCCUGAUCGGCGCCCAGCUGGGACUGCUGACAGAUGCCAAGAUCCAGAGAGCCGCUGCAGCCGUGGAUCUGGGCA<br>UCAAGGCCACACUGGCCGCCACCAUCAUCCCAAACGCCCUGGGCAGCGCCGCCUUCAAAAAUGCCGUGAUUGCCAACCU<br>GGUGGCCGCCGGCAUCGAUAAGCACCUGGCCAGAGCCACAGCCGUGGCCAUCGUGGCCACAGCCCUGAAUCCCGCACUG<br>GGACCUAUUGCCAAGUUCGAACUCAUUAAGGCCGAAAUCGCAGCCCAAGCCGCCCUGCUGAUUCGGCGGGGCGUGCACC<br>UGCAGAAAGCCGCCAUUGAGCACGUGAUCGGCAGAGCCUUCGAUGCCGCUGUGGCCACCGCCAUCAUCUCCUCUCCUAU<br>CCUGUCUGCUAGAAUCGUGACCCACCUGGUCAGAGCCGGAAUCGACAAGUCUAUCGCUAUCAGCCUGGCCCCCCACAUC<br>GUGAAGAGACUGGCCAAAGAGCCCCUGCUGGCCUUCAACACAGCCAAGCUCAUGAAGAAUAUCACCAGACAGAUCGUGG<br>ACGUGAUCACCGCCGACAAGGCCAUCAAAACCGCUGAGCAGCUGGAGAAGGAGCUGCCCGCCCUGGAUGACCUGGUGAA<br>GAAGGCCAGCAGCCCCCCCAAGCCUACACCUACACCUACCCCAACCCCUACAGCCGGCCCUACAGUGACCGUGAUUCCU<br>GUGGGCAGAGAAGGAGGCGACAUCACCAUCAGCGGAAAGGGCUUCUCUACCACAGGCUUCGGCGUGUACGUGGCCGUGG<br>CCCCUGCCUCCGUGCCCGAAUUCUACGGCAACAGCGACAAGUUCUACGGCUACGACCCCAGCAAAGACACCACAGAGAG<br>CCCUUCCACCAUCUGGGUGUACACCCCUUCCCAGAAGGCCAUCGGCAGCAGAUUCGCUCAGGGCAGACCUAUGAAUAAC<br>GACGGCUCUUUCACCAUCACAAUGAAGGCCCCCCCUUCGAGCAGGGCAAAGACUUCGUGGUGCUGACAACCAAGGCCC<br>ACGGCGUGGGCAAGACAGAUCACUCCGACGACACCCGGACCCCUGUGACCUACAGAGAGGCAACACCUGCUCCCACCGG<br>GCCAAAGACCCCUAUC | 373 |
| 386 | AUGGUGGAGCCCACAACCACAAUCUCUGCCACAAGCACCCACGAGCUGUCUGCCAGCGACGCCAGAAACUCCAUCCAGC<br>UGCUGAAUGCCCACAUCGCCACACUGCAGAGCGUGCAGAAAUCCGUGCCUGGCAGCGAUUACAGCGACCAGAUCCGGGA<br>CCUGCUGAAGGCCGCCUUUGAUCUGAGAGGCCUGAUCGAAACCCUGGCCCACGGCGGCAUUCCCUUCUAUGACCCCUCC<br>ACCAUCAUGCCCAGAAUCAAGCUGGUGGCCACCACCAUCGACACCAUCCACACAGCUACAACCACCCUGCAGAACAAGG<br>UGCGGCCAGCCCAUGUGGAACUGGGCCUGGAGGUGACAAAGGCCGUGCUGCUGACCGCCAAUCCUGCCAGCACAGCAAA<br>AGAACUGGACGCCGAGGGAGCUGCUCUGAAGGCCAGACUGGAAAAGGUGAGCCAGUACCCCGACCUGACACCUAAUGAU<br>GUGGCCACAGUGUACGUGAGAACCAAUUUCAGCAAGACCAUCUGGCAGGUGAGAGCCAACAGAGAUCGGUACAUCCUGG<br>GCCACAAGUCCGCCGCCGUGUACAAGACCCUGAAUCACGCCAUCACCAAGGCCGUGGGCGUGCGGCUGAAUCCUAAGAC<br>CACCGUGGGCAACAUCCAGGCCGCCAGAACCGAACUGCUGGCCGCCUACCAGACCGCCUUCAACAGCCCCGAUGUGAAG<br>AAGGCCGCUAGCUCCAAUAGACCCAGAUCCGUGGCCCAGGCCGCCAUCGCCACAGAUGGCAAGGGGAUCAUCGACAAGG<br>AUUCCAGAGACGCUGUGAUCAACGACGCAAAGCUGAGAGCCGCCAUCGCCGGAGCUCUGGUGAAGGCCGGCUUUAGCAG<br>CGCCGACGCCGUGGCACUGGCCCCCAGAAUUGCAAAGGAGAUGGCAAAGGAGGGCGUGCUGCUGAUCAAUCACCACAAG<br>CUGAAGGCCCUGAUCGGCGCACAGCUGGGCCUGCUGACCGACGCAAAGAUUCAGAGAGCCGCCGCAGCCGUGGACCUGG<br>GCAUCAAGGCCACCCUGGCUGCCACCAUCAUCCCUAACGCCCUGGGCAGCGCCGCCUUCAAGAAUGCAGUGAUCGCCAA<br>CCUGGUGGCCGCCGGAAUCGACAAGCACCUGGCCAGAGCCACAGCCGUCGCUAUCGUGGCCACAGCCCUGAAUCCCGCC<br>CUGGGCCCCAUCGCCAAAUUUGAACUGAUCAAGGCAGAAAUCGCUGCCCAGGCCGCCCUGCUCAUCAGAAGAGGCGUCC<br>AUCUGCAGAAGGCCGCCAUCGAGCACGUGAUUGGCAGAGCCUUCGACGCCGCCGUGGCCACAGCUAUCAUUUCUUCCCC<br>UAUCCUGUCUGCCAGAAUCGUGACACACCUGGUGAGAGCCGGAAUCGACAAGUCCAUCGCCAUCUCCCUGGCCCCCCAC<br>AUCGUGAAGAGACUGGCUAAGGAGCCUCUGCUGGCCUUCAAUACAGCCAAGCUGAUGAAGAACAUCACAAGACAGAUCG<br>UGGACGUGAUCACCGCCGACAAGGCCAUCAAGACAGCCGAGCAGCUGGAGAAGGAACUGCCAGCCCUGGACGACCUGGU<br>GAAGAAGGCCAGCAGCCCUCCCAAGCCUACCCCUACCCCAACCCCUACACCUACAGCCGGACCUACCGUGACCGUGAUC<br>CCUGUGGGCAGAGAGGGCGGCGACAUCACCAUCAGCGGCAAGGGCUUCAGCACAACAGGCUUUGGCGUGUACGUGGCCG<br>UGGCCCCAGCCAGCGUGCCUGAGUUUUACGGCAAUAGCGACAAGUUCUACGGCUACGACCCCUCCAAGGACACCACCGA<br>GAGCCCAAGCACCAUCUGGGUGUACACACCUAGCCAGAAGGCCAUCGGCAGCAGAUUUGCCCAGGGCAGGCCUAUGAAU<br>AAUGACGGCAGCUUCACAAUCACAAUGAAGGCCCCCCCUUUGAGCAGGGCAAGGACUUCGUGGUGCUGACCACCAAGG<br>CCCACGGCGUGGGCAAGACAGAUCACAGCGACGACACCCGGACCCCCGUGACCUACAGAGAAGCAACACCUGCCCCUAC<br>CGGGCCUAAGACACCCAUC | 374 |
| 387 | GUGGAGCCUACCACCACAAUCAGCGCCACCAGCACCCACGAGCUGAGCGCCAGCGAUGCCAGAAAUAGCAUCCAGCUGC<br>UGAAUGCCCACAUCGCCACCCUGCAGUCCGUGCAGAAAAGCGUGCCUGGAAGCGAUUACAGCGAUCAGAUCAGGGACCU<br>GCUGAAGGCCGCCUUCGAUCUGAGAGGCCUGAUCGAGACACUGGCCCACGGCGGCAUCCCUUUCUACGACCCCAGCACC<br>AUCAUGCCUAGAAUCAAACUGGUGGCCACCACCAUCGACACCAUCCACACCGCAACAACAACCCUGCAGAAUAAGGUGC<br>GGCCUGCCCACGUGGAACUGGGACUGGAAGUGACAAAGGCCGUGCUGCUGACCGCUAAUCCCGCCUCCACCGCCAAGGA<br>GCUGGAUGCCGAAGGAGCUGCCCUGAAAGCCAGACUGGAGAAGGUGAGCCAGUACCCUGAUCUGACCCCUAACGACGUG<br>GCCACCGUGUACGUGAGAACCAAUUUCAGCAAGACCAUCUGGCAGGUGAGAGCCAAUCGGGACAGAUACAUCCUGGGCC<br>ACAAGUCUGCCGCCGUGUAUAAAACCCUGAAUCACGCCAUCACCAAGGCCGUGGGCGUGAGACUGAACCCUAAGACAAC | 374 |

TABLE 8-continued

| SEQ ID NO | Nucleotide sequence | Encodes polypeptide sequence according to SEQ ID NO |
|---|---|---|
| | CGUGGGCAACAUCCAGGCCGCCAGAACAGAGCUGCUGGCCGCCUACCAGACAGCCUUCAAUAGCCCCGACGUGAAGAAG<br>GCCGCUUCCAGCAAUAGACCCCGGAGCGUGGCACAGGCUGCUAUUGCCACCGACGGAAAGGGCAUCAUCGAUAAAGACA<br>GCCGGGAUGCCGUGAUCAAUGACGCCAAGCUGAGAGCAGCAAUCGCCGGCGCUCUGGUGAAGGCAGGCUUCAGCAGCGC<br>CGACGCCGUGGCUCUGGCCCCUAGAAUCGCUAAGGAGAUGGCCAAGGAGGGCGUGCUGCUGAUCAAUCACCACAAGCUG<br>AAGGCCCUGAUCGGCGCCCAGCUGGGACUGCUGACAGAUGCCAAGAUCCAGAGAGCCGCUGCAGCCGUGGAUCUGGGCA<br>UCAAGGCCACACUGGCCGCCACCAUCAUCCCAAACGCCCUGGGCAGCGCCGCCUUCAAAAAUGCCGUGAUUGCCAACCU<br>GGUGGCCGCCGGCAUCGAUAAGCACCUGGCCAGAGCCACAGCCGUGGCCAUCGUGGCCACAGCCCUGAAUCCCGCACUG<br>GGACCUAUUGCCAAGUUCGAACUCAUUAAGGCCGAAAUCGCAGCCCAAGCCGCCCUGCUGAUUCGGCGGGGCGUGCACC<br>UGCAGAAAGCCGCCAUUGAGCACGUGAUCGGCAGAGCCUUCGAUGCCGCUGUGGCCACCGCCAUCAUCUCCUCUCCUAU<br>CCUGUCUGCUAGAAUCGUGACCCACCUGGUCAGAGCCGGAAUCGACAAGUCUAUCGCUAUCAGCCUGGCCCCCCACAUC<br>GUGAAGAGACUGGCCAAAGAGCCCCUGCUGGCCUUCAACACAGCCAAGCUCAUGAAGAAUAUCACCAGACAGAUCGUGG<br>ACGUGAUCACCGCCGACAAGGCCAUCAAAACCGCUGAGCAGCUGGAGAAGGAGCUGCCCGCCCUGGAUGACCUGGUGAA<br>GAAGGCCAGCAGCCCCCCCAAGCCUACACCUACACCUACCCCAACCCCUACAGCCGGCCCUACAGUGACCGUGAUUCCU<br>GUGGGCAGAGAAGGAGGCGACAUCACCAUCAGCGGAAAGGGCUUCUCUACCACAGGCUUCGGCGUGUACGUGGCCGUGG<br>CCCCUGCCUCCGUGCCCGAAUUCUACGGCAACAGCGACAAGUUCUACGGCUACGACCCCAGCAAAGACACCACAGAGAG<br>CCCUUCCACCAUCUGGGUGUACACCCCUUCCCAGAAGGCCAUCGGCAGCAGAUUCGCUCAGGGCAGACCUAUGAAUAAC<br>GACGGCUCUUUCACCAUCACAAUGAAGGCCCCCCCUUCGAGCAGGGCAAAGACUUCGUGGUGCUGACAACCAAGGCCC<br>ACGGCGUGGGCAAGACAGAUCACUCCGACGACACCCGGACCCCUGUGACCUACAGAGAGGCAACACCUGCUCCCACCGG<br>GCCAAAGACCCCUAUC | |
| 388 | GUGGAGCCCACAACCACAAUCUCUGCCACAAGCACCCACGAGCUGUCUGCCAGCGACGCCAGAAACUCCAUCCAGCUGC<br>UGAAUGCCCACAUCGCCACACUGCAGAGCGUGCAGAAAUCCGUGCCUGGCAGCGAUUACAGCGACCAGAUCCGGGACCU<br>GCUGAAGGCCGCCUUUGAUCUGAGAGGCCUGAUCGAAACCCUGGCCCACGGCGGCAUUCCCUUCUAUGACCCCUCCACC<br>AUCAUGCCCAGAAUCAAGCUGGUGGCCACCACCAUCGACACCAUCCACACAGCUACAACCACCCUGCAGAACAAGGUGC<br>GGCCAGCCCAUGUGGAACUGGGCCUGGAGGUGACAAAGGCCGUGCUGCUGACCGCCAAUCCUGCCAGCACAGCAAAAGA<br>ACUGGACGCCGAGGGAGCUGCUCUGAAGGCCAGACUGGAAAAGGUGAGCCAGUACCCCGACCUGACACCUAAUGAUGUG<br>GCCACAAGCUCCAAUAGACCCAGAUCCGUGGCCCAGGCCGCCAUCGCCACAGAUGGCAAGGGGAUCAUCGACAAGGAUU<br>CCAGAGACGCUGUGAUCAACGACGCAAAGCUGAGAGCCGCCAUCGCCGGAGCUCUGGUGAAGGCCGGCUUUAGCAGCGC<br>CGACGCCGUGGCACUGGCCCCCAGAAUUGCAAAGGAGAUGGCAAAGGAGGGCGUGCUGCUGAUCAAUCACCACAAGCUG<br>AAGGCCCUGAUCGGCGCACAGCUGGGCCUGCUGACCGACGCAAAGAUUCAGAGAGCCGCCGCAGCCGUGGACCUGGGCA<br>UCAAGGCCACCCUGGCUGCCACCAUCAUCCCUAACGCCCUGGGCAGCGCCGCCUUCAAGAAUGCAGUGAUCGCCAACCU<br>GGUGGCCGCCGGAAUCGACAAGCACCUGGCCAGAGCCACAGCCGUCGCUAUCGUGGCCACAGCCCUGAAUCCCGCCCUG<br>GGCCCCAUCGCCAAAUUUGAACUGAUCAAGGCAGAAAUCGCUGCCCAGGCCGCCCUGCUCAUCAGAAGAGGCGUCCAUC<br>UGCAGAAGGCCGCCAUCGAGCACGUGAUUGGCAGAGCCUUCGACGCCGCCGUGGCCACAGCUAUCAUUUCUUCCCCUAU<br>CCUGUCUGCCAGAAUCGUGACACACCUGGUGAGAGCCGGAAUCGACAAGUCCAUCGCCAUCUCCCUGGCCCCCCACAUC<br>GUGAAGAGACUGGCUAAGGAGCCUCUGCUGGCCUUCAAUACAGCCAAGCUGAUGAAGAACAUCACAAGACAGAUCGUGG<br>ACGUGAUCACCGCCGACAAGGCCAUCAAGACAGCCGAGCAGCUGGAGAAGGAACUGCCAGCCCUGGACGACCUGGUGAA<br>GAAGGCCAGCAGCCCUCCCAAGCCUACCCCUACCCCAACCCCUACACCUACAGCCGGACCUACCGUGACCGUGAUCCCU<br>GUGGGCAGAGAGGGCGGCGACAUCACCAUCAGCGGCAAGGGCUUCAGCACAACAGGCUUUGGCGUGUACGUGGCCGUGG<br>CCCCAGCCAGCGUGCCUGAGUUUUACGGCAAUAGCGACAAGUUCUACGGCUACGACCCCUCCAAGGACACCACCGAGAG<br>CCCAAGCACCAUCUGGGUGUACACACCUAGCCAGAAGGCCAUCGGCAGCAGAUUUGCCCAGGGCAGGCCUAUGAAUAAU<br>GACGGCAGCUUCACAAUCACAAUGAAGGCCCCCCCUUUGAGCAGGGCAAGGACUUCGUGGUGCUGACCACCAAGGCCC<br>ACGGCGUGGGCAAGACAGAUCACAGCGACGACACCCGGACCCCCGUGACCUACAGAGAAGCAACACCUGCCCCUACCGG<br>GCCUAAGACACCCAUC | 375 |
| 389 | GUGGAGCCUACCACCACAAUCAGCGCCACCAGCACCCACGAGCUGAGCGCCAGCGAUGCCAGAAAUAGCAUCCAGCUGC<br>UGAAUGCCCACAUCGCCACCCUGCAGUCCGUGCAGAAAAGCGUGCCUGGAAGCGAUUACAGCGAUCAGAUCAGGGACCU<br>GCUGAAGGCCGCCUUCGAUCUGAGAGGCCUGAUCGAGACACUGGCCCACGGCGGCAUCCCUUUCUACGACCCCAGCACC<br>AUCAUGCCUAGAAUCAAACUGGUGGCCACCACCAUCGACACCAUCCACACCGCAACAACAACCCUGCAGAAUAAGGUGC<br>GGCCUGCCCACGUGGAACUGGGACUGGAAGUGACAAAGGCCGUGCUGCUGACCGCUAAUCCCGCCUCCACCGCCAAGGA<br>GCUGGAUGCCGAAGGAGCUGCCCUGAAAGCCAGACUGGAGAAGGUGAGCCAGUACCCUGAUCUGACCCCUAACGACGUG<br>GCCACCUCCAGCAAUAGACCCCGGAGCGUGGCACAGGCUGCUAUUGCCACCGACGGAAAGGGCAUCAUCGAUAAAGACA<br>GCCGGGAUGCCGUGAUCAAUGACGCCAAGCUGAGAGCAGCAAUCGCCGGCGCUCUGGUGAAGGCAGGCUUCAGCAGCGC<br>CGACGCCGUGGCUCUGGCCCCUAGAAUCGCUAAGGAGAUGGCCAAGGAGGGCGUGCUGCUGAUCAAUCACCACAAGCUG<br>AAGGCCCUGAUCGGCGCCCAGCUGGGACUGCUGACAGAUGCCAAGAUCCAGAGAGCCGCUGCAGCCGUGGAUCUGGGCA<br>UCAAGGCCACACUGGCCGCCACCAUCAUCCCAAACGCCCUGGGCAGCGCCGCCUUCAAAAAUGCCGUGAUUGCCAACCU<br>GGUGGCCGCCGGCAUCGAUAAGCACCUGGCCAGAGCCACAGCCGUGGCCAUCGUGGCCACAGCCCUGAAUCCCGCACUG<br>GGACCUAUUGCCAAGUUCGAACUCAUUAAGGCCGAAAUCGCAGCCCAAGCCGCCCUGCUGAUUCGGCGGGGCGUGCACC<br>UGCAGAAAGCCGCCAUUGAGCACGUGAUCGGCAGAGCCUUCGAUGCCGCUGUGGCCACCGCCAUCAUCUCCUCUCCUAU<br>CCUGUCUGCUAGAAUCGUGACCCACCUGGUCAGAGCCGGAAUCGACAAGUCUAUCGCUAUCAGCCUGGCCCCCCACAUC<br>GUGAAGAGACUGGCCAAAGAGCCCCUGCUGGCCUUCAACACAGCCAAGCUCAUGAAGAAUAUCACCAGACAGAUCGUGG<br>ACGUGAUCACCGCCGACAAGGCCAUCAAAACCGCUGAGCAGCUGGAGAAGGAGCUGCCCGCCCUGGAUGACCUGGUGAA<br>GAAGGCCAGCAGCCCCCCCAAGCCUACACCUACACCUACCCCAACCCCUACAGCCGGCCCUACAGUGACCGUGAUUCCU<br>GUGGGCAGAGAAGGAGGCGACAUCACCAUCAGCGGAAAGGGCUUCUCUACCACAGGCUUCGGCGUGUACGUGGCCGUGG<br>CCCCUGCCUCCGUGCCCGAAUUCUACGGCAACAGCGACAAGUUCUACGGCUACGACCCCAGCAAAGACACCACAGAGAG<br>CCCUUCCACCAUCUGGGUGUACACCCCUUCCCAGAAGGCCAUCGGCAGCAGAUUCGCUCAGGGCAGACCUAUGAAUAAC<br>GACGGCUCUUUCACCAUCACAAUGAAGGCCCCCCCUUCGAGCAGGGCAAAGACUUCGUGGUGCUGACAACCAAGGCCC<br>ACGGCGUGGGCAAGACAGAUCACUCCGACGACACCCGGACCCCUGUGACCUACAGAGAGGCAACACCUGCUCCCACCGG<br>GCCAAAGACCCCUAUC | 375 |
| 390 | UCCAGCAAUAGACCCCGGAGCGUGGCACAGGCUGCUAUUGCCACCGACGGAAAGGGCAUCAUCGAUAAAGACAGCCGGG<br>AUGCCGUGAUCAAUGACGCCAAGCUGAGAGCAGCAAUCGCCGGCGCUCUGGUGAAGGCAGGCUUCAGCAGCGCCGACGC<br>CGUGGCUCUGGCCCCUAGAAUCGCUAAGGAGAUGGCCAAGGAGGGCGUGCUGCUGAUCAAUCACCACAAGCUGAAGGCC<br>CUGAUCGGCGCCCAGCUGGGACUGCUGACAGAUGCCAAGAUCCAGAGAGCCGCUGCAGCCGUGGAUCUGGGCAUCAAGG | 376 |

TABLE 8-continued

| SEQ ID NO | Nucleotide sequence | Encodes polypeptide sequence according to SEQ ID NO |
|---|---|---|
| | CCACACUGGCCGCCACCAUCAUCCCAAACGCCCUGGGCAGCGCCGCCUUCAAAAAUGCCGUGAUUGCCAACCUGGUGGC<br>CGCCGGCAUCGAUAAGCACCUGGCCAGAGCCACAGCCGUGGCCAUCGUGGCCACAGCCCUGAAUCCCGCACUGGGACCU<br>AUUGCCAAGUUCGAACUCAUUAAGGCCGAAAUCGCAGCCCAAGCCGCCCUGCUGAUUCGGCGGGGCGUGCACCUGCAGA<br>AAGCCGCCAUUGAGCACGUGAUCGGCAGAGCCUUCGAUGCCGCUGUGGCCACCGCCAUCAUCUCCUCUCCUAUCCUGUC<br>UGCUAGAAUCGUGACCCACCUGGUCAGAGCCGGAAUCGACAAGUCUAUCGCUAUCAGCCUGGCCCCCCACAUCGUGAAG<br>AGACUGGCCAAAGAGCCCCUGCUGGCCUUCAACACAGCCAAGCUCAUGAAGAAUAUCACCAGACAGAUCGUGGACGUGA<br>UCACCGCCGACAAGGCCAUCAAAACCGCUGAGCAGCUGGAGAAGGAGCUGCCCGCCCUGGAUGACCUGGUGAAGAAGGC<br>CAGCAGCCCCCCCAAGCCUACACCUACACCUACCCCAACCCCUACAGCCGGCCCUACAGUGACCGUGAUUCCUGUGGGC<br>AGAGAAGGAGGCGACAUCACCAUCAGCGGAAAGGGCUUCUCUACCACAGGCUUCGGCGUGUACGUGGCCGUGGCCCCUG<br>CCUCCGUGCCCGAAUUCUACGGCAACAGCGACAAGUUCUACGGCUACGACCCCAGCAAAGACACCACAGAGAGCCCUUC<br>CACCAUCUGGGUGUACACCCCUUCCCAGAAGGCCAUCGGCAGCAGAUUCGCUCAGGGCAGACCUAUGAAUAACGACGGC<br>UCUUUCACCAUCACAAUGAAGGCCCCCCCUUCGAGCAGGGCAAAGACUUCGUGGUGCUGACAACCAAGGCCCACGGCG<br>UGGGCAAGACAGAUCACUCCGACGACACCCGGACCCCUGUGACCUACAGAGAGGCAACACCUGCUCCCACCGGGCCAAA<br>GACCCCUAUCGUGUACGUGAGAACCAAUUUCAGCAAGACCAUCUGGCAGGUGAGAGCCAAUCGGGACAGAUACAUCCUG<br>GGCCACAAGUCUGCCGCCGUGUAUAAAACCCUGAAUCACGCCAUCACCAAGGCCGUGGGCGUGAGACUGAACCCUAAGA<br>CAACCGUGGGCAACAUCCAGGCCGCCAGAACAGAGCUGCUGGCCGCCUACCAGACAGCCUUCAAUAGCCCCGACGUGAA<br>GAAGGCCGCU | |
| 393 | AGCUCCAAUAGACCCAGAUCCGUGGCCCAGGCCGCCAUCGCCACAGAUGGCAAGGGGAUCAUCGACAAGGAUUCCAGAG<br>ACGCUGUGAUCAACGACGCAAAGCUGAGAGCCGCCAUCGCCGGAGCUCUGGUGAAGGCCGGCUUUAGCAGCGCCGACGC<br>CGUGGCACUGGCCCCCAGAAUUGCAAAGGAGAUGGCAAAGGAGGGCGUGCUGCUGAUCAAUCACCACAAGCUGAAGGCC<br>CUGAUCGGCGCACAGCUGGGCCUGCUGACCGACGCAAAGAUUCAGAGAGCCGCCGCAGCCGUGGACCUGGGCAUCAAGG<br>CCACCCUGGCUGCCACCAUCAUCCCUAACGCCCUGGGCAGCGCCGCCUUCAAGAAUGCAGUGAUCGCCAACCUGGUGGC<br>CGCCGGAAUCGACAAGCACCUGGCCAGAGCCACAGCCGUCGCUAUCGUGGCCACAGCCCUGAAUCCCGCCCUGGGCCCC<br>AUCGCCAAAUUUGAACUGAUCAAGGCAGAAAUCGCUGCCCAGGCCGCCCUGCUCAUCAGAAGAGGCGUCCAUCUGCAGA<br>AGGCCGCCAUCGAGCACGUGAUUGGCAGAGCCUUCGACGCCGCCGUGGCCACAGCUAUCAUUUCUUCCCCUAUCCUGUC<br>UGCCAGAAUCGUGACACACCUGGUGAGAGCCGGAAUCGACAAGUCCAUCGCCAUCUCCCUGGCCCCCCACAUCGUGAAG<br>AGACUGGCUAAGGAGCCUCUGCUGGCCUUCAAUACAGCCAAGCUGAUGAAGAACAUCACAAGACAGAUCGUGGACGUGA<br>UCACCGCCGACAAGGCCAUCAAGACAGCCGAGCAGCUGGAGAAGGAACUGCCAGCCCUGGACGACCUGGUGAAGAAGGC<br>CAGCAGCCCUCCCAAGCCUACCCCUACCCCAACCCCUACACCUACAGCCGGACCUACCGUGACCGUGAUCCCUGUGGGC<br>AGAGAGGGCGGCGACAUCACCAUCAGCGGCAAGGGCUUCAGCACAACAGGCUUUGGCGUGUACGUGGCCGUGGCCCCAG<br>CCAGCGUGCCUGAGUUUUACGGCAAUAGCGACAAGUUCUACGGCUACGACCCCUCCAAGGACACCACCGAGAGCCCAAG<br>CACCAUCUGGGUGUACACACCUAGCCAGAAGGCCAUCGGCAGCAGAUUUGCCCAGGGCAGGCCUAUGAAUAAUGACGGC<br>AGCUUCACAAUCACAAUGAAGGCCCCCCCUUUGAGCAGGGCAAGGACUUCGUGGUGCUGACCACCAAGGCCCACGGCG<br>UGGGCAAGACAGAUCACAGCGACGACACCCGGACCCCCGUGACCUACAGAGAAGCAACACCUGCCCCUACCGGGCCUAA<br>GACACCCAUCGUGUACGUGAGAACCAAUUUCAGCAAGACCAUCUGGCAGGUGAGAGCCAACAGAGAUCGGUACAUCCUG<br>GGCCACAAGUCCGCCGCCGUGUACAAGACCCUGAAUCACGCCAUCACCAAGGCCGUGGGCGUGCGGCUGAAUCCUAAGA<br>CCACCGUGGGCAACAUCCAGGCCGCCAGAACCGAACUGCUGGCCGCCUACCAGACCGCCUUCAACAGCCCCGAUGUGAA<br>GAAGGCCGCU | 376 |
| 395 | AGCGGCAGCAUCCUGGCUAUCUACAGCACAGUGGCUUCUAGCCUGGUGCUGCUGGUGUCUCUGGGCGCCAUCAGCUUUG<br>GCAGCGGC | 84 |
| 396 | AGCGGAAGCAUCCUGGCCAUCUAUAGCACCGUGGCUAGCUCUCUGGUGCUGCUGGUGAGCCUGGGAGCUAUCAGCUUUG<br>GGAGCGGC | 84 |

The invention claimed is:

1. A nucleic acid comprising a nucleotide sequence encoding a modified *Cutibacterium acnes* (*C. acnes*) Christie-Atkins-Munch-Petersen factor 2 (CAMP2) polypeptide, wherein the modified *C. acnes* CAMP2 polypeptide comprises an amino acid sequence comprising a *C. acnes* CAMP2 polypeptide sequence and a transmembrane domain sequence, wherein the nucleic acid is a messenger RNA (mRNA).

2. The nucleic acid of claim 1, wherein:

(A) (a) the transmembrane domain sequence is positioned at the C terminus of the modified *C. acnes* CAMP2 polypeptide; and/or (b) the transmembrane domain sequence comprises a viral transmembrane domain sequence, which is selected from the group consisting of: an influenza hemagglutinin (HA) transmembrane domain sequence, a SARS COV-2 spike transmembrane domain sequence, a VZV gB transmembrane domain sequence, a VZV gE transmembrane domain sequence, a VZV gI transmembrane domain sequence, a VZV gK transmembrane domain sequence, a measles F-protein transmembrane domain sequence, a rubella E1 protein transmembrane domain sequence, a rubella E2 protein transmembrane domain sequence, a mumps F-protein transmembrane domain sequence, an Ebola GP protein transmembrane domain sequence and a rabies transmembrane domain sequence; and/or (B) the modified *C. acnes* CAMP2 polypeptide comprises a non-native secretion signal peptide sequence wherein:

(a) the secretion signal peptide sequence is positioned at the N terminus of the modified *C. acnes* CAMP2 polypeptide; and/or (b) the secretion signal peptide sequence is a viral secretion signal peptide sequence, which is selected from the group consisting of: an influenza hemagglutinin (HA) secretion signal peptide sequence, a SARS COV-2 spike secretion signal peptide sequence, a VZV gB secretion signal peptide sequence, a VZV gE secretion signal peptide sequence, a VZV gI secretion signal peptide sequence, a VZV gK secretion signal peptide sequence, a measles F-protein secretion signal peptide sequence, a rubella E1 protein secretion signal peptide sequence, a rubella E2 protein secretion signal peptide sequence, a mumps F-protein secretion signal peptide sequence, an Ebola GP protein secretion signal peptide sequence, a smallpox 6 kDa IC protein secretion signal peptide sequence and a rabies G protein secretion signal peptide sequence.

3. The nucleic acid of claim 1, wherein the transmembrane domain comprises an amino acid sequence selected from the group consisting of sequences set forth by SEQ ID NO: 208-209 and 241-253.

4. The nucleic acid of claim 1, wherein the mRNA comprises a 5' cap, at least one 5' untranslated region (5' UTR), at least one 3' untranslated region (3' UTR), and/or at least one polyadenylation (poly(A)) sequence.

5. The nucleic acid of claim 1, wherein:

(a) the modified *C. acnes* CAMP2 polypeptide comprises a sequence selected from the group consisting of sequences set forth by SEQ ID NO: 207 and SEQ ID NO: 5-9, or a sequence having at least 60% identity thereto; and/or (b) the nucleic acid comprises a nucleotide sequence selected from the group consisting of sequences set forth by SEQ ID NO: 90-94 and SEQ ID NO: 391-392, or a sequence having at least 50% identity thereto; and/or (c) the nucleic acid is a mRNA comprising or consisting of the following structural elements:

(i) a 5' cap with the following structure:

(ii) a 5' untranslated region (5' UTR) having the nucleic acid sequence according to SEQ ID NO: 265;

(iii) a protein coding region having the nucleic acid sequence selected from the group consisting of sequences set forth by SEQ ID NO: 90-91 and SEQ ID NO: 391-392;

(iv) a 3' untranslated region (3' UTR) having the nucleic acid sequence according to SEQ ID NO: 266; and (v) a poly A tail.

6. A composition comprising the nucleic acid of claim 1.

7. The composition of claim 6, wherein the composition further comprises one or more of:

(i) a nucleic acid comprising a nucleotide sequence encoding a *C. acnes* dermatan sulfate-adhesin 1 (DsA1) polypeptide;

(ii) a nucleic acid comprising a nucleotide sequence encoding a *C. acnes* dermatan sulfate-adhesin 2 (DsA2) polypeptide;

(iii) a nucleic acid comprising a nucleotide sequence encoding a *C. acnes* putative iron-transport protein (PITP) polypeptide;

(iv) a nucleic acid comprising a nucleotide sequence encoding a chimeric *C. acnes* DsA1/DsA2 polypeptide; and (v) a nucleic acid comprising a nucleotide sequence encoding a chimeric *C. acnes* DsA1/DsA2/PITP polypeptide.

8. The composition of claim 6, wherein the composition comprises:

(A) a first mRNA comprising or consisting of the following structural elements:

(i) a 5' cap;

(ii) a 5' UTR having the nucleic acid sequence according to SEQ ID NO: 265;

(iii) a protein coding region having the nucleic acid sequence according to SEQ ID NO: 91;

(iv) a 3' UTR having the nucleic acid sequence according to SEQ ID NO: 266; and (v) a poly A tail;

(B) a second mRNA comprising or consisting of the following structural elements:

(i) a 5' cap;

(ii) a 5' UTR having the nucleic acid sequence according to SEQ ID NO: 265;

(iii) a protein coding region having the nucleic acid sequence according to SEQ ID NO: 113;

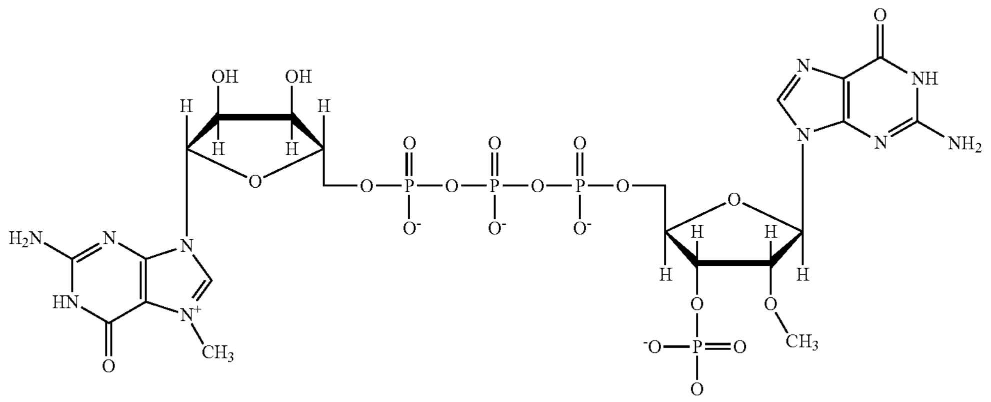

(iv) a 3' UTR having the nucleic acid sequence according to SEQ ID NO: 266; and (v) a poly A tail; and (C) a third mRNA comprising or consisting of the following structural elements:

(i) a 5' cap;

(ii) a 5' UTR having the nucleic acid sequence according to SEQ ID NO: 265;

(iii) a protein coding region having the nucleic acid sequence according to SEQ ID NO: 115;

(iv) a 3' UTR having the nucleic acid sequence according to SEQ ID NO: 266; and (v) a poly A tail;

wherein the 5' cap has the following structure:

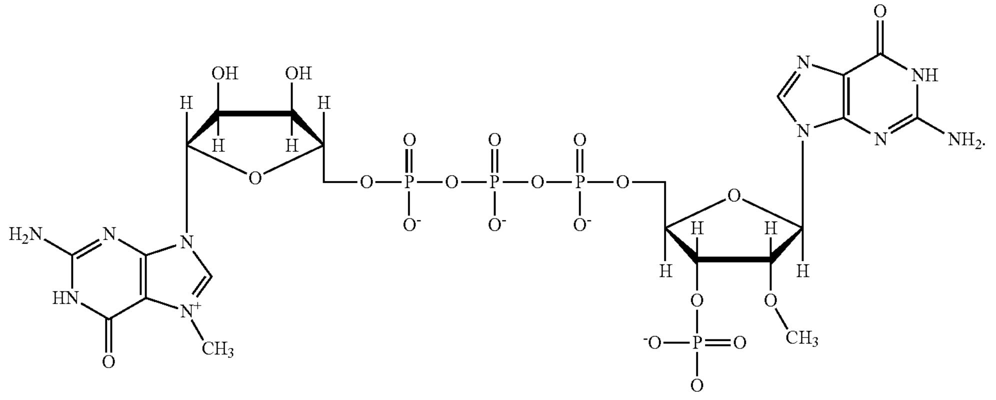

9. The composition of claim 6, wherein:

the composition comprises a total of about 45 μg, about 120 μg, or about 225 μg of the one or more nucleic acid(s).

10. A composition comprising a nucleic acid comprising a nucleotide sequence encoding a *C. acnes* CAMP2 polypeptide and one or more of:

(i) a nucleic acid comprising a nucleotide sequence encoding a *C. acnes* DsA1 polypeptide;

(ii) a nucleic acid comprising a nucleotide sequence encoding a *C. acnes* DsA2 polypeptide;

(iii) a nucleic acid comprising a nucleotide sequence encoding a *C. acnes* PITP polypeptide;

(iv) a nucleic acid comprising a nucleotide sequence encoding a chimeric *C. acnes* DsA1/DsA2 polypeptide; and (v) a nucleic acid comprising a nucleotide sequence encoding a chimeric *C. acnes* DsA1/DsA2/PITP polypeptide.

11. The composition of claim 10, wherein the composition comprises the nucleic acid according to (iii) and/or the nucleic acid according to (iv).

12. The composition of claim 10, wherein any two or more nucleic acids are located on the same nucleic acid molecule or on different nucleic acid molecules.

13. The composition of claim 10, wherein:

(a) the *C. acnes* CAMP2 polypeptide comprises a sequence selected from the group consisting of sequences set forth by SEQ ID NO: 203, SEQ ID NO: 43-58, SEQ ID NO: 1-4, SEQ ID NO: 10-16 and SEQ ID NO: 339-363 or a sequence having at least 60% identity thereto;

(b) the *C. acnes* DsA1 polypeptide comprises a sequence selected from the group consisting of sequences set forth by SEQ ID NO: 204, SEQ ID NO: 17-19 and SEQ ID NO: 59-61, or a sequence having at least 75% identity thereto;

(c) the *C. acnes* DsA2 polypeptide comprises a sequence selected from the group consisting of sequences set forth by SEQ ID NO: 205, SEQ ID NO: 20-27 and SEQ ID NO: 62-69 or a sequence having at least 75% identity thereto;

(d) the *C. acnes* PITP polypeptide comprises a sequence selected from the group consisting of sequences set forth by SEQ ID NO: 206, SEQ ID NO: 31-37, and SEQ ID NO: 73-79 or a sequence having at least 75% identity thereto;

(e) the chimeric *C. acnes* DsA1/DsA2 polypeptide comprises a sequence selected from the group consisting of sequences set forth by SEQ ID NO: 28-30, SEQ ID NO: 39, SEQ ID NO: 70-72 and SEQ ID NO: 81, or a sequence having at least 90% identity thereto; and/or (f) the chimeric *C. acnes* DsA1/DsA2/PITP polypeptide comprises (i) a sequence selected from the group consisting of sequences set forth by SEQ ID NO: 28-30, SEQ ID NO:

39, SEQ ID NO: 70-72 and SEQ ID NO: 81, or a sequence having at least 90% identity thereto; and (ii) a PITP polypeptide sequence.

14. A nucleic acid comprising a nucleotide sequence encoding a chimeric *C. acnes* DsA1/DsA2/PITP/CAMP2 polypeptide, wherein the chimeric *C. acnes* DsA1/DsA2/PITP/CAMP2 polypeptide comprises:

(a) a chimeric *C. acnes* DsA1/DsA2 polypeptide;

(b) an immunogenic fragment of a *C. acnes* PITP polypeptide; and (c) a *C. acnes* CAMP2 polypeptide or an immunogenic fragment thereof.

15. The nucleic acid comprising a nucleotide sequence encoding a chimeric C *acnes* DsA1/DsA2/PITP/CAMP2 polypeptide of claim 14, wherein:

i, the chimeric *C. acnes* DsA1/DsA2/PITP/CAMP2 polypeptide comprises a first conserved sub-domain (CSD1) of a *C. acnes* DsA1 polypeptide, a second conserved sub-domain (CSD2) of a *C. acnes* DsA2 polypeptide and a third conserved sub-domain (CSD3) of a *C. acnes* DsA1 polypeptide;

ii, the immunogenic fragment of a *C. acnes* PITP polypeptide in (b) comprising an extended neocarzinostatin family domain (ENFD) of a *C. acnes* PITP polypeptide comprises the sequence corresponding to amino acid residues 1-133 or residues 1-146 of SEQ ID NO: 73 or a sequence having at least 90% identity thereto; and/or iii. (c) is (1) a *C. acnes* CAMP2 polypeptide; or (2) an immunogenic fragment of a *C. acnes* CAMP2 polypeptide comprising a N-terminal domain of a *C. acnes* CAMP2 polypeptide.

16. The nucleic acid of claim 14, wherein:

(i) the chimeric C *acnes* DsA1/DsA2/PITP/CAMP2 polypeptide comprises a sequence selected from the group consisting of sequences set forth by SEQ ID NO: 374-375;

(ii) the chimeric *C. acnes* DsA1/DsA2/PITP/CAMP2 polypeptide comprises a sequence according to SEQ ID NO: 373 and a transmembrane domain sequence, (iii) the nucleotide sequence encoding the chimeric *C. acnes* DsA1/DsA2/PITP/CAMP2 polypeptide comprises a sequence selected from the group consisting of sequences set forth by SEQ ID NO: 377-382 and 384-389; and/or (iv) the nucleotide sequence encoding the chimeric *C. acnes* DsA1/DsA2/PITP/CAMP2 polypeptide comprises a sequence according to SEQ ID NO: 384 and a sequence according to SEQ ID NO: 395; or a sequence according to SEQ ID NO: 385 and a sequence according to SEQ ID NO: 396.

17. A chimeric *C. acnes* DsA1/DsA2/PITP/CAMP2 polypeptide encoded by the nucleic acid of claim 14.

18. A composition, optionally an immunogenic composition, comprising the nucleic acid as defined in claim 14.

19. A composition, optionally an immunogenic composition, comprising the chimeric *C. acnes* DsA1/DsA2/PITP/CAMP2 polypeptide as defined in claim 17.

20. An immunogenic composition comprising a nucleic acid comprising a nucleotide sequence encoding a *C. acnes* CAMP2 polypeptide, wherein the nucleic acid is a mRNA.

21. A method of treating or preventing *C. acnes* infection in a subject, the method comprising administering the nucleic acid of claim 1 to the subject.

22. A method of treating or preventing at least one symptom of a *C. acnes* infection in a subject, the method comprising administering the composition of claim 10 to the subject.

23. A method of treating or preventing at least one symptom of a *C. acnes* infection in a subject, the method comprising administering the nucleic acid of claim 14 to the subject.

24. A method of treating or preventing at least one symptom of a *C. acnes* infection in a subject, the method comprising administering the polypeptide of claim 17 to the subject.

25. A method of treating or preventing at least one symptom of a *C. acnes* infection in a subject, the method comprising administering the immunogenic composition of claim 20 to the subject.

26. The nucleic acid of claim 1, wherein the mRNA is unmodified.

27. The nucleic acid of claim 1, wherein the mRNA comprises at least one chemical modification.

28. The nucleic acid of claim 1, wherein the mRNA is a self-replicating mRNA.

29. The nucleic acid of claim 1, wherein the mRNA is a non-replicating mRNA.

30. The nucleic acid of claim 5, wherein the polyA tail comprises at least 75 adenosine nucleotides or at least 100 adenosine nucleotides.

31. The composition of claim 6, wherein the composition is in a frozen liquid form or in a lyophilized form.

32. The composition of claim 7, wherein:

the modified *C. acnes* CAMP2 polypeptide comprises a sequence having at least 60% identity to SEQ ID NO: 207;

the chimeric *C. acnes* DsA1/DsA2 polypeptide comprises a sequence having at least 90% identity to SEQ ID NO: 70; and the *C. acnes* PITP polypeptide comprises a sequence having at least 75% identity to SEQ ID NO: 73.

33. The composition of claim 6, wherein the composition further comprises a nucleic acid comprising a nucleotide sequence encoding a chimeric *C. acnes* DsA1/DsA2 polypeptide and a nucleic acid comprising a nucleotide sequence encoding a *C. acnes* PITP polypeptide, wherein:

the modified *C. acnes* CAMP2 polypeptide comprises or consists of a sequence according to SEQ ID NO: 207;

the chimeric *C. acnes* DsA1/DsA2 polypeptide comprises or consists of a sequence according to SEQ ID NO: 70; and the *C. acnes* PITP polypeptide comprises or consists of a sequence according to SEQ ID NO: 73.

34. The composition of claim 7, wherein:

the nucleotide sequence encoding the modified *C. acnes* CAMP2 polypeptide comprises a sequence having at least 50% identity to SEQ ID NO: 91;

the nucleotide sequence encoding the chimeric *C. acnes* DsA1/DsA2 polypeptide comprises a sequence having at least 75% identity to SEQ ID NO: 113; and the nucleotide sequence encoding the *C. acnes* PITP polypeptide comprises a sequence having at least 50% identity to SEQ ID NO: 115.

35. The composition of claim 6, wherein the composition further comprises a nucleic acid comprising a nucleotide sequence encoding a chimeric *C. acnes* DsA1/DsA2 polypeptide and a nucleic acid comprising a nucleotide sequence encoding a *C. acnes* PITP polypeptide, wherein:

the nucleotide sequence encoding the modified *C. acnes* CAMP2 polypeptide comprises or consists of a sequence according to SEQ ID NO: 91;

the nucleotide sequence encoding the chimeric *C. acnes* DsA1/DsA2 polypeptide comprises or consists of a sequence according to SEQ ID NO: 113; and the nucleotide sequence encoding the *C. acnes* PITP polypeptide comprises or consists of a sequence according to SEQ ID NO: 115.

36. The composition of claim 6, wherein the composition further comprises a lipid nanoparticle (LNP).

37. The composition of claim 36, wherein any one or more nucleic acids are encapsulated in the LNP.

38. The composition of claim 7, wherein any two or more nucleic acids are co-encapsulated in a single LNP.

39. The composition of claim 33, wherein the nucleic acid comprising a nucleotide sequence encoding the modified *C. acnes* CAMP2 polypeptide, the nucleic acid comprising a nucleotide sequence encoding the *C. acnes* PITP polypeptide, and the nucleic acid comprising a nucleotide sequence encoding the chimeric *C. acnes* DsA1/DsA2 polypeptide are encapsulated in an LNP.

40. The composition of claim 33, wherein the nucleic acid comprising a nucleotide sequence encoding the modified *C. acnes* CAMP2 polypeptide, the nucleic acid comprising a nucleotide sequence encoding the *C. acnes* PITP polypeptide, and the nucleic acid comprising a nucleotide sequence encoding the chimeric *C. acnes* DsA1/DsA2 polypeptide are co-encapsulated in a single LNP.

41. The composition of claim 33, wherein the nucleic acid comprising a nucleotide sequence encoding the modified *C. acnes* CAMP2 polypeptide, the nucleic acid comprising a nucleotide sequence encoding the *C. acnes* PITP polypeptide, and the nucleic acid comprising a nucleotide sequence encoding the chimeric *C. acnes* DsA1/DsA2 polypeptide are present in a weight ratio of 1:1:1.

42. The composition of claim 35, wherein the nucleic acid comprising a nucleotide sequence encoding the modified *C. acnes* CAMP2 polypeptide, the nucleic acid comprising a nucleotide sequence encoding the *C. acnes* PITP polypeptide, and the nucleic acid comprising a nucleotide sequence encoding the chimeric *C. acnes* DsA1/DsA2 polypeptide are co-encapsulated in a single LNP.

43. The composition of claim 35, wherein the nucleic acid comprising a nucleotide sequence encoding the modified *C. acnes* CAMP2 polypeptide, the nucleic acid comprising a nucleotide sequence encoding the *C. acnes* PITP polypeptide, and the nucleic acid comprising a nucleotide sequence encoding the chimeric *C. acnes* DsA1/DsA2 polypeptide are present in a weight ratio of 1:1:1.

44. The composition of claim 7, wherein any two or more nucleic acids are encapsulated in separate LNPs.

45. The composition of claim 36, wherein: the LNP comprises at least one cationic lipid and wherein the cationic lipid is selected from the group consisting of OF-02, cKK-E10, IM-001, IS-001 and GL-HEPES-E3-E12-DS-4-E10; and/or the LNP comprises a polyethylene glycol (PEG) conjugated (PEGylated) lipid, a cholesterol-based lipid, and a helper lipid.

46. The composition of claim 45, wherein the LNP comprises GL-HEPES-E3-E12-DS-4-E10, DMG-PEG2000, cholesterol and DOPE.

47. The composition of claim 46, wherein the LNP comprises GL-HEPES-E3-E12-DS-4-E10 at a molar ratio of 40%, DMG-PEG2000 at a molar ratio of 1.5%, cholesterol at a molar ratio of 28.5%, and DOPE at a molar ratio of 30%.

48. The composition of claim 10, wherein the composition is an immunogenic composition.

49. The composition of claim 10, wherein the composition is in a frozen liquid form or in a lyophilized form.

50. The composition of claim 10, wherein the *C. acnes* DsA1 polypeptide comprises a sequence selected from the group consisting of sequences set forth by SEQ ID NO: 204, SEQ ID NO: 17-19 and SEQ ID NO: 59-61, or a sequence having at least 75% identity thereto.

51. The composition of claim 10, wherein the *C. acnes* DsA2 polypeptide comprises a sequence selected from the group consisting of sequences set forth by SEQ ID NO: 205, SEQ ID NO: 20-27 and SEQ ID NO: 62-69 or a sequence having at least 75% identity thereto.

52. The composition of claim 10, wherein the *C. acnes* PITP polypeptide comprises a sequence selected from the group consisting of sequences set forth by SEQ ID NO: 206, SEQ ID NO: 31-37, and SEQ ID NO: 73-79 or a sequence having at least 75% identity thereto.

53. The composition of claim 10, wherein the chimeric *C. acnes* DsA1/DsA2 polypeptide comprises a sequence selected from the group consisting of sequences set forth by SEQ ID NO: 28-30, SEQ ID NO: 39, SEQ ID NO: 70-72 and SEQ ID NO: 81, or a sequence having at least 90% identity thereto.

54. The composition of claim 10, wherein the chimeric *C. acnes* DsA1/DsA2/PITP polypeptide comprises (i) a sequence selected from the group consisting of sequences set forth by SEQ ID NO: 28-30, SEQ ID NO: 39, or SEQ ID NO: 70-72 and SEQ ID NO: 81, or a sequence having at least 90% identity thereto; and (ii) a PITP polypeptide sequence.

55. The nucleic acid of claim 14, wherein the immunogenic fragment of a *C. acnes* PITP polypeptide of (b) comprises an extended neocarzinostatin family domain (ENFD) of a *C. acnes* PITP polypeptide.

56. The nucleic acid of claim 15, wherein the chimeric *C. acnes* DsA1/DsA2 polypeptide of (a) comprises a sequence according to SEQ ID NO: 70, or a sequence having at least 90% identity thereto.

57. The nucleic acid of claim 15, wherein the *C. acnes* CAMP2 polypeptide of (c) (1) comprises SEQ ID NO: 203 or a sequence having at least 90% identity thereto.

58. The nucleic acid of claim 15, wherein the chimeric *C. acnes* DsA1/DsA2/PITP/CAMP2 polypeptide comprises a transmembrane domain sequence.

59. The nucleic acid of claim 58, wherein the transmembrane domain sequence comprises an amino acid sequence according to SEQ ID NO: 84.

60. The composition of claim 11, wherein the *C. acnes* CAMP2 polypeptide comprises a sequence according to SEQ ID NO: 203 or a sequence having at least 60% identity thereto; the chimeric *C. acnes* DsA1/DsA2 polypeptide comprises a sequence according to SEQ ID NO: 70 or a sequence having at least 90% identity thereto; and the *C. acnes* PITP polypeptide comprises a sequence according to SEQ ID NO: 73 or a sequence having at least 75% identity thereto.

61. A composition comprising:

a messenger RNA (mRNA) comprising a nucleotide sequence encoding a modified *C. acnes* CAMP2 polypeptide comprising or consisting of a sequence according to SEQ ID NO: 207;

a mRNA comprising a nucleotide sequence encoding a chimeric *C. acnes* DsA1/DsA2 polypeptide comprising or consisting of a sequence according to SEQ ID NO: 70; and a mRNA comprising a nucleotide sequence encoding a *C. acnes* PITP polypeptide comprising or consisting of a sequence according to SEQ ID NO: 73, wherein the mRNAs are encapsulated in an LNP.

62. The composition of claim 61, wherein the mRNAs are co-encapsulated in the same LNP.

63. The composition of claim 61, wherein the mRNAs are present in a weight ratio of 1:1:1.

64. The composition of claim 61, wherein the mRNAs are present in a weight ratio of 1:1:1 and are co-encapsulated in the same LNP.

65. A method of generating an immune response against a *C. acnes* infection in a subject, the method comprising administering the composition of claim 10 to the subject.

66. A method of generating an immune response against a *C. acnes* infection in a subject, the method comprising administering the nucleic acid of claim 14 to the subject.

67. A method of generating an immune response against a *C. acnes* infection in a subject, the method comprising administering the polypeptide of claim 17 to the subject.

68. A method of generating an immune response against a *C. acnes* infection in a subject, the method comprising administering the immunogenic composition of claim 20 to the subject.

* * * * *

SEQUENCE LISTING

Sequence total quantity: 399
SEQ ID NO: 1 moltype = AA length = 240
FEATURE Location/Qualifiers
source 1..240
mol_type = protein
organism = synthetic construct
SEQUENCE: 1
MVEPTTTISA TSTHELSASD ARNSIQLLNA HIATLQSVQK SVPGSDYSDQ IRDLLKAAFD 60
LRGLIETLAH GGIPFYDPST IMPRIKLVAT TIDTIHTATT TLQNKVRPAH VELGLEVTKA 120
VLLTANPAST AKELDAEGAA LKARLEKVSQ YPDLTPNDVA TVYVRTNFSK TIWQVRANRD 180
RYILGHKSAA VYKTLNHAIT KAVGVRLNPK TTVGNIQAAR TELLAAYQTA FNSPDVKKAA 240

SEQ ID NO: 2 moltype = AA length = 256
FEATURE Location/Qualifiers
source 1..256
mol_type = protein
organism = synthetic construct
SEQUENCE: 2
MKAKLLVLLC TFTATYAVEP TTTISATSTH ELSASDARNS IQLLNAHIAT LQSVQKSVPG 60
SDYSDQIRDL LKAAFDLRGL IETLAHGGIP FYDPSTIMPR IKLVATTIDT IHTATTTLQN 120
KVRPAHVELG LEVTKAVLLT ANPASTAKEL DAEGAALKAR LEKVSQYPDL TPNDVATVYV 180

```
RTNFSKTIWQ VRANRDRYIL GHKSAAVYKT LNHAITKAVG VRLNPKTTVG NIQAARTELL  240
AAYQTAFNSP DVKKAA                                                  256

SEQ ID NO: 3           moltype = AA  length = 256
FEATURE                Location/Qualifiers
source                 1..256
                       mol_type = protein
                       organism = synthetic construct
SEQUENCE: 3
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAA                                                  256

SEQ ID NO: 4           moltype = AA  length = 256
FEATURE                Location/Qualifiers
source                 1..256
                       mol_type = protein
                       organism = synthetic construct
SEQUENCE: 4
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAA                                                  256

SEQ ID NO: 5           moltype = AA  length = 285
FEATURE                Location/Qualifiers
source                 1..285
                       mol_type = protein
                       organism = synthetic construct
SEQUENCE: 5
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAASGSI LAIYSTVASS LVLLVSLGAI SFGSG                  285

SEQ ID NO: 6           moltype = AA  length = 285
FEATURE                Location/Qualifiers
source                 1..285
                       mol_type = protein
                       organism = synthetic construct
SEQUENCE: 6
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAASGSI LAIYSTVASS LVLLVSLGAI SFGSG                  285

SEQ ID NO: 7           moltype = AA  length = 271
FEATURE                Location/Qualifiers
source                 1..271
                       mol_type = protein
                       organism = synthetic construct
SEQUENCE: 7
MNPNQKIITI GSISIAIGII SLMLQIGNIS GSVEPTTTIS ATSTHELSAS DARNSIQLLN  60
AHIATLQSVQ KSVPGSDYSD QIRDLLKAAF DLRGLIETLA HGGIPFYDPS TIMPRIKLVA  120
TTIDTIHTAT TTLQNKVRPA HVELGLEVTK AVLLTANPAS TAKELDAEGA ALKARLEKVS  180
QYPDLTPNDV ATVYVRTNFS KTIWQVRANR DRYILGHKSA AVYKTLNHAI TKAVGVRLNP  240
KTTVGNIQAA RTELLAAYQT AFNSPDVKKA A                                 271

SEQ ID NO: 8           moltype = AA  length = 271
FEATURE                Location/Qualifiers
source                 1..271
                       mol_type = protein
                       organism = synthetic construct
SEQUENCE: 8
MNPNQKIITI GSISIAIGII SLMLQIGNIS GSVEPTTTIS ATSTHELSAS DARNSIQLLN  60
AHIATLQSVQ KSVPGSDYSD QIRDLLKAAF DLRGLIETLA HGGIPFYDPS TIMPRIKLVA  120
TTIDTIHTAT TTLQNKVRPA HVELGLEVTK AVLLTANPAS TAKELDAEGA ALKARLEKVS  180
QYPDLTPNDV ATVYVRTSFS KTIWQVRANR DRYILGHKSA AVYKTLNHAI TKAVGVRLNP  240
KTTVGNIQAA RTELLAAYQT AFNSPDVKKA A                                 271

SEQ ID NO: 9           moltype = AA  length = 285
FEATURE                Location/Qualifiers
source                 1..285
                       mol_type = protein
```

-continued

```
                       organism = synthetic construct
SEQUENCE: 9
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTSFSKTIWQ VRANRDRYIL GHKSAAVYKT LNHAITKAVG VRLNPKTTVG NIQAARTELL  240
AAYQTAFNSP DVKKAASGSI LAIYSTVASS LVLLVSLGAI SFGSG                 285

SEQ ID NO: 10          moltype = AA  length = 256
FEATURE                Location/Qualifiers
source                 1..256
                       mol_type = protein
                       organism = synthetic construct
SEQUENCE: 10
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAA                                                 256

SEQ ID NO: 11          moltype = AA  length = 256
FEATURE                Location/Qualifiers
source                 1..256
                       mol_type = protein
                       organism = synthetic construct
SEQUENCE: 11
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAA                                                 256

SEQ ID NO: 12          moltype = AA  length = 256
FEATURE                Location/Qualifiers
source                 1..256
                       mol_type = protein
                       organism = synthetic construct
SEQUENCE: 12
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTSFSKTIWQ VRANRDRYIL GHKSAAVYKT LNHAITKAVG VRLNPKTTVG NIQAARTELL  240
AAYQTAFNSP DVKKAA                                                 256

SEQ ID NO: 13          moltype = AA  length = 256
FEATURE                Location/Qualifiers
source                 1..256
                       mol_type = protein
                       organism = synthetic construct
SEQUENCE: 13
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPGG TPNGVGGVYV  180
RTNFSKTIWQ VRANRDRYIL GHKSAAVYKT LNHAITKAVG VRLNPKTTVG NIQAARTELL  240
AAYQTAFNSP DVKKAA                                                 256

SEQ ID NO: 14          moltype = AA  length = 256
FEATURE                Location/Qualifiers
source                 1..256
                       mol_type = protein
                       organism = synthetic construct
SEQUENCE: 14
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPGG TPNGVGGVYV  180
RTSFSKTIWQ VRANRDRYIL GHKSAAVYKT LNHAITKAVG VRLNPKTTVG NIQAARTELL  240
AAYQTAFNSP DVKKAA                                                 256

SEQ ID NO: 15          moltype = AA  length = 256
FEATURE                Location/Qualifiers
source                 1..256
                       mol_type = protein
                       organism = synthetic construct
SEQUENCE: 15
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VAANADRYIA GHKSAAVAKT LAHAIAKAAG VRANPKTTVG NIQAARTELL  240
AAYQTAFNSP DVKKAA                                                 256
```

-continued

```
SEQ ID NO: 16          moltype = AA  length = 256
FEATURE                Location/Qualifiers
source                 1..256
                       mol_type = protein
                       organism = synthetic construct
SEQUENCE: 16
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTSFSKTIWQ VAANADRYIA GHKSAAVAKT LAHAIAKAAG VRANPKTTVG NIQAARTELL  240
AAYQTAFNSP DVKKAA                                                256

SEQ ID NO: 17          moltype = AA  length = 342
FEATURE                Location/Qualifiers
source                 1..342
                       mol_type = protein
                       organism = synthetic construct
SEQUENCE: 17
MKAKLLVLLC TFTATYASSN RPRSVAQAAI ATDGKGIINK DCRDAVINDA KLRAAIAGAL  60
VKAGFSSADA VALAPRIARE MAKEGVLLIN HHKLKALIGA QVGLLTDAKI QRAAAAVDLG  120
IKATLAATII PNALHSAAFK DAVVANLVAA GVDKKLAKAT AVAIAATALN PALGPIAKTE  180
AIKAEIGAQA ALLVSRGVHL KKAAIEHIIG RSFDAAVATA IVSSPILNAR IVTHLVRAGI  240
DKSLAVQIAP RIIDRLAKEP LLALNTAKLM KNITRQIVDV ITADKAIKTA EQLEKELPAL  300
DDLVKKACSS PKPTPTILAI YSTVASSLVL LVSLGAISFG SG                   342

SEQ ID NO: 18          moltype = AA  length = 309
FEATURE                Location/Qualifiers
source                 1..309
                       mol_type = protein
                       organism = synthetic construct
SEQUENCE: 18
MKAKLLVLLC TFTATYASSN RPRSVAQAAI ATDGKGIINK DCRDAVINDA KLRAAIAGAL  60
VKAGFSSADA VALAPRIARE MAKEGVLLIN HHKLKALIGA QVGLLTDAKI QRAAAAVDLG  120
IKATLAATII PNALHSAAFK DAVVANLVAA GVDKKLAKAT AVAIAATALN PALGPIAKTE  180
AIKAEIGAQA ALLVSRGVHL KKAAIEHIIG RSFDAAVATA IVSSPILNAR IVTHLVRAGI  240
DKSLAVQIAP RIIDRLAKEP LLALNTAKLM KNITRQIVDV ITADKAIKTA EQLEKELPAL  300
DDLVKKACS                                                        309

SEQ ID NO: 19          moltype = AA  length = 338
FEATURE                Location/Qualifiers
source                 1..338
                       mol_type = protein
                       organism = synthetic construct
SEQUENCE: 19
MKAKLLVLLC TFTATYASSN RPRSVAQAAI ATDGKGIINK DCRDAVINDA KLRAAIAGAL  60
VKAGFSSADA VALAPRIARE MAKEGVLLIN HHKLKALIGA QVGLLTDAKI QRAAAAVDLG  120
IKATLAATII PNALHSAAFK DAVVANLVAA GVDKKLAKAT AVAIAATALN PALGPIAKTE  180
AIKAEIGAQA ALLVSRGVHL KKAAIEHIIG RSFDAAVATA IVSSPILNAR IVTHLVRAGI  240
DKSLAVQIAP RIIDRLAKEP LLALNTAKLM KNITRQIVDV ITADKAIKTA EQLEKELPAL  300
DDLVKKACSS GSILAIYSTV ASSLVLLVSL GAISFGSG                        338

SEQ ID NO: 20          moltype = AA  length = 342
FEATURE                Location/Qualifiers
source                 1..342
                       mol_type = protein
                       organism = synthetic construct
SEQUENCE: 20
MKAKLLVLLC TFTATYAASN GNSSITQSAA FSPRATTKIS EDCRKAIIND LKLRGAIVGA  60
LVKAGLSAAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT PEPTPTILAI YSTVASSLVL LVSLGAISFG SG                   342

SEQ ID NO: 21          moltype = AA  length = 339
FEATURE                Location/Qualifiers
source                 1..339
                       mol_type = protein
                       organism = synthetic construct
SEQUENCE: 21
MKAKLLVLLC TFTATYAASN GNSSITQSAA FSPRATTKIS EDCRKAIIND LKLRGAIVGA  60
LVKAGLSAAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT SGSILAIYST VASSLVLLVS LGAISFGSG                       339

SEQ ID NO: 22          moltype = AA  length = 310
```

```
FEATURE                Location/Qualifiers
source                 1..310
                       mol_type = protein
                       organism = synthetic construct
SEQUENCE: 22
MKAKLLVLLC TFTATYAASN GNSSITQSAA FSPRATTKIS EDCRKAIIND LKLRGAIVGA  60
LVKAGLSAAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT                                                        310

SEQ ID NO: 23          moltype = AA  length = 310
FEATURE                Location/Qualifiers
source                 1..310
                       mol_type = protein
                       organism = synthetic construct
SEQUENCE: 23
MKAKLLVLLC TFTATYAASN GNSSITQSAA FSPRATTKIS EDCRKAIIND LKLRGAIVGA  60
LVKAGLSVAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT                                                        310

SEQ ID NO: 24          moltype = AA  length = 342
FEATURE                Location/Qualifiers
source                 1..342
                       mol_type = protein
                       organism = synthetic construct
SEQUENCE: 24
MKAKLLVLLC TFTATYAASN GNSSITQSAA FSPRATTKIS EDCRKAIIND LKLRGAIVGA  60
LVKAGLSVAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT PEPTPTILAI YSTVASSLVL LVSLGAISFG SG                    342

SEQ ID NO: 25          moltype = AA  length = 339
FEATURE                Location/Qualifiers
source                 1..339
                       mol_type = protein
                       organism = synthetic construct
SEQUENCE: 25
MKAKLLVLLC TFTATYAASN GNSSITQSAA FSPRATTKIS EDCRKAIIND LKLRGAIVGA  60
LVKAGLSVAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT SGSILAIYST VASSLVLLVS LGAISFGSG                        339

SEQ ID NO: 26          moltype = AA  length = 339
FEATURE                Location/Qualifiers
source                 1..339
                       mol_type = protein
                       organism = synthetic construct
SEQUENCE: 26
MKAKLLVLLC TFTATYAASN GQSSITQSAA FSPRATTKIS EDCRKAIIND LKLRGAIVGA  60
LVKAGLSAAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT SGSILAIYST VASSLVLLVS LGAISFGSG                        339

SEQ ID NO: 27          moltype = AA  length = 342
FEATURE                Location/Qualifiers
source                 1..342
                       mol_type = protein
                       organism = synthetic construct
SEQUENCE: 27
MKAKLLVLLC TFTATYAASN GQSSITQSAA FSPRATTKIS EDCRKAIIND LKLRGAIVGA  60
LVKAGLSAAD AAALAPRIAA EMAAEGTLTI NHHRLKVLVA SQLGLVADAA VQHAAAAIDL  120
SFKAILGASI IPNALGSAAF KNAVIANLVA AGIDKHLARA TAVAIVATAL NPALGPIAKF  180
ELIKAEIAAQ AALLIRRGVH LQKAAIEHVI GRAFDAAVAT AIISSPILSA RIVTHLVRAG  240
IDKSIAISLA PHIVKRLAKE PLLAFNTAKL VKDIARQIVD IRNTQEAIAV YKQLKAELPT  300
LDGLVQKACT PEPTPTILAI YSTVASSLVL LVSLGAISFG SG                    342

SEQ ID NO: 28          moltype = AA  length = 322
FEATURE                Location/Qualifiers
```

```
source                  1..322
                        mol_type = protein
                        organism = synthetic construct
SEQUENCE: 28
MKAKLLVLLC TFTATYASSN RPRSVAQAAI ATDGKGIIDK DSRDAVINDA KLRAAIAGAL  60
VKAGFSSADA VALAPRIAKE MAKEGVLLIN HHKLKALIGA QLGLLTDAKI QRAAAAVDLG  120
IKATLAATII PNALGSAAFK NAVIANLVAA GIDKHLARAT AVAIVATALN PALGPIAKFE  180
LIKAEIAAQA ALLIRRGVHL QKAAIEHVIG RAFDAAVATA IISSPILSAR IVTHLVRAGI  240
DKSIAISLAP HIVKRLAKEP LLAFNTAKLM KNITRQIVDV ITADKAIKTA EQLEKELPAL  300
DDLVKKASSP PKPTPTPTPT PT                                            322

SEQ ID NO: 29           moltype = AA  length = 306
FEATURE                 Location/Qualifiers
source                  1..306
                        mol_type = protein
                        organism = synthetic construct
SEQUENCE: 29
MSSNRPRSVA QAAIATDGKG IIDKDSRDAV INDAKLRAAI AGALVKAGFS SADAVALAPR  60
IAKEMAKEGV LLINHHKLKA LIGAQLGLLT DAKIQRAAAA VDLGIKATLA ATIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLMKNITRQ IVDVITADKA IKTAEQLEKE LPALDDLVKK ASSPPKPTPT  300
PTPTPT                                                              306

SEQ ID NO: 30           moltype = AA  length = 322
FEATURE                 Location/Qualifiers
source                  1..322
                        mol_type = protein
                        organism = synthetic construct
SEQUENCE: 30
MKAKLLVLLC TFTATYASSN RPRSVAQAAI ATDGKGIIDK DSRDAVINDA KLRAAIAGAL  60
VKAGFSSADA VALAPRIAKE MAKEGVLLIN HHKLKALIGA QLGLLTDAKI QRAAAAVDLG  120
IKATLAATII PNALGSAAFK NAVIANLVAA GIDKHLARAT AVAIVATALN PALGPIAKFE  180
LIKAEIAAQA ALLIRRGVHL QKAAIEHVIG RAFDAAVATA IISSPILSAR IVTHLVRAGI  240
DKSIAISLAP HIVKRLAKEP LLAFNTAKLM KQITRQIVDV ITADKAIKTA EQLEKELPAL  300
DDLVKKASSP PKPTPTPTPT PT                                            322

SEQ ID NO: 31           moltype = AA  length = 416
FEATURE                 Location/Qualifiers
source                  1..416
                        mol_type = protein
                        organism = synthetic construct
SEQUENCE: 31
MKAKLLVLLC TFTATYAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVSTIG ASKVTSGSLT WGIRTSFTSY  240
LRGPIANGSW KLSGGANWNG SAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTNL TLSAEKVSHN VTVDAVTGKV IGDDSGKGAG RGLPVT       416

SEQ ID NO: 32           moltype = AA  length = 400
FEATURE                 Location/Qualifiers
source                  1..400
                        mol_type = protein
                        organism = synthetic construct
SEQUENCE: 32
MAGPTVTVIP VGREGGDITI SGKGFSTTGF GVYVAVAPAS VPEFYGNSDK FYGYDPSKDT  60
TESPSTIWVY TPSQKAIGSR FAQGRPMNND GSFTITMKAP PFEQGKDFVV LTTKAHGVGK  120
TDHSDDTRTP VTYREATPAP TGPKTPIAPS KQPSKQAAPS KQVKPSKQAG PNKQSTTPQQ  180
KTAEHRSQTP AAHRTMTKQV STIGASKVTS GSLTWGIRTS FTSYLRGPIA NGSWKLSGGA  240
NWNGSAFTFP LTSGSFDPAT KSGSLKYSGS VHMTGHHGIL DMTLAEPSLQ IKGSTGHLYL  300
DVKSSSMDGK KTNYGRVDFA TFGVSVSGNA AIKGSPVKLT ATGAKAFAGF YRAGEPMNPL  360
STNLTLSAEK VSHNVTVDAV TGKVIGDDSG KGAGRGLPVT                         400

SEQ ID NO: 33           moltype = AA  length = 416
FEATURE                 Location/Qualifiers
source                  1..416
                        mol_type = protein
                        organism = synthetic construct
SEQUENCE: 33
MKAKLLVLLC TFTATYAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVCTIG ASKVTSGSLT WGIRTSFTSY  240
LRGPIANGSW KLSGGANWNG SAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTNL TLSAEKVCHN VTVDAVTGKV IGDDSGKGAG RGLPVT       416
```

-continued

```
SEQ ID NO: 34          moltype = AA  length = 416
FEATURE                Location/Qualifiers
source                 1..416
                       mol_type = protein
                       organism = synthetic construct
SEQUENCE: 34
MKAKLLVLLC TFTATYAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVCTIG ASKVTSGSLT WGIRTSFTSY  240
LRGPIAKGSW KLSGGANWNG GAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTQL TLSAEKVCHS VTVDAVTGKV IGDDSGKGAG RGLPVT      416

SEQ ID NO: 35          moltype = AA  length = 416
FEATURE                Location/Qualifiers
source                 1..416
                       mol_type = protein
                       organism = synthetic construct
SEQUENCE: 35
MKAKLLVLLC TFTATYAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVSTIG ASKVTSGSLT WGIRTSFTSY  240
LRGPIAKGSW KLSGGANWNG GAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTQL TLSAEKVSHS VTVDAVTGKV IGDDSGKGAG RGLPVT      416

SEQ ID NO: 36          moltype = AA  length = 445
FEATURE                Location/Qualifiers
source                 1..445
                       mol_type = protein
                       organism = synthetic construct
SEQUENCE: 36
MKAKLLVLLC TFTATYAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVCTIG ASKVTSGSLT WGIRTSFTSY  240
LRGPIANGSW KLSGGANWNG SAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTNL TLSAEKVCHN VTVDAVTGKV IGDDSGKGAG RGLPVTSGSI  420
LAIYSTVASS LVLLVSLGAI SFGSG                                        445

SEQ ID NO: 37          moltype = AA  length = 445
FEATURE                Location/Qualifiers
source                 1..445
                       mol_type = protein
                       organism = synthetic construct
SEQUENCE: 37
MKAKLLVLLC TFTATYAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVCTIG ASKVTSGSLT WGIRTSFTSY  240
LRGPIAKGSW KLSGGANWNG GAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTQL TLSAEKVCHS VTVDAVTGKV IGDDSGKGAG RGLPVTSGSI  420
LAIYSTVASS LVLLVSLGAI SFGSG                                        445

SEQ ID NO: 38          moltype = AA  length = 468
FEATURE                Location/Qualifiers
source                 1..468
                       mol_type = protein
                       organism = synthetic construct
SEQUENCE: 38
MKAKLLVLLC TFTATYASSN RPRSVAQAAI ATDGKGIIDK DSRDAVINDA KLRAAIAGAL  60
VKAGFSSADA VALAPRIAKE MAKEGVLLIN HHKLKALIGA QLGLLTDAKI QRAAAAVDLG  120
IKATLAATII PNALGSAAFK NAVIANLVAA GIDKHLARAT AVAIVATALN PALGPIAKFE  180
LIKAEIAAQA ALLIRRGVHL QKAAIEHVIG RAFDAAVATA IISSPILSAR IVTHLVRAGI  240
DKSIAISLAP HIVKRLAKEP LLAFNTAKLM KNITRQIVDV ITADKAIKTA EQLEKELPAL  300
DDLVKKASSP PKPTPTPTPT PTAGPTVTVI PVGREGGDIT ISGKGFSTTG FGVYVAVAPA  360
SVPEFYGNSD KFYGYDPSKD TTESPSTIWV YTPSQKAIGS RFAQGRPMNN DGSFTITMKA  420
PPFEQGKDFV VLTTKAHGVG KTDHSDDTRT PVTYREATPA PTGPKTPI               468

SEQ ID NO: 39          moltype = AA  length = 307
FEATURE                Location/Qualifiers
source                 1..307
                       mol_type = protein
                       organism = synthetic construct
SEQUENCE: 39
```

```
MKAKLLVLLC TFTATYAVAQ AAIATDGKGI IDKDSRDAVI NDAKLRAAIA GALVKAGFSS  60
ADAVALAPRI AKEMAKEGVL LINHHKLKAL IGAQLGLLTD AKIQRAAAAV DLGIKATLAA  120
TIIPNALGSA AFKNAVIANL VAAGIDKHLA RATAVAIVAT ALNPALGPIA KFELIKAEIA  180
AQAALLIRRG VHLQKAAIEH VIGRAFDAAV ATAIISSPIL SARIVTHLVR AGIDKSIAIS  240
LAPHIVKRLA KEPLLAFNTA KLMKAITRQI VDVITADKAI KTAEQLEKEL PALDDLVKKA  300
MGPPKPT                                                           307

SEQ ID NO: 40          moltype = AA  length = 452
FEATURE                Location/Qualifiers
source                 1..452
                       mol_type = protein
                       organism = synthetic construct
SEQUENCE: 40
MKAKLLVLLC TFTATYASSN RPRSVAQAAI ATDGKGIIDK DSRDAVINDA KLRAAIAGAL  60
VKAGFSSADA VALAPRIAKE MAKEGVLLIN HHKLKALIGA QLGLLTDAKI QRAAAAVDLG  120
IKATLAATII PNALGSAAFK NAVIANLVAA GIDKHLARAT AVAIVATALN PALGPIAKFE  180
LIKAEIAAQA ALLIRRGVHL QKAAIEHVIG RAFDAAVATA IISSPILSAR IVTHLVRAGI  240
DKSIAISLAP HIVKRLAKEP LLAFNTAKLM KNITRQIVDV ITADKAIKTA EQLEKELPAL  300
DDLVKKAMGP PKPTGGGGGA GPTVTVIPVG REGGDITISG KGFSTTGFGV YVAVAPASVP  360
EFYGNSDKFY GYDPSKDTTE SPSTIWVYTP SQKAIGSRFA QGRPMNNDGS FTITMKAPPF  420
EQGKDFVVLT TKAHGVGKGD HGDDTRTPVG YR                               452

SEQ ID NO: 41          moltype = AA  length = 455
FEATURE                Location/Qualifiers
source                 1..455
                       mol_type = protein
                       organism = synthetic construct
SEQUENCE: 41
MKAKLLVLLC TFTATYASSN RPRSVAQAAI ATDGKGIIDK DSRDAVINDA KLRAAIAGAL  60
VKAGFSSADA VALAPRIAKE MAKEGVLLIN HHKLKALIGA QLGLLTDAKI QRAAAAVDLG  120
IKATLAATII PNALGSAAFK NAVIANLVAA GIDKHLARAT AVAIVATALN PALGPIAKFE  180
LIKAEIAAQA ALLIRRGVHL QKAAIEHVIG RAFDAAVATA IISSPILSAR IVTHLVRAGI  240
DKSIAISLAP HIVKRLAKEP LLAFNTAKLM KNITRQIVDV ITADKAIKTA EQLEKELPAL  300
DDLVKKASSP PKPTPTPTPT PTAGPTVTVI PVGREGGDIT ISGKGFSTTG FGVYVAVAPA  360
SVPEFYGNSD KFYGYDPSKD TTESPSTIWV YTPSQKAIGS RFAQGRPMNN DGSFTITMKA  420
PPFEQGKDFV VLTTKAHGVG KTDHSDDTRT PVTYR                            455

SEQ ID NO: 42          moltype = AA  length = 17
FEATURE                Location/Qualifiers
source                 1..17
                       mol_type = protein
                       organism = synthetic construct
SEQUENCE: 42
MKAKLLVLLC TFTATYA                                                17

SEQ ID NO: 43          moltype = AA  length = 240
FEATURE                Location/Qualifiers
source                 1..240
                       mol_type = protein
                       organism = synthetic construct
SEQUENCE: 43
MVEPTTTISA TSTHELSASD ARNSIQLLNA HIATLQSVQK SVPGSDYSDQ IRDLLKAAFD  60
LRGLIETLAH GGIPFYDPST IMPRIKLVAT TIDTIHTATT TLQNKVRPAH VELGLEVTKA  120
VLLTANPAST AKELDAEGAA LKARLEKVSQ YPDLTPNDVA TVYVRTNFSK TIWQVRANRD  180
RYILGHKSAA VYKTLNHAIT KAVGVRLNPK TTVGNIQAAR TELLAAYQTA FNSPDVKKAA  240

SEQ ID NO: 44          moltype = AA  length = 239
FEATURE                Location/Qualifiers
source                 1..239
                       mol_type = protein
                       organism = synthetic construct
SEQUENCE: 44
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 45          moltype = AA  length = 239
FEATURE                Location/Qualifiers
source                 1..239
                       mol_type = protein
                       organism = synthetic construct
SEQUENCE: 45
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 46          moltype = AA  length = 239
```

-continued

```
FEATURE                Location/Qualifiers
source                 1..239
                       mol_type = protein
                       organism = synthetic construct
SEQUENCE: 46
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 47          moltype = AA  length = 239
FEATURE                Location/Qualifiers
source                 1..239
                       mol_type = protein
                       organism = synthetic construct
SEQUENCE: 47
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 48          moltype = AA  length = 239
FEATURE                Location/Qualifiers
source                 1..239
                       mol_type = protein
                       organism = synthetic construct
SEQUENCE: 48
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 49          moltype = AA  length = 239
FEATURE                Location/Qualifiers
source                 1..239
                       mol_type = protein
                       organism = synthetic construct
SEQUENCE: 49
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 50          moltype = AA  length = 239
FEATURE                Location/Qualifiers
source                 1..239
                       mol_type = protein
                       organism = synthetic construct
SEQUENCE: 50
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTSFSKT IWQVRANRDR  180
YILGHKSAAV YKTLNHAITK AVGVRLNPKT TVGNIQAART ELLAAYQTAF NSPDVKKAA   239

SEQ ID NO: 51          moltype = AA  length = 239
FEATURE                Location/Qualifiers
source                 1..239
                       mol_type = protein
                       organism = synthetic construct
SEQUENCE: 51
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTSFSKT IWQVRANRDR  180
YILGHKSAAV YKTLNHAITK AVGVRLNPKT TVGNIQAART ELLAAYQTAF NSPDVKKAA   239

SEQ ID NO: 52          moltype = AA  length = 239
FEATURE                Location/Qualifiers
source                 1..239
                       mol_type = protein
                       organism = synthetic construct
SEQUENCE: 52
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 53          moltype = AA  length = 239
FEATURE                Location/Qualifiers
source                 1..239
```

```
                         mol_type = protein
                         organism = synthetic construct
SEQUENCE: 53
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 54            moltype = AA  length = 239
FEATURE                  Location/Qualifiers
source                   1..239
                         mol_type = protein
                         organism = synthetic construct
SEQUENCE: 54
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTSFSKT IWQVRANRDR  180
YILGHKSAAV YKTLNHAITK AVGVRLNPKT TVGNIQAART ELLAAYQTAF NSPDVKKAA   239

SEQ ID NO: 55            moltype = AA  length = 239
FEATURE                  Location/Qualifiers
source                   1..239
                         mol_type = protein
                         organism = synthetic construct
SEQUENCE: 55
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PGGTPNGVGG VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 56            moltype = AA  length = 239
FEATURE                  Location/Qualifiers
source                   1..239
                         mol_type = protein
                         organism = synthetic construct
SEQUENCE: 56
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PGGTPNGVGG VYVRTSFSKT IWQVRANRDR  180
YILGHKSAAV YKTLNHAITK AVGVRLNPKT TVGNIQAART ELLAAYQTAF NSPDVKKAA   239

SEQ ID NO: 57            moltype = AA  length = 239
FEATURE                  Location/Qualifiers
source                   1..239
                         mol_type = protein
                         organism = synthetic construct
SEQUENCE: 57
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVAANADR  180
YIAGHKSAAV AKTLAHAIAK AAGVRANPKT TVGNIQAART ELLAAYQTAF NSPDVKKAA   239

SEQ ID NO: 58            moltype = AA  length = 239
FEATURE                  Location/Qualifiers
source                   1..239
                         mol_type = protein
                         organism = synthetic construct
SEQUENCE: 58
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTSFSKT IWQVAANADR  180
YIAGHKSAAV AKTLAHAIAK AAGVRANPKT TVGNIQAART ELLAAYQTAF NSPDVKKAA   239

SEQ ID NO: 59            moltype = AA  length = 299
FEATURE                  Location/Qualifiers
source                   1..299
                         mol_type = protein
                         organism = synthetic construct
SEQUENCE: 59
SSNRPRSVAQ AAIATDGKGI INKDCRDAVI NDAKLRAAIA GALVKAGFSS ADAVALAPRI  60
AREMAKEGVL LINHHKLKAL IGAQVGLLTD AKIQRAAAAV DLGIKATLAA TIIPNALHSA  120
AFKDAVVANL VAAGVDKKLA KATAVAIAAT ALNPALGPIA KTEAIKAEIG AQAALLVSRG  180
VHLKKAAIEH IIGRSFDAAV ATAIVSSPIL NARIVTHLVR AGIDKSLAVQ IAPRIIDRLA  240
KEPLLALNTA KLMKNITRQI VDVITADKAI KTAEQLEKEL PALDDLVKKA CSSPKPTPT   299

SEQ ID NO: 60            moltype = AA  length = 292
FEATURE                  Location/Qualifiers
source                   1..292
                         mol_type = protein
```

```
                        organism = synthetic construct
SEQUENCE: 60
SSNRPRSVAQ AAIATDGKGI INKDCRDAVI NDAKLRAAIA GALVKAGFSS ADAVALAPRI  60
AREMAKEGVL LINHHKLKAL IGAQVGLLTD AKIQRAAAAV DLGIKATLAA TIIPNALHSA  120
AFKDAVVANL VAAGVDKKLA KATAVAIAAT ALNPALGPIA KTEAIKAEIG AQAALLVSRG  180
VHLKKAAIEH IIGRSFDAAV ATAIVSSPIL NARIVTHLVR AGIDKSLAVQ IAPRIIDRLA  240
KEPLLALNTA KLMKNITRQI VDVITADKAI KTAEQLEKEL PALDDLVKKA CS          292

SEQ ID NO: 61           moltype = AA  length = 292
FEATURE                 Location/Qualifiers
source                  1..292
                        mol_type = protein
                        organism = synthetic construct
SEQUENCE: 61
SSNRPRSVAQ AAIATDGKGI INKDCRDAVI NDAKLRAAIA GALVKAGFSS ADAVALAPRI  60
AREMAKEGVL LINHHKLKAL IGAQVGLLTD AKIQRAAAAV DLGIKATLAA TIIPNALHSA  120
AFKDAVVANL VAAGVDKKLA KATAVAIAAT ALNPALGPIA KTEAIKAEIG AQAALLVSRG  180
VHLKKAAIEH IIGRSFDAAV ATAIVSSPIL NARIVTHLVR AGIDKSLAVQ IAPRIIDRLA  240
KEPLLALNTA KLMKNITRQI VDVITADKAI KTAEQLEKEL PALDDLVKKA CS          292

SEQ ID NO: 62           moltype = AA  length = 299
FEATURE                 Location/Qualifiers
source                  1..299
                        mol_type = protein
                        organism = synthetic construct
SEQUENCE: 62
ASNGNSSITQ SAAFSPRATT KISEDCRKAI INDLKLRGAI VGALVKAGLS AADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACTPEPTPT   299

SEQ ID NO: 63           moltype = AA  length = 293
FEATURE                 Location/Qualifiers
source                  1..293
                        mol_type = protein
                        organism = synthetic construct
SEQUENCE: 63
ASNGNSSITQ SAAFSPRATT KISEDCRKAI INDLKLRGAI VGALVKAGLS AADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACT         293

SEQ ID NO: 64           moltype = AA  length = 293
FEATURE                 Location/Qualifiers
source                  1..293
                        mol_type = protein
                        organism = synthetic construct
SEQUENCE: 64
ASNGNSSITQ SAAFSPRATT KISEDCRKAI INDLKLRGAI VGALVKAGLS AADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACT         293

SEQ ID NO: 65           moltype = AA  length = 293
FEATURE                 Location/Qualifiers
source                  1..293
                        mol_type = protein
                        organism = synthetic construct
SEQUENCE: 65
ASNGNSSITQ SAAFSPRATT KISEDCRKAI INDLKLRGAI VGALVKAGLS VADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACT         293

SEQ ID NO: 66           moltype = AA  length = 299
FEATURE                 Location/Qualifiers
source                  1..299
                        mol_type = protein
                        organism = synthetic construct
SEQUENCE: 66
ASNGNSSITQ SAAFSPRATT KISEDCRKAI INDLKLRGAI VGALVKAGLS VADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACTPEPTPT   299
```

```
SEQ ID NO: 67          moltype = AA  length = 293
FEATURE                Location/Qualifiers
source                 1..293
                       mol_type = protein
                       organism = synthetic construct
SEQUENCE: 67
ASNGNSSITQ SAAFSPRATT KISEDCRKAI INDLKLRGAI VGALVKAGLS VADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACT         293

SEQ ID NO: 68          moltype = AA  length = 293
FEATURE                Location/Qualifiers
source                 1..293
                       mol_type = protein
                       organism = synthetic construct
SEQUENCE: 68
ASNGQSSITQ SAAFSPRATT KISEDCRKAI INDLKLRGAI VGALVKAGLS AADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACT         293

SEQ ID NO: 69          moltype = AA  length = 299
FEATURE                Location/Qualifiers
source                 1..299
                       mol_type = protein
                       organism = synthetic construct
SEQUENCE: 69
ASNGQSSITQ SAAFSPRATT KISEDCRKAI INDLKLRGAI VGALVKAGLS AADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACTPEPTPT   299

SEQ ID NO: 70          moltype = AA  length = 305
FEATURE                Location/Qualifiers
source                 1..305
                       mol_type = protein
                       organism = synthetic construct
SEQUENCE: 70
SSNRPRSVAQ AAIATDGKGI IDKDSRDAVI NDAKLRAAIA GALVKAGFSS ADAVALAPRI  60
AKEMAKEGVL LINHHKLKAL IGAQLGLLTD AKIQRAAAAV DLGIKATLAA TIIPNALGSA  120
AFKNAVIANL VAAGIDKHLA RATAVAIVAT ALNPALGPIA KFELIKAEIA AQAALLIRRG  180
VHLQKAAIEH VIGRAFDAAV ATAIISSPIL SARIVTHLVR AGIDKSIAIS LAPHIVKRLA  240
KEPLLAFNTA KLMKNITRQI VDVITADKAI KTAEQLEKEL PALDDLVKKA SSPPKPTPTP  300
TPTPT                                                              305

SEQ ID NO: 71          moltype = AA  length = 306
FEATURE                Location/Qualifiers
source                 1..306
                       mol_type = protein
                       organism = synthetic construct
SEQUENCE: 71
MSSNRPRSVA QAAIATDGKG IIDKDSRDAV INDAKLRAAI AGALVKAGFS SADAVALAPR  60
IAKEMAKEGV LLINHHKLKA LIGAQLGLLT DAKIQRAAAA VDLGIKATLA ATIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLMKNITRQ IVDVITADKA IKTAEQLEKE LPALDDLVKK ASSPPKPTPT  300
PTPTPT                                                             306

SEQ ID NO: 72          moltype = AA  length = 305
FEATURE                Location/Qualifiers
source                 1..305
                       mol_type = protein
                       organism = synthetic construct
SEQUENCE: 72
SSNRPRSVAQ AAIATDGKGI IDKDSRDAVI NDAKLRAAIA GALVKAGFSS ADAVALAPRI  60
AKEMAKEGVL LINHHKLKAL IGAQLGLLTD AKIQRAAAAV DLGIKATLAA TIIPNALGSA  120
AFKNAVIANL VAAGIDKHLA RATAVAIVAT ALNPALGPIA KFELIKAEIA AQAALLIRRG  180
VHLQKAAIEH VIGRAFDAAV ATAIISSPIL SARIVTHLVR AGIDKSIAIS LAPHIVKRLA  240
KEPLLAFNTA KLMKQITRQI VDVITADKAI KTAEQLEKEL PALDDLVKKA SSPPKPTPTP  300
TPTPT                                                              305

SEQ ID NO: 73          moltype = AA  length = 399
FEATURE                Location/Qualifiers
source                 1..399
```

```
                        mol_type = protein
                        organism = synthetic construct
SEQUENCE: 73
AGPTVTVIPV GREGGDITIS GKGFSTTGFG VYVAVAPASV PEFYGNSDKF YGYDPSKDTT  60
ESPSTIWVYT PSQKAIGSRF AQGRPMNNDG SFTITMKAPP FEQGKDFVVL TTKAHGVGKT  120
DHSDDTRTPV TYREATPAPT GPKTPIAPSK QPSKQAAPSK QVKPSKQAGP NKQSTTPQQK  180
TAEHRSQTPA AHRTMTKQVS TIGASKVTSG SLTWGIRTSF TSYLRGPIAN GSWKLSGGAN  240
WNGSAFTFPL TSGSFDPATK SGSLKYSGSV HMTGHHGILD MTLAEPSLQI KGSTGHLYLD  300
VKSSSMDGKK TNYGRVDFAT FGVSVSGNAA IKGSPVKLTA TGAKAFAGFY RAGEPMNPLS  360
TNLTLSAEKV SHNVTVDAVT GKVIGDDSGK GAGRGLPVT                         399

SEQ ID NO: 74           moltype = AA  length = 400
FEATURE                 Location/Qualifiers
source                  1..400
                        mol_type = protein
                        organism = synthetic construct
SEQUENCE: 74
MAGPTVTVIP VGREGGDITI SGKGFSTTGF GVYVAVAPAS VPEFYGNSDK FYGYDPSKDT  60
TESPSTIWVY TPSQKAIGSR FAQGRPMNND GSFTITMKAP PFEQGKDFVV LTTKAHGVGK  120
TDHSDDTRTP VTYREATPAP TGPKTPIAPS KQPSKQAAPS KQVKPSKQAG PNKQSTTPQQ  180
KTAEHRSQTP AAHRTMTKQV STIGASKVTS GSLTWGIRTS FTSYLRGPIA NGSWKLSGGA  240
NWNGSAFTFP LTSGSFDPAT KSGSLKYSGS VHMTGHHGIL DMTLAEPSLQ IKGSTGHLYL  300
DVKSSSMDGK KTNYGRVDFA TFGVSVSGNA AIKGSPVKLT ATGAKAFAGF YRAGEPMNPL  360
STNLTLSAEK VSHNVTVDAV TGKVIGDDSG KGAGRGLPVT                        400

SEQ ID NO: 75           moltype = AA  length = 399
FEATURE                 Location/Qualifiers
source                  1..399
                        mol_type = protein
                        organism = synthetic construct
SEQUENCE: 75
AGPTVTVIPV GREGGDITIS GKGFSTTGFG VYVAVAPASV PEFYGNSDKF YGYDPSKDTT  60
ESPSTIWVYT PSQKAIGSRF AQGRPMNNDG SFTITMKAPP FEQGKDFVVL TTKAHGVGKT  120
DHSDDTRTPV TYREATPAPT GPKTPIAPSK QPSKQAAPSK QVKPSKQAGP NKQSTTPQQK  180
TAEHRSQTPA AHRTMTKQVC TIGASKVTSG SLTWGIRTSF TSYLRGPIAN GSWKLSGGAN  240
WNGSAFTFPL TSGSFDPATK SGSLKYSGSV HMTGHHGILD MTLAEPSLQI KGSTGHLYLD  300
VKSSSMDGKK TNYGRVDFAT FGVSVSGNAA IKGSPVKLTA TGAKAFAGFY RAGEPMNPLS  360
TNLTLSAEKV CHNVTVDAVT GKVIGDDSGK GAGRGLPVT                         399

SEQ ID NO: 76           moltype = AA  length = 399
FEATURE                 Location/Qualifiers
source                  1..399
                        mol_type = protein
                        organism = synthetic construct
SEQUENCE: 76
AGPTVTVIPV GREGGDITIS GKGFSTTGFG VYVAVAPASV PEFYGNSDKF YGYDPSKDTT  60
ESPSTIWVYT PSQKAIGSRF AQGRPMNNDG SFTITMKAPP FEQGKDFVVL TTKAHGVGKT  120
DHSDDTRTPV TYREATPAPT GPKTPIAPSK QPSKQAAPSK QVKPSKQAGP NKQSTTPQQK  180
TAEHRSQTPA AHRTMTKQVC TIGASKVTSG SLTWGIRTSF TSYLRGPIAK GSWKLSGGAN  240
WNGGAFTFPL TSGSFDPATK SGSLKYSGSV HMTGHHGILD MTLAEPSLQI KGSTGHLYLD  300
VKSSSMDGKK TNYGRVDFAT FGVSVSGNAA IKGSPVKLTA TGAKAFAGFY RAGEPMNPLS  360
TQLTLSAEKV CHSVTVDAVT GKVIGDDSGK GAGRGLPVT                         399

SEQ ID NO: 77           moltype = AA  length = 399
FEATURE                 Location/Qualifiers
source                  1..399
                        mol_type = protein
                        organism = synthetic construct
SEQUENCE: 77
AGPTVTVIPV GREGGDITIS GKGFSTTGFG VYVAVAPASV PEFYGNSDKF YGYDPSKDTT  60
ESPSTIWVYT PSQKAIGSRF AQGRPMNNDG SFTITMKAPP FEQGKDFVVL TTKAHGVGKT  120
DHSDDTRTPV TYREATPAPT GPKTPIAPSK QPSKQAAPSK QVKPSKQAGP NKQSTTPQQK  180
TAEHRSQTPA AHRTMTKQVS TIGASKVTSG SLTWGIRTSF TSYLRGPIAK GSWKLSGGAN  240
WNGGAFTFPL TSGSFDPATK SGSLKYSGSV HMTGHHGILD MTLAEPSLQI KGSTGHLYLD  300
VKSSSMDGKK TNYGRVDFAT FGVSVSGNAA IKGSPVKLTA TGAKAFAGFY RAGEPMNPLS  360
TQLTLSAEKV SHSVTVDAVT GKVIGDDSGK GAGRGLPVT                         399

SEQ ID NO: 78           moltype = AA  length = 399
FEATURE                 Location/Qualifiers
source                  1..399
                        mol_type = protein
                        organism = synthetic construct
SEQUENCE: 78
AGPTVTVIPV GREGGDITIS GKGFSTTGFG VYVAVAPASV PEFYGNSDKF YGYDPSKDTT  60
ESPSTIWVYT PSQKAIGSRF AQGRPMNNDG SFTITMKAPP FEQGKDFVVL TTKAHGVGKT  120
DHSDDTRTPV TYREATPAPT GPKTPIAPSK QPSKQAAPSK QVKPSKQAGP NKQSTTPQQK  180
TAEHRSQTPA AHRTMTKQVC TIGASKVTSG SLTWGIRTSF TSYLRGPIAN GSWKLSGGAN  240
WNGSAFTFPL TSGSFDPATK SGSLKYSGSV HMTGHHGILD MTLAEPSLQI KGSTGHLYLD  300
VKSSSMDGKK TNYGRVDFAT FGVSVSGNAA IKGSPVKLTA TGAKAFAGFY RAGEPMNPLS  360
```

-continued

```
TNLTLSAEKV CHNVTVDAVT GKVIGDDSGK GAGRGLPVT                        399

SEQ ID NO: 79          moltype = AA  length = 399
FEATURE                Location/Qualifiers
source                 1..399
                       mol_type = protein
                       organism = synthetic construct
SEQUENCE: 79
AGPTVTVIPV GREGGDITIS GKGFSTTGFG VYVAVAPASV PEFYGNSDKF YGYDPSKDTT  60
ESPSTIWVYT PSQKAIGSRF AQGRPMNNDG SFTITMKAPP FEQGKDFVVL TTKAHGVGKT  120
DHSDDTRTPV TYREATPAPT GPKTPIAPSK QPSKQAAPSK QVKPSKQAGP NKQSTTPQQK  180
TAEHRSQTPA AHRTMTKQVC TIGASKVTSG SLTWGIRTSF TSYLRGPIAK GSWKLSGGAN  240
WNGGAFTFPL TSGSFDPATK SGSLKYSGSV HMTGHHGILD MTLAEPSLQI KGSTGHLYLD  300
VKSSSMDGKK TNYGRVDFAT FGVSVSGNAA IKGSPVKLTA TGAKAFAGFY RAGEPMNPLS  360
TQLTLSAEKV CHSVTVDAVT GKVIGDDSGK GAGRGLPVT                        399

SEQ ID NO: 80          moltype = AA  length = 451
FEATURE                Location/Qualifiers
source                 1..451
                       mol_type = protein
                       organism = synthetic construct
SEQUENCE: 80
SSNRPRSVAQ AAIATDGKGI IDKDSRDAVI NDAKLRAAIA GALVKAGFSS ADAVALAPRI  60
AKEMAKEGVL LINHHKLKAL IGAQLGLLTD AKIQRAAAAV DLGIKATLAA TIIPNALGSA  120
AFKNAVIANL VAAGIDKHLA RATAVAIVAT ALNPALGPIA KFELIKAEIA AQAALLIRRG  180
VHLQKAAIEH VIGRAFDAAV ATAIISSPIL SARIVTHLVR AGIDKSIAIS LAPHIVKRLA  240
KEPLLAFNTA KLMKNITRQI VDVITADKAI KTAEQLEKEL PALDDLVKKA SSPPKPTPTP  300
TPTPTAGPTV TVIPVGREGG DITISGKGFS TTGFGVYVAV APASVPEFYG NSDKFYGYDP  360
SKDTTESPST IWVYTPSQKA IGSRFAQGRP MNNDGSFTIT MKAPPFEQGK DFVVLTTKAH  420
GVGKTDHSDD TRTPVTYREA TPAPTGPKTP I                                451

SEQ ID NO: 81          moltype = AA  length = 290
FEATURE                Location/Qualifiers
source                 1..290
                       mol_type = protein
                       organism = synthetic construct
SEQUENCE: 81
VAQAAIATDG KGIIDKDSRD AVINDAKLRA AIAGALVKAG FSSADAVALA PRIAKEMAKE  60
GVLLINHHKL KALIGAQLGL LTDAKIQRAA AAVDLGIKAT LAATIIPNAL GSAAFKNAVI  120
ANLVAAGIDK HLARATAVAI VATALNPALG PIAKFELIKA EIAAQAALLI RRGVHLQKAA  180
IEHVIGRAFD AAVATAIISS PILSARIVTH LVRAGIDKSI AISLAPHIVK RLAKEPLLAF  240
NTAKLMKAIT RQIVDVITAD KAIKTAEQLE KELPALDDLV KKAMGPPKPT            290

SEQ ID NO: 82          moltype = AA  length = 435
FEATURE                Location/Qualifiers
source                 1..435
                       mol_type = protein
                       organism = synthetic construct
SEQUENCE: 82
SSNRPRSVAQ AAIATDGKGI IDKDSRDAVI NDAKLRAAIA GALVKAGFSS ADAVALAPRI  60
AKEMAKEGVL LINHHKLKAL IGAQLGLLTD AKIQRAAAAV DLGIKATLAA TIIPNALGSA  120
AFKNAVIANL VAAGIDKHLA RATAVAIVAT ALNPALGPIA KFELIKAEIA AQAALLIRRG  180
VHLQKAAIEH VIGRAFDAAV ATAIISSPIL SARIVTHLVR AGIDKSIAIS LAPHIVKRLA  240
KEPLLAFNTA KLMKNITRQI VDVITADKAI KTAEQLEKEL PALDDLVKKA MGPPKPTGGG  300
GGAGPTVTVI PVGREGGDIT ISGKGFSTTG FGVYVAVAPA SVPEFYGNSD KFYGYDPSKD  360
TTESPSTIWV YTPSQKAIGS RFAQGRPMNN DGSFTITMKA PPFEQGKDFV VLTTKAHGVG  420
KGDHGDDTRT PVGYR                                                  435

SEQ ID NO: 83          moltype = AA  length = 438
FEATURE                Location/Qualifiers
source                 1..438
                       mol_type = protein
                       organism = synthetic construct
SEQUENCE: 83
SSNRPRSVAQ AAIATDGKGI IDKDSRDAVI NDAKLRAAIA GALVKAGFSS ADAVALAPRI  60
AKEMAKEGVL LINHHKLKAL IGAQLGLLTD AKIQRAAAAV DLGIKATLAA TIIPNALGSA  120
AFKNAVIANL VAAGIDKHLA RATAVAIVAT ALNPALGPIA KFELIKAEIA AQAALLIRRG  180
VHLQKAAIEH VIGRAFDAAV ATAIISSPIL SARIVTHLVR AGIDKSIAIS LAPHIVKRLA  240
KEPLLAFNTA KLMKNITRQI VDVITADKAI KTAEQLEKEL PALDDLVKKA SSPPKPTPTP  300
TPTPTAGPTV TVIPVGREGG DITISGKGFS TTGFGVYVAV APASVPEFYG NSDKFYGYDP  360
SKDTTESPST IWVYTPSQKA IGSRFAQGRP MNNDGSFTIT MKAPPFEQGK DFVVLTTKAH  420
GVGKTDHSDD TRTPVTYR                                               438

SEQ ID NO: 84          moltype = AA  length = 29
FEATURE                Location/Qualifiers
source                 1..29
                       mol_type = protein
                       organism = synthetic construct
SEQUENCE: 84
```

-continued

```
SGSILAIYST VASSLVLLVS LGAISFGSG                                   29

SEQ ID NO: 85          moltype = AA  length = 26
FEATURE                Location/Qualifiers
source                 1..26
                       mol_type = protein
                       organism = synthetic construct
SEQUENCE: 85
ILAIYSTVAS SLVLLVSLGA ISFGSG                                      26

SEQ ID NO: 86          moltype = AA  length = 26
FEATURE                Location/Qualifiers
source                 1..26
                       mol_type = protein
                       organism = synthetic construct
SEQUENCE: 86
ILAIYSTVAS SLVLLVSLGA ISFGSG                                      26

SEQ ID NO: 87          moltype = RNA  length = 771
FEATURE                Location/Qualifiers
source                 1..771
                       mol_type = other RNA
                       organism = synthetic construct
SEQUENCE: 87
atgaaggcca agctgctggt gctgctgtgc acctttacag ccacctacgc cgtggaaccc  60
accaccacaa tcagcgccac aagcacacac gagctgagcg cctccgatgc cagaaactct  120
atccagctgc tgaacgccca cattgccaca ctgcagagcg tgcagaaaag cgtgccaggc  180
agcgactaca gcgaccagat cagagatctg ctgaaggccg ccttcgacct gagaggcctg  240
attgaaacac tggcccacgg cggcatccca ttctacgatc ctagcaccat catgccccgg  300
atcaagctgg tggccacaac catcgatacc atccacaccg ccaccacaac tctgcagaac  360
aaagtgcggc ctgctcacgt ggaactgggc ctcgaagtga caaaagccgt gctgctgaca  420
gccaatcctg ccagcacagc caaagagctg gacgctgaag gcgccgctct gaaggccaga  480
ctggaaaaag tgtctcagta ccccgatctg accoctaacg acgtggccac agtgtacgtg  540
cggaccaact tcagcaagac catctggcaa gtgcgggcca acagagatcg gtacatcctg  600
ggacacaaga gcgccgctgt gtacaagacc ctgaaccacg ccatcacaaa ggccgtgggc  660
gtcagactga accccaagac cacagtgggc aacatccagg ccgccagaac agaactgctg  720
gccgcctatc agaccgcctt caacagcccc gatgtgaaga aagccgctta a           771

SEQ ID NO: 88          moltype = RNA  length = 771
FEATURE                Location/Qualifiers
source                 1..771
                       mol_type = other RNA
                       organism = synthetic construct
SEQUENCE: 88
atgaaagcaa agctgctggt gctgctgtgc accttcaccg ctacctacgc cgtcgagcct  60
acaacaacaa tcagcgccac aagcacccac gagctgagcg cctctgatgc ccggaactct  120
atccagctgc tgaacgccca catcgccacc ctgcagagcg tgcagaagtc tgtgccaggc  180
agcgactaca gcgaccagat cagagatctg cttaaagccg ctttcgacct gagaggcctg  240
atcgagacac tggcccacgg cggaatcccc ttctacgacc ccagcaccat catgcctaga  300
atcaagctgg tcgccaccac catcgacacc atccacaccg ccacaaccac cctgcagaac  360
aaggtgcggc ctgcccatgt ggaactggga ctggaggtga caaaagccgt gctgctcacc  420
gccaacccag ctagcacagc caaggaactg gacgccgagg gcgccgccct gaaggccaga  480
ctggaaaagg tgtcccagta ccccgacctg accoctaacg acgtggccac cgtgtacgtg  540
cgcaccaact tcagcaagac catttggcag gtgcgggcca atagagatag atacatcctg  600
ggccacaagt ccgctgccgt gtacaagaca ctgaatcacg ccatcaccaa ggctgttggc  660
gtgcggctga accctaagac cactgtgggc aacatccagg ccgctagaac agagctgctg  720
gccgcctatc aaacagcttt taacagccct gatgtgaaga aagccgctta a           771

SEQ ID NO: 89          moltype = RNA  length = 771
FEATURE                Location/Qualifiers
source                 1..771
                       mol_type = other RNA
                       organism = synthetic construct
SEQUENCE: 89
atgaaggcca agctgctggt gctgctctgc accttcaccg ccacctacgc cgtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg acaccaaacg atgtggccac tgtgtacgtg  540
agaaccaact tctccaagac catctggcag gtcagagcca accgcgatcg ctacatcctg  600
ggccacaagt ccgccgccgt gtataagacc ctgaaccatg ccatcaccaa ggccgtgggc  660
gtcagactga accccaagac caccgtgggc aacatccagg ccgctagaac agagctgctg  720
gccgcctacc agaccgcctt caattcaccc gacgtgaaga aggccgctta a           771

SEQ ID NO: 90          moltype = RNA  length = 858
```

```
FEATURE                Location/Qualifiers
source                 1..858
                       mol_type = other RNA
                       organism = synthetic construct
SEQUENCE: 90
atgaaggcca agctgctggt gctgctgtgc accttcaccg ccacctatgc cgtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg acccccaacg acgtggccac tgtgtacgtg  540
cggaccaact tcagcaagac catttggcag gtcagggcca atagagacag atacatcctg  600
gggcacaaaa gcgccgccgt gtacaagacc ctgaaccacg ccatcaccaa ggccgtggga  660
gtgcggctga atccaaagac caccgtgggc aacattcagg ccgccagaac cgagctgctg  720
gccgcctacc agacagcttt caatagcccc gacgtgaaga aggccgcctc cggcagcatc  780
ctggccatct actccaccgt ggcctccagc ctggtgctgc tggtgagcct gggcgctatc  840
tccttcgggt ctgggtaa                                                 858

SEQ ID NO: 91          moltype = RNA  length = 861
FEATURE                Location/Qualifiers
source                 1..861
                       mol_type = other RNA
                       organism = synthetic construct
SEQUENCE: 91
atgaaagcca agctgctggt gctgctctgc acttttaccg ccacctacgc cgtggagccc  60
accacaacaa tcagcgccac atccacccac gaactgagcg cctccgacgc cagaaattcc  120
atccagctgc tgaacgccca catcgccacc ctgcagagcg tgcagaaaag cgtgcccggc  180
tctgattaca gcgaccagat ccgggacctg ctgaaggccg cctttgacct gagaggcctg  240
atcgagacac tggcccacgg aggcatccct ttctacgatc ctagcaccat catgcctcgg  300
atcaagctgg tggccacaac aatcgacacc atccacaccg ccaccaccac actgcagaac  360
aaagtgcggc ctgcccatgt ggaactgggc ctggaagtga ccaaggccgt gctgctgaca  420
gccaatcctg ctagcacagc caaggaactg gatgccgagg gagccgccct gaaggctaga  480
ctggagaagg tgagccagta ccccgacctg acccccaatg acgtggcaac cgtgtacgtg  540
agaaccaatt tcagcaagac catctggcag gtgcgggcca atcgggacag atacatcctg  600
ggccacaaga gcgccgccgt gtacaagacc ctgaatcacg ccatcaccaa ggccgtgggc  660
gtgcggctga atcctaagac caccgtgggc aatatccagg ccgcccggac agaactgctg  720
gccgcctacc agacagcctt taatagccct gatgtgaaga aggccgccag cgggagcatt  780
ctggccatct actctaccgt ggcctctagc ctggtgctgc tggtgtctct gggagccatt  840
agcttcggat ctggctgata a                                             861

SEQ ID NO: 92          moltype = RNA  length = 816
FEATURE                Location/Qualifiers
source                 1..816
                       mol_type = other RNA
                       organism = synthetic construct
SEQUENCE: 92
atgaacccca accagaaaat catcaccatc ggctctattt ctatcgccat cggaatcatc  60
tccctgatgc tgcagatcgg caacatcagc ggcagcgtgg aacctaccac aaccatcagc  120
gccaccagca cacacgagct gagcgcttct gatgcccgga acagcatcca actgctgaat  180
gcccacatcg ccacactcca gagcgtccag aagagcgtcc ccggcagcga ctacagcgat  240
cagatcagag acctgctgaa ggccgctttc gacctgagag gcctgatcga gacacttgcc  300
cacggcggca tcccccttcta cgaccccagc accatcatgc ctagaatcaa gctggtggcc  360
accaccatcg acaccatcca caccgccaca actaccctgc aaaacaaggt gcgcccagcc  420
catgtggaac tgggcctgga ggtgaccaag gcagttctgc tgacagctaa tcctgcctct  480
accgctaaag agctggacgc cgagggcgcc gccctgaaag ccagactgga aaaggtgtcc  540
cagtaccctg atctgacccc taacgacgtg gccacagtgt acgtgcggac caacttcagc  600
aagaccatct ggcaggtgcg ggccaacaga gatagataca tcctgggaca caagtccgcc  660
gccgtgtaca agaccctgaa ccacgccatt accaaagccg tgggcgtgcg gctgaaccct  720
aagacaaccg tgggaaatat ccaggccgct agaaccgagc tgctggccgc ttatcagaca  780
gcctttaaca gccctgacgt gaagaaggcc gcctga                             816

SEQ ID NO: 93          moltype = RNA  length = 816
FEATURE                Location/Qualifiers
source                 1..816
                       mol_type = other RNA
                       organism = synthetic construct
SEQUENCE: 93
atgaacccca accagaagat cattaccatc ggcagcatca gcatcgccat cggcatcatc  60
agtctgatgc tgcagattgg caacatctcc ggcagcgtcg agcctaccac aaccatcagc  120
gccacatcta cacacgagct gagcgccagc gacgccagaa acagcatcca gctgctgaac  180
gcccacatcg ccacactgca gagcgtgcag aaatctgtgc ccggctccga ttacagcgat  240
cagatcagag acctgcttaa agccgctttc gacctgagag gactgatcga gacactggcc  300
cacggaggca tccccttcta cgaccccagc accatcatgc ctagaatcaa gctggtggcc  360
accaccatcg acactatcca caccgctacc acaaccctgc aaaacaaggt gcggcctgcc  420
catgtggaac tgggcctgga agtgaccaaa gccgtgctgc tgaccgccaa ccctgcttct  480
accgccaagg aactggacgc cgagggcgcc gctctgaaag cgcggctgga gaaggtttct  540
```

```
cagtaccctg atctgacccc taacgacgtg gccacagtgt acgtgaggac cagcttcagc  600
aagaccatct ggcaggtgcg ggccaataga gatagataca tcctgggcca caagtccgcc  660
gccgtgtata agacactgaa ccacgccatc accaaggctg tcggagtgcg gctgaatcca  720
aagaccaccg tgggcaatat ccaagccgct agaaccgagc tgctcgccgc ctaccagaca  780
gcttttaaca gccctgacgt gaagaaggcc gcctga                            816

SEQ ID NO: 94          moltype = RNA  length = 858
FEATURE                Location/Qualifiers
source                 1..858
                       mol_type = other RNA
                       organism = synthetic construct
SEQUENCE: 94
atgaaggcca agctgctggt gctgctgtgc accttcaccg ccacatacgc cgtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg acccccaacg atgtggccac cgtgtatgtg  540
cggacctcct tctccaagac catctggcag gtcagagcca atcgggaccg gtacatcctg  600
ggccacaaga gcgccgctgt gtacaagacc ctgaaccatg ccatcaccaa ggcagtgggc  660
gtgcgcctga acccaaaaac caccgtgggc aacattcagg ccgccagaac cgagctgctg  720
gccgcctacc agaccgcttt caatagcccc gacgtgaaga aggccgccag cggctccatc  780
ctggccatct actctaccgt ggccagcagc ctggtgctgc tggtctccct gggagccatc  840
tccttcggct ccgggtaa                                                858

SEQ ID NO: 95          moltype = RNA  length = 771
FEATURE                Location/Qualifiers
source                 1..771
                       mol_type = other RNA
                       organism = synthetic construct
SEQUENCE: 95
atgaaggcca agctgctggt gctgctgtgc acctttacag ccacctacgc cgtggaaccc  60
accaccacaa tcagcgccac aagcacacac gagctgagcg cctccgatgc cagaaactct  120
atccagctgc tgaacgccca cattgccaca ctgcagagcg tgcagaaaag cgtgccaggc  180
agcgactaca gcgaccagat cagagatctg ctgaaggccg ccttcgacct gagaggcctg  240
attgaaacac tggcccacgg cggcatccca ttctacgatc ctagcaccat catgcccccgg  300
atcaagctgg tggccacaac catcgatacc atccacaccg ccaccacaac tctgcagaac  360
aaagtgcggc ctgctcacgt ggaactgggc ctcgaagtga caaaagccgt gctgctgaca  420
gccaatcctg ccagcacagc caaagagctg gacgctgaag gcgccgctct gaaggccaga  480
ctggaaaaag tgtctcagta ccccgatctg acccctaacg acgtggccac agtgtacgtg  540
cggaccaact tcagcaagac catctggcaa gtgcgggcca acagagatcg gtacatcctg  600
ggacacaaga gcgccgctgt gtacaagacc ctgaaccacg ccatcacaaa ggccgtgggc  660
gtcagactga accccaagac cacagtgggc aacatccagg ccgccagaac agaactgctg  720
gccgcctatc agaccgcctt caacagcccc gatgtgaaga aagccgctta a           771

SEQ ID NO: 96          moltype = RNA  length = 771
FEATURE                Location/Qualifiers
source                 1..771
                       mol_type = other RNA
                       organism = synthetic construct
SEQUENCE: 96
atgaaagcaa agctgctggt gctgctgtgc accttcaccg ctacctacgc cgtcgagcct  60
acaacaacaa tcagcgccac aagcacccac gagctgagcg cctctgatgc ccggaactct  120
atccagctgc tgaacgccca catcgccacc ctgcagagcg tgcagaagtc tgtgccaggc  180
agcgactaca gcgaccagat cagagatctg cttaaagccg ctttcgacct gagaggcctg  240
atcgagacac tggcccacgg cggaatcccc ttctacgacc ccagcaccat catgcctaga  300
atcaagctgg tcgccaccac catcgacacc atccacaccg ccacaaccac cctgcagaac  360
aaggtgcggc ctgcccatgt ggaactggga ctggaggtga caaaagccgt gctgctcacc  420
gccaacccag ctagcacagc caaggaactg gacgccgagg gcgccgccct gaaggccaga  480
ctggaaaagg tgtcccagta ccccgacctg acccctaacg acgtggccac cgtgtacgtg  540
cgcaccaact tcagcaagac catttggcag gtgcgggcca atagagatag atacatcctg  600
ggccacaagt ccgctgccgt gtacaagaca ctgaatcacg ccatcaccaa ggctgttggc  660
gtgcggctga accctaagac cactgtgggc aacatccagg ccgctagaac agagctgctg  720
gccgcctatc aaacagcttt taacagccct gatgtgaaga aagccgctta a           771

SEQ ID NO: 97          moltype = RNA  length = 771
FEATURE                Location/Qualifiers
source                 1..771
                       mol_type = other RNA
                       organism = synthetic construct
SEQUENCE: 97
atgaaggcca agctgctggt gctgctgtgc accttcaccg ccacctacgc cgtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
```

```
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg accccaaatg acgtggccac cgtgtacgtg  540
cggacctcct tctccaagac catctggcaa gtgcgggcta acagagacag gtacattctg  600
ggccacaagt ccgccgccgt gtacaaaacc ctgaatcacg ccatcaccaa ggccgtgggc  660
gtgagactga accccaagac caccgtgggc aacattcagg ctgccaggac cgagctgctg  720
gccgcttatc agaccgcctt caacagcccc gacgtgaaga aagccgccta a           771

SEQ ID NO: 98          moltype = RNA  length = 771
FEATURE                Location/Qualifiers
source                 1..771
                       mol_type = other RNA
                       organism = synthetic construct
SEQUENCE: 98
atgaaggcaa agctgctggt gctgctgtgc accttcaccg ccacatacgc agtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccggcggg acacctaacg gcgtgggagg cgtgtatgtg  540
aggacaaact tcagcaagac aatctggcag gtcagggcca accgcgatag atacatcctg  600
ggccacaaga gcgccgccgt ctacaagaca ctgaaccacg ctatcacaaa agccgtgggg  660
gtgaggctga accccaagac caccgtgggg aacatccagg ccgctagaac tgagctgctg  720
gccgcctacc agaccgcttt caatagcccc gacgtgaaga aggccgccta a           771

SEQ ID NO: 99          moltype = RNA  length = 771
FEATURE                Location/Qualifiers
source                 1..771
                       mol_type = other RNA
                       organism = synthetic construct
SEQUENCE: 99
atgaaagcca agctgctggt gctgctgtgc accttcaccg ccacatacgc cgtggaacct  60
acaaccacaa tcagcgccac atctacacac gagctgagcg ccagcgacgc ccggaacagc  120
atccagctgc tgaacgccca catcgccacc ctccagagcg tgcagaaatc cgtgcctgga  180
tctgattaca gcgaccagat cagagatctg ctgaaggccg cttttgacct gagaggcctg  240
atcgagacac tggcccatgg cggcatcccc ttctacgacc ctagcacaat tatgcctaga  300
atcaagctgg tcgccaccac catcgacacc atccacaccg ccaccacaac cctgcagaac  360
aaggtcagac cagcccacgt ggaactcggc ctggaggtga ccaaggctgt gctgcttaca  420
gctaatcctg ctagcaccgc taaagagctg gacgccgagg gcgccgccct gaaggcccgc  480
ctggaaaaag tgtcccagta ccccggcgga accccctaacg gcgttggcgg agtgtacgtg  540
cggaccagct tcagcaagac catctggcag gtgcgggcta atagagatag atacatcctg  600
ggccacaagt ccgccgcggt gtataagaca ctgaaccacg ccatcaccaa ggctgtgggc  660
gtgcggctga accccaagac cacagtgggc aacatccaag ccgccagaac cgagctgctg  720
gccgcctacc agaccgcctt caactctcca gacgtgaaga aggccgcctg a           771

SEQ ID NO: 100         moltype = RNA  length = 771
FEATURE                Location/Qualifiers
source                 1..771
                       mol_type = other RNA
                       organism = synthetic construct
SEQUENCE: 100
atgaaggcca agctgctggt gctgctgtgc accttcacag ccacctacgc cgtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg acccccaacg atgtggctac cgtctatgtg  540
cggactaatt tcagtaagac catctggcag gtcgccgcca acgccgatag atatatcgcc  600
ggccacaaat ccgccgccgt cgcaaagacc cttgctcacg ctattgccaa ggccgctggc  660
gtgagagcta acccaaagac caccgtcggc aacatccagg ccgccaggac agagctgctt  720
gccgcctatc agactgcctt caacagccct gacgtgaaga aggcagccta a           771

SEQ ID NO: 101         moltype = RNA  length = 771
FEATURE                Location/Qualifiers
source                 1..771
                       mol_type = other RNA
                       organism = synthetic construct
SEQUENCE: 101
atgaaggcca agctgctggt gctgctgtgc actttcaccg caacatacgc cgtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
```

```
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg acccccaacg acgtggccac cgtgtatgtg  540
agaaccagct tcagcaaaac aatctggcag gtcgccgcca acgccgacag atacatcgca  600
ggccacaaga gtgctgccgt ggcgaaaacc ctggcacacg caattgccaa ggccgcaggc  660
gtgcgggcca atcctaagac cactgtgggc aatatccagg ccgccaggac tgaactgctg  720
gctgcctacc agacagcctt caacagccca gacgtgaaga aggccgccta a           771

SEQ ID NO: 102         moltype = RNA  length = 1029
FEATURE                Location/Qualifiers
source                 1..1029
                       mol_type = other RNA
                       organism = synthetic construct
SEQUENCE: 102
atgaaggcaa agctgctggt gctgctgtgc acatttactg ccacttacgc aagctccaac  60
cggccaagaa gcgtcgccca ggcagccatc gcaacagacg gcaaggggat catcaataag  120
gactgcagag acgccgtgat caatgatgcc aaactgaggg ccgccatcgc cggagctctg  180
gtgaaggccg ggttttctag cgccgacgct gtggcactgg cacctagaat cgctcgggaa  240
atggccaagg agggggttct gctgattaac caccacaagc tgaaagcact gatcggagcc  300
caggtgggac tgctgacaga tgccaagatc cagagagccg cagctgcagt ggacctgggc  360
atcaaagcca cactggccgc aaccattatc cccaatgccc tgcactccgc agccttcaag  420
gatgctgtgg tggccaacct ggtggcagct ggggttgata agaagctggc caaggccacc  480
gcagttgcca ttgctgccac agccctgaat cctgcactgg gacccatcgc aaagactgag  540
gcaatcaagg ccgagattgg cgcacaggcc gctctgctgg tgagcagagg agtgcacctg  600
aagaaggccg ccattgagca catcattggg agatcctttg acgccgcagt ggccaccgcc  660
attgttagct cccccatcct gaatgcccgg atcgtgaccc acctcgtgcg ggcaggaatt  720
gacaagagcc tcgcagtgca gattgcccca cggattatag atagactggc caaggagccg  780
ctgctggccc tgaacactgc aaagctgatg aaaaacatca caaggcagat cgtcgacgtg  840
attaccgccg acaaggcaat taagaccgcc gagcagctgg agaaggagct gcctgccctg  900
gacgacctgg tgaagaaggc ctgctcctcc cccaagccta ctccaaccat tctggcaatc  960
tatagcaccg tggctagcag cctggtgctg ctggtgtctc tgggagccat cagcttcggc  1020
tctggctaa                                                        1029

SEQ ID NO: 103         moltype = RNA  length = 930
FEATURE                Location/Qualifiers
source                 1..930
                       mol_type = other RNA
                       organism = synthetic construct
SEQUENCE: 103
atgaaggcca agctgctggt gctgctgtgc acattcacag caacctatgc atccagcaac  60
cggcctagaa gcgtggccca ggctgccatc gccacagatg gcaagggcat catcaacaag  120
gactgtagag acgccgtgat caatgacgcc aagctgagag ccgccatcgc cggagccctg  180
gtgaaggccg gctttagcag cgccgacgcc gtggccctgg cccctcggat cgcccgggag  240
atggccaagg agggagtgct gctgatcaat catcacaagc tgaaggccct gattggcgcc  300
caggtgggac tgctgaccga cgccaagatt cagagagccg ccgctgccgt ggatctgggc  360
atcaaggcca ccctggccgc caccatcatc cctaacgccc tgcactccgc cgcttttaag  420
gatgccgtgg tggctaacct ggtggctgcc ggcgtggaca agaagctggc caaagctacc  480
gccgttgcca tcgccgctac agctctgaat cctgccctgg ggcccatcgc caagacagag  540
gccattaagg ccgaaattgg agcccaggcc gcactgctgg tgtccagagg cgtgcacctg  600
aagaaggccg ccatcgagca catcattggc agatccttcg atgctgccgt ggctaccgcc  660
atcgtgagca gccctatcct gaatgccaga atcgtgaccc acctggtgag agcaggcatc  720
gacaagagcc tggccgtgca gatcgcccct cggattatcg accggctggc caaggagccc  780
ctgctggccc tgaacaccgc caagctgatg aagaacatca ccagacagat cgtggatgtg  840
atcaccgccg ataaggccat caaaacagcc gagcagctgg agaaggagct gcctgccctg  900
gatgacctgg tgaagaaggc ctgtagctaa                                 930

SEQ ID NO: 104         moltype = RNA  length = 1017
FEATURE                Location/Qualifiers
source                 1..1017
                       mol_type = other RNA
                       organism = synthetic construct
SEQUENCE: 104
atgaaggcaa agctgctggt gctgctgtgc acatttactg ccacttacgc aagctccaac  60
cggccaagaa gcgtcgccca ggcagccatc gcaacagacg gcaaggggat catcaataag  120
gactgcagag acgccgtgat caatgatgcc aaactgaggg ccgccatcgc cggagctctg  180
gtgaaggccg ggttttctag cgccgacgct gtggcactgg cacctagaat cgctcgggaa  240
atggccaagg agggggttct gctgattaac caccacaagc tgaaagcact gatcggagcc  300
caggtgggac tgctgacaga tgccaagatc cagagagccg cagctgcagt ggacctgggc  360
atcaaagcca cactggccgc aaccattatc cccaatgccc tgcactccgc agccttcaag  420
gatgctgtgg tggccaacct ggtggcagct ggggttgata agaagctggc caaggccacc  480
gcagttgcca ttgctgccac agccctgaat cctgcactgg gacccatcgc aaagactgag  540
gcaatcaagg ccgagattgg cgcacaggcc gctctgctgg tgagcagagg agtgcacctg  600
aagaaggccg ccattgagca catcattggg agatcctttg acgccgcagt ggccaccgcc  660
attgttagct cccccatcct gaatgcccgg atcgtgaccc acctcgtgcg ggcaggaatt  720
gacaagagcc tcgcagtgca gattgcccca cggattatag atagactggc caaggagccg  780
ctgctggccc tgaacactgc aaagctgatg aaaaacatca caaggcagat cgtcgacgtg  840
attaccgccg acaaggcaat taagaccgcc gagcagctgg agaaggagct gcctgccctg  900
```

-continued

```
gacgacctgg tgaagaaggc ctgctccagc ggcagcattc tggcaatcta tagcaccgtg  960
gctagcagcc tggtgctgct ggtgtctctg ggagccatca gcttcggctc tggctaa     1017

SEQ ID NO: 105          moltype = RNA  length = 1029
FEATURE                 Location/Qualifiers
source                  1..1029
                        mol_type = other RNA
                        organism = synthetic construct
SEQUENCE: 105
atgaaggcaa agctgctggt gctgctgtgc acatttactg ccacttacgc agccagcaat  60
ggcaacagct ccatcaccca gagcgccgcc ttcagcccta gagctaccac aaagatcagc  120
gaagattgca gaaaggccat tatcaatgat ctgaaactga gaggcgccat cgtgggagct  180
ctggtgaagg ccggcctgtc tgccgccgac gccgccgccc tggcccctag aattgccgcc  240
gaaatggccg ccgaaggcac cctgaccatc aatcaccacc ggctgaaggt gctggtcgcc  300
tctcaactgg gcctggtggc cgatgctgca gtgcaacatg ccgcagccgc catcgacctg  360
agcttcaagg ccatcctggg cgccagcatc atccctaatg ccctgggctc cgccgctttc  420
aagaatgccg tgatcgctaa tctcgtggcc gccggcattg acaagcacct ggccagagcc  480
acagcagtgg ccatcgttgc cacagcactg aatcccgctc tgggtcctat cgccaagttc  540
gagctgatca aggccgagat cgccgcccag gccgccctgc tgatcagaag aggcgtgcat  600
ctgcagaaag ctgccatcga gcacgtgatc ggacgggcat tcgacgctgc cgtggccaca  660
gccatcatca gcagccctat cctgtctgcc agaatcgtga cacacctggt gagagccggc  720
attgacaaat ctatcgccat cagcctggcc cctcacatcg tgaagagact ggccaaggag  780
cccctgctgg ccttcaatac agccaagctg gtgaaggata tcgccagaca gattgtggac  840
atccggaata cccaggaggc catcgccgtg tacaagcagc tgaaggccga gctgcctacc  900
ctggatggcc tggtgcagaa ggcttgcacc ccagaaccta cacccaccat tctggcaatc  960
tatagcaccg tggctagcag cctggtgctg ctggtgtctc tgggagccat cagcttcggc  1020
tctggctaa                                                          1029

SEQ ID NO: 106          moltype = RNA  length = 1020
FEATURE                 Location/Qualifiers
source                  1..1020
                        mol_type = other RNA
                        organism = synthetic construct
SEQUENCE: 106
atgaaggcaa agctgctggt gctgctgtgc acatttactg ccacttacgc agccagcaat  60
ggcaacagct ccatcaccca gagcgccgcc ttcagcccta gagctaccac aaagatcagc  120
gaagattgca gaaaggccat tatcaatgat ctgaaactga gaggcgccat cgtgggagct  180
ctggtgaagg ccggcctgtc tgccgccgac gccgccgccc tggcccctag aattgccgcc  240
gaaatggccg ccgaaggcac cctgaccatc aatcaccacc ggctgaaggt gctggtcgcc  300
tctcaactgg gcctggtggc cgatgctgca gtgcaacatg ccgcagccgc catcgacctg  360
agcttcaagg ccatcctggg cgccagcatc atccctaatg ccctgggctc cgccgctttc  420
aagaatgccg tgatcgctaa tctcgtggcc gccggcattg acaagcacct ggccagagcc  480
acagcagtgg ccatcgttgc cacagcactg aatcccgctc tgggtcctat cgccaagttc  540
gagctgatca aggccgagat cgccgcccag gccgccctgc tgatcagaag aggcgtgcat  600
ctgcagaaag ctgccatcga gcacgtgatc ggacgggcat tcgacgctgc cgtggccaca  660
gccatcatca gcagccctat cctgtctgcc agaatcgtga cacacctggt gagagccggc  720
attgacaaat ctatcgccat cagcctggcc cctcacatcg tgaagagact ggccaaggag  780
cccctgctgg ccttcaatac agccaagctg gtgaaggata tcgccagaca gattgtggac  840
atccggaata cccaggaggc catcgccgtg tacaagcagc tgaaggccga gctgcctacc  900
ctggatggcc tggtgcagaa ggcttgcacc agcggcagca ttctggcaat ctatagcacc  960
gtggctagca gcctggtgct gctggtgtct ctgggagcca tcagcttcgg ctctggctaa  1020

SEQ ID NO: 107          moltype = RNA  length = 933
FEATURE                 Location/Qualifiers
source                  1..933
                        mol_type = other RNA
                        organism = synthetic construct
SEQUENCE: 107
atgaaggcca agctgctggt gctgctgtgc acattcacag caacctatgc agctagcaat  60
ggaaactcct ctattacaca gtctgccgcc ttcagcccaa gagctaccac aaagatcagc  120
gaggattgta gaaaggccat cattaacgat ctgaagctgc ggggcgccat cgtgggcgct  180
ctcgtgaaag ccggactgtc tgcagcagac gctgcagcac tggctccaag gatcgccgct  240
gagatggcag cagaggggac actgactatt aaccaccata ggctgaaagt gctggtcgct  300
tcccagctgg gcctggttgc agatgcagcc gtgcagcatg ctgccgctgc aattgacctg  360
agcttcaaag ctatcctggg cgcctctatc attccaaatg ctctcgggag cgcagccttc  420
aaaaacgccg tgattgccaa cctggtggct gcaggaattg acaagcacct ggccagagcc  480
actgctgtgg caattgtggc cactgctctg aatccagcac tgggacccat cgcaaagttt  540
gagctgatta aggcagaaat tgccgctcaa gcagccctgc tgattagacg gggagtgcac  600
ctgcagaagg ccgcaattga acacgtgatc ggccgggcat ttgacgccgc tgttgctact  660
gccatcatca gcagccctat tctgtccgcc aggattgtca cccacctggt cagggcaggc  720
attgataaga gcattgctat cagcctggcc ccacacatcg ttaagcggct ggccaaagaa  780
cccctgctgg cttttaatac tgctaagctg gtgaaagaca ttgcccgcca gatcgtggac  840
attaggaata ctcaggaggc catcgccgtg tataaacagc tcaaggcaga actgcctacc  900
ctggacggcc tggtgcagaa agcctgtaca taa                               933

SEQ ID NO: 108          moltype = RNA  length = 933
FEATURE                 Location/Qualifiers
source                  1..933
                        mol_type = other RNA
```

-continued

```
                          organism = synthetic construct
SEQUENCE: 108
atgaaggcca agctgctggt gctgctgtgc acattcacag caacctatgc agctagcaat  60
ggaaactcct ctattacaca gtctgccgcc ttcagcccaa gagctaccac aaagatcagc  120
gaggattgta gaaaggccat cattaacgat ctgaagctgc ggggcgccat cgtgggcgct  180
ctcgtgaaag ccggactgtc tgtggcagac gctgcagcac tggctccaag gatcgccgct  240
gagatggcag cagaggggac actgactatt aaccaccata ggctgaaagt gctggtcgct  300
tcccagctgg gcctggttgc agatgcagcc gtgcagcatg ctgccgctgc aattgacctg  360
agcttcaaag ctatcctggg cgcctctatc attccaaatg ctctcgggag cgcagccttc  420
aaaaacgccg tgattgccaa cctggtggct gcaggaattg acaagcacct ggccagagcc  480
actgctgtgg caattgtggc cactgctctg aatccagcac tgggacccat cgcaaagttt  540
gagctgatta aggcagaaat tgccgctcaa gcagccctgc tgattagacg gggagtgcac  600
ctgcagaagg ccgcaattga acacgtgatc ggccgggcat ttgacgccgc tgttgctact  660
gccatcatca gcagccctat tctgtccgcc aggattgtca cccacctggt cagggcaggc  720
attgataaga gcattgctat cagcctggcc ccacacatcg ttaagcggct ggccaaagaa  780
cccctgctgg cttttaatac tgctaagctg gtgaaagaca ttgcccgcca gatcgtggac  840
attaggaata ctcaggaggc catcgccgtg tataaacagc tcaaggcaga actgcctacc  900
ctggacggcc tggtgcagaa agcctgtaca taa                              933

SEQ ID NO: 109            moltype = RNA  length = 1029
FEATURE                   Location/Qualifiers
source                    1..1029
                          mol_type = other RNA
                          organism = synthetic construct
SEQUENCE: 109
atgaaggcaa agctgctggt gctgctgtgc acatttactg ccacttacgc agccagcaat  60
ggcaacagct ccatcaccca gagcgccgcc ttcagcccta gagctaccac aaagatcagc  120
gaagattgca gaaaggccat tatcaatgat ctgaaactga gaggcgccat cgtgggagct  180
ctggtgaagg ccggcctgtc tgtggccgac gccgccgccc tggcccctag aattgccgcc  240
gaaatggccg ccgaaggcac cctgaccatc aatcaccacc ggctgaaggt gctggtcgcc  300
tctcaactgg gcctggtggc cgatgctgca gtgcaacatg ccgcagccgc catcgacctg  360
agcttcaagg ccatcctggg cgccagcatc atccctaatg ccctgggctc cgccgctttc  420
aagaatgccg tgatcgctaa tctcgtggcc gccggcattg acaagcacct ggccagagcc  480
acagcagtgg ccatcgttgc cacagcactg aatcccgctc tgggtcctat cgccaagttc  540
gagctgatca aggccgagat cgccgcccag gccgccctgc tgatcagaag aggcgtgcat  600
ctgcagaaag ctgccatcga gcacgtgatc ggacgggcat tcgacgctgc cgtggccaca  660
gccatcatca gcagccctat cctgtctgcc agaatcgtga cacacctggt gagagccggc  720
attgacaaat ctatcgccat cagcctggcc cctcacatcg tgaagagact ggccaaggag  780
cccctgctgg ccttcaatac agccaagctg gtgaaggata tcgccagaca gattgtggac  840
atccggaata cccaggaggc catcgccgtg tacaagcagc tgaaggccga gctgcctacc  900
ctggatggcc tggtgcagaa ggcttgcacc ccagaaccta cacccaccat tctggcaatc  960
tatagcaccg tggctagcag cctggtgctg ctggtgtctc tgggagccat cagcttcggc  1020
tctggctaa                                                         1029

SEQ ID NO: 110            moltype = RNA  length = 1020
FEATURE                   Location/Qualifiers
source                    1..1020
                          mol_type = other RNA
                          organism = synthetic construct
SEQUENCE: 110
atgaaggcca agctgctggt gctgctgtgc acattcacag caacctatgc agctagcaat  60
ggaaactcct ctattacaca gtctgccgcc ttcagcccaa gagctaccac aaagatcagc  120
gaggattgta gaaaggccat cattaacgat ctgaagctgc ggggcgccat cgtgggcgct  180
ctcgtgaaag ccggactgtc tgtggcagac gctgcagcac tggctccaag gatcgccgct  240
gagatggcag cagaggggac actgactatt aaccaccata ggctgaaagt gctggtcgct  300
tcccagctgg gcctggttgc agatgcagcc gtgcagcatg ctgccgctgc aattgacctg  360
agcttcaaag ctatcctggg cgcctctatc attccaaatg ctctcgggag cgcagccttc  420
aaaaacgccg tgattgccaa cctggtggct gcaggaattg acaagcacct ggccagagcc  480
actgctgtgg caattgtggc cactgctctg aatccagcac tgggacccat cgcaaagttt  540
gagctgatta aggcagaaat tgccgctcaa gcagccctgc tgattagacg gggagtgcac  600
ctgcagaagg ccgcaattga acacgtgatc ggccgggcat ttgacgccgc tgttgctact  660
gccatcatca gcagccctat tctgtccgcc aggattgtca cccacctggt cagggcaggc  720
attgataaga gcattgctat cagcctggcc ccacacatcg ttaagcggct ggccaaagaa  780
cccctgctgg cttttaatac tgctaagctg gtgaaagaca ttgcccgcca gatcgtggac  840
attaggaata ctcaggaggc catcgccgtg tataaacagc tcaaggcaga actgcctacc  900
ctggacggcc tggtgcagaa agcctgtaca agcggctcta ttctggccat ctacagcaca  960
gtggccagct ctctggtgct gctggttagc ctgggcgcca tcagcttcgg cagcggctaa  1020

SEQ ID NO: 111            moltype = RNA  length = 1020
FEATURE                   Location/Qualifiers
source                    1..1020
                          mol_type = other RNA
                          organism = synthetic construct
SEQUENCE: 111
atgaaggcca agctgctggt gctgctgtgc acattcacag caacctatgc agctagcaat  60
ggacagtcct ctattacaca gtctgccgcc ttcagcccaa gagctaccac aaagatcagc  120
gaggattgta gaaaggccat cattaacgat ctgaagctgc ggggcgccat cgtgggcgct  180
ctcgtgaaag ccggactgtc tgcagcagac gctgcagcac tggctccaag gatcgccgct  240
gagatggcag cagaggggac actgactatt aaccaccata ggctgaaagt gctggtcgct  300
```

```
tcccagctgg gcctggttgc agatgcagcc gtgcagcatg ctgccgctgc aattgacctg  360
agcttcaaag ctatcctggg cgcctctatc attccaaatg ctctcgggag cgcagccttc  420
aaaaacgccg tgattgccaa cctggtggct gcaggaattg acaagcacct ggccagagcc  480
actgctgtgg caattgtggc cactgctctg aatccagcac tgggacccat cgcaaagttt  540
gagctgatta aggcagaaat tgccgctcaa gcagccctgc tgattagacg gggagtgcac  600
ctgcagaagg ccgcaattga acacgtgatc ggccgggcat ttgacgccgc tgttgctact  660
gccatcatca gcagccctat tctgtccgcc aggattgtca cccacctggt cagggcaggc  720
attgataaga gcattgctat cagcctggcc ccacacatcg ttaagcggct ggccaaagaa  780
cccctgctgg cttttaatac tgctaagctg gtgaaagaca ttgcccgcca gatcgtggac  840
attaggaata ctcaggaggc catcgccgtg tataaacagc tcaaggcaga actgcctacc  900
ctggacggcc tggtgcagaa agcctgtaca agcggctcta ttctggccat ctacagcaca  960
gtggccagct ctctggtgct gctggttagc ctgggcgcca tcagcttcgg cagcggctaa  1020

SEQ ID NO: 112          moltype = RNA  length = 1029
FEATURE                 Location/Qualifiers
source                  1..1029
                        mol_type = other RNA
                        organism = synthetic construct
SEQUENCE: 112
atgaaggcca agctgctggt gctgctgtgc acattcacag caacctatgc agctagcaat  60
ggacagtcct ctattacaca gtctgccgcc ttcagcccaa gagctaccac aaagatcagc  120
gaggattgta gaaaggccat cattaacgat ctgaagctgc ggggcgccat cgtgggcgct  180
ctcgtgaaag ccggactgtc tgcagcagac gctgcagcac tggctccaag gatcgccgct  240
gagatggcag cagaggggac actgactatt aaccaccata ggctgaaagt gctggtcgct  300
tcccagctgg gcctggttgc agatgcagcc gtgcagcatg ctgccgctgc aattgacctg  360
agcttcaaag ctatcctggg cgcctctatc attccaaatg ctctcgggag cgcagccttc  420
aaaaacgccg tgattgccaa cctggtggct gcaggaattg acaagcacct ggccagagcc  480
actgctgtgg caattgtggc cactgctctg aatccagcac tgggacccat cgcaaagttt  540
gagctgatta aggcagaaat tgccgctcaa gcagccctgc tgattagacg gggagtgcac  600
ctgcagaagg ccgcaattga acacgtgatc ggccgggcat ttgacgccgc tgttgctact  660
gccatcatca gcagccctat tctgtccgcc aggattgtca cccacctggt cagggcaggc  720
attgataaga gcattgctat cagcctggcc ccacacatcg ttaagcggct ggccaaagaa  780
cccctgctgg cttttaatac tgctaagctg gtgaaagaca ttgcccgcca gatcgtggac  840
attaggaata ctcaggaggc catcgccgtg tataaacagc tcaaggcaga actgcctacc  900
ctggacggcc tggtgcagaa agcctgtaca cccgagccta cacctaccat tctggccatc  960
tacagcacag tggccagctc tctggtgctg ctggttagcc tgggcgccat cagcttcggc  1020
agcggctaa                                                         1029

SEQ ID NO: 113          moltype = RNA  length = 969
FEATURE                 Location/Qualifiers
source                  1..969
                        mol_type = other RNA
                        organism = synthetic construct
SEQUENCE: 113
atgaaggcca agctgctggt gctgctgtgc acattcacag caacctatgc atcatccaac  60
aggcctcgct ccgtggccca ggctgctatt gctaccgacg gcaagggaat catcgataaa  120
gactccaggg atgccgtgat caacgatgcc aagctccggg ccgcaattgc cggagccctg  180
gtgaaagccg ggttcagctc cgccgatgct gtggctctgg ctccaaggat tgctaaggag  240
atggccaaag agggggtgct gctgattaac caccacaagc tgaaggcact gatcggagca  300
cagctgggac tgctgactga cgccaaaatc cagcgcgccg ctgcagcagt cgacctgggc  360
atcaaggcca cactggctgc taccatcatt cctaacgctc tgggcagcgc agcctttaag  420
aatgccgtta tcgccaatct cgtggctgct ggaattgata agcacctggc cagagccaca  480
gctgtggcca tcgtggccac tgccctgaac ccagcattgg gccctatcgc taagtttgag  540
ctgattaagg ccgagatcgc cgctcaggct gccctgctga ttcgcagggg agtgcacctg  600
cagaaggctg ccatcgagca cgtcatcggc agagcattcg acgccgctgt cgccactgct  660
atcatctcta gcccaatcct gagcgccagg atcgtcactc acctggtgag agctgggatt  720
gacaaatcca tcgctatcag cctggcccct cacatcgtga agaggctggc taaggaacca  780
ctgctggctt ttaacactgc taagctgatg aagaatatta caagacagat cgtggacgtc  840
atcaccgccg acaaagccat caagacagcc gagcagctcg agaaggagct gcctgccctg  900
gatgacctgg tgaagaaggc atcctccccc cctaagccaa cccctacccc aacccctaca  960
cctacttaa                                                         969

SEQ ID NO: 114          moltype = RNA  length = 969
FEATURE                 Location/Qualifiers
source                  1..969
                        mol_type = other RNA
                        organism = synthetic construct
SEQUENCE: 114
atgaaggcca agctgctggt gctgctgtgc acattcacag caacctatgc atcatccaac  60
aggcctcgct ccgtggccca ggctgctatt gctaccgacg gcaagggaat catcgataaa  120
gactccaggg atgccgtgat caacgatgcc aagctccggg ccgcaattgc cggagccctg  180
gtgaaagccg ggttcagctc cgccgatgct gtggctctgg ctccaaggat tgctaaggag  240
atggccaaag agggggtgct gctgattaac caccacaagc tgaaggcact gatcggagca  300
cagctgggac tgctgactga cgccaaaatc cagcgcgccg ctgcagcagt cgacctgggc  360
atcaaggcca cactggctgc taccatcatt cctaacgctc tgggcagcgc agcctttaag  420
aatgccgtta tcgccaatct cgtggctgct ggaattgata agcacctggc cagagccaca  480
gctgtggcca tcgtggccac tgccctgaac ccagcattgg gccctatcgc taagtttgag  540
ctgattaagg ccgagatcgc cgctcaggct gccctgctga ttcgcagggg agtgcacctg  600
cagaaggctg ccatcgagca cgtcatcggc agagcattcg acgccgctgt cgccactgct  660
```

```
atcatctcta gcccaatcct gagcgccagg atcgtcactc acctggtgag agctgggatt  720
gacaaatcca tcgctatcag cctggcccct cacatcgtga agaggctggc taaggaacca  780
ctgctggctt ttaacactgc taagctgatg aagcagatta caagacagat cgtggacgtc  840
atcaccgccg acaaagccat caagacagcc gagcagctcg agaaggagct gcctgccctg  900
gatgacctgg tgaagaaggc atcctccccc cctaagccaa cccctacccc aacccctaca  960
cctacttaa                                                          969

SEQ ID NO: 115         moltype = RNA  length = 1251
FEATURE                Location/Qualifiers
source                 1..1251
                       mol_type = other RNA
                       organism = synthetic construct
SEQUENCE: 115
atgaaggcaa agctgctggt gctgctgtgc acatttactg ccacttacgc agcaggccct  60
accgtcacag tgatccctgt gggcagagaa ggtggcgaca tcaccatcag cggcaagggc  120
ttcagcacca caggctttgg cgtgtacgtg gccgtggcac ctgctagcgt gcccgaattc  180
tacggcaata gcgacaagtt ctacggctac gaccccagca aggacaccac cgagagccct  240
agcaccatct gggtgtacac ccctagccag aaggccatcg gctctcggtt cgcccagggc  300
agacccatga acaatgacgg cagcttcaca atcaccatga aggccccccc tttcgagcag  360
ggcaaagact tcgtggtgct gaccacaaag gcccatggcg tgggcaaaac cgatcacagc  420
gacgacacac ggacacctgt cacctacaga gaggctaccc ctgcccctac aggccctaag  480
acacccatcg cccctagcaa gcagcctagc aagcaggccg cccctagcaa gcaggtgaag  540
ccttctaagc aggccggccc caacaagcag tccaccacac ctcagcagaa gacagccgag  600
cacagaagcc agacccctgc cgcccaccgg accatgacaa agcaggtgag caccatcggc  660
gccagcaagg tgacaagcgg ctctctgacc tggggcatca gaacctcttt tacctcctac  720
ctgagaggcc ctatcgccaa cggctcttgg aagctgagcg gaggcgccaa ttggaatggc  780
tccgccttca ccttccctct gaccagcggc agcttcgacc cagccaccaa gtccggaagc  840
ctgaagtaca gcggcagcgt gcacatgaca ggccaccacg gcatcctgga catgaccctg  900
gccgagccaa gcctgcagat caagggaagc accggccacc tgtatctgga cgtgaaaagc  960
agcagcatgg acggcaagaa gaccaattac ggcagagtgg acttcgccac cttcggagtg  1020
agcgtgtctg gcaacgccgc catcaagggc agccctgtga agctgaccgc cacaggcgct  1080
aaggcttttg ccggcttcta cagagccggc gagcctatga accctctgag caccaatctg  1140
accctgagcg ccgagaaggt gtcccacaac gtgaccgtgg acgcagtgac aggcaaggtg  1200
atcggcgacg actctggcaa gggagccggc cggggcctgc ccgtgacata a           1251

SEQ ID NO: 116         moltype =   length =
SEQUENCE: 116
000

SEQ ID NO: 117         moltype = RNA  length = 1251
FEATURE                Location/Qualifiers
source                 1..1251
                       mol_type = other RNA
                       organism = synthetic construct
SEQUENCE: 117
atgaaggcca agctgctggt gctgctgtgc acattcacag caacctatgc agctgggcca  60
acagtgacag tgatccccgt gggacgcgag ggcggagaca ttaccatctc cgggaagggc  120
tttagcacaa cagggttcgg tgtgtatgtg gctgtggccc cagcaagcgt gccagagttc  180
tacgggaact ccgataaatt ttatgggtat gaccccagta aagacacaac cgagagcccc  240
agcacaattt gggtttacac cccctctcag aaagctattg gctcccggtt cgcccagggc  300
agaccaatga ataatgacgg gagctttacc atcactatga aggccccccc attcgagcag  360
ggaaaggact ttgtggtcct gactaccaag gctcacggag tgggcaaaac cgaccactct  420
gacgacactc ggacaccggt gacataccgg gaggctactc ccgctccaac aggccctaaa  480
actccaatcg cccccagcaa gcagccttca aagcaggctg cccccagcaa gcaggtgaag  540
cctagcaagc aggctggccc caacaagcag agcactactc ctcagcagaa gaccgcagag  600
cacagatctc agaccccagc agctcatcgc actatgacta agcaggtgtg taccatcgga  660
gcctcaaagg tgaccagcgg atccctgaca tggggaatcc ggactagctt tacttcctac  720
ctgcgcgggc ccatcgcaaa cggcagctgg aagctgtctg gggggcgccaa ttggaacggc  780
agcgccttca cattccccact gacttctgga tccttcgacc ccgccaccaa atccggctca  840
ctgaagtaca gcgggagcgt gcacatgact ggacaccatg gaattctgga catgacactc  900
gctgaaccct ctctgcagat caagggctct actgggcacc tgtatctgga tgtgaagtcc  960
tcttctatgg acggcaagaa gacaaactat gggagagtgg attttgccac cttcggagtg  1020
agcgtgagcg gaaatgctgc aatcaaaggg tcccccgtga aactgaccgc taccggagca  1080
aaagcctttg ccggctttta cagagcagga gagcccatga accccctgag caccaatctg  1140
acactgagcg ctgagaaagt ttgtcacaat gtgaccgttg atgcagttac cgggaaagtg  1200
atcggcgacg attccggaaa gggggcagga aggggactgc ctgtcactta a           1251

SEQ ID NO: 118         moltype = RNA  length = 1251
FEATURE                Location/Qualifiers
source                 1..1251
                       mol_type = other RNA
                       organism = synthetic construct
SEQUENCE: 118
atgaaggcca agctgctggt gctgctgtgc acattcacag caacctatgc agctgggcca  60
acagtgacag tgatccccgt gggacgcgag ggcggagaca ttaccatctc cgggaagggc  120
tttagcacaa cagggttcgg tgtgtatgtg gctgtggccc cagcaagcgt gccagagttc  180
tacgggaact ccgataaatt ttatgggtat gaccccagta aagacacaac cgagagcccc  240
agcacaattt gggtttacac cccctctcag aaagctattg gctcccggtt cgcccagggc  300
agaccaatga ataatgacgg gagctttacc atcactatga aggccccccc attcgagcag  360
```

```
ggaaaggact ttgtggtcct gactaccaag gctcacggag tgggcaaaac cgaccactct  420
gacgacactc ggacaccggt gacataccgg gaggctactc ccgctccaac aggccctaaa  480
actccaatcg cccccagcaa gcagccttca aagcaggctg cccccagcaa gcaggtgaag  540
cctagcaagc aggctggccc caacaagcag agcactactc ctcagcagaa gaccgcagag  600
cacagatctc agaccccagc agctcatcgc actatgacta agcaggtgtg taccatcgga  660
gcctcaaagg tgaccagcgg atccctgaca tggggaatcc ggactagctt tacttcctac  720
ctgcgcgggc ccatcgcaaa gggcagctgg aagctgtctg ggggggccaa ttggaacgga  780
ggcgccttca cattcccact gacttctgga tccttcgacc ccgccaccaa atccggctca  840
ctgaagtaca gcgggagcgt gcacatgact ggacaccatg gaattctgga catgacactc  900
gctgaaccct ctctgcagat caagggctct actgggcacc tgtatctgga tgtgaagtcc  960
tcttctatgg acggcaagaa gacaaactat gggagagtgg attttgccac cttcggagtg  1020
agcgtgagcg gaaatgctgc aatcaaaggg tcccccgtga aactgaccgc taccggagca  1080
aaagcctttg ccggctttta cagagcagga gagcccatga accccctgag cacccagctg  1140
acactgagcg ctgagaaagt ttgtcacagc gtgaccgttg atgcagttac cgggaaagtg  1200
atcggcgacg attccggaaa gggggcagga aggggactgc ctgtcactta a           1251
```

```
SEQ ID NO: 119          moltype = RNA  length = 1251
FEATURE                 Location/Qualifiers
source                  1..1251
                        mol_type = other RNA
                        organism = synthetic construct
SEQUENCE: 119
atgaaggcaa agctgctggt gctgctgtgc acatttactg ccacttacgc agcaggccct  60
accgtcacag tgatccctgt gggcagagaa ggtggcgaca tcaccatcag cggcaagggc  120
ttcagcacca caggctttgg cgtgtacgtg gccgtggcac ctgctagcgt gcccgaattc  180
tacggcaata gcgacaagtt ctacggctac gaccccagca aggacaccac cgagagccct  240
agcaccatct gggtgtacac ccctagccag aaggccatcg gctctcggtt cgcccagggc  300
agacccatga acaatgacgg cagcttcaca atcaccatga aggccccccc tttcgagcag  360
ggcaaagact tcgtggtgct gaccacaaag gcccatggcg tgggcaaaac cgatcacagc  420
gacgacacac ggacacctgt cacctacaga gaggctaccc ctgcccctac aggccctaag  480
acacccatcg cccctagcaa gcagcctagc aagcaggccg cccctagcaa gcaggtgaag  540
ccttctaagc aggccggccc caacaagcag tccaccacac ctcagcagaa gacagccgag  600
cacagaagcc agacccctgc cgcccaccgg accatgacaa agcaggtgag caccatcggc  660
gccagcaagg tgacaagcgg ctctctgacc tggggcatca gaacctcttt tacctcctac  720
ctgagaggcc ctatcgccaa gggctcttgg aagctgagcg gaggcgccaa ttggaatggc  780
ggcgccttca ccttccctct gaccagcggc agcttcgacc cagccaccaa gtccggaagc  840
ctgaagtaca gcggcagcgt gcacatgaca ggccaccacg gcatcctgga catgaccctg  900
gccgagccaa gcctgcagat caagggaagc accggccacc tgtatctgga cgtgaaaagc  960
agcagcatgg acggcaagaa gaccaattac ggcagagtgg acttcgccac cttcggagtg  1020
agcgtgtctg gcaacgccgc catcaagggc agccctgtga agctgaccgc cacaggcgct  1080
aaggcttttg ccggcttcta cagagccggc gagcctatga accctctgag cacccagctg  1140
accctgagcg ccgagaaggt gtcccacagc gtgaccgtgg acgcagtgac aggcaaggtg  1200
atcggcgacg actctggcaa gggagccggc cggggcctgc ccgtgacata a           1251
```

```
SEQ ID NO: 120          moltype = RNA  length = 1338
FEATURE                 Location/Qualifiers
source                  1..1338
                        mol_type = other RNA
                        organism = synthetic construct
SEQUENCE: 120
atgaaggcaa agctgctggt gctgctgtgc acatttactg ccacttacgc agccggtcca  60
acagtgacag tgatccctgt gggcagagaa ggcggcgata tcacaatcag cggcaagggc  120
ttctctacaa caggattcgg agtgtatgtg gctgtcgccc ctgccagcgt gcccgaattc  180
tatggaaaca gcgacaagtt ctacggctac gaccccagca aggatacaac cgagagcccc  240
tccaccatct gggtgtacac ccccagccag aaggccatcg gcagcagatt cgcccagggc  300
agacctatga ataatgacgg ctccttcacc atcaccatga aggcccctcc attcgagcag  360
ggcaaggatt tcgtggtgct gaccaccaaa gcccacggcg tgggcaaaac agaccacagc  420
gatgataccc ggacccccgt gacatacaga gaagccacac cagcccctac cggccctaag  480
acccctatcg ccccttctaa gcagcctagc aagcaggccg ccccatccaa acaggtgaag  540
cctagcaagc aggccgggcc caataagcag agcacaaccc cccagcagaa gaccgccgaa  600
cacagaagcc agacacccgc cgcccacaga acaatgacca agcaggtgtg caccatcggc  660
gcctccaagg tgaccagcgg cagcctgacc tggggcatta gaaccagctt taccagctac  720
ctgagaggcc ctatcgccaa cggcagctgg aagctgtccg gcggcgccaa ttggaacggc  780
agcgccttta ccttccccct gacaagcggc agcttcgacc ctgccaccaa gtctggcagc  840
ctgaagtaca gcggcagcgt gcatatgacc ggccaccacg gcatcctgga tatgaccctg  900
gccgaaccta gcctgcagat caagggcagc accggccacc tgtacctgga cgtgaaaagc  960
agcagcatgg acggcaagaa gacaaattac ggcagagtgg acttcgccac cttcggcgtg  1020
agcgtgagcg gaaatgccgc catcaaagga agccctgtga agctgaccgc caccggcgcc  1080
aaggcctttg ccggcttcta cagagccggc gagcctatga atcctctgag caccaatctg  1140
accctgagcg ccgaaaaggt gtgccacaat gtgacagtcg acgccgtgac aggcaaggtc  1200
atcggcgatg actctggcaa aggagccggc agaggcctgc ccgtgacaag cggcagcatt  1260
ctggcaatct atagcaccgt ggctagcagc ctggtgctgc tggtgtctct gggagccatc  1320
agcttcggct ctggctaa                                                1338
```

```
SEQ ID NO: 121          moltype = RNA  length = 1338
FEATURE                 Location/Qualifiers
source                  1..1338
                        mol_type = other RNA
                        organism = synthetic construct
```

```
SEQUENCE: 121
atgaaggcca agctgctggt gctgctgtgc acattcacag caacctatgc agctgggcca  60
acagtgacag tgatccccgt gggacgcgag ggcggagaca ttaccatctc cgggaagggc  120
tttagcacaa cagggttcgg tgtgtatgtg gctgtggccc cagcaagcgt gccagagttc  180
tacgggaact ccgataaatt ttatgggtat gaccccagta aagacacaac cgagagcccc  240
agcacaattt gggtttacac cccctctcag aaagctattg gctcccggtt cgcccagggc  300
agaccaatga ataatgacgg gagctttacc atcactatga aggccccccc attcgagcag  360
ggaaaggact ttgtggtcct gactaccaag gctcacggag tgggcaaaac cgaccactct  420
gacgacactc ggacaccggt gacataccgg gaggctactc ccgctccaac aggccctaaa  480
actccaatcg cccccagcaa gcagccttca aagcaggctg cccccagcaa gcaggtgaag  540
cctagcaagc aggctggccc caacaagcag agcactactc ctcagcagaa gaccgcagag  600
cacagatctc agaccccagc agctcatcgc actatgacta agcaggtgtg taccatcgga  660
gcctcaaagg tgaccagcgg atccctgaca tggggaatcc ggactagctt tacttcctac  720
ctgcgcgggc ccatcgcaaa gggcagctgg aagctgtctg ggggggccaa ttggaacgga  780
ggcgccttca cattcccact gacttctgga tccttcgacc ccgccaccaa atccggctca  840
ctgaagtaca gcgggagcgt gcacatgact ggacaccatg gaattctgga catgacactc  900
gctgaaccct ctctgcagat caagggctct actgggcacc tgtatctgga tgtgaagtcc  960
tcttctatgg acggcaagaa gacaaactat gggagagtgg attttgccac cttcggagtg  1020
agcgtgagcg gaaatgctgc aatcaaaggg tccccccgtga aactgaccgc taccggagca  1080
aaagcctttg ccggctttta cagagcagga gagcccatga accccctgag cacccagctg  1140
acactgagcg ctgagaaagt ttgtcacagc gtgaccgttg atgcagttac cgggaaagtg  1200
atcggcgacg attccggaaa gggggcagga aggggactgc ctgtcactag cggctctatt  1260
ctggccatct acagcacagt ggccagctct ctggtgctgc tggttagcct gggcgccatc  1320
agcttcggca gcggctaa                                                1338

SEQ ID NO: 122          moltype = RNA  length = 1410
FEATURE                 Location/Qualifiers
source                  1..1410
                        mol_type = other RNA
                        organism = synthetic construct
SEQUENCE: 122
atgaaggcca aactgctggt gctgctgtgt acctttacag ccacatatgc ctcctctaat  60
agaccaagat ccgtggctca ggccgccatc gctacagatg ggaaaggaat catcgataag  120
gatagtcggg atgcagtgat caacgacgcc aaactccgag ctgccatcgc cggcgccctg  180
gtgaaggctg ggttttccag cgccgacgca gtggccctgg cacctagaat cgccaaggag  240
atggcaaagg agggcgtcct gctgattaat caccacaagc tgaaagctct gattggggct  300
cagctcggac tgctgactga cgccaagatc cagagggccg cagctgccgt ggatctgggg  360
atcaaggcca ctctggccgc tactattatt cctaacgctc tggggtctgc cgccttcaag  420
aatgctgtca ttgccaacct ggtggctgct ggcatcgaca aacacctcgc cagggctacc  480
gctgtggcca tcgttgccac agccctgaat cctgccctgg gcccaatcgc taaatttgag  540
ctgattaagg ctgagatcgc cgcccaggcc gcactgctga tcagaagggg ggtccatctg  600
cagaaggccg ctattgaaca tgtgatcggc cgcgcattcg acgctgccgt ggccaccgct  660
atcatttcct ctccaatcct gagcgcacgg attgtgaccc acctggtgag ggctggaatt  720
gataaaagca tcgctatctc cctggctcct catatcgtga agcgcctggc caaggagccc  780
ctgctggctt tcaacaccgc caagctgatg aagaatatta caagacagat cgttgacgtg  840
atcacagccg ataaagccat caaaacagct gagcagctgg aaaaggagct ccccgccctg  900
gacgacctgg tcaaaaaagc tagctcccct cctaagccta cccccacacc tactccaacc  960
cccaccgccg ggcccaccgt gacagtgatc cccgtgggaa gggagggggg cgacattacc  1020
attagcggaa aagggttctc cacaaccggg ttcggcgtct acgtggccgt ggctcctgcc  1080
tctgtgccag agttctatgg caatagcgac aagttctatg ggtacgatcc atctaaggac  1140
accaccgaaa gtcccagcac catctgggtg tatacaccat cccagaaagc aatcggcagc  1200
agattcgccc aaggcaggcc catgaataat gatggctctt tcaccattac aatgaaggcc  1260
cctcctttcg agcagggaaa ggatttcgtg gtgctgacca ccaaagcaca tggcgttgga  1320
aagaccgacc acagcgacga tactcggacc cctgtgactt acagagaggc cacccctgct  1380
ccaaccggcc ctaaaactcc catctgataa                                  1410

SEQ ID NO: 123          moltype = RNA  length = 927
FEATURE                 Location/Qualifiers
source                  1..927
                        mol_type = other RNA
                        organism = synthetic construct
SEQUENCE: 123
atgaaggcca agctcctggt gctgctgtgt accttcactg ccacttacgc cgtggctcag  60
gccgctattg ctacagatgg aaagggcatc atcgataagg actcccgcga tgccgtgatc  120
aatgatgcca agctgagggc tgctattgct ggcgccctgg tgaaggctgg cttcagctcc  180
gccgatgcag tggcactggc tcctcggatc gctaaggaga tggccaagga gggcgtgctc  240
ctgatcaacc accacaaact gaaggccctg attggggccc agctgggcct gctcacagac  300
gccaagatcc agcgggccgc tgcagccgtg gacctgggca tcaaggccac tctggctgct  360
acaatcatcc caaacgcact cgggtccgcc gccttcaaga atgccgtgat cgccaacctg  420
gttgcagccg gaatcgacaa acatctggcc agagccacag ccgtggccat cgtggctacc  480
gctctgaacc cagctctggg gcctatcgcc aagtttgaac tgatcaaggc tgagatcgcc  540
gcacaggccg ccctgctgat cagaagagga gtgcacctgc agaaagccgc tatcgagcac  600
gtgatcggac gcgcctttga cgcagccgtg gctactgcca tcatcagctc tccaattctg  660
agcgcaagga tcgtgacaca cctggtgagg gccggcatcg acaagagcat cgcaatttcc  720
ctggcccctc acatcgtgaa gcggctggct aaggagccac tgctcgcctt taataccgca  780
aaactgatga aggctattac acgccagatc gtggatgtga tcaccgctga taaggcaatc  840
aagaccgccg aacagctgga aaaggaactg cctgccctgg atgacctggt gaaaaaggct  900
atgggccccc ctaagcctac ctgataa                                     927
```

```
SEQ ID NO: 124          moltype = RNA  length = 1362
FEATURE                 Location/Qualifiers
source                  1..1362
                        mol_type = other RNA
                        organism = synthetic construct
SEQUENCE: 124
atgaaggcca agctgctggt gctgctgtgc accttcaccg ccacctacgc ctccagcaac  60
cggcctagaa gcgtggccca ggccgccatc gccaccgacg gcaagggcat catcgacaag  120
gattcccggg acgccgtgat caatgacgcc aagctgagag ccgccatcgc cggcgccctg  180
gtgaaggccg gcttcagcag cgccgacgcc gtggccctgg cccccagaat cgccaaggag  240
atggccaagg aaggcgtgct gctgatcaat caccacaagc tgaaggccct gatcggcgcc  300
cagctgggcc tgctgacaga tgccaagatc cagagagccg ctgccgccgt ggacctgggc  360
atcaaggcca ccctggccgc caccatcatc cctaacgccc tgggcagcgc tgccttcaag  420
aatgccgtga tcgccaacct ggtggccgcc ggcatcgaca agcacctggc cagagccaca  480
gccgtggcca tcgtggccac cgccctgaat cctgccctgg gccccatcgc caagttcgag  540
ctgatcaagg ccgagatcgc cgcccaggcc gccctgctga tccggcgggg cgtgcacctg  600
cagaaggccg ccatcgaaca cgtgatcggc agagccttcg atgccgccgt ggccaccgcc  660
atcatcagct cccccatcct gagcgccaga atcgtgaccc acctggtgcg ggccggcatc  720
gacaagtcca tcgccattag cctggcccct cacatcgtga agcgcctggc caaggagccc  780
ctgctggcct tcaataccgc caagctgatg aagaatatca ccagacagat cgtggatgtg  840
atcaccgccg ataaggccat caagaccgcc gagcagctgg agaaagagct gcccgccctg  900
gacgacctgg tgaaaaaggc catgggcccc cctaagccta caggcggcgg cggaggcgct  960
ggacctaccg tgaccgtgat ccccgtgggc agagagggcg gcgatatcac catcagcggc  1020
aagggcttca gcaccaccgg cttcggcgtg tacgtggccg tggcccctgc cagcgtgccc  1080
gagttctacg gcaatagcga caagttctac ggctacgacc ccagcaagga caccacagaa  1140
tctcccagca ccatctgggt gtacaccccc agccagaagg ccattggcag ccggttcgcc  1200
cagggccggc ctatgaacaa tgatggcagc ttcacaatca ccatgaaggc cccacccttc  1260
gagcagggca aggacttcgt ggtgctgacc accaaggccc acggagtggg caagggcgac  1320
cacggcgacg acacacggac ccccgtgggc tacagatgat aa                    1362

SEQ ID NO: 125          moltype = RNA  length = 1371
FEATURE                 Location/Qualifiers
source                  1..1371
                        mol_type = other RNA
                        organism = synthetic construct
SEQUENCE: 125
atgaaagcca agctgctggt gctgctgtgt acttttactg caacctacgc cagcagcaac  60
cgcccaaggt ctgtcgcaca ggctgctatc gccacagatg gcaagggaat cattgataag  120
gacagcaggg atgctgtgat caacgacgca aaactgagag ccgccatcgc cggcgcactg  180
gtgaaagccg gcttttcttc cgccgacgca gtggctctgg ctcccagaat cgctaaggaa  240
atggccaagg agggagtgct gctgatcaat caccacaaac tgaaggctct gatcggggct  300
cagctgggcc tgctgactga cgctaagatt cagagagcag cagcagctgt cgacctggga  360
atcaaggcaa ccctggcagc cactatcatt ccaaatgctc tgggctctgc cgccttcaaa  420
aacgccgtga ttgccaatct cgtggcagct ggaatcgata agcacctggc acgggccacc  480
gccgtggcta tcgtggccac cgctctgaat cccgccctgg gccctattgc caagtttgaa  540
ctgatcaaag ccgagatcgc tgcacaggcc gccctgctca tccgcagggg ggtccacctg  600
cagaaagcag ccatcgagca cgtgatcggc agggcctttg atgcagccgt cgccactgcc  660
atcatcagct ctccaatcct gtctgcccgg attgtgactc acctggtgcg cgccggcatc  720
gataagtcca tcgcaatctc tctggcccca cacatcgtga agagactggc caaagaacca  780
ctcctggctt tcaataccgc caaactcatg aaaaacatca cccggcagat cgtcgatgtg  840
attaccgccg acaaggctat caagaccgcc gagcagctcg aaaaggagct gcctgccctg  900
gacgacctgg tgaagaaagc ctcctctcca cccaaaccca ccccaactcc aactccaacc  960
cctacagctg gccccaccgt gaccgtcatc ccagtgggaa gggaaggagg agacatcaca  1020
atctctggaa aggggtttag cacaaccgga tttggagtgt acgtcgccgt ggcccccgca  1080
tccgtgccag aattctacgg caattccgat aaattctacg ggtacgaccc ctccaaggac  1140
actacagaga gcccctctac aatttgggtg tacaccccaa gccagaaggc catcggaagc  1200
agatttgctc agggccggcc aatgaacaac gacggatcct tcacaatcac aatgaaagca  1260
cctccctttg agcagggcaa ggattttgtg gtgctgacca ccaaggctca cggggtcgga  1320
aagaccgatc acagcgacga tacaagaacc cccgtgacat accggtgata a          1371

SEQ ID NO: 126          moltype = RNA  length = 51
FEATURE                 Location/Qualifiers
source                  1..51
                        mol_type = other RNA
                        organism = synthetic construct
SEQUENCE: 126
atgaaggcca agctgctggt gctgctgtgc acctttacag ccacctacgc c          51

SEQ ID NO: 127          moltype = RNA  length = 51
FEATURE                 Location/Qualifiers
source                  1..51
                        mol_type = other RNA
                        organism = synthetic construct
SEQUENCE: 127
atgaaagcaa agctgctggt gctgctgtgc accttcaccg ctacctacgc c          51

SEQ ID NO: 128          moltype = RNA  length = 51
FEATURE                 Location/Qualifiers
source                  1..51
```

```
                         mol_type = other RNA
                         organism = synthetic construct
SEQUENCE: 128
atgaaggcca agctgctggt gctgctctgc accttcaccg ccacctacgc c           51

SEQ ID NO: 129           moltype = RNA  length = 51
FEATURE                  Location/Qualifiers
source                   1..51
                         mol_type = other RNA
                         organism = synthetic construct
SEQUENCE: 129
atgaaggcca agctgctggt gctgctgtgc accttcaccg ccacctatgc c           51

SEQ ID NO: 130           moltype = RNA  length = 51
FEATURE                  Location/Qualifiers
source                   1..51
                         mol_type = other RNA
                         organism = synthetic construct
SEQUENCE: 130
atgaaagcca agctgctggt gctgctctgc actttaccg ccacctacgc c            51

SEQ ID NO: 131           moltype = RNA  length = 51
FEATURE                  Location/Qualifiers
source                   1..51
                         mol_type = other RNA
                         organism = synthetic construct
SEQUENCE: 131
atgaaggcca agctgctggt gctgctgtgc accttcaccg ccacatacgc c           51

SEQ ID NO: 132           moltype = RNA  length = 51
FEATURE                  Location/Qualifiers
source                   1..51
                         mol_type = other RNA
                         organism = synthetic construct
SEQUENCE: 132
atgaaggcca agctgctggt gctgctgtgc accttcaccg ccacctacgc c           51

SEQ ID NO: 133           moltype = RNA  length = 51
FEATURE                  Location/Qualifiers
source                   1..51
                         mol_type = other RNA
                         organism = synthetic construct
SEQUENCE: 133
atgaaggcaa agctgctggt gctgctgtgc accttcaccg ccacatacgc a           51

SEQ ID NO: 134           moltype = RNA  length = 51
FEATURE                  Location/Qualifiers
source                   1..51
                         mol_type = other RNA
                         organism = synthetic construct
SEQUENCE: 134
atgaaggcca agctgctggt gctgctgtgc accttcacag ccacctacgc c           51

SEQ ID NO: 135           moltype = RNA  length = 51
FEATURE                  Location/Qualifiers
source                   1..51
                         mol_type = other RNA
                         organism = synthetic construct
SEQUENCE: 135
atgaaggcca agctgctggt gctgctgtgc actttcaccg caacatacgc c           51

SEQ ID NO: 136           moltype = RNA  length = 51
FEATURE                  Location/Qualifiers
source                   1..51
                         mol_type = other RNA
                         organism = synthetic construct
SEQUENCE: 136
atgaaggcaa agctgctggt gctgctgtgc acatttactg ccacttacgc a           51

SEQ ID NO: 137           moltype = RNA  length = 51
FEATURE                  Location/Qualifiers
source                   1..51
                         mol_type = other RNA
                         organism = synthetic construct
SEQUENCE: 137
atgaaggcca agctgctggt gctgctgtgc acattcacag caacctatgc a           51

SEQ ID NO: 138           moltype = RNA  length = 51
FEATURE                  Location/Qualifiers
```

```
source                  1..51
                        mol_type = other RNA
                        organism = synthetic construct
SEQUENCE: 138
atgaaggcaa agctgctggt gctgctgtgc acatttactg ccacttacgc a           51

SEQ ID NO: 139          moltype = RNA  length = 51
FEATURE                 Location/Qualifiers
source                  1..51
                        mol_type = other RNA
                        organism = synthetic construct
SEQUENCE: 139
atgaaggcaa agctgctggt gctgctgtgc acatttactg ccacttacgc a           51

SEQ ID NO: 140          moltype = RNA  length = 51
FEATURE                 Location/Qualifiers
source                  1..51
                        mol_type = other RNA
                        organism = synthetic construct
SEQUENCE: 140
atgaaggcca agctgctggt gctgctgtgc acattcacag caacctatgc a           51

SEQ ID NO: 141          moltype = RNA  length = 51
FEATURE                 Location/Qualifiers
source                  1..51
                        mol_type = other RNA
                        organism = synthetic construct
SEQUENCE: 141
atgaaggcca agctgctggt gctgctgtgc acattcacag caacctatgc a           51

SEQ ID NO: 142          moltype = RNA  length = 51
FEATURE                 Location/Qualifiers
source                  1..51
                        mol_type = other RNA
                        organism = synthetic construct
SEQUENCE: 142
atgaaggcaa agctgctggt gctgctgtgc acatttactg ccacttacgc a           51

SEQ ID NO: 143          moltype = RNA  length = 51
FEATURE                 Location/Qualifiers
source                  1..51
                        mol_type = other RNA
                        organism = synthetic construct
SEQUENCE: 143
atgaaggcca agctgctggt gctgctgtgc acattcacag caacctatgc a           51

SEQ ID NO: 144          moltype = RNA  length = 51
FEATURE                 Location/Qualifiers
source                  1..51
                        mol_type = other RNA
                        organism = synthetic construct
SEQUENCE: 144
atgaaggcca agctgctggt gctgctgtgc acattcacag caacctatgc a           51

SEQ ID NO: 145          moltype = RNA  length = 51
FEATURE                 Location/Qualifiers
source                  1..51
                        mol_type = other RNA
                        organism = synthetic construct
SEQUENCE: 145
atgaaggcaa agctgctggt gctgctgtgc acatttactg ccacttacgc a           51

SEQ ID NO: 146          moltype = RNA  length = 51
FEATURE                 Location/Qualifiers
source                  1..51
                        mol_type = other RNA
                        organism = synthetic construct
SEQUENCE: 146
atgaaggcca agctgctggt gctgctgtgc acattcacag caacctatgc a           51

SEQ ID NO: 147          moltype = RNA  length = 51
FEATURE                 Location/Qualifiers
source                  1..51
                        mol_type = other RNA
                        organism = synthetic construct
SEQUENCE: 147
atgaaggcaa agctgctggt gctgctgtgc acatttactg ccacttacgc a           51

SEQ ID NO: 148          moltype = RNA  length = 51
```

-continued

```
FEATURE                 Location/Qualifiers
source                  1..51
                        mol_type = other RNA
                        organism = synthetic construct
SEQUENCE: 148
atgaaggcaa agctgctggt gctgctgtgc acatttactg ccacttacgc a           51

SEQ ID NO: 149          moltype = RNA  length = 51
FEATURE                 Location/Qualifiers
source                  1..51
                        mol_type = other RNA
                        organism = synthetic construct
SEQUENCE: 149
atgaaggcca aactgctggt gctgctgtgt acctttacag ccacatatgc c           51

SEQ ID NO: 150          moltype = RNA  length = 51
FEATURE                 Location/Qualifiers
source                  1..51
                        mol_type = other RNA
                        organism = synthetic construct
SEQUENCE: 150
atgaaggcca agctcctggt gctgctgtgt accttcactg ccacttacgc c           51

SEQ ID NO: 151          moltype = RNA  length = 51
FEATURE                 Location/Qualifiers
source                  1..51
                        mol_type = other RNA
                        organism = synthetic construct
SEQUENCE: 151
atgaaggcca agctgctggt gctgctgtgc accttcaccg ccacctacgc c           51

SEQ ID NO: 152          moltype = RNA  length = 51
FEATURE                 Location/Qualifiers
source                  1..51
                        mol_type = other RNA
                        organism = synthetic construct
SEQUENCE: 152
atgaaagcca agctgctggt gctgctgtgt actttactg caacctacgc c            51

SEQ ID NO: 153          moltype = RNA  length = 720
FEATURE                 Location/Qualifiers
source                  1..720
                        mol_type = other RNA
                        organism = synthetic construct
SEQUENCE: 153
gtggaaccca ccaccacaat cagcgccaca agcacacacg agctgagcgc ctccgatgcc  60
agaaactcta tccagctgct gaacgcccac attgccacac tgcagagcgt gcagaaaagc  120
gtgccaggca gcgactacag cgaccagatc agagatctgc tgaaggccgc cttcgacctg  180
agaggcctga ttgaaacact ggcccacggc ggcatcccat tctacgatcc tagcaccatc  240
atgccccgga tcaagctggt ggccacaacc atcgatacca tccacaccgc caccacaact  300
ctgcagaaca aagtgcggcc tgctcacgtg gaactgggcc tcgaagtgac aaaagccgtg  360
ctgctgacag ccaatcctgc cagcacagcc aaagagctgg acgctgaagg cgccgctctg  420
aaggccagac tggaaaaagt gtctcagtac cccgatctga cccctaacga cgtggccaca  480
gtgtacgtgc ggaccaactt cagcaagacc atctggcaag tgcgggccaa cagagatcgg  540
tacatcctgg gacacaagag cgccgctgtg tacaagaccc tgaaccacgc catcacaaag  600
gccgtgggcg tcagactgaa ccccaagacc acagtgggca acatccaggc cgccagaaca  660
gaactgctgg ccgcctatca gaccgccttc aacagccccg atgtgaagaa agccgcttaa  720

SEQ ID NO: 154          moltype = RNA  length = 720
FEATURE                 Location/Qualifiers
source                  1..720
                        mol_type = other RNA
                        organism = synthetic construct
SEQUENCE: 154
gtcgagccta caacaacaat cagcgccaca agcacccacg agctgagcgc ctctgatgcc  60
cggaactcta tccagctgct gaacgcccac atcgccaccc tgcagagcgt gcagaagtct  120
gtgccaggca gcgactacag cgaccagatc agagatctgc ttaaagccgc tttcgacctg  180
agaggcctga tcgagacact ggcccacggc ggaatcccct tctacgaccc cagcaccatc  240
atgcctagaa tcaagctggt cgccaccacc atcgacacca tccacaccgc cacaaccacc  300
ctgcagaaca aggtgcggcc tgcccatgtg gaactgggac tggaggtgac aaaagccgtg  360
ctgctcaccg ccaacccagc tagcacagcc aaggaactgg acgccgaggg cgccgccctg  420
aaggccagac tggaaaaggt gtcccagtac cccgacctga cccctaacga cgtggccacc  480
gtgtacgtgc gcaccaactt cagcaagacc atttggcagg tgcgggccaa tagagataga  540
tacatcctgg gccacaagtc cgctgccgtg tacaagacac tgaatcacgc catcaccaag  600
gctgttggcg tgcggctgaa ccctaagacc actgtgggca acatccaggc cgctagaaca  660
gagctgctgg ccgcctatca aacagctttt aacagccctg atgtgaagaa agccgcttaa  720

SEQ ID NO: 155          moltype = RNA  length = 720
FEATURE                 Location/Qualifiers
```

```
source                  1..720
                        mol_type = other RNA
                        organism = synthetic construct
SEQUENCE: 155
gtcgagccca ccaccaccat ctccgccaca tccacacacg aactgtccgc aagcgacgcc  60
agaaacagca tccagctgct gaacgcccac atcgccaccc tccagagcgt gcagaagagt  120
gtgcccggca gcgattatag cgaccagatc cgggacctgc tcaaggccgc attcgacctg  180
cgcggcctga tcgagacact ggctcatggc gggatcccct tctatgatcc cagcaccatc  240
atgcccagga tcaagctggt cgccactacc atcgacacca tccacaccgc caccaccacc  300
ctgcagaaca aagtgcgccc cgcccacgtg gagctggggc tggaggtgac caaagcggtg  360
ctgctgacag ccaaccctgc atccaccgcc aaggagctgg acgcagaggg cgctgcactg  420
aaggcccggc tcgagaaggt gtcccagtat cccgacctga caccaaacga tgtggccact  480
gtgtacgtga gaaccaactt ctccaagacc atctggcagg tcagagccaa ccgcgatcgc  540
tacatcctgg gccacaagtc cgccgccgtg tataagaccc tgaaccatgc catcaccaag  600
gccgtgggcg tcagactgaa ccccaagacc accgtgggca acatccaggc cgctagaaca  660
gagctgctgg ccgcctacca gaccgccttc aattcacccg acgtgaagaa ggccgcttaa  720

SEQ ID NO: 156          moltype = RNA  length = 717
FEATURE                 Location/Qualifiers
source                  1..717
                        mol_type = other RNA
                        organism = synthetic construct
SEQUENCE: 156
gtcgagccca ccaccaccat ctccgccaca tccacacacg aactgtccgc aagcgacgcc  60
agaaacagca tccagctgct gaacgcccac atcgccaccc tccagagcgt gcagaagagt  120
gtgcccggca gcgattatag cgaccagatc cgggacctgc tcaaggccgc attcgacctg  180
cgcggcctga tcgagacact ggctcatggc gggatcccct tctatgatcc cagcaccatc  240
atgcccagga tcaagctggt cgccactacc atcgacacca tccacaccgc caccaccacc  300
ctgcagaaca aagtgcgccc cgcccacgtg gagctggggc tggaggtgac caaagcggtg  360
ctgctgacag ccaaccctgc atccaccgcc aaggagctgg acgcagaggg cgctgcactg  420
aaggcccggc tcgagaaggt gtcccagtat cccgacctga cccccaacga cgtggccact  480
gtgtacgtgc ggaccaactt cagcaagacc atttggcagg tcagggccaa tagagacaga  540
tacatcctgg ggcacaaaag cgccgccgtg tacaagaccc tgaaccacgc catcaccaag  600
gccgtgggag tgcggctgaa tccaaagacc accgtgggca acattcaggc cgccagaacc  660
gagctgctgg ccgcctacca gacagctttc aatagccccg acgtgaagaa ggccgcc     717

SEQ ID NO: 157          moltype = RNA  length = 717
FEATURE                 Location/Qualifiers
source                  1..717
                        mol_type = other RNA
                        organism = synthetic construct
SEQUENCE: 157
gtggagccca ccacaacaat cagcgccaca tccacccacg aactgagcgc ctccgacgcc  60
agaaattcca tccagctgct gaacgcccac atcgccaccc tgcagagcgt gcagaaaagc  120
gtgcccggct ctgattacag cgaccagatc cgggacctgc tgaaggccgc ctttgacctg  180
agaggcctga tcgagacact ggcccacgga ggcatccctt tctacgatcc tagcaccatc  240
atgcctcgga tcaagctggt ggccacaaca atcgacacca tccacaccgc caccaccaca  300
ctgcagaaca aagtgcggcc tgcccatgtg gaactgggcc tggaagtgac caaggccgtg  360
ctgctgacag ccaatcctgc tagcacagcc aaggaactgg atgccgaggg agccgccctg  420
aaggctagac tggagaaggt gagccagtac cccgacctga cccccaatga cgtggcaacc  480
gtgtacgtga gaaccaattt cagcaagacc atctggcagg tgcgggccaa tcgggacaga  540
tacatcctgg gccacaagag cgccgccgtg tacaagaccc tgaatcacgc catcaccaag  600
gccgtgggcg tgcggctgaa tcctaagacc accgtgggca atatccaggc cgcccggaca  660
gaactgctgg ccgcctacca gacagccttt aatagccctg atgtgaagaa ggccgcc     717

SEQ ID NO: 158          moltype = RNA  length = 720
FEATURE                 Location/Qualifiers
source                  1..720
                        mol_type = other RNA
                        organism = synthetic construct
SEQUENCE: 158
gtggaaccta ccacaaccat cagcgccacc agcacacacg agctgagcgc ttctgatgcc  60
cggaacagca tccaactgct gaatgcccac atcgccacac tccagagcgt ccagaagagc  120
gtccccggca gcgactacag cgatcagatc agagacctgc tgaaggccgc tttcgacctg  180
agaggcctga tcgagacact tgcccacggc ggcatcccct tctacgaccc cagcaccatc  240
atgcctagaa tcaagctggt ggccaccacc atcgacacca tccacaccgc cacaactacc  300
ctgcaaaaca aggtgcgccc agcccatgtg gaactgggcc tggaggtgac caaggcagtt  360
ctgctgacag ctaatcctgc ctctaccgct aaagagctgg acgccgaggg cgccgccctg  420
aaagccagac tggaaaaggt gtcccagtac cctgatctga ccccctaacga cgtggccaca  480
gtgtacgtgc ggaccaactt cagcaagacc atctggcagg tgcgggccaa cagagataga  540
tacatcctgg gacacaagtc cgccgccgtg tacaagaccc tgaaccacgc cattaccaaa  600
gccgtgggcg tgcggctgaa ccctaagaca accgtgggaa atatccaggc cgctagaacc  660
gagctgctgg ccgcttatca gacagccttt aacagccctg acgtgaagaa ggccgcctga  720

SEQ ID NO: 159          moltype = RNA  length = 720
FEATURE                 Location/Qualifiers
source                  1..720
                        mol_type = other RNA
                        organism = synthetic construct
```

```
SEQUENCE: 159
gtcgagccta ccacaaccat cagcgccaca tctacacacg agctgagcgc cagcgacgcc  60
agaaacagca tccagctgct gaacgcccac atcgccacac tgcagagcgt gcagaaatct  120
gtgcccggct ccgattacag cgatcagatc agagacctgc ttaaagccgc tttcgacctg  180
agaggactga tcgagacact ggcccacgga ggcatcccct tctacgaccc cagcaccatc  240
atgcctagaa tcaagctggt ggccaccacc atcgacacta tccacaccgc taccacaacc  300
ctgcaaaaca aggtgcggcc tgcccatgtg gaactgggcc tggaagtgac caaagccgtg  360
ctgctgaccg ccaaccctgc ttctaccgcc aaggaactgg acgccgaggg cgccgctctg  420
aaagcgcggc tggagaaggt ttctcagtac cctgatctga cccctaacga cgtggccaca  480
gtgtacgtga ggaccagctt cagcaagacc atctggcagg tgcgggccaa tagagataga  540
tacatcctgg gccacaagtc cgccgccgtg tataagacac tgaaccacgc catcaccaag  600
gctgtcggag tgcggctgaa tccaaagacc accgtgggca atatccaagc cgctagaacc  660
gagctgctcg ccgcctacca gacagctttt aacagccctg acgtgaagaa ggccgcctga  720

SEQ ID NO: 160         moltype = RNA  length = 717
FEATURE                Location/Qualifiers
source                 1..717
                       mol_type = other RNA
                       organism = synthetic construct
SEQUENCE: 160
gtcgagccca ccaccaccat ctccgccaca tccacacacg aactgtccgc aagcgacgcc  60
agaaacagca tccagctgct gaacgcccac atcgccaccc tccagagcgt gcagaagagt  120
gtgcccggca gcgattatag cgaccagatc cgggacctgc tcaaggccgc attcgacctg  180
cgcggcctga tcgagacact ggctcatggc gggatcccct tctatgatcc cagcaccatc  240
atgcccagga tcaagctggt cgccactacc atcgacacca tccacaccgc caccaccacc  300
ctgcagaaca aagtgcgccc cgcccacgtg gagctggggc tggaggtgac caaagcggtg  360
ctgctgacag ccaaccctgc atccaccgcc aaggagctgg acgcagaggg cgctgcactg  420
aaggcccggc tcgagaaggt gtcccagtat cccgacctga cccccaacga tgtggccacc  480
gtgtatgtgc ggacctcctt ctccaagacc atctggcagg tcagagccaa tcgggaccgg  540
tacatcctgg gccacaagag cgccgctgtg tacaagaccc tgaaccatgc catcaccaag  600
gcagtgggcg tgcgcctgaa cccaaaaacc accgtgggca acattcaggc cgccagaacc  660
gagctgctgg ccgcctacca gaccgctttc aatagccccg acgtgaagaa ggccgcc     717

SEQ ID NO: 161         moltype = RNA  length = 720
FEATURE                Location/Qualifiers
source                 1..720
                       mol_type = other RNA
                       organism = synthetic construct
SEQUENCE: 161
gtggaaccca ccaccacaat cagcgccaca agcacacacg agctgagcgc ctccgatgcc  60
agaaactcta tccagctgct gaacgcccac attgccacac tgcagagcgt gcagaaaagc  120
gtgccaggca gcgactacag cgaccagatc agagatctgc tgaaggccgc cttcgacctg  180
agaggcctga ttgaaacact ggcccacggc ggcatcccat tctacgatcc tagcaccatc  240
atgccccgga tcaagctggt ggccacaacc atcgatacca tccacaccgc caccacaact  300
ctgcagaaca aagtgcggcc tgctcacgtg gaactgggcc tcgaagtgac aaaagccgtg  360
ctgctgacag ccaatcctgc cagcacagcc aaagagctgg acgctgaagg cgccgctctg  420
aaggccagac tggaaaaagt gtctcagtac cccgatctga cccctaacga cgtggccaca  480
gtgtacgtgc ggaccaactt cagcaagacc atctggcaag tgcgggccaa cagagatcgg  540
tacatcctgg gacacaagag cgccgctgtg tacaagaccc tgaaccacgc catcacaaag  600
gccgtgggcg tcagactgaa ccccaagacc acagtgggca acatccaggc cgccagaaca  660
gaactgctgg ccgcctatca gaccgccttc aacagccccg atgtgaagaa agccgcttaa  720

SEQ ID NO: 162         moltype = RNA  length = 720
FEATURE                Location/Qualifiers
source                 1..720
                       mol_type = other RNA
                       organism = synthetic construct
SEQUENCE: 162
gtcgagccta caacaacaat cagcgccaca agcacccacg agctgagcgc ctctgatgcc  60
cggaactcta tccagctgct gaacgcccac atcgccaccc tgcagagcgt gcagaagtct  120
gtgccaggca gcgactacag cgaccagatc agagatctgc ttaaagccgc tttcgacctg  180
agaggcctga tcgagacact ggcccacggc ggaatcccct tctacgaccc cagcaccatc  240
atgcctagaa tcaagctggt cgccaccacc atcgacacca tccacaccgc cacaaccacc  300
ctgcagaaca aggtgcggcc tgcccatgtg gaactgggac tggaggtgac aaaagccgtg  360
ctgctcaccg ccaacccagc tagcacagcc aaggaactgg acgccgaggg cgccgccctg  420
aaggccagac tggaaaaggt gtcccagtac cccgacctga cccctaacga cgtggccacc  480
gtgtacgtgc gcaccaactt cagcaagacc atttggcagg tgcgggccaa tagagataga  540
tacatcctgg gccacaagtc cgctgccgtg tacaagacac tgaatcacgc catcaccaag  600
gctgttggcg tgcggctgaa ccctaagacc actgtgggca acatccaggc cgctagaaca  660
gagctgctgg ccgcctatca aacagctttt aacagccctg atgtgaagaa agccgcttaa  720

SEQ ID NO: 163         moltype = RNA  length = 720
FEATURE                Location/Qualifiers
source                 1..720
                       mol_type = other RNA
                       organism = synthetic construct
SEQUENCE: 163
gtcgagccca ccaccaccat ctccgccaca tccacacacg aactgtccgc aagcgacgcc  60
agaaacagca tccagctgct gaacgcccac atcgccaccc tccagagcgt gcagaagagt  120
```

```
gtgcccggca gcgattatag cgaccagatc cgggacctgc tcaaggccgc attcgacctg  180
cgcggcctga tcgagacact ggctcatggc gggatcccct tctatgatcc cagcaccatc  240
atgcccagga tcaagctggt cgccactacc atcgacacca tccacaccgc caccaccacc  300
ctgcagaaca aagtgcgccc cgcccacgtg gagctggggc tggaggtgac caaagcggtg  360
ctgctgacag ccaaccctgc atccaccgcc aaggagctgg acgcagaggg cgctgcactg  420
aaggcccggc tcgagaaggt gtcccagtat cccgacctga ccccaaatga cgtggccacc  480
gtgtacgtgc ggacctcctt ctccaagacc atctggcaag tgcgggctaa cagagacagg  540
tacattctgg gccacaagtc cgccgccgtg tacaaaaccc tgaatcacgc catcaccaag  600
gccgtgggcg tgagactgaa ccccaagacc accgtgggca acattcaggc tgccaggacc  660
gagctgctgg ccgcttatca gaccgccttc aacagccccg acgtgaagaa agccgcctaa  720

SEQ ID NO: 164         moltype = RNA  length = 720
FEATURE                Location/Qualifiers
source                 1..720
                       mol_type = other RNA
                       organism = synthetic construct
SEQUENCE: 164
gtcgagccca ccaccaccat ctccgccaca tccacacacg aactgtccgc aagcgacgcc  60
agaaacagca tccagctgct gaacgcccac atcgccaccc tccagagcgt gcagaagagt  120
gtgcccggca gcgattatag cgaccagatc cgggacctgc tcaaggccgc attcgacctg  180
cgcggcctga tcgagacact ggctcatggc gggatcccct tctatgatcc cagcaccatc  240
atgcccagga tcaagctggt cgccactacc atcgacacca tccacaccgc caccaccacc  300
ctgcagaaca aagtgcgccc cgcccacgtg gagctggggc tggaggtgac caaagcggtg  360
ctgctgacag ccaaccctgc atccaccgcc aaggagctgg acgcagaggg cgctgcactg  420
aaggcccggc tcgagaaggt gtcccagtat cccggcggga cacctaacgg cgtgggaggc  480
gtgtatgtga ggacaaactt cagcaagaca atctggcagg tcagggccaa ccgcgataga  540
tacatcctgg gccacaagag cgccgccgtc tacaagacac tgaaccacgc tatcacaaaa  600
gccgtggggg tgaggctgaa ccccaagacc accgtgggga acatccaggc cgctagaact  660
gagctgctgg ccgcctacca gaccgctttc aatagccccg acgtgaagaa ggccgcctaa  720

SEQ ID NO: 165         moltype = RNA  length = 720
FEATURE                Location/Qualifiers
source                 1..720
                       mol_type = other RNA
                       organism = synthetic construct
SEQUENCE: 165
gtggaaccta caaccacaat cagcgccaca tctacacacg agctgagcgc cagcgacgcc  60
cggaacagca tccagctgct gaacgcccac atcgccaccc tccagagcgt gcagaaatcc  120
gtgcctggat ctgattacag cgaccagatc agagatctgc tgaaggccgc ttttgacctg  180
agaggcctga tcgagacact ggcccatggc ggcatcccct tctacgaccc tagcacaatt  240
atgcctagaa tcaagctggt cgccaccacc atcgacacca tccacaccgc caccacaacc  300
ctgcagaaca aggtcagacc agcccacgtg gaactcggcc tggaggtgac caaggctgtg  360
ctgcttacag ctaatcctgc tagcaccgct aaagagctgg acgccgaggg cgccgccctg  420
aaggcccgcc tggaaaaagt gtcccagtac cccggcggaa cccctaacgg cgttggcgga  480
gtgtacgtgc ggaccagctt cagcaagacc atctggcagg tgcgggctaa tagagataga  540
tacatcctgg gccacaagtc cgccgcggtg tataagacac tgaaccacgc catcaccaag  600
gctgtgggcg tgcggctgaa ccccaagacc acagtgggca acatccaagc cgccagaacc  660
gagctgctgg ccgcctacca gaccgccttc aactctccag acgtgaagaa ggccgcctga  720

SEQ ID NO: 166         moltype = RNA  length = 720
FEATURE                Location/Qualifiers
source                 1..720
                       mol_type = other RNA
                       organism = synthetic construct
SEQUENCE: 166
gtcgagccca ccaccaccat ctccgccaca tccacacacg aactgtccgc aagcgacgcc  60
agaaacagca tccagctgct gaacgcccac atcgccaccc tccagagcgt gcagaagagt  120
gtgcccggca gcgattatag cgaccagatc cgggacctgc tcaaggccgc attcgacctg  180
cgcggcctga tcgagacact ggctcatggc gggatcccct tctatgatcc cagcaccatc  240
atgcccagga tcaagctggt cgccactacc atcgacacca tccacaccgc caccaccacc  300
ctgcagaaca aagtgcgccc cgcccacgtg gagctggggc tggaggtgac caaagcggtg  360
ctgctgacag ccaaccctgc atccaccgcc aaggagctgg acgcagaggg cgctgcactg  420
aaggcccggc tcgagaaggt gtcccagtat cccgacctga cccccaacga tgtggctacc  480
gtctatgtgc ggactaattt cagtaagacc atctggcagg tcgccgccaa cgccgataga  540
tatatcgccg gccacaaatc cgccgccgtc gcaaagaccc ttgctcacgc tattgccaag  600
gccgctggcg tgagagctaa cccaaagacc accgtcggca acatccaggc cgccaggaca  660
gagctgcttg ccgcctatca gactgccttc aacagccctg acgtgaagaa ggcagcctaa  720

SEQ ID NO: 167         moltype = RNA  length = 720
FEATURE                Location/Qualifiers
source                 1..720
                       mol_type = other RNA
                       organism = synthetic construct
SEQUENCE: 167
gtcgagccca ccaccaccat ctccgccaca tccacacacg aactgtccgc aagcgacgcc  60
agaaacagca tccagctgct gaacgcccac atcgccaccc tccagagcgt gcagaagagt  120
gtgcccggca gcgattatag cgaccagatc cgggacctgc tcaaggccgc attcgacctg  180
cgcggcctga tcgagacact ggctcatggc gggatcccct tctatgatcc cagcaccatc  240
atgcccagga tcaagctggt cgccactacc atcgacacca tccacaccgc caccaccacc  300
```

```
ctgcagaaca aagtgcgccc cgcccacgtg gagctggggc tggaggtgac caaagcggtg  360
ctgctgacag ccaaccctgc atccaccgcc aaggagctgg acgcagaggg cgctgcactg  420
aaggcccggc tcgagaaggt gtcccagtat cccgacctga cccccaacga cgtggccacc  480
gtgtatgtga gaaccagctt cagcaaaaca atctggcagg tcgccgccaa cgccgacaga  540
tacatcgcag gccacaagag tgctgccgtg gcgaaaaccc tggcacacgc aattgccaag  600
gccgcaggcg tgcgggccaa tcctaagacc actgtgggca atatccaggc cgccaggact  660
gaactgctgg ctgcctacca gacagccttc aacagcccag acgtgaagaa ggccgcctaa  720

SEQ ID NO: 168         moltype = RNA  length = 897
FEATURE                Location/Qualifiers
source                 1..897
                       mol_type = other RNA
                       organism = synthetic construct
SEQUENCE: 168
agctccaacc ggccaagaag cgtcgcccag gcagccatcg caacagacgg caaggggatc  60
atcaataagg actgcagaga cgccgtgatc aatgatgcca aactgagggc cgccatcgcc  120
ggagctctgg tgaaggccgg gttttctagc gccgacgctg tggcactggc acctagaatc  180
gctcgggaaa tggccaagga gggggttctg ctgattaacc accacaagct gaaagcactg  240
atcggagccc aggtgggact gctgacagat gccaagatcc agagagccgc agctgcagtg  300
gacctgggca tcaaagccac actggccgca accattatcc ccaatgccct gcactccgca  360
gccttcaagg atgctgtggt ggccaacctg gtggcagctg ggttgataa gaagctggcc  420
aaggccaccg cagttgccat tgctgccaca gccctgaatc ctgcactggg acccatcgca  480
aagactgagg caatcaaggc cgagattggc gcacaggccg ctctgctggt gagcagagga  540
gtgcacctga agaaggccgc cattgagcac atcattggga gatcctttga cgccgcagtg  600
gccaccgcca ttgttagctc cccatcctg aatgcccgga tcgtgaccca cctcgtgcgg  660
gcaggaattg acaagagcct cgcagtgcag attgccccac ggattataga tagactggcc  720
aaggagccgc tgctggccct gaacactgca aagctgatga aaaacatcac aaggcagatc  780
gtcgacgtga ttaccgccga caaggcaatt aagaccgccg agcagctgga gaaggagctg  840
cctgccctgg acgacctggt gaagaaggcc tgctcctccc ccaagcctac tccaacc     897

SEQ ID NO: 169         moltype = RNA  length = 879
FEATURE                Location/Qualifiers
source                 1..879
                       mol_type = other RNA
                       organism = synthetic construct
SEQUENCE: 169
tccagcaacc ggcctagaag cgtggcccag gctgccatcg ccacagatgg caagggcatc  60
atcaacaagg actgtagaga cgccgtgatc aatgacgcca agctgagagc cgccatcgcc  120
ggagccctgg tgaaggccgg ctttagcagc gccgacgccg tggccctggc ccctcggatc  180
gcccgggaga tggccaagga gggagtgctg ctgatcaatc atcacaagct gaaggccctg  240
attggcgccc aggtgggact gctgaccgac gccaagattc agagagccgc cgctgccgtg  300
gatctgggca tcaaggccac cctggccgcc accatcatcc ctaacgccct gcactccgcc  360
gcttttaagg atgccgtggt ggctaacctg gtggctgccg gcgtggacaa gaagctggcc  420
aaagctaccg ccgttgccat cgccgctaca gctctgaatc ctgccctggg gcccatcgcc  480
aagacagagg ccattaaggc cgaaattgga gcccaggccg cactgctggt gtccagaggc  540
gtgcacctga agaaggccgc catcgagcac atcattggca gatccttcga tgctgccgtg  600
gctaccgcca tcgtgagcag ccctatcctg aatgccagaa tcgtgaccca cctggtgaga  660
gcaggcatcg acaagagcct ggccgtgcag atcgcccctc ggattatcga ccggctggcc  720
aaggagcccc tgctggccct gaacaccgcc aagctgatga agaacatcac cagacagatc  780
gtggatgtga tcaccgccga taaggccatc aaaacagccg agcagctgga gaaggagctg  840
cctgccctgg atgacctggt gaagaaggcc tgtagctaa                          879

SEQ ID NO: 170         moltype = RNA  length = 876
FEATURE                Location/Qualifiers
source                 1..876
                       mol_type = other RNA
                       organism = synthetic construct
SEQUENCE: 170
agctccaacc ggccaagaag cgtcgcccag gcagccatcg caacagacgg caaggggatc  60
atcaataagg actgcagaga cgccgtgatc aatgatgcca aactgagggc cgccatcgcc  120
ggagctctgg tgaaggccgg gttttctagc gccgacgctg tggcactggc acctagaatc  180
gctcgggaaa tggccaagga gggggttctg ctgattaacc accacaagct gaaagcactg  240
atcggagccc aggtgggact gctgacagat gccaagatcc agagagccgc agctgcagtg  300
gacctgggca tcaaagccac actggccgca accattatcc ccaatgccct gcactccgca  360
gccttcaagg atgctgtggt ggccaacctg gtggcagctg ggttgataa gaagctggcc  420
aaggccaccg cagttgccat tgctgccaca gccctgaatc ctgcactggg acccatcgca  480
aagactgagg caatcaaggc cgagattggc gcacaggccg ctctgctggt gagcagagga  540
gtgcacctga agaaggccgc cattgagcac atcattggga gatcctttga cgccgcagtg  600
gccaccgcca ttgttagctc cccatcctg aatgcccgga tcgtgaccca cctcgtgcgg  660
gcaggaattg acaagagcct cgcagtgcag attgccccac ggattataga tagactggcc  720
aaggagccgc tgctggccct gaacactgca aagctgatga aaaacatcac aaggcagatc  780
gtcgacgtga ttaccgccga caaggcaatt aagaccgccg agcagctgga gaaggagctg  840
cctgccctgg acgacctggt gaagaaggcc tgctcc                             876

SEQ ID NO: 171         moltype = RNA  length = 897
FEATURE                Location/Qualifiers
source                 1..897
                       mol_type = other RNA
                       organism = synthetic construct
```

```
SEQUENCE: 171
gccagcaatg gcaacagctc catcacccag agcgccgcct tcagccctag agctaccaca  60
aagatcagcg aagattgcag aaaggccatt atcaatgatc tgaaactgag aggcgccatc  120
gtgggagctc tggtgaaggc cggcctgtct gccgccgacg ccgccgccct ggcccctaga  180
attgccgccg aaatggccgc cgaaggcacc ctgaccatca atcaccaccg gctgaaggtg  240
ctggtcgcct ctcaactggg cctggtggcc gatgctgcag tgcaacatgc cgcagccgcc  300
atcgacctga gcttcaaggc catcctgggc gccagcatca tccctaatgc cctgggctcc  360
gccgctttca agaatgccgt gatcgctaat ctcgtggccg ccggcattga caagcacctg  420
gccagagcca cagcagtggc catcgttgcc acagcactga atcccgctct gggtcctatc  480
gccaagttcg agctgatcaa ggccgagatc gccgcccagg ccgccctgct gatcagaaga  540
ggcgtgcatc tgcagaaagc tgccatcgag cacgtgatcg gacgggcatt cgacgctgcc  600
gtggccacag ccatcatcag cagccctatc ctgtctgcca gaatcgtgac acacctggtg  660
agagccggca ttgacaaatc tatcgccatc agcctggccc ctcacatcgt gaagagactg  720
gccaaggagc cctgctggc cttcaataca gccaagctgg tgaaggatat cgccagacag  780
attgtggaca tccggaatac ccaggaggcc atcgccgtgt acaagcagct gaaggccgag  840
ctgcctaccc tggatggcct ggtgcagaag gcttgcaccc cagaacctac acccacc     897

SEQ ID NO: 172          moltype = RNA  length = 879
FEATURE                 Location/Qualifiers
source                  1..879
                        mol_type = other RNA
                        organism = synthetic construct
SEQUENCE: 172
gccagcaatg gcaacagctc catcacccag agcgccgcct tcagccctag agctaccaca  60
aagatcagcg aagattgcag aaaggccatt atcaatgatc tgaaactgag aggcgccatc  120
gtgggagctc tggtgaaggc cggcctgtct gccgccgacg ccgccgccct ggcccctaga  180
attgccgccg aaatggccgc cgaaggcacc ctgaccatca atcaccaccg gctgaaggtg  240
ctggtcgcct ctcaactggg cctggtggcc gatgctgcag tgcaacatgc cgcagccgcc  300
atcgacctga gcttcaaggc catcctgggc gccagcatca tccctaatgc cctgggctcc  360
gccgctttca agaatgccgt gatcgctaat ctcgtggccg ccggcattga caagcacctg  420
gccagagcca cagcagtggc catcgttgcc acagcactga atcccgctct gggtcctatc  480
gccaagttcg agctgatcaa ggccgagatc gccgcccagg ccgccctgct gatcagaaga  540
ggcgtgcatc tgcagaaagc tgccatcgag cacgtgatcg gacgggcatt cgacgctgcc  600
gtggccacag ccatcatcag cagccctatc ctgtctgcca gaatcgtgac acacctggtg  660
agagccggca ttgacaaatc tatcgccatc agcctggccc ctcacatcgt gaagagactg  720
gccaaggagc cctgctggc cttcaataca gccaagctgg tgaaggatat cgccagacag  780
attgtggaca tccggaatac ccaggaggcc atcgccgtgt acaagcagct gaaggccgag  840
ctgcctaccc tggatggcct ggtgcagaag gcttgcacc                        879

SEQ ID NO: 173          moltype = RNA  length = 882
FEATURE                 Location/Qualifiers
source                  1..882
                        mol_type = other RNA
                        organism = synthetic construct
SEQUENCE: 173
gctagcaatg gaaactcctc tattacacag tctgccgcct tcagcccaag agctaccaca  60
aagatcagcg aggattgtag aaaggccatc attaacgatc tgaagctgcg gggcgccatc  120
gtgggcgctc tcgtgaaagc cggactgtct gcagcagacg ctgcagcact ggctccaagg  180
atcgccgctg agatggcagc agaggggaca ctgactatta accaccatag gctgaaagtg  240
ctggtcgctt cccagctggg cctggttgca gatgcagccg tgcagcatgc tgccgctgca  300
attgacctga gcttcaaagc tatcctgggc gcctctatca ttccaaatgc tctcgggagc  360
gcagccttca aaaacgccgt gattgccaac ctggtggctg caggaattga caagcacctg  420
gccagagcca ctgctgtggc aattgtggcc actgctctga atccagcact gggacccatc  480
gcaaagtttg agctgattaa ggcagaaatt gccgctcaag cagccctgct gattagacgg  540
ggagtgcacc tgcagaaggc cgcaattgaa cacgtgatcg gccgggcatt tgacgccgct  600
gttgctactg ccatcatcag cagccctatt ctgtccgcca ggattgtcac ccacctggtc  660
agggcaggca ttgataagag cattgctatc agcctggccc cacacatcgt taagcggctg  720
gccaaagaac ccctgctggc ttttaatact gctaagctgg tgaaagacat tgcccgccag  780
atcgtggaca ttaggaatac tcaggaggcc atcgccgtgt ataaacagct caaggcagaa  840
ctgcctaccc tggacggcct ggtgcagaaa gcctgtacat aa                    882

SEQ ID NO: 174          moltype = RNA  length = 882
FEATURE                 Location/Qualifiers
source                  1..882
                        mol_type = other RNA
                        organism = synthetic construct
SEQUENCE: 174
gctagcaatg gaaactcctc tattacacag tctgccgcct tcagcccaag agctaccaca  60
aagatcagcg aggattgtag aaaggccatc attaacgatc tgaagctgcg gggcgccatc  120
gtgggcgctc tcgtgaaagc cggactgtct gtggcagacg ctgcagcact ggctccaagg  180
atcgccgctg agatggcagc agaggggaca ctgactatta accaccatag gctgaaagtg  240
ctggtcgctt cccagctggg cctggttgca gatgcagccg tgcagcatgc tgccgctgca  300
attgacctga gcttcaaagc tatcctgggc gcctctatca ttccaaatgc tctcgggagc  360
gcagccttca aaaacgccgt gattgccaac ctggtggctg caggaattga caagcacctg  420
gccagagcca ctgctgtggc aattgtggcc actgctctga atccagcact gggacccatc  480
gcaaagtttg agctgattaa ggcagaaatt gccgctcaag cagccctgct gattagacgg  540
ggagtgcacc tgcagaaggc cgcaattgaa cacgtgatcg gccgggcatt tgacgccgct  600
gttgctactg ccatcatcag cagccctatt ctgtccgcca ggattgtcac ccacctggtc  660
agggcaggca ttgataagag cattgctatc agcctggccc cacacatcgt taagcggctg  720
```

```
gccaaagaac ccctgctggc ttttaatact gctaagctgg tgaaagacat tgcccgccag  780
atcgtggaca ttaggaatac tcaggaggcc atcgccgtgt ataaacagct caaggcagaa  840
ctgcctaccc tggacggcct ggtgcagaaa gcctgtacat aa                     882

SEQ ID NO: 175          moltype = RNA  length = 897
FEATURE                 Location/Qualifiers
source                  1..897
                        mol_type = other RNA
                        organism = synthetic construct
SEQUENCE: 175
gccagcaatg gcaacagctc catcacccag agcgccgcct tcagccctag agctaccaca  60
aagatcagcg aagattgcag aaaggccatt atcaatgatc tgaaactgag aggcgccatc  120
gtgggagctc tggtgaaggc cggcctgtct gtggccgacg ccgccgccct ggcccctaga  180
attgccgccg aaatggccgc cgaaggcacc ctgaccatca atcaccaccg gctgaaggtg  240
ctggtcgcct ctcaactggg cctggtggcc gatgctgcag tgcaacatgc cgcagccgcc  300
atcgacctga gcttcaaggc catcctgggc gccagcatca tccctaatgc cctgggctcc  360
gccgctttca agaatgccgt gatcgctaat ctcgtggccg ccggcattga caagcacctg  420
gccagagcca cagcagtggc catcgttgcc acagcactga atcccgctct gggtcctatc  480
gccaagttcg agctgatcaa ggccgagatc gccgcccagg ccgccctgct gatcagaaga  540
ggcgtgcatc tgcagaaagc tgccatcgag cacgtgatcg gacgggcatt cgacgctgcc  600
gtggccacag ccatcatcag cagccctatc ctgtctgcca gaatcgtgac acacctggtg  660
agagccggca ttgacaaatc tatcgccatc agcctggccc ctcacatcgt gaagagactg  720
gccaaggagc ccctgctggc cttcaataca gccaagctgg tgaaggatat cgccagacag  780
attgtggaca tccggaatac ccaggaggcc atcgccgtgt acaagcagct gaaggccgag  840
ctgcctaccc tggatggcct ggtgcagaag gcttgcaccc cagaacctac acccacc     897

SEQ ID NO: 176          moltype = RNA  length = 879
FEATURE                 Location/Qualifiers
source                  1..879
                        mol_type = other RNA
                        organism = synthetic construct
SEQUENCE: 176
gctagcaatg gaaactcctc tattacacag tctgccgcct tcagcccaag agctaccaca  60
aagatcagcg aggattgtag aaaggccatc attaacgatc tgaagctgcg gggcgccatc  120
gtgggcgctc tcgtgaaagc cggactgtct gtggcagacg ctgcagcact ggctccaagg  180
atcgccgctg agatggcagc agaggggaca ctgactatta accaccatag gctgaaagtg  240
ctggtcgctt cccagctggg cctggttgca gatgcagccg tgcagcatgc tgccgctgca  300
attgacctga gcttcaaagc tatcctgggc gcctctatca ttccaaatgc tctcgggagc  360
gcagccttca aaaacgccgt gattgccaac ctggtggctg caggaattga caagcacctg  420
gccagagcca ctgctgtggc aattgtggcc actgctctga atccagcact gggacccatc  480
gcaaagtttg agctgattaa ggcagaaatt gccgctcaag cagccctgct gattagacgg  540
ggagtgcacc tgcagaaggc cgcaattgaa cacgtgatcg gccgggcatt tgacgccgct  600
gttgctactg ccatcatcag cagccctatt ctgtccgcca ggattgtcac ccacctggtc  660
agggcaggca ttgataagag cattgctatc agcctggccc cacacatcgt taagcggctg  720
gccaaagaac ccctgctggc ttttaatact gctaagctgg tgaaagacat tgcccgccag  780
atcgtggaca ttaggaatac tcaggaggcc atcgccgtgt ataaacagct caaggcagaa  840
ctgcctaccc tggacggcct ggtgcagaaa gcctgtaca                         879

SEQ ID NO: 177          moltype = RNA  length = 879
FEATURE                 Location/Qualifiers
source                  1..879
                        mol_type = other RNA
                        organism = synthetic construct
SEQUENCE: 177
gctagcaatg gacagtcctc tattacacag tctgccgcct tcagcccaag agctaccaca  60
aagatcagcg aggattgtag aaaggccatc attaacgatc tgaagctgcg gggcgccatc  120
gtgggcgctc tcgtgaaagc cggactgtct gcagcagacg ctgcagcact ggctccaagg  180
atcgccgctg agatggcagc agaggggaca ctgactatta accaccatag gctgaaagtg  240
ctggtcgctt cccagctggg cctggttgca gatgcagccg tgcagcatgc tgccgctgca  300
attgacctga gcttcaaagc tatcctgggc gcctctatca ttccaaatgc tctcgggagc  360
gcagccttca aaaacgccgt gattgccaac ctggtggctg caggaattga caagcacctg  420
gccagagcca ctgctgtggc aattgtggcc actgctctga atccagcact gggacccatc  480
gcaaagtttg agctgattaa ggcagaaatt gccgctcaag cagccctgct gattagacgg  540
ggagtgcacc tgcagaaggc cgcaattgaa cacgtgatcg gccgggcatt tgacgccgct  600
gttgctactg ccatcatcag cagccctatt ctgtccgcca ggattgtcac ccacctggtc  660
agggcaggca ttgataagag cattgctatc agcctggccc cacacatcgt taagcggctg  720
gccaaagaac ccctgctggc ttttaatact gctaagctgg tgaaagacat tgcccgccag  780
atcgtggaca ttaggaatac tcaggaggcc atcgccgtgt ataaacagct caaggcagaa  840
ctgcctaccc tggacggcct ggtgcagaaa gcctgtaca                         879

SEQ ID NO: 178          moltype = RNA  length = 897
FEATURE                 Location/Qualifiers
source                  1..897
                        mol_type = other RNA
                        organism = synthetic construct
SEQUENCE: 178
gctagcaatg gacagtcctc tattacacag tctgccgcct tcagcccaag agctaccaca  60
aagatcagcg aggattgtag aaaggccatc attaacgatc tgaagctgcg gggcgccatc  120
gtgggcgctc tcgtgaaagc cggactgtct gcagcagacg ctgcagcact ggctccaagg  180
```

```
atcgccgctg agatggcagc agaggggaca ctgactatta accaccatag gctgaaagtg  240
ctggtcgctt cccagctggg cctggttgca gatgcagccg tgcagcatgc tgccgctgca  300
attgacctga gcttcaaagc tatcctgggc gcctctatca ttccaaatgc tctcgggagc  360
gcagccttca aaaacgccgt gattgccaac ctggtggctg caggaattga caagcacctg  420
gccagagcca ctgctgtggc aattgtggcc actgctctga atccagcact gggacccatc  480
gcaaagtttg agctgattaa ggcagaaatt gccgctcaag cagccctgct gattagacgg  540
ggagtgcacc tgcagaaggc cgcaattgaa cacgtgatcg gccgggcatt tgacgccgct  600
gttgctactg ccatcatcag cagccctatt ctgtccgcca ggattgtcac ccacctggtc  660
agggcaggca ttgataagag cattgctatc agcctggccc cacacatcgt taagcggctg  720
gccaaagaac ccctgctggc ttttaatact gctaagctgg tgaaagacat tgcccgccag  780
atcgtggaca ttaggaatac tcaggaggcc atcgccgtgt ataaacagct caaggcagaa  840
ctgcctaccc tggacggcct ggtgcagaaa gcctgtacac ccgagcctac acctacc     897

SEQ ID NO: 179          moltype = RNA  length = 918
FEATURE                 Location/Qualifiers
source                  1..918
                        mol_type = other RNA
                        organism = synthetic construct
SEQUENCE: 179
tcatccaaca ggcctcgctc cgtggcccag gctgctattg ctaccgacgg caagggaatc  60
atcgataaag actccaggga tgccgtgatc aacgatgcca agctccgggc cgcaattgcc  120
ggagccctgg tgaaagccgg gttcagctcc gccgatgctg tggctctggc tccaaggatt  180
gctaaggaga tggccaaaga gggggtgctg ctgattaacc accacaagct gaaggcactg  240
atcggagcac agctgggact gctgactgac gccaaaatcc agcgcgccgc tgcagcagtc  300
gacctgggca tcaaggccac actggctgct accatcattc ctaacgctct gggcagcgca  360
gcctttaaga atgccgttat cgccaatctc gtggctgctg gaattgataa gcacctggcc  420
agagccacag ctgtggccat cgtggccact gccctgaacc cagcattggg ccctatcgct  480
aagtttgagc tgattaaggc cgagatcgcc gctcaggctg ccctgctgat tcgcagggga  540
gtgcacctgc agaaggctgc catcgagcac gtcatcggca gagcattcga cgccgctgtc  600
gccactgcta tcatctctag cccaatcctg agcgccagga tcgtcactca cctggtgaga  660
gctgggattg acaaatccat cgctatcagc ctggcccctc acatcgtgaa gaggctggct  720
aaggaaccac tgctggcttt taacactgct aagctgatga agaatattac aagacagatc  780
gtggacgtca tcaccgccga caaagccatc aagacagccg agcagctcga gaaggagctg  840
cctgccctgg atgacctggt gaagaaggca tcctcccccc ctaagccaac ccctacccca  900
acccctacac ctacttaa                                                918

SEQ ID NO: 180          moltype =   length =
SEQUENCE: 180
000

SEQ ID NO: 181          moltype = RNA  length = 918
FEATURE                 Location/Qualifiers
source                  1..918
                        mol_type = other RNA
                        organism = synthetic construct
SEQUENCE: 181
tcatccaaca ggcctcgctc cgtggcccag gctgctattg ctaccgacgg caagggaatc  60
atcgataaag actccaggga tgccgtgatc aacgatgcca agctccgggc cgcaattgcc  120
ggagccctgg tgaaagccgg gttcagctcc gccgatgctg tggctctggc tccaaggatt  180
gctaaggaga tggccaaaga gggggtgctg ctgattaacc accacaagct gaaggcactg  240
atcggagcac agctgggact gctgactgac gccaaaatcc agcgcgccgc tgcagcagtc  300
gacctgggca tcaaggccac actggctgct accatcattc ctaacgctct gggcagcgca  360
gcctttaaga atgccgttat cgccaatctc gtggctgctg gaattgataa gcacctggcc  420
agagccacag ctgtggccat cgtggccact gccctgaacc cagcattggg ccctatcgct  480
aagtttgagc tgattaaggc cgagatcgcc gctcaggctg ccctgctgat tcgcagggga  540
gtgcacctgc agaaggctgc catcgagcac gtcatcggca gagcattcga cgccgctgtc  600
gccactgcta tcatctctag cccaatcctg agcgccagga tcgtcactca cctggtgaga  660
gctgggattg acaaatccat cgctatcagc ctggcccctc acatcgtgaa gaggctggct  720
aaggaaccac tgctggcttt taacactgct aagctgatga agcagattac aagacagatc  780
gtggacgtca tcaccgccga caaagccatc aagacagccg agcagctcga gaaggagctg  840
cctgccctgg atgacctggt gaagaaggca tcctcccccc ctaagccaac ccctacccca  900
acccctacac ctacttaa                                                918

SEQ ID NO: 182          moltype = RNA  length = 1200
FEATURE                 Location/Qualifiers
source                  1..1200
                        mol_type = other RNA
                        organism = synthetic construct
SEQUENCE: 182
gcaggcccta ccgtcacagt gatccctgtg ggcagagaag gtggcgacat caccatcagc  60
ggcaagggct tcagcaccac aggctttggc gtgtacgtgg ccgtggcacc tgctagcgtg  120
cccgaattct acggcaatag cgacaagttc tacggctacg accccagcaa ggacaccacc  180
gagagcccta gcaccatctg ggtgtacacc cctagccaga aggccatcgg ctctcggttc  240
gcccagggca gacccatgaa caatgacggc agcttcacaa tcaccatgaa ggcccccccct  300
ttcgagcagg gcaaagactt cgtggtgctg accacaaagg cccatggcgt gggcaaaacc  360
gatcacagcg acgacacacg gacacctgtc acctacagag aggctacccc tgcccctaca  420
ggccctaaga cacccatcgc ccctagcaag cagcctagca agcaggccgc ccctagcaag  480
caggtgaagc cttctaagca ggccggcccc aacaagcagt ccaccacacc tcagcagaag  540
acagccgagc acagaagcca gaccccctgcc gcccaccgga ccatgacaaa gcaggtgagc  600
```

```
accatcggcg ccagcaaggt gacaagcggc tctctgacct ggggcatcag aacctctttt  660
acctcctacc tgagaggccc tatcgccaac ggctcttgga agctgagcgg aggcgccaat  720
tggaatggct ccgccttcac cttccctctg accagcggca gcttcgaccc agccaccaag  780
tccggaagcc tgaagtacag cggcagcgtg cacatgacag gccaccacgg catcctggac  840
atgaccctgg ccgagccaag cctgcagatc aagggaagca ccggccacct gtatctggac  900
gtgaaaagca gcagcatgga cggcaagaag accaattacg gcagagtgga cttcgccacc  960
ttcggagtga gcgtgtctgg caacgccgcc atcaagggca gccctgtgaa gctgaccgcc  1020
acaggcgcta aggcttttgc cggcttctac agagccggcg agcctatgaa ccctctgagc  1080
accaatctga ccctgagcgc cgagaaggtg tcccacaacg tgaccgtgga cgcagtgaca  1140
ggcaaggtga tcggcgacga ctctggcaag ggagccggcc ggggcctgcc cgtgacataa  1200

SEQ ID NO: 183          moltype =   length =
SEQUENCE: 183
000

SEQ ID NO: 184          moltype = RNA  length = 1200
FEATURE                 Location/Qualifiers
source                  1..1200
                        mol_type = other RNA
                        organism = synthetic construct
SEQUENCE: 184
gctgggccaa cagtgacagt gatccccgtg ggacgcgagg gcggagacat taccatctcc  60
gggaagggct ttagcacaac agggttcggt gtgtatgtgg ctgtggcccc agcaagcgtg  120
ccagagttct acgggaactc cgataaattt tatgggtatg accccagtaa agacacaacc  180
gagagcccca gcacaatttg ggtttacacc ccctctcaga aagctattgg ctcccggttc  240
gcccagggca gaccaatgaa taatgacggg agctttacca tcactatgaa ggccccccca  300
ttcgagcagg gaaaggactt tgtggtcctg actaccaagg ctcacggagt gggcaaaacc  360
gaccactctg acgacactcg gacaccggtg acataccggg aggctactcc cgctccaaca  420
ggccctaaaa ctccaatcgc ccccagcaag cagccttcaa agcaggctgc ccccagcaag  480
caggtgaagc ctagcaagca ggctggcccc aacaagcaga gcactactcc tcagcagaag  540
accgcagagc acagatctca gaccccagca gctcatcgca ctatgactaa gcaggtgtgt  600
accatcggag cctcaaaggt gaccagcgga tccctgacat ggggaatccg gactagcttt  660
acttcctacc tgcgcgggcc catcgcaaac ggcagctgga agctgtctgg gggggccaat  720
tggaacggca gcgccttcac attcccactg acttctggat ccttcgaccc cgccaccaaa  780
tccggctcac tgaagtacag cgggagcgtg cacatgactg gacaccatgg aattctggac  840
atgacactcg ctgaaccctc tctgcagatc aagggctcta ctgggcacct gtatctggat  900
gtgaagtcct cttctatgga cggcaagaag acaaactatg ggagagtgga ttttgccacc  960
ttcggagtga gcgtgagcgg aaatgctgca atcaaagggt cccccgtgaa actgaccgct  1020
accggagcaa aagcctttgc cggcttttac agagcaggag agcccatgaa ccccctgagc  1080
accaatctga cactgagcgc tgagaaagtt tgtcacaatg tgaccgttga tgcagttacc  1140
gggaaagtga tcggcgacga ttccggaaag ggggcaggaa ggggactgcc tgtcacttaa  1200

SEQ ID NO: 185          moltype = RNA  length = 1200
FEATURE                 Location/Qualifiers
source                  1..1200
                        mol_type = other RNA
                        organism = synthetic construct
SEQUENCE: 185
gctgggccaa cagtgacagt gatccccgtg ggacgcgagg gcggagacat taccatctcc  60
gggaagggct ttagcacaac agggttcggt gtgtatgtgg ctgtggcccc agcaagcgtg  120
ccagagttct acgggaactc cgataaattt tatgggtatg accccagtaa agacacaacc  180
gagagcccca gcacaatttg ggtttacacc ccctctcaga aagctattgg ctcccggttc  240
gcccagggca gaccaatgaa taatgacggg agctttacca tcactatgaa ggccccccca  300
ttcgagcagg gaaaggactt tgtggtcctg actaccaagg ctcacggagt gggcaaaacc  360
gaccactctg acgacactcg gacaccggtg acataccggg aggctactcc cgctccaaca  420
ggccctaaaa ctccaatcgc ccccagcaag cagccttcaa agcaggctgc ccccagcaag  480
caggtgaagc ctagcaagca ggctggcccc aacaagcaga gcactactcc tcagcagaag  540
accgcagagc acagatctca gaccccagca gctcatcgca ctatgactaa gcaggtgtgt  600
accatcggag cctcaaaggt gaccagcgga tccctgacat ggggaatccg gactagcttt  660
acttcctacc tgcgcgggcc catcgcaaag ggcagctgga agctgtctgg gggggccaat  720
tggaacggag gcgccttcac attcccactg acttctggat ccttcgaccc cgccaccaaa  780
tccggctcac tgaagtacag cgggagcgtg cacatgactg gacaccatgg aattctggac  840
atgacactcg ctgaaccctc tctgcagatc aagggctcta ctgggcacct gtatctggat  900
gtgaagtcct cttctatgga cggcaagaag acaaactatg ggagagtgga ttttgccacc  960
ttcggagtga gcgtgagcgg aaatgctgca atcaaagggt cccccgtgaa actgaccgct  1020
accggagcaa aagcctttgc cggcttttac agagcaggag agcccatgaa ccccctgagc  1080
acccagctga cactgagcgc tgagaaagtt tgtcacagcg tgaccgttga tgcagttacc  1140
gggaaagtga tcggcgacga ttccggaaag ggggcaggaa ggggactgcc tgtcacttaa  1200

SEQ ID NO: 186          moltype = RNA  length = 1200
FEATURE                 Location/Qualifiers
source                  1..1200
                        mol_type = other RNA
                        organism = synthetic construct
SEQUENCE: 186
gcaggcccta ccgtcacagt gatccctgtg ggcagagaag gtggcgacat caccatcagc  60
ggcaagggct tcagcaccac aggctttggc gtgtacgtgg ccgtggcacc tgctagcgtg  120
cccgaattct acggcaatag cgacaagttc tacggctacg accccagcaa ggacaccacc  180
gagagcccta gcaccatctg ggtgtacacc cctagccaga aggccatcgg ctctcggttc  240
```

-continued

```
gcccagggca gacccatgaa caatgacggc agcttcacaa tcaccatgaa ggcccccccct 300
ttcgagcagg gcaaagactt cgtggtgctg accacaaagg cccatggcgt gggcaaaacc 360
gatcacagcg acgacacacg gacacctgtc acctacagag aggctacccc tgcccctaca 420
ggccctaaga cacccatcgc ccctagcaag cagcctagca agcaggccgc ccctagcaag 480
caggtgaagc cttctaagca ggccggcccc aacaagcagt ccaccacacc tcagcagaag 540
acagccgagc acagaagcca gacccctgcc gcccaccgga ccatgacaaa gcaggtgagc 600
accatcggcg ccagcaaggt gacaagcggc tctctgacct ggggcatcag aacctctttt 660
acctcctacc tgagaggccc tatcgccaag ggctcttgga agctgagcgg aggcgccaat 720
tggaatggcg gcgccttcac cttccctctg accagcggca gcttcgaccc agccaccaag 780
tccggaagcc tgaagtacag cggcagcgtg cacatgacag gccaccacgg catcctggac 840
atgaccctgg ccgagccaag cctgcagatc aagggaagca ccggccacct gtatctggac 900
gtgaaaagca gcagcatgga cggcaagaag accaattacg gcagagtgga cttcgccacc 960
ttcggagtga gcgtgtctgg caacgccgcc atcaagggca gccctgtgaa gctgaccgcc 1020
acaggcgcta aggcttttgc cggcttctac agagccggcg agcctatgaa ccctctgagc 1080
acccagctga ccctgagcgc cgagaaggtg tcccacagcg tgaccgtgga cgcagtgaca 1140
ggcaaggtga tcggcgacga ctctggcaag ggagccggcc ggggcctgcc cgtgacataa 1200

SEQ ID NO: 187         moltype = RNA  length = 1197
FEATURE                Location/Qualifiers
source                 1..1197
                       mol_type = other RNA
                       organism = synthetic construct
SEQUENCE: 187
gccggtccaa cagtgacagt gatccctgtg ggcagagaag gcggcgatat cacaatcagc 60
ggcaagggct tctctacaac aggattcgga gtgtatgtgg ctgtcgcccc tgccagcgtg 120
cccgaattct atggaaacag cgacaagttc tacggctacg accccagcaa ggatacaacc 180
gagagcccct ccaccatctg ggtgtacacc cccagccaga aggccatcgg cagcagattc 240
gcccagggca gacctatgaa taatgacggc tccttcacca tcaccatgaa ggcccctcca 300
ttcgagcagg gcaaggattt cgtggtgctg accaccaaag cccacggcgt gggcaaaaca 360
gaccacagcg atgatacccg gacccccgtg acatacagag aagccacacc agcccctacc 420
ggccctaaga cccctatcgc cccttctaag cagcctagca agcaggccgc cccatccaaa 480
caggtgaagc ctagcaagca ggccgggccc aataagcaga gcacaacccc ccagcagaag 540
accgccgaac acagaagcca gacacccgcc gcccacagaa caatgaccaa gcaggtgtgc 600
accatcggcg cctccaaggt gaccagcggc agcctgacct ggggcattag aaccagcttt 660
accagctacc tgagaggccc tatcgccaac ggcagctgga agctgtccgg cggcgccaat 720
tggaacggca gcgcctttac cttcccccctg acaagcggca gcttcgaccc tgccaccaag 780
tctggcagcc tgaagtacag cggcagcgtg catatgaccg gccaccacgg catcctggat 840
atgaccctgg ccgaacctag cctgcagatc aagggcagca ccggccacct gtacctggac 900
gtgaaaagca gcagcatgga cggcaagaag acaaattacg gcagagtgga cttcgccacc 960
ttcggcgtga gcgtgagcgg aaatgccgcc atcaaaggaa gccctgtgaa gctgaccgcc 1020
accggcgcca aggcctttgc cggcttctac agagccggcg agcctatgaa tcctctgagc 1080
accaatctga ccctgagcgc cgaaaaggtg tgccacaatg tgacagtcga cgccgtgaca 1140
ggcaaggtca tcggcgatga ctctggcaaa ggagccggca gaggcctgcc cgtgaca 1197

SEQ ID NO: 188         moltype = RNA  length = 1197
FEATURE                Location/Qualifiers
source                 1..1197
                       mol_type = other RNA
                       organism = synthetic construct
SEQUENCE: 188
gctgggccaa cagtgacagt gatccccgtg ggacgcgagg gcggagacat taccatctcc 60
gggaagggct ttagcacaac agggttcggt gtgtatgtgg ctgtggcccc agcaagcgtg 120
ccagagttct acgggaactc cgataaattt tatgggtatg accccagtaa agacacaacc 180
gagagcccca gcacaatttg ggtttacacc ccctctcaga aagctattgg ctcccggttc 240
gcccagggca gaccaatgaa taatgacggg agctttacca tcactatgaa ggcccccccca 300
ttcgagcagg gaaaggactt tgtggtcctg actaccaagg ctcacggagt gggcaaaacc 360
gaccactctg acgacactcg gacaccggtg acataccggg aggctactcc cgctccaaca 420
ggccctaaaa ctccaatcgc cccccagcaag cagccttcaa agcaggctgc cccccagcaag 480
caggtgaagc ctagcaagca ggctggcccc aacaagcaga gcactactcc tcagcagaag 540
accgcagagc acagatctca gaccccagca gctcatcgca ctatgactaa gcaggtgtgt 600
accatcggag cctcaaaggt gaccagcgga tccctgacat ggggaatccg gactagcttt 660
acttcctacc tgcgcgggcc catcgcaaag ggcagctgga agctgtctgg gggggccaat 720
tggaacggag gcgccttcac attcccactg acttctggat ccttcgaccc cgccaccaaa 780
tccggctcac tgaagtacag cgggagcgtg cacatgactg gacaccatgg aattctggac 840
atgacactcg ctgaaccctc tctgcagatc aagggctcta ctgggcacct gtatctggat 900
gtgaagtcct cttctatgga cggcaagaag acaaactatg ggagagtgga ttttgccacc 960
ttcggagtga gcgtgagcgg aaatgctgca atcaaagggt cccccgtgaa actgaccgct 1020
accggagcaa aagcctttgc cggcttttac agagcaggag agcccatgaa ccccctgagc 1080
acccagctga cactgagcgc tgagaaagtt tgtcacagcg tgaccgttga tgcagttacc 1140
gggaaagtga tcggcgacga ttccggaaag ggggcaggaa ggggactgcc tgtcact 1197

SEQ ID NO: 189         moltype = RNA  length = 1359
FEATURE                Location/Qualifiers
source                 1..1359
                       mol_type = other RNA
                       organism = synthetic construct
SEQUENCE: 189
tcctctaata gaccaagatc cgtggctcag gccgccatcg ctacagatgg gaaaggaatc 60
atcgataagg atagtcggga tgcagtgatc aacgacgcca aactccgagc tgccatcgcc 120
```

-continued

```
ggcgccctgg tgaaggctgg gttttccagc gccgacgcag tggccctggc acctagaatc  180
gccaaggaga tggcaaagga gggcgtcctg ctgattaatc accacaagct gaaagctctg  240
attggggctc agctcggact gctgactgac gccaagatcc agagggccgc agctgccgtg  300
gatctgggga tcaaggccac tctggccgct actattattc ctaacgctct ggggtctgcc  360
gccttcaaga atgctgtcat tgccaacctg gtggctgctg gcatcgacaa acacctcgcc  420
agggctaccg ctgtggccat cgttgccaca gccctgaatc ctgccctggg cccaatcgct  480
aaatttgagc tgattaaggc tgagatcgcc gcccaggccg cactgctgat cagaaggggg  540
gtccatctgc agaaggccgc tattgaacat gtgatcggcc gcgcattcga cgctgccgtg  600
gccaccgcta tcatttcctc tccaatcctg agcgcacgga ttgtgaccca cctggtgagg  660
gctggaattg ataaaagcat cgctatctcc ctggctcctc atatcgtgaa gcgcctggcc  720
aaggagcccc tgctggcttt caacaccgcc aagctgatga agaatattac aagacagatc  780
gttgacgtga tcacagccga taaagccatc aaaacagctg agcagctgga aaaggagctc  840
cccgccctgg acgacctggt caaaaaagct agctcccctc ctaagcctac cccacacct  900
actccaaccc ccaccgccgg gcccaccgtg acagtgatcc ccgtgggaag ggagggggc  960
gacattacca ttagcggaaa agggttctcc acaaccgggt tcggcgtcta cgtggccgtg  1020
gctcctgcct ctgtgccaga gttctatggc aatagcgaca agttctatgg gtacgatcca  1080
tctaaggaca ccaccgaaag tcccagcacc atctgggtgt atacaccatc ccagaaagca  1140
atcggcagca gattcgccca aggcaggccc atgaataatg atggctcttt caccattaca  1200
atgaaggccc ctcctttcga gcagggaaag gatttcgtgg tgctgaccac caaagcacat  1260
ggcgttggaa agaccgacca cagcgacgat actcggaccc ctgtgactta cagagaggcc  1320
acccctgctc caaccggccc taaaactccc atctgataa                        1359

SEQ ID NO: 190         moltype = RNA  length = 876
FEATURE                Location/Qualifiers
source                 1..876
                       mol_type = other RNA
                       organism = synthetic construct
SEQUENCE: 190
gtggctcagg ccgctattgc tacagatgga aagggcatca tcgataagga ctcccgcgat  60
gccgtgatca atgatgccaa gctgagggct gctattgctg gcgccctggt gaaggctggc  120
ttcagctccg ccgatgcagt ggcactggct cctcggatcg ctaaggagat ggccaaggag  180
ggcgtgctcc tgatcaacca ccacaaactg aaggccctga ttggggccca gctgggcctg  240
ctcacagacg ccaagatcca gcgggccgct gcagccgtgg acctgggcat caaggccact  300
ctggctgcta caatcatccc aaacgcactc gggtccgccg ccttcaagaa tgccgtgatc  360
gccaacctgg ttgcagccgg aatcgacaaa catctggcca gagccacagc cgtggccatc  420
gtggctaccg ctctgaaccc agctctgggg cctatcgcca agtttgaact gatcaaggct  480
gagatcgccg cacaggccgc cctgctgatc agaagaggag tgcacctgca gaaagccgct  540
atcgagcacg tgatcggacg cgcctttgac gcagccgtgg ctactgccat catcagctct  600
ccaattctga gcgcaaggat cgtgacacac ctggtgaggg ccggcatcga caagagcatc  660
gcaatttccc tggcccctca catcgtgaag cggctggcta aggagccact gctcgccttt  720
aataccgcaa aactgatgaa ggctattaca cgccagatcg tggatgtgat caccgctgat  780
aaggcaatca agaccgccga acagctggaa aaggaactgc ctgccctgga tgacctggtg  840
aaaaaggcta tgggcccccc taagcctacc tgataa                          876

SEQ ID NO: 191         moltype = RNA  length = 1308
FEATURE                Location/Qualifiers
source                 1..1308
                       mol_type = other RNA
                       organism = synthetic construct
SEQUENCE: 191
tccagcaacc ggcctagaag cgtggcccag gccgccatcg ccaccgacgg caagggcatc  60
atcgacaagg attcccggga cgccgtgatc aatgacgcca agctgagagc cgccatcgcc  120
ggcgccctgg tgaaggccgg cttcagcagc gccgacgccg tggccctggc ccccagaatc  180
gccaaggaga tggccaagga aggcgtgctg ctgatcaatc accacaagct gaaggccctg  240
atcggcgccc agctgggcct gctgacagat gccaagatcc agagagccgc tgccgccgtg  300
gacctgggca tcaaggccac cctggccgcc accatcatcc ctaacgccct gggcagcgct  360
gccttcaaga atgccgtgat cgccaacctg gtggccgccg gcatcgacaa gcacctggcc  420
agagccacag ccgtggccat cgtggccacc gccctgaatc ctgccctggg ccccatcgcc  480
aagttcgagc tgatcaaggc cgagatcgcc gcccaggccg ccctgctgat ccggcggggc  540
gtgcacctgc agaaggccgc catcgaacac gtgatcggca gagccttcga tgccgccgtg  600
gccaccgcca tcatcagctc ccccatcctg agcgccagaa tcgtgaccca cctggtgcgg  660
gccggcatcg acaagtccat cgccattagc ctggcccctc acatcgtgaa gcgcctggcc  720
aaggagcccc tgctggcctt caataccgcc aagctgatga agaatatcac cagacagatc  780
gtggatgtga tcaccgccga taaggccatc aagaccgccg agcagctgga gaaagagctg  840
cccgccctgg acgacctggt gaaaaaggcc atgggccccc ctaagcctac aggcggcggc  900
ggaggcgctg gacctaccgt gaccgtgatc cccgtgggca gagagggcgg cgatatcacc  960
atcagcggca agggcttcag caccaccggc ttcggcgtgt acgtggccgt ggcccctgcc  1020
agcgtgcccg agttctacgg caatagcgac aagttctacg gctacgaccc cagcaaggac  1080
accacagaat ctcccagcac catctgggtg tacaccccca gccagaaggc cattggcagc  1140
cggttcgccc agggccggcc tatgaacaat gatggcagct tcacaatcac catgaaggcc  1200
ccacccttcg agcagggcaa ggacttcgtg gtgctgacca ccaaggccca cggagtgggc  1260
aagggcgacc acggcgacga cacacggacc cccgtgggct acagatga              1308

SEQ ID NO: 192         moltype = RNA  length = 1320
FEATURE                Location/Qualifiers
source                 1..1320
                       mol_type = other RNA
                       organism = synthetic construct
SEQUENCE: 192
```

```
agcagcaacc gcccaaggtc tgtcgcacag gctgctatcg ccacagatgg caagggaatc  60
attgataagg acagcaggga tgctgtgatc aacgacgcaa aactgagagc cgccatcgcc  120
ggcgcactgg tgaaagccgg cttttcttcc gccgacgcag tggctctggc tcccagaatc  180
gctaaggaaa tggccaagga gggagtgctg ctgatcaatc accacaaact gaaggctctg  240
atcggggctc agctgggcct gctgactgac gctaagattc agagagcagc agcagctgtc  300
gacctgggaa tcaaggcaac cctggcagcc actatcattc caaatgctct gggctctgcc  360
gccttcaaaa acgccgtgat tgccaatctc gtggcagctg gaatcgataa gcacctggca  420
cgggccaccg ccgtggctat cgtggccacc gctctgaatc ccgccctggg ccctattgcc  480
aagtttgaac tgatcaaagc cgagatcgct gcacaggccg ccctgctcat ccgcaggggg  540
gtccacctgc agaaagcagc catcgagcac gtgatcggca gggcctttga tgcagccgtc  600
gccactgcca tcatcagctc tccaatcctg tctgcccgga ttgtgactca cctggtgcgc  660
gccggcatcg ataagtccat cgcaatctct ctggccccac acatcgtgaa gagactggcc  720
aaagaaccac tcctggcttt caataccgcc aaactcatga aaaacatcac ccggcagatc  780
gtcgatgtga ttaccgccga caaggctatc aagaccgccg agcagctcga aaaggagctg  840
cctgccctgg acgacctggt gaagaaagcc tcctctccac ccaaacccac cccaactcca  900
actccaaccc ctacagctgg ccccaccgtg accgtcatcc cagtgggaag ggaaggagga  960
gacatcacaa tctctggaaa ggggtttagc acaaccggat ttggagtgta cgtcgccgtg  1020
gcccccgcat ccgtgccaga attctacggc aattccgata aattctacgg gtacgacccc  1080
tccaaggaca ctacagagag cccctctaca atttgggtgt acaccccaag ccagaaggcc  1140
atcggaagca gatttgctca gggccggcca atgaacaacg acggatcctt cacaatcaca  1200
atgaaagcac ctcccttga gcagggcaag gattttgtgg tgctgaccac caaggctcac  1260
ggggtcggaa agaccgatca cagcgacgat acaagaaccc ccgtgacata ccggtgataa  1320

SEQ ID NO: 193         moltype = RNA  length = 90
FEATURE                Location/Qualifiers
source                 1..90
                       mol_type = other RNA
                       organism = synthetic construct
SEQUENCE: 193
tccggcagca tcctggccat ctactccacc gtggcctcca gcctggtgct gctggtgagc  60
ctgggcgcta tctccttcgg gtctgggtaa                                  90

SEQ ID NO: 194         moltype = RNA  length = 87
FEATURE                Location/Qualifiers
source                 1..87
                       mol_type = other RNA
                       organism = synthetic construct
SEQUENCE: 194
agcgggagca ttctggccat ctactctacc gtggcctcta gcctggtgct gctggtgtct  60
ctgggagcca ttagcttcgg atctggc                                     87

SEQ ID NO: 195         moltype = RNA  length = 87
FEATURE                Location/Qualifiers
source                 1..87
                       mol_type = other RNA
                       organism = synthetic construct
SEQUENCE: 195
agcggctcca tcctggccat ctactctacc gtggccagca gcctggtgct gctggtgtcc  60
ctgggagcca tctccttcgg ctccggg                                     87

SEQ ID NO: 196         moltype = RNA  length = 81
FEATURE                Location/Qualifiers
source                 1..81
                       mol_type = other RNA
                       organism = synthetic construct
SEQUENCE: 196
attctggcaa tctatagcac cgtggctagc agcctggtgc tgctggtgtc tctgggagcc  60
atcagcttcg gctctggcta a                                           81

SEQ ID NO: 197         moltype = RNA  length = 90
FEATURE                Location/Qualifiers
source                 1..90
                       mol_type = other RNA
                       organism = synthetic construct
SEQUENCE: 197
agcggcagca ttctggcaat ctatagcacc gtggctagca gcctggtgct gctggtgtct  60
ctgggagcca tcagcttcgg ctctggctaa                                  90

SEQ ID NO: 198         moltype = RNA  length = 90
FEATURE                Location/Qualifiers
source                 1..90
                       mol_type = other RNA
                       organism = synthetic construct
SEQUENCE: 198
agcggcagca ttctggcaat ctatagcacc gtggctagca gcctggtgct gctggtgtct  60
ctgggagcca tcagcttcgg ctctggctaa                                  90

SEQ ID NO: 199         moltype = RNA  length = 81
FEATURE                Location/Qualifiers
```

-continued

```
source                  1..81
                        mol_type = other RNA
                        organism = synthetic construct
SEQUENCE: 199
attctggcaa tctatagcac cgtggctagc agcctggtgc tgctggtgtc tctgggagcc  60
atcagcttcg gctctggcta a                                            81

SEQ ID NO: 200          moltype = RNA  length = 90
FEATURE                 Location/Qualifiers
source                  1..90
                        mol_type = other RNA
                        organism = synthetic construct
SEQUENCE: 200
agcggctcta ttctggccat ctacagcaca gtggccagct ctctggtgct gctggttagc  60
ctgggcgcca tcagcttcgg cagcggctaa                                   90

SEQ ID NO: 201          moltype = RNA  length = 90
FEATURE                 Location/Qualifiers
source                  1..90
                        mol_type = other RNA
                        organism = synthetic construct
SEQUENCE: 201
agcggcagca ttctggcaat ctatagcacc gtggctagca gcctggtgct gctggtgtct  60
ctgggagcca tcagcttcgg ctctggctaa                                   90

SEQ ID NO: 202          moltype = AA  length = 267
FEATURE                 Location/Qualifiers
source                  1..267
                        mol_type = protein
                        organism = Cutibacterium acnes
SEQUENCE: 202
MKKTHLVAPL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTID  120
TIHTATTTLQ NKVRPAHVEL GLEVTKAVLL TANPASTAKE LDAEGAALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                      267

SEQ ID NO: 203          moltype = AA  length = 239
FEATURE                 Location/Qualifiers
source                  1..239
                        mol_type = protein
                        organism = Cutibacterium acnes
SEQUENCE: 203
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 204          moltype = AA  length = 377
FEATURE                 Location/Qualifiers
source                  1..377
                        mol_type = protein
                        organism = Cutibacterium acnes
SEQUENCE: 204
SSNRPRSVAQ AAIATDGKGI IDKDCRDAVI NDAKLRAAIA GALVKAGFSS ADAVALAPRI  60
AKEMAKEGVL LINHHKLKAL IGAQLGLLTD AKIQRAAAAV DLGIKATLAA TIIPNALHSA  120
AFKDAVVANL VAAGVDKKLA KATAVAIAAT ALNPALGPIA KTEAIKAEIA AQAALLVGRG  180
VHLKKAAIEH IIGRSFDAAV ATAIVSSPIL NARIVTHLVR AGIDKSLAVQ IAPRIIDRLA  240
KEPLLALNTA KLMKNITRQI VDVITADKAI KTAEQLEKEL PALDDLVKKA CSCPKPTPTP  300
TPTPTPTPKP TPTPTPKPTP TPKPKPTPAP APTSGATSDE STSRSGGHSQ GGSGTHYIHH  360
GVAPVLTHSS DLPSTGF                                                 377

SEQ ID NO: 205          moltype = AA  length = 392
FEATURE                 Location/Qualifiers
source                  1..392
                        mol_type = protein
                        organism = Cutibacterium acnes
SEQUENCE: 205
ASNGNSSITQ SAAFSPRATT KISEDCRKAI INDLKLRGAI VGALVKAGLS AADAAALAPR  60
IAAEMAAEGT LTINHHRLKV LVASQLGLVA DAAVQHAAAA IDLSFKAILG ASIIPNALGS  120
AAFKNAVIAN LVAAGIDKHL ARATAVAIVA TALNPALGPI AKFELIKAEI AAQAALLIRR  180
GVHLQKAAIE HVIGRAFDAA VATAIISSPI LSARIVTHLV RAGIDKSIAI SLAPHIVKRL  240
AKEPLLAFNT AKLVKDIARQ IVDIRNTQEA IAVYKQLKAE LPTLDGLVQK ACTPEPTPTP  300
TPTPTPTPTP APTPTPAPTP TPAPTPAPTP TPAPTPTPTP TPTPTPTPTH GATTTTPISR  360
TTDRHNLGSH HTRIAAPALI HAKALPATGT GA                                392

SEQ ID NO: 206          moltype = AA  length = 436
FEATURE                 Location/Qualifiers
source                  1..436
```

```
                        mol_type = protein
                        organism = Cutibacterium acnes
SEQUENCE: 206
AGPTVTVIPV GREGGDITIS GKGFSTTGFG VYVAVAPASV PEFYGNSDKF YGYDPSKDTT  60
ESPSTIWVYT PSQKAIGSRF AQGRPMNNDG SFTITMKAPP FEQGKDFVVL TTKAHGVGKT  120
DHSDDTRTPV TYREATPAPT GPKTPIAPSK QPSKQAAPSK QVKPSKQAGP NKQSTTPQQK  180
TAEHRSQTPA AHRTMTKQVC TIGASKVTSG SLTWGIRTSF TSYLRGPIAN GSWKLSGGAN  240
WNGSAFTFPL TSGSFDPATK SGSLKYSGSV HMTGHHGILD MTLAEPSLQI KGSTGHLYLD  300
VKSSSMDGKK TNYGRVDFAT FGVSVSGNAA IKGSPVKLTA TGAKAFAGFY RAGEPMNPLS  360
TNLTLSAEKV CHNVTVDAVT GKVIGDDSGK GAGRGLPVTG AEGPSSDEID LGIVGGLALT  420
AVVSTVVVCR RYAARI                                                 436

SEQ ID NO: 207          moltype = AA  length = 268
FEATURE                 Location/Qualifiers
source                  1..268
                        mol_type = protein
                        organism = synthetic construct
SEQUENCE: 207
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAAS  240
GSILAIYSTV ASSLVLLVSL GAISFGSG                                    268

SEQ ID NO: 208          moltype = AA  length = 23
FEATURE                 Location/Qualifiers
source                  1..23
                        mol_type = protein
                        organism = Influenza virus
SEQUENCE: 208
ILAIYSTVAS SLVLLVSLGA ISF                                         23

SEQ ID NO: 209          moltype = AA  length = 23
FEATURE                 Location/Qualifiers
source                  1..23
                        mol_type = protein
                        organism = Influenza virus
SEQUENCE: 209
ILAIYSTVAS SLVLVVSLGA ISF                                         23

SEQ ID NO: 210          moltype = AA  length = 17
FEATURE                 Location/Qualifiers
source                  1..17
                        mol_type = protein
                        organism = Influenza A virus
SEQUENCE: 210
MKAKLLVLLC TFTATYA                                                17

SEQ ID NO: 211          moltype = AA  length = 17
FEATURE                 Location/Qualifiers
source                  1..17
                        mol_type = protein
                        organism = Influenza A virus
SEQUENCE: 211
MKAILVVLLY TFATANA                                                17

SEQ ID NO: 212          moltype = AA  length = 16
FEATURE                 Location/Qualifiers
source                  1..16
                        mol_type = protein
                        organism = Influenza A virus
SEQUENCE: 212
MKTIIALSYI LCLVFA                                                 16

SEQ ID NO: 213          moltype = AA  length = 15
FEATURE                 Location/Qualifiers
source                  1..15
                        mol_type = protein
                        organism = Influenza B virus
SEQUENCE: 213
MKAIIVLLMV VTSNA                                                  15

SEQ ID NO: 214          moltype = AA  length = 12
FEATURE                 Location/Qualifiers
source                  1..12
                        mol_type = protein
                        organism = SARS CoV-2 virus
SEQUENCE: 214
MFVFLVLLPL VS                                                     12
```

```
SEQ ID NO: 215         moltype = AA  length = 21
FEATURE                Location/Qualifiers
source                 1..21
                       mol_type = protein
                       organism = SARS CoV-2 virus
SEQUENCE: 215
MFLLTTKRTM FVFLVLLPLV S                                            21

SEQ ID NO: 216         moltype = AA  length = 71
FEATURE                Location/Qualifiers
source                 1..71
                       mol_type = protein
                       organism = Varicella-zoster virus
SEQUENCE: 216
MSPCGYYSKW RNRDRPEYRR NLRFRRFFSS IHPNAAAGSG FNGPGVFITS VTGVWLCFLC  60
IFSMFVTAVV S                                                       71

SEQ ID NO: 217         moltype = AA  length = 30
FEATURE                Location/Qualifiers
source                 1..30
                       mol_type = protein
                       organism = Varicella-zoster virus
SEQUENCE: 217
MGTVNKPVVG VLMGFGIITG TLRITNPVRA                                   30

SEQ ID NO: 218         moltype = AA  length = 20
FEATURE                Location/Qualifiers
source                 1..20
                       mol_type = protein
                       organism = Varicella-zoster virus
SEQUENCE: 218
MFLIQCLISA VIFYIQVTNA                                              20

SEQ ID NO: 219         moltype = AA  length = 21
FEATURE                Location/Qualifiers
source                 1..21
                       mol_type = protein
                       organism = Varicella-zoster virus
SEQUENCE: 219
MQALGIKTEH FIIMCLLSGH A                                            21

SEQ ID NO: 220         moltype = AA  length = 23
FEATURE                Location/Qualifiers
source                 1..23
                       mol_type = protein
                       organism = Measles virus
SEQUENCE: 220
MGLKVNVSAI FMAVLLTLQT PTG                                          23

SEQ ID NO: 221         moltype = AA  length = 21
FEATURE                Location/Qualifiers
source                 1..21
                       mol_type = protein
                       organism = Rubella virus
SEQUENCE: 221
MGAAAALTAV VLQGYNPPAY G                                            21

SEQ ID NO: 222         moltype = AA  length = 23
FEATURE                Location/Qualifiers
source                 1..23
                       mol_type = protein
                       organism = Rubella virus
SEQUENCE: 222
MGAPQAFLAG LLLAAVAVGT ARA                                          23

SEQ ID NO: 223         moltype = AA  length = 19
FEATURE                Location/Qualifiers
source                 1..19
                       mol_type = protein
                       organism = Mumps virus
SEQUENCE: 223
MKVFLVTCLG FAVFSSSVC                                               19

SEQ ID NO: 224         moltype = AA  length = 32
FEATURE                Location/Qualifiers
source                 1..32
                       mol_type = protein
                       organism = Ebola virus
```

```
SEQUENCE: 224
MGVTGILQLP RDRFKRTSFF LWVIILFQRT FS                            32

SEQ ID NO: 225          moltype = AA  length = 16
FEATURE                 Location/Qualifiers
source                  1..16
                        mol_type = protein
                        organism = Smallpox virus
SEQUENCE: 225
MRSLIIFLLF PSIIYS                                              16

SEQ ID NO: 226          moltype = AA  length = 19
FEATURE                 Location/Qualifiers
source                  1..19
                        mol_type = protein
                        organism = Rabies virus
SEQUENCE: 226
MVPQALLFVP LLVFPLCFG                                           19

SEQ ID NO: 227          moltype = AA  length = 17
FEATURE                 Location/Qualifiers
source                  1..17
                        mol_type = protein
                        organism = Influenza A virus
SEQUENCE: 227
MKAILVVLLY TFTTANA                                             17

SEQ ID NO: 228          moltype = AA  length = 17
FEATURE                 Location/Qualifiers
source                  1..17
                        mol_type = protein
                        organism = Influenza A virus
SEQUENCE: 228
MKVKLLVLLC TFTATYA                                             17

SEQ ID NO: 229          moltype = AA  length = 17
FEATURE                 Location/Qualifiers
source                  1..17
                        mol_type = protein
                        organism = Influenza A virus
SEQUENCE: 229
MKAILVVMLY TFTTANA                                             17

SEQ ID NO: 230          moltype = AA  length = 16
FEATURE                 Location/Qualifiers
source                  1..16
                        mol_type = protein
                        organism = Influenza A virus
SEQUENCE: 230
MKTIIALSYI LCLVFT                                              16

SEQ ID NO: 231          moltype = AA  length = 16
FEATURE                 Location/Qualifiers
source                  1..16
                        mol_type = protein
                        organism = synthetic construct
SEQUENCE: 231
MKTIIALSNI LCLVFA                                              16

SEQ ID NO: 232          moltype = AA  length = 16
FEATURE                 Location/Qualifiers
source                  1..16
                        mol_type = protein
                        organism = synthetic construct
SEQUENCE: 232
MKAIIALSNI LCLVFA                                              16

SEQ ID NO: 233          moltype = AA  length = 16
FEATURE                 Location/Qualifiers
source                  1..16
                        mol_type = protein
                        organism = Influenza A virus
SEQUENCE: 233
MKTIIALSCI LCLVFA                                              16

SEQ ID NO: 234          moltype = AA  length = 16
FEATURE                 Location/Qualifiers
source                  1..16
                        mol_type = protein
```

```
                        organism = Influenza A virus
SEQUENCE: 234
MKTIIALSHI LCLVFA                                                   16

SEQ ID NO: 235          moltype = AA  length = 15
FEATURE                 Location/Qualifiers
source                  1..15
                        mol_type = protein
                        organism = Influenza B virus
SEQUENCE: 235
MKAIIVLLMV VTSSA                                                    15

SEQ ID NO: 236          moltype = AA  length = 15
FEATURE                 Location/Qualifiers
source                  1..15
                        mol_type = protein
                        organism = Influenza B virus
SEQUENCE: 236
MEAIIVLLMV VTSNA                                                    15

SEQ ID NO: 237          moltype = AA  length = 17
FEATURE                 Location/Qualifiers
source                  1..17
                        mol_type = protein
                        organism = Influenza B virus
VARIANT                 3
                        note = A or V
VARIANT                 4
                        note = I or K
VARIANT                 6
                        note = V or L
VARIANT                 8
                        note = L or M
VARIANT                 10
                        note = Y or C
VARIANT                 13
                        note = T or A
VARIANT                 16
                        note = N or Y
VARIANT                 14
                        note = T or A
VARIANT                 15
                        note = T or A
SEQUENCE: 237
MKXXLXVXLX TFXXXXA                                                  17

SEQ ID NO: 238          moltype = AA  length = 16
FEATURE                 Location/Qualifiers
source                  1..16
                        mol_type = protein
                        organism = Influenza B virus
VARIANT                 3
                        note = T or A
VARIANT                 9
                        note = Y, N, C or H
VARIANT                 16
                        note = T or A
SEQUENCE: 238
MKXIIALSXI LCLVFX                                                   16

SEQ ID NO: 239          moltype = AA  length = 15
FEATURE                 Location/Qualifiers
source                  1..15
                        mol_type = protein
                        organism = Influenza B virus
VARIANT                 14
                        note = S or N
SEQUENCE: 239
MKAIIVLLMV VTSXA                                                    15

SEQ ID NO: 240          moltype = AA  length = 15
FEATURE                 Location/Qualifiers
source                  1..15
                        mol_type = protein
                        organism = Influenza B virus
VARIANT                 2
                        note = K or E
SEQUENCE: 240
MXAIIVLLMV VTSNA                                                    15
```

```
SEQ ID NO: 241         moltype = AA  length = 21
FEATURE                Location/Qualifiers
source                 1..21
                       mol_type = protein
                       organism = Influenza virus
SEQUENCE: 241
ILWISFAISC FLLCVVLLGF I                                              21

SEQ ID NO: 242         moltype = AA  length = 21
FEATURE                Location/Qualifiers
source                 1..21
                       mol_type = protein
                       organism = Influenza virus
SEQUENCE: 242
STAASSLAVT LMLAIFIVYM V                                              21

SEQ ID NO: 243         moltype = AA  length = 21
FEATURE                Location/Qualifiers
source                 1..21
                       mol_type = protein
                       organism = SARS CoV-2 virus
SEQUENCE: 243
WYIWLGFIAG LIAIVMVTIM L                                              21

SEQ ID NO: 244         moltype = AA  length = 21
FEATURE                Location/Qualifiers
source                 1..21
                       mol_type = protein
                       organism = Varicella-zoster virus
SEQUENCE: 244
FGALAVGLLV LAGLVAAFFA Y                                              21

SEQ ID NO: 245         moltype = AA  length = 21
FEATURE                Location/Qualifiers
source                 1..21
                       mol_type = protein
                       organism = Varicella-zoster virus
SEQUENCE: 245
AAWTGGLAAV VLLCLVIFLI C                                              21

SEQ ID NO: 246         moltype = AA  length = 21
FEATURE                Location/Qualifiers
source                 1..21
                       mol_type = protein
                       organism = Varicella-zoster virus
SEQUENCE: 246
IIIPIVASVM ILTAMVIVIV I                                              21

SEQ ID NO: 247         moltype = AA  length = 21
FEATURE                Location/Qualifiers
source                 1..21
                       mol_type = protein
                       organism = Varicella-zoster virus
SEQUENCE: 247
YFWCVQLKMI FFAWFVYGMY L                                              21

SEQ ID NO: 248         moltype = AA  length = 21
FEATURE                Location/Qualifiers
source                 1..21
                       mol_type = protein
                       organism = Measles virus
SEQUENCE: 248
IVYILIAVCL GGLIGIPALI C                                              21

SEQ ID NO: 249         moltype = AA  length = 21
FEATURE                Location/Qualifiers
source                 1..21
                       mol_type = protein
                       organism = Rubella virus
SEQUENCE: 249
LDHAFAAFVL LVPWVLIFMV C                                              21

SEQ ID NO: 250         moltype = AA  length = 21
FEATURE                Location/Qualifiers
source                 1..21
                       mol_type = protein
                       organism = Rubella virus
SEQUENCE: 250
```

```
WWQLTLGAIC ALLLAGLLAC C                                            21

SEQ ID NO: 251          moltype = AA  length = 21
FEATURE                 Location/Qualifiers
source                  1..21
                        mol_type = protein
                        organism = Mumps virus
SEQUENCE: 251
IVAALVLSIL SIIISLLFCC W                                            21

SEQ ID NO: 252          moltype = AA  length = 21
FEATURE                 Location/Qualifiers
source                  1..21
                        mol_type = protein
                        organism = Ebola virus
SEQUENCE: 252
WIPAGIGVTG VIIAVIALFC I                                            21

SEQ ID NO: 253          moltype = AA  length = 21
FEATURE                 Location/Qualifiers
source                  1..21
                        mol_type = protein
                        organism = Rabies virus
SEQUENCE: 253
VLLSAGALTA LMLIIFLMTC W                                            21

SEQ ID NO: 254          moltype = AA  length = 5
FEATURE                 Location/Qualifiers
source                  1..5
                        mol_type = protein
                        organism = synthetic construct
SEQUENCE: 254
DGGGS                                                              5

SEQ ID NO: 255          moltype = AA  length = 5
FEATURE                 Location/Qualifiers
source                  1..5
                        mol_type = protein
                        organism = synthetic construct
SEQUENCE: 255
TGEKP                                                              5

SEQ ID NO: 256          moltype = AA  length = 4
FEATURE                 Location/Qualifiers
source                  1..4
                        mol_type = protein
                        organism = synthetic construct
SEQUENCE: 256
GGRR                                                               4

SEQ ID NO: 257          moltype = AA  length = 5
FEATURE                 Location/Qualifiers
source                  1..5
                        mol_type = protein
                        organism = synthetic construct
REPEAT                  1..5
                        note = 1, 2, 3, 4 or 5 repeats
SEQUENCE: 257
GGGGS                                                              5

SEQ ID NO: 258          moltype = AA  length = 14
FEATURE                 Location/Qualifiers
source                  1..14
                        mol_type = protein
                        organism = synthetic construct
SEQUENCE: 258
EGKSSGSGSE SKVD                                                    14

SEQ ID NO: 259          moltype = AA  length = 18
FEATURE                 Location/Qualifiers
source                  1..18
                        mol_type = protein
                        organism = synthetic construct
SEQUENCE: 259
KESGSVSSEQ LAQFRSLD                                                18

SEQ ID NO: 260          moltype = AA  length = 8
FEATURE                 Location/Qualifiers
source                  1..8
```

```
                        mol_type = protein
                        organism = synthetic construct
SEQUENCE: 260
GGRRGGGS                                                            8

SEQ ID NO: 261          moltype = AA  length = 9
FEATURE                 Location/Qualifiers
source                  1..9
                        mol_type = protein
                        organism = synthetic construct
SEQUENCE: 261
LRQRDGERP                                                           9

SEQ ID NO: 262          moltype = AA  length = 12
FEATURE                 Location/Qualifiers
source                  1..12
                        mol_type = protein
                        organism = synthetic construct
SEQUENCE: 262
LRQKDGGGSE RP                                                       12

SEQ ID NO: 263          moltype = AA  length = 18
FEATURE                 Location/Qualifiers
source                  1..18
                        mol_type = protein
                        organism = synthetic construct
SEQUENCE: 263
GSTSGSGKPG SGEGSTKG                                                 18

SEQ ID NO: 264          moltype = RNA  length = 11
FEATURE                 Location/Qualifiers
source                  1..11
                        mol_type = other RNA
                        organism = synthetic construct
SEQUENCE: 264
gggatcctac c                                                        11

SEQ ID NO: 265          moltype = RNA  length = 140
FEATURE                 Location/Qualifiers
source                  1..140
                        mol_type = other RNA
                        organism = synthetic construct
SEQUENCE: 265
ggacagatcg cctggagacg ccatccacgc tgttttgacc tccatagaag acaccgggac  60
cgatccagcc tccgcggccg ggaacggtgc attggaacgc ggattccccg tgccaagagt  120
gactcaccgt ccttgacacg                                               140

SEQ ID NO: 266          moltype = RNA  length = 100
FEATURE                 Location/Qualifiers
source                  1..100
                        mol_type = other RNA
                        organism = synthetic construct
SEQUENCE: 266
cgggtggcat ccctgtgacc cctccccagt gcctctcctg gccctggaag ttgccactcc  60
agtgcccacc agccttgtcc taataaaatt aagttgcatc                         100

SEQ ID NO: 267          moltype = RNA  length = 110
FEATURE                 Location/Qualifiers
source                  1..110
                        mol_type = other RNA
                        organism = synthetic construct
SEQUENCE: 267
aaaaaaaaaa aaaaaaaaaa aaaaaaaaaa gcatatgact aaaaaaaaaa aaaaaaaaaa  60
aaaaaaaaaa aaaaaaaaaa aaaaaaaaaa aaaaaaaaaa aaaaaaaaaa             110

SEQ ID NO: 268          moltype = AA  length = 256
FEATURE                 Location/Qualifiers
source                  1..256
                        mol_type = protein
                        organism = synthetic construct
SEQUENCE: 268
MKAILVVLLY TFATANAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAA                                                   256

SEQ ID NO: 269          moltype = AA  length = 254
FEATURE                 Location/Qualifiers
```

-continued

```
source                  1..254
                        mol_type = protein
                        organism = synthetic construct
SEQUENCE: 269
MKAIIVLLMV VTSNAVEPTT TISATSTHEL SASDARNSIQ LLNAHIATLQ SVQKSVPGSD  60
YSDQIRDLLK AAFDLRGLIE TLAHGGIPFY DPSTIMPRIK LVATTIDTIH TATTTLQNKV  120
RPAHVELGLE VTKAVLLTAN PASTAKELDA EGAALKARLE KVSQYPDLTP NDVATVYVRT  180
NFSKTIWQVR ANRDRYILGH KSAAVYKTLN HAITKAVGVR LNPKTTVGNI QAARTELLAA  240
YQTAFNSPDV KKAA                                                    254

SEQ ID NO: 270          moltype = AA  length = 258
FEATURE                 Location/Qualifiers
source                  1..258
                        mol_type = protein
                        organism = synthetic construct
SEQUENCE: 270
MVPQALLFVP LLVFPLCFGV EPTTTISATS THELSASDAR NSIQLLNAHI ATLQSVQKSV  60
PGSDYSDQIR DLLKAAFDLR GLIETLAHGG IPFYDPSTIM PRIKLVATTI DTIHTATTTL  120
QNKVRPAHVE LGLEVTKAVL LTANPASTAK ELDAEGAALK ARLEKVSQYP DLTPNDVATV  180
YVRTNFSKTI WQVRANRDRY ILGHKSAAVY KTLNHAITKA VGVRLNPKTT VGNIQAARTE  240
LLAAYQTAFN SPDVKKAA                                                258

SEQ ID NO: 271          moltype = AA  length = 259
FEATURE                 Location/Qualifiers
source                  1..259
                        mol_type = protein
                        organism = synthetic construct
SEQUENCE: 271
MFLIQCLISA VIFYIQVTNA VEPTTTISAT STHELSASDA RNSIQLLNAH IATLQSVQKS  60
VPGSDYSDQI RDLLKAAFDL RGLIETLAHG GIPFYDPSTI MPRIKLVATT IDTIHTATTT  120
LQNKVRPAHV ELGLEVTKAV LLTANPASTA KELDAEGAAL KARLEKVSQY PDLTPNDVAT  180
VYVRTNFSKT IWQVRANRDR YILGHKSAAV YKTLNHAITK AVGVRLNPKT TVGNIQAART  240
ELLAAYQTAF NSPDVKKAA                                               259

SEQ ID NO: 272          moltype = AA  length = 271
FEATURE                 Location/Qualifiers
source                  1..271
                        mol_type = protein
                        organism = synthetic construct
SEQUENCE: 272
MGVTGILQLP RDRFKRTSFF LWVIILFQRT FSVEPTTTIS ATSTHELSAS DARNSIQLLN  60
AHIATLQSVQ KSVPGSDYSD QIRDLLKAAF DLRGLIETLA HGGIPFYDPS TIMPRIKLVA  120
TTIDTIHTAT TTLQNKVRPA HVELGLEVTK AVLLTANPAS TAKELDAEGA ALKARLEKVS  180
QYPDLTPNDV ATVYVRTNFS KTIWQVRANR DRYILGHKSA AVYKTLNHAI TKAVGVRLNP  240
KTTVGNIQAA RTELLAAYQT AFNSPDVKKA A                                 271

SEQ ID NO: 273          moltype = AA  length = 285
FEATURE                 Location/Qualifiers
source                  1..285
                        mol_type = protein
                        organism = synthetic construct
SEQUENCE: 273
MKAILVVLLY TFATANAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATVYV  180
RTNFSKTIWQ VRANRDRYIL GHKSAAVYKT LNHAITKAVG VRLNPKTTVG NIQAARTELL  240
AAYQTAFNSP DVKKAASGSI LAIYSTVASS LVLVVSLGAI SFGSG                  285

SEQ ID NO: 274          moltype = AA  length = 281
FEATURE                 Location/Qualifiers
source                  1..281
                        mol_type = protein
                        organism = synthetic construct
SEQUENCE: 274
MKAIIVLLMV VTSNAVEPTT TISATSTHEL SASDARNSIQ LLNAHIATLQ SVQKSVPGSD  60
YSDQIRDLLK AAFDLRGLIE TLAHGGIPFY DPSTIMPRIK LVATTIDTIH TATTTLQNKV  120
RPAHVELGLE VTKAVLLTAN PASTAKELDA EGAALKARLE KVSQYPDLTP NDVATVYVRT  180
NFSKTIWQVR ANRDRYILGH KSAAVYKTLN HAITKAVGVR LNPKTTVGNI QAARTELLAA  240
YQTAFNSPDV KKAASGSSTA ASSLAVTLML AIFIVYMVGS G                      281

SEQ ID NO: 275          moltype = AA  length = 285
FEATURE                 Location/Qualifiers
source                  1..285
                        mol_type = protein
                        organism = synthetic construct
SEQUENCE: 275
MVPQALLFVP LLVFPLCFGV EPTTTISATS THELSASDAR NSIQLLNAHI ATLQSVQKSV  60
PGSDYSDQIR DLLKAAFDLR GLIETLAHGG IPFYDPSTIM PRIKLVATTI DTIHTATTTL  120
QNKVRPAHVE LGLEVTKAVL LTANPASTAK ELDAEGAALK ARLEKVSQYP DLTPNDVATV  180
```

```
YVRTNFSKTI WQVRANRDRY ILGHKSAAVY KTLNHAITKA VGVRLNPKTT VGNIQAARTE  240
LLAAYQTAFN SPDVKKAASG SVLLSAGALT ALMLIIFLMT CWGSG                  285

SEQ ID NO: 276          moltype = AA  length = 286
FEATURE                 Location/Qualifiers
source                  1..286
                        mol_type = protein
                        organism = synthetic construct
SEQUENCE: 276
MFLIQCLISA VIFYIQVTNA VEPTTTISAT STHELSASDA RNSIQLLNAH IATLQSVQKS  60
VPGSDYSDQI RDLLKAAFDL RGLIETLAHG GIPFYDPSTI MPRIKLVATT IDTIHTATTT  120
LQNKVRPAHV ELGLEVTKAV LLTANPASTA KELDAEGAAL KARLEKVSQY PDLTPNDVAT  180
VYVRTNFSKT IWQVRANRDR YILGHKSAAV YKTLNHAITK AVGVRLNPKT TVGNIQAART  240
ELLAAYQTAF NSPDVKKAAS GSIIIPIVAS VMILTAMVIV IVIGSG                 286

SEQ ID NO: 277          moltype = AA  length = 298
FEATURE                 Location/Qualifiers
source                  1..298
                        mol_type = protein
                        organism = synthetic construct
SEQUENCE: 277
MGVTGILQLP RDRFKRTSFF LWVIILFQRT FSVEPTTTIS ATSTHELSAS DARNSIQLLN  60
AHIATLQSVQ KSVPGSDYSD QIRDLLKAAF DLRGLIETLA HGGIPFYDPS TIMPRIKLVA  120
TTIDTIHTAT TTLQNKVRPA HVELGLEVTK AVLLTANPAS TAKELDAEGA ALKARLEKVS  180
QYPDLTPNDV ATVYVRTNFS KTIWQVRANR DRYILGHKSA AVYKTLNHAI TKAVGVRLNP  240
KTTVGNIQAA RTELLAAYQT AFNSPDVKKA ASGSWIPAGI GVTGVIIAVI ALFCIGSG    298

SEQ ID NO: 278          moltype = AA  length = 400
FEATURE                 Location/Qualifiers
source                  1..400
                        mol_type = protein
                        organism = synthetic construct
SEQUENCE: 278
MAGPTVTVIP VGREGGDITI SGKGFSTTGF GVYVAVAPAS VPEFYGNSDK FYGYDPSKDT  60
TESPSTIWVY TPSQKAIGSR FAQGRPMNND GSFTITMKAP PFEQGKDFVV LTTKAHGVGK  120
TDHSDDTRTP VTYREATPAP TGPKTPIAPS KQPSKQAAPS KQVKPSKQAG PNKQSTTPQQ  180
KTAEHRSQTP AAHRTMTKQV CTIGASKVTS GSLTWGIRTS FTSYLRGPIA NGSWKLSGGA  240
NWNGSAFTFP LTSGSFDPAT KSGSLKYSGS VHMTGHHGIL DMTLAEPSLQ IKGSTGHLYL  300
DVKSSSMDGK KTNYGRVDFA TFGVSVSGNA AIKGSPVKLT ATGAKAFAGF YRAGEPMNPL  360
STNLTLSAEK VCHNVTVDAV TGKVIGDDSG KGAGRGLPVT                        400

SEQ ID NO: 279          moltype = AA  length = 416
FEATURE                 Location/Qualifiers
source                  1..416
                        mol_type = protein
                        organism = synthetic construct
SEQUENCE: 279
MKAILVVLLY TFATANAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVCTIG ASKVTSGSLT WGIRTSFTSY  240
LRGPIANGSW KLSGGANWNG SAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTNL TLSAEKVCHN VTVDAVTGKV IGDDSGKGAG RGLPVT      416

SEQ ID NO: 280          moltype = AA  length = 414
FEATURE                 Location/Qualifiers
source                  1..414
                        mol_type = protein
                        organism = synthetic construct
SEQUENCE: 280
MKAIIVLLMV VTSNAAGPTV TVIPVGREGG DITISGKGFS TTGFGVYVAV APASVPEFYG  60
NSDKFYGYDP SKDTTESPST IWVYTPSQKA IGSRFAQGRP MNNDGSFTIT MKAPPFEQGK  120
DFVVLTTKAH GVGKTDHSDD TRTPVTYREA TPAPTGPKTP IAPSKQPSKQ AAPSKQVKPS  180
KQAGPNKQST TPQQKTAEHR SQTPAAHRTM TKQVCTIGAS KVTSGSLTWG IRTSFTSYLR  240
GPIANGSWKL SGGANWNGSA FTFPLTSGSF DPATKSGSLK YSGSVHMTGH HGILDMTLAE  300
PSLQIKGSTG HLYLDVKSSS MDGKKTNYGR VDFATFGVSV SGNAAIKGSP VKLTATGAKA  360
FAGFYRAGEP MNPLSTNLTL SAEKVCHNVT VDAVTGKVIG DDSGKGAGRG LPVT        414

SEQ ID NO: 281          moltype = AA  length = 418
FEATURE                 Location/Qualifiers
source                  1..418
                        mol_type = protein
                        organism = synthetic construct
SEQUENCE: 281
MVPQALLFVP LLVFPLCFGA GPTVTVIPVG REGGDITISG KGFSTTGFGV YVAVAPASVP  60
EFYGNSDKFY GYDPSKDTTE SPSTIWVYTP SQKAIGSRFA QGRPMNNDGS FTITMKAPPF  120
EQGKDFVVLT TKAHGVGKTD HSDDTRTPVT YREATPAPTG PKTPIAPSKQ PSKQAAPSKQ  180
VKPSKQAGPN KQSTTPQQKT AEHRSQTPAA HRTMTKQVCT IGASKVTSGS LTWGIRTSFT  240
```

-continued

```
SYLRGPIANG SWKLSGGANW NGSAFTFPLT SGSFDPATKS GSLKYSGSVH MTGHHGILDM  300
TLAEPSLQIK GSTGHLYLDV KSSSMDGKKT NYGRVDFATF GVSVSGNAAI KGSPVKLTAT  360
GAKAFAGFYR AGEPMNPLST NLTLSAEKVC HNVTVDAVTG KVIGDDSGKG AGRGLPVT    418

SEQ ID NO: 282          moltype = AA  length = 419
FEATURE                 Location/Qualifiers
source                  1..419
                        mol_type = protein
                        organism = synthetic construct
SEQUENCE: 282
MFLIQCLISA VIFYIQVTNA AGPTVTVIPV GREGGDITIS GKGFSTTGFG VYVAVAPASV  60
PEFYGNSDKF YGYDPSKDTT ESPSTIWVYT PSQKAIGSRF AQGRPMNNDG SFTITMKAPP  120
FEQGKDFVVL TTKAHGVGKT DHSDDTRTPV TYREATPAPT GPKTPIAPSK QPSKQAAPSK  180
QVKPSKQAGP NKQSTTPQQK TAEHRSQTPA AHRTMTKQVC TIGASKVTSG SLTWGIRTSF  240
TSYLRGPIAN GSWKLSGGAN WNGSAFTFPL TSGSFDPATK SGSLKYSGSV HMTGHHGILD  300
MTLAEPSLQI KGSTGHLYLD VKSSSMDGKK TNYGRVDFAT FGVSVSGNAA IKGSPVKLTA  360
TGAKAFAGFY RAGEPMNPLS TNLTLSAEKV CHNVTVDAVT GKVIGDDSGK GAGRGLPVT   419

SEQ ID NO: 283          moltype = AA  length = 431
FEATURE                 Location/Qualifiers
source                  1..431
                        mol_type = protein
                        organism = synthetic construct
SEQUENCE: 283
MGVTGILQLP RDRFKRTSFF LWVIILFQRT FSAGPTVTVI PVGREGGDIT ISGKGFSTTG  60
FGVYVAVAPA SVPEFYGNSD KFYGYDPSKD TTESPSTIWV YTPSQKAIGS RFAQGRPMNN  120
DGSFTITMKA PPFEQGKDFV VLTTKAHGVG KTDHSDDTRT PVTYREATPA PTGPKTPIAP  180
SKQPSKQAAP SKQVKPSKQA GPNKQSTTPQ QKTAEHRSQT PAAHRTMTKQ VCTIGASKVT  240
SGSLTWGIRT SFTSYLRGPI ANGSWKLSGG ANWNGSAFTF PLTSGSFDPA TKSGSLKYSG  300
SVHMTGHHGI LDMTLAEPSL QIKGSTGHLY LDVKSSSMDG KKTNYGRVDF ATFGVSVSGN  360
AAIKGSPVKL TATGAKAFAG FYRAGEPMNP LSTNLTLSAE KVCHNVTVDA VTGKVIGDDS  420
GKGAGRGLPV T                                                       431

SEQ ID NO: 284          moltype = AA  length = 445
FEATURE                 Location/Qualifiers
source                  1..445
                        mol_type = protein
                        organism = synthetic construct
SEQUENCE: 284
MKAILVVLLY TFATANAAGP TVTVIPVGRE GGDITISGKG FSTTGFGVYV AVAPASVPEF  60
YGNSDKFYGY DPSKDTTESP STIWVYTPSQ KAIGSRFAQG RPMNNDGSFT ITMKAPPFEQ  120
GKDFVVLTTK AHGVGKTDHS DDTRTPVTYR EATPAPTGPK TPIAPSKQPS KQAAPSKQVK  180
PSKQAGPNKQ STTPQQKTAE HRSQTPAAHR TMTKQVCTIG ASKVTSGSLT WGIRTSFTSY  240
LRGPIANGSW KLSGGANWNG SAFTFPLTSG SFDPATKSGS LKYSGSVHMT GHHGILDMTL  300
AEPSLQIKGS TGHLYLDVKS SSMDGKKTNY GRVDFATFGV SVSGNAAIKG SPVKLTATGA  360
KAFAGFYRAG EPMNPLSTNL TLSAEKVCHN VTVDAVTGKV IGDDSGKGAG RGLPVTSGSI  420
LAIYSTVASS LVLVVSLGAI SFGSG                                        445

SEQ ID NO: 285          moltype = AA  length = 441
FEATURE                 Location/Qualifiers
source                  1..441
                        mol_type = protein
                        organism = synthetic construct
SEQUENCE: 285
MKAIIVLLMV VTSNAAGPTV TVIPVGREGG DITISGKGFS TTGFGVYVAV APASVPEFYG  60
NSDKFYGYDP SKDTTESPST IWVYTPSQKA IGSRFAQGRP MNNDGSFTIT MKAPPFEQGK  120
DFVVLTTKAH GVGKTDHSDD TRTPVTYREA TPAPTGPKTP IAPSKQPSKQ AAPSKQVKPS  180
KQAGPNKQST TPQQKTAEHR SQTPAAHRTM TKQVCTIGAS KVTSGSLTWG IRTSFTSYLR  240
GPIANGSWKL SGGANWNGSA FTFPLTSGSF DPATKSGSLK YSGSVHMTGH HGILDMTLAE  300
PSLQIKGSTG HLYLDVKSSS MDGKKTNYGR VDFATFGVSV SGNAAIKGSP VKLTATGAKA  360
FAGFYRAGEP MNPLSTNLTL SAEKVCHNVT VDAVTGKVIG DDSGKGAGRG LPVTSGSSTA  420
ASSLAVTLML AIFIVYMVGS G                                            441

SEQ ID NO: 286          moltype = AA  length = 445
FEATURE                 Location/Qualifiers
source                  1..445
                        mol_type = protein
                        organism = synthetic construct
SEQUENCE: 286
MVPQALLFVP LLVFPLCFGA GPTVTVIPVG REGGDITISG KGFSTTGFGV YVAVAPASVP  60
EFYGNSDKFY GYDPSKDTTE SPSTIWVYTP SQKAIGSRFA QGRPMNNDGS FTITMKAPPF  120
EQGKDFVVLT TKAHGVGKTD HSDDTRTPVT YREATPAPTG PKTPIAPSKQ PSKQAAPSKQ  180
VKPSKQAGPN KQSTTPQQKT AEHRSQTPAA HRTMTKQVCT IGASKVTSGS LTWGIRTSFT  240
SYLRGPIANG SWKLSGGANW NGSAFTFPLT SGSFDPATKS GSLKYSGSVH MTGHHGILDM  300
TLAEPSLQIK GSTGHLYLDV KSSSMDGKKT NYGRVDFATF GVSVSGNAAI KGSPVKLTAT  360
GAKAFAGFYR AGEPMNPLST NLTLSAEKVC HNVTVDAVTG KVIGDDSGKG AGRGLPVTSG  420
SVLLSAGALT ALMLIIFLMT CWGSG                                        445

SEQ ID NO: 287          moltype = AA  length = 446
```

```
FEATURE                Location/Qualifiers
source                 1..446
                       mol_type = protein
                       organism = synthetic construct
SEQUENCE: 287
MFLIQCLISA VIFYIQVTNA AGPTVTVIPV GREGGDITIS GKGFSTTGFG VYVAVAPASV  60
PEFYGNSDKF YGYDPSKDTT ESPSTIWVYT PSQKAIGSRF AQGRPMNNDG SFTITMKAPP  120
FEQGKDFVVL TTKAHGVGKT DHSDDTRTPV TYREATPAPT GPKTPIAPSK QPSKQAAPSK  180
QVKPSKQAGP NKQSTTPQQK TAEHRSQTPA AHRTMTKQVC TIGASKVTSG SLTWGIRTSF  240
TSYLRGPIAN GSWKLSGGAN WNGSAFTFPL TSGSFDPATK SGSLKYSGSV HMTGHHGILD  300
MTLAEPSLQI KGSTGHLYLD VKSSSMDGKK TNYGRVDFAT FGVSVSGNAA IKGSPVKLTA  360
TGAKAFAGFY RAGEPMNPLS TNLTLSAEKV CHNVTVDAVT GKVIGDDSGK GAGRGLPVTS  420
GSIIIPIVAS VMILTAMVIV IVIGSG                                       446

SEQ ID NO: 288         moltype = AA  length = 458
FEATURE                Location/Qualifiers
source                 1..458
                       mol_type = protein
                       organism = synthetic construct
SEQUENCE: 288
MGVTGILQLP RDRFKRTSFF LWVIILFQRT FSAGPTVTVI PVGREGGDIT ISGKGFSTTG  60
FGVYVAVAPA SVPEFYGNSD KFYGYDPSKD TTESPSTIWV YTPSQKAIGS RFAQGRPMNN  120
DGSFTITMKA PPFEQGKDFV VLTTKAHGVG KTDHSDDTRT PVTYREATPA PTGPKTPIAP  180
SKQPSKQAAP SKQVKPSKQA GPNKQSTTPQ QKTAEHRSQT PAAHRTMTKQ VCTIGASKVT  240
SGSLTWGIRT SFTSYLRGPI ANGSWKLSGG ANWNGSAFTF PLTSGSFDPA TKSGSLKYSG  300
SVHMTGHHGI LDMTLAEPSL QIKGSTGHLY LDVKSSSMDG KKTNYGRVDF ATFGVSVSGN  360
AAIKGSPVKL TATGAKAFAG FYRAGEPMNP LSTNLTLSAE KVCHNVTVDA VTGKVIGDDS  420
GKGAGRGLPV TSGSWIPAGI GVTGVIIAVI ALFCIGSG                          458

SEQ ID NO: 289         moltype = RNA  length = 723
FEATURE                Location/Qualifiers
source                 1..723
                       mol_type = other RNA
                       organism = synthetic construct
SEQUENCE: 289
atggtcgagc ccaccaccac catctccgcc acatccacac acgaactgtc cgcaagcgac  60
gccagaaaca gcatccagct gctgaacgcc cacatcgcca ccctccagag cgtgcagaag  120
agtgtgcccg gcagcgatta tagcgaccag atccgggacc tgctcaaggc cgcattcgac  180
ctgcgcggcc tgatcgagac actggctcat ggcgggatcc ccttctatga tcccagcacc  240
atcatgccca ggatcaagct ggtcgccact accatcgaca ccatccacac cgccaccacc  300
accctgcaga acaaagtgcg ccccgcccac gtggagctgg ggctggaggt gaccaaagcg  360
gtgctgctga cagccaaccc tgcatccacc gccaaggagc tggacgcaga gggcgctgca  420
ctgaaggccc ggctcgagaa ggtgtcccag tatcccgacc tgacaccaaa cgatgtggcc  480
actgtgtacg tgagaaccaa cttctccaag accatctggc aggtcagagc caaccgcgat  540
cgctacatcc tgggccacaa gtccgccgcc gtgtataaga ccctgaacca tgccatcacc  600
aaggccgtgg gcgtcagact gaaccccaag accaccgtgg gcaacatcca ggccgctaga  660
acagagctgc tggccgccta ccagaccgcc ttcaattcac ccgacgtgaa gaaggccgct  720
taa                                                                723

SEQ ID NO: 290         moltype = RNA  length = 771
FEATURE                Location/Qualifiers
source                 1..771
                       mol_type = other RNA
                       organism = synthetic construct
SEQUENCE: 290
atgaaggcca ttctggtggt gctgctgtac acatttgcta cagccaacgc cgtcgagccc  60
accaccacca tctccgccac atccacacac gaactgtccg caagcgacgc cagaaacagc  120
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg acaccaaacg atgtggccac tgtgtacgtg  540
agaaccaact tctccaagac catctggcag gtcagagcca accgcgatcg ctacatcctg  600
ggccacaagt ccgccgccgt gtataagacc ctgaaccatg ccatcaccaa ggccgtgggc  660
gtcagactga accccaagac caccgtgggc aacatccagg ccgctagaac agagctgctg  720
gccgcctacc agaccgcctt caattcaccc gacgtgaaga aggccgctta a           771

SEQ ID NO: 291         moltype = RNA  length = 765
FEATURE                Location/Qualifiers
source                 1..765
                       mol_type = other RNA
                       organism = synthetic construct
SEQUENCE: 291
atgaaggcta tcatcgtgct gctgatggtg gtgacctcca acgccgtcga gcccaccacc  60
accatctccg ccacatccac acacgaactg tccgcaagcg acgccagaaa cagcatccag  120
ctgctgaacg cccacatcgc caccctccag agcgtgcaga agagtgtgcc cggcagcgat  180
tatagcgacc agatccggga cctgctcaag gccgcattcg acctgcgcgg cctgatcgag  240
```

-continued

```
acactggctc atggcgggat ccccttctat gatcccagca ccatcatgcc caggatcaag  300
ctggtcgcca ctaccatcga caccatccac accgccacca ccaccctgca gaacaaagtg  360
cgccccgccc acgtggagct ggggctggag gtgaccaaag cggtgctgct gacagccaac  420
cctgcatcca ccgccaagga gctggacgca gagggcgctg cactgaaggc ccggctcgag  480
aaggtgtccc agtatcccga cctgacacca aacgatgtgg ccactgtgta cgtgagaacc  540
aacttctcca agaccatctg gcaggtcaga gccaaccgcg atcgctacat cctgggccac  600
aagtccgccg ccgtgtataa gaccctgaac catgccatca ccaaggccgt gggcgtcaga  660
ctgaacccca agaccaccgt gggcaacatc caggccgcta gaacagagct gctggccgcc  720
taccagaccg ccttcaattc acccgacgtg aagaaggccg cttaa                 765

SEQ ID NO: 292          moltype = RNA  length = 777
FEATURE                 Location/Qualifiers
source                  1..777
                        mol_type = other RNA
                        organism = synthetic construct
SEQUENCE: 292
atggtgcccc aggcactgct gttcgtgcca ctgctggtgt ttccactgtg tttcggcgtc  60
gagcccacca ccaccatctc cgccacatcc acacacgaac tgtccgcaag cgacgccaga  120
aacagcatcc agctgctgaa cgcccacatc gccaccctcc agagcgtgca gaagagtgtg  180
cccggcagcg attatagcga ccagatccgg gacctgctca aggccgcatt cgacctgcgc  240
ggcctgatcg agacactggc tcatggcggg atccccttct atgatcccag caccatcatg  300
cccaggatca agctggtcgc cactaccatc gacaccatcc acaccgccac caccaccctg  360
cagaacaaag tgcgccccgc ccacgtggag ctggggctgg aggtgaccaa agcggtgctg  420
ctgacagcca accctgcatc caccgccaag gagctggacg cagagggcgc tgcactgaag  480
gcccggctcg agaaggtgtc ccagtatccc gacctgacac caaacgatgt ggccactgtg  540
tacgtgagaa ccaacttctc caagaccatc tggcaggtca gagccaaccg cgatcgctac  600
atcctgggcc acaagtccgc cgccgtgtat aagaccctga accatgccat caccaaggcc  660
gtgggcgtca gactgaaccc caagaccacc gtgggcaaca tccaggccgc tagaacagag  720
ctgctggccg cctaccagac cgccttcaat tcacccgacg tgaagaaggc cgcttaa     777

SEQ ID NO: 293          moltype = RNA  length = 780
FEATURE                 Location/Qualifiers
source                  1..780
                        mol_type = other RNA
                        organism = synthetic construct
SEQUENCE: 293
atgttcctga tccagtgtct gatctccgcc gtgatcttct atatccaggt gaccaacgca  60
gtcgagccca ccaccaccat ctccgccaca tccacacacg aactgtccgc aagcgacgcc  120
agaaacagca tccagctgct gaacgcccac atcgccaccc tccagagcgt gcagaagagt  180
gtgcccggca gcgattatag cgaccagatc cgggacctgc tcaaggccgc attcgacctg  240
cgcggcctga tcgagacact ggctcatggc gggatcccct tctatgatcc cagcaccatc  300
atgcccagga tcaagctggt cgccactacc atcgacacca tccacaccgc caccaccacc  360
ctgcagaaca aagtgcgccc cgcccacgtg gagctggggc tggaggtgac caaagcggtg  420
ctgctgacag ccaaccctgc atccaccgcc aaggagctgg acgcagaggg cgctgcactg  480
aaggcccggc tcgagaaggt gtcccagtat cccgacctga caccaaacga tgtggccact  540
gtgtacgtga gaaccaactt ctccaagacc atctggcagg tcagagccaa ccgcgatcgc  600
tacatcctgg gccacaagtc cgccgccgtg tataagaccc tgaaccatgc catcaccaag  660
gccgtgggcg tcagactgaa ccccaagacc accgtgggca acatccaggc cgctagaaca  720
gagctgctgg ccgcctacca gaccgccttc aattcacccg acgtgaagaa ggccgcttaa  780

SEQ ID NO: 294          moltype = RNA  length = 816
FEATURE                 Location/Qualifiers
source                  1..816
                        mol_type = other RNA
                        organism = synthetic construct
SEQUENCE: 294
atgggagtga ccggaatcct gcagctgccc agagataggt tcaagcggac cagcttcttc  60
ctgtgggtca ttatcctgtt tcagagaaca ttctctgtcg agcccaccac caccatctcc  120
gccacatcca cacacgaact gtccgcaagc gacgccagaa acagcatcca gctgctgaac  180
gcccacatcg ccaccctcca gagcgtgcag aagagtgtgc ccggcagcga ttatagcgac  240
cagatccggg acctgctcaa ggccgcattc gacctgcgcg gcctgatcga gacactggct  300
catggcggga tccccttcta tgatcccagc accatcatgc ccaggatcaa gctggtcgcc  360
actaccatcg acaccatcca caccgccacc accaccctgc agaacaaagt gcgccccgcc  420
cacgtggagc tggggctgga ggtgaccaaa gcggtgctgc tgacagccaa ccctgcatcc  480
accgccaagg agctggacgc agagggcgct gcactgaagg cccggctcga gaaggtgtcc  540
cagtatcccg acctgacacc aaacgatgtg gccactgtgt acgtgagaac caacttctcc  600
aagaccatct ggcaggtcag agccaaccgc gatcgctaca tcctgggcca caagtccgcc  660
gccgtgtata agaccctgaa ccatgccatc accaaggccg tgggcgtcag actgaacccc  720
aagaccaccg tgggcaacat ccaggccgct agaacagagc tgctggccgc ctaccagacc  780
gccttcaatt cacccgacgt gaagaaggcc gcttaa                            816

SEQ ID NO: 295          moltype = RNA  length = 858
FEATURE                 Location/Qualifiers
source                  1..858
                        mol_type = other RNA
                        organism = synthetic construct
SEQUENCE: 295
atgaaggcca ttctggtggt gctgctgtac acatttgcta cagccaacgc cgtcgagccc  60
accaccacca tctccgccac atccacacac gaactgtccg caagcgacgc cagaaacagc  120
```

```
atccagctgc tgaacgccca catcgccacc ctccagagcg tgcagaagag tgtgcccggc  180
agcgattata gcgaccagat ccgggacctg ctcaaggccg cattcgacct gcgcggcctg  240
atcgagacac tggctcatgg cgggatcccc ttctatgatc ccagcaccat catgcccagg  300
atcaagctgg tcgccactac catcgacacc atccacaccg ccaccaccac cctgcagaac  360
aaagtgcgcc ccgcccacgt ggagctgggg ctggaggtga ccaaagcggt gctgctgaca  420
gccaaccctg catccaccgc caaggagctg gacgcagagg gcgctgcact gaaggcccgg  480
ctcgagaagg tgtcccagta tcccgacctg acaccaaacg atgtggccac tgtgtacgtg  540
agaaccaact tctccaagac catctggcag gtcagagcca accgcgatcg ctacatcctg  600
ggccacaagt ccgccgccgt gtataagacc ctgaaccatg ccatcaccaa ggccgtgggc  660
gtcagactga accccaagac caccgtgggc aacatccagg ccgctagaac agagctgctg  720
gccgcctacc agaccgcctt caattcaccc gacgtgaaga aggccgcttc cggcagcatc  780
ctggccatct acagcaccgt ggctagctcc ctggtgctgg tggtgagcct gggagctatt  840
agctttggaa gcggataa                                                858

SEQ ID NO: 296         moltype = RNA  length = 846
FEATURE                Location/Qualifiers
source                 1..846
                       mol_type = other RNA
                       organism = synthetic construct
SEQUENCE: 296
atgaaggcta tcatcgtgct gctgatggtg gtgacctcca acgccgtcga gcccaccacc  60
accatctccg ccacatccac acacgaactg tccgcaagcg acgccagaaa cagcatccag  120
ctgctgaacg cccacatcgc caccctccag agcgtgcaga agagtgtgcc cggcagcgat  180
tatagcgacc agatccggga cctgctcaag gccgcattcg acctgcgcgg cctgatcgag  240
acactggctc atggcgggat ccccttctat gatcccagca ccatcatgcc caggatcaag  300
ctggtcgcca ctaccatcga caccatccac accgccacca ccaccctgca gaacaaagtg  360
cgccccgccc acgtggagct ggggctggag gtgaccaaag cggtgctgct gacagccaac  420
cctgcatcca ccgccaagga gctggacgca gagggcgctg cactgaaggc ccggctcgag  480
aaggtgtccc agtatcccga cctgacacca aacgatgtgg ccactgtgta cgtgagaacc  540
aacttctcca agaccatctg gcaggtcaga gccaaccgcg atcgctacat cctgggccac  600
aagtccgccg ccgtgtataa gaccctgaac catgccatca ccaaggccgt gggcgtcaga  660
ctgaacccca agaccaccgt gggcaacatc caggccgcta gaacagagct gctggccgcc  720
taccagaccg ccttcaattc acccgacgtg aagaaggccg ctagcggcag ctctacagcc  780
gcaagcagcc tggctgtgac actgatgctg gccattttca ttgtgtacat ggtgggctcc  840
ggataa                                                             846

SEQ ID NO: 297         moltype = RNA  length = 858
FEATURE                Location/Qualifiers
source                 1..858
                       mol_type = other RNA
                       organism = synthetic construct
SEQUENCE: 297
atggtgcccc aggcactgct gttcgtgcca ctgctggtgt ttccactgtg tttcggcgtc  60
gagcccacca ccaccatctc cgccacatcc acacacgaac tgtccgcaag cgacgccaga  120
aacagcatcc agctgctgaa cgcccacatc gccaccctcc agagcgtgca gaagagtgtg  180
cccggcagcg attatagcga ccagatccgg gacctgctca aggccgcatt cgacctgcgc  240
ggcctgatcg agacactggc tcatggcggg atccccttct atgatcccag caccatcatg  300
cccaggatca agctggtcgc cactaccatc gacaccatcc acaccgccac caccaccctg  360
cagaacaaag tgcgccccgc ccacgtggag ctggggctgg aggtgaccaa agcggtgctg  420
ctgacagcca accctgcatc caccgccaag gagctggacg cagagggcgc tgcactgaag  480
gcccggctcg agaaggtgtc ccagtatccc gacctgacac caaacgatgt ggccactgtg  540
tacgtgagaa ccaacttctc caagaccatc tggcaggtca gagccaaccg cgatcgctac  600
atcctgggcc acaagtccgc cgccgtgtat aagaccctga accatgccat caccaaggcc  660
gtgggcgtca gactgaaccc caagaccacc gtgggcaaca tccaggccgc tagaacagag  720
ctgctggccg cctaccagac cgccttcaat tcacccgacg tgaagaaggc cgctagcgga  780
tccgtgctgc tgtctgccgg agctctgaca gcactgatgc tgatcatttt cctgatgacc  840
tgctggggca gcggctaa                                                858

SEQ ID NO: 298         moltype = RNA  length = 861
FEATURE                Location/Qualifiers
source                 1..861
                       mol_type = other RNA
                       organism = synthetic construct
SEQUENCE: 298
atgttcctga tccagtgtct gatctccgcc gtgatcttct atatccaggt gaccaacgca  60
gtcgagccca ccaccaccat ctccgccaca tccacacacg aactgtccgc aagcgacgcc  120
agaaacagca tccagctgct gaacgcccac atcgccaccc tccagagcgt gcagaagagt  180
gtgcccggca gcgattatag cgaccagatc cgggacctgc tcaaggccgc attcgacctg  240
cgcggcctga tcgagacact ggctcatggc gggatcccct tctatgatcc cagcaccatc  300
atgcccagga tcaagctggt cgccactacc atcgacacca tccacaccgc caccaccacc  360
ctgcagaaca aagtgcgccc cgcccacgtg gagctggggc tggaggtgac caaagcggtg  420
ctgctgacag ccaaccctgc atccaccgcc aaggagctgg acgcagaggg cgctgcactg  480
aaggcccggc tcgagaaggt gtcccagtat cccgacctga caccaaacga tgtggccact  540
gtgtacgtga gaaccaactt ctccaagacc atctggcagg tcagagccaa ccgcgatcgc  600
tacatcctgg gccacaagtc cgccgccgtg tataagaccc tgaaccatgc catcaccaag  660
gccgtgggcg tcagactgaa ccccaagacc accgtgggca acatccaggc cgctagaaca  720
gagctgctgg ccgcctacca gaccgccttc aattcacccg acgtgaagaa ggccgctagc  780
ggaagcatta ttatccccat cgtggcctct gtgatgatcc tgaccgcaat ggtcattgtg  840
atcgtgatcg gcagcggcta a                                             861
```

```
SEQ ID NO: 299         moltype = RNA  length = 897
FEATURE                Location/Qualifiers
source                 1..897
                       mol_type = other RNA
                       organism = synthetic construct
SEQUENCE: 299
atgggagtga ccggaatcct gcagctgccc agagataggt tcaagcggac cagcttcttc  60
ctgtgggtca ttatcctgtt tcagagaaca ttctctgtcg agcccaccac caccatctcc  120
gccacatcca cacacgaact gtccgcaagc gacgccagaa acagcatcca gctgctgaac  180
gcccacatcg ccaccctcca gagcgtgcag aagagtgtgc ccggcagcga ttatagcgac  240
cagatccggg acctgctcaa ggccgcattc gacctgcgcg gcctgatcga gacactggct  300
catggcggga tccccttcta tgatcccagc accatcatgc ccaggatcaa gctggtcgcc  360
actaccatcg acaccatcca caccgccacc accaccctgc agaacaaagt gcgccccgcc  420
cacgtggagc tggggctgga ggtgaccaaa gcggtgctgc tgacagccaa ccctgcatcc  480
accgccaagg agctggacgc agagggcgct gcactgaagg cccggctcga gaaggtgtcc  540
cagtatcccg acctgacacc aaacgatgtg gccactgtgt acgtgagaac caacttctcc  600
aagaccatct ggcaggtcag agccaaccgc gatcgctaca tcctgggcca caagtccgcc  660
gccgtgtata agaccctgaa ccatgccatc accaaggccg tgggcgtcag actgaacccc  720
aagaccaccg tgggcaacat ccaggccgct agaacagagc tgctggccgc ctaccagacc  780
gccttcaatt cacccgacgt gaagaaggcc gcttctggat cctggatccc tgccggaatc  840
ggggtgaccg gcgtgatcat cgccgtgatc gccctgttct gtattggcag cggataa     897

SEQ ID NO: 300         moltype = RNA  length = 1203
FEATURE                Location/Qualifiers
source                 1..1203
                       mol_type = other RNA
                       organism = synthetic construct
SEQUENCE: 300
atggctgggc caacagtgac agtgatcccc gtgggacgcg agggcggaga cattaccatc  60
tccgggaagg gctttagcac aacagggttc ggtgtgtatg tggctgtggc cccagcaagc  120
gtgccagagt tctacgggaa ctccgataaa ttttatgggt atgaccccag taaagacaca  180
accgagagcc ccagcacaat ttgggtttac accccctctc agaaagctat tggctcccgg  240
ttcgcccagg gcagaccaat gaataatgac gggagcttta ccatcactat gaaggccccc  300
ccattcgagc agggaaagga ctttgtggtc ctgactacca aggctcacgg agtgggcaaa  360
accgaccact ctgacgacac tcggacaccg gtgacatacc gggaggctac tcccgctcca  420
acaggcccta aaactccaat cgcccccagc aagcagcctt caaagcaggc tgcccccagc  480
aagcaggtga agcctagcaa gcaggctggc cccaacaagc agagcactac tcctcagcag  540
aagaccgcag agcacagatc tcagacccca gcagctcatc gcactatgac taagcaggtg  600
tgtaccatcg gagcctcaaa ggtgaccagc ggatccctga catggggaat ccggactagc  660
tttacttcct acctgcgcgg gcccatcgca aacggcagct ggaagctgtc tgggggggcc  720
aattggaacg gcagcgcctt cacattccca ctgacttctg gatccttcga ccccgccacc  780
aaatccggct cactgaagta cagcgggagc gtgcacatga ctggacacca tggaattctg  840
gacatgacac tcgctgaacc ctctctgcag atcaagggct ctactgggca cctgtatctg  900
gatgtgaagt cctcttctat ggacggcaag aagacaaact atgggagagt ggattttgcc  960
accttcggag tgagcgtgag cggaaatgct gcaatcaaag ggtcccccgt gaaactgacc  1020
gctaccggag caaaagcctt tgccggcttt tacagagcag gagagcccat gaaccccctg  1080
agcaccaatc tgacactgag cgctgagaaa gtttgtcaca atgtgaccgt tgatgcagtt  1140
accgggaaag tgatcggcga cgattccgga aagggggcag gaaggggact gcctgtcact  1200
tga                                                                1203

SEQ ID NO: 301         moltype = RNA  length = 1251
FEATURE                Location/Qualifiers
source                 1..1251
                       mol_type = other RNA
                       organism = synthetic construct
SEQUENCE: 301
atgaaggcca ttctggtggt gctgctgtac acatttgcta cagccaacgc cgctgggcca  60
acagtgacag tgatccccgt gggacgcgag ggcggagaca ttaccatctc cgggaagggc  120
tttagcacaa cagggttcgg tgtgtatgtg gctgtggccc cagcaagcgt gccagagttc  180
tacgggaact ccgataaatt ttatgggtat gaccccagta aagacacaac cgagagcccc  240
agcacaattt gggtttacac cccctctcag aaagctattg gctcccggtt cgcccagggc  300
agaccaatga ataatgacgg gagctttacc atcactatga aggccccccc attcgagcag  360
ggaaaggact ttgtggtcct gactaccaag gctcacggag tgggcaaaac cgaccactct  420
gacgacactc ggacaccggt gacataccgg gaggctactc ccgctccaac aggccctaaa  480
actccaatcg cccccagcaa gcagccttca aagcaggctg cccccagcaa gcaggtgaag  540
cctagcaagc aggctggccc caacaagcag agcactactc ctcagcagaa gaccgcagag  600
cacagatctc agaccccagc agctcatcgc actatgacta agcaggtgtg taccatcgga  660
gcctcaaagg tgaccagcgg atccctgaca tggggaatcc ggactagctt tacttcctac  720
ctgcgcgggc ccatcgcaaa cggcagctgg aagctgtctg ggggggccaa ttggaacggc  780
agcgccttca cattcccact gacttctgga tccttcgacc ccgccaccaa atccggctca  840
ctgaagtaca gcgggagcgt gcacatgact ggacaccatg gaattctgga catgacactc  900
gctgaaccct ctctgcagat caagggctct actgggcacc tgtatctgga tgtgaagtcc  960
tcttctatgg acggcaagaa gacaaactat gggagagtgg attttgccac cttcggagtg  1020
agcgtgagcg gaaatgctgc aatcaaaggg tcccccgtga aactgaccgc taccggagca  1080
aaagcctttg ccggctttta cagagcagga gagcccatga accccctgag caccaatctg  1140
acactgagcg ctgagaaagt ttgtcacaat gtgaccgttg atgcagttac cgggaaagtg  1200
atcggcgacg attccggaaa gggggcagga aggggactgc ctgtcacttg a           1251
```

-continued

```
SEQ ID NO: 302         moltype = RNA  length = 1245
FEATURE                Location/Qualifiers
source                 1..1245
                       mol_type = other RNA
                       organism = synthetic construct
SEQUENCE: 302
atgaaggcta tcatcgtgct gctgatggtg gtgacctcca acgccgctgg gccaacagtg  60
acagtgatcc ccgtgggacg cgagggcgga gacattacca tctccgggaa gggctttagc  120
acaacagggt tcggtgtgta tgtggctgtg gccccagcaa gcgtgccaga gttctacggg  180
aactccgata aattttatgg gtatgacccc agtaaagaca caaccgagag ccccagcaca  240
atttgggttt acaccccctc tcagaaagct attggctccc ggttcgccca gggcagacca  300
atgaataatg acgggagctt taccatcact atgaaggccc ccccattcga gcagggaaag  360
gactttgtgg tcctgactac caaggctcac ggagtgggca aaaccgacca ctctgacgac  420
actcggacac cggtgacata ccgggaggct actcccgctc caacaggccc taaaactcca  480
atcgccccca gcaagcagcc ttcaaagcag gctgccccca gcaagcaggt gaagcctagc  540
aagcaggctg gccccaacaa gcagagcact actcctcagc agaagaccgc agagcacaga  600
tctcagaccc cagcagctca tcgcactatg actaagcagg tgtgtaccat cggagcctca  660
aaggtgacca gcggatccct gacatgggga atccggacta gctttacttc ctacctgcgc  720
gggcccatcg caaacggcag ctggaagctg tctggggggg ccaattggaa cggcagcgcc  780
ttcacattcc cactgacttc tggatccttc gaccccgcca ccaaatccgg ctcactgaag  840
tacagcggga gcgtgcacat gactggacac catggaattc tggacatgac actcgctgaa  900
ccctctctgc agatcaaggg ctctactggg cacctgtatc tggatgtgaa gtcctcttct  960
atggacggca agaagacaaa ctatgggaga gtggattttg ccaccttcgg agtgagcgtg  1020
agcggaaatg ctgcaatcaa aggtcccccc gtgaaactga ccgctaccgg agcaaaagcc  1080
tttgccggct tttacagagc aggagagccc atgaaccccc tgagcaccaa tctgacactg  1140
agcgctgaga aagtttgtca caatgtgacc gttgatgcag ttaccgggaa agtgatcggc  1200
gacgattccg gaaagggggc aggaagggga ctgcctgtca cttga                 1245

SEQ ID NO: 303         moltype = RNA  length = 1257
FEATURE                Location/Qualifiers
source                 1..1257
                       mol_type = other RNA
                       organism = synthetic construct
SEQUENCE: 303
atggtgcccc aggcactgct gttcgtgcca ctgctggtgt ttccactgtg tttcggcgct  60
gggccaacag tgacagtgat ccccgtggga cgcgagggcg gagacattac catctccggg  120
aagggcttta gcacaacagg gttcggtgtg tatgtggctg tggccccagc aagcgtgcca  180
gagttctacg ggaactccga taaattttat gggtatgacc ccagtaaaga cacaaccgag  240
agccccagca caatttgggt ttacaccccc tctcagaaag ctattggctc ccggttcgcc  300
cagggcagac caatgaataa tgacgggagc tttaccatca ctatgaaggc ccccccattc  360
gagcagggaa aggactttgt ggtcctgact accaaggctc acggagtggg caaaaccgac  420
cactctgacg acactcggac accggtgaca taccgggagg ctactcccgc tccaacaggc  480
cctaaaactc caatcgcccc cagcaagcag ccttcaaagc aggctgcccc cagcaagcag  540
gtgaagccta gcaagcaggc tggccccaac aagcagagca ctactcctca gcagaagacc  600
gcagagcaca gatctcagac cccagcagct catcgcacta tgactaagca ggtgtgtacc  660
atcggagcct caaaggtgac cagcggatcc ctgacatggg gaatccggac tagctttact  720
tcctacctgc gcgggcccat cgcaaacggc agctggaagc tgtctggggg ggccaattgg  780
aacggcagcg ccttcacatt cccactgact tctggatcct tcgaccccgc caccaaatcc  840
ggctcactga agtacagcgg gagcgtgcac atgactggac accatggaat tctggacatg  900
acactcgctg aaccctctct gcagatcaag ggctctactg ggcacctgta tctggatgtg  960
aagtcctctt ctatggacgg caagaagaca aactatggga gagtggattt tgccaccttc  1020
ggagtgagcg tgagcggaaa tgctgcaatc aaagggtccc ccgtgaaact gaccgctacc  1080
ggagcaaaag cctttgccgg cttttacaga gcaggagagc ccatgaaccc cctgagcacc  1140
aatctgacac tgagcgctga gaaagtttgt cacaatgtga ccgttgatgc agttaccggg  1200
aaagtgatcg gcgacgattc cggaaagggg gcaggaaggg gactgcctgt cacttga     1257

SEQ ID NO: 304         moltype = RNA  length = 1260
FEATURE                Location/Qualifiers
source                 1..1260
                       mol_type = other RNA
                       organism = synthetic construct
SEQUENCE: 304
atgttcctga tccagtgtct gatctccgcc gtgatcttct atatccaggt gaccaacgca  60
gctgggccaa cagtgacagt gatccccgtg ggacgcgagg gcggagacat taccatctcc  120
gggaagggct ttagcacaac agggttcggt gtgtatgtgg ctgtggcccc agcaagcgtg  180
ccagagttct acgggaactc cgataaattt tatgggtatg accccagtaa agacacaacc  240
gagagcccca gcacaatttg ggtttacacc ccctctcaga aagctattgg ctcccggttc  300
gcccagggca gaccaatgaa taatgacggg agctttacca tcactatgaa ggccccccca  360
ttcgagcagg gaaaggactt tgtggtcctg actaccaagg ctcacggagt gggcaaaacc  420
gaccactctg acgacactcg gacaccggtg acataccggg aggctactcc cgctccaaca  480
ggccctaaaa ctccaatcgc ccccagcaag cagccttcaa agcaggctgc ccccagcaag  540
caggtgaagc ctagcaagca ggctggcccc aacaagcaga gcactactcc tcagcagaag  600
accgcagagc acagatctca gaccccagca gctcatcgca ctatgactaa gcaggtgtgt  660
accatcggag cctcaaaggt gaccagcgga tccctgacat ggggaatccg gactagcttt  720
acttcctacc tgcgcgggcc catcgcaaac ggcagctgga agctgtctgg gggggccaat  780
tggaacggca gcgccttcac attcccactg acttctggat ccttcgaccc cgccaccaaa  840
tccggctcac tgaagtacag cgggagcgtg cacatgactg gacaccatgg aattctggac  900
atgacactcg ctgaaccctc tctgcagatc aagggctcta ctgggcacct gtatctggat  960
gtgaagtcct cttctatgga cggcaagaag acaaactatg ggagagtgga ttttgccacc  1020
```

-continued

```
ttcggagtga gcgtgagcgg aaatgctgca atcaaagggt cccccgtgaa actgaccgct  1080
accggagcaa aagcctttgc cggcttttac agagcaggag agcccatgaa ccccctgagc  1140
accaatctga cactgagcgc tgagaaagtt tgtcacaatg tgaccgttga tgcagttacc  1200
gggaaagtga tcggcgacga ttccggaaag ggggcaggaa ggggactgcc tgtcacttga  1260

SEQ ID NO: 305          moltype = RNA  length = 1296
FEATURE                 Location/Qualifiers
source                  1..1296
                        mol_type = other RNA
                        organism = synthetic construct
SEQUENCE: 305
atgggagtga ccggaatcct gcagctgccc agagataggt tcaagcggac cagcttcttc  60
ctgtgggtca ttatcctgtt tcagagaaca ttctctgctg ggccaacagt gacagtgatc  120
cccgtgggac gcgagggcgg agacattacc atctccggga agggctttag cacaacaggg  180
ttcggtgtgt atgtggctgt ggccccagca agcgtgccag agttctacgg gaactccgat  240
aaattttatg ggtatgaccc cagtaaagac acaaccgaga gccccagcac aatttgggtt  300
tacaccccct ctcagaaagc tattggctcc cggttcgccc agggcagacc aatgaataat  360
gacgggagct ttaccatcac tatgaaggcc cccccattcg agcagggaaa ggactttgtg  420
gtcctgacta ccaaggctca cggagtgggc aaaaccgacc actctgacga cactcggaca  480
ccggtgacat accgggaggc tactcccgct ccaacaggcc ctaaaactcc aatcgccccc  540
agcaagcagc cttcaaagca ggctgccccc agcaagcagg tgaagcctag caagcaggct  600
ggccccaaca agcagagcac tactcctcag cagaagaccg cagagcacag atctcagacc  660
ccagcagctc atcgcactat gactaagcag gtgtgtacca tcggagcctc aaaggtgacc  720
agcggatccc tgacatgggg aatccggact agctttactt cctacctgcg cgggcccatc  780
gcaaacggca gctggaagct gtctgggggg gccaattgga acggcagcgc cttcacattc  840
ccactgactt ctggatcctt cgaccccgcc accaaatccg gctcactgaa gtacagcggg  900
agcgtgcaca tgactggaca ccatggaatt ctggacatga cactcgctga accctctctg  960
cagatcaagg gctctactgg gcacctgtat ctggatgtga agtcctcttc tatggacggc  1020
aagaagacaa actatgggag agtggatttt gccaccttcg gagtgagcgt gagcggaaat  1080
gctgcaatca aagggtcccc cgtgaaactg accgctaccg gagcaaaagc ctttgccggc  1140
ttttacagag caggagagcc catgaacccc ctgagcacca atctgacact gagcgctgag  1200
aaagtttgtc acaatgtgac cgttgatgca gttaccggga aagtgatcgg cgacgattcc  1260
ggaaaggggg caggaagggg actgcctgtc acttga                          1296

SEQ ID NO: 306          moltype = RNA  length = 1338
FEATURE                 Location/Qualifiers
source                  1..1338
                        mol_type = other RNA
                        organism = synthetic construct
SEQUENCE: 306
atgaaggcca ttctggtggt gctgctgtac acatttgcta cagccaacgc cgctgggcca  60
acagtgacag tgatccccgt gggacgcgag ggcggagaca ttaccatctc cgggaagggc  120
tttagcacaa cagggttcgg tgtgtatgtg gctgtggccc cagcaagcgt gccagagttc  180
tacgggaact ccgataaatt ttatgggtat gaccccagta aagacacaac cgagagcccc  240
agcacaattt gggtttacac cccctctcag aaagctattg gctcccggtt cgcccagggc  300
agaccaatga ataatgacgg gagctttacc atcactatga aggccccccc attcgagcag  360
ggaaaggact ttgtggtcct gactaccaag gctcacggag tgggcaaaac cgaccactct  420
gacgacactc ggacaccggt gacataccgg gaggctactc ccgctccaac aggccctaaa  480
actccaatcg cccccagcaa gcagccttca aagcaggctg cccccagcaa gcaggtgaag  540
cctagcaagc aggctggccc caacaagcag agcactactc ctcagcagaa gaccgcagag  600
cacagatctc agaccccagc agctcatcgc actatgacta agcaggtgtg taccatcgga  660
gcctcaaagg tgaccagcgg atccctgaca tggggaatcc ggactagctt tacttcctac  720
ctgcgcgggc ccatcgcaaa cggcagctgg aagctgtctg ggggggccaa ttggaacggc  780
agcgccttca cattcccact gacttctgga tccttcgacc ccgccaccaa atccggctca  840
ctgaagtaca gcgggagcgt gcacatgact ggacaccatg gaattctgga catgacactc  900
gctgaaccct ctctgcagat caagggctct actgggcacc tgtatctgga tgtgaagtcc  960
tcttctatgg acggcaagaa gacaaactat gggagagtgg attttgccac cttcggagtg  1020
agcgtgagcg gaaatgctgc aatcaaaggg tcccccgtga aactgaccgc taccggagca  1080
aaagcctttg ccggctttta cagagcagga gagcccatga accccctgag caccaatctg  1140
acactgagcg ctgagaaagt ttgtcacaat gtgaccgttg atgcagttac cgggaaagtg  1200
atcggcgacg attccggaaa gggggcagga aggggactgc ctgtcacttc cggcagcatc  1260
ctggccatct acagcaccgt ggctagctcc ctggtgctgg tggtgagcct gggagctatt  1320
agctttggaa gcggatga                                              1338

SEQ ID NO: 307          moltype = RNA  length = 1326
FEATURE                 Location/Qualifiers
source                  1..1326
                        mol_type = other RNA
                        organism = synthetic construct
SEQUENCE: 307
atgaaggcta tcatcgtgct gctgatggtg gtgacctcca acgccgctgg gccaacagtg  60
acagtgatcc ccgtgggacg cgagggcgga gacattacca tctccgggaa gggctttagc  120
acaacagggt tcggtgtgta tgtggctgtg gccccagcaa gcgtgccaga gttctacggg  180
aactccgata aattttatgg gtatgacccc agtaaagaca caaccgagag ccccagcaca  240
atttgggttt acaccccctc tcagaaagct attggctccc ggttcgccca gggcagacca  300
atgaataatg acgggagctt taccatcact atgaaggccc ccccattcga gcagggaaag  360
gactttgtgg tcctgactac caaggctcac ggagtgggca aaaccgacca ctctgacgac  420
actcggacac cggtgacata ccgggaggct actcccgctc caacaggccc taaaactcca  480
atcgccccca gcaagcagcc ttcaaagcag gctgccccca gcaagcaggt gaagcctagc  540
```

```
aagcaggctg gccccaacaa gcagagcact actcctcagc agaagaccgc agagcacaga  600
tctcagaccc cagcagctca tcgcactatg actaagcagg tgtgtaccat cggagcctca  660
aaggtgacca gcggatccct gacatgggga atccggacta gctttacttc ctacctgcgc  720
gggcccatcg caaacggcag ctggaagctg tctggggggg ccaattggaa cggcagcgcc  780
ttcacattcc cactgacttc tggatccttc gaccccgcca ccaaatccgg ctcactgaag  840
tacagcggga gcgtgcacat gactggacac catggaattc tggacatgac actcgctgaa  900
ccctctctgc agatcaaggg ctctactggg cacctgtatc tggatgtgaa gtcctcttct  960
atggacggca agaagacaaa ctatgggaga gtggattttg ccaccttcgg agtgagcgtg  1020
agcggaaatg ctgcaatcaa agggtccccc gtgaaactga ccgctaccgg agcaaaagcc  1080
tttgccggct tttacagagc aggagagccc atgaaccccc tgagcaccaa tctgacactg  1140
agcgctgaga aagtttgtca caatgtgacc gttgatgcag ttaccgggaa agtgatcggc  1200
gacgattccg gaaagggggc aggaagggga ctgcctgtca ctagcggcag ctctacagcc  1260
gcaagcagcc tggctgtgac actgatgctg gccattttca ttgtgtacat ggtgggctcc  1320
ggatga                                                             1326

SEQ ID NO: 308          moltype = RNA  length = 1338
FEATURE                 Location/Qualifiers
source                  1..1338
                        mol_type = other RNA
                        organism = synthetic construct
SEQUENCE: 308
atggtgcccc aggcactgct gttcgtgcca ctgctggtgt ttccactgtg tttcggcgct  60
gggccaacag tgacagtgat ccccgtggga cgcgagggcg gagacattac catctccggg  120
aagggcttta gcacaacagg gttcggtgtg tatgtggctg tggccccagc aagcgtgcca  180
gagttctacg ggaactccga taaattttat gggtatgacc ccagtaaaga cacaaccgag  240
agccccagca caatttgggt ttacaccccc tctcagaaag ctattggctc ccggttcgcc  300
cagggcagac caatgaataa tgacgggagc tttaccatca ctatgaaggc ccccccattc  360
gagcagggaa aggactttgt ggtcctgact accaaggctc acggagtggg caaaaccgac  420
cactctgacg acactcggac accggtgaca taccgggagg ctactcccgc tccaacaggc  480
cctaaaactc caatcgcccc cagcaagcag ccttcaaagc aggctgcccc cagcaagcag  540
gtgaagccta gcaagcaggc tggccccaac aagcagagca ctactcctca gcagaagacc  600
gcagagcaca gatctcagac cccagcagct catcgcacta tgactaagca ggtgtgtacc  660
atcggagcct caaaggtgac cagcggatcc ctgacatggg gaatccggac tagctttact  720
tcctacctgc gcgggcccat cgcaaacggc agctggaagc tgtctggggg ggccaattgg  780
aacggcagcg ccttcacatt cccactgact tctggatcct tcgaccccgc caccaaatcc  840
ggctcactga agtacagcgg gagcgtgcac atgactggac accatggaat tctggacatg  900
acactcgctg aaccctctct gcagatcaag ggctctactg ggcacctgta tctggatgtg  960
aagtcctctt ctatggacgg caagaagaca aactatggga gagtggattt tgccaccttc  1020
ggagtgagcg tgagcggaaa tgctgcaatc aaagggtccc ccgtgaaact gaccgctacc  1080
ggagcaaaag cctttgccgg cttttacaga gcaggagagc ccatgaaccc cctgagcacc  1140
aatctgacac tgagcgctga gaaagtttgt cacaatgtga ccgttgatgc agttaccggg  1200
aaagtgatcg gcgacgattc cggaaagggg gcaggaaggg gactgcctgt cactagcgga  1260
tccgtgctgc tgtctgccgg agctctgaca gcactgatgc tgatcatttt cctgatgacc  1320
tgctggggca gcggctga                                                1338

SEQ ID NO: 309          moltype = RNA  length = 1341
FEATURE                 Location/Qualifiers
source                  1..1341
                        mol_type = other RNA
                        organism = synthetic construct
SEQUENCE: 309
atgttcctga tccagtgtct gatctccgcc gtgatcttct atatccaggt gaccaacgca  60
gctgggccaa cagtgacagt gatccccgtg ggacgcgagg gcggagacat taccatctcc  120
gggaagggct ttagcacaac agggttcggt gtgtatgtgg ctgtggcccc agcaagcgtg  180
ccagagttct acgggaactc cgataaattt tatgggtatg accccagtaa agacacaacc  240
gagagcccca gcacaatttg ggtttacacc ccctctcaga aagctattgg ctcccggttc  300
gcccagggca gaccaatgaa taatgacggg agctttacca tcactatgaa ggccccccca  360
ttcgagcagg gaaaggactt tgtggtcctg actaccaagg ctcacggagt gggcaaaacc  420
gaccactctg acgacactcg gacaccggtg acataccggg aggctactcc cgctccaaca  480
ggccctaaaa ctccaatcgc ccccagcaag cagccttcaa agcaggctgc ccccagcaag  540
caggtgaagc ctagcaagca ggctggcccc aacaagcaga gcactactcc tcagcagaag  600
accgcagagc acagatctca gaccccagca gctcatcgca ctatgactaa gcaggtgtgt  660
accatcggag cctcaaaggt gaccagcgga tccctgacat ggggaatccg gactagcttt  720
acttcctacc tgcgcgggcc catcgcaaac ggcagctgga agctgtctgg gggggccaat  780
tggaacggca gcgccttcac attcccactg acttctggat ccttcgaccc cgccaccaaa  840
tccggctcac tgaagtacag cgggagcgtg cacatgactg gacaccatgg aattctggac  900
atgacactcg ctgaaccctc tctgcagatc aagggctcta ctgggcacct gtatctggat  960
gtgaagtcct cttctatgga cggcaagaag acaaactatg ggagagtgga ttttgccacc  1020
ttcggagtga gcgtgagcgg aaatgctgca atcaaagggt cccccgtgaa actgaccgct  1080
accggagcaa aagcctttgc cggcttttac agagcaggag agcccatgaa ccccctgagc  1140
accaatctga cactgagcgc tgagaaagtt tgtcacaatg tgaccgttga tgcagttacc  1200
gggaaagtga tcggcgacga ttccggaaag ggggcaggaa ggggactgcc tgtcactagc  1260
ggaagcatta ttatccccat cgtggcctct gtgatgatcc tgaccgcaat ggtcattgtg  1320
atcgtgatcg gcagcggctg a                                            1341

SEQ ID NO: 310          moltype = RNA  length = 1377
FEATURE                 Location/Qualifiers
source                  1..1377
                        mol_type = other RNA
```

```
                          organism = synthetic construct
SEQUENCE: 310
atgggagtga ccggaatcct gcagctgccc agagataggt tcaagcggac cagcttcttc  60
ctgtgggtca ttatcctgtt tcagagaaca ttctctgctg ggccaacagt gacagtgatc  120
cccgtgggac gcgagggcgg agacattacc atctccggga agggctttag cacaacaggg  180
ttcggtgtgt atgtggctgt ggccccagca agcgtgccag agttctacgg gaactccgat  240
aaattttatg ggtatgaccc cagtaaagac acaaccgaga gccccagcac aatttgggtt  300
tacacccccct ctcagaaagc tattggctcc cggttcgccc agggcagacc aatgaataat  360
gacgggagct ttaccatcac tatgaaggcc cccccattcg agcagggaaa ggactttgtg  420
gtcctgacta ccaaggctca cggagtgggc aaaaccgacc actctgacga cactcggaca  480
ccggtgacat accgggaggc tactcccgct ccaacaggcc ctaaaactcc aatcgccccc  540
agcaagcagc cttcaaagca ggctgccccc agcaagcagg tgaagcctag caagcaggct  600
ggccccaaca agcagagcac tactcctcag cagaagaccg cagagcacag atctcagacc  660
ccagcagctc atcgcactat gactaagcag gtgtgtacca tcggagcctc aaaggtgacc  720
agcggatccc tgacatgggg aatccggact agctttactt cctacctgcg cgggcccatc  780
gcaaacggca gctggaagct gtctgggggg gccaattgga acggcagcgc cttcacattc  840
ccactgactt ctggatcctt cgaccccgcc accaaatccg gctcactgaa gtacagcggg  900
agcgtgcaca tgactggaca ccatggaatt ctggacatga cactcgctga accctctctg  960
cagatcaagg gctctactgg gcacctgtat ctggatgtga agtcctcttc tatggacggc  1020
aagaagacaa actatgggag agtggatttt gccaccttcg gagtgagcgt gagcggaaat  1080
gctgcaatca aagggtcccc cgtgaaactg accgctaccg gagcaaaagc ctttgccggc  1140
ttttacagag caggagagcc catgaacccc ctgagcacca atctgacact gagcgctgag  1200
aaagtttgtc acaatgtgac cgttgatgca gttaccggga aagtgatcgg cgacgattcc  1260
ggaaaggggg caggaagggg actgcctgtc acttctggat cctggatccc tgccggaatc  1320
ggggtgaccg gcgtgatcat cgccgtgatc gccctgttct gtattggcag cggatga     1377

SEQ ID NO: 311          moltype = RNA  length = 51
FEATURE                 Location/Qualifiers
source                  1..51
                        mol_type = other RNA
                        organism = synthetic construct
SEQUENCE: 311
atgaaagcca agctgctggt gctgctgtgc accttcaccg ccacatacgc c           51

SEQ ID NO: 312          moltype = RNA  length = 81
FEATURE                 Location/Qualifiers
source                  1..81
                        mol_type = other RNA
                        organism = synthetic construct
SEQUENCE: 312
attctggcca tctacagcac agtggccagc tctctggtgc tgctggttag cctgggcgcc  60
atcagcttcg gcagcggcta a                                            81

SEQ ID NO: 313          moltype = AA  length = 267
FEATURE                 Location/Qualifiers
source                  1..267
                        mol_type = protein
                        organism = Cutibacterium acnes
SEQUENCE: 313
MKKTHLVAPL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTID  120
TIHTATTTLQ NKVSPAHVEL GLEVTKAVLL TANPASTAKE LDAEGAALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                      267

SEQ ID NO: 314          moltype = AA  length = 267
FEATURE                 Location/Qualifiers
source                  1..267
                        mol_type = protein
                        organism = Cutibacterium acnes
SEQUENCE: 314
MKKTHLVATL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTID  120
TIHTATTTLQ NKVSPAHVEL GLEVTKAVLL TANPASTAKE LDAEGAALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                      267

SEQ ID NO: 315          moltype = AA  length = 267
FEATURE                 Location/Qualifiers
source                  1..267
                        mol_type = protein
                        organism = Cutibacterium acnes
SEQUENCE: 315
MKKTHLVTPL LIGAMLVPAT LSAPSAHAVE PTTTISATAT HELSASDAHN SLQLLNARIA  60
TLQSVQKSVP GSDYSDQIRD LLKAAFDLRG LIDTLAHGGI PFYDPSTIMP RIKLAATTID  120
TIHTATTTLQ NKVRPAHVEL GLEVTKAVLL TANPASTAKE LDAEGAALKA RLDKVSQYPD  180
LAPNDVATVY VRTNFSRTIW QVRADRNRYI LGHKSAEVYK TLNHAITKAV GVRLNPKTTV  240
GNIQAARTKL LAAYQTAFNS PDVKKAA                                      267
```

-continued

```
SEQ ID NO: 316         moltype = AA  length = 267
FEATURE                Location/Qualifiers
source                 1..267
                       mol_type = protein
                       organism = Cutibacterium acnes
SEQUENCE: 316
MKKTHLVTPL LIGAMLVPAT LSAPSAHAVE PTTTISTTAT HELSASDAHN SLQLLNARIA  60
TLQSVQKSVP GSDYSDQIRD LLKAAFDLRG LIDTLAHGGI PFYDPSTIMP RIKLAATTID  120
TIHTATTTLQ NKVRPAHVEL GLEVTKAVLL TANPASTAKE LDAEGAALKA RLDKVSQYPD  180
LAPNDVATVY VRTNFSRTIW QVRADRNRYI LGHKSAEVYK TLNHAITKAV GVRLNPKTTV  240
GNIQAARTKL LAAYQTAFNS PDVKKAA                                      267

SEQ ID NO: 317         moltype = AA  length = 267
FEATURE                Location/Qualifiers
source                 1..267
                       mol_type = protein
                       organism = Cutibacterium acnes
SEQUENCE: 317
MKKTHLVAPL LVGAMLVPAA LSAPSAHAVE PTTTIISATST HELSASDARN SIQLLNPHIA  60
TLQSVQKSVP GSDYSDQIRD LLKAAFDLRG LIETLAHGGI PFYDPSTIMP RIKLVATTID  120
TIHTATTTLQ NKVRPAHVEL GLEVTKAVLL TANPASTAKE LDAEGAALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                      267

SEQ ID NO: 318         moltype = AA  length = 267
FEATURE                Location/Qualifiers
source                 1..267
                       mol_type = protein
                       organism = Cutibacterium acnes
SEQUENCE: 318
MKKTHLVAPL LVGAMLVPAA LSAPSAHAVE PTTTISATST HELSASYARN SIQLLNAHIA  60
TLQSVQKSVP GSDYSDQIRD LLKAAFDLRG LIETLAHGGI PFYDPSTIMP RIKLVATTID  120
TIHTATTTLQ NKVRPAHVEL GLEVTKAVLL TANPATTAKE LDAEGTALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                      267

SEQ ID NO: 319         moltype = AA  length = 267
FEATURE                Location/Qualifiers
source                 1..267
                       mol_type = protein
                       organism = Cutibacterium acnes
SEQUENCE: 319
MKKTHLVAPL LVGAMLVPAA LSAPSAHAVE PTTTISATST HELSANEAHN SMQLLNARIA  60
TLQSVQKSVP GSDYSDQIRD LLKAAFDLHG LIETLAHGGI PFYDPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                      267

SEQ ID NO: 320         moltype = AA  length = 267
FEATURE                Location/Qualifiers
source                 1..267
                       mol_type = protein
                       organism = Cutibacterium acnes
SEQUENCE: 320
MKKTHLVAPL LVGAMLVPAA LSAPSAHAVE PTTTISATST HELSANEARN SMQLLNARIA  60
TLQSVQKSVP GSDYSDQIRD LLKAAFDLRG LIETLTHGGI PFYDPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                      267

SEQ ID NO: 321         moltype = AA  length = 267
FEATURE                Location/Qualifiers
source                 1..267
                       mol_type = protein
                       organism = Cutibacterium acnes
SEQUENCE: 321
MKKTHLVAPL LVGAMLVPAA LSAPSAHAVE PTTTISATST HELSANEARN SMQLLNARIA  60
TLQSVQKSVP GSDYSDQIRD LLKAAFDLRG LIETLAHGGI PFYNPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                      267

SEQ ID NO: 322         moltype = AA  length = 267
FEATURE                Location/Qualifiers
source                 1..267
                       mol_type = protein
                       organism = Cutibacterium acnes
SEQUENCE: 322
MKKTHLVAPL LVGAMLVPAA LSAPSAHAVE PTTTISATST HELSANEARN SMQLLNARIA  60
```

-continued

```
TLQSVQKSVP GSDYSDQIRD LLKAAFDLHG LIETLAHGGI PFYDPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                     267

SEQ ID NO: 323          moltype = AA  length = 267
FEATURE                 Location/Qualifiers
source                  1..267
                        mol_type = protein
                        organism = Cutibacterium acnes
SEQUENCE: 323
MKKTHLVAPL LVGAMLVPAA LSAPSAHAVE PTTTISATST HELSANEARN SMQLLNARIA  60
TLQSVQKSVP GSDYSDQIRD LLKAAFDLRG LIETLAHGGI PFYDPSTIMP RIKLVATTVD  120
TIHTATTTLQ NKVRPAHVEL GLEVTNAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                     267

SEQ ID NO: 324          moltype = AA  length = 267
FEATURE                 Location/Qualifiers
source                  1..267
                        mol_type = protein
                        organism = Cutibacterium acnes
SEQUENCE: 324
MKKTHLVAPL LVGAMLVPAA LSAPSAHAVE PTTTISATST HELSANEARN SMQLLNARIA  60
TLQSVQKSVP GSDYSDQIRD LLKAAFDLRG LIETLAHGGI PFYDPSTIMP RIKLVATTVD  120
TIHTATTTLQ NKVRPAHVEL GLEVTKAVLL TANPASTAKE LDAEGAALKA HLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                     267

SEQ ID NO: 325          moltype = AA  length = 267
FEATURE                 Location/Qualifiers
source                  1..267
                        mol_type = protein
                        organism = Cutibacterium acnes
SEQUENCE: 325
MKKTHLVAPL LVGAMLVPAA LSAPSAHAVE PTTTISATST HELSANEARN SMQLLNARIA  60
TLQSVQKSVP GSDYSNQIRD LLKAAFDLRG LIETLAHGGI PFYDPSTIMP RIKLVATTVD  120
TIHTAKTILQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                     267

SEQ ID NO: 326          moltype = AA  length = 267
FEATURE                 Location/Qualifiers
source                  1..267
                        mol_type = protein
                        organism = Cutibacterium acnes
SEQUENCE: 326
MKKTHLVAPL LVGAMLVPAA LSAPSAHAVE PTTTISATST HELSASDARN SIQLLNAHIA  60
TLQSAQKSVP GSDYSDQIRD LLKAAFDLRG LIETLAHGGI PFYDPSTIMP RIKLVATTID  120
TIHTATTTLQ NKVRPAHVEL GLEVTKAVLL TANPATTAKE LDAEGTALKA RLEKVSQYPD  180
LTPNDVATVY VRTNFSKTIW QVRANRHRYI LGHKSAAVYK TLNHAITKAV GVRLNPKTTV  240
GNIQAARTEL LAAYQTAFNS PDVKKAA                                     267

SEQ ID NO: 327          moltype = AA  length = 267
FEATURE                 Location/Qualifiers
source                  1..267
                        mol_type = protein
                        organism = Cutibacterium acnes
SEQUENCE: 327
MKKTHLVAPL LVGAMLVPAA LSAPSAHAVE PTTTISATST HELSASDARN SIQLLNAHIA  60
TLQSAQKSVP GSDYSDQIRD LLKAAFDLRG LIETLAHGGI PFYDPSTIMP RIKLVATTID  120
TIHTATTTLQ NKVSPAHVEL GLEVTKAVLL TANPASTAKE LDAEGAALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 328          moltype = AA  length = 267
FEATURE                 Location/Qualifiers
source                  1..267
                        mol_type = protein
                        organism = Cutibacterium acnes
SEQUENCE: 328
MKKTHLVAPL LVGAMLVPAA LSAPSAHAVE PTTTISATST HELSASDARN SIQLLNAHIA  60
TLQSAQKSVP GSDYSDQIRD LLKAAFDLRG LIETLAHGGI PFYDPSTIMP RIKLVATTID  120
TIHTATTTLQ NKVRPAHVEL GLEVTKAVLL TANPATTAKE LDAEGTALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 329          moltype = AA  length = 267
FEATURE                 Location/Qualifiers
```

```
source                  1..267
                        mol_type = protein
                        organism = Cutibacterium acnes
SEQUENCE: 329
MKKTHLVAPL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTID  120
TIHTATTTLQ NKVRPAHVEL GLEVTKAVLL TANPATTAKE LDAEGTALKA RLEKVSQYPD  180
LTPNDVATVY VRTNFSKTIW QVRANRDRYI LGHKSAAVYK TLNHAITKAV GVRLNPKTTV  240
GNIQAARTEL FAAYQTAFNS PDVKKAA                                     267

SEQ ID NO: 330          moltype = AA  length = 267
FEATURE                 Location/Qualifiers
source                  1..267
                        mol_type = protein
                        organism = Cutibacterium acnes
SEQUENCE: 330
MKKTHLVAPL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTIG  120
TIHTATTTLQ NKVSPAHVEL GLEVTKAVLL TANPASTAKE LDAEGAALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 331          moltype = AA  length = 267
FEATURE                 Location/Qualifiers
source                  1..267
                        mol_type = protein
                        organism = Cutibacterium acnes
SEQUENCE: 331
MKKTHLVAPL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTID  120
TIHTATTTLQ NKVSPAHVEL GLEVTKAVLL TANPASTAKE LDAEGAALKA RLKKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 332          moltype = AA  length = 267
FEATURE                 Location/Qualifiers
source                  1..267
                        mol_type = protein
                        organism = Cutibacterium acnes
SEQUENCE: 332
MKKTHLVAPL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 333          moltype = AA  length = 267
FEATURE                 Location/Qualifiers
source                  1..267
                        mol_type = protein
                        organism = Cutibacterium acnes
SEQUENCE: 333
MKKTHLVAPL LVGAMLVPAA LSAPSAHAVE PTTTISATST HELSASDARN SIQLLNAHIA  60
TLQSVQKSVP GSDYSDQIRD LLKAAFDLRG LIETLAHGGI PFYDPSTIMP RIKLVATTID  120
TIHTATTTLQ NKVRPAHVEL GLEVTKAVLL TANPATTAKE LDAEGTALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 334          moltype = AA  length = 267
FEATURE                 Location/Qualifiers
source                  1..267
                        mol_type = protein
                        organism = Cutibacterium acnes
SEQUENCE: 334
MKKTHLVAPL LVGAMLVPAA LSAPSAHAVE PTTTISATST HELSANEARN SMQLLNARIA  60
TLQSVQKSVP GSDYSNQIRD LLKAAFDLRG LIETLAHGGI PFYDPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                     267

SEQ ID NO: 335          moltype = AA  length = 267
FEATURE                 Location/Qualifiers
source                  1..267
                        mol_type = protein
                        organism = Cutibacterium acnes
SEQUENCE: 335
MKKTHLVAPL LVGAMLVPAA LSAPSAHAVE PTTTISATST HELSASDARN SIQLLNPHIA  60
TLQSVQKSVP GSDYSDQIRD LLKAAFDLRG LIETLAHGGI PFYDPSTIMP RIKLVATTID  120
TIHTATTTLQ NKVRPAHVEL GLEVTKAVLL TANPASTAKE LDAEGAALKA RLEKVSQYPD  180
```

-continued

```
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 336         moltype = AA  length = 267
FEATURE                Location/Qualifiers
source                 1..267
                       mol_type = protein
                       organism = Cutibacterium acnes
SEQUENCE: 336
MKKTHLVAPL LVGAMLVPAA LSAPSAHAVE PTTTISATST HELSANEARN SMQLLNARIA  60
TLQSVQKSVP GSDYSDQIRD LLKAAFDLRG LIETLAHGGI PFYDPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLAPKTTV  240
GNIQAARTEL LAAYQTAFNS PDVKKAA                                     267

SEQ ID NO: 337         moltype = AA  length = 267
FEATURE                Location/Qualifiers
source                 1..267
                       mol_type = protein
                       organism = Cutibacterium acnes
SEQUENCE: 337
MKKTHLVAPL LVGAMLVPAA LSAPSAHAVE PTTTISATST HELSANEARN SMQLLNARIA  60
TLQSVQKSVP GSDYSDQIRD LLKAAFDLRG LIETLAHGGI PFYDPSTIMP RIKLVATTVD  120
TIHTATTTLQ NKVRPAHVEL GLEVTKAVLL TANPASTAKE LDAEGAALKA RLEKVSQYPD  180
LTPNDVATVY VRTNFSKTIW QVRADRDRYI LGHKSAAVYK TLNHAITKAV GVRLDPKTTV  240
GNIQAARTEL LAAYQTAFNS PDVKKAA                                     267

SEQ ID NO: 338         moltype = AA  length = 267
FEATURE                Location/Qualifiers
source                 1..267
                       mol_type = protein
                       organism = Cutibacterium acnes
SEQUENCE: 338
MKKTHLVAPL LVGAMLVPAA LSAPSAHAVE PTTTISATST HELSASDARN STQLLNAHIA  60
TLQSVQKSVP GSDYSDQIRD LLKAAFDLRG LIETLAHGGI PFYDPSTIMP RIKLVATTID  120
TIHTATTTLQ NKVRPAHVEL GLEVTKAVLL TANPATTAKE LDAEGTALKA RLEKVSQYPD  180
LTPNDVATVY VRTNFSKTIW QVRANRDRYI LGHKSAAVYK TLNHAITKAV GVRLNPKTTV  240
GNIQAARTEL LAAYQTAFNS PDVKKAA                                     267

SEQ ID NO: 339         moltype = AA  length = 239
FEATURE                Location/Qualifiers
source                 1..239
                       mol_type = protein
                       organism = Cutibacterium acnes
SEQUENCE: 339
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVSPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 340         moltype = AA  length = 239
FEATURE                Location/Qualifiers
source                 1..239
                       mol_type = protein
                       organism = Cutibacterium acnes
SEQUENCE: 340
VEPTTTISAT ATHELSASDA HNSLQLLNAR IATLQSVQKS VPGSDYSDQI RDLLKAAFDL  60
RGLIDTLAHG GIPFYDPSTI MPRIKLAATT IDTIHTATTT LQNKVRPAHV ELGLEVTKAV  120
LLTANPASTA KELDAEGAAL KARLDKVSQY PDLAPNDVAT VYVRTNFSRT IWQVRADRNR  180
YILGHKSAEV YKTLNHAITK AVGVRLNPKT TVGNIQAART KLLAAYQTAF NSPDVKKAA   239

SEQ ID NO: 341         moltype = AA  length = 239
FEATURE                Location/Qualifiers
source                 1..239
                       mol_type = protein
                       organism = Cutibacterium acnes
SEQUENCE: 341
VEPTTTISTT ATHELSASDA HNSLQLLNAR IATLQSVQKS VPGSDYSDQI RDLLKAAFDL  60
RGLIDTLAHG GIPFYDPSTI MPRIKLAATT IDTIHTATTT LQNKVRPAHV ELGLEVTKAV  120
LLTANPASTA KELDAEGAAL KARLDKVSQY PDLAPNDVAT VYVRTNFSRT IWQVRADRNR  180
YILGHKSAEV YKTLNHAITK AVGVRLNPKT TVGNIQAART KLLAAYQTAF NSPDVKKAA   239

SEQ ID NO: 342         moltype = AA  length = 239
FEATURE                Location/Qualifiers
source                 1..239
                       mol_type = protein
                       organism = Cutibacterium acnes
SEQUENCE: 342
VEPTTIISAT STHELSASDA RNSIQLLNPH IATLQSVQKS VPGSDYSDQI RDLLKAAFDL  60
```

```
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 343         moltype = AA  length = 239
FEATURE                Location/Qualifiers
source                 1..239
                       mol_type = protein
                       organism = Cutibacterium acnes
SEQUENCE: 343
VEPTTTISAT STHELSASYA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPATTA KELDAEGTAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 344         moltype = AA  length = 239
FEATURE                Location/Qualifiers
source                 1..239
                       mol_type = protein
                       organism = Cutibacterium acnes
SEQUENCE: 344
VEPTTTISAT STHELSANEA HNSMQLLNAR IATLQSVQKS VPGSDYSDQI RDLLKAAFDL  60
HGLIETLAHG GIPFYDPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRADRDR  180
YILGHKSAAV YKTLNHAITK AVGVRLDPKT TVGNIQAART ELLAAYQTAF NSPDVKKAA   239

SEQ ID NO: 345         moltype = AA  length = 239
FEATURE                Location/Qualifiers
source                 1..239
                       mol_type = protein
                       organism = Cutibacterium acnes
SEQUENCE: 345
VEPTTTISAT STHELSANEA RNSMQLLNAR IATLQSVQKS VPGSDYSDQI RDLLKAAFDL  60
RGLIETLTHG GIPFYDPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRADRDR  180
YILGHKSAAV YKTLNHAITK AVGVRLDPKT TVGNIQAART ELLAAYQTAF NSPDVKKAA   239

SEQ ID NO: 346         moltype = AA  length = 239
FEATURE                Location/Qualifiers
source                 1..239
                       mol_type = protein
                       organism = Cutibacterium acnes
SEQUENCE: 346
VEPTTTISAT STHELSANEA RNSMQLLNAR IATLQSVQKS VPGSDYSDQI RDLLKAAFDL  60
RGLIETLAHG GIPFYNPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRADRDR  180
YILGHKSAAV YKTLNHAITK AVGVRLDPKT TVGNIQAART ELLAAYQTAF NSPDVKKAA   239

SEQ ID NO: 347         moltype = AA  length = 239
FEATURE                Location/Qualifiers
source                 1..239
                       mol_type = protein
                       organism = Cutibacterium acnes
SEQUENCE: 347
VEPTTTISAT STHELSANEA RNSMQLLNAR IATLQSVQKS VPGSDYSDQI RDLLKAAFDL  60
HGLIETLAHG GIPFYDPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRADRDR  180
YILGHKSAAV YKTLNHAITK AVGVRLDPKT TVGNIQAART ELLAAYQTAF NSPDVKKAA   239

SEQ ID NO: 348         moltype = AA  length = 239
FEATURE                Location/Qualifiers
source                 1..239
                       mol_type = protein
                       organism = Cutibacterium acnes
SEQUENCE: 348
VEPTTTISAT STHELSANEA RNSMQLLNAR IATLQSVQKS VPGSDYSDQI RDLLKAAFDL  60
RGLIETLAHG GIPFYDPSTI MPRIKLVATT VDTIHTATTT LQNKVRPAHV ELGLEVTNAV  120
LLTANPASTA KELDAEGAAL KARLEKVSQY PDLTPNDVAT VYVRTNFSKT IWQVRADRDR  180
YILGHKSAAV YKTLNHAITK AVGVRLDPKT TVGNIQAART ELLAAYQTAF NSPDVKKAA   239

SEQ ID NO: 349         moltype = AA  length = 239
FEATURE                Location/Qualifiers
source                 1..239
                       mol_type = protein
                       organism = Cutibacterium acnes
SEQUENCE: 349
VEPTTTISAT STHELSANEA RNSMQLLNAR IATLQSVQKS VPGSDYSDQI RDLLKAAFDL  60
RGLIETLAHG GIPFYDPSTI MPRIKLVATT VDTIHTATTT LQNKVRPAHV ELGLEVTKAV  120
LLTANPASTA KELDAEGAAL KAHLEKVSQY PDLTPNDVAT VYVRTNFSKT IWQVRADRDR  180
```

YILGHKSAAV YKTLNHAITK AVGVRLDPKT TVGNIQAART ELLAAYQTAF NSPDVKKAA 239

SEQ ID NO: 350 moltype = AA length = 239
FEATURE Location/Qualifiers
source 1..239
mol_type = protein
organism = Cutibacterium acnes
SEQUENCE: 350
VEPTTTISAT STHELSANEA RNSMQLLNAR IATLQSVQKS VPGSDYSNQI RDLLKAAFDL 60
RGLIETLAHG GIPFYDPSTI MPRIKLVATT VDTIHTAKTI LQNKVRPAHV ELGLEVTKAV 120
LLTANPASTA KELDAEGAAL KARLEKVSQY PDLTPNDVAT VYVRTNFSKT IWQVRADRDR 180
YILGHKSAAV YKTLNHAITK AVGVRLDPKT TVGNIQAART ELLAAYQTAF NSPDVKKAA 239

SEQ ID NO: 351 moltype = AA length = 239
FEATURE Location/Qualifiers
source 1..239
mol_type = protein
organism = Cutibacterium acnes
SEQUENCE: 351
VEPTTTISAT STHELSASDA RNSIQLLNAH IATLQSAQKS VPGSDYSDQI RDLLKAAFDL 60
RGLIETLAHG GIPFYDPSTI MPRIKLVATT IDTIHTATTT LQNKVRPAHV ELGLEVTKAV 120
LLTANPATTA KELDAEGTAL KARLEKVSQY PDLTPNDVAT VYVRTNFSKT IWQVRANRHR 180
YILGHKSAAV YKTLNHAITK AVGVRLNPKT TVGNIQAART ELLAAYQTAF NSPDVKKAA 239

SEQ ID NO: 352 moltype = AA length = 239
FEATURE Location/Qualifiers
source 1..239
mol_type = protein
organism = Cutibacterium acnes
SEQUENCE: 352
VEPTTTISAT STHELSASDA RNSIQLLNAH IATLQSAQKS VPGSDYSDQI RDLLKAAFDL 60
RGLIETLAHG GIPFYDPSTI MPRIKLVATT IDTIHTATTT LQNKVSPAHV ELGLEVTKAV 120
LLTANPASTA KELDAEGAAL KARLEKVSQY PDLTPNDVAT VYVRTNFSKT IWQVRANRDR 180
YILGHKSAAV YKTLNHAITK AVGVRLNPKT TVGNIQAART ELLAAYQTAF NSPDVKKAA 239

SEQ ID NO: 353 moltype = AA length = 239
FEATURE Location/Qualifiers
source 1..239
mol_type = protein
organism = Cutibacterium acnes
SEQUENCE: 353
VEPTTTISAT STHELSASDA RNSIQLLNAH IATLQSAQKS VPGSDYSDQI RDLLKAAFDL 60
RGLIETLAHG GIPFYDPSTI MPRIKLVATT IDTIHTATTT LQNKVRPAHV ELGLEVTKAV 120
LLTANPATTA KELDAEGTAL KARLEKVSQY PDLTPNDVAT VYVRTNFSKT IWQVRANRDR 180
YILGHKSAAV YKTLNHAITK AVGVRLNPKT TVGNIQAART ELLAAYQTAF NSPDVKKAA 239

SEQ ID NO: 354 moltype = AA length = 239
FEATURE Location/Qualifiers
source 1..239
mol_type = protein
organism = Cutibacterium acnes
SEQUENCE: 354
VEPTTTISAT STHELSASDA RNSIQLLNAH IATLQSVQKS VPGSDYSDQI RDLLKAAFDL 60
RGLIETLAHG GIPFYDPSTI MPRIKLVATT IDTIHTATTT LQNKVRPAHV ELGLEVTKAV 120
LLTANPATTA KELDAEGTAL KARLEKVSQY PDLTPNDVAT VYVRTNFSKT IWQVRANRDR 180
YILGHKSAAV YKTLNHAITK AVGVRLNPKT TVGNIQAART ELFAAYQTAF NSPDVKKAA 239

SEQ ID NO: 355 moltype = AA length = 239
FEATURE Location/Qualifiers
source 1..239
mol_type = protein
organism = Cutibacterium acnes
SEQUENCE: 355
VEPTTTISAT STHELSASDA RNSIQLLNAH IATLQSVQKS VPGSDYSDQI RDLLKAAFDL 60
RGLIETLAHG GIPFYDPSTI MPRIKLVATT IGTIHTATTT LQNKVSPAHV ELGLEVTKAV 120
LLTANPASTA KELDAEGAAL KARLEKVSQY PDLTPNDVAT VYVRTNFSKT IWQVRANRDR 180
YILGHKSAAV YKTLNHAITK AVGVRLNPKT TVGNIQAART ELLAAYQTAF NSPDVKKAA 239

SEQ ID NO: 356 moltype = AA length = 239
FEATURE Location/Qualifiers
source 1..239
mol_type = protein
organism = Cutibacterium acnes
SEQUENCE: 356
VEPTTTISAT STHELSASDA RNSIQLLNAH IATLQSVQKS VPGSDYSDQI RDLLKAAFDL 60
RGLIETLAHG GIPFYDPSTI MPRIKLVATT IDTIHTATTT LQNKVSPAHV ELGLEVTKAV 120
LLTANPASTA KELDAEGAAL KARLKKVSQY PDLTPNDVAT VYVRTNFSKT IWQVRANRDR 180
YILGHKSAAV YKTLNHAITK AVGVRLNPKT TVGNIQAART ELLAAYQTAF NSPDVKKAA 239

-continued

```
SEQ ID NO: 357         moltype = AA  length = 239
FEATURE                Location/Qualifiers
source                 1..239
                       mol_type = protein
                       organism = Cutibacterium acnes
SEQUENCE: 357
VEPTTTISAT STHELSASDA RNSIQLLNAH IATLQSVQKS VPGSDYSDQI RDLLKAAFDL  60
RGLIETLAHG GIPFYDPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 358         moltype = AA  length = 239
FEATURE                Location/Qualifiers
source                 1..239
                       mol_type = protein
                       organism = Cutibacterium acnes
SEQUENCE: 358
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPATTA KELDAEGTAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 359         moltype = AA  length = 239
FEATURE                Location/Qualifiers
source                 1..239
                       mol_type = protein
                       organism = Cutibacterium acnes
SEQUENCE: 359
VEPTTTISAT STHELSANEA RNSMQLLNAR IATLQSVQKS VPGSDYSNQI RDLLKAAFDL  60
RGLIETLAHG GIPFYDPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRADRDR  180
YILGHKSAAV YKTLNHAITK AVGVRLDPKT TVGNIQAART ELLAAYQTAF NSPDVKKAA   239

SEQ ID NO: 360         moltype = AA  length = 239
FEATURE                Location/Qualifiers
source                 1..239
                       mol_type = protein
                       organism = Cutibacterium acnes
SEQUENCE: 360
VEPTTTISAT STHELSASDA RNSIQLLNPH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 361         moltype = AA  length = 239
FEATURE                Location/Qualifiers
source                 1..239
                       mol_type = protein
                       organism = Cutibacterium acnes
SEQUENCE: 361
VEPTTTISAT STHELSANEA RNSMQLLNAR IATLQSVQKS VPGSDYSDQI RDLLKAAFDL  60
RGLIETLAHG GIPFYDPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRADRDR  180
YILGHKSAAV YKTLNHAITK AVGVRLAPKT TVGNIQAART ELLAAYQTAF NSPDVKKAA   239

SEQ ID NO: 362         moltype = AA  length = 239
FEATURE                Location/Qualifiers
source                 1..239
                       mol_type = protein
                       organism = Cutibacterium acnes
SEQUENCE: 362
VEPTTTISAT STHELSANEA RNSMQLLNAR IATLQSVQKS VPGSDYSDQI RDLLKAAFDL  60
RGLIETLAHG GIPFYDPSTI MPRIKLVATT VDTIHTATTT LQNKVRPAHV ELGLEVTKAV  120
LLTANPASTA KELDAEGAAL KARLEKVSQY PDLTPNDVAT VYVRTNFSKT IWQVRADRDR  180
YILGHKSAAV YKTLNHAITK AVGVRLDPKT TVGNIQAART ELLAAYQTAF NSPDVKKAA   239

SEQ ID NO: 363         moltype = AA  length = 239
FEATURE                Location/Qualifiers
source                 1..239
                       mol_type = protein
                       organism = Cutibacterium acnes
SEQUENCE: 363
VEPTTTISAT STHELSASDA RNSTQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPATTA KELDAEGTAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAA   239

SEQ ID NO: 364         moltype =   length =
SEQUENCE: 364
```

000

SEQ ID NO: 365 moltype = length =
SEQUENCE: 365
000

SEQ ID NO: 366 moltype = length =
SEQUENCE: 366
000

SEQ ID NO: 367 moltype = AA length = 445
FEATURE Location/Qualifiers
source 1..445
mol_type = protein
organism = synthetic construct
SEQUENCE: 367
MKAKLLVLLC TFTATYAVAQ AAIATDGKGI IDKDSRDAVI NDAKLRAAIA GALVKAGFSS 60
ADAVALAPRI AKEMAKEGVL LINHHKLKAL IGAQLGLLTD AKIQRAAAAV DLGIKATLAA 120
TIIPNALGSA AFKNAVIANL VAAGIDKHLA RATAVAIVAT ALNPALGPIA KFELIKAEIA 180
AQAALLIRRG VHLQKAAIEH VIGRAFDAAV ATAIISSPIL SARIVTHLVR AGIDKSIAIS 240
LAPHIVKRLA KEPLLAFNTA KLMKAITRQI VDVITADKAI KTAEQLEKEL PALDDLVKKA 300
MGPPKPTGGG GGAGPTVTVI PVGREGGDIT ISGKGFSTTG FGVYVAVAPA SVPEFYGNSD 360
KFYGYDPSKD TTESPSTIWV YTPSQKAIGS RFAQGRPMNN DGSFTITMKA PPFEQGKDFV 420
VLTTKAHGVG KGDHGDDTRT PVGYR 445

SEQ ID NO: 368 moltype = AA length = 428
FEATURE Location/Qualifiers
source 1..428
mol_type = protein
organism = synthetic construct
SEQUENCE: 368
VAQAAIATDG KGIIDKDSRD AVINDAKLRA AIAGALVKAG FSSADAVALA PRIAKEMAKE 60
GVLLINHHKL KALIGAQLGL LTDAKIQRAA AAVDLGIKAT LAATIIPNAL GSAAFKNAVI 120
ANLVAAGIDK HLARATAVAI VATALNPALG PIAKFELIKA EIAAQAALLI RRGVHLQKAA 180
IEHVIGRAFD AAVATAIISS PILSARIVTH LVRAGIDKSI AISLAPHIVK RLAKEPLLAF 240
NTAKLMKAIT RQIVDVITAD KAIKTAEQLE KELPALDDLV KKAMGPPKPT GGGGGAGPTV 300
TVIPVGREGG DITISGKGFS TTGFGVYVAV APASVPEFYG NSDKFYGYDP SKDTTESPST 360
IWVYTPSQKA IGSRFAQGRP MNNDGSFTIT MKAPPFEQGK DFVVLTTKAH GVGKGDHGDD 420
TRTPVGYR 428

SEQ ID NO: 369 moltype = AA length = 736
FEATURE Location/Qualifiers
source 1..736
mol_type = protein
organism = synthetic construct
SEQUENCE: 369
MKAKLLVLLC TFTATYAVEP TTTISATSTH ELSASDARNS IQLLNAHIAT LQSVQKSVPG 60
SDYSDQIRDL LKAAFDLRGL IETLAHGGIP FYDPSTIMPR IKLVATTIDT IHTATTTLQN 120
KVRPAHVELG LEVTKAVLLT ANPASTAKEL DAEGAALKAR LEKVSQYPDL TPNDVATVYV 180
RTNFSKTIWQ VRANRDRYIL GHKSAAVYKT LNHAITKAVG VRLNPKTTVG NIQAARTELL 240
AAYQTAFNSP DVKKAASSNR PRSVAQAAIA TDGKGIIDKD SRDAVINDAK LRAAIAGALV 300
KAGFSSADAV ALAPRIAKEM AKEGVLLINH HKLKALIGAQ LGLLTDAKIQ RAAAAVDLGI 360
KATLAATIIP NALGSAAFKN AVIANLVAAG IDKHLARATA VAIVATALNP ALGPIAKFEL 420
IKAEIAAQAA LLIRRGVHLQ KAAIEHVIGR AFDAAVATAI ISSPILSARI VTHLVRAGID 480
KSIAISLAPH IVKRLAKEPL LAFNTAKLMK NITRQIVDVI TADKAIKTAE QLEKELPALD 540
DLVKKASSPP KPTPTPTPTP TAGPTVTVIP VGREGGDITI SGKGFSTTGF GVYVAVAPAS 600
VPEFYGNSDK FYGYDPSKDT TESPSTIWVY TPSQKAIGSR FAQGRPMNND GSFTITMKAP 660
PFEQGKDFVV LTTKAHGVGK TDHSDDTRTP VTYREATPAP TGPKTPISGS ILAIYSTVAS 720
SLVLLVSLGA ISFGSG 736

SEQ ID NO: 370 moltype = AA length = 707
FEATURE Location/Qualifiers
source 1..707
mol_type = protein
organism = synthetic construct
SEQUENCE: 370
MKAKLLVLLC TFTATYAVEP TTTISATSTH ELSASDARNS IQLLNAHIAT LQSVQKSVPG 60
SDYSDQIRDL LKAAFDLRGL IETLAHGGIP FYDPSTIMPR IKLVATTIDT IHTATTTLQN 120
KVRPAHVELG LEVTKAVLLT ANPASTAKEL DAEGAALKAR LEKVSQYPDL TPNDVATVYV 180
RTNFSKTIWQ VRANRDRYIL GHKSAAVYKT LNHAITKAVG VRLNPKTTVG NIQAARTELL 240
AAYQTAFNSP DVKKAASSNR PRSVAQAAIA TDGKGIIDKD SRDAVINDAK LRAAIAGALV 300
KAGFSSADAV ALAPRIAKEM AKEGVLLINH HKLKALIGAQ LGLLTDAKIQ RAAAAVDLGI 360
KATLAATIIP NALGSAAFKN AVIANLVAAG IDKHLARATA VAIVATALNP ALGPIAKFEL 420
IKAEIAAQAA LLIRRGVHLQ KAAIEHVIGR AFDAAVATAI ISSPILSARI VTHLVRAGID 480
KSIAISLAPH IVKRLAKEPL LAFNTAKLMK NITRQIVDVI TADKAIKTAE QLEKELPALD 540
DLVKKASSPP KPTPTPTPTP TAGPTVTVIP VGREGGDITI SGKGFSTTGF GVYVAVAPAS 600
VPEFYGNSDK FYGYDPSKDT TESPSTIWVY TPSQKAIGSR FAQGRPMNND GSFTITMKAP 660
PFEQGKDFVV LTTKAHGVGK TDHSDDTRTP VTYREATPAP TGPKTPI 707

```
SEQ ID NO: 371         moltype = AA  length = 628
FEATURE                Location/Qualifiers
source                 1..628
                       mol_type = protein
                       organism = synthetic construct
SEQUENCE: 371
MKAKLLVLLC TFTATYAVEP TTTISATSTH ELSASDARNS IQLLNAHIAT LQSVQKSVPG  60
SDYSDQIRDL LKAAFDLRGL IETLAHGGIP FYDPSTIMPR IKLVATTIDT IHTATTTLQN  120
KVRPAHVELG LEVTKAVLLT ANPASTAKEL DAEGAALKAR LEKVSQYPDL TPNDVATSSN  180
RPRSVAQAAI ATDGKGIIDK DSRDAVINDA KLRAAIAGAL VKAGFSSADA VALAPRIAKE  240
MAKEGVLLIN HHKLKALIGA QLGLLTDAKI QRAAAAVDLG IKATLAATII PNALGSAAFK  300
NAVIANLVAA GIDKHLARAT AVAIVATALN PALGPIAKFE LIKAEIAAQA ALLIRRGVHL  360
QKAAIEHVIG RAFDAAVATA IISSPILSAR IVTHLVRAGI DKSIAISLAP HIVKRLAKEP  420
LLAFNTAKLM KNITRQIVDV ITADKAIKTA EQLEKELPAL DDLVKKASSP PKPTPTPTPT  480
PTAGPTVTVI PVGREGGDIT ISGKGFSTTG FGVYVAVAPA SVPEFYGNSD KFYGYDPSKD  540
TTESPSTIWV YTPSQKAIGS RFAQGRPMNN DGSFTITMKA PPFEQGKDFV VLTTKAHGVG  600
KTDHSDDTRT PVTYREATPA PTGPKTPI                                     628

SEQ ID NO: 372         moltype = AA  length = 547
FEATURE                Location/Qualifiers
source                 1..547
                       mol_type = protein
                       organism = synthetic construct
SEQUENCE: 372
MKAKLLVLLC TFTATYASSN RPRSVAQAAI ATDGKGIIDK DSRDAVINDA KLRAAIAGAL  60
VKAGFSSADA VALAPRIAKE MAKEGVLLIN HHKLKALIGA QLGLLTDAKI QRAAAAVDLG  120
IKATLAATII PNALGSAAFK NAVIANLVAA GIDKHLARAT AVAIVATALN PALGPIAKFE  180
LIKAEIAAQA ALLIRRGVHL QKAAIEHVIG RAFDAAVATA IISSPILSAR IVTHLVRAGI  240
DKSIAISLAP HIVKRLAKEP LLAFNTAKLM KNITRQIVDV ITADKAIKTA EQLEKELPAL  300
DDLVKKASSP PKPTPTPTPT PTAGPTVTVI PVGREGGDIT ISGKGFSTTG FGVYVAVAPA  360
SVPEFYGNSD KFYGYDPSKD TTESPSTIWV YTPSQKAIGS RFAQGRPMNN DGSFTITMKA  420
PPFEQGKDFV VLTTKAHGVG KTDHSDDTRT PVTYREATPA PTGPKTPIVY VRTNFSKTIW  480
QVRANRDRYI LGHKSAAVYK TLNHAITKAV GVRLNPKTTV GNIQAARTEL LAAYQTAFNS  540
PDVKKAA                                                            547

SEQ ID NO: 373         moltype = AA  length = 690
FEATURE                Location/Qualifiers
source                 1..690
                       mol_type = protein
                       organism = synthetic construct
SEQUENCE: 373
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAAS  240
SNRPRSVAQA AIATDGKGII DKDSRDAVIN DAKLRAAIAG ALVKAGFSSA DAVALAPRIA  300
KEMAKEGVLL INHHKLKALI GAQLGLLTDA KIQRAAAAVD LGIKATLAAT IIPNALGSAA  360
FKNAVIANLV AAGIDKHLAR ATAVAIVATA LNPALGPIAK FELIKAEIAA QAALLIRRGV  420
HLQKAAIEHV IGRAFDAAVA TAIISSPILS ARIVTHLVRA GIDKSIAISL APHIVKRLAK  480
EPLLAFNTAK LMKNITRQIV DVITADKAIK TAEQLEKELP ALDDLVKKAS SPPKPTPTPT  540
PTPTAGPTVT VIPVGREGGD ITISGKGFST TGFGVYVAVA PASVPEFYGN SDKFYGYDPS  600
KDTTESPSTI WVYTPSQKAI GSRFAQGRPM NNDGSFTITM KAPPFEQGKD FVVLTTKAHG  660
VGKTDHSDDT RTPVTYREAT PAPTGPKTPI                                   690

SEQ ID NO: 374         moltype = AA  length = 690
FEATURE                Location/Qualifiers
source                 1..690
                       mol_type = protein
                       organism = synthetic construct
SEQUENCE: 374
VEPTTTISAT STHELSASDA RNSIQLLNAH IATLQSVQKS VPGSDYSDQI RDLLKAAFDL  60
RGLIETLAHG GIPFYDPSTI MPRIKLVATT IDTIHTATTT LQNKVRPAHV ELGLEVTKAV  120
LLTANPASTA KELDAEGAAL KARLEKVSQY PDLTPNDVAT VYVRTNFSKT IWQVRANRDR  180
YILGHKSAAV YKTLNHAITK AVGVRLNPKT TVGNIQAART ELLAAYQTAF NSPDVKKAAS  240
SNRPRSVAQA AIATDGKGII DKDSRDAVIN DAKLRAAIAG ALVKAGFSSA DAVALAPRIA  300
KEMAKEGVLL INHHKLKALI GAQLGLLTDA KIQRAAAAVD LGIKATLAAT IIPNALGSAA  360
FKNAVIANLV AAGIDKHLAR ATAVAIVATA LNPALGPIAK FELIKAEIAA QAALLIRRGV  420
HLQKAAIEHV IGRAFDAAVA TAIISSPILS ARIVTHLVRA GIDKSIAISL APHIVKRLAK  480
EPLLAFNTAK LMKNITRQIV DVITADKAIK TAEQLEKELP ALDDLVKKAS SPPKPTPTPT  540
PTPTAGPTVT VIPVGREGGD ITISGKGFST TGFGVYVAVA PASVPEFYGN SDKFYGYDPS  600
KDTTESPSTI WVYTPSQKAI GSRFAQGRPM NNDGSFTITM KAPPFEQGKD FVVLTTKAHG  660
VGKTDHSDDT RTPVTYREAT PAPTGPKTPI                                   690

SEQ ID NO: 375         moltype = AA  length = 611
FEATURE                Location/Qualifiers
source                 1..611
                       mol_type = protein
                       organism = synthetic construct
SEQUENCE: 375
```

-continued

VEPTTTISAT STHELSASDA RNSIQLLNAH IATLQSVQKS VPGSDYSDQI RDLLKAAFDL 60
RGLIETLAHG GIPFYDPSTI MPRIKLVATT IDTIHTATTT LQNKVRPAHV ELGLEVTKAV 120
LLTANPASTA KELDAEGAAL KARLEKVSQY PDLTPNDVAT SSNRPRSVAQ AAIATDGKGI 180
IDKDSRDAVI NDAKLRAAIA GALVKAGFSS ADAVALAPRI AKEMAKEGVL LINHHKLKAL 240
IGAQLGLLTD AKIQRAAAAV DLGIKATLAA TIIPNALGSA AFKNAVIANL VAAGIDKHLA 300
RATAVAIVAT ALNPALGPIA KFELIKAEIA AQAALLIRRG VHLQKAAIEH VIGRAFDAAV 360
ATAIISSPIL SARIVTHLVR AGIDKSIAIS LAPHIVKRLA KEPLLAFNTA KLMKNITRQI 420
VDVITADKAI KTAEQLEKEL PALDDLVKKA SSPPKPTPTP TPTPTAGPTV TVIPVGREGG 480
DITISGKGFS TTGFGVYVAV APASVPEFYG NSDKFYGYDP SKDTTESPST IWVYTPSQKA 540
IGSRFAQGRP MNNDGSFTIT MKAPPFEQGK DFVVLTTKAH GVGKTDHSDD TRTPVTYREA 600
TPAPTGPKTP I 611

SEQ ID NO: 376 moltype = AA length = 530
FEATURE Location/Qualifiers
source 1..530
mol_type = protein
organism = synthetic construct
SEQUENCE: 376
SSNRPRSVAQ AAIATDGKGI IDKDSRDAVI NDAKLRAAIA GALVKAGFSS ADAVALAPRI 60
AKEMAKEGVL LINHHKLKAL IGAQLGLLTD AKIQRAAAAV DLGIKATLAA TIIPNALGSA 120
AFKNAVIANL VAAGIDKHLA RATAVAIVAT ALNPALGPIA KFELIKAEIA AQAALLIRRG 180
VHLQKAAIEH VIGRAFDAAV ATAIISSPIL SARIVTHLVR AGIDKSIAIS LAPHIVKRLA 240
KEPLLAFNTA KLMKNITRQI VDVITADKAI KTAEQLEKEL PALDDLVKKA SSPPKPTPTP 300
TPTPTAGPTV TVIPVGREGG DITISGKGFS TTGFGVYVAV APASVPEFYG NSDKFYGYDP 360
SKDTTESPST IWVYTPSQKA IGSRFAQGRP MNNDGSFTIT MKAPPFEQGK DFVVLTTKAH 420
GVGKTDHSDD TRTPVTYREA TPAPTGPKTP IVYVRTNFSK TIWQVRANRD RYILGHKSAA 480
VYKTLNHAIT KAVGVRLNPK TTVGNIQAAR TELLAAYQTA FNSPDVKKAA 530

SEQ ID NO: 377 moltype = RNA length = 2214
FEATURE Location/Qualifiers
source 1..2214
mol_type = other RNA
organism = synthetic construct
SEQUENCE: 377
atgaaggcca agctgctggt gctgctgtgt accttcactg caacatatgc tgtggagccc 60
acaaccacaa tctctgccac aagcacccac gagctgtctg ccagcgacgc cagaaactcc 120
atccagctgc tgaatgccca catcgccaca ctgcagagcg tgcagaaatc cgtgcctggc 180
agcgattaca gcgaccagat ccgggacctg ctgaaggccg cctttgatct gagaggcctg 240
atcgaaaccc tggcccacgg cggcattccc ttctatgacc cctccaccat catgcccaga 300
atcaagctgg tggccaccac catcgacacc atccacacag ctacaaccac cctgcagaac 360
aaggtgcggc cagcccatgt ggaactgggc ctggaggtga caaaggccgt gctgctgacc 420
gccaatcctg ccagcacagc aaaagaactg gacgccgagg gagctgctct gaaggccaga 480
ctggaaaagg tgagccagta ccccgacctg acacctaatg atgtggccac agtgtacgtg 540
agaaccaatt tcagcaagac catctggcag gtgagagcca acagagatcg gtacatcctg 600
ggccacaagt ccgccgccgt gtacaagacc ctgaatcacg ccatcaccaa ggccgtgggc 660
gtgcggctga atcctaagac caccgtgggc aacatccagg ccgccagaac cgaactgctg 720
gccgcctacc agaccgcctt caacagcccc gatgtgaaga aggccgctag ctccaataga 780
cccagatccg tggcccaggc cgccatcgcc acagatggca aggggatcat cgacaaggat 840
tccagagacg ctgtgatcaa cgacgcaaag ctgagagccg ccatcgccgg agctctggtg 900
aaggccggct ttagcagcgc cgacgccgtg gcactggccc ccagaattgc aaaggagatg 960
gcaaaggagg gcgtgctgct gatcaatcac cacaagctga aggccctgat cggcgcacag 1020
ctgggcctgc tgaccgacgc aaagattcag agagccgccg cagccgtgga cctgggcatc 1080
aaggccaccc tggctgccac catcatccct aacgccctgg gcagcgccgc cttcaagaat 1140
gcagtgatcg ccaacctggt ggccgccgga atcgacaagc acctggccag agccacagcc 1200
gtcgctatcg tggccacagc cctgaatccc gccctgggcc ccatcgccaa atttgaactg 1260
atcaaggcag aaatcgctgc ccaggccgcc ctgctcatca gaagaggcgt ccatctgcag 1320
aaggccgcca tcgagcacgt gattggcaga gccttcgacg ccgccgtggc cacagctatc 1380
atttcttccc ctatcctgtc tgccagaatc gtgacacacc tggtgagagc cggaatcgac 1440
aagtccatcg ccatctccct ggccccccac atcgtgaaga gactggctaa ggagcctctg 1500
ctggccttca atacagccaa gctgatgaag aacatcacaa gacagatcgt ggacgtgatc 1560
accgccgaca aggccatcaa gacagccgag cagctggaga aggaactgcc agccctggac 1620
gacctggtga agaaggccag cagccctccc aagcctaccc ctaccccaac ccctacacct 1680
acagccggac ctaccgtgac cgtgatccct gtgggcagag agggcggcga catcaccatc 1740
agcggcaagg gcttcagcac aacaggcttt ggcgtgtacg tggccgtggc cccagccagc 1800
gtgcctgagt tttacggcaa tagcgacaag ttctacggct acgacccctc caaggacacc 1860
accgagagcc caagcaccat ctgggtgtac acacctagcc agaaggccat cggcagcaga 1920
tttgcccagg gcaggcctat gaataatgac ggcagcttca caatcacaat gaaggccccc 1980
ccctttgagc agggcaagga cttcgtggtg ctgaccacca aggcccacgg cgtgggcaag 2040
acagatcaca gcgacgacac ccggaccccc gtgacctaca gagaagcaac acctgcccct 2100
accgggccta agacacccat cagcggcagc atcctggcta tctacagcac agtggcttct 2160
agcctggtgc tgctggtgtc tctgggcgcc atcagctttg gcagcggctg ataa 2214

SEQ ID NO: 378 moltype = RNA length = 2214
FEATURE Location/Qualifiers
source 1..2214
mol_type = other RNA
organism = synthetic construct
SEQUENCE: 378
atgaaggcta agctgctggt gctgctgtgc acattcacag ccacctacgc cgtggagcct 60

-continued accaccacaa tcagcgccac cagcacccac gagctgagcg ccagcgatgc cagaaatagc 120
atccagctgc tgaatgccca catcgccacc ctgcagtccg tgcagaaaag cgtgcctgga 180
agcgattaca gcgatcagat cagggacctg ctgaaggccg ccttcgatct gagaggcctg 240
atcgagacac tggcccacgg cggcatccct ttctacgacc ccagcaccat catgcctaga 300
atcaaactgg tggccaccac catcgacacc atccacaccg caacaacaac cctgcagaat 360
aaggtgcggc ctgcccacgt ggaactggga ctggaagtga caaaggccgt gctgctgacc 420
gctaatcccg cctccaccgc caaggagctg gatgccgaag gagctgccct gaaagccaga 480
ctggagaagg tgagccagta ccctgatctg accccctaacg acgtggccac cgtgtacgtg 540
agaaccaatt tcagcaagac catctggcag gtgagagcca atcgggacag atacatcctg 600
ggccacaagt ctgccgccgt gtataaaacc ctgaatcacg ccatcaccaa ggccgtgggc 660
gtgagactga accctaagac aaccgtgggc aacatccagg ccgccagaac agagctgctg 720
gccgcctacc agacagcctt caatagcccc gacgtgaaga aggccgcttc cagcaataga 780
ccccggagcg tggcacaggc tgctattgcc accgacggaa agggcatcat cgataaagac 840
agccgggatg ccgtgatcaa tgacgccaag ctgagagcag caatcgccgg cgctctggtg 900
aaggcaggct tcagcagcgc cgacgccgtg gctctggccc ctagaatcgc taaggagatg 960
gccaaggagg gcgtgctgct gatcaatcac cacaagctga aggccctgat cggcgcccag 1020
ctgggactgc tgacagatgc caagatccag agagccgctg cagccgtgga tctgggcatc 1080
aaggccacac tggccgccac catcatccca aacgccctgg gcagcgccgc cttcaaaaat 1140
gccgtgattg ccaacctggt ggccgccggc atcgataagc acctggccag agccacagcc 1200
gtggccatcg tggccacagc cctgaatccc gcactgggac ctattgccaa gttcgaactc 1260
attaaggccg aaatcgcagc ccaagccgcc ctgctgattc ggcggggcgt gcacctgcag 1320
aaagccgcca ttgagcacgt gatcggcaga gccttcgatg ccgctgtggc caccgccatc 1380
atctcctctc ctatcctgtc tgctagaatc gtgacccacc tggtcagagc cggaatcgac 1440
aagtctatcg ctatcagcct ggccccccac atcgtgaaga gactggccaa agagcccctg 1500
ctggccttca acacagccaa gctcatgaag aatatcacca gacagatcgt ggacgtgatc 1560
accgccgaca aggccatcaa aaccgctgag cagctggaga aggagctgcc cgccctggat 1620
gacctggtga agaaggccag cagccccccc aagcctacac ctacacctac cccaacccct 1680
acagccggcc ctacagtgac cgtgattcct gtgggcagag aaggaggcga catcaccatc 1740
agcggaaagg gcttctctac cacaggcttc ggcgtgtacg tggccgtggc cccctgcctcc 1800
gtgcccgaat tctacggcaa cagcgacaag ttctacggct acgaccccag caaagacacc 1860
acagagagcc cttccaccat ctgggtgtac accccttccc agaaggccat cggcagcaga 1920
ttcgctcagg gcagacctat gaataacgac ggctctttca ccatcacaat gaaggccccc 1980
cccttcgagc agggcaaaga cttcgtggtg ctgacaacca aggcccacgg cgtgggcaag 2040
acagatcact ccgacgacac ccggacccct gtgacctaca gagaggcaac acctgctccc 2100
accgggccaa agacccctat cagcggaagc atcctggcca tctatagcac cgtggctagc 2160
tctctggtgc tgctggtgag cctgggagct atcagctttg ggagcggctg ataa 2214

SEQ ID NO: 379 moltype = RNA length = 2130
FEATURE Location/Qualifiers
source 1..2130
mol_type = other RNA
organism = synthetic construct
SEQUENCE: 379
atgaaggcca agctgctggt gctgctgtgt accttcactg caacatatgc tatggtggag 60
cccacaacca caatctctgc cacaagcacc cacgagctgt ctgccagcga cgccagaaac 120
tccatccagc tgctgaatgc ccacatcgcc acactgcaga gcgtgcagaa atccgtgcct 180
ggcagcgatt acagcgacca gatccgggac ctgctgaagg ccgcctttga tctgagaggc 240
ctgatcgaaa ccctggccca cggcggcatt cccttctatg acccctccac catcatgccc 300
agaatcaagc tggtggccac caccatcgac accatccaca cagctacaac caccctgcag 360
aacaaggtgc ggccagccca tgtggaactg ggcctggagg tgacaaaggc cgtgctgctg 420
accgccaatc ctgccagcac agcaaaagaa ctggacgccg agggagctgc tctgaaggcc 480
agactggaaa aggtgagcca gtaccccgac ctgacaccta atgatgtggc cacagtgtac 540
gtgagaacca atttcagcaa gaccatctgg caggtgagag ccaacagaga tcggtacatc 600
ctgggccaca agtccgccgc cgtgtacaag accctgaatc acgccatcac caaggccgtg 660
ggcgtgcggc tgaatcctaa gaccaccgtg ggcaacatcc aggccgccag aaccgaactg 720
ctggccgcct accagaccgc cttcaacagc cccgatgtga agaaggccgc tagctccaat 780
agacccagat ccgtggccca ggccgccatc gccacagatg gcaaggggat catcgacaag 840
gattccagag acgctgtgat caacgacgca aagctgagag ccgccatcgc cggagctctg 900
gtgaaggccg gctttagcag cgccgacgcc gtggcactgg cccccagaat tgcaaaggag 960
atggcaaagg agggcgtgct gctgatcaat caccacaagc tgaaggccct gatcggcgca 1020
cagctgggcc tgctgaccga cgcaaagatt cagagagccg ccgcagccgt ggacctgggc 1080
atcaaggcca ccctggctgc caccatcatc cctaacgccc tgggcagcgc cgccttcaag 1140
aatgcagtga tcgccaacct ggtggccgcc ggaatcgaca agcacctggc cagagccaca 1200
gccgtcgcta tcgtggccac agccctgaat cccgccctgg gccccatcgc caaatttgaa 1260
ctgatcaagg cagaaatcgc tgcccaggcc gccctgctca tcagaagagg cgtccatctg 1320
cagaaggccg ccatcgagca cgtgattggc agagccttcg acgccgccgt ggccacagct 1380
atcatttctt cccctatcct gtctgccaga atcgtgacac acctggtgag agccggaatc 1440
gacaagtcca tcgccatctc cctggccccc cacatcgtga agagactggc taaggagcct 1500
ctgctggcct tcaatacagc caagctgatg aagaacatca caagacagat cgtggacgtg 1560
atcaccgccg acaaggccat caagacagcc gagcagctgg agaaggaact gccagccctg 1620
gacgacctgg tgaagaaggc cagcagccct cccaagccta cccctacccc aacccctaca 1680
cctacagccg gacctaccgt gaccgtgatc cctgtgggca gagagggcgg cgacatcacc 1740
atcagcggca agggcttcag cacaacaggc tttggcgtgt acgtggccgt ggccccagcc 1800
agcgtgcctg agttttacgg caatagcgac aagttctacg gctacgaccc ctccaaggac 1860
accaccgaga gcccaagcac catctgggtg tacacaccta gccagaaggc catcggcagc 1920
agatttgccc agggcaggcc tatgaataat gacggcagct tcacaatcac aatgaaggcc 1980
ccccccttttg agcagggcaa ggacttcgtg gtgctgacca ccaaggccca cggcgtgggc 2040
aagacagatc acagcgacga cacccggacc cccgtgacct acagagaagc aacacctgcc 2100
cctaccgggc ctaagacacc catctgataa 2130

```
SEQ ID NO: 380          moltype = RNA  length = 2127
FEATURE                 Location/Qualifiers
source                  1..2127
                        mol_type = other RNA
                        organism = synthetic construct
SEQUENCE: 380
atgaaggcta agctgctggt gctgctgtgc acattcacag ccacctacgc cgtggagcct  60
accaccacaa tcagcgccac cagcacccac gagctgagcg ccagcgatgc cagaaatagc  120
atccagctgc tgaatgccca catcgccacc ctgcagtccg tgcagaaaag cgtgcctgga  180
agcgattaca gcgatcagat cagggacctg ctgaaggccg ccttcgatct gagaggcctg  240
atcgagacac tggcccacgg cggcatccct ttctacgacc ccagcaccat catgcctaga  300
atcaaactgg tggccaccac catcgacacc atccacaccg caacaacaac cctgcagaat  360
aaggtgcggc ctgcccacgt ggaactggga ctggaagtga caaaggccgt gctgctgacc  420
gctaatcccg cctccaccgc caaggagctg gatgccgaag gagctgccct gaaagccaga  480
ctggagaagg tgagccagta ccctgatctg acccctaacg acgtggccac cgtgtacgtg  540
agaaccaatt tcagcaagac catctggcag gtgagagcca atcgggacag atacatcctg  600
ggccacaagt ctgccgccgt gtataaaacc ctgaatcacg ccatcaccaa ggccgtgggc  660
gtgagactga accctaagac aaccgtgggc aacatccagg ccgccagaac agagctgctg  720
gccgcctacc agacagcctt caatagcccc gacgtgaaga aggccgcttc cagcaataga  780
ccccggagcg tggcacaggc tgctattgcc accgacggaa agggcatcat cgataaagac  840
agccgggatg ccgtgatcaa tgacgccaag ctgagagcag caatcgccgg cgctctggtg  900
aaggcaggct tcagcagcgc cgacgccgtg gctctggccc ctagaatcgc taaggagatg  960
gccaaggagg gcgtgctgct gatcaatcac cacaagctga aggccctgat cggcgcccag  1020
ctgggactgc tgacagatgc caagatccag agagccgctg cagccgtgga tctgggcatc  1080
aaggccacac tggccgccac catcatccca aacgccctgg gcagcgccgc cttcaaaaat  1140
gccgtgattg ccaacctggt ggccgccggc atcgataagc acctggccag agccacagcc  1200
gtggccatcg tggccacagc cctgaatccc gcactgggac ctattgccaa gttcgaactc  1260
attaaggccg aaatcgcagc ccaagccgcc ctgctgattc ggcggggcgt gcacctgcag  1320
aaagccgcca ttgagcacgt gatcggcaga gccttcgatg ccgctgtggc caccgccatc  1380
atctcctctc ctatcctgtc tgctagaatc gtgacccacc tggtcagagc cggaatcgac  1440
aagtctatcg ctatcagcct ggccccccac atcgtgaaga gactggccaa agagcccctg  1500
ctggccttca acacagccaa gctcatgaag aatatcacca gacagatcgt ggacgtgatc  1560
accgccgaca aggccatcaa aaccgctgag cagctggaga aggagctgcc cgccctggat  1620
gacctggtga agaaggccag cagccccccc aagcctacac ctacacctac cccaacccct  1680
acagccggcc ctacagtgac cgtgattcct gtgggcagag aaggaggcga catcaccatc  1740
agcggaaagg gcttctctac cacaggcttc ggcgtgtacg tggccgtggc cctgcctcc  1800
gtgcccgaat tctacggcaa cagcgacaag ttctacggct acgaccccag caaagacacc  1860
acagagagcc cttccaccat ctgggtgtac accccttccc agaaggccat cggcagcaga  1920
ttcgctcagg gcagacctat gaataacgac ggctctttca ccatcacaat gaaggccccc  1980
cccttcgagc agggcaaaga cttcgtggtg ctgacaacca aggcccacgg cgtgggcaag  2040
acagatcact ccgacgacac ccggacccct gtgacctaca gagaggcaac acctgctccc  2100
accgggccaa agacccctat ctgataa                                      2127

SEQ ID NO: 381          moltype = RNA  length = 1890
FEATURE                 Location/Qualifiers
source                  1..1890
                        mol_type = other RNA
                        organism = synthetic construct
SEQUENCE: 381
atgaaggcca agctgctggt gctgctgtgt accttcactg caacatatgc tgtggagccc  60
acaaccacaa tctctgccac aagcacccac gagctgtctg ccagcgacgc cagaaactcc  120
atccagctgc tgaatgccca catcgccaca ctgcagagcg tgcagaaatc cgtgcctggc  180
agcgattaca gcgaccagat ccgggacctg ctgaaggccg cctttgatct gagaggcctg  240
atcgaaaccc tggcccacgg cggcattccc ttctatgacc cctccaccat catgcccaga  300
atcaagctgg tggccaccac catcgacacc atccacacag ctacaaccac cctgcagaac  360
aaggtgcggc cagcccatgt ggaactgggc ctggaggtga caaaggccgt gctgctgacc  420
gccaatcctg ccagcacagc aaaagaactg gacgccgagg gagctgctct gaaggccaga  480
ctggaaaagg tgagccagta ccccgacctg acacctaatg atgtggccac aagctccaat  540
agacccagat ccgtggccca ggccgccatc gccacagatg gcaaggggat catcgacaag  600
gattccagag acgctgtgat caacgacgca aagctgagag ccgccatcgc cggagctctg  660
gtgaaggccg gctttagcag cgccgacgcc gtggcactgg cccccagaat tgcaaaggag  720
atggcaaagg agggcgtgct gctgatcaat caccacaagc tgaaggccct gatcggcgca  780
cagctgggcc tgctgaccga cgcaaagatt cagagagccg ccgcagccgt ggacctgggc  840
atcaaggcca ccctggctgc caccatcatc cctaacgccc tgggcagcgc cgccttcaag  900
aatgcagtga tcgccaacct ggtggccgcc ggaatcgaca agcacctggc cagagccaca  960
gccgtcgcta tcgtggccac agccctgaat cccgccctgg gccccatcgc caaatttgaa  1020
ctgatcaagg cagaaatcgc tgcccaggcc gccctgctca tcagaagagg cgtccatctg  1080
cagaaggccg ccatcgagca cgtgattggc agagccttcg acgccgccgt ggccacagct  1140
atcatttctt cccctatcct gtctgccaga atcgtgacac acctggtgag agccggaatc  1200
gacaagtcca tcgccatctc cctggccccc cacatcgtga agagactggc taaggagcct  1260
ctgctggcct tcaatacagc caagctgatg aagaacatca caagacagat cgtggacgtg  1320
atcaccgccg acaaggccat caagacagcc gagcagctgg agaaggaact gccagccctg  1380
gacgacctgg tgaagaaggc cagcagccct cccaagccta cccctacccc aacccctaca  1440
cctacagccg gacctaccgt gaccgtgatc cctgtgggca gagagggcgg cgacatcacc  1500
atcagcggca agggcttcag cacaacaggc tttggcgtgt acgtggccgt ggccccagcc  1560
agcgtgcctg agttttacgg caatagcgac aagttctacg gctacgaccc ctccaaggac  1620
accaccgaga gcccaagcac catctgggtg tacacaccta gccagaaggc catcggcagc  1680
agatttgccc agggcaggcc tatgaataat gacggcagct tcacaatcac aatgaaggcc  1740
```

-continued

```
ccccccttg agcagggcaa ggacttcgtg gtgctgacca ccaaggccca cggcgtgggc  1800
aagacagatc acagcgacga cacccggacc cccgtgacct acagagaagc aacacctgcc  1860
cctaccgggc ctaagacacc catctgataa                                  1890

SEQ ID NO: 382          moltype = RNA  length = 1890
FEATURE                 Location/Qualifiers
source                  1..1890
                        mol_type = other RNA
                        organism = synthetic construct
SEQUENCE: 382
atgaaggcta agctgctggt gctgctgtgc acattcacag ccacctacgc cgtggagcct  60
accaccacaa tcagcgccac cagcacccac gagctgagcg ccagcgatgc cagaaatagc  120
atccagctgc tgaatgccca catcgccacc ctgcagtccg tgcagaaaag cgtgcctgga  180
agcgattaca gcgatcagat cagggacctg ctgaaggccg ccttcgatct gagaggcctg  240
atcgagacac tggcccacgg cggcatccct ttctacgacc ccagcaccat catgcctaga  300
atcaaactgg tggccaccac catcgacacc atccacaccg caacaacaac cctgcagaat  360
aaggtgcggc ctgcccacgt ggaactggga ctggaagtga caaaggccgt gctgctgacc  420
gctaatcccg cctccaccgc caaggagctg gatgccgaag gagctgccct gaaagccaga  480
ctggagaagg tgagccagta ccctgatctg acccctaacg acgtggccac ctccagcaat  540
agaccccgga gcgtggcaca ggctgctatt gccaccgacg gaaagggcat catcgataaa  600
gacagccggg atgccgtgat caatgacgcc aagctgagag cagcaatcgc cggcgctctg  660
gtgaaggcag gcttcagcag cgccgacgcc gtggctctgg cccctagaat cgctaaggag  720
atggccaagg agggcgtgct gctgatcaat caccacaagc tgaaggccct gatcggcgcc  780
cagctgggac tgctgacaga tgccaagatc cagagagccg ctgcagccgt ggatctgggc  840
atcaaggcca cactggccgc caccatcatc ccaaacgccc tgggcagcgc cgccttcaaa  900
aatgccgtga ttgccaacct ggtggccgcc ggcatcgata agcacctggc cagagccaca  960
gccgtggcca tcgtggccac agccctgaat cccgcactgg gacctattgc caagttcgaa  1020
ctcattaagg ccgaaatcgc agcccaagcc gccctgctga ttcggcgggg cgtgcacctg  1080
cagaaagccg ccattgagca cgtgatcggc agagccttcg atgccgctgt ggccaccgcc  1140
atcatctcct ctcctatcct gtctgctaga atcgtgaccc acctggtcag agccggaatc  1200
gacaagtcta tcgctatcag cctggccccc cacatcgtga agagactggc caaagagccc  1260
ctgctggcct tcaacacagc caagctcatg aagaatatca ccagacagat cgtggacgtg  1320
atcaccgccg acaaggccat caaaaccgct gagcagctgg agaaggagct gcccgccctg  1380
gatgacctgg tgaagaaggc cagcagcccc cccaagccta cacctacacc taccccaacc  1440
cctacagccg gccctacagt gaccgtgatt cctgtgggca gagaaggagg cgacatcacc  1500
atcagcggaa agggcttctc taccacaggc ttcggcgtgt acgtggccgt ggcccctgcc  1560
tccgtgcccg aattctacgg caacagcgac aagttctacg gctacgaccc cagcaaagac  1620
accacagaga gcccttccac catctgggtg tacacccctt cccagaaggc catcggcagc  1680
agattcgctc agggcagacc tatgaataac gacggctctt tcaccatcac aatgaaggcc  1740
ccccccttcg agcagggcaa agacttcgtg gtgctgacaa ccaaggccca cggcgtgggc  1800
aagacagatc actccgacga cacccggacc cctgtgacct acagagaggc aacacctgct  1860
cccaccgggc caaagacccc tatctgataa                                  1890

SEQ ID NO: 383          moltype = RNA  length = 1647
FEATURE                 Location/Qualifiers
source                  1..1647
                        mol_type = other RNA
                        organism = synthetic construct
SEQUENCE: 383
atgaaggcta agctgctggt gctgctgtgc acattcacag ccacctacgc ctccagcaat  60
agaccccgga gcgtggcaca ggctgctatt gccaccgacg gaaagggcat catcgataaa  120
gacagccggg atgccgtgat caatgacgcc aagctgagag cagcaatcgc cggcgctctg  180
gtgaaggcag gcttcagcag cgccgacgcc gtggctctgg cccctagaat cgctaaggag  240
atggccaagg agggcgtgct gctgatcaat caccacaagc tgaaggccct gatcggcgcc  300
cagctgggac tgctgacaga tgccaagatc cagagagccg ctgcagccgt ggatctgggc  360
atcaaggcca cactggccgc caccatcatc ccaaacgccc tgggcagcgc cgccttcaaa  420
aatgccgtga ttgccaacct ggtggccgcc ggcatcgata agcacctggc cagagccaca  480
gccgtggcca tcgtggccac agccctgaat cccgcactgg gacctattgc caagttcgaa  540
ctcattaagg ccgaaatcgc agcccaagcc gccctgctga ttcggcgggg cgtgcacctg  600
cagaaagccg ccattgagca cgtgatcggc agagccttcg atgccgctgt ggccaccgcc  660
atcatctcct ctcctatcct gtctgctaga atcgtgaccc acctggtcag agccggaatc  720
gacaagtcta tcgctatcag cctggccccc cacatcgtga agagactggc caaagagccc  780
ctgctggcct tcaacacagc caagctcatg aagaatatca ccagacagat cgtggacgtg  840
atcaccgccg acaaggccat caaaaccgct gagcagctgg agaaggagct gcccgccctg  900
gatgacctgg tgaagaaggc cagcagcccc cccaagccta cacctacacc taccccaacc  960
cctacagccg gccctacagt gaccgtgatt cctgtgggca gagaaggagg cgacatcacc  1020
atcagcggaa agggcttctc taccacaggc ttcggcgtgt acgtggccgt ggcccctgcc  1080
tccgtgcccg aattctacgg caacagcgac aagttctacg gctacgaccc cagcaaagac  1140
accacagaga gcccttccac catctgggtg tacacccctt cccagaaggc catcggcagc  1200
agattcgctc agggcagacc tatgaataac gacggctctt tcaccatcac aatgaaggcc  1260
ccccccttcg agcagggcaa agacttcgtg gtgctgacaa ccaaggccca cggcgtgggc  1320
aagacagatc actccgacga cacccggacc cctgtgacct acagagaggc aacacctgct  1380
cccaccgggc caaagacccc tatcgtgtac gtgagaacca atttcagcaa gaccatctgg  1440
caggtgagag ccaatcggga cagatacatc ctgggccaca agtctgccgc cgtgtataaa  1500
accctgaatc acgccatcac caaggccgtg ggcgtgagac tgaaccctaa gacaaccgtg  1560
ggcaacatcc aggccgccag aacagagctg ctggccgcct accagacagc cttcaatagc  1620
cccgacgtga agaaggccgc ttgataa                                     1647

SEQ ID NO: 384          moltype = RNA  length = 2070
```

```
FEATURE                Location/Qualifiers
source                 1..2070
                       mol_type = other RNA
                       organism = synthetic construct
SEQUENCE: 384
gtggagccca caaccacaat ctctgccaca agcacccacg agctgtctgc cagcgacgcc  60
agaaactcca tccagctgct gaatgcccac atcgccacac tgcagagcgt gcagaaatcc  120
gtgcctggca gcgattacag cgaccagatc cgggacctgc tgaaggccgc ctttgatctg  180
agaggcctga tcgaaaccct ggcccacggc ggcattccct tctatgaccc ctccaccatc  240
atgcccagaa tcaagctggt ggccaccacc atcgacacca tccacacagc tacaaccacc  300
ctgcagaaca aggtgcggcc agcccatgtg gaactgggcc tggaggtgac aaaggccgtg  360
ctgctgaccg ccaatcctgc cagcacagca aaagaactgg acgccgaggg agctgctctg  420
aaggccagac tggaaaaggt gagccagtac cccgacctga cacctaatga tgtggccaca  480
gtgtacgtga gaaccaattt cagcaagacc atctggcagg tgagagccaa cagagatcgg  540
tacatcctgg gccacaagtc cgccgccgtg tacaagaccc tgaatcacgc catcaccaag  600
gccgtgggcg tgcggctgaa tcctaagacc accgtgggca acatccaggc cgccagaacc  660
gaactgctgg ccgcctacca gaccgccttc aacagccccg atgtgaagaa ggccgctagc  720
tccaatagac ccagatccgt ggcccaggcc gccatcgcca cagatggcaa ggggatcatc  780
gacaaggatt ccagagacgc tgtgatcaac gacgcaaagc tgagagccgc catcgccgga  840
gctctggtga aggccggctt tagcagcgcc gacgccgtgg cactggcccc cagaattgca  900
aaggagatgg caaaggaggg cgtgctgctg atcaatcacc acaagctgaa ggccctgatc  960
ggcgcacagc tgggcctgct gaccgacgca aagattcaga gagccgccgc agccgtggac  1020
ctgggcatca aggccaccct ggctgccacc atcatcccta acgccctggg cagcgccgcc  1080
ttcaagaatg cagtgatcgc caacctggtg gccgccggaa tcgacaagca cctggccaga  1140
gccacagccg tcgctatcgt ggccacagcc ctgaatcccg ccctgggccc catcgccaaa  1200
tttgaactga tcaaggcaga aatcgctgcc caggccgccc tgctcatcag aagaggcgtc  1260
catctgcaga aggccgccat cgagcacgtg attggcagag ccttcgacgc cgccgtggcc  1320
acagctatca tttcttcccc tatcctgtct gccagaatcg tgacacacct ggtgagagcc  1380
ggaatcgaca agtccatcgc catctccctg gccccccaca tcgtgaagag actggctaag  1440
gagcctctgc tggccttcaa tacagccaag ctgatgaaga acatcacaag acagatcgtg  1500
gacgtgatca ccgccgacaa ggccatcaag acagccgagc agctggagaa ggaactgcca  1560
gccctggacg acctggtgaa gaaggccagc agccctccca agcctacccc taccccaacc  1620
cctacaccta cagccggacc taccgtgacc gtgatccctg tgggcagaga gggcggcgac  1680
atcaccatca gcggcaaggg cttcagcaca acaggctttg gcgtgtacgt ggccgtggcc  1740
ccagccagcg tgcctgagtt ttacggcaat agcgacaagt tctacggcta cgacccctcc  1800
aaggacacca ccgagagccc aagcaccatc tgggtgtaca cacctagcca gaaggccatc  1860
ggcagcagat ttgcccaggg caggcctatg aataatgacg gcagcttcac aatcacaatg  1920
aaggcccccc cctttgagca gggcaaggac ttcgtggtgc tgaccaccaa ggcccacggc  1980
gtgggcaaga cagatcacag cgacgacacc cggacccccg tgacctacag agaagcaaca  2040
cctgccccta ccgggcctaa gacacccatc                                  2070

SEQ ID NO: 385         moltype = RNA  length = 2070
FEATURE                Location/Qualifiers
source                 1..2070
                       mol_type = other RNA
                       organism = synthetic construct
SEQUENCE: 385
gtggagccta ccaccacaat cagcgccacc agcacccacg agctgagcgc cagcgatgcc  60
agaaatagca tccagctgct gaatgcccac atcgccaccc tgcagtccgt gcagaaaagc  120
gtgcctggaa gcgattacag cgatcagatc agggacctgc tgaaggccgc cttcgatctg  180
agaggcctga tcgagacact ggcccacggc ggcatccctt tctacgaccc cagcaccatc  240
atgcctagaa tcaaactggt ggccaccacc atcgacacca tccacaccgc aacaacaacc  300
ctgcagaata aggtgcggcc tgcccacgtg gaactgggac tggaagtgac aaaggccgtg  360
ctgctgaccg ctaatcccgc ctccaccgcc aaggagctgg atgccgaagg agctgccctg  420
aaagccagac tggagaaggt gagccagtac cctgatctga cccctaacga cgtggccacc  480
gtgtacgtga gaaccaattt cagcaagacc atctggcagg tgagagccaa tcgggacaga  540
tacatcctgg gccacaagtc tgccgccgtg tataaaaccc tgaatcacgc catcaccaag  600
gccgtgggcg tgagactgaa ccctaagaca accgtgggca acatccaggc cgccagaaca  660
gagctgctgg ccgcctacca gacagccttc aatagccccg acgtgaagaa ggccgcttcc  720
agcaatagac cccggagcgt ggcacaggct gctattgcca ccgacggaaa gggcatcatc  780
gataaagaca gccgggatgc cgtgatcaat gacgccaagc tgagagcagc aatcgccggc  840
gctctggtga aggcaggctt cagcagcgcc gacgccgtgg ctctggcccc tagaatcgct  900
aaggagatgg ccaaggaggg cgtgctgctg atcaatcacc acaagctgaa ggccctgatc  960
ggcgcccagc tgggactgct gacagatgcc aagatccaga gagccgctgc agccgtggat  1020
ctgggcatca aggccacact ggccgccacc atcatcccaa acgccctggg cagcgccgcc  1080
ttcaaaaatg ccgtgattgc caacctggtg gccgccggca tcgataagca cctggccaga  1140
gccacagccg tggccatcgt ggccacagcc ctgaatcccg cactgggacc tattgccaag  1200
ttcgaactca ttaaggccga aatcgcagcc caagccgccc tgctgattcg gcggggcgtg  1260
cacctgcaga aagccgccat tgagcacgtg atcggcagag ccttcgatgc cgctgtggcc  1320
accgccatca tctcctctcc tatcctgtct gctagaatcg tgacccacct ggtcagagcc  1380
ggaatcgaca agtctatcgc tatcagcctg gccccccaca tcgtgaagag actggccaaa  1440
gagcccctgc tggccttcaa cacagccaag ctcatgaaga atatcaccag acagatcgtg  1500
gacgtgatca ccgccgacaa ggccatcaaa accgctgagc agctggagaa ggagctgccc  1560
gccctggatg acctggtgaa gaaggccagc agcccccccca agcctacacc tacacctacc  1620
ccaaccccta cagccggccc tacagtgacc gtgattcctg tgggcagaga aggaggcgac  1680
atcaccatca gcggaaaggg cttctctacc acaggcttcg gcgtgtacgt ggccgtggcc  1740
cctgcctccg tgcccgaatt ctacggcaac agcgacaagt tctacggcta cgaccccagc  1800
aaagacacca cagagagccc ttccaccatc tgggtgtaca ccccttccca gaaggccatc  1860
ggcagcagat tcgctcaggg cagacctatg aataacgacg gctctttcac catcacaatg  1920
```

```
aaggcccccc ccttcgagca gggcaaagac ttcgtggtgc tgacaaccaa ggcccacggc  1980
gtgggcaaga cagatcactc cgacgacacc cggacccctg tgacctacag agaggcaaca  2040
cctgctccca ccgggccaaa gacccctatc                                   2070

SEQ ID NO: 386          moltype = RNA  length = 2073
FEATURE                 Location/Qualifiers
source                  1..2073
                        mol_type = other RNA
                        organism = synthetic construct
SEQUENCE: 386
atggtggagc ccacaaccac aatctctgcc acaagcaccc acgagctgtc tgccagcgac  60
gccagaaact ccatccagct gctgaatgcc cacatcgcca cactgcagag cgtgcagaaa  120
tccgtgcctg gcagcgatta cagcgaccag atccgggacc tgctgaaggc cgcctttgat  180
ctgagaggcc tgatcgaaac cctggcccac ggcggcattc ccttctatga cccctccacc  240
atcatgccca gaatcaagct ggtggccacc accatcgaca ccatccacac agctacaacc  300
accctgcaga acaaggtgcg gccagcccat gtggaactgg gcctggaggt gacaaaggcc  360
gtgctgctga ccgccaatcc tgccagcaca gcaaaagaac tggacgccga gggagctgct  420
ctgaaggcca gactggaaaa ggtgagccag taccccgacc tgacacctaa tgatgtggcc  480
acagtgtacg tgagaaccaa tttcagcaag accatctggc aggtgagagc caacagagat  540
cggtacatcc tgggccacaa gtccgccgcc gtgtacaaga ccctgaatca cgccatcacc  600
aaggccgtgg gcgtgcggct gaatcctaag accaccgtgg gcaacatcca ggccgccaga  660
accgaactgc tggccgccta ccagaccgcc ttcaacagcc ccgatgtgaa gaaggccgct  720
agctccaata gacccagatc cgtggcccag gccgccatcg ccacagatgg caaggggatc  780
atcgacaagg attccagaga cgctgtgatc aacgacgcaa agctgagagc cgccatcgcc  840
ggagctctgg tgaaggccgg ctttagcagc gccgacgccg tggcactggc ccccagaatt  900
gcaaaggaga tggcaaagga gggcgtgctg ctgatcaatc accacaagct gaaggccctg  960
atcggcgcac agctgggcct gctgaccgac gcaaagattc agagagccgc cgcagccgtg  1020
gacctgggca tcaaggccac cctggctgcc accatcatcc ctaacgccct gggcagcgcc  1080
gccttcaaga atgcagtgat cgccaacctg gtggccgccg gaatcgacaa gcacctggcc  1140
agagccacag ccgtcgctat cgtggccaca gccctgaatc ccgccctggg ccccatcgcc  1200
aaatttgaac tgatcaaggc agaaatcgct gcccaggccg ccctgctcat cagaagaggc  1260
gtccatctgc agaaggccgc catcgagcac gtgattggca gagccttcga cgccgccgtg  1320
gccacagcta tcatttcttc ccctatcctg tctgccagaa tcgtgacaca cctggtgaga  1380
gccggaatcg acaagtccat cgccatctcc ctggcccccc acatcgtgaa gagactggct  1440
aaggagcctc tgctggcctt caatacagcc aagctgatga agaacatcac aagacagatc  1500
gtggacgtga tcaccgccga caaggccatc aagacagccg agcagctgga gaaggaactg  1560
ccagccctgg acgacctggt gaagaaggcc agcagccctc ccaagcctac ccctacccca  1620
acccctacac ctacagccgg acctaccgtg accgtgatcc ctgtgggcag agagggcggc  1680
gacatcacca tcagcggcaa gggcttcagc acaacaggct ttggcgtgta cgtggccgtg  1740
gccccagcca gcgtgcctga gttttacggc aatagcgaca agttctacgg ctacgacccc  1800
tccaaggaca ccaccgagag cccaagcacc atctgggtgt acacacctag ccagaaggcc  1860
atcggcagca gatttgccca gggcaggcct atgaataatg acggcagctt cacaatcaca  1920
atgaaggccc ccccctttga gcagggcaag gacttcgtgg tgctgaccac caaggcccac  1980
ggcgtgggca agacagatca cagcgacgac acccggaccc ccgtgaccta cagagaagca  2040
acacctgccc ctaccgggcc taagacaccc atc                               2073

SEQ ID NO: 387          moltype = RNA  length = 2070
FEATURE                 Location/Qualifiers
source                  1..2070
                        mol_type = other RNA
                        organism = synthetic construct
SEQUENCE: 387
gtggagccta ccaccacaat cagcgccacc agcacccacg agctgagcgc cagcgatgcc  60
agaaatagca tccagctgct gaatgcccac atcgccaccc tgcagtccgt gcagaaaagc  120
gtgcctggaa gcgattacag cgatcagatc agggacctgc tgaaggccgc cttcgatctg  180
agaggcctga tcgagacact ggcccacggc ggcatccctt tctacgaccc cagcaccatc  240
atgcctagaa tcaaactggt ggccaccacc atcgacacca tccacaccgc aacaacaacc  300
ctgcagaata aggtgcggcc tgcccacgtg gaactgggac tggaagtgac aaaggccgtg  360
ctgctgaccg ctaatcccgc ctccaccgcc aaggagctgg atgccgaagg agctgccctg  420
aaagccagac tggagaaggt gagccagtac cctgatctga cccctaacga cgtggccacc  480
gtgtacgtga gaaccaattt cagcaagacc atctggcagg tgagagccaa tcgggacaga  540
tacatcctgg gccacaagtc tgccgccgtg tataaaaccc tgaatcacgc catcaccaag  600
gccgtgggcg tgagactgaa ccctaagaca accgtgggca acatccaggc cgccagaaca  660
gagctgctgg ccgcctacca gacagccttc aatagccccg acgtgaagaa ggccgcttcc  720
agcaatagac cccggagcgt ggcacaggct gctattgcca ccgacggaaa gggcatcatc  780
gataaagaca gccgggatgc cgtgatcaat gacgccaagc tgagagcagc aatcgccggc  840
gctctggtga aggcaggctt cagcagcgcc gacgccgtgg ctctggcccc tagaatcgct  900
aaggagatgg ccaaggaggg cgtgctgctg atcaatcacc acaagctgaa ggccctgatc  960
ggcgcccagc tgggactgct gacagatgcc aagatccaga gagccgctgc agccgtggat  1020
ctgggcatca aggccacact ggccgccacc atcatcccaa acgccctggg cagcgccgcc  1080
ttcaaaaatg ccgtgattgc caacctggtg gccgccggca tcgataagca cctggccaga  1140
gccacagccg tggccatcgt ggccacagcc ctgaatcccg cactgggacc tattgccaag  1200
ttcgaactca ttaaggccga aatcgcagcc caagccgccc tgctgattcg gcggggcgtg  1260
cacctgcaga aagccgccat tgagcacgtg atcggcagag ccttcgatgc cgctgtggcc  1320
accgccatca tctcctctcc tatcctgtct gctagaatcg tgacccacct ggtcagagcc  1380
ggaatcgaca agtctatcgc tatcagcctg gccccccaca tcgtgaagag actggccaaa  1440
gagcccctgc tggccttcaa cacagccaag ctcatgaaga atatcaccag acagatcgtg  1500
gacgtgatca ccgccgacaa ggccatcaaa accgctgagc agctggagaa ggagctgccc  1560
gccctggatg acctggtgaa gaaggccagc agccccccca agcctacacc tacacctacc  1620
```

```
ccaaccccta cagccggccc tacagtgacc gtgattcctg tgggcagaga aggaggcgac  1680
atcaccatca gcggaaaggg cttctctacc acaggcttcg gcgtgtacgt ggccgtggcc  1740
cctgcctccg tgcccgaatt ctacggcaac agcgacaagt tctacggcta cgaccccagc  1800
aaagacacca cagagagccc ttccaccatc tgggtgtaca cccccttccca gaaggccatc  1860
ggcagcagat tcgctcaggg cagacctatg aataacgacg gctctttcac catcacaatg  1920
aaggcccccc ccttcgagca gggcaaagac ttcgtggtgc tgacaaccaa ggcccacggc  1980
gtgggcaaga cagatcactc cgacgacacc cggacccctg tgacctacag agaggcaaca  2040
cctgctccca ccgggccaaa gacccctatc                                  2070

SEQ ID NO: 388         moltype = RNA  length = 1833
FEATURE                Location/Qualifiers
source                 1..1833
                       mol_type = other RNA
                       organism = synthetic construct
SEQUENCE: 388
gtggagccca caaccacaat ctctgccaca agcacccacg agctgtctgc cagcgacgcc  60
agaaactcca tccagctgct gaatgcccac atcgccacac tgcagagcgt gcagaaatcc  120
gtgcctggca gcgattacag cgaccagatc cgggacctgc tgaaggccgc ctttgatctg  180
agaggcctga tcgaaaccct ggcccacggc ggcattccct tctatgaccc ctccaccatc  240
atgcccagaa tcaagctggt ggccaccacc atcgacacca tccacacagc tacaaccacc  300
ctgcagaaca aggtgcggcc agcccatgtg gaactgggcc tggaggtgac aaaggccgtg  360
ctgctgaccg ccaatcctgc cagcacagca aaagaactgg acgccgaggg agctgctctg  420
aaggccagac tggaaaaggt gagccagtac cccgacctga cacctaatga tgtggccaca  480
agctccaata gacccagatc cgtggcccag gccgccatcg ccacagatgg caaggggatc  540
atcgacaagg attccagaga cgctgtgatc aacgacgcaa agctgagagc cgccatcgcc  600
ggagctctgg tgaaggccgg ctttagcagc gccgacgccg tggcactggc ccccagaatt  660
gcaaaggaga tggcaaagga gggcgtgctg ctgatcaatc accacaagct gaaggccctg  720
atcggcgcac agctgggcct gctgaccgac gcaaagattc agagagccgc cgcagccgtg  780
gacctgggca tcaaggccac cctggctgcc accatcatcc ctaacgccct gggcagcgcc  840
gccttcaaga atgcagtgat cgccaacctg gtggccgccg gaatcgacaa gcacctggcc  900
agagccacag ccgtcgctat cgtggccaca gccctgaatc ccgccctggg ccccatcgcc  960
aaatttgaac tgatcaaggc agaaatcgct gcccaggccg ccctgctcat cagaagaggc  1020
gtccatctgc agaaggccgc catcgagcac gtgattggca gagccttcga cgccgccgtg  1080
gccacagcta tcatttcttc ccctatcctg tctgccagaa tcgtgacaca cctggtgaga  1140
gccggaatcg acaagtccat cgccatctcc ctggcccccc acatcgtgaa gagactggct  1200
aaggagcctc tgctggcctt caatacagcc aagctgatga agaacatcac aagacagatc  1260
gtggacgtga tcaccgccga caaggccatc aagacagccg agcagctgga gaaggaactg  1320
ccagccctgg acgacctggt gaagaaggcc agcagccctc ccaagcctac ccctacccca  1380
acccctacac ctacagccgg acctaccgtg accgtgatcc ctgtgggcag agagggcggc  1440
gacatcacca tcagcggcaa gggcttcagc acaacaggct ttggcgtgta cgtggccgtg  1500
gccccagcca gcgtgcctga gttttacggc aatagcgaca agttctacgg ctacgacccc  1560
tccaaggaca ccaccgagag cccaagcacc atctgggtgt acacacctag ccagaaggcc  1620
atcggcagca gatttgccca gggcaggcct atgaataatg acggcagctt cacaatcaca  1680
atgaaggccc ccccctttga gcagggcaag gacttcgtgg tgctgaccac caaggcccac  1740
ggcgtgggca agacagatca cagcgacgac acccggaccc ccgtgaccta cagagaagca  1800
acacctgccc ctaccgggcc taagacaccc atc                              1833

SEQ ID NO: 389         moltype = RNA  length = 1833
FEATURE                Location/Qualifiers
source                 1..1833
                       mol_type = other RNA
                       organism = synthetic construct
SEQUENCE: 389
gtggagccta ccaccacaat cagcgccacc agcacccacg agctgagcgc cagcgatgcc  60
agaaatagca tccagctgct gaatgcccac atcgccaccc tgcagtccgt gcagaaaagc  120
gtgcctggaa gcgattacag cgatcagatc agggacctgc tgaaggccgc cttcgatctg  180
agaggcctga tcgagacact ggcccacggc ggcatccctt tctacgaccc cagcaccatc  240
atgcctagaa tcaaactggt ggccaccacc atcgacacca tccacaccgc aacaacaacc  300
ctgcagaata aggtgcggcc tgcccacgtg gaactgggac tggaagtgac aaaggccgtg  360
ctgctgaccg ctaatcccgc ctccaccgcc aaggagctgg atgccgaagg agctgccctg  420
aaagccagac tggagaaggt gagccagtac cctgatctga cccctaacga cgtggccacc  480
tccagcaata gaccccggag cgtggcacag gctgctattg ccaccgacgg aaagggcatc  540
atcgataaag acagccggga tgccgtgatc aatgacgcca agctgagagc agcaatcgcc  600
ggcgctctgg tgaaggcagg cttcagcagc gccgacgccg tggctctggc ccctagaatc  660
gctaaggaga tggccaagga gggcgtgctg ctgatcaatc accacaagct gaaggccctg  720
atcggcgccc agctgggact gctgacagat gccaagatcc agagagccgc tgcagccgtg  780
gatctgggca tcaaggccac actggccgcc accatcatcc caaacgccct gggcagcgcc  840
gccttcaaaa atgccgtgat tgccaacctg gtggccgccg gcatcgataa gcacctggcc  900
agagccacag ccgtggccat cgtggccaca gccctgaatc ccgcactggg acctattgcc  960
aagttcgaac tcattaaggc cgaaatcgca gcccaagccg ccctgctgat tcggcggggc  1020
gtgcacctgc agaaagccgc cattgagcac gtgatcggca gagccttcga tgccgctgtg  1080
gccaccgcca tcatctcctc tcctatcctg tctgctagaa tcgtgaccca cctggtcaga  1140
gccggaatcg acaagtctat cgctatcagc ctggcccccc acatcgtgaa gagactggcc  1200
aaagagcccc tgctggcctt caacacagcc aagctcatga agaatatcac cagacagatc  1260
gtggacgtga tcaccgccga caaggccatc aaaaccgctg agcagctgga gaaggagctg  1320
cccgccctgg atgacctggt gaagaaggcc agcagccccc ccaagcctac acctacacct  1380
accccaaccc ctacagccgg ccctacagtg accgtgattc ctgtgggcag agaaggaggc  1440
gacatcacca tcagcggaaa gggcttctct accacaggct tcggcgtgta cgtggccgtg  1500
gcccctgcct ccgtgcccga attctacggc aacagcgaca agttctacgg ctacgacccc  1560
```

```
agcaaagaca ccacagagag cccttccacc atctgggtgt acacccctte ccagaaggcc  1620
atcggcagca gattcgctca gggcagacct atgaataacg acggctcttt caccatcaca  1680
atgaaggccc ccccettcga gcagggcaaa gacttcgtgg tgctgacaac caaggcccac  1740
ggcgtgggca agacagatca ctccgacgac acccggaccc ctgtgaccta cagagaggca  1800
acacctgctc ccaccgggcc aaagacccct atc                              1833

SEQ ID NO: 390         moltype = RNA  length = 1590
FEATURE                Location/Qualifiers
source                 1..1590
                       mol_type = other RNA
                       organism = synthetic construct
SEQUENCE: 390
tccagcaata gaccccggag cgtggcacag gctgctattg ccaccgacgg aaagggcatc  60
atcgataaag acagccggga tgccgtgatc aatgacgcca agctgagagc agcaatcgcc  120
ggcgctctgg tgaaggcagg cttcagcagc gccgacgccg tggctctggc ccctagaatc  180
gctaaggaga tggccaagga gggcgtgctg ctgatcaatc accacaagct gaaggccctg  240
atcggcgccc agctgggact gctgacagat gccaagatcc agagagccgc tgcagccgtg  300
gatctgggca tcaaggccac actggccgcc accatcatcc caaacgccct gggcagcgcc  360
gccttcaaaa atgccgtgat tgccaacctg gtggccgccg gcatcgataa gcacctggcc  420
agagccacag ccgtggccat cgtggccaca gccctgaatc ccgcactggg acctattgcc  480
aagttcgaac tcattaaggc cgaaatcgca gcccaagccg ccctgctgat tcggcggggc  540
gtgcacctgc agaaagccgc cattgagcac gtgatcggca gagccttcga tgccgctgtg  600
gccaccgcca tcatctcctc tcctatcctg tctgctagaa tcgtgaccca cctggtcaga  660
gccggaatcg acaagtctat cgctatcagc ctggcccccc acatcgtgaa gagactggcc  720
aaagagcccc tgctggcctt caacacagcc aagctcatga agaatatcac cagacagatc  780
gtggacgtga tcaccgccga caaggccatc aaaaccgctg agcagctgga gaaggagctg  840
cccgccctgg atgacctggt gaagaaggcc agcagccccc ccaagcctac acctacacct  900
accccaaccc ctacagccgg ccctacagtg accgtgattc ctgtgggcag agaaggaggc  960
gacatcacca tcagcggaaa gggcttctct accacaggct tcggcgtgta cgtggccgtg  1020
gcccctgcct ccgtgcccga attctacggc aacagcgaca agttctacgg ctacgacccc  1080
agcaaagaca ccacagagag cccttccacc atctgggtgt acacccctte ccagaaggcc  1140
atcggcagca gattcgctca gggcagacct atgaataacg acggctcttt caccatcaca  1200
atgaaggccc ccccettcga gcagggcaaa gacttcgtgg tgctgacaac caaggcccac  1260
ggcgtgggca agacagatca ctccgacgac acccggaccc ctgtgaccta cagagaggca  1320
acacctgctc ccaccgggcc aaagacccct atcgtgtacg tgagaaccaa tttcagcaag  1380
accatctggc aggtgagagc caatcgggac agatacatcc tgggccacaa gtctgccgcc  1440
gtgtataaaa ccctgaatca cgccatcacc aaggccgtgg gcgtgagact gaaccctaag  1500
acaaccgtgg gcaacatcca ggccgccaga acagagctgc tggccgccta ccagacagcc  1560
ttcaatagcc ccgacgtgaa gaaggccgct                                   1590

SEQ ID NO: 391         moltype = RNA  length = 858
FEATURE                Location/Qualifiers
source                 1..858
                       mol_type = other RNA
                       organism = synthetic construct
SEQUENCE: 391
atgaaggcca agctgctggt gctgctgtgc accttcaccg ccacctacgc tgtggagccc  60
accaccacca tcagcgcaac ctccacccac gaactgtccg cctccgatgc taggaactca  120
atccagctgc tgaacgccca catcgccaca ctgcagagcg tccagaaatc agtgcccggc  180
agcgactact ccgaccagat ccgggatctc ctgaaggctg cattcgacct gcgcggcctc  240
atcgaaacac tggcccacgg aggcatcccc ttctatgacc catccaccat catgccccgg  300
atcaagctgg tggccaccac aatcgacacc atccacaccg ccaccaccac cctgcagaac  360
aaggtgaggc ccgcacacgt ggagctgggg ctggaggtga ctaaggccgt gctgctgaca  420
gcaaaccccg cctcaaccgc gaaggagttg gatgccgagg gcgccgcact gaaggcccgc  480
ctggagaagg tgagccagta tcccgatctg acccccaacg acgtggccac cgtgtatgtg  540
aggaccaatt tctccaagac catctggcag gtcagagcca acagagacag gtatatcctg  600
ggccacaaga gcgctgccgt gtacaagacc ctgaaccacg ccatcaccaa ggccgtgggg  660
gtgcggctga accctaagac caccgtgggg aacatccagg ctgccagaac cgagctgctg  720
gccgcctatc agaccgcatt caattccccc gatgtgaaga aggccgccag cggctccatc  780
ctggccatct actccaccgt ggctagtagc ctggtgctgc tggtgtccct gggagccatc  840
agcttcggga gcggctaa                                               858

SEQ ID NO: 392         moltype = RNA  length = 858
FEATURE                Location/Qualifiers
source                 1..858
                       mol_type = other RNA
                       organism = synthetic construct
SEQUENCE: 392
atgaaagcca agctgctcgt gctgctgtgt accttcaccg ccacctacgc cgtggaaccc  60
accaccacaa tctccgccac ctccacccac gagctgagcg ccagcgacgc cagaaacagc  120
attcagctgc tgaatgccca catcgccacc ctgcagagcg tgcagaagtc cgtgcctggc  180
agcgactaca gcgaccagat ccgggacctg ctgaaggccg ccttcgacct gagaggcctg  240
attgagacac tggcccacgg cggcattcct ttctacgatc cttctaccat catgcctaga  300
atcaagctgg tggccaccac catcgatacc atccacacag ccaccaccac actgcagaac  360
aaggtgcggc ctgctcacgt ggaactgggc ctggaagtga ccaaggccgt gctgctgacc  420
gccaatcctg cctccaccgc caaggagctg gacgcagaag gcgctgccct gaaggccaga  480
ctggagaagg tgagccagta tcccgacctg accccaaacg atgtggccac cgtgtacgtg  540
cggacaaact tcagcaagac catctggcag gtgagagcca accgggacag atacatcctg  600
ggccacaaga gcgccgccgt gtataagacc ctgaaccacg ccatcacaaa ggccgtgggc  660
```

```
gtgagactga accccaagac cacagtgggc aacatccagg ccgccaggac cgaactgctg  720
gccgcctacc agaccgcctt caattcccct gacgtgaaga aggccgcctc tggcagcatc  780
ctggccatct acagcaccgt ggccagctct ctggtgctgc tggtgtctct gggcgccatc  840
agcttcggca gcggctga                                                858

SEQ ID NO: 393         moltype = RNA  length = 1590
FEATURE                Location/Qualifiers
source                 1..1590
                       mol_type = other RNA
                       organism = synthetic construct
SEQUENCE: 393
agctccaata gacccagatc cgtggcccag gccgccatcg ccacagatgg caaggggatc  60
atcgacaagg attccagaga cgctgtgatc aacgacgcaa agctgagagc cgccatcgcc  120
ggagctctgg tgaaggccgg ctttagcagc gccgacgccg tggcactggc ccccagaatt  180
gcaaaggaga tggcaaagga gggcgtgctg ctgatcaatc accacaagct gaaggccctg  240
atcggcgcac agctgggcct gctgaccgac gcaaagattc agagagccgc cgcagccgtg  300
gacctgggca tcaaggccac cctggctgcc accatcatcc ctaacgccct gggcagcgcc  360
gccttcaaga atgcagtgat cgccaacctg gtggccgccg gaatcgacaa gcacctggcc  420
agagccacag ccgtcgctat cgtggccaca gccctgaatc ccgccctggg ccccatcgcc  480
aaatttgaac tgatcaaggc agaaatcgct gcccaggccg ccctgctcat cagaagaggc  540
gtccatctgc agaaggccgc catcgagcac gtgattggca gagccttcga cgccgccgtg  600
gccacagcta tcatttcttc ccctatcctg tctgccagaa tcgtgacaca cctggtgaga  660
gccggaatcg acaagtccat cgccatctcc ctggcccccc acatcgtgaa gagactggct  720
aaggagcctc tgctggcctt caatacagcc aagctgatga agaacatcac aagacagatc  780
gtggacgtga tcaccgccga caaggccatc aagacagccg agcagctgga gaaggaactg  840
ccagccctgg acgacctggt gaagaaggcc agcagccctc ccaagcctac ccctacccca  900
acccctacac ctacagccgg acctaccgtg accgtgatcc ctgtgggcag agagggcggc  960
gacatcacca tcagcggcaa gggcttcagc acaacaggct ttggcgtgta cgtggccgtg  1020
gccccagcca gcgtgcctga gttttacggc aatagcgaca agttctacgg ctacgacccc  1080
tccaaggaca ccaccgagag cccaagcacc atctgggtgt acacacctag ccagaaggcc  1140
atcggcagca gatttgccca gggcaggcct atgaataatg acggcagctt cacaatcaca  1200
atgaaggccc ccccctttga gcagggcaag gacttcgtgg tgctgaccac caaggcccac  1260
ggcgtgggca agacagatca cagcgacgac acccggaccc ccgtgaccta cagagaagca  1320
acacctgccc ctaccgggcc taagacaccc atcgtgtacg tgagaaccaa tttcagcaag  1380
accatctggc aggtgagagc caacagagat cggtacatcc tgggccacaa gtccgccgcc  1440
gtgtacaaga ccctgaatca cgccatcacc aaggccgtgg gcgtgcggct gaatcctaag  1500
accaccgtgg gcaacatcca ggccgccaga accgaactgc tggccgccta ccagaccgcc  1560
ttcaacagcc ccgatgtgaa gaaggccgct                                   1590

SEQ ID NO: 394         moltype = RNA  length = 1647
FEATURE                Location/Qualifiers
source                 1..1647
                       mol_type = other RNA
                       organism = synthetic construct
SEQUENCE: 394
atgaaggcca agctgctggt gctgctgtgt accttcactg caacatatgc tagctccaat  60
agacccagat ccgtggccca ggccgccatc gccacagatg gcaaggggat catcgacaag  120
gattccagag acgctgtgat caacgacgca aagctgagag ccgccatcgc cggagctctg  180
gtgaaggccg gctttagcag cgccgacgcc gtggcactgg cccccagaat tgcaaaggag  240
atggcaaagg agggcgtgct gctgatcaat caccacaagc tgaaggccct gatcggcgca  300
cagctgggcc tgctgaccga cgcaaagatt cagagagccg ccgcagccgt ggacctgggc  360
atcaaggcca ccctggctgc caccatcatc cctaacgccc tgggcagcgc cgccttcaag  420
aatgcagtga tcgccaacct ggtggccgcc ggaatcgaca agcacctggc cagagccaca  480
gccgtcgcta tcgtggccac agccctgaat cccgccctgg gccccatcgc caaatttgaa  540
ctgatcaagg cagaaatcgc tgcccaggcc gccctgctca tcagaagagg cgtccatctg  600
cagaaggccg ccatcgagca cgtgattggc agagccttcg acgccgccgt ggccacagct  660
atcatttctt cccctatcct gtctgccaga atcgtgacac acctggtgag agccggaatc  720
gacaagtcca tcgccatctc cctggccccc cacatcgtga agagactggc taaggagcct  780
ctgctggcct tcaatacagc caagctgatg aagaacatca caagacagat cgtggacgtg  840
atcaccgccg acaaggccat caagacagcc gagcagctgg agaaggaact gccagccctg  900
gacgacctgg tgaagaaggc cagcagccct cccaagccta cccctacccc aacccctaca  960
cctacagccg gacctaccgt gaccgtgatc cctgtgggca gagagggcgg cgacatcacc  1020
atcagcggca agggcttcag cacaacaggc tttggcgtgt acgtggccgt ggccccagcc  1080
agcgtgcctg agttttacgg caatagcgac aagttctacg gctacgaccc ctccaaggac  1140
accaccgaga gcccaagcac catctgggtg tacacaccta gccagaaggc catcggcagc  1200
agatttgccc agggcaggcc tatgaataat gacggcagct tcacaatcac aatgaaggcc  1260
ccccctttg agcagggcaa ggacttcgtg gtgctgacca ccaaggccca cggcgtgggc  1320
aagacagatc acagcgacga cacccggacc cccgtgacct acagagaagc aacacctgcc  1380
cctaccgggc ctaagacacc catcgtgtac gtgagaacca atttcagcaa gaccatctgg  1440
caggtgagag ccaacagaga tcggtacatc ctgggccaca agtccgccgc cgtgtacaag  1500
accctgaatc acgccatcac caaggccgtg ggcgtgcggc tgaatcctaa gaccaccgtg  1560
ggcaacatcc aggccgccag aaccgaactg ctggccgcct accagaccgc cttcaacagc  1620
cccgatgtga agaaggccgc ttgataa                                      1647

SEQ ID NO: 395         moltype = RNA  length = 87
FEATURE                Location/Qualifiers
source                 1..87
                       mol_type = other RNA
                       organism = synthetic construct
```

-continued

```
SEQUENCE: 395
agcggcagca tcctggctat ctacagcaca gtggcttcta gcctggtgct gctggtgtct  60
ctgggcgcca tcagctttgg cagcggc                                      87

SEQ ID NO: 396         moltype = RNA  length = 87
FEATURE                Location/Qualifiers
source                 1..87
                       mol_type = other RNA
                       organism = synthetic construct
SEQUENCE: 396
agcggaagca tcctggccat ctatagcacc gtggctagct ctctggtgct gctggtgagc  60
ctgggagcta tcagctttgg gagcggc                                      87

SEQ ID NO: 397         moltype =   length =
SEQUENCE: 397
000

SEQ ID NO: 398         moltype = RNA  length = 858
FEATURE                Location/Qualifiers
source                 1..858
                       mol_type = other RNA
                       organism = synthetic construct
SEQUENCE: 398
atgaargcca agctgctsgt gctgctstgy acyttyaccg ccacctaygc ygtsgarccc  60
accacmacaa tcwgcgcmac mtccacmcac garctgwscg cmwccgaygc yagraaywsm  120
atycagctgc tgaaygccca catcgccacm ctscagagcg tscagaarws hgtgccyggc  180
wsygaytayw scgaccagat ccgggaycts ctsaaggcyg cmttygacct gmgmggccts  240
atygaracac tggcycaygg mggsatyccy ttctaygayc chwsyaccat catgccymgr  300
atcaagctgg tsgccachac matcgayacc atccacacmg ccaccaccac mctgcagaac  360
aargtgmgsc cygchcaygt ggarctgggs ctggargtga cyaargcsgt gctgctgacm  420
gcmaayccyg chwsmacmgc saaggarytg gaygcmgarg gmgcygcmct gaaggcymgv  480
ctsgagaagg tgwsccagta ycccgayctg accccmaayg aygtggcmac ygtgtaygtg  540
mgracmaayt tcwscaagac catytggcag gtsmgggcca aymgrgacag rtayatcctg  600
ggscacaara gcgcygccgt gtayaagacc ctgaaycacg ccatcacmaa ggccgtgggv  660
gtgmgrctga aycchaagac cacmgtgggs aayatycagg cygccmgrac mgarctgctg  720
gccgcctayc agacmgchtt yaatwscccy gaygtgaaga aggccgccws yggswscaty  780
ctggccatct acwsyaccgt ggcywsywsy ctggtgctgc tggtgwsyct gggmgcyaty  840
wscttcggvw syggstra                                                858

SEQ ID NO: 399         moltype = RNA  length = 858
FEATURE                Location/Qualifiers
source                 1..858
                       mol_type = other RNA
                       organism = synthetic construct
SEQUENCE: 399
atgaargcca agctgctsgt gctgctstgy acyttyaccg ccacctaygc cgtsgarccc  60
accacmacaa tcwgcgccac mtccacmcac garctgwscg cmwccgacgc cagaaaywsc  120
atycagctgc tgaaygccca catcgccacc ctscagagcg tgcagaarws ygtgccyggc  180
wsygaytaya gcgaccagat ccgggacctg ctsaaggccg cmttygacct gmgmggcctg  240
atygagacac tggcycaygg mggsatyccy ttctaygatc cywsyaccat catgccymgr  300
atcaagctgg tsgccachac matcgayacc atccacacmg ccaccaccac mctgcagaac  360
aargtgcgsc cygcycaygt ggarctgggs ctggargtga ccaargcsgt gctgctgacm  420
gccaayccts chwscacmgc caaggarctg gaygcmgarg gmgcygcmct gaaggcymgr  480
ctsgagaagg tgwsccagta ycccgacctg accccmaayg aygtggcmac ygtgtacgtg  540
mgracmaayt tcagcaagac catytggcag gtsmgggcca aymgrgacag atacatcctg  600
ggscacaara gcgccgccgt gtayaagacc ctgaaycacg ccatcacmaa ggccgtgggm  660
gtgmgrctga aycchaagac cacmgtgggc aayatycagg ccgccmgrac mgarctgctg  720
gccgcctacc agacmgcytt yaatwscccy gaygtgaaga aggccgccws yggsagcaty  780
ctggccatct acwsyaccgt ggccwsywsy ctggtgctgc tggtgwsyct gggmgcyaty  840
wscttcggvw syggstra                                                858
```